(12) United States Patent
Park et al.

(10) Patent No.: US 9,353,385 B2
(45) Date of Patent: May 31, 2016

(54) SCLAREOL AND LABDENEDIOL DIPHOSPHATE SYNTHASE POLYPEPTIDES, ENCODING NUCLEIC ACID MOLECULES AND USES THEREOF

(71) Applicants: Grace Eunyoung Park, Lexington, KY (US); Bryan N. Julien, Lexington, KY (US); Richard Burlingame, Nicholasville, KY (US)

(72) Inventors: Grace Eunyoung Park, Lexington, KY (US); Bryan N. Julien, Lexington, KY (US); Richard Burlingame, Nicholasville, KY (US)

(73) Assignee: Evolva, Inc., Reinach (CH)

( * ) Notice: Subject to any disclaimer, the term of this patent is extended or adjusted under 35 U.S.C. 154(b) by 78 days.

(21) Appl. No.: 13/987,493

(22) Filed: Jul. 30, 2013

(65) Prior Publication Data

US 2014/0073020 A1   Mar. 13, 2014
US 2014/0349352 A9   Nov. 27, 2014

Related U.S. Application Data

(60) Provisional application No. 61/741,959, filed on Jul. 30, 2012.

(51) Int. Cl.
| *C12P 7/02* | (2006.01) |
| *C12P 9/00* | (2006.01) |
| *C12N 9/88* | (2006.01) |
| *C12P 7/18* | (2006.01) |

(52) U.S. Cl.
CPC ... *C12P 7/02* (2013.01); *C12N 9/88* (2013.01); *C12P 7/18* (2013.01); *C12P 9/00* (2013.01); *C12Y 402/03* (2013.01); *Y02P 20/52* (2015.11)

(58) Field of Classification Search
None
See application file for complete search history.

(56) References Cited

U.S. PATENT DOCUMENTS

| 4,701,543 A | 10/1987 | Naef et al. ............... 549/458 |
| 4,734,530 A | 3/1988 | Whitesides et al. ........ 568/567 |
| 4,814,469 A | 3/1989 | Whitesides et al. ........ 549/458 |
| 4,952,496 A | 8/1990 | Studier et al. ............. 435/91 |
| 4,970,163 A | 11/1990 | Farbood et al. ............ 435/255 |
| 5,012,040 A | 4/1991 | Whitaker ................... 800/200 |
| 5,177,306 A | 1/1993 | Whitaker ................... 800/200 |
| 5,212,078 A | 5/1993 | Farbood et al. ............ 435/126 |
| 5,290,955 A | 3/1994 | Asanuma et al. ........... 549/458 |
| 5,463,089 A | 10/1995 | Barton et al. .............. 549/458 |
| 5,525,728 A | 6/1996 | Schneider et al. .......... 549/299 |
| 5,605,793 A | 2/1997 | Stemmer ..................... 435/6 |
| 5,811,238 A | 9/1998 | Stemmer et al. .............. 435/6 |
| 5,824,774 A | 10/1998 | Chappell et al. ........... 530/350 |
| 5,830,721 A | 11/1998 | Stemmer et al. .......... 435/172.1 |
| 5,834,252 A | 11/1998 | Stemmer et al. .......... 435/91.1 |
| 5,837,458 A | 11/1998 | Minshull et al. ............. 435/6 |
| 6,072,045 A | 6/2000 | Chappell et al. ........... 536/23.1 |
| 6,531,303 B1 | 3/2003 | Millis et al. ............. 435/155 |
| 6,689,593 B2 | 2/2004 | Millis et al. ............. 435/155 |
| 7,186,891 B1 | 3/2007 | Chappell et al. ........... 800/298 |
| 7,238,514 B2 | 7/2007 | Matsuda et al. .......... 435/252.3 |
| 7,622,614 B2 | 11/2009 | Julien et al. ............. 568/327 |
| 7,838,279 B2 | 11/2010 | Millis et al. ........... 435/254.2 |
| 7,842,497 B2 | 11/2010 | Millis et al. ........... 435/254.2 |
| 7,906,710 B2 | 3/2011 | Karunanandaa et al. ..... 800/306 |
| 8,106,260 B2 | 1/2012 | Chappell et al. ........... 800/298 |
| 8,124,811 B2 | 2/2012 | Julien et al. ............. 568/367 |
| 8,362,309 B2 | 1/2013 | Julien et al. ............. 583/360 |
| 8,481,286 B2 | 7/2013 | Julien et al. ............. 435/69.1 |
| 2004/0072323 A1 | 4/2004 | Matsuda et al. .......... 435/252.3 |
| 2004/0249219 A1 | 12/2004 | Saucy ..................... 568/388 |
| 2006/0223883 A1 | 10/2006 | Rahman et al. ............ 514/468 |
| 2007/0231861 A1 | 10/2007 | Millis et al. ............ 435/69.1 |
| 2007/0238157 A1 | 10/2007 | Millis et al. ............. 435/166 |
| 2007/0238159 A1 | 10/2007 | Millis et al. .......... 435/252.33 |
| 2007/0238160 A1 | 10/2007 | Millis et al. .......... 435/252.33 |
| 2007/0254354 A1 | 11/2007 | Millis et al. .......... 435/252.33 |
| 2008/0233622 A1 | 9/2008 | Julien et al. ............. 435/148 |
| 2009/0123984 A1 | 5/2009 | Chappell et al. ........... 435/166 |
| 2010/0035329 A1 | 2/2010 | Millis et al. ........... 435/254.2 |
| 2010/0129306 A1 | 5/2010 | Julien et al. ............. 424/65 |
| 2010/0151519 A1 | 6/2010 | Julien et al. ............ 435/69.1 |
| 2010/0151555 A1 | 6/2010 | Julien et al. ............. 435/193 |
| 2010/0311134 A1 | 12/2010 | Schalk .................. 435/156 |
| 2011/0041218 A1 | 2/2011 | Schalk .................. 800/298 |
| 2011/0081703 A1 | 4/2011 | Chappell et al. ........... 435/193 |
| 2011/0189717 A1 | 8/2011 | Ajikumar et al. ........... 435/29 |
| 2012/0129235 A1 | 5/2012 | Julien et al. ............. 435/166 |
| 2012/0135477 A1 | 5/2012 | Breuer et al. ............. 435/126 |
| 2012/0246767 A1 | 9/2012 | Amick et al. ............. 800/316 |

(Continued)

FOREIGN PATENT DOCUMENTS

| WO | WO 97/07205 | 2/1997 |
| WO | WO 97/38703 | 10/1997 |
| WO | WO 2006/010287 | 2/2006 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
US 8,486,659, Jul. 16, 2013, Julien et al. (withdrawn).
Letter/Written Disclosure of the Information Disclosure Statement for the above-referenced application, mailed on the same day herewith, 2 pages.
Partial International Search Report, issued Oct. 16, 2013, in connection with corresponding International Patent Application No. PCT/US2013/052784, 7 pages.
International Search Report, issued Nov. 26, 2013, in connection with corresponding International Patent Application No. PCT/US2013/052784, 17 pages.
Allylix, "Protein engineering and chembiosynthesis to produce novel sesquiterpenoids," Presentation at BIO World Congress on Industrial Biotechnology & Bioprocessing, Washington, D.C. on Jun. 28, 2010, 19 pages.

(Continued)

*Primary Examiner* — Christian Fronda
(74) *Attorney, Agent, or Firm* — McDonnell Boehnen Hulbert & Berghoff LLP

(57) ABSTRACT

Provided are labdenediol diphosphate synthase polypeptides, sclareol synthase polypeptides, nucleic acid molecules encoding the labdenediol diphosphate synthase polypeptides and sclareol synthase polypeptides, and methods of using the labdenediol diphosphate synthase polypeptides, sclareol synthase polypeptides. Also provided are methods for producing labdenediol diphosphate, sclareol and (−)-ambroxide.

11 Claims, 27 Drawing Sheets

(56) References Cited

U.S. PATENT DOCUMENTS

| | | | | |
|---|---|---|---|---|
| 2013/0122560 | A1 | 5/2013 | Julien et al. | 435/148 |
| 2013/0236943 | A1 | 9/2013 | Julien et al. | 435/166 |

FOREIGN PATENT DOCUMENTS

| | | |
|---|---|---|
| WO | WO 2008/007031 | 1/2008 |
| WO | WO 2009/044336 | 4/2009 |
| WO | WO 2009/095366 | 8/2009 |
| WO | WO 2009/101126 | 8/2009 |
| WO | WO 2010/019696 | 2/2010 |
| WO | WO 2012/058636 | 5/2012 |
| WO | WO 2013/075239 | 5/2013 |

OTHER PUBLICATIONS

Altschul et al., "Basic local alignment search tool," J. Mol. Biol. 215(3):403-410 (1990).

Arnold et al., "The SWISS-MODEL workspace: a web-based environment for protein structure homology modelling," Bioinformatics 22:195-201 2006.

ATCC Accession No. 20918, "Cryptococcus magnus," [online][retrieved on Sep. 13, 2013] Retrieved from:<URL:atcc.org/products/all/20918.aspx, 2 pages.

Banthorpe et al., "Accumulation of the anti-fungal diterpene sclareol by cell cultures of Salvia sclarea and Nicotiana glutinosa," Phytochem. 29(7):2145-2148 (1990).

Banthorpe et al., "Partial purification of farnesyl pyrophosphate: drimenol cyclase and geranylgeranyl pyrophosphate: sclareol cyclase, using cell culture as a source of material," Phytochem. 31(10):3391-3395 (1992).

Barrero et al., "Synthesis of Ambrox® from (−)-sclareol and (+)-cis-abienol," Tetrahedron 49(45):10405-10412 (1993).

Barrero et al., "Degradation of the side chain of (−)-sclareol: a very short synthesis of nor-ambreinolide and Ambrox," Synth. Comm. 34(19):3631-3643 (2004).

Beier, D. and E. Young, "Characterization of a regulatory region upstream of the ADR2 locus of S. cerevisiae," Nature 300:724-728 (1982).

Bohlmann et al., "Plant terpenoid synthases: molecular biology and phylogenetic analysis," Proc. Natl. Acad. Sci. U.S.A. 95:4126-4133 (1998).

Brodelius et al., "Fusion of farnesyldiphosphate synthase and epi-aristolochene synthase, a sesquiterpene cyclase involved in capsidiol biosynthesis in Nicotiana tabacum," Eur. J. Biochem. 269:3570-3577 (2002).

Brown et al., "Codon utilisation in the pathogenic yeast, Candida albicans," Nucleic Acids Res. 19(15):4298 (1991).

Caniard et al., "Discovery and functional characterization of two diterpene synthases for sclareol biosynthesis in Salvia sclarea (L.) and their relevance for perfume manufacture," BMC Plant Biol. 12:119, 13 pages (2012).

Cao et al., "Diterpene cyclases and the nature of the isoprene fold," Proteins 78:2417-2432 (2010).

Carrillo et al., "The multiple sequence alignment problem in biology," SIAM J. Appl. Math. 48(5):1073-1082 (1988).

Christianson, D., "Unearthing the roots of the terpenome," Curr. Opin. Chem. Biol. 12(2):141-150 (2008).

Crameri et al., "DNA shuffling of a family of genes from diverse species accelerates directed evolution," Nature 391:288-291 (1998).

Cyr et al., "A modular approach for facile biosynthesis of labdane-related diterpenes," J. Am. Chem. Soc. 129(21):6684-6685 (2007).

de Boer et al., "The tac promoter: a functional hybrid derived from the trp and lac promoters," Proc. Natl. Acad. Sci. U.S.A. 80:21-25 (1983).

Dolan, K., "Allylix sniffs out biotech for new fragrances," found in Forbes Magazine dated Nov. 8, 2010, Published on Oct. 21, 2010 [online][retrieved on Jun. 1, 2012] Retrieved from :<URL: forbes.com/forbes/2010/1108/technology-allylix-fragrances-flavor-carolyn-fritz-smell-test.html?partner=email, 1 page.

Emanuelsson et al., "ChloroP, a neural network-based method for predicting chloroplast transit peptides and their cleavage sites," Protein Sci. 8:978-984 (1999).

English language machine translation of WO 2008/007031 (Item CF), published Jan. 17, 2008, entitled "Genes coding for cis-labda-12,14-dien-9 alpha-ol (cis-abienol) synthase and syn-copalyl-8-ol diphosphate synthase and uses thereof," World Intellectual Property Organization Patentscope translation tool, 10 pages [Patent originally in French].

Falara et al, "A copal-8-ol diphosphate synthase from the angiosperm Cistus creticus subsp. Creticus is a putative key enzyme for the formation of pharmacologically active, oxygen-containing labdane-type diterpenes," Plant Physiol. 154(1):301-310 (2010).

Fleer et al., "High-level secretion of correctly processed recombinant human interleukin-1β in Kluyveromyces lactis," Gene 107:285-295 (1991).

Forsburg, S., "Codon usage table for Schizosaccharomyces pombe," Yeast 10(8):1045-1047 (1994).

Gilbert et al., "Useful proteins from recombinant bacteria," Sci. Am. 242(3):74-94 (1980).

Greenhagen et al., "Identifying and manipulating structural determinates linking catalytic specificities in terpene synthases," Proc. Natl. Acad. Sci. U.S.A. 103:9826-9831 (2006).

Gribskov et al., "Sigma factors from E.coli, B.subtilis, phage SP01, and phage T4 are homologous proteins," Nucleic Acids Res. 14(16):6745-6763 (1986).

Guex et al., "SWISS-MODEL and the Swiss-Pdb Viewer: an environment for comparative protein modeling," Electrophoresis 18:2714-2723 (1997).

Guo et al., "Biosynthesis of labdenediol and sclareol in cell-free extracts from trichomes of Nicotiana glutinosa," Planta 197:627-632 (1995).

Hess et al., "Cooperation of glycolytic enzymes," Adv. Enzyme Reg. 7:149-167 (1969).

Hitzeman et al., "Isolation and characterization of the yeast 3-phosphoglycerokinase gene (PGK) by an immunological screening technique," J. Biol. Chem. 255:12073-12080 (1980).

Holland, M. and J. Holland, "Isolation and identification of yeast messenger ribonucleic acids coding for enolase, glyceraldehyde-3-phosphate dehydrogenase, and phosphoglycerate kinase," Biochem. 17:4900-4907 (1978).

Huang et al., "A time-efficient, linear-space local similarity algorithm," Adv. Appl. Math. 12:337-357 (1991).

IUPAC-IUB Commission on Biochemical Nomenclature, "A one-letter notation for amino acid sequences. Tentative rules," J. Biol. Chem. 243(13):3557-3559 (1968).

IUPAC-IUB Commission on Bio-Chemical Nomenclature Symbols for Amino-Acid Derivatives and Peptides, "Recommendations," Biochem. 11(9):1726-1732 (1972).

Jay et al., "Construction of a general vector for efficient expression of mammalian proteins in bacteria: use of a synthetic ribosome binding site," Proc. Natl. Acad. Sci. U.S.A. 78(9):5543-5548 (1981).

Keeling et al., "Identification and functional characterization of monofunctional ent-copalyl diphosphate and ent-kaurene synthases in white spruce reveal different patterns for diterpene synthase evolution for primary and secodary metabolism in gymnosperms," Plant Physiol. 152(3):1197-1208 (2010).

Kiefer et al., "The SWISS-MODEL repository and associated resources," Nucleic Acids Res. 37:D387-D392 (2009).

Köksal et al., "Taxadiene synthase structure and evolution of modular architecture in terpene biosynthesis," Nature 469:116-120 (2011).

Köksal et al., "Structure and mechanism of the diterpene cyclase ent-copalyl diphosphate synthase," Nat. Chem. Biol. 7(7):431-433 (2011).

Lesburg et al., "Managing and manipulating carbocations in biology: terpenoid cyclase structure and mechanism," Curr. Opin. Struc. Biol. 8:695-703 (1998).

Liang et al., "Structure, mechanism and function of prenyltransferases," Eur. J. Biochem. 269:3339-3354 (2002).

Mann et al., "A single residue switch for Mg2+-dependent inhibition characterizes plant class II diterpene cyclases from primary and secondary metabolism," J. Biol. Chem. 285(27):20558-20563 (2010).

(56) References Cited

OTHER PUBLICATIONS

Mau, C. and C. West, "Cloning of casbene synthase cDNA: evidence for conserved structural features among terpenoid cyclases in plants," Proc. Natl. Acad. Sci. U.S.A. 91:8497-8501 (1994).

Mayfield et al., "Expression and assembly of a fully active antibody in algae," Proc. Natl. Acad. Sci. U.S.A. 100(2):438-442 (2003).

Muneta et al., "Large-scale production of porcine mature interleukin-18 (IL-18) in silkworms using a hybrid baculovirus expression system," J. Vet. Med. Sci. 65(2):219-223 (2003).

NCBI Accession No. AAS98912.1 "terpenoid cyclase [Nicotiana tabacum]," Published on Feb. 1, 2005 [online][retrieved on Sep. 13, 2013] Retrieved from:<URL:ncbi.nlm.nih.gov/protein/AAS98912.1, 1 page.

NCBI Accession No. ACO56896.1, "terpene synthase [Solanum lycopersicum]," Published on Jul. 8, 2009 [online][retrieved on Sep. 13, 2013] Retrieved from:<URL:ncbi.nlm.nih.gov/protein/ACO56896.1, 2 pages.

NCBI Accession No. ADJ93862, "copal-8-ol diphosphate synthase [Cistus creticus subsp. creticus]," Published on Jun. 30, 2010 [online][retrieved on Sep. 13, 2013] Retrieved from:<URL:ncbi.nlm.nih.gov/protem/ADJ93862, 2 pages.

Needleman, S. and C. Wunsch, "A general method applicable to the search for similarities in the amino acid sequence of two proteins," J. Mol. Biol. 48:443-453 (1970).

Park et al., "Metabolic engineering of Saccharomyces cerevisiae for the fermentative production of high-value terpenoid compounds," Abstract of presentation at Society for Industrial Microbiology Annual Meeting and Exhibition, Denver, CO, Jul. 30, 2007, 1 page.

Park et al., "Using Saccharomyces cerevisiae for production of terpenoid compounds for use as fragrances and flavorings," Abstract of presentation at Society for Industrial Microbiology Annual Meeting and Exhibition, San Diego, CA presented on Aug. 31, 2008, 1 page.

PDB Accession No. 3PYB, "Crystal structure of ent-copalyl diphosphate synthase from Arabidopsis thaliana in complex with 13-aza-13,14-dihydrocopalyl diphosphate," Published on Dec. 12, 2010 [online][retrieved on Sep. 13, 2013] Retrieved from:<URL:rcsb.org/pdb/explore/explore.do?structureId=3pyb, 1 page.

PDB Accession No. 3S9V, "abietadiene synthase from Abies grandis," Published on Jun. 2, 2011 [online][retrieved on Sep. 13, 2013] Retrieved from:<URL:rcsb.org/pdb/explore/explore.do?structureId=3s9v, 1 page.

Peitsch, M., "Protein modeling by e-mail," Nature Biotechnol. 13:658-660 (1995).

Peters et al., "Bifunctional abietadiene synthase: free diffusive transfer of the (+)-copalyl diphosphate intermediate between two distinct active sites," J. Am. Chem. Soc. 123:8974-8978 (2001).

Peters et al., "Abietadiene synthase catalysis: conserved residues involved in protonation-initiated cyclization of geranylgeranyl diphosphate to (+)-copalyl diphosphate," Biochem. 41:1836-1842 (2002).

Pham et al., "Large-scale transient transfection of serum-free suspension-growing HEK293 EBNA1 cells: peptone additives improve cell growth and transfection efficiency," Biotechnol. Bioeng. 84(3):332-342 (2003).

Quigley, K., "Allylix raises $18.2M, announces launch of new product for fragrance market," San Diego Business Journal, Published on Mar. 14, 2012 [online][retrieved on Jun. 1, 2012] Retrieved from:<URL:sdbj.com/news/2012/mar/14/allylix-raises-182m-announces-launch-new-product-f/, 1 page.

Richmond, T., "Precompiled codon-usage tables," Genome Biol. 1:241 (2000).

Russell et al., "Nucleotide sequence of the yeast alcohol dehydrogenase II gene," J. Biol. Chem. 258:2674-2682 (1982).

Schwartz, R. and M. Dayhoff, eds., Atlas of Protein Sequence and Structure, National Biomedical Research Foundation, pp. 353-358 (1979).

Sharp et al., "Codon usage patterns in Escherichia coli, Bacillus subtilis, Saccharomyces cerevisiae, Schizosaccharomyces pombe, Drosophila melanogaster and Homo sapiens; a review of the considerable within-species diversity," Nucleic Acids Res. 16(17):8207-8211 (1988).

Sharp et al., "Synonymous codon usage in Saccharomyces cerevisiae," Yeast 7(7):657-678 (1991).

Smith, T. and M. Waterman, "Comparison of biosequences," Advances in Applied Mathematics 2:482-489 (1981).

Starks et al., "Structural basis for cyclic terpene biosynthesis by tobacco 5-epi-aristolochene synthase," Science 277:1815-1820 (1997).

Stemmer, W., "DNA shuffling by random fragmentation and reassembly: in vitro recombination for molecular evolution," Proc. Natl. Acad. Sci. U.S.A. 91:10747-10751 (1994).

Stemmer et al., "Rapid evolution of a protein in vitro by DNA shuffling," Nature 370(6488):389-391 (1994).

Takahashi et al., "Metabolic engineering of sesquiterpene metabolism in yeast," Biotechnol. Bioeng. 97:170-181 (2007).

Thai et al., "Farnesol is utilized for isoprenoid biosynthesis in plant cells via farnesyl pyrophosphate formed by successive monophosphorylation reactions," Proc. Natl. Acad. Sci. U.S.A. 96:13080-13085 (1999).

Thompson et al., "CLUSTAL W: improving the sensitivity of progressive multiple sequence alignment through sequence weighting, position-specific gap penalties and weight matrix choice," Nucleic Acids Res. 11(22):4673-4680 (1994).

Threlfall, D. and I. Whitehead, "Co-ordinated inhibition of squalene synthetase and induction of enzymes of sesquiterpenoid phytoalexin biosynthesis in cultures of Nicotiana tabacum," Phytochemistry 27:2567-2580 (1988).

van den Berg et al., "Kluyveromyces as a host for heterologous gene expression: expression and secretion of prochymosin," Biotechnol. 8:135-139 (1990).

Watson et al., Molecular Biology of the Gene, 4th Edition, The Benjamin/Cummings Pub. co., p. 224 (1987).

Wendt et al., "Structure and function of a squalene cyclase," Science 277:1811-1815 (1997).

Zhou et al., "Insights into diterpene cyclization from structure of bifunctional abietadiene synthase from Abies grandis," J. Biol. Chem. 287:6840-6850 (2012).

\* cited by examiner

B. Conversion of GGPP to LPP by LPP Synthase:

C. Conversion of LPP to Sclareol by Sclareol Synthase:

```
NgLPP2-1-2  (2)   MQVKITSSHRLFCHFHQLKSATSLSAQKTEFRKYGPGNSLFQTEGSLLYKPVRLNCAPID    60
CPS        (83)   MSLQYHVLNSIPSTTFLSSTKTTISSSFLTISGSPLNVARDKSRSGSIHCSKLRTQEYIN    60
                  *  ::      .         *::*::.     .  :    ..  :: :.   .   *  :

NgLPP2-1-2  (2)   ASYLGYLNELESNFSNNPEEKDIQVSR---TIQIKNLTEEIKCKLNSMEDGRSSVSAYDT   117
CPS        (83)   SQEVQHDLPLIHEWQQLQGEDAPQISVGSNSNAFKEAVKSVKTILRNLTDGEITISAYDT   120
                  :    : :  :  :.: * ::  *  .    :  :   *:*  . :  *   :::****

NgLPP2-1-2  (2)   AWVSFIPNTTNNGNDQRPMFPSCLQWIIDNQLCDGSWGEESVFCIYDRLLNTLACVVALT   177
CPS        (83)   AWVALID-----AGDKTPAFPSAVKWIAENQLSDGSWGDAYLFSYHDRLINTLACVVALR   175
                  ***::*       . :.* ***  ***::***.*****:: :  *.**:*********

NgLPP2-1-2  (2)   LWNTCLPKRNKGVMFIKENLIKLETGEVEHMTCGFEFVFPALLEKAQQLNIDIPYDAPVL   237
CPS        (83)   SWNLFPHQCNKGITFFRENIGKLEDENDEHMPIGFEVAFPSLLEIARGINIDVPYDSPVL   235
                  .**  :.:. **: *:::** *** ::  **  ***.**:** * : :***:***:***

NgLPP2-1-2  (2)   KDIYARREVKFTRIPKEIVHTIPTTALLSLEGLRDDLDWQRLLNFQMPDGSFLSAPASTA   297
CPS        (83)   KDIYAKKELKLTRIPKEIMHKIPTTLLHSLEGMR-DLDWEKLLKLQSQDGSFLFSPSSTA   294
                  *****::*:*:*******:*.****:*:****:* ****::**::*..***** :*:***

NgLPP2-1-2  (2)   FAFMKTNDEKCLAYLQNVVQKSNGGAR-HYPLDLLTRLWAIDRLQRLGISYYFAEEFKEL   356
CPS        (83)   FAFMQTRDSNCLEYLRNAVKRFNGGVPNVFPVDLFEHIWIVDRLQRLGISRYFEEEIKEC   354
                  ****:*.*.:**.**:*.*:: ***.  . *:**:.::* :********* ** :*:**

NgLPP2-1-2  (2)   LNHVFRYWDEENGIFSGRNSNVCDVDDTCMAIRLLRLHGYDVSPDALNNFTDGDQFFCLR   416
CPS        (83)   LDYVHRYWT-DNGICWARCSHVQDIDDTAMAFRLLRQHGYQVSADVFKNFEKEGEFFCFV   413
                  *::*.***. *:**   *.*:* *:*** **:****:***:**.**::**.:* :***:

NgLPP2-1-2  (2)   GEVDGSPTHMFNLYRCSQVLFPGEKILEEAKNFTYNFLQQCLANNRCLDKWVIAKDIPGE   476
CPS        (83)   GQSNQAVTGMFNLYRASQLAFPREEILKNAKEFSYNYLLEKREEELIDKWIIMKDLPGE   473
                  *:.: :.* *****.**:.**.:*** :**:*:**:* :  : :*.***:*:**:***
```

FIGURE 3A

```
NgLPP2-1-2  (2)   IRYALKFPWYASLPRVESRLYIEQYGGANDIWIGKTLYRMPDVSNNVYLQAAKLDYNRCQ  536
CPS        (83)   IGFALEIPWYASLPRVETRFYIDQYGGENDVWIGKTLYRMPYVNNNGYLELAKQDYNNCQ  533
                  * :****************:.***:******* ****** * ***.**: ** ****.**

NgLPP2-1-2  (2)   SQHRFEWLIMQQWFDKCNFQQFGISKKYLLVSYFLAAASIFEVEKSRERLAWAKSRIICK  596
CPS        (83)   AQHQLEWDIFQKWYEENRLSEWGVRRSELLECYYLAAATIFESERSHERMVWAKSSVLVK  593
                  :.*::**  :*:*::: .: ..:.. :. **   ****:***.***:**:.****  :*

NgLPP2-1-2  (2)   MITSYYNEEATTWTSRNSLLMEFKGSDDPSRKNGNE------TKEIIVLKNLRQFL     646
CPS        (83)   AISSSFGESSDSRRSFSDQFHEYIANARRSDHHFNDRNMRLDRPGSVQASRLAGVLIGTL  653
                  *:**  .*: :: :* .  : *:  .  ** :.:**:        .: ..* .*:  *

NgLPP2-1-2  (2)   HQLSEETFEDLGKDIHHQLQNAWKTWLAFLREEKNTCQEEAELLVRTINLSGGHMIHDEI  706
CPS        (83)   NQMSFDLFMSHGRDVNNLLYLSWGDWMEKWKLYGD--BGEGELMVKMIILMKNNDLTN-F  710
                   *:*   *  :*:**::: * ..  **  :*: *    *:***:: *::: .:: : *

NgLPP2-1-2  (2)   LFDADYKNLSNLTNKVCCMLSELQNDKVTGSSKNTD-IELNMQALVKLVFGNTSSNINQD  765
CPS        (83)   FTHTHFVRLAEIINRICLPRQYLKARRNDEKEKTIKSMEKEMGKMVELALS--ESDTFRD  768
                   :     :*::: *:  ::.* :  :     .::.::* ::.:*: *.*:.  *: *:*

NgLPP2-1-2  (2)   IKQTFFTVVKTFYYSAHASEEIINFHISKVLFHQVQ   801
CPS        (83)   VSITFLDVAKAFYYFALCGDHLQ-THISKVLFQKV-   802
                  :. ***  *:.***:* .. ::   .:******:::*

FIGURE 3B
```

```
NgSs S3F1-1  (36)  --MILGLRSTIIPLPDHKLGN--------------------IKLGSVTNSNFPRP   33
AgAs         (84)  MAMPSSSLSSQIPTAAHHLTANAQSIPHFSTTLNAGSSASKRRSLYLRWGKGSNKIIACV  60
                     *  *:.**  . * *:*                    :: *. :*. ..

NgSs S3F1-1  (36)  SRVRCS--------------------------------------HSTASSLEEAK      50
AgAs         (84)  GEGGATSVPYQSAEKNDSLSSSTLVKREFPPGFWKDDLIDSLTSSHKVAASDEKRIETLI 120
                    .  :                                        *  . :*

NgSs S3F1-1  (36)  ERI---RETFVKNELSPSSYDTAWVAMVPSRYSMNQPCFPRCLDWILENQREDGSWGLNP 107
AgAs         (84)  SEIKNMFRCMGYGETNPSAYDTAWVARIPAVDGSDNPHFPETVEWILQNQLKDGSWGEG- 179
                    . *     * ***:******::*:  :  ::** . :******.:*:*****  .

NgSs S3F1-1  (36)  SHPLLVKDSLSSTLACLLALRKWRIGDNQVQRGLGFIETHG-WAVDNVDQISPLGFDIIF 166
AgAs         (84)  -FYFLAYDRILATLACIITLTLWRTGETQVQKGIEFFRTQAGKMEDEADSHRPSGFEIVF 238
                    : *.  * :.:******:::: ** *:.****:*:* *:*.  * **  * ::**:*:*

NgSs S3F1-1  (36)  PSMIKYAEKLNLDLPFDPNLVNMMLREREELTIERALKNEFEGNMANVEYFAEGLGELCHW 226
AgAs         (84)  PAMLKEAKILGLDLPYDLPFLKQIIEKREAKLKRIPTDVLYALPTTLLYSLEGLQEIVDW 298
                   *:*:*:** *   ***:* **   :*** ** :   *. *:*:  ***   * . .  *

NgSs S3F1-1  (36)  KEIMLHQRRNGSLFDSPATTAAALIYHQDEKCFGYLSSILKLHENWVPTIYPTKVHSNL  286
AgAs         (84)  QKIMKLQSKDGSFLSSPASTAAVFMRTG-NKKCLDFLNFVLKKFGNHVPCHYPLDLFERL 357
                   ::* *   :: :* ::**:*****.::::   *.:**.::** : * *** :**    :

NgSs S3F1-1  (36)  FLVDALQNLGVNRYFKTELKSVLDEIYRLWLEK----NEEIFSDIAHCAMAFRLLRMNN  341
AgAs         (84)  WAVDTVERLGIDRHFKEEIKEALDYVYSHWDERGIGWARENPVPDIDDTAMGLRILRLHG 417
                    .**.  :**::*:**.::*.:** :*. * :*    . :* .: :***. ***   .
```

FIGURE 3C

```
NgSs S3F1-1  (36)  YEVSSEELEGFVDQEH-FFTTSGGKLISHVAILELHRASQVDIQEGKDLILDKISTWTRN  400
AgAs        (84)  YNVSSDVLKTFRDENGEFFCFLGQTQRGVTDMLNVNRCSHVSFPG--ETIMEEAKLCTER  475
                  *:****.*: .*** .**::    .    .:*::**:****::.     *:::: *..

NgSs S3F1-1  (36)  FMEQELLDNQILD-----RSKKEMEFAMR-KFYGTFDRVETRRYIESYKMDSFKILKAA   453
AgAs        (84)  YLRNALENVDAFDKWAFKKNIRGEVEYALKYPWHKSMPRLEARSYIENYGPDDVWLGKTV 535
                   : . *::* : *     *..::   *:: :: .. **: *:* **:.*  *.. *..

NgSs S3F1-1  (36)  YRSSNINNIDLLKFSEHDFNLCQARHKEELQQIKRWFADCKLEQVGSSQNYLYTSYFPIA  513
AgAs        (84)  YMMPYISNEKYLELAKLDFNKVQSIHQTELQDLRRWWKSSGFTDLNFTRERVTEIYFSPA  595
                  *  . *.*: **:.: ***: *: *: ***::*.*:..     .*:* ** :* **.*

NgSs S3F1-1  (36)  AILFEPEYGDARLAFAKCGIIATTVDDFFDGFACNEELQNIIELVERWDGYPTVGFRSER  573
AgAs        (84)  SFIFEPEFSKCREVYTKTSNFTVILDDLYDAHGSLDDLKLFTESVKRWD-LSLVDQMPQQ  654
                  : :****:..   . :. . ::* :** :*.:.. :*: :: .***.* ::*:   . :

NgSs S3F1-1  (36)  VRIFFLALYKMVEEIAAKAETKQGRCVKDLLINLWIDLLKCMLVELDLWKIKSTTPSIEE  633
AgAs        (84)  MKICFVGFYNTFNDIAKEGRERQGRDVLGYIQNVWKVQLEAYTKEAEWSEAK-YVPSFNE  713
                  :.* *. :*: .::**:.  ::*** *  :*:: :.::*  ::   *.:*: *.**::*

NgSs S3F1-1  (36)  YLSIACVTTGVKCLILISLHLLGPKLSKDVTESSE-VSALWNCTAVVARLNNDIHSYKRE  692
AgAs        (84)  YIENASVSIALGTVVLISALFTGEVLTDEVLSKIDRESRFLQLMGLTGRLVNDTKTYQAE  773
                  *:. *.*:..  .::***:*: * :*::* .*.::  *. :  .. ..**.**: *: *

NgSs S3F1-1  (36)  QAESSTNMVAILISQSQRTISEEEAIRQIKEMMESKRRELLGMVLQNKESQLPQVCKDLF  752
AgAs        (84)  RGQGEVASAIQCYMKDHPKISEEEALQHVYSVMENALEELNREFVNN---KIPDIYKRLV  830
                  :..  . .:*  :.:.:::*****::::: :*:. :.*: .: ::.   *:*:: *.*.

NgSs S3F1-1  (36)  WTTFKAAYSIYTHGDEYRFP--QELKNHINDVIYKPLNQYSP    792
AgAs        (84)  FETARIMQLFYMQGDGLTLSHDMEIKEHVKNCLFQPVA----    868
                  : *  : : :* *.*     ..*:*:::::::  *..
```

FIGURE 3D

```
SsLPP   (58)   -------------MTSVNLSRAPAAITRRRLQLQPEFHAECSWLKS-SSKHAPLTLSCQ-IR   47
SsLPP   (59)   -------------MTSVNLSRAPAAIIRRRLQLQPEFHAECSWLKS-SSKHAPFTLSCQ-IR   47
NgLPP   (2)    MQVKITSSHRLFCHFHQLKSATSLSAQKTEFRKYGPGNSLFQTEGSLLYKPVRLNCAPID     60
NgLPP   (10)   -------------------------------------------------MCAPID         6
                                                                  *

SsLPP   (58)   PKQLSQIAELRVTSLDASQASEKDISLVQTPHKVEVNEKIEESIEYVQNLLMTSGDGRIS   107
SsLPP   (59)   PKQLSQIAELRVTSLDASQASEKDISLVQTPHKVEVNEKIEESIEYVQNLLMTSGDGRIS   107
NgLPP   (2)    ASYLGYLNELESN--FSNNPEEKDIQVSRTIQIKNLTEEIKCKLNSME------DGRSS    111
NgLPP   (10)   ASYLGYLNELESN--FSNNPEEKDIQVSRTIQIKNLTEEIKCKLNSME------DGRSS     57
                 *          *  ****                      *    *       ***  *

SsLPP   (58)   VSPYDTAVIALIKDLK--GRD-APQFPSCLEWIAHHQLADGSWG-DEFFCIYDRILNTLA   163
SsLPP   (59)   VSPYDTAVIALIKDLK--GRD-APQFPSCLEWIAHHQLADGSWG-DEFFCIYDRILNTLA   163
NgLPP   (2)    VSAYDTAWVSFIPNTTNNGNDQRPMFPSCLQWIIDNQLCDGSWGEESVFCIYDRLLNTLA   171
NgLPP   (10)   VSAYDTAWVSFIPNTTNNGNDQRPMFPSCLQWIIDNQLCDGSWGEESVFCIYDRLLNTLA   117
               ** *** *   *        *    *  **** **  ::  ****    ****::****

SsLPP   (58)   CVVALKSWNLHSDIIEKGVTYIKENVHKLKGANVEHRTAGFELVVPTFMQMATDLGIQDL   223
SsLPP   (59)   CVVALKSWNLQSDIIEKGVTYIKENVHKLKGANVEHRTAGFELVVPTFMQMATDLGIQGL   223
NgLPP   (2)    CVVALTLWNTCLPKRNKGVMFIKENLIKLETGEVBHMTCGFEFVFPALLEKAQQLNID-I   230
NgLPP   (10)   CVVALTLWNTCLPKRNKGVMFIKENLIKLETGEVBHMTCGFEFVFPALLEKAQQLNID-I   176
               *****. *   *: :* ** :**** :*  * :*..: .**:.:*.: :::      .:

SsLPP   (58)   PYDHPLIKEIADTKQQRLKEIPKDLVYQMPTNLLYSLEGLG-DLEWERLLKLQSGNGSFL   282
SsLPP   (59)   PYDHPLIKEIADTKQQRLKEIPKDLVYQMPTNLLYSLEGLG-DLEWERLLKLQSGNGSFL   282
NgLPP   (2)    PYDAPVLKDIYARREVKFTRIPKEIVHTIPTTALLSLEGLRDDLDWQRLLNFQMPDGSFL   290
NgLPP   (10)   PYDAPVLKDIYARREVKFTRIPKEIVHTIPTTALLSLEGLRDDLDWQRLLNFQMPDGSFL   236
               *** *::*:*  :. *:  **::*:  :**::*****: *:**:**::  . ****
```

FIGURE 4A

| | | |
|---|---|---|
| SsLPP (58) | TSPSSTAAVLMHTKDEKCLKYIENALKNCDGGAPHTYPVDIFSRLWAIDRLQRLGISRFF | 342 |
| SsLPP (59) | TSPSSTAAVLMHTKDEKCLKYIENALKNCDGGAPHTYPVDIFSRLWAIDRLQRLGISRFF | 342 |
| NgLPP (2)  | SAPASTAFAFMKTNDEKCLAYLQNVVQKSNGGARH-YPLDLLTRLWAIDRLQRLGISYYF | 349 |
| NgLPP (10) | SAPASTAFAFMKTNDEKCLAYLQNVVQKSNGGARH-YPLDLLTRLWAIDRLQRLGISYYF | 295 |
| | .:*:**  ****::*:*.**.:.:: * ::..:::*******:  :* | |

| | | |
|---|---|---|
| SsLPP (58) | QHEIKYFLDHIESVW-EETGVFSGRYTKFSDIDDTSMGVRLLKMHGYDVDPNVLKHFKQQ | 401 |
| SsLPP (59) | QHEIKYFLDHIESVW-EETGVFSGRYTKFSDIDDTSMGVRLLKMHGYDVDPNVLKHFKQQ | 401 |
| NgLPP (2)  | AEEFKELLNHVFRYWDEENGIFSGRNSNVCDVDDTCMAIRLLRLHGYDVSPDALNNFTDG | 409 |
| NgLPP (10) | AEEFKELLNHVFRYWDEENGIFSGRNSNVCDVDDTCMAIRLLRLHGYDVSPDALNNFTDG | 355 |
| | .*:. : *::::: * :::*:***.::.: *:***.:*:*::*.* **::* | |

| | | |
|---|---|---|
| SsLPP (58) | DGKFSCYIGQSVESASPMYNLYRAAQLRFPGEEVLEEATKFAFNFLQEMLVKDRLQERWV | 461 |
| SsLPP (59) | DGKFSCYIGQSVESASPMYNLYRAAQLRFPGEEVLEEATKFAFNFLQEMLVKDRLQERWV | 461 |
| NgLPP (2)  | D-QFFCLRGEVDGSPTHMFNLYRCSQVLFPGEKILEEAKNFTYNFLQQCLANNRCLDKWV | 468 |
| NgLPP (10) | D-QFFCLRGEVDGSPTHMFNLYRCSQVLFPGEKILEEAKNFTYNFLQQCLANNRCLDKWV | 414 |
| | * :* *: * .**..*::****.:*:**::::::***::*.::* :::** | |

| | | |
|---|---|---|
| SsLPP (58) | ISDHLFDEIKLGLKMPWYATLPRVEAAYYLDHYAGSGDVWIGKSFYRMPEISNDTYKELA | 521 |
| SsLPP (59) | ISDHLFDEIKLGLKMPWYATLPRVEAAYYLDHYAGSGDVWIGKSFYRMPEISNDTYKELA | 521 |
| NgLPP (2)  | IAKDIPGEIRYALKFPWYASLPRVESRLYIEQYGGANDIWIGKTLYRMPDVSNNVYLQAA | 528 |
| NgLPP (10) | IAKDIPGEIRYALKFPWYASLPRVESRLYIEQYGGANDIWIGKTLYRMPDVSNNVYLQAA | 474 |
| | *:.. : :  **:*: :::* .:*:**::::::* : * | |

| | | |
|---|---|---|
| SsLPP (58) | ILDFNRCQTQHQLEWIHMQEWYDRCSLSEFGISKRELLRSYFLAAATIFEPERTQERLLW | 581 |
| SsLPP (59) | ILDFNRCQTQHQLEWIQMQEWYDRCSLSEFGISKRELLRSYFLAAATIFEPERTQERLLW | 581 |
| NgLPP (2)  | KLDYNRCQSQHRFEWLIMQQWFDKCNFQQFGISKKYLLVSYFLAAASIFEVEKSRERLAW | 588 |
| NgLPP (10) | KLDYNRCQSQHRFEWLIMQQWFDKCNFQQFGISKKYLLVSYFLAAASIFEVEKSRERLAW | 534 |
| |  ::::::*:*:*.:.:***:::******:*  : ****:* | |

FIGURE 4B

```
SsLPP  (58)  AKTRILSKMITSFVNISGTTLS-----LDYNFNGLDEIISSANEDQGLAGTLLATFHQLLD  637
SsLPP  (59)  AKTRILSKMITSFVNISGTTLS-----LDYNFNGLDEIIS-ANEDQGLAGTLLATFHQLLD  636
NgLPP  (2)   AKSRIICKMITSYYNEEATTWTSRNSLLMEFKGSDDPSR-KNGNETKEIIVLKNLRQFLH  647
NgLPP  (10)  AKSRIICKMITSYYNEEATTWTSRNSLLMEFKGSDDPSR-KNGNETKEIIVLKNLRQFLH  593
             **::.**::.******:   *   .:***   :** .:**::.*     ..::*.:::*:.

SsLPP  (58)  GFDIYT------LHQLKHVWSQWFMKVQQGEGSGGEDAVLLANTLNICAG--LNEDVL  687
SsLPP  (59)  GFDIYT------LHQLKHVWSQWFMKVQQGEGSGGEDAVLLANTLNICAG--LNEDVL  686
NgLPP  (2)   QLSEETFEDLGKDIHHQLQNAWKTWLAFLREEKNTCQBEAELLVRTINLSGGHMIHDEIL  707
NgLPP  (10)  QLSEETFEDLGKDIHHQLQNAWKTWLAFLREEKNTCQEEAELLVRTINLSGGHMIHDEIL  653
              :*       **::*:.*  *:  . . :::      * :**  **..:.  :::*

SsLPP  (58)  SNNEYTALSTLTNKICNRLAQIQDNKILQVVDGSIKDKELEQDMQALVKLVLQENGGAVD  747
SsLPP  (59)  SNNEYTALSTLTNKICNRLAQIQDNKILQVVDGSIKDKELEQDMQALVKLVLQENGGAVD  746
NgLPP  (2)   FDADYKNLSNLTNKVCCMLSELQNDK----VTGSSKNTDIELNMQALVKLVFGNTSSNIN  763
NgLPP  (10)  FDADYKNLSNLTNKVCCMLSELQNDK----VTGSSKNTDIELNMQALVKLVFGNTSSNIN  709
              . :  *::*** * :*::::::*::    *.**.*: :*:::******:.:...::

SsLPP  (58)  RNIRHTFLSVSKTFYYDAYHDDETTDLHIFKVLFRPVV  785
SsLPP  (59)  RNIRHTFLSVSKTFYYDAYHDDETTDLHIFKVLFRPVV  784
NgLPP  (2)   QDIKQTFFTVVKTFYYSAHASEEIINFHISKVLFHQVQ  801
NgLPP  (10)  QDIKQTFFTVVKTFYYSAHASEEIINFHISKVLFQQVQ  747
              :*:::** :*.****.*: :*::::::***:***::*
```

FIGURE 4C

```
NgSs  (36)   MILGLRSTIIPLPDHKLGNIKLGSVTNSNFPRPSRVRCSHSTASSLEEAKERIRETFVKN   60
NgSs  (40)   ----------------------------------------MSHSTASSLEEAKERIRETFGKN   23
SsSs  (62)   --MSLPLSTCNGSHFRRYRLSPASASAMETGLQTATSAKIASMPACFEETRGRIAKLFHKD   58
SsSs  (60)   ------------------------------------------------------------

NgSs  (36)   ELSPSSYDTAWVAMVPSRYSMNQPCFPRCLDWILENQREDGSWGLNPSHPLLVKDSLSST   120
NgSs  (40)   ELSSSSYDTAWVAMVPSRYSMNQPCFPRCLDWILENQREDGSWGLNPSLPLLVKDSLSST    83
SsSs  (62)   ELSVSTYDTAWVAMVPSPTSLEEPCFPDCLNWLLENQCHDGSWARPHHHSLLMKDVLSST   118
SsSs  (60)   ---------------------------------------------------------MS     2
                                                                      ..

NgSs  (36)   LACLLALRKWRIGDNQVQRGLGFIETHGWAVDNVDQISPLGFDIIFPSMIKYAEKLNLDL   180
NgSs  (40)   LACLLALRKWRIGDNQVQRGLGFIETHGWAVDNVDQISPLGFDIIFPSMIKYAEKLNLDL   143
SsSs  (62)   LACILALKKWGVGEKQINRGLHFMELNFASATEKCQITPMGFDIVFPAMLDYARDFSLDM   178
SsSs  (60)   LAFNVGVTPFSGQR----------------VGSRKEKFPVQGFPVTTPNRSRLIVNCSLTT    47
             *.*   .     :.                   ::  **    *                *

NgSs  (36)   PFDPNLVNMLREREITIERALKNEFEGNMANVEYFAEGLGELCHWKEIMLHQRRNGSLF   240
NgSs  (40)   PFDPNLVNMMLREREITIERALKNEFEGNMANVEYFAEGLGELCHWKEIMLHQRRNGSPF   203
SsSs  (62)   HLEPTTLNDLIHKRDLELKSKPDFSSDG-EAYWAYIAEGMGNLRNWESVMKYQRRNGSLF   237
SsSs  (60)   IDFMAKMKENFKREDDKFP-----------------------------------------    66
              :     ..  :                          :: *  * ::  * *:    :

NgSs  (36)   DSPATTAAALIYHQHDEKCFGYLSSILKLHENWVPTIYPTKVHSNLFLVDALQNLGVNRY   300
NgSs  (40)   DSPATTAAALIYHQHDEKCFGYLSSILKLHENWVPTIYPTKVHSNLFFVDALQNLGVDRY   263
SsSs  (62)   NCPSTTAAAFVALGNSD-CLNYLHSALKKFGNAVPAVYPLDIYSHLCIVDNLERLGISRY   296
SsSs  (60)   ----------------TTTTLRSEDIPSNLCIIDTLQRLGVDQF                  94
                              .  :  .   . *..:.   * * *::.. ::

FIGURE 4D
```

```
NgSs  (36)  FKTELKSVLDEIYRLWLEKNEEIFSDIAHCAMAFRLLRMNNYEVSSEELEGFVDQEHFFT  360
NgSs  (40)  FKTELKSVLDEIYRLWLEKNEEIFSDIAHCAMAFRLLRMNNYEVSSEELEGFVDQEHFFT  323
SsSs  (62)  FLTEIQSVLDETHRCWMQGNEEIFMDASTCALAFRILRLNGYDVTSDPVT-KIQHECFSS  355
SsSs  (60)  FQYEINTILDNTFRLWQEKHKVIYGNVTTHAMAFRLLRVKGYEVSSEELAPYGNQEAVSQ  154
              *  *::**  .  * .*:****.***:.*::*:*::.:  .

NgSs  (36)  TSGGKLISHVAILELHRASQVDIQ-EGKDLILDKISTWTRNFMEQELLD----NQILDRS  415
NgSs  (40)  TSGGKLISHVAILELHRASQVDIQ-EGKDLILDKISTWTRNFMEQELLD----NQILDRS  378
SsSs  (62)  SFHGNVMDINTTLELYRASELILYPDERDLVRQNLR--LKQILEQELSNGFIQSCQLGRS  413
SsSs  (60)  QTN----DLPMIIELYRAANERIY--EEERSLEKILAWTTIFLNKQVQD----NSIPDKK  204
              : *  : ** .:   :         .

NgSs  (36)  K-KEMEFAMR--KFYGTFDRVETRRYIESYKMDSFKILKAAYRSSNINNIDLLKFSEHDFN  473
NgSs  (40)  K-KEMEFAMR--KFYGTFDRVETRRYIESYKMDSFKILKAAYRSSNINNIDLLKFSEHDFN  436
SsSs  (62)  VNAEVNQAIEYPFYAIMDRVAKRKNIENYNFDNTRILKTSYCSPNFGNKDFLFLSVEDFN  473
SsSs  (60)  LHKLVEFYLR--NYKGITIRLGARRNLELYDMTYYQALKSTNRFSNLCNEDFLVFAKQDFD  263
              : :**.*   . *: ::  : :   . ::

NgSs  (36)  LCQARHKEELQQIKRWFADCKLEQVGSSQNYLYTSYFPIAAILFEPEYGDARLAFAKCGI  533
NgSs  (40)  LCQARHKEELQQIKRWFADCKLEQVGSSQNYLYTSYFPIAAILFEPEYGDARLAFAKCGI  496
SsSs  (62)  LCQATHREELRELERWVVENRLDELQFARSKSAYCYFSAAATFSAPELRDARMSWAKGGV  533
SsSs  (60)  IHEAQNQKGLQQLQRWYADCRLDTLNFGRDVVIIANYLASLLIGDHAFDYVRLAFAKTSV  323
              : .  : .*  :* ** :.*:*:

NgSs  (36)  IATTVDDFFDGFACNEELQNIIELVERWDGYPTVGFRSERVRIFFLALYKMVEEIAAKAE  593
NgSs  (40)  IATTVDDFFDGFACNEELQNIIELVERWDGYPTVGFRSERVRIFFLALYKMIEEIAAKAE  556
SsSs  (62)  LTTVIDDFFDVGGSMEELKNLIHLVEKWDVDVSTECSSHNVQIIFSALKSTIREIGYKGL  593
SsSs  (60)  LVTIMDDFFDCHGSSQECDKIIELVKEWKENPDAEYGSEELEILFMALYNTVNELAERAR  383
              : .*:****     : :*:::  **:*      .    : :* * *
```

FIGURE 4E

```
NgSs  (36)   TKQGRCVKDLLINLWIDLLKCMLVELDLWKIKSTTPSIEEYLSIACVTTGVKCLILISLH   653
NgSs  (40)   TKQGRCVKDLLINLWIDLLKCMLVELDLWKIKSTTPSIEEYLSIACVTTGVKCLILISLH   616
SsSs  (62)   KLQGRCITNHIIGIWLDLLNSMMKET-EWARDNYVPTIDEYMSNAYVSFALGPIVLPTLY   652
SsSs  (60)   VEQGRSVKEFLVKLWVEILSAFKIELDTWSNG-TQQSFDEYISSSWLSNGSRLTGLLTMQ   442
             * ::  *      ::    :   * :: **:.:.*  : :     :   ::: .

NgSs  (36)   LLGPKLSKDVTESSEVSALWNCTAVVARLNNDIHSYKREQAE---SSTNMVAILISQSQR   710
NgSs  (40)   LLGPKLSKDVTESSEVSALWNCTAVVARLNNDIHSYKREQAE---SSTNMVAILISQSQR   673
SsSs  (62)   LVGPKLSEEMANHPEYYKLFKLMSTCGRLLNDIRGYERELKD---GKLNALSLYMANHGG   709
SsSs  (60)   FVGVKLSDEMLMSEECTDLARHVCMVGRLLNDVCSSEREREENIAGKSYSILLATEKDGR   502
             : * ***.:      .    : :::.:**:::  *:*:  :      :  :: :  .

NgSs  (36)   TISEEEAIRQIKEMMESKRRELLGMVLQNKESQLPQVCKDLFWTTFKAAYSIYTHGDEYR   770
NgSs  (40)   TISEEEAIRQIKEMMESKRRELLGMVLQNKESQLPQVCKDLFWTTFKAAYSIYTHGDEYR   733
SsSs  (62)   EVSKEAAISEIKSWIESSRRELLRLVLEGKKKSVLPKPCKELFWHMCSVVHLFYSKDDGFT   769
SsSs  (60)   KVSEDEAIAEINEMVEYHWRKVLQIVYK-KESILPRRCKDVFLEMAKGTFYAYGINDELT   561
             . *::.**  * :  :   . :*:: : ::: :*: **::* .  . ::  .  :  :

NgSs  (36)   FPQELKNHINDVIYKPLNQYSP------   792
NgSs  (40)   FPQELKNHINDVIYKPLNQYSP------   755
SsSs  (62)   S-QDLIQVVNAIIHKPIVLKEQTGARI   795
SsSs  (60)   SPQQSKEDMKSFVF-------------   575
             .  :     :  .  :
```

FIGURE 4F

| | | |
|---|---|---|
| SEQ ID NO:54 | MQVKITSSHRLFCHFHQLKSATSLSAQKTEIR---KYGPGNSLFQTEGSLLYKPVRLNCA | 57 |
| SEQ ID NO:58 | MTSVNLSRAPAAITRRRLQLQPEFHAECSWLKSSSKHAPLTLSCQIRPKQLSQIAELRVT | 60 |
| | * * .:*. : .:.* * * . .* . | |
| SEQ ID NO:54 | PIDASYLGYLNELESNFSNNPEEKDIQVSRTIQIKNLTEEIKCCKLNSMEDGRSSVSAYDT | 117 |
| SEQ ID NO:58 | SLDAS----QASEKDISLVQTPHKVEVNEKIEES--IEYVQNLLMTSGDGRISVSPYDT | 113 |
| | .:*** :: *.:.* :. :::.:*: . * :* | |
| SEQ ID NO:54 | AWVSFIPNTTNNGNDQRPMFPSCLQWIIDNQLCDGSWGEESVFCIYDRLLNTLACVVALT | 177 |
| SEQ ID NO:58 | AVIALIKDLK--GRD-APQFPSCLEWIAHHQLADGSWG-DEFFCIYDRLINTLACVVALK | 169 |
| | * :::** . *.* :*****.* : * :**:****. | |
| SEQ ID NO:54 | LWNTCLPKRNKGVMFIKENLIKLETGEVEHMTCGFEFVFPALLEKAQQLNI-DIPYDAPV | 236 |
| SEQ ID NO:58 | SWNLHSDIIEKGVTYIKENVHKLKGANVEHRTAGFELVPTFMQMATDLGIQDLPYDHPL | 229 |
| | ** :****: **:.* :.* .* ** *:* .: * :*****:*: | |
| SEQ ID NO:54 | LKDIYARREVKFTRIPKEIVHTIPTTALLSLEGLRDDLDWQRLLNFQMPDGSFLSAPAST | 296 |
| SEQ ID NO:58 | IKEIADTKQQRLKEIPKDLVYQMPTNLLYSLEGLGEDLEWERLLKLQSGNGSFLTSPSST | 288 |
| | :*:** :::.* .*** :* .:::*::****.:::*:::. :*:::*** | |
| SEQ ID NO:54 | AFAFMKTNDEKCLAYLQNVVQKSNGGARH-YPLDLLTRLWAIDRLQRLGISYYFAEEFKE | 355 |
| SEQ ID NO:58 | AAVLMHTKDEKCLKYIENALKNCDGGAPHTYPVDIFSRLNLWAIDRLQRLGISRFFQHEIKY | 348 |
| | *. :*:*:**** *::* ::* :*** * **:*::*:***:*. :*.: : | |
| SEQ ID NO:54 | LLNHVFRYWDEENGIFSGRNSNVCDVDDTCMAIRLLRLHGYDVSPDALNNFTDGD-QFFC | 414 |
| SEQ ID NO:58 | FLDHIESVW-EETGVFSGRYTKFSDIDDTSMGVRLLKMHGYDVDPNVLKHFKQQDGKFSC | 407 |
| | :*:*: .* ** *.***: .:.*:*. :*::*****.*.. *:*. *.. :* | |
| SEQ ID NO:54 | LRGEVDGSPTHMFNLYRCSQVLFPGEKILEEAKNFTYNFLQQCLANNRCLDKWVIAKDIP | 474 |
| SEQ ID NO:58 | YIGQSVESASPMYNLYRAAQLRFPGEEVLEEATKFAFNFLQEMLVKDRLQERWVISDHLF | 467 |
| | : :.. .*::****.:*:***::**::*: ****: *..:* ::***:.*:: | |

FIGURE 6A

```
SEQ ID NO:54    GEIRYALKFPWYASLPRVESRLYIEQYGGANDIWIGKTLYRMPDVSNNVYLQAAKLDYNR  534
SEQ ID NO:58    DEIKLGLKMPWYATLPRVEAAYYLDHYAGSGDVWIGKSFYRMPEISNDTYKELAILDFNR  527
                 *:  .:**:****** :*  * :::*: **.* ***:.:* **:*:*.* : * :*:**

SEQ ID NO:54    CQSQHRFEWLIMQQWFDKCNFQQFGISKKYLLVSYFLAAASIFEVEKSRERLAWAKSRII  594
SEQ ID NO:58    CQTQHQLEWIHMQEWYDRCSLSEFGISKRELLRSYFLAAATIFEPERTQERLLWAKTRIL  587
                **:**::***:**:*:*:*.:*::****: *** ******:*** *: :*** ***:**:

SEQ ID NO:54    CKMITSYYNEEATTWTSRNSLLMEFKGSDDPSRKNGNETKEIIVLKNLRQFLHQLSEETF  654
SEQ ID NO:58    SKMITSFVNISGTTLS----LDYNFNGLDEIIS-SANEDQGLAG--TLLATFHQL----L  636
                 *****: *: .:*::*    *:.*:  :*  . * *:: ::*   ** ::***     :

SEQ ID NO:54    EDLGKDHHQLQNAWKTWLAFLREEKNTCQEEAELLVRTINLSGGHMIHDEILFDADYKN  714
SEQ ID NO:58    DGFDIYLHQLKHVWSQWFMKVQQGEGSGGEDAVLLANTLNICAG--LNEDVLSNNEYTA  694
                :.: :  :***::.*. *: :::..: . :* *::* * *:.*.  :*:*:* :::* .

SEQ ID NO:54    LSNLTNKVCCMLSELQNDK---VTGSSKNTDIELNMQALVKLVFGNTSSNINQDIKQTF  770
SEQ ID NO:58    LSTLTNKICNRLAQIQDNKILQVVDGSIKDKELEQDMQALVKLVLQENGGAVDRNIRHTF  754
                **.****:* **::*:**   *.**.*: :** :****:***.  * .:::* *:**

SEQ ID NO:54    FAVVKTFYYSAHVSEEIINFHISKVLEQVQ   801
SEQ ID NO:58    LSVSKTFYYDAYHDDETTDLHIFKVLERPVV  785
                 :* ******.*: :: :  :*:***:  *
```

FIGURE 6B

```
SEQ ID NO:54       MQVKITSSHRLFCHFHQLKSATSLSAQKTELRKYGPGNSLFQTEGSLLYKPVRLNCAPID    60
SEQ ID NO:10       ------------------------------------------------MCAPID     6
                                                                   *****

SEQ ID NO:54       ASYLGYLNELESNFSNNPEEKDIQVSRTIQIKNLTEEIKCKLNSMEDGRSSVSAYDTAWV   120
SEQ ID NO:10       ASYLGYLNELESNFSNNPEEKDIQVSRTIQIKNLTEEIKCKLNSMEDGRSSVSAYDTAWV    66
                   ************************************************************

SEQ ID NO:54       SFIPNTTNNGNDQRPMFPSCLQWIIDNQLCDGSWGEESVFCIYDRLLNTLACVVALTLWN   180
SEQ ID NO:10       SFIPNTTNNGNDQRPMFPSCLQWIIDNQLCDGSWGEESVFCIYDRLLNTLACVVALTLWN   126
                   ************************************************************

SEQ ID NO:54       TCLPKRNKGVMFIKENLIKLETGEVEHMTCGFEFVFPALLEKAQQLNIDIPYDAPVLKDI   240
SEQ ID NO:10       TCLPKRNKGVMFIKENLIKLETGEVEHMTCGFEFVFPALLEKAQQLNIDIPYDAPVLKDI   186
                   ************************************************************

SEQ ID NO:54       YARREVKFTRIPKEIVHTIPTTALLSLEGLRDDLDWQRLLNFQMPDGSFLSAPASTAFAF   300
SEQ ID NO:10       YARREVKFTRIPKEIVHTIPTTALLSLEGLRDDLDWQRLLNFQMPDGSFLSAPASTAFAF   246
                   ************************************************************

SEQ ID NO:54       MKTNDEKCLAYLQNVVQKSNGGARHYPLDLLTRLWAIDRLQRLGISYYFAEEFKELLNHV   360
SEQ ID NO:10       MKTNDEKCLAYLQNVVQKSNGGARHYPLDLLTRLWAIDRLQRLGISYYFAEEFKELLNHV   306
                   ************************************************************

SEQ ID NO:54       FRYWDEENGIFSGRNSNVCDVDDTCMAIRLLRLHGYDVSPDALNNFTDGDQFFCLRGEVD   420
SEQ ID NO:10       FRYWDEENGIFSGRNSNVCDVDDTCMAIRLLRLHGYDVSPDALNNFTDGDQFFCLRGEVD   366
                   ************************************************************

SEQ ID NO:54       GSPTHMFNLYRCSQVLFPGEKILEEAKNFTYNFLQQCLANNRCLDKWVIAKDIPGEIRYA   480
SEQ ID NO:10       GSPTHMFNLYRCSQVLFPGEKILEEAKNFTYNFLQQCLANNRCLDKWVIAKDIPGEIRYA   426
                   ************************************************************
```

FIGURE 6C

```
SEQ ID NO:54   LKFPWYASLPRVESRLYIEQYGGANDIWIGKTLYRMPDVSNNVYLQAAKLDYNRCQSQHR   540
SEQ ID NO:10   LKFPWYASLPRVESRLYIEQYGGANDIWIGKTLYRMPDVSNNVYLQAAKLDYNRCQSQHR   486
               ************************************************************

SEQ ID NO:54   FEWLIMQQWFDKCNFQQFGISKKYLLVSYFLAAASIFEVEKSRERLAWAKSRIICKMITS   600
SEQ ID NO:10   FEWLIMQQWFDKCNFQQFGISKKYLLVSYFLAAASIFEVEKSRERLAWAKSRIICKMITS   546
               ************************************************************

SEQ ID NO:54   YYNEEATTWTSRNSLLMEFKGSDDPSRKNGNETKEIIVLKNLRQFLHQLSEETFEDLGKD   660
SEQ ID NO:10   YYNEEATTWTSRNSLLMEFKGSDDPSRKNGNETKEIIVLKNLRQFLHQLSEETFEDLGKD   606
               ************************************************************

SEQ ID NO:54   THHQLQNAWKTWLAFLREEKNTCQEEAELLVRTINLSGGHMIHDEILFDADYKNLSNLTN   720
SEQ ID NO:10   HHHQLQNAWKTWLAFLREEKNTCQEEAELLVRTINLSGGHMIHDEILFDADYKNLSNLTN   666
                ***********************************************************

SEQ ID NO:54   KVCCMLSELQNDKVTGSSKNTDIELNMQALVKLVFGNTSSNINQDIKQTFFAVVKTFYYS   780
SEQ ID NO:10   KVCCMLSELQNDKVTGSSKNTDIELNMQALVKLVFGNTSSNINQDIKQTFFEVVKTFYYS   726
               ***************************************************:********

SEQ ID NO:54   AHVSEEIINFHISKVLHQQVQ   801
SEQ ID NO:10   AHASEEIINFHISKVLRQQVQ   747
               **:*************:****
```

FIGURE 6D

```
SEQ ID NO:31    MILGLRSTIIPLPDHKLGNIKLGSVTKDSNFHRPSRVRCSHSTASSLEEAKGRIRETFGK    60
SEQ ID NO:60    MSLAFNVGVTPFSGQRVGSRKEKFPVQGFPVETPNRSRLIVNCSLTTIDFMAKMKENFKR    60
                * *..    ..  .* ::::.*. .      .     .      . ::::..*.   *

SEQ ID NO:31    NELSPSSYDTAWVAMVPSRYSMNQPCFPRCLDWILENQREDGSWGLNPSHPLLVKDSLSS   120
SEQ ID NO:60    E-----------------------------------------------------------    61
                :

SEQ ID NO:31    TLACLLALRKWRIGDNQVQRGLGFIETHGWAVDNVDQISPLGFDIIFPSMIKYAEKLNLD   180
SEQ ID NO:60    -----------------------------------------DDKFPT------------    67
                                                         *  *  :

SEQ ID NO:31    LPFDPNLVNMMLRERELTIERALKNEFEGNMANVEYFAEGLGELCHWKEIMLHQRRNGSL   240
SEQ ID NO:60    ------------------------------------------------------------

SEQ ID NO:31    FDSPATTAAALIYHQDEKCFGYLSSILKLHENWVPTIYPTKVHSNLFEVDALQNLGVDR   300
SEQ ID NO:60    -------------------------------TTTLRSEDIPSNLCMIDTLQRLGVDQ    93
                                               .*  .  .::  ***:* :* :*:***

SEQ ID NO:31    YFKTELKSVLDEIYRLWLEKNEEIFSDIAHCAMAFRLLRMNNYEVSSELEGFVDQEHFF   360
SEQ ID NO:60    FFQYEINTILDNTFRLWQEKHKVIYGNVTTHAMAFRLLRVKGYEVSSEELAPYGNQEAVS  153
                :*:  :.: *: :***:**::: :. : .  ********:: *****.**    :*

SEQ ID NO:31    TTSGGKLISHVAILELHRASQVDIQEGKDLLILDKISTWTRNFMEQELLDNQILDR-SKKE  419
SEQ ID NO:60    QQTN----DLPMIIELYRAANERIYE-EERSLEKILAWTTIFLNKQVQDNSIPDKKLHKL  208
                 : .    :*::**  **::: :  : :: **:*: * .*::: * *:*  *.  ..

SEQ ID NO:31    MEFAMRKFYGTFDRVETRRYIESYKMDSFKILKAAYRSSNINNIDLLKFSEHDFNLCQAR  479
SEQ ID NO:60    VEFYLRNYKGITIRLGARRNLELYDMTYYQALKSTNRFSNLCNEDFLVFAKQDFDIHEAQ  268
                :** :*::*    * *  **  * * .: :****:..*.*:* *::**::*:  :

FIGURE 6E
```

| | | |
|---|---|---|
| SEQ ID NO:31 | HKEELQQIKRWFADCKLEQVGSSQNYLYTSYFPIAAILFEPEYGDARLAFAKCGIIATTV | 539 |
| SEQ ID NO:60 | NQKGLQQLQRWYADCRLDTLNFGRDVVIIANYLASLIIGDHAFDYVRLAFAKTSVLVTIM | 328 |
| | :::.*:::.:****.:*:: .: .::: :: .* :*:*.. .:.****** .::.* .: | |
| SEQ ID NO:31 | DDFFDGFACNEELQNIIELVERWDGYPTVGFRSERVRIFFLALYKMTEEIAAKAETKQGR | 599 |
| SEQ ID NO:60 | DDFFDCHGSSQECDKIIELVKEWKENPDAEYGSEELEILFMALYNTVNELAERARVEQGR | 388 |
| | *****  .: . ::: ****:* . :. * * **::*:****: :* *: *.:*** | |

| | | |
|---|---|---|
| SEQ ID NO:31 | CVKDLLINLWIDLLKCMLVELDLWKIKSTTPSIEEYLSIACVTTGVKCLILISLHLLGPK | 659 |
| SEQ ID NO:60 | SVKEFLVKLWVEILSAFKIELDTWSNG-TQQSFDEYISSSWLSNGSRLTGLLTMQFVGVK | 447 |
| | .**::*  **::*.  :******:*. *:* ****:*. . :*: * :*::  :*  * | |

| | | |
|---|---|---|
| SEQ ID NO:31 | LSKDVTESSEVSALWNCTAVVARLNNDIHSYKREQAESSTNMVAILISQSQ--RTISEE | 716 |
| SEQ ID NO:60 | LSDEMLMSEECTDLARHVCMVGRLLNDVCSSEREREENIAGKSYSILLATEKDGRKVSED | 507 |
| | **.:  :* :* . .*:.. .* :: ** :*.:.. .:*::: :. *..* | |

| | | |
|---|---|---|
| SEQ ID NO:31 | EAIRQIKEVMESKRRELLGMVLQNKESQLPQVCKDLFWTTFKAAYSIYTHGDEYRFPQEL | 776 |
| SEQ ID NO:60 | EAIAEINEMVEYHWRKVLQIVYK-KESILPRRCKDVFLEMAKGTFYAYGINDELTSPQQS | 566 |
| | *** :*:*:** . *:.::*:  * :*::*. .:*.*  :. . .: | |

| | | |
|---|---|---|
| SEQ ID NO:31 | KNHINDVIYKPLNQYSP | 793 |
| SEQ ID NO:60 | KEDMKSFVF-------- | 575 |
| | *.:::..::. | |

FIGURE 6F

```
SEQ ID NO:31    MILGLRSTIIPLPDHKLGNIKLGSVTKDSNFHRPSRVRCSHSTASSLEEAKGRIRETFCK     60
SEQ ID NO:62    --MSLPLSTCNGSHFRRYRLSPASASMETGLQTATSAKIAS-MPACFEETRGRIAKLFHK     57
                  :.*     .   ..   :: ...   .  * .** :::***  **  ::***:.**:.*

SEQ ID NO:31    NELSPSSYDTAWVAMVPSRYSMNQPCFPRCLDWILENQREDGSWGLNPSHPLLVKDSLSS    120
SEQ ID NO:62    DELSVSTYDTAWVAMVPSPTSLEEPCFPDCLNWLLENQCHDGSWARPHHHSLLMKDVLSS    117
                 :** *:**********. *: ::****: *:*:**** :****  *::* *::**.***

SEQ ID NO:31    TLACLLALRKWRIGDNQVQRGLGFIETHGWAVDNVDQISPLGFDIIFPSMIKYAEKLNLD    180
SEQ ID NO:62    TLACILALKKWGVGEKQINRGLHFMELNFASATEKCQITPMGFDIVFPAMLDYARDFSLD    177
                ****:***::*  *::*::***.*:* . .*.:::  *:* ****:**:*  **.:.**

SEQ ID NO:31    LPFDPNLVNMMLRERELTIERALKNEFEGNMANVEYFAEGLGELCHWKEIMLHQRRNGSL    240
SEQ ID NO:62    MHLEPTTLNDLIHKRDLELKSKPDFSSDG-EAYWAYIAEGMGNLRNWESVMKYQRRNGSL    236
                :  :* .*::::::*::* :::..:::.   :*  :****:*:* :*: :: ******

SEQ ID NO:31    FDSPATTAAALIYHQHDEKCFGYLSSILKLHENWVPTIYPTKVHSNLFEVDALQNLGVDR    300
SEQ ID NO:62    FNCPSTTAAAFVALGNSD-CLNYLHSALKKFGNAVPAVYPLDIYSHLCVDNLERLGISR    295
                *:.*:******::  ::*  :.** *:**::.*.**::**  ::*:*: **.*:** *

SEQ ID NO:31    YFKTELKSVLDEIYRLWLEKNEEIFSDIAHCAMAFRLLRMNNYEVSSEELEGFVDQEHFF    360
SEQ ID NO:62    YFLTEIQSVLDETHRCWMQGNEEIFMDASTCALAFRILRLNGYDVTSDPVT-KIQHECFS    354
                ** **::***** :* *::.**** **: **:***:**:*.*:*:*:  :  :::*.*

SEQ ID NO:31    TTSGGKLISHVAILELHRASQVDIQ-EGKDLILDKISTWTRNFMEQELLD---NQILDR    415
SEQ ID NO:62    SSFHGNVMDINTTLELYRASELILYPDERDLVRQNLR--LKQILEQELSNGFIQSCQLGR    412
                 :: *::: .: ***:***::*:   :.:**: ::*.   ::: ****.:   *  * *

SEQ ID NO:31    SK-KEMEFAMR-KFYGTFDRVETRRYIESYKMDSFKILKAAYRSSNINNIDLLKFSEHDF    473
SEQ ID NO:62    SVNAEVNQAIEYPFYAIMDRVAKRKNIENYNFDNTRILKTSYCSPNFGNKDFLFLSVEDF    472
                *   *::::::  ** :.***.  ::*.*:.*.:::**::* * *: ::* *: *.:**

FIGURE 6G
```

```
SEQ ID NO:31    NLCQARHKEELQQIKRWFADCKLEQVGSSQNYLYTSYFPIAAILFEPEYGDARLAFAKCG  533
SEQ ID NO:62    NLCQATHREELRELERWVVENRLDELQFARSKSAYCYFSAAATFSAPELRDARMSWAKGG  532
                ***** *:***: *.::* :: :*.**::.**:*:*.:  :*:*** ****:   ***

SEQ ID NO:31    IIATTVDDFFDGFACNEELQNIIELVERWDGYPTVGFRSERVRIFFLALYKMTEEIAAKA  593
SEQ ID NO:62    VLTTVIDDFFDVGGSMEELKNLIHLVEKWDVDVSTECSSHNVQIIFSALKSTTREIGYKG  592
                ::.**:***** .. :***::*: **:**  .*.    .*: :*:**:*: **:. *

SEQ ID NO:31    ETKQGRCVKDLLINLWIDLLKCMLVELDLWKIKSTTPSIEEYLSIACVTTGVKCLILISL  653
SEQ ID NO:62    LKLQGRCITNHIIGIWLDLLNSMMKET-EWARDNYVPTIDEYMSNAYVSFALGPIVLPTL  651
                 * ****: ::::: *:****:.*:.:* **:..*. ***:**:*.*.*:: *:::* *

SEQ ID NO:31    HLLGPKLSKDVTESSEVSALWNCTAVVARLNNDIHSYKREQAESSTNMVAILISQSQRTI  713
SEQ ID NO:62    YLVGPKLSEEMANHPEYYKLFKLMSTCGRLLNDIRGYERELKDGKLNALSLYMANHGGEV  711
                :*:*****::  .. * .:*:: .:.**::**:..*:**: : .:*..: :: :. .:

SEQ ID NO:31    SEEEAIRQIKEVMESKRRELLGMVLQNKESQLPQVCKDLFWTTFKAAYSIYTHGDEYRFP  773
SEQ ID NO:62    SKEAAISEIKSWIESSRRELLRLVLEGKKKSVLPKPCKELFWHMCSVVHLFYSKDDGFTS-  770
                *::*** :**. :**.**** :**:.*:.  :*: **:***   .. . :.. *:   :

SEQ ID NO:31    QELKNHINDVIYKPLNQYSP-----  793
SEQ ID NO:62    QDLIQVVNAIIHKPIVLKEQTGARI  795
                *:*::  *:*::**:  :.
```

FIGURE 6H

```
SEQ ID NO:31                                                                    
SEQ ID NO:40   MILGLRSTIIPLPDHKLGNIKLGSVTKDSNFHHRPSRVRCSHSTASSLEEAKGRIRETFGK  60
                                             ----MSHSTASSLEEAKERIRETFGK  22
                                                  ******************

SEQ ID NO:31   NELSPSSYDTAWVAMVPSRYSMNQPCFPRCLDWILENQREDGSWGLNPSHPLLVKDSLSS 120
SEQ ID NO:40   NELSSSSYDTAWVAMVPSRYSMNQPCFPRCLDWILENQREDGSWGLNPSLPLLVKDSLSS  82
               ****  ******************************************* ********

SEQ ID NO:31   TLACLLALRKWRIGDNQVQRGLGFIETHGWAVDNVDQISPLGFDIIFPSMIKYAEKLNLD 180
SEQ ID NO:40   TLACLLALRKWRIGDNQVQRGLGFIETHGWAVDNVDQISPLGFDIIFPSMIKYAEKLNLD 142
               ************************************************************

SEQ ID NO:31   LPFDPNLVNMMLRERELTIERALKNEFEGNMANVEYFAEGLGELCHWKEIMLHQRRNGSL 240
SEQ ID NO:40   LPFDPNLVNMMLRERELTIERALKNEFEGNMANVEYFAEGLGELCHWKEIMLHQRRNGSP 202
               ************************************************************

SEQ ID NO:31   FDSPATTAAALIYHQDEKCFGYLSSILKLHENWVPTIYPTKVHSNLFEVDALQNLGVDR  300
SEQ ID NO:40   FDSPATTAAALIYHQDEKCFGYLSSILKLHENWVPTIYPTKVHSNLFEVDALQNLGVDR  262
               ************************************************************

SEQ ID NO:31   YFKTELKSVLDEIYRLWLEKNEEIFSDIAHCAMAFRLLRMNNYEVSSEELEGFVDQEHFF 360
SEQ ID NO:40   YFKTELKSVLDEIYRLWLEKNEEIFSDIAHCAMAFRLLRMNNYEVSSEELEGFVDQEHFF 322
               ************************************************************

SEQ ID NO:31   TTSGGKLISHVAILELHRASQVDIQEGKDLLILDKISTWTRNFMEQELLDNQILDRSKKEM 420
SEQ ID NO:40   TTSGGKLISHVAILELHRASQVDIQEGKDLLILDKISTWTRNFMEQELLDNQILDRSKKEM 382
               ************************************************************

SEQ ID NO:31   EFAMRKFYGTFDRVETRRYIESYKMDSFKILKAAYRSSNINNIDLLKFSEHDFNLCQARH 480
SEQ ID NO:40   EFAMRKFYGTFDRVETRRYIESYKMDSFKILKAAYRSSNINNIDLLKFSEHDFNLCQARH 442
               ************************************************************
```

FIGURE 6I

```
SEQ ID NO:31    KEELQQIKRWFADCKLEQVGSSQNYLYTSYFPIAAILFEPEYGDARLAFAKCGIIATTVD    540
SEQ ID NO:40    KEELQQIKRWFADCKLEQVGSSQNYLYTSYFPIAAILFEPEYGDARLAFAKCGIIATTVD    502
                ************************************************************

SEQ ID NO:31    DFFDGFACNEELQNIIELVERWDGYPTVGFRSERVRIFFLALYKMIEEIAAKAETKQGRC    600
SEQ ID NO:40    DFFDGFACNEELQNIIELVERWDGYPTVGFRSERVRIFFLALYKMIEEIAAKAETKQGRC    562
                ************************************************************

SEQ ID NO:31    VKDLLINLWIDLLKCMLVELDLWKIKSTTPSIEEYLSIACVTTGVKCLILISLHLLGPKL    660
SEQ ID NO:40    VKDLLINLWIDLLKCMLVELDLWKIKSTTPSIEEYLSIACVTTGVKCLILISLHLLGPKL    622
                ************************************************************

SEQ ID NO:31    SKDVTESSEVSALWNCTAVVARLNNDIHSYKREQAESSTNMVAILISQSQRTISEEEAIR    720
SEQ ID NO:40    SKDVTESSEVSALWNCTAVVARLNNDIHSYKREQAESSTNMVAILISQSQRTISEEEAIR    682
                ************************************************************

SEQ ID NO:31    QIKEVMESKRRELLGMVLQNKESQLPQVCKDLFWTTFKAAYSIYTHGDEYRFPQELKNHI    780
SEQ ID NO:40    QIKEMMESKRRELLGMVLQNKESQLPQVCKDLFWTTFKAAYSIYTHGDEYRFPQELKNHI    742
                ****:*******************************************************

SEQ ID NO:31    NDVIYKPLNQYSP    793
SEQ ID NO:40    NDVIYKPLNQYSP    755
                *************
```

FIGURE 6J ly. The text file, created Oct. 25, 2013, is 560 kilobytes in size and titled 219SE0002.txt.
SCLAREOL AND LABDENEDIOL DIPHOSPHATE SYNTHASE POLYPEPTIDES, ENCODING NUCLEIC ACID MOLECULES AND USES THEREOF

RELATED APPLICATIONS

Benefit of priority is claimed to U.S. Provisional Application Serial No. 61/741,959, filed Jul. 30, 2012, entitled "SCLAREOL AND LABDENEDIOL DIPHOSPHATE SYNTHASE POLYPEPTIDES, ENCODING NUCLEIC ACID MOLECULES AND USES THEREOF." The subject matter of the above-noted application is incorporated by reference in its entirety.

This application is related to International PCT Application No. PCT/US2013/052784, filed the same day herewith, entitled "SCLAREOL AND LABDENEDIOL DIPHOSPHATE SYNTHASE POLYPEPTIDES, ENCODING NUCLEIC ACID MOLECULES AND USES THEREOF," which also claims priority to U.S. Provisional Application Ser. No. 61/741,959.

The subject matter of each of the above-noted applications is incorporated by reference in its entirety.

INCORPORATION BY REFERENCE OF SEQUENCE LISTING PROVIDED ON COMPACT DISCS

An electronic version on compact disc (CD-R) of the Sequence Listing is filed herewith in duplicate (labeled Copy #1 and Copy #2), the contents of which are incorporated by reference in their entirety. The computer-readable file on each of the aforementioned compact discs, created on Jul. 29, 2013, is identical, 561 kilobytes in size, and titled 219SEQ.001.txt. A substitute Sequence Listing is filed electronically herewith, the contents of which are incorporated by reference in their entirety. The text file, created Oct. 25, 2013, is 560 kilobytes in size and titled 219SE0002.txt.

FIELD OF THE INVENTION

Provided are sclareol synthase and labdenediol diphosphate synthase (designated LPP synthase), nucleic acid molecules encoding the sclareol and LPP synthases, and methods for producing products whose synthesis includes reactions catalyzed by one or both of sclareol and LPP synthases. Included among the products are ambroxide and precursors and derivatives thereof.

BACKGROUND

Labdenediol diphosphate and sclareol are diterpenes that occur in plants. Labdenediol diphosphate is derived from cyclization of the acyclic pyrophosphate terpene precursor geranylgeranyl diphosphate (GGPP), and sclareol is derived from labdenediol diphosphate. Sclareol can be converted to ambroxide, a compound that is used widely in the perfume industry to impart ambergris notes. Thus, among the objects herein is the provision of labdenediol diphosphate synthase polypeptides, sclareol synthase polypeptides and methods for the production of labdenediol diphosphate and sclareol and ambroxide.

SUMMARY

Provided herein are isolated *Nicotiana glutinosa* labdenediol diphosphate synthases. Also provided herein are isolated nucleic acid molecules encoding *Nicotiana glutinosa* labdenediol diphosphate synthase polypeptides. For example, provided herein are isolated nucleic acid molecules encoding a labdenediol diphosphate synthase polypeptides, wherein the labdenediol diphosphate synthase polypeptide has a sequence of amino acids set forth in any of SEQ ID NOS:2, 4, 6, 8, 10, 12, 14 or 54; or the labdenediol diphosphate synthase polypeptide has a sequence of amino acids that has at least 95% sequence identity to a labdenediol diphosphate synthase polypeptide set forth in any of SEQ ID NOS:2, 4, 6, 8, 10, 12, 14 or 54. In some examples, the isolated nucleic acid molecule encoding the labdenediol diphosphate synthase polypeptide has a sequence of amino acids that has at least 50% amino acid sequence identity to a sequence of amino acids set forth in any of SEQ ID NOS:2, 4, 6, 8, 10, 12, 14 or 54; and the labdenediol diphosphate synthase catalyzes the formation of labdenediol diphosphate from an acyclic pyrophosphate terpene precursor. For example, the isolated nucleic acid molecule encoding the labdenediol diphosphate synthase polypeptide exhibits at least 55%, 60%, 65%, 70%, 75%, 80%, 85%, 86%, 87%, 88%, 89%, 90%, 91%, 92%, 93%, 94%, 95%, 96%, 97%, 98% or 99% amino acid sequence identity to a sequence of amino acids set forth in any of SEQ ID NOS:2, 4, 6, 8, 10, 12, 14 or 54.

In some examples, the isolated nucleic acid molecule encoding a labdenediol diphosphate synthase polypeptide has a sequence of nucleic acids set forth in any of SEQ ID NOS:1, 3, 5, 7, 9, 11, 13 and 53. In other examples, the isolated nucleic acid molecule encoding a labdenediol diphosphate synthase polypeptide has a sequence of nucleic acids having at least 95% sequence identity to a sequence of nucleic acids set forth in any of SEQ ID NOS:1, 3, 5, 7, 9, 11, 13 and 53. Also provided herein are degenerates of any of the provided isolated nucleic acid molecules encoding a labdenediol diphosphate synthase polypeptide. In particular examples, the isolated nucleic acid molecule encoding a labdenediol diphosphate synthase polypeptide has a sequence of nucleic acids set forth in any of SEQ ID NOS:1, 3, 5, 7, 9, 11, 13 and 53.

Provided herein are isolated nucleic acid molecules encoding a labdenediol diphosphate synthase polypeptide wherein the encoded labdenediol diphosphate synthase polypeptide has a sequence of amino acids set forth in any of SEQ ID NOS:2, 4, 6, 8, 10, 12, 14 or 54. Also provided herein are isolated nucleic acid molecules encoding a labdenediol diphosphate synthase polypeptide wherein the encoded labdenediol diphosphate synthase polypeptide has a sequence of amino acids that has at least 95% sequence identity to a labdenediol diphosphate synthase set forth in any of SEQ ID NOS:2, 4, 6, 8, 10, 12, 14 or 54. In particular examples, the encoded labdenediol diphosphate synthase polypeptide has a sequence of amino acids set forth in any of SEQ ID NOS:2, 4, 6, 8, 10, 12, 14 or 54.

Also provided herein are nucleic acid molecules encoding modified *Nicotiana glutinosa* labdenediol diphosphate synthase polypeptides. In some examples, the encoded modified labdenediol diphosphate synthase polypeptide contains at least one amino acid replacement, addition or deletion compared to the labdenediol diphosphate synthase polypeptide not containing the modification. In a particular example, the modification is an amino acid replacement. Provided herein are nucleic acid molecules encoding modified *Nicotiana glutinosa* labdenediol diphosphate synthase polypeptides wherein the encoded modified labdenediol diphosphate synthase polypeptide exhibits at least 65% sequence identity to the sequence of amino acids set forth in SEQ ID NO:54. For example, the encoded modified labdenediol diphosphate synthase polypeptide exhibits at least 70%, 75%, 80%, 85%, 86%, 87%, 88%, 89%, 90%, 91%, 92%, 93%, 94%, 95%, 96%, 97%, 98% or 99% amino acid sequence identity to the sequence of amino acids set forth in SEQ ID NO:54. In some examples, the amino acid replacement is in a labdenediol diphosphate synthase polypeptide that has a sequence of amino acids set forth in any of SEQ ID NOS:2, 4, 6, 8, 10, 12 or 14; or is in a labdenediol diphosphate synthase that has a sequence of amino acids that is at least 80%, 85%, 86%, 87%, 88%, 89%, 90%, 91%, 92%, 93%, 94%, 95%, 96%, 97%, 98%, 99% identical to any of SEQ ID NOS:2, 4, 6, 8, 10, 12 or 14.

The labdenediol diphosphate synthase polypeptides encoded by the nucleic acids molecules provided herein catalyze the formation of labdenediol pyrophosphate from an acyclic pyrophosphate terpene precursor. For example, the encoded labdenediol diphosphate synthase polypeptides catalyze the formation of labdenediol pyrophosphate from the pyrophosphate terpene precursor geranylgeranyl diphosphate (GGPP). In some examples, the encoded labdenediol diphosphate synthase polypeptide produces labdenediol diphosphate from GGPP in a host cell, whereby the host cell is a cell that produces GGPP, for example, a yeast cell.

Also provided herein are labdenediol diphosphate synthases encoded by any of the nucleic acid molecules provided herein. The labdenediol diphosphate synthases provided herein catalyze the formation of labdenediol diphosphate from an acyclic pyrophosphate terpene precursor, for example, an acyclic pyrophosphate terpene precursor that is geranylgeranyl diphosphate (GGPP). In some examples, the labdenediol diphosphate synthase polypeptides produce labdenediol diphosphate from GGPP in a host cell, whereby the host cell is a cell that produces GGPP, for example, a yeast cell.

Provided herein are isolated *Nicotiana glutinosa* sclareol synthases. Also provided herein are isolated nucleic acid molecules encoding *Nicotiana glutinosa* sclareol synthase polypeptides. For example, provided herein are isolated nucleic acid molecules encoding *Nicotiana glutinosa* sclareol synthase polypeptides, wherein the sclareol synthase polypeptide has a sequence of amino acids set forth in any of SEQ ID NOS: 31, 36, 38, 40 or 78; or the sclareol synthase polypeptide has a sequence of amino acids that has at least 95% sequence identity to a sclareol synthase polypeptide set forth in any of SEQ ID NOS: 31, 36, 38, 40 or 78. In some examples, the isolated nucleic acid molecule encoding the sclareol synthase polypeptide has a sequence of amino acids that has at least 50% amino acid sequence identity to a sequence of amino acids set forth in any of SEQ ID NOS: 31, 36, 38, 40 or 78, and the sclareol synthase catalyzes the formation of sclareol from labdenediol diphosphate. For example, the encoded sclareol synthase polypeptide exhibits at least 55%, 60%, 65%, 70%, 75%, 80%, 85%, 86%, 87%, 88%, 89%, 90%, 91%, 92%, 93%, 94%, 95%, 96%, 97%, 98% or 99% amino acid sequence identity to a sequence of amino acids set forth in any of SEQ ID NOS: 31, 36, 38, 40 or 78.

In some examples, the isolated nucleic acid molecule encoding a sclareol synthase polypeptide has a sequence of nucleic acids set forth in any of SEQ ID NOS:30, 35, 37, 39 or 77. In other examples, the isolated nucleic acid molecule encoding a sclareol synthase polypeptide has a sequence of nucleic acids having at least 95% sequence identity to a sequence of nucleic acids set forth in any of SEQ ID NOS:30, 35, 37, 39 or 77. Also provided herein are degenerates of any of the provided isolated nucleic acid molecules encoding a sclareol synthase polypeptide. In particular examples, the isolated nucleic acid molecule encoding a sclareol synthase polypeptide has a sequence of nucleic acids set forth in any of SEQ ID NOS:30, 35, 37, 39 or 77.

Provided herein are isolated nucleic acid molecules encoding a sclareol synthase polypeptide wherein the encoded sclareol synthase polypeptide has a sequence of amino acids set forth in any of SEQ ID NOS: 31, 36, 38, 40 or 78; or the encoded sclareol synthase polypeptide has a sequence of amino acids that has at least 95% sequence identity to a sclareol synthase set forth in any of SEQ ID NOS: 31, 36, 38, 40 or 78. In a particular example, the encoded sclareol synthase polypeptide has a sequence of amino acids set forth in any of SEQ ID NOS: 31, 36, 38, 40 or 78.

Also provided herein are nucleic acid molecules encoding modified *Nicotiana glutinosa* sclareol synthase polypeptides. In some examples, the modified *Nicotiana glutinosa* sclareol synthase polypeptide contains at least one amino acid replacement, addition or deletion compared to the sclareol synthase polypeptide not containing the modification. In a particular example, the modification is an amino acid replacement. Provided herein are nucleic acid molecules encoding modified *Nicotiana glutinosa* sclareol synthase polypeptides wherein the encoded modified sclareol synthase polypeptide exhibits at least 65% sequence identity to the sequence of amino acids set forth in SEQ ID NO:31. For example, the encoded modified sclareol synthase polypeptide exhibits at least 70%, 75%, 80%, 85%, 86%, 87%, 88%, 89%, 90%, 91%, 92%, 93%, 94%, 95%, 96%, 97%, 98% or 99% amino acid sequence identity to the sequence of amino acids set forth in SEQ ID NO:31. In some examples, the amino acid replacement is in a sclareol synthase polypeptide that has a sequence of amino acids set forth in any of SEQ ID NOS: 31, 36, 38, 40 or 78; or is in a sclareol synthase polypeptide that has a sequence of amino acids that is at least 80%, 85%, 86%, 87%, 88%, 89%, 90%, 91%, 92%, 93%, 94%, 95%, 96%, 97%, 98%, 99% identical to any of SEQ ID NOS:31, 36, 38, 40 or 78. The sclareol synthase polypeptides encoded by the nucleic acids molecules provided herein catalyze the formation of sclareol from labdenediol diphosphate. For example, the encoded sclareol synthase polypeptides catalyze the formation of sclareol from labdenediol diphosphate.

Provided herein are nucleic acid molecules encoding modified labdenediol diphosphate synthase polypeptides containing one or more heterologous domains or portions thereof from one or more terpene synthases, wherein the domain is selected from among Helix A; Loop 1; Helix B; Loop 2; Helix C; Loop 3; Helix D; Loop 4; Helix E; Loop 5; Helix F1; Loop 7; Helix G; Loop 8; Helix H; Loop 9; Helix I; Loop 10; Helix J; Loop 11; Helix K; Loop 12; Helix L; Loop 13; Helix M; Loop 14; Helix N; Loop 15; Helix O; Loop 16; Helix P; Loop 17; Helix Q; Loop 18; Helix R; Loop 19; Helix S; Loop 20; Helix T; Loop 21; Helix U; Loop 22; Helix V; Loop 23; Helix W; Loop 24; Helix X; Loop 25; Helix Y; Loop 26; Helix Z1; Loop 28; Helix AA; Loop 29; Helix AB; Loop 30; Helix AC and/or Loop 31. For example, provided herein is a nucleic acid molecule encoding a modified labdenediol diphosphate synthase polypeptide, wherein the encoded modified labdenediol diphosphate synthase polypeptide has one or more heterologous domains or portions thereof from one or more terpene synthases, wherein the domain is selected from among Helix A; Loop 1; Helix B; Loop 2; Helix C; Loop 3; Helix D; Loop 4; Helix E; Loop 5; Helix F1; Loop 7; Helix G; Loop 8; Helix H; Loop 9; Helix I; Loop 10; Helix J; Loop 11; Helix K; Loop 12; Helix L; Loop 13; Helix M; Loop 14; Helix N; Loop 15; Helix O; Loop 16; Helix P; Loop 17; Helix Q; Loop 18; Helix R; Loop 19; Helix S; Loop 20; Helix T; Loop 21; Helix U; Loop 22; Helix V; Loop 23; Helix W; Loop 24; Helix X; Loop 25; Helix Y; Loop 26; Helix Z1; Loop 28; Helix AA; Loop 29; Helix AB; Loop 30; Helix AC and/or Loop 31.

In some examples, the heterologous domain or a contiguous portion thereof replaces all or a contiguous portion of the corresponding native domain of the labdenediol diphosphate synthase not containing the heterologous domain. In other examples, the encoded modified labdenediol diphosphate synthase polypeptide contains all of a heterologous domain of a different terpene synthase. In other examples, the encoded modified labdenediol diphosphate synthase polypeptide contains at least 50%, 60%, 70%, 80%, 90%, or 95% of contiguous amino acids of a heterologous domain from one or more different terpene synthases. In some examples, the different terpene synthase is a diterpene synthase, for example, a class II diterpene synthase. In one example, the different diterpene synthase is a labdenediol diphosphate synthase from a species other than *Nicotiana glutinosa*. For example, the diterpene synthase is a *Salvia sclarea* labdenediol diphosphate synthase.

Provided herein are nucleic acid molecules encoding modified sclareol synthase polypeptides containing one or more heterologous domains or portions thereof from one or more terpene synthases, wherein the domain is selected from among Loop 1; Helix A; Loop 2; Helix B; Loop 3; Helix C; Loop 4; Helix D; Loop 5; Helix E; Loop 6; Helix F; Loop 7; Helix G; Loop 8; Helix H; Loop 9; Helix I; Loop 10; Helix J; Loop 11; Helix K; Loop 12; Helix L; Loop 13; Helix M; Loop 14; Helix N; Loop 15; Helix O; Loop 16; Helix P; Loop 17; Helix Q; Loop 18; Helix R; Loop 19; Helix S; Loop 20; Helix T; Loop 21; Helix U; Loop 22; Helix V; Loop 23; Helix W; Loop 24; Helix X; Loop 25; Helix Y; Loop 26; Helix Z; Loop 27; Helix AA; Loop 28; Helix AB; Loop 29; Helix AC; Loop 30; Helix AD; Loop 31; Helix AE; Loop 32; Helix AF; Loop 33; Helix AG; Loop 34; Helix AH; and/or Loop 35. For example, provided herein is a nucleic acid molecule encoding a modified sclareol synthase polypeptide, wherein the encoded modified sclareol synthase polypeptide has one or more heterologous domains or portions thereof from one or more terpene synthases, wherein the domain is selected from among Loop 1; Helix A; Loop 2; Helix B; Loop 3; Helix C; Loop 4; Helix D; Loop 5; Helix E; Loop 6; Helix F; Loop 7; Helix G; Loop 8; Helix H; Loop 9; Helix I; Loop 10; Helix J; Loop 11; Helix K; Loop 12; Helix L; Loop 13; Helix M; Loop 14; Helix N; Loop 15; Helix O; Loop 16; Helix P; Loop 17; Helix Q; Loop 18; Helix R; Loop 19; Helix S; Loop 20; Helix T; Loop 21; Helix U; Loop 22; Helix V; Loop 23; Helix W; Loop 24; Helix X; Loop 25; Helix Y; Loop 26; Helix Z; Loop 27; Helix AA; Loop 28; Helix AB; Loop 29; Helix AC; Loop 30; Helix AD; Loop 31; Helix AE; Loop 32; Helix AF; Loop 33; Helix AG; Loop 34; Helix AH; and/or Loop 35.

In some examples, the heterologous domain or a contiguous portion thereof replaces all or a contiguous portion of the corresponding native domain of the sclareol synthase not containing the heterologous domain. In other examples, the encoded modified sclareol synthase polypeptide contains all of a heterologous domain of a different terpene synthase. In other examples, the encoded modified sclareol synthase polypeptide contains at least 50%, 60%, 70%, 80%, 90%, or 95% of contiguous amino acids of a heterologous domain from one or more different terpene synthases. In some examples, the different terpene synthase is a diterpene synthase, for example, a class I diterpene synthase. In one example, the different diterpene synthase is a sclareol synthase from a species other than *Nicotiana glutinosa*. For example, the diterpene synthase is a *Salvia sclarea* sclareol synthase. For example, provided herein is a nucleic acid molecule encoding a modified sclareol synthase polypeptide having a sequence of amino acids set forth in SEQ ID NO:86; or a sequence of amino acids that has at least 95% sequence identity to a sequence of amino acids set forth in SEQ ID NO:86. In another example, provided herein is a nucleic acid molecule encoding a modified sclareol synthase polypeptide having a sequence of nucleic acids set forth in SEQ ID NO:87; or having a sequence of nucleic acids that has at least 95% sequence identity to a sequence of nucleic acids set forth in SEQ ID NO:87; and degenerates thereof.

Also provided herein are nucleic acid molecules encoding fusion proteins containing a *Nicotiana glutinosa* labdenediol diphosphate synthase and a *Nicotiana glutinosa* sclareol synthase. For example, provided herein is a nucleic acid molecule encoding a fusion protein having a labdenediol diphosphate synthase and a sclareol synthase, wherein the labdenediol diphosphate synthase is any synthase nucleic acid molecule encoding a labdenediol diphosphate provided herein and the sclareol synthase is any nucleic acid molecule encoding a sclareol synthase polypeptide provided herein. The labdenediol diphosphate synthase and sclareol synthase can be linked directly or via a linker. In some examples, the fusion protein contains a *Nicotiana glutinosa* labdenediol diphosphate synthase provided herein and the sclareol synthase that is a *Salvia sclarea* sclareol synthase, for example, a sclareol synthase that has a sequence of amino acid set forth in any of SEQ ID NOS:60-62. In other examples, the fusion protein contains a *Salvia sclarea* labdenediol diphosphate synthase and the sclareol synthase is a *Nicotiana glutinosa* labdenediol diphosphate synthase provided herein. For example, the *Salvia sclarea* labdenediol diphosphate synthase has a sequence of amino acid set forth in SEQ ID NO:58 or 59. Provided herein are nucleic acids encoding a fusion protein having a sequence of amino acids set forth in SEQ ID NO:94; or a sequence of amino acids that has at least 95% sequence identity to a sequence of amino acids set forth in SEQ ID NO:94. Provided herein are nucleic acids encoding a fusion protein having a sequence of nucleic acids set forth in SEQ ID NO:95; or a sequence of nucleic acids that has at least 95% sequence identity to a sequence of nucleic acids set forth in SEQ ID NO:95; and degenerates thereof.

Also provided herein are nucleic acid molecules encoding a sclareol synthase fused to a protein domain that facilitates increased expression of the sclareol synthase. The sclareol synthase and protein domain can be linked directly or via a linker. In some examples, the protein domain is a green fluorescent protein or a cellulose binding domain. In some examples, the nucleic acid molecule encodes a *Nicotiana glutinosa* sclareol synthase, for example, any of the nucleic acid molecules provided herein. Provided herein is a nucleic acid molecule encoding a sclareol synthase fused to a protein domain that facilitates increased expression of the sclareol synthase that encodes a sequence of amino acids set forth in SEQ ID NO:90 or 92; or a sequence of amino acids that has at least 95% sequence identity to a sequence of amino acids set forth in SEQ ID NO:90 or 92. Also provided herein is a nucleic acid molecule encoding a sclareol synthase fused to a protein domain that facilitates increased expression of the sclareol synthase having a sequence of nucleic acids set forth in SEQ ID NO:91 or 93; or a sequence of nucleic acids that has at least 95% sequence identity to a sequence of nucleic acids set forth in SEQ ID NO:91 or 93; and degenerates thereof.

Also provided herein are vectors containing any of the nucleic acid molecules encoding a labdenediol diphosphate synthase polypeptide or a sclareol synthase polypeptide provided herein. In some examples, the vector is a prokaryotic vector, a viral vector, or an eukaryotic vector. For example, the vector is a yeast vector. Also provided herein are cells containing any of the vectors or nucleic acid molecules provided herein. The cell can be a prokaryotic cell or an eukaryotic cell. For example, the cell is selected from among a bacteria, yeast, insect, plant or mammalian cell. In a particular example, the cell is a yeast cell that is a *Saccharomyces* genus cell or a *Pichia* genus cell. In one example, the yeast cell is a *Saccharomyces cerevisiae* cell. In another example, the cell is a bacterial cell that is an *Escherichia coli* cell. In particular examples, the cells produce geranylgeranyl diphosphate (GGPP). For example, the cell produces GGPP natively or is modified to produce more GGPP compared to an unmodified cell. In a particular example, the cell is modified to produce more GGPP compared to an unmodified cell. The cells provided herein can express a sclareol synthase polypeptide. Also provided herein are sclareol synthases produced by any of the cells provided herein. Also provided herein are transgenic plants containing any of the vectors provided herein. In one example, the transgenic plant is a tobacco plant.

Provided herein is a method for producing a labdenediol diphosphate synthase polypeptide wherein a nucleic acid molecule or vector encoding a labdenediol diphosphate synthase polypeptide provided herein is introduced into a cell, the cell is cultured under conditions suitable for expression of the labdenediol diphosphate synthase polypeptide encoded by the nucleic acid or vector; and, optionally, the labdenediol diphosphate synthase polypeptide is isolated. Provided herein is a method for producing a sclareol synthase polypeptide wherein a nucleic acid molecule or vector encoding a sclareol synthase polypeptide provided herein is introduced into a cell, the cell is cultured under conditions suitable for expression of the sclareol synthase polypeptide encoded by the nucleic acid or vector; and, optionally, the sclareol synthase polypeptide is isolated.

Provided herein is a method for producing labdenediol diphosphate, wherein an acyclic pyrophosphate terpene precursor is contacted with any labdenediol diphosphate synthase polypeptide provided herein, under conditions suitable for the formation of labdenediol diphosphate from the acyclic pyrophosphate terpene precursor, and optionally, isolating the labdenediol diphosphate. In some examples, the step of contacting the acyclic pyrophosphate terpene precursor with the labdenediol synthase polypeptide is effected in vitro or in vivo. In some examples, the acyclic pyrophosphate terpene precursor is geranylgeranyl diphosphate (GGPP).

Provided herein is a method for producing labdenediol diphosphate, wherein a cell transformed with a nucleic acid molecule encoding a labdenediol diphosphate synthase provided herein is cultured; whereby the cell produces an acyclic pyrophosphate terpene precursor; the labdenediol diphosphate synthase polypeptide encoded by the nucleic acid molecule or vector is expressed; and the labdenediol diphosphate synthase polypeptide catalyzes the formation of labdenediol diphosphate from the acyclic pyrophosphate terpene precursor. In some examples, the acyclic pyrophosphate terpene precursor is geranylgeranyl diphosphate (GGPP). In other examples, the cell is selected from among a bacteria, yeast, insect, plant or mammalian cell. For example, the cell is a yeast cell that is a *Saccharomyces cerevisiae* cell. In some examples, the cell is modified to produce more GGPP compared to an unmodified cell.

Also provided herein is a method for producing labdenediol diphosphate, wherein a cell transformed with a nucleic acid molecule encoding a labdenediol diphosphate synthase provided herein is cultured; whereby the cell produces an acyclic pyrophosphate terpene precursor; the labdenediol diphosphate synthase polypeptide encoded by the nucleic acid molecule or vector is expressed; the labdenediol diphosphate synthase polypeptide catalyzes the formation of labdenediol diphosphate from the acyclic pyrophosphate terpene precursor; and the labdenediol diphosphate is isolated. In some examples of the method, the labdenediol diphosphate is converted to labdenediol, for example, the conversion is effected by addition of an alkaline phosphatase. In some examples, the labdenediol is isolated, for example, by extraction with an organic solvent and/or column chromatography.

Provided herein is a method for producing sclareol, wherein a labdenediol diphosphate is contacted with any sclareol synthase polypeptide provided herein or any sclareol synthase polypeptide encoded by a nucleic acid molecule provided herein, under conditions suitable for the formation of sclareol from the labdenediol diphosphate; and optionally, the sclareol is isolated.

Provided herein is a method for producing sclareol, wherein a cell is transformed with a nucleic acid molecule or vector encoding a sclareol synthase polypeptide provided herein in a medium that contains labdenediol diphosphate; the sclareol synthase polypeptide encoded by the nucleic acid molecule or vector is expressed; and the sclareol synthase polypeptide catalyzes the formation of sclareol from the labdenediol diphosphate.

Provided herein is a method for producing sclareol, wherein the method includes (a) contacting geranylgeranyl diphosphate with a labdenediol diphosphate synthase polypeptide provided herein or a labdenediol diphosphate synthase polypeptide encoded by a nucleic acid provided herein; (b) contacting labdenediol diphosphate with a sclareol synthase polypeptide provided herein or a sclareol synthase polypeptide encoded by the nucleic acid molecule provided herein; and (c) optionally isolating the sclareol produced in step (b).

Provided herein is a method for producing sclareol, wherein the method includes culturing a cell encoding (a) a nucleic acid molecule or vector encoding a labdenediol diphosphate synthase polypeptide provided herein; (b) the nucleic acid molecule or the vector encoding a sclareol synthase polypeptide provided herein; and (c) optionally isolating the sclareol produced in step (b); wherein the cell produces an acyclic pyrophosphate terpene precursor; the labdenediol diphosphate synthase and sclareol synthase polypeptides encoded by the nucleic acid molecule or vector are expressed; the labdenediol diphosphate synthase polypeptide catalyzes the formation of labdenediol diphosphate from the acyclic pyrophosphate terpene precursor; and the sclareol synthase polypeptide catalyzes the formation of sclareol from labdenediol diphosphate. Steps a) and b) can be carried out simultaneously or sequentially.

Provided herein is a method for producing sclareol, wherein the method includes culturing a cell encoding (a) the nucleic acid molecule encoding a fusion protein containing a *Nicotiana glutinosa* labdenediol diphosphate synthase and a *Nicotiana glutinosa* sclareol synthase; and (b) optionally isolating the sclareol produced in step (a); wherein the cell produces an acyclic pyrophosphate terpene precursor; the labdenediol diphosphate synthase and sclareol synthase polypeptides encoded by the nucleic acid molecule are expressed; the labdenediol diphosphate synthase polypeptide catalyzes the formation of labdenediol diphosphate from the acyclic pyrophosphate terpene precursor; and the sclareol synthase polypeptide catalyzes the formation of sclareol from labdenediol diphosphate. Steps a) and b) can be carried out simultaneously or sequentially. In some examples, in step (b), the sclareol is isolated by extraction with an organic solvent and/or column chromatography.

Provided herein is a method for producing (−)-ambroxide, wherein the method includes (a) contacting geranylgeranyl diphosphate with the labdenediol diphosphate synthase polypeptide provided herein or the labdenediol diphosphate synthase polypeptide encoded by the nucleic acid molecule provided herein; (b) contacting labdenediol diphosphate with the sclareol synthase polypeptide provided herein or the sclareol synthase polypeptide encoded by the nucleic acid molecule provided herein; (c) isolating the sclareol produced in step (b); (d) converting the sclareol to ambroxide; and (e) isolating the ambroxide.

Provided herein is a method for producing (−)-ambroxide, wherein the method includes culturing a cell encoding (a) a nucleic acid molecule or vector encoding a labdenediol diphosphate synthase polypeptide; (b) a nucleic acid molecule or a vector encoding a sclareol synthase polypeptide; (c) isolating the sclareol produced in step (b); (d) converting the sclareol to (−)-ambroxide; and (e) isolating the (−)-ambroxide; wherein the cell produces an acyclic pyrophosphate terpene precursor; the labdenediol diphosphate synthase polypeptide and sclareol synthase polypeptides encoded by the nucleic acid molecule or vector are expressed; the labdenediol diphosphate synthase polypeptide catalyzes the formation of labdenediol diphosphate from the acyclic pyrophosphate terpene precursor; and the sclareol synthase polypeptide catalyzes the formation of sclareol from labdenediol diphosphate.

In any of the methods for producing (−)-ambroxide provided herein, in step (c), the sclareol can be isolated by extraction with an organic solvent and/or column chromatography. In any of the methods for producing (−)-ambroxide provided herein, in step (d), the sclareol can be converted to (−)-ambroxide biosynthetically, chemically or both biosynthetically and chemically. The oxidation to (−)-ambroxide can be performed in one step or multiple steps.

For example, the sclareol is converted to (−)-ambroxide according to Scheme II

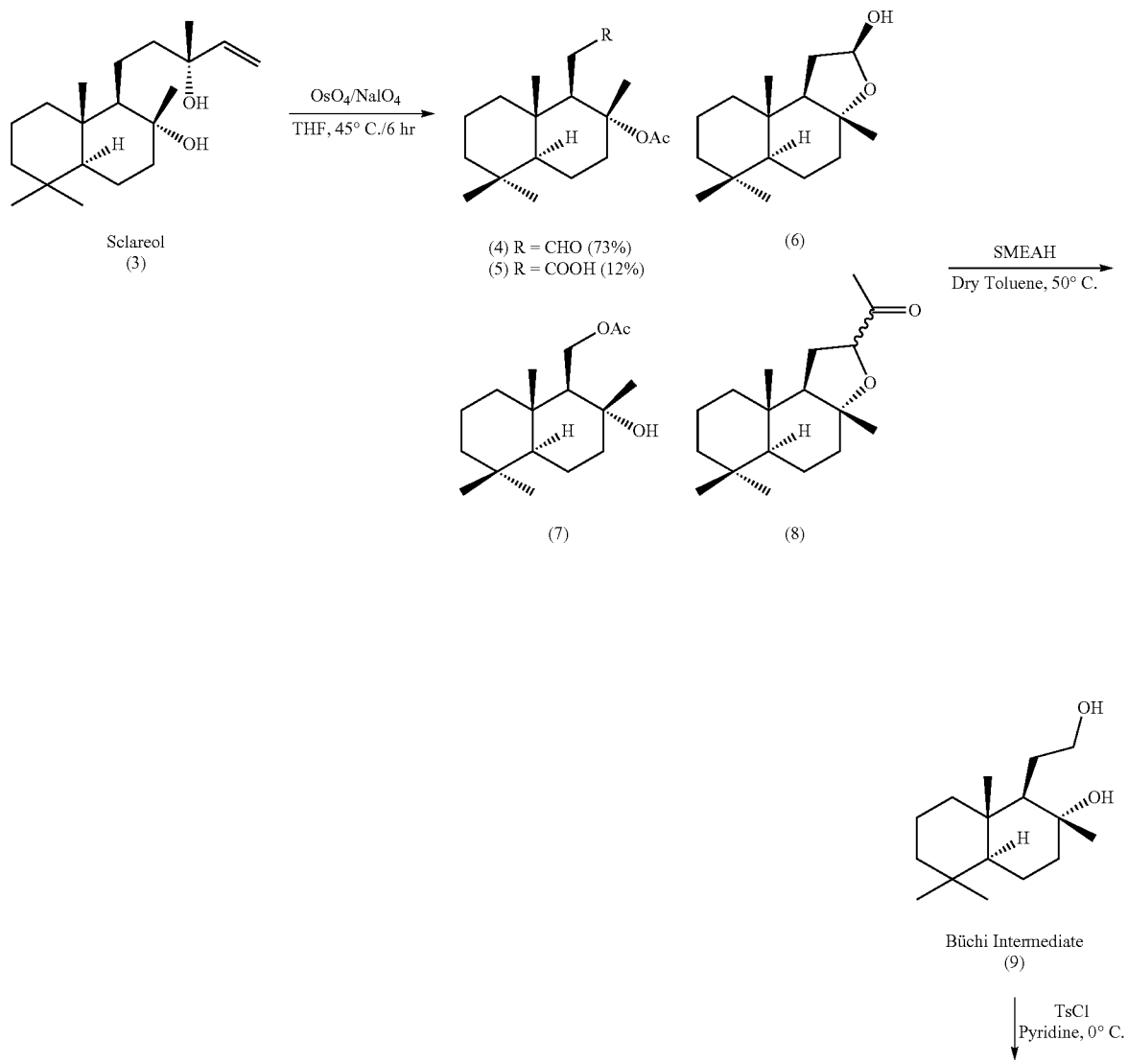

-continued

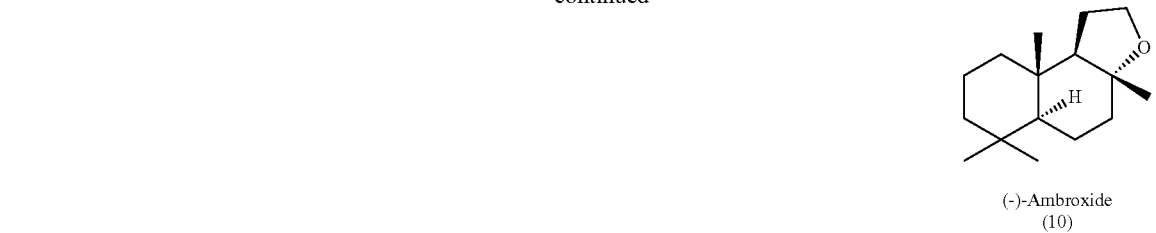

(-)-Ambroxide
(10)

or Scheme III

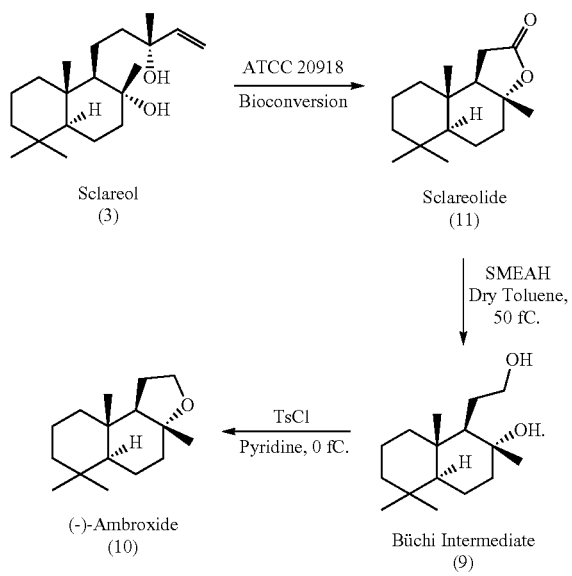

In any of the methods for producing (−)-ambroxide provided herein, in step (e), the (−)-ambroxide is isolated by extraction with an organic solvent and/or column chromatography. In any of the methods for producing (−)-ambroxide provided herein, steps a) and b) can be carried out simultaneously or sequentially.

BRIEF DESCRIPTION OF THE FIGURES

FIG. 2A illustrates a scheme involving oxidative degradation followed by reduction and cyclization. FIG. 2B illustrates a scheme involving biochemical conversion to sclareolide followed by reduction and cyclization. FIG. 2C illustrates a scheme for the conversion of GGPP to (−)-ambroxide.

FIGS. 3A-3D depict exemplary alignments of Nicotiana glutinosa labdenediol diphosphate synthase and sclareol synthase with other diterpene synthases. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position. For example, FIGS. 3A-3B depict the alignment of Nicotiana glutinosa labdenediol diphosphate synthase NgLPP2-1-2 set forth in SEQ ID NO:2 with Arabidopsis thaliana ent-copalyl diphosphate synthase set forth in SEQ ID NO:83. FIGS. 3C-3D depicts the alignment of Nicotiana glutinosa sclareol synthase NgSs S3F1-1 set forth in SEQ ID NO:36 with Abies grandis abietadiene synthase set forth in SEQ ID NO:84.

FIGS. 4A-4F depict exemplary alignments of Nicotiana glutinosa labdenediol diphosphate synthases (NgLPP) and sclareol synthases (NgSs) with Salvia sclarea labdenediol diphosphate synthases (SsLPP) and sclareol synthases (SsSs). A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position. For example, FIGS. 4A-4C depict the alignment of Nicotiana glutinosa labdenediol diphosphate synthase NgLPP2-1-2 set forth in SEQ ID NO:2, Nicotiana glutinosa labdenediol diphosphate synthase NgLPP2-2-2 set forth in SEQ ID NO:10 and Salvia sclarea labdenediol diphosphate synthases set forth in SEQ ID NOS:58 and 59. FIGS. 4D-4F depict the alignment of Nicotiana glutinosa sclareol synthase S3F1-1 set forth in SEQ ID NO:36, Nicotiana glutinosa sclareol synthase S3F2-3 set forth in SEQ ID NO:40 and Salvia sclarea sclareol synthases set forth in SEQ ID NOS:60 and 62.

FIGS. 6A-6J depict exemplary alignments of Nicotiana glutinosa labdenediol diphosphate and sclareol synthases. A "*" means that the aligned residues are identical, a ":" means that aligned residues are not identical, but are similar and contain conservative amino acids residues at the aligned position, and a "." means that the aligned residues are similar and contain semi-conservative amino acid residues at the aligned position. Exemplary, non-limiting, corresponding positions for amino acid replacements are indicated by highlighting. For example, FIGS. 6A-6B depict the alignment of a Nicotiana glutinosa labdenediol diphosphate synthase set forth in SEQ ID NO:54 with a Salvia sclarea labdenediol diphosphate synthase set forth in SEQ ID NO:58. FIGS. 6C-6D depict the alignment of a Nicotiana glutinosa labdenediol diphosphate synthase set forth in SEQ ID NO:54 with a Nicotiana glutinosa labdenediol diphosphate synthase set forth in SEQ ID NO:10. FIGS. 6E-6F depict the alignment of a Nicotiana glutinosa sclareol synthase set forth in SEQ ID NO:31 with a Salvia sclarea sclareol synthase set forth in SEQ ID NO:60.

FIGS. 6G-6H depict the alignment of a *Nicotiana glutinosa* sclareol synthase set forth in SEQ ID NO:31 with a *Salvia sclarea* sclareol synthase set forth in SEQ ID NO:62. FIGS. 6I-6J depict the alignment of a *Nicotiana glutinosa* sclareol synthase set forth in SEQ ID NO:31 with a *Nicotiana glutinosa* sclareol synthase set forth in SEQ ID NO:40.

DETAILED DESCRIPTION

Outline

Figure 1A:
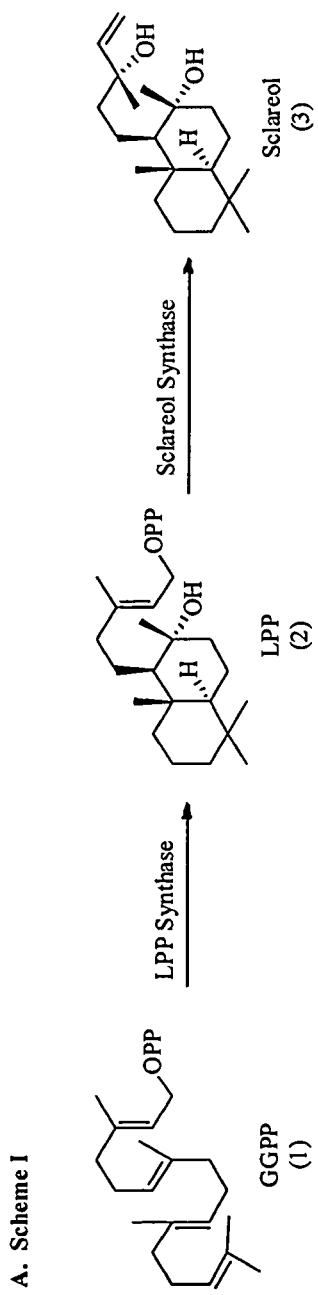
FIG. 1A depicts the formation of labdenediol diphosphate (LPP) and sclareol from the acyclic pyrophosphate terpene precursor geranylgeranyl diphosphate (GGPP) by the enzymes labdenediol diphosphate synthase (LPP synthase) and sclareol synthase.

A. Definitions
B. Pathways and products—overview
　Pathway
　Diterpene synthases
　　1. Labdenediol Diphosphate (LPP) Synthase
　　　a. Structure
　　　b. Activity
　　2. Sclareol Synthase
　　　a. Structure
　　　b. Activity
　　3. (−)-Ambroxide
C. Labdenediol diphosphate (LPP) synthase and sclareol synthase polypeptides and encoding nucleic acid molecules
　　1. Labdenediol diphosphate (LPP) synthase polypeptides
　　　a. Modified labdenediol diphosphate synthase polypeptides
　　　b. Truncated LPP synthase polypeptides
　　　c. LPP synthase polypeptides with altered activities or properties
　　　d. Domain Swaps
　　　e. Additional variants
　　2. Sclareol synthase polypeptides
　　　a. Modified sclareol synthase polypeptides
　　　b. Truncated sclareol synthase polypeptides
　　　c. Altered activities or properties
　　　d. Domain Swaps
　　　e. Additional Variants
　　3. Fusion or chimeric LPP synthase and sclareol synthase polypeptides
D. Methods for producing modified LPP and sclareol synthases and encoding nucleic acid molecules
E. Expression of LPP synthase and sclareol synthase polypeptides and encoding nucleic acid molecules
　　1. Isolation of nucleic acid encoding LPP synthase and sclareol synthase
　　2. Generation of mutant or modified nucleic acid
　　3. Vectors and Cells
　　4. Expression systems
　　　a. Prokaryotic cells
　　　b. Yeast cells
　　　c. Plants and plant cells
　　　d. Insects and insect cells
　　　e. Mammalian cells
　　5. Purification
　　6. Fusion proteins
F. Methods for producing terpenes catalyzed by LPP and sclareol synthases and methods for detecting such products and the activity of the LPP and sclareol synthases
　　1. Labdenediol diphosphate and labdenediol
　　2. Sclareol
　　3. Production of labdenediol diphosphate and sclareol
　　　a. Exemplary cells
　　　b. Culture of cells
　　　c. Isolation and assessment
　　4. Production of (−)-ambroxide
G. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the interne can come and go, but equivalent information can be found by searching the internet. Reference thereto evidences the availability and public dissemination of such information.

As used herein, an acyclic pyrophosphate terpene precursor is any acyclic pyrophosphate compound that is a precursor to the production of at least one terpene, including, but not limited to, farnesyl-pyrophosphate (FPP), geranyl-pyrophosphate (GPP), and geranylgeranyl-pyrophosphate (GGPP). Acyclic pyrophosphate terpene precursors are thus substrates for terpene synthases.

As used herein, a terpene is an unsaturated hydrocarbon based on the isoprene unit ($C_5H_8$), and having a general formula $C_{5x}H_{8x}$, such as $C_{10}H_{16}$. Reference to a terpene includes acyclic, monocyclic and polycyclic terpenes. Terpenes include, but are not limited to, monoterpenes, which contain 10 carbon atoms; sesquiterpenes, which contain 15 carbon atoms; diterpenes, which contain 20 carbon atoms, and triterpenes, which contain 30 carbon atoms. Reference to a terpene also includes stereoisomers of the terpene.

As used herein, a terpene synthase is a polypeptide capable of catalyzing the formation of one or more terpenes from a pyrophosphate terpene precursor. In some examples, a terpene synthase catalyzes the formation of one or more terpenes from an acyclic pyrophosphate terpene precursor, for example, FPP, GPP or GGPP. In other examples, a terpene synthase catalyzes the formation of one or more terpenes from a cyclic pyrophosphate terpene precursor, including, but not limited to, labdenediol diphosphate.

As used herein, a "labdenediol diphosphate synthase" or "LPP synthase" or "labdenediol diphosphate synthase polypeptide" or "LPP synthase polypeptide" is a polypeptide capable of catalyzing the formation of labdenediol diphosphate from an acyclic pyrophosphate precursor, typically geranylgeranyl diphosphate (GGPP). Labdenediol diphosphate can be the only product or one of a mixture of products formed from the reaction of an acyclic pyrophosphate terpene precursor with a labdenediol diphosphate synthase. The amount of labdenediol diphosphate produced from the reaction of a labdenediol diphosphate synthase with an acyclic pyrophosphate terpene precursor typically is at least or at least about 1%, 5%, 10%, 20%, 30%, 40%, 50%, 60%, 70%, 80%, 90% or more of the total amount of terpenes produced in the reaction. In some instances, labdenediol diphosphate is the predominant terpene produced (i.e. present in greater amounts than any other single terpene produced from the reaction of an acyclic pyrophosphate terpene precursor with a labdenediol diphosphate synthase).

For purposes herein, labdenediol diphosphate synthases provided herein are enzymes with LPP synthase activity and have greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, when aligned with the LPP synthase sequence set forth in SEQ ID NO:54. Reference to a labdenediol diphosphate synthase includes any labdenediol diphosphate synthase polypeptide including, but not limited to, a recombinantly produced polypeptide, synthetically produced polypeptide and a labdenediol diphosphate synthase polypeptide extracted or isolated from cells or plant matter, including, but not limited to, leaves of the tobacco plant. Exemplary of labdenediol diphosphate synthase polypeptides include those isolated from *Nicotiana glutinosa*. Reference to a labdenediol diphosphate synthase includes labdenediol diphosphate synthase from any genus or species, and includes allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity to the labdenediol diphosphate synthase set forth in SEQ ID NO:54 when aligned therewith. Labdenediol diphosphate synthase also includes catalytically active fragments thereof that retain labdenediol diphosphate synthase activity.

As used herein, "labdenediol diphosphate synthase activity" (also referred to herein as catalytic activity) refers to the ability to catalyze the formation of labdenediol diphosphate from an acyclic pyrophosphate terpene precursor, such as geranylgeranyl diphosphate (GGPP). Methods to assess labdenediol diphosphate formation from the reaction of a synthase with an acyclic pyrophosphate terpene precursor, such as GGPP, are well known in the art and described herein. For example, the synthase can be expressed in a host cell, such as a yeast cell, that also produces GGPP. The production of labdenediol diphosphate then can be assessed and quantified by methods such as, for example, gas chromatography-mass spectrometry (GC-MS) (see Examples below). A synthase exhibits labdenediol diphosphate synthase activity or the ability to catalyze the formation of labdenediol diphosphate from an acyclic pyrophosphate terpene precursor such as GGPP if the amount of labdenediol diphosphate produced from the reaction is at least or at least about 0.5%, 1%, 5%, 10%, 20%, 30%, 40%, 50%, 60%, 70%, 80%, 90% or more of the total amount of terpene produced in the reaction.

As used herein, labdenediol diphosphate is a diterpene having the following structure or isomers thereof:

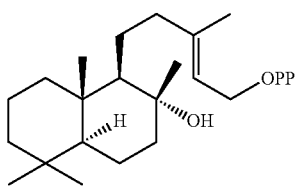

As used herein, labdenediol is a diterpene having the following structure or isomers thereof:

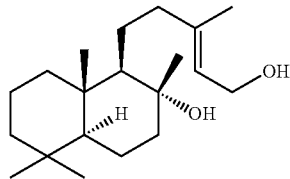

As used herein, a "sclareol synthase" or "sclareol synthase polypeptide" refers to a polypeptide capable of catalyzing the formation of sclareol from labdenediol diphosphate. Sclareol can be the only product or one of a mixture of products formed from the reaction of labdenediol diphosphate with a sclareol synthase. The amount of sclareol produced from the reaction of a sclareol synthase with labdenediol diphosphate typically is at least or at least about 0.5%, 1%, 5%, 10%, 20%, 30%, 40%, 50%, 60%, 70%, 80%, 90% or more of the total amount of terpenes produced in the reaction. In some instances, sclareol is the predominant terpene produced (i.e. present in greater amounts than any other single terpene produced from the reaction of labdenediol diphosphate with a sclareol synthase).

Reference to a sclareol synthase includes any sclareol synthase polypeptide including, but not limited to, a recombinantly produced polypeptide, synthetically produced polypeptide and a sclareol synthase polypeptide extracted or isolated from cells or plant matter, including, but not limited to, leaves of the tobacco plant. Exemplary sclareol synthase polypeptides include those isolated from *Nicotiana glutinosa*. For purposes herein, a sclareol synthase provided herein has greater than or greater than about or 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity, upon alignment, with the sclareol synthase set forth in SEQ ID NO:31.

Thus, reference to a sclareol synthase includes sclareol synthase from any genus or species, and includes allelic or species variants, variants encoded by splice variants, and other variants thereof, including polypeptides that have at least or at least about 50%, 55%, 60%, 65%, 70%, 75%, 80%, 85%, 90%, 95%, 96%, 97%, 98%, 99% or more sequence identity, upon alignment, to the sclareol synthase set forth in SEQ ID NO:31. Sclareol synthase also includes fragments thereof that retain catalytic activity.

As used herein, "sclareol synthase activity" (also referred to herein as catalytic activity) refers to the ability of the polypeptide to catalyze the formation of sclareol from labdenediol diphosphate. Methods to assess sclareol formation from the reaction of a synthase with labdenediol diphosphate are well known in the art and described herein. For example, the synthase can be expressed in a host cell, such as an *E. coli* or yeast cell, and incubated with labdenediol diphosphate. The production of sclareol then can be assessed and quantified by methods, including, for example, gas chromatography-mass spectrometry (GC-MS) (see Examples below). A synthase is considered to exhibit sclareol synthase activity or the ability to catalyze the formation of sclareol from labdenediol diphosphate if the amount of sclareol produced from the reaction is at least or at least about 0.5%, 1%, 5%, 10%, 20%, 30%, 40%, 50%, 60%, 70%, 80%, 90% or more of the total amount of terpene produced in the reaction.

As used herein, sclareol is a diterpene having the following structure or isomers thereof:

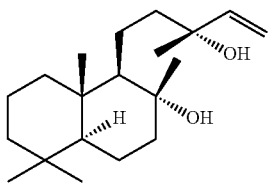

As used herein, "wild type" or "native" with reference to a labdenediol diphosphate synthase or sclareol synthase refers to a labdenediol diphosphate synthase polypeptide or sclareol synthase polypeptide encoded by a native or naturally occurring labdenediol diphosphate synthase gene or sclareol synthase gene, including allelic variants, that are present in an organism, including a plant, in nature. Reference to wild type labdenediol diphosphate synthase or sclareol synthase without reference to a species is intended to encompass any species of a wild type labdenediol diphosphate synthase or sclareol synthase.

As used herein, species variants refer to variants in polypeptides among different species, including different tobacco species, such *Nicotiana glutinosa* and *Nicotiana tabacum*. Generally, species variants share at least or at least about 70%, 75%, 80%, 85%, 90%, 91%, 92%, 93%, 94%, 95%, 96%, 97%, 98% or more sequence identity. Corresponding residues between and among species variants can be determined by comparing and aligning sequences to maximize the number of matching nucleotides or amino acid residues, for example, such that identity between the sequences is equal to or greater than 95%, equal to or greater than 96%, equal to or greater than 97%, equal to or greater than 98% or equal to greater than 99%. The position of interest is then given the number assigned in the reference nucleic acid molecule or polypeptide. Alignment can be effected manually or by eye, particularly, where sequence identity is greater than 80%. To determine sequence identity among a plurality of variants, alignments are effected one-by-one against the same reference polypeptide.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wild type form and/or predominant form of a polypeptide from a population or single reference member of a species. Typically, allelic variants, which include variants between and among species typically, have at least 80%, 90% or greater amino acid identity with a wild type and/or predominant form from the same species; the degree of identity depends upon the gene and whether comparison is interspecies or intraspecies. Generally, intraspecies allelic variants have at least about 80%, 85%, 90% or 95% identity or greater with a wild type and/or predominant form, including 96%, 97%, 98%, 99% or greater identity with a wild type and/or predominant form of a polypeptide. Reference to an allelic variant herein generally refers to variations n proteins among members of the same species.

As used herein, a splice variant refers to a variant produced by differential processing of a primary transcript of genomic DNA that results in more than one type of mRNA.

As used herein, a "modified labdenediol diphosphate synthase polypeptide" refers to a labdenediol diphosphate synthase polypeptide that has one or more amino acid differences compared to an unmodified or wild type labdenediol diphosphate synthase polypeptide. The one or more amino acid differences can be amino acid mutations such as one or more amino acid replacements (substitutions), insertions or deletions, or can be insertions or deletions or replacements of entire domains or portions thereof, and any combination thereof. Modification can be effected by any mutational protocol, including gene shuffling methods. Typically, a modified labdenediol diphosphate synthase polypeptide has one or more modifications in the primary sequence compared to an unmodified labdenediol diphosphate synthase polypeptide. For example, a modified labdenediol diphosphate synthase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified labdenediol diphosphate synthase polypeptide. Typically, the LPP will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one labdenediol diphosphate synthase activity associated with a wild type labdenediol diphosphate synthase polypeptide, such as, for example, catalytic activity, the ability to bind GGPP, and/or the ability to catalyze the formation of labdenediol diphosphate from GGPP. Generally, the resulting LPP enzyme will have at least 50% sequence identity with the wild type LPP provided herein.

As used herein, a "modified sclareol synthase polypeptide" refers to a sclareol synthase polypeptide that has one or more amino acid differences compared to an unmodified or wild type sclareol synthase polypeptide. The one or more amino acid differences can be amino acid mutations such as one or more amino acid replacements (substitutions), insertions or deletions, or can be insertions or deletions of entire domains, and any combination thereof. Typically, a sclareol synthase polypeptide has one or more modifications in the primary sequence compared to an unmodified sclareol synthase polypeptide. For example, a modified sclareol synthase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified sclareol synthase polypeptide. Typically, the sclareol synthase will have 1, 2, 3, 4, 5, 6, 7, 8, 9, 10, 11, 12, 13, 14 or 15 amino acid replacements, but can include more, particularly when domains or portions thereof are swapped. Any modification is contemplated as long as the resulting polypeptide has at least one sclareol synthase activity associated with a wild type sclareol synthase polypeptide, such as, for example, catalytic activity, the ability to bind to or interact with labdenediol diphosphate, and/or the ability to catalyze the formation of sclareol from labdenediol diphosphate. Generally, the resulting sclareol synthase will have at least 50% sequence identity with the wild type sclareol synthase provided herein.

As used herein, ambroxide is the compound having the following structure or a mixture of isomers thereof:

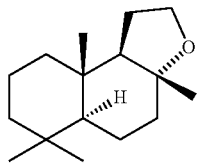

As used herein, corresponding residues refers to residues that occur at aligned loci. Related or variant polypeptides are aligned by any method known to those of skill in the art. Such methods typically maximize matches, and include methods such as manual alignments and those produced by the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. For example, corresponding residues between a *Nicotiana glutinosa* LPP synthase and *Arabidopsis thaliana* ent-copalyl diphosphate synthase are shown in FIGS. 3A-3B and corresponding residues between a *Nicotiana glutinosa* sclareol synthase and *Abies grandis* abietadiene synthase are shown in FIGS. 3C-3D.

As used herein, domain or region (typically a sequence of at least three or more, generally 5 or 7 or more amino acids) refers to a portion of a molecule, such as a protein or the encoding nucleic acids, that is structurally and/or functionally distinct from other portions of the molecule and is identifiable. A protein can have one, or more than one, distinct domains. For example, a domain can be identified, defined or distinguished by homology of the sequence therein to related family members, such as other terpene synthases. A domain can be a linear sequence of amino acids or a non-linear sequence of amino acids. Many polypeptides contain a plurality of domains. Such domains are known, and can be identified by, those of skill in the art. For exemplification herein, definitions are provided, but it is understood that it is well within the skill in the art to recognize particular domains by name. If needed, appropriate software can be employed to identify domains. For example, as discussed above, corresponding domains in different terpene synthases can be identified by sequence alignments, such as using tools and algorithms well known in the art (for example, BLASTP).

As used herein, a functional domain refers to those portions of a polypeptide that is recognized by virtue of a functional activity, such as catalytic activity. A functional domain can be distinguished by its function, such as by catalytic activity, or an ability to interact with a biomolecule, such as substrate binding or metal binding. In some examples, a domain independently can exhibit a biological function or property such that the domain independently or fused to another molecule can perform an activity, such as, for example catalytic activity or substrate binding.

As used herein, a structural domain refers to those portions of a polypeptide chain that can form an independently folded structure within a protein made up of one or more structural motifs.

As used herein, "heterologous" with respect to an amino acid or nucleic acid sequence refers to portions of a sequence that is not present in a native polypeptide or encoded by a polynucleotide. For example, a portion of amino acids of a polypeptide, such as a domain or region or portion thereof, for a sclareol synthase is heterologous thereto if such amino acids are not present in a native or wild type sclareol synthase (e.g. as set forth in SEQ ID NO:31), or encoded by the polynucleotide encoding therefor. Polypeptides containing such heterologous amino acids or polynucleotides encoding therefor are referred to as "chimeric polypeptides" or "chimeric polynucleotides," respectively.

As used herein, the phrase "a property of the modified terpene synthase is improved compared to the first terpene synthase" refers to a desirable change in a property of a modified terpene synthase compared to a terpene synthase that does not contain the modification(s). Typically, the property or properties are improved such that the amount of a desired terpene produced from the reaction of a substrate with the modified terpene synthase is increased compared to the amount of the desired terpene produced from the reaction of a substrate with a terpene synthase that is not so modified. Exemplary properties that can be improved in a modified terpene synthase include, for example, terpene production, catalytic activity, product distribution, substrate specificity, regioselectivity and stereoselectivity. One or more of the properties can be assessed using methods well known in the art to determine whether the property had been improved (i.e. has been altered to be more desirable for the production of a desired terpene or terpenes).

As used herein, terpene production (also referred to as terpene yield) refers to the amount (in weight or weight/volume) of terpene produced from the reaction of an acyclic pyrophosphate terpene precursor with a terpene synthase. Reference to total terpene production refers to the total amount of all terpenes produced from the reaction, while reference to specific terpene production refers to the amount of a specific terpene (e.g. labdenediol diphosphate or sclareol), produced from the reaction.

As used herein, an improved terpene production refers to an increase in the total amount of terpene (i.e. improved total terpene production) or an increase in the specific amount of terpene (i.e. improved specific terpene production) produced from the reaction of an acyclic pyrophosphate terpene precursor with a modified terpene synthase compared to the amount produced from the reaction of the same acyclic pyrophosphate terpene precursor with a terpene synthase that is not so modified. The amount of terpene (total or specific) produced from the reaction of an acyclic pyrophosphate terpene precursor with a modified terpene synthase can be increased by at least or at least about 1%, 3%, 5%, 10%, 15%, 20%, 30%, 40%, 50%, 60%, 70%, 80%, 90%, 100% or more compared to the amount of terpene produced from the reaction of the same acyclic pyrophosphate terpene precursor under the same conditions with a terpene synthase that is not so modified.

As used herein, substrate specificity refers to the preference of a synthase for one target substrate over another, such as one acyclic pyrophosphate terpene precursor (e.g. farnesyl-pyrophosphate (FPP), geranyl-pyrophosphate (GPP), or geranylgeranyl-pyrophosphate (GGPP)) over another. Substrate specificity can be assessed using methods well known in the art, such as those that calculate $k_{cat}/K_m$. For example, the substrate specificity can be assessed by comparing the relative $K_{cat}/K_m$, which is a measure of catalytic efficiency, of the enzyme against various substrates (e.g. GPP, FPP and GGPP).

As used herein, altered specificity refers to a change in substrate specificity of a modified terpene synthase polypeptide (such as a modified labdenediol diphosphate synthase polypeptide or sclareol synthase polypeptide) compared to a terpene synthase that is not so modified (such as, for example, a wild type labdenediol diphosphate synthase or sclareol synthase). The specificity (e.g. $k_{cat}/K_m$) of a modified terpene synthase polypeptide for a substrate, such as FPP, GPP, GGPP or labdenediol diphosphate, can be altered by at least or at least about 10%, 15%, 20%, 30%, 40%, 50%, 60%, 70%, 80%, 90%, 100% or more compared to the specificity of a starting labdenediol diphosphate synthase or sclareol synthase for the same substrate.

As used herein, improved substrate specificity refers to a change or alteration in the substrate specificity to a more desired specificity. For example, an improved substrate specificity can include an increase in substrate specificity of a modified terpene synthase polypeptide for a desired substrate, such as FPP, GPP or GGPP. The specificity (e.g. $k_{cat}/K_m$) of a modified terpene synthase polypeptide for a substrate, such as FPP, GPP or GGPP, can be increased by at least or at least about 10%, 15%, 20%, 30%, 40%, 50%, 60%, 70%, 80%, 90%, 100% or more compared to the specificity of a terpene synthase that is not so modified.

As used herein, "product distribution" refers to the relative amounts of different terpenes produced from the reaction between an acyclic pyrophosphate terpene precursor, such as GGPP, and a terpene synthase, including the modified labdenediol diphosphate synthase polypeptides provided herein. The amount of a produced terpene can be depicted as a percentage of the total products produced by the terpene synthase. For example, the product distribution resulting from reaction of GGPP with a labdenediol diphosphate synthase can be 90% (weight/volume) labdenediol diphosphate and 10% (weight/volume) manoyl oxides. Methods for assessing the type and amount of a terpene in a solution are well known in the art and described herein, and include, for example, gas chromatography-mass spectrometry (GC-MS) (see Examples below).

As used herein, an altered product distribution refers to a change in the relative amount of individual terpenes produced from the reaction between an acyclic pyrophosphate terpene precursor, such as GGPP, and a terpene synthase, such as labdenediol diphosphate synthase. Typically, the change is assessed by determining the relative amount of individual terpenes produced from the acyclic pyrophosphate terpene precursor using a first synthase (e.g. wild type synthase) and then comparing it to the relative amount of individual terpenes produced using a second synthase (e.g. a modified synthase). An altered product distribution is considered to occur if the relative amount of any one or more terpenes is increased or decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, an improved product distribution refers to a change in the product distribution to one that is more desirable, i.e. contains more desirable relative amounts of terpenes. For example, an improved product distribution can contain an increased amount of a desired terpene and/or a decreased amount of a terpene that is not so desired. The amount of desired terpene in an improved production distribution can be increased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more. The amount of a terpene that is not desired in an improved production distribution can be decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, nucleic acids or nucleic acid molecules include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, heterologous nucleic acid is nucleic acid that is not normally produced in vivo by the cell in which it is expressed or that is produced by the cell but is at a different locus or expressed differently or that mediates or encodes mediators that alter expression of endogenous nucleic acid, such as DNA, by affecting transcription, translation, or other regulatable biochemical processes. Heterologous nucleic acid is generally not endogenous to the cell into which it is introduced, but has been obtained from another cell or prepared synthetically. Heterologous nucleic acid can be endogenous, but is nucleic acid that is expressed from a different locus or altered in its expression. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, is found in a genome. It also can refer to a nucleic acid molecule from another organism or species (i.e., exogenous).

Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a peptide refers to a polypeptide that is from 2 to 40 amino acids in length.

As used herein, the amino acids that occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

In keeping with standard polypeptide nomenclature described in *J. Biol. Chem.*, 243: 3557-3559 (1969), and adopted 37 C.F.R. §§1.821-1.822, abbreviations for the amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the naturally-occurring amino acids and include, but are not limited to, the D-isostereomers of amino acids. Exemplary non-natural amino acids are known to those of skill in the art and can be included in a modified labdenediol diphosphate synthase polypeptides or sclareol synthase polypeptides provided herein.

As used herein, modification is in reference to modification of the primary sequence of amino acids of a polypeptide or a sequence of nucleotides in a nucleic acid molecule and includes deletions, insertions, and replacements and rearrangements of amino acids and nucleotides. For purposes herein, amino acid replacements (or substitutions), deletions and/or insertions, can be made in any of the labdenediol diphosphate synthases or sclareol synthases provided herein. Modifications can be made by making conservative amino acid replacements and also non-conservative amino acid substitutions as well as by insertions, domain swaps and other such changes in primary sequence. For example, amino acid replacements that desirably or advantageously alter properties of the labdenediol diphosphate synthase or sclareol synthase can be made. For example, amino acid replacements can be made to the labdenediol diphosphate synthase such that the resulting modified labdenediol diphosphate synthase can produce more labdenediol diphosphate from GGPP compared to an unmodified labdenediol diphosphate synthase. For example, amino acid replacements can be made to the sclareol synthase such that the resulting sclareol synthase can produce more sclareol from labdenediol diphosphate compared to an unmodified sclareol synthase. Modifications also can include post-translational modifications or other changes to the molecule that can occur due to conjugation or linkage, directly or indirectly, to another moiety, but when such modifications are contemplated they are referred to as post-translational modifications or conjugates or other such term as appropriate. Methods of modifying a polypeptide are routine to those of skill in the art, and can be performed by standard methods, such as site directed mutations, amplification methods, and gene shuffling methods.

As used herein, amino acid replacements or substitutions contemplated include, but are not limited to, conservative substitutions, including, but not limited to, those set forth in Table 2. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224). Conservative amino acid substitutions are made, for example, in accordance with those set forth in Table 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |

TABLE 2-continued

| Original residue | Conservative substitution |
| --- | --- |
| Ser (S) | Thr |
| Thr (T) | Ser |
| Trp (W) | Tyr |
| Tyr (Y) | Trp; Phe |
| Val (V) | Ile; Leu; Met |

Other conservative substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, "at a position corresponding to" or recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. For purposes herein, alignment of a labdenediol diphosphate synthase sequence is to the amino acid sequence set forth in any of SEQ ID NOS:2, 4, 6, 8, 10, 12, 14 or 54, and in particular SEQ ID NO:54. For purposes herein, alignment of a sclareol synthase sequence is to the amino acid sequence set forth in any of SEQ ID NOS:31, 36, 38, 40 or 78, and in particular SEQ ID NO:31. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). FIGS. 6A-6J exemplify exemplary alignments and identification of exemplary corresponding residues for replacement.

As used herein, "sequence identity" refers to the number of identical or similar amino acids or nucleotide bases in a comparison between a test and a reference poly-peptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence× 100. When using gap penalties, sequence identity can be determined with no penalty for end gaps (e.g. terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. (1970) *J. Mol. Biol.* 48: 443). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequence, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2:482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier or manually. Default parameters for the GAP program can include: (1) a unary comparison matrix (containing a value of 1 for identities and 0 for non identities) and the weighted comparison matrix of Gribskov et al. (1986) *Nucl. Acids Res.* 14:6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (Adv. Appl. Math. (1991) 12:337-357)); and program from Xiaoqui Huang available at deepc2.psi.iastate.edu/aat/align/align.html. Generally, when comparing nucleotide sequences herein, an alignment with penalty for end gaps is used. Local alignment also can be used when the sequences being compared are substantially the same length.

As used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polypeptide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result reasonably independent of the program and gap parameters set; such high levels of identity can be assessed readily, often without relying on software.

As used herein, the terms "substantially identical" or "similar" varies with the context as understood by those skilled in the relevant art, but that those of skill can assess such.

As used herein, an aligned sequence refers to the use of homology (similarity and/or identity) to align corresponding positions in a sequence of nucleotides or amino acids. Typically, two or more sequences that are related by about or 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, substantially free of cellular material includes preparations of labdenediol diphosphate synthase, sclareol synthase or terpene products in which the labdenediol diphosphate synthase, sclareol synthase or terpene product is separated from cellular components of the cells from which it is isolated or produced. In one embodiment, the term substantially free of cellular material includes preparations of labdenediol diphosphate synthase, sclareol synthase or terpene products having less that about or less than 30%, 20%, 10%, 5% or less (by dry weight) of non-labdenediol synthase, non-sclareol synthase or terpene proteins or products, including cell culture medium. When the synthase is recombinantly produced, it also is substantially free of culture medium, i.e., culture medium represents less than about or at 20%, 10% or 5% of the volume of the synthase protein preparation.

As used herein, the term substantially free of chemical precursors or other chemicals includes preparations of synthase proteins in which the protein is separated from chemical precursors or other chemicals that are involved in the synthesis of the protein. The term includes preparations of synthase proteins having less than about or less than 30% (by dry weight), 20%, 10%, 5% or less of chemical precursors or non-synthase chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors.

As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, a "chimeric protein" or "fusion protein" refers to a polypeptide operatively-linked to a different polypeptide. For example, a polypeptide encoded by a nucleic acid sequence containing a coding sequence from one nucleic acid molecule and the coding sequence from another nucleic acid molecule in which the coding sequences are in the same reading frame such that when the fusion construct is transcribed and translated in a host cell, the protein is produced containing the two proteins. The two molecules can be adjacent in the construct or separated by a linker polypeptide that contains, 1, 2, 3, or more, but typically fewer than 10, 9, 8, 7, or 6 amino acids. The protein product encoded by a fusion construct is referred to as a fusion polypeptide. A chimeric or fusion protein provided herein can include one or more labdenediol diphosphate synthase polypeptides, or a portion thereof, and/or one or more sclareol synthase polypeptides, or a portion thereof, and/or one or more other polypeptides for any one or more of a transcriptional/translational control signals, signal sequences, a tag for localization, a tag for purification, part of a domain of an immunoglobulin G, and/or a targeting agent. A chimeric labdenediol diphosphate synthase polypeptide or sclareol synthase polypeptide also includes those having their endogenous domains or regions of the polypeptide exchanged with another polypeptide. These chimeric or fusion proteins include those produced by recombinant means as fusion proteins, those produced by chemical means, such as by chemical coupling, through, for example, coupling to sulfhydryl groups, and those produced by any other method whereby at least one polypeptide (i.e. labdenediol diphosphate synthase and/or sclareol synthase), or a portion thereof, is linked, directly or indirectly via linker(s) to another polypeptide.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, recitation that a polypeptide "consists essentially" of a recited sequence of amino acids means that only the recited portion, or a fragment thereof, of the full-length polypeptide is present. The polypeptide can optionally, and generally will, include additional amino acids from another source or can be inserted into another polypeptide As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where said event or circumstance occurs and instances where it does not. For example, an optional step of isolating labdenediol diphosphate means that the labdenediol diphosphate is isolated or is not isolated, or, an optional stop of isolating sclareol means that the sclareol is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. PATHWAYS AND PRODUCTS—OVERVIEW

Plant extracts provide valuable sources of oils for perfumes, biofuels and other such products. Generally the price and availability of plant natural extracts depends on the abundance, oil yield and geographical location of the plants. In addition, the availability and quality of natural extracts depends on climate and other local conditions leading to variability from year to year, rendering the use of such ingredients in high quality perfumery very difficult or even impossible some years. Sclareol is one such product. Sclareol is a starting material for the synthesis of fragrance molecules with ambergris notes. Ambergris is a waxy substance secreted by the intestines of sperm whale that is used as a perfume ingredient due to its pleasant odor. Due to its high price and increasing demand for ambergris, in combination with the protection of whale species, chemical syntheses of ambergris and ambergris-like fragrance molecules have been developed. One such molecule is (−)-ambroxide (1,5,5,9-tetra-13-oxatricyclo[8.3.0.0$^{4,9}$]tridecane; (3aR,5aS,9aS,9bR)-3a,6,6,9a-tetramethyl-2,4,5,5a,7,8,9,9b-octahydro-1H-benzo[e][1]benzofuran) which is widely used as a substitute for ambergris.

Although chemical approaches have been taken to generate sclareol, its highly complex structure renders economic synthetic process for its preparation in large quantities unattainable. There remains a need for efficient, cost-effective syntheses of sclareol, and additionally (−)-ambroxide. Thus, provided herein are LPP and sclareol synthases from *Nicotiana glutinosa*, and variants and modified forms thereof, for production of sclareol from GGPP. Also provided herein are methods of making sclareol from GGPP using the provided LPP and sclareol synthases. Also provided herein are methods of making (−)-ambroxide from either (1) geranylgeranyl diphosphate and/or (2) sclareol. The provided LPP and sclareol synthases provide for production of these valuable products, including sclareol and (−)-ambroxide in commercially useful quantities and in a cost effective and energy efficient manner.

Pathway

Provided herein are synthases sclareol synthase and LPP synthase that together in a two step reaction catalyze the production of sclareol from GGPP. LPP synthase catalyzes production of LPP from GGPP, and sclareol synthase catalyzes the production of sclareol from LPP. Sclareol then can be converted into ambroxide via various chemical conversions, including but not limited to 1) oxidative degradation followed by reduction and cyclization (see FIG. 2A); and 2) biochemical conversion to sclareolide followed by reduction and cyclization (see FIG. 2B).

Sclareol ((−)-(13R)-14-labdene-8α,13-diol) is a diterpene that occurs in plants, including in the foliage of the tobacco plant *Nicotiana glutinosa*, flowerheads of clary sage (*Salvia sclarea*), *Astragalus brachystachys, Cistus labdaniferus, Cupressu sempervivens* and *Nicotiana tabacum* (see, e.g., Banthorpe et al. (1990) *Phytochemistry* 29:2145-2148 and Banthorpe et al. (1992) *Phytochemistry* 31:3391-3395). Sclareol is produced biosynthetically in a two step process from GGPP (see FIGS. 1A-1C). In the first step, the class II diterpene synthase labdenediol diphosphate (LPP) synthase catalyzes production of labdenediol diphosphate (LPP) from GGPP, and in the second step, the class I diterpene synthase sclareol synthase catalyzes production of sclareol from labdenediol diphosphate. Sclareol also can be generated non-catalytically from labdenediol diphosphate by acid rearrangement under acidic conditions. Diterpene synthases labdenediol diphosphate synthase and sclareol synthase are described in further detail herein below.

Diterpene Synthases

Diterpene synthases are among terpene synthases which are classified based upon the terpene products whose production they catalyze. Diterpene synthases contain an element that is conserved in sequence and position among almost all diterpene synthase regardless of cyclization mechanisms (see, e.g., Bohlmann et al., (1998) *Proc. Natl. Acad. Sci. USA* 95:4126-4133; Mau et al. (1994) *Proc Natl Acad Sci USA* 91:8497-8501). Because of this element diterpene synthases contain about 210 more amino acids than monoterpene synthases. In plants, diterpene synthases occur in plastids. Transport between compartments is controlled by a transport mechanism that recognizes a N-terminal transit peptide signal. Thus, diterpene synthases are generally expressed as pre-proteins and are processed in the plastids by cleavage of the peptide signal, resulting in the mature protein.

1. Labdenediol Diphosphate (LPP) Synthase

Figure 1B:
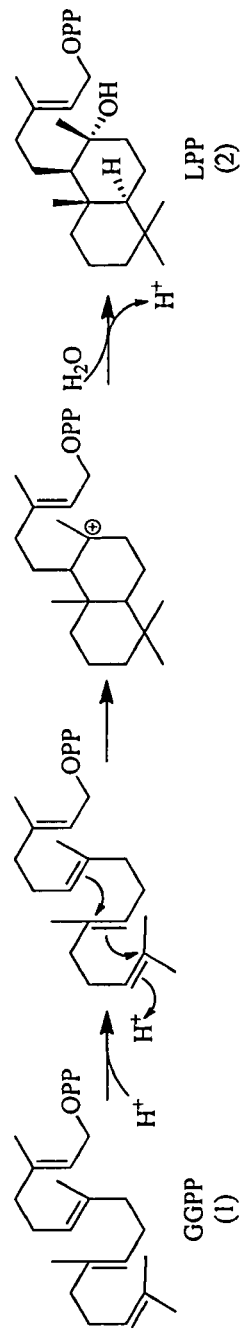
FIG. 1B illustrates the conversion of GGPP to LPP by LPP synthase.

Labdenediol diphosphate synthases are class II plant terpene cyclases, or terpene synthases, isoprenoid synthases or terpene cyclases, which convert geranylgeranyl diphosphate (GGPP) into the diterpene labdenediol diphosphate (see FIG. 1B). Labdenediol diphosphate then can be converted to sclareol by the class I plant terpene cyclase sclareol synthase. LPP synthases have been isolated from flower buds of the clary sage (*Salvia sclarea*) (SEQ ID NOS:57-59) (see, International PCT application Nos. WO2009/044336, WO2009/095366 and WO2009/101126). The LPP synthases provided herein possess less than 50% sequence homology with the LPP synthase from clary sage. For example, the LPP synthase exemplified herein (SEQ ID NO: 10) possesses only 44% sequence identity to the LPP synthase from clary sage (SEQ ID NO:58). Alignments of *S. sclarea* and *N. glutinosa* labdenediol diphosphate synthases are shown in FIGS. 4A-4C.

a. Structure

Class II diterpene cyclases include a diverse group of terpene synthases that share a common modular assembly of three α-helical domains (Köksal et al. (2011) *Nat. Chem. Biol.* 7(7):431-433). Although diverse in sequence, class II terpene cyclases have homologous structures and highly conserved motifs and/or residues. In its catalytic site, each terpene cyclase provides a template that binds the flexible isoprenoid substrate with an orientation and conformation such that upon cyclization, a specific intramolecular carbon-carbon bond is formed. The structure of each enzyme's catalytic site dictates the resulting cyclic monoterpenes, sesquiterpenes and diterpenes. Class II terpenoid cyclases initiate carbocation formation by acid catalysis using an aspartic acid of the DxDD motif (SEQ ID NO:103) to protonate an isoprenoid double bond.

X-ray crystal structure of ent-copalyl diphosphate synthase (Köksal et al. (2011) *Nat. Chem. Biol.* 7(7):431-433) reveals that class II diterpene synthases contain three α-helical domains, including the α domain, β domain and γ domain. The γ domain is inserted into the β domain, thus splitting the β domain into the β1 and β2 domains. The C-terminal catalytic domain, or α domain, has a class I terpenoid cyclase fold that lacks the class I active site motifs, while the N-terminal domain, or β domain, and the insertion domain, or γ domain, adopt a double α-barrel class II terpenoid synthase fold. The class II active site DxDD motif (SEQ ID NO:103) is located in the β domain. The active site is located in a deep cavity at the βγ interface and is generally hydrophobic being lined by numerous aliphatic and aromatic residues.

Amino acids 537-801 of SEQ ID NO:31 form the C-terminal α domain of *N. glutinosa* labdenediol diphosphate synthase. Amino acids 111-326 are part of the γ domain, or insertion domain, which are inserted into the β domain, set forth in amino acids 88-110 and 327-536 of SEQ ID NO:31. The active site DXDDTXM motif (SEQ ID NO:79) is located in the β2 domain, in Loop 14 and Helix N. The structural domains are as follows: Helix A, amino acids 89-103 of SEQ ID NO:2; Loop 1, amino acids 104-113 of SEQ ID NO:2; Helix B, amino acids 114-121 of SEQ ID NO:2; Loop 2, amino acids 122-138 of SEQ ID NO:2; Helix C, amino acids 139-146 of SEQ ID NO:2; Loop 3, amino acids 147-161 of SEQ ID NO:2; Helix D, amino acids 162-177 of SEQ ID NO:2; Loop 4, amino acids 178-182 of SEQ ID NO:2; Helix E, amino acids 183-200 of SEQ ID NO:2; Loop 5, amino acids 201-211 of SEQ ID NO:2; Helix F1, amino acids 212-225 of SEQ ID NO:2; Loop 7, amino acids 226-239 of SEQ ID NO:2; Helix G, amino acids 240-248 of SEQ ID NO:2; Loop 8, amino acids 249-252 of SEQ ID NO:2; Helix H, amino acids 253-256 of SEQ ID NO:2; Loop 9, amino acids 257-275 of SEQ ID NO:2; Helix I, amino acids 276-281 of SEQ ID NO:2; Loop 10, amino acids 282-292 of SEQ ID NO:2; Helix J, amino acids 293-302 of SEQ ID NO:2; Loop 11, amino acids 303-306 of SEQ ID NO:2; Helix K, amino acids 307-318 of SEQ ID NO:2; Loop 12, amino acids 319-328 of SEQ ID NO:2; Helix L, amino acids 329-343 of SEQ ID NO:2; Loop 13, amino acids 344-349 of SEQ ID NO:2; Helix M, amino acids 350-363 of SEQ ID NO:2; Loop 14, amino acids 364-380 of SEQ ID NO:2; Helix N, amino acids 381-394 of SEQ ID NO:2; Loop 15, amino acids 395-422 of SEQ ID NO:2; Helix O, amino acids 423-433 of SEQ ID NO:2; Loop 16, amino acids 434-441 of SEQ ID NO:2; Helix P, amino acids 442-460 of SEQ ID NO:2; Loop 17, amino acids 461-472 of SEQ ID NO:2; Helix Q, amino acids 473-482 of SEQ ID NO:2; Loop 18, amino acids 483-489 of SEQ ID NO:2; Helix R, amino acids 490-498 of SEQ ID NO:2; Loop 19, amino acids 499-522 of SEQ ID NO:2; Helix S, amino acids 523-551 of SEQ ID NO:2; Loop 20, amino acids 552-561 of SEQ ID NO:2; Helix T, amino acids 562-575 of SEQ ID NO:2; Loop 21, amino acids of 576-581 SEQ ID NO:2; Helix U, amino acids 582-600 of SEQ ID NO:2; Loop 22, amino acids 601-613 of SEQ ID NO:2; Helix V, amino acids 614-623 of SEQ ID NO:2; Loop 23, amino acids 624-633 of SEQ ID NO:2; Helix W, amino acids 634-654 of SEQ ID NO:2; Loop 24, amino acids 655-661 of SEQ ID NO:2; Helix X, amino acids 662-675 of SEQ ID NO:2; Loop 25, amino acids 676-678 of SEQ ID NO:2; Helix Y, amino acids 679-686 of SEQ ID NO:2; Loop 26, amino acids 687-709 of SEQ ID NO:2; Helix Z1, amino acids 710-730 of SEQ ID NO:2; Loop 28, amino acids 731-737 of SEQ ID NO:2; Helix AA, amino acids 738-754 of SEQ ID NO:2; Loop 29, amino acids 755-764 of SEQ ID NO:2; Helix AB, amino acids 765-782 of SEQ ID NO:2; Loop 30, amino acids 783-788 of SEQ ID NO:2; Helix AC, amino acids 789-796 of SEQ ID NO:2 and Loop 31, amino acids 797-801 of SEQ ID NO:2.

b. Activity

Figure 1C:
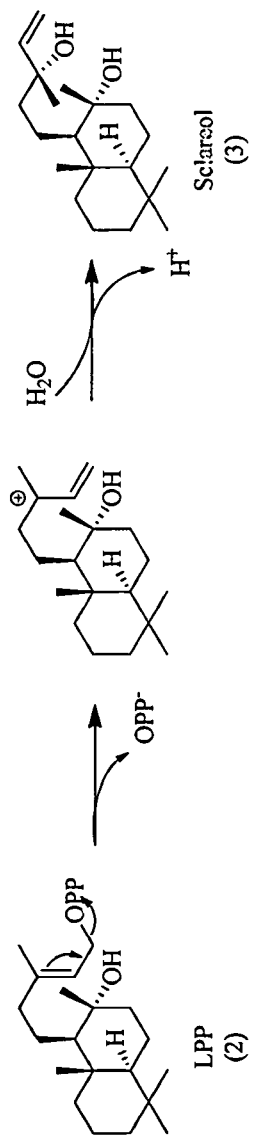
FIG. 1C illustrates the conversion of LPP to sclareol by sclareol synthase.

Labdenediol diphosphate synthase catalyzes the formation of labdenediol diphosphate (13-E)-labda-13-ene-8α,15-diol) from geranylgeranyl diphosphate by protonating the terminal bond of GGPP, leading to internal rearrangement and proton elimination, thereby yielding labdenediol diphosphate (see FIG. 1C).

2. Sclareol Synthase

Sclareol synthase can catalyze conversion of LPP to sclareol. Sclareol synthases or sclareol cyclases are class 1 plant terpene cyclases, or terpene synthases, isoprenoid synthases or terpenoid cyclases that catalyze conversion of labdenediol diphosphate into the diterpene sclareol (see FIG. 1C). Sclareol has been identified in the foliage of the tobacco plant *Nicotiana glutinosa* and in flowerheads of clary sage (*Salvia sclarea*). Sclareol synthases have been isolated from flowers of the clary sage (*Salvia sclarea*) (SEQ ID NOS:60-62) (see, e.g., International PCT application Nos. WO2009/044336, WO2009/095366 and WO2009/101126). The sclareol synthases provided herein possess less than 50% sequence homology with the sclareol synthases from clary sage. For example, the sclareol synthase exemplified herein in SEQ ID NO:40 shares only 32 percent homology with the sclareol synthase from clary sage (SEQ ID NO:60). Alignments of *S. sclarea* and *N. glutinosa* sclareol synthases are shown in FIGS. 4D-4F.

a. Structure

Class I plant terpene cyclases include a diverse group of monomeric terpene synthases that share a common alpha helical architecture termed the class 1 terpenoid cyclase fold (see, e.g., Köksal et al. (2011) *Nature* 469:116-120; Zhou et al. (2012) *J. Biol. Chem.* 287:6840-6850). Class I plant terpene cyclases share homologous structures and some highly conserved motifs and/or residues. Class I terpenoid cyclases use a trinuclear metal, e.g. $Mg^{2+}$, cluster, bound to conserved metal binding motifs DDxxD (SEQ ID NO:80) and [N/D]xxx[S/T]xxxE (NTE motif; SEQ ID NO:99) to trigger ionization of the isoprenoid substrate diphosphate group, which generates a carbocation to initiate catalysis.

X-ray crystal structures of diterpene cyclases taxadiene synthase and abietadiene synthase (Köksal et al. (2011) *Nature* 469:116-120; Zhou et al. (2012) *J. Biol. Chem.* 287: 6840-6850) reveal that these enzymes contain three α-helical domains, including the α domain, β domain and γ domain. The γ domain is inserted into the β domain, thus splitting the β domain into the β1 and β2 domains. The C-terminal catalytic domain, or α domain, is a class I terpenoid cyclase containing a three-metal ion cluster while the N-terminal domain, or β domain, and the insertion domain, or γ domain, adopt a double α-barrel class II terpenoid synthase fold that lacks the class II active site motif. The class I active site aspartic acid motifs DDXXD (SEQ ID NO:80) and (N/D)DXX(S/T)XXXE (NTE motif; SEQ ID NO:101) are located in the α domain.

Amino acids 477-788 of SEQ ID NO:36 form the C-terminal α domain of *N. glutinosa* sclareol synthase. Amino acids 63-278 form the γ, or insertion, domain, which is inserted into the β domain, set forth in amino acids 107-135 and 349-552 of SEQ ID NO:36. The DDXXD motif (539-DDFFD-543 of SEQ ID NO:36) and the NTE motif (684-NDIHSYKRE-692 of SEQ ID NO:26) of sclareol synthase are located in the α domain, in Helix V (DDXXD motif) and Helix AC and Loop 30 (NTE motif). Sclareol synthase contains the following structural domains: Loop 1, amino acids 40-41 of SEQ ID NO:36; Helix A, amino acids 42-54 of SEQ ID NO:36; Loop 2, amino acids 55-65 of SEQ ID NO:36; Helix B, amino acids 66-73 of SEQ ID NO:36; Loop 3, amino acids 74-87 of SEQ ID NO:36; Helix C, amino acids 88-95 of SEQ ID NO:36; Loop 4, amino acids 96-112 of SEQ ID NO:36; Helix D, amino acids 113-129 of SEQ ID NO:36; Loop 5, amino acids 130-133 of SEQ ID NO:36; Helix E, amino acids 134-148 of SEQ ID NO:36; Loop 6, amino acids 149-161 of SEQ ID NO:36; Helix F, amino acids 162-176 of SEQ ID NO:36; Loop 7, amino acids 177-184 of SEQ ID NO:36; Helix G, amino acids 185-199 of SEQ ID NO:36; Loop 8, amino acids 200-202 of SEQ ID NO:36; Helix H, amino acids 203-207 of SEQ ID NO:36; Loop 9, amino acids 208-225 of SEQ ID NO:36; Helix I, amino acids 226-230 of SEQ ID NO:36; Loop 10, amino acids 231-242 of SEQ ID NO:36; Helix J, amino acids 243-251 of SEQ ID NO:36; Loop 11, amino acids 242-257 of SEQ ID NO:36; Helix K, amino acids 258-270 of SEQ ID NO:36; Loop 12, amino acids 271-280 of SEQ ID NO:36; Helix L, amino acids 281-295 of SEQ ID NO:36; Loop 13, amino acids 296-301 of SEQ ID NO:36; Helix M, amino acids 302-315 of SEQ ID NO:36; Loop 14, amino acids 316-326 of SEQ ID NO:36; Helix N, amino acids 327-339 of SEQ ID NO:36; Loop 15, amino acids 340-346 of SEQ ID NO:36; Helix O, amino acids 347-351 of SEQ ID NO:36; Loop 16, amino acids 352-368 of SEQ ID NO:36; Helix P, amino acids 369-379 of SEQ ID NO:36; Loop 17, amino acids 380-389 of SEQ ID NO:36; Helix Q, amino acids 390-406 of SEQ ID NO:36; Loop 18, amino acids 407-414 of SEQ ID NO:36; Helix R, amino acids 415-424 of SEQ ID NO:36, amino acids 425-430 of SEQ ID NO:36; Loop 19, amino acids 431-441 of SEQ ID NO:36; Helix S, amino acids 442-462 of SEQ ID NO:36; Loop 20, amino acids 463-491 of SEQ ID NO:36; Helix T, amino acids 492-501 of SEQ ID NO:36; Loop 21; Helix U, amino acids 505-513 of SEQ ID NO:36; Loop 22, amino acids 514-521 of SEQ ID NO:36; Helix V, amino acids 522-543 of SEQ ID NO:36; Loop 23, amino acids 544-547 of SEQ ID NO:36; Helix W, amino acids 548-560 of SEQ ID NO:36; Loop 24, amino acids 561-571 of SEQ ID NO:36; Helix X, amino acids 572-596 of SEQ ID NO:36; Loop 25, amino acids 579-600 of SEQ ID NO:36; Helix Y, amino acids 601-619 of SEQ ID NO:36; Loop 26, amino acids 620-630 of SEQ ID NO:36; Helix Z, amino acids 631-641 of SEQ ID NO:36; Loop 27, amino acids 642-644 of SEQ ID NO:36; Helix AA, amino acids 645-652 of SEQ ID NO:36; Loop 28, amino acids 653-660 of SEQ ID NO:36; Helix AB, amino acids 661-664 of SEQ ID NO:36; Loop 29, amino acids 665-670 of SEQ ID NO:36; Helix AC, amino acids 671-685 of SEQ ID NO:36; Loop 30, amino acids 686-688 of SEQ ID NO:36; Helix AD, amino acids 689-692 of SEQ ID NO:36; Loop 31, amino acids 693-700 of SEQ ID NO:36; Helix AE, amino acids 701-708 of SEQ ID NO:36; Loop 32, amino acids 709-713 of SEQ ID NO:36; Helix AF, amino acids 714-738 of SEQ ID NO:36; Loop 33, amino acids 739-746 of SEQ ID NO:36; Helix AG, amino acids 747-762 of SEQ ID NO:36; Loop 34, amino acids 763-774 of SEQ ID NO:36; Helix AH, amino acids 775-785 of SEQ ID NO:36; and Loop 35, amino acids 783-788 of SEQ ID NO:36.

b. Activity

Sclareol synthases catalyzes the formation of sclareol ((−)-(13R)-14-labdene-8α,13-diol) from labdenediol diphosphate (13-E)-labda-13-ene-8α,15-diol) by catalyzing the ionization of the diphosphate ester functional group of LPP followed by the reaction of the carbocation with an internal double bond (see FIG. 1C).

3. (−)-Ambroxide

Figure 2A:
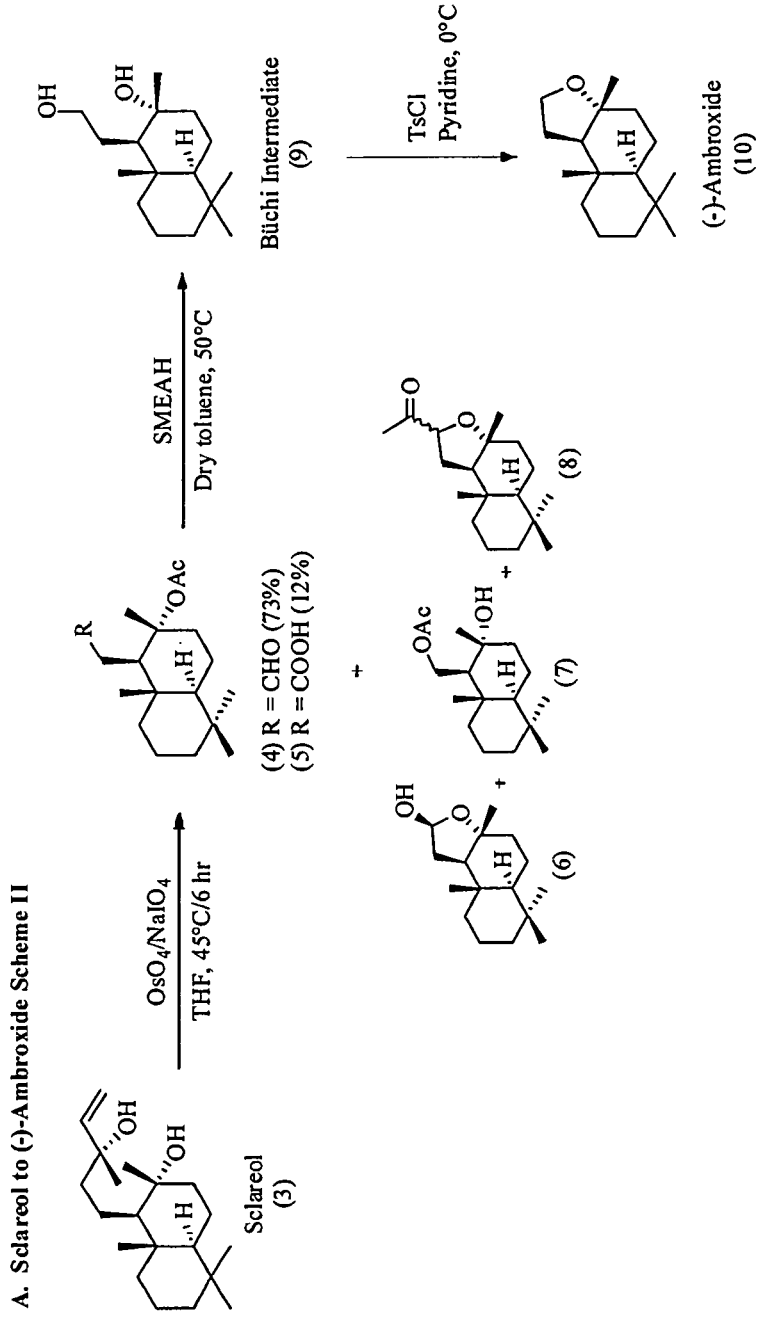
FIGS. 2A-2C depict pathways for the conversion of sclareol to (−)-ambroxide and geranylgeranyl diphosphate (GGPP) to (−)-ambroxide. For example.
Figure 2B:
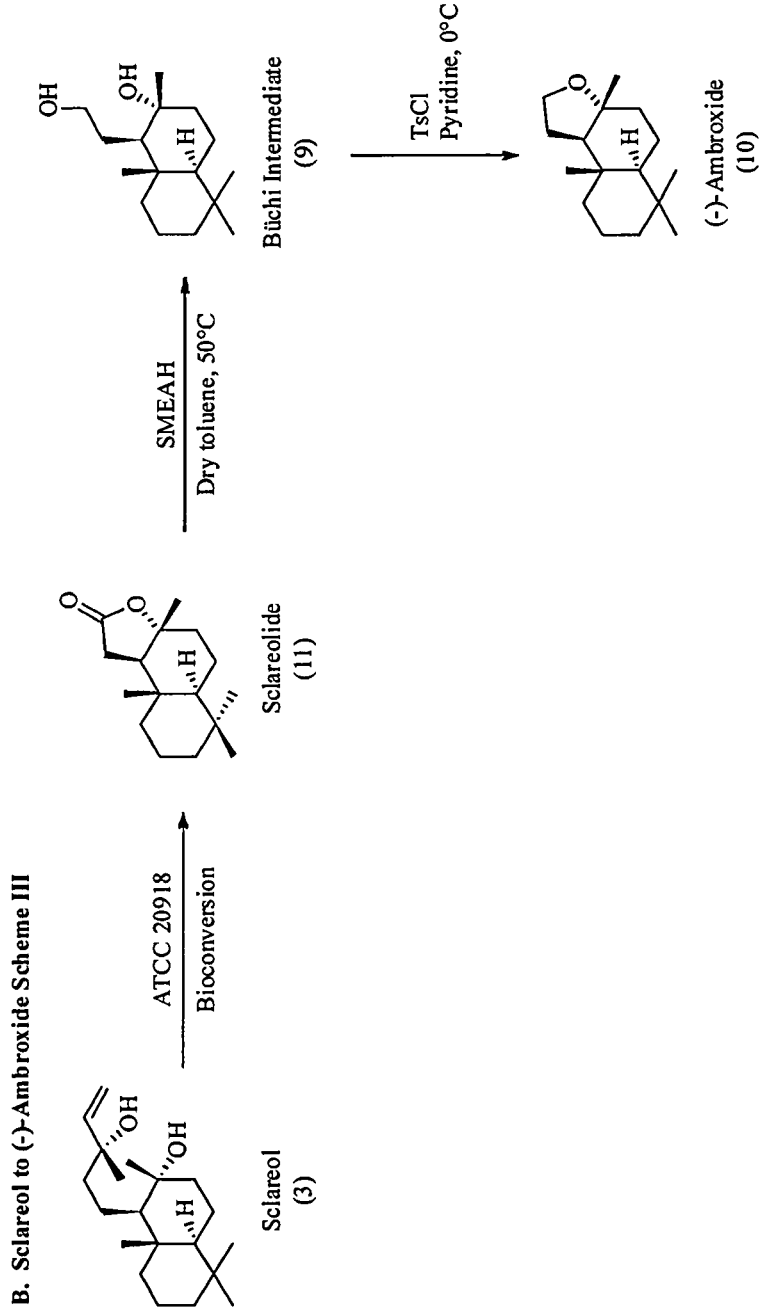
Figure 2C:
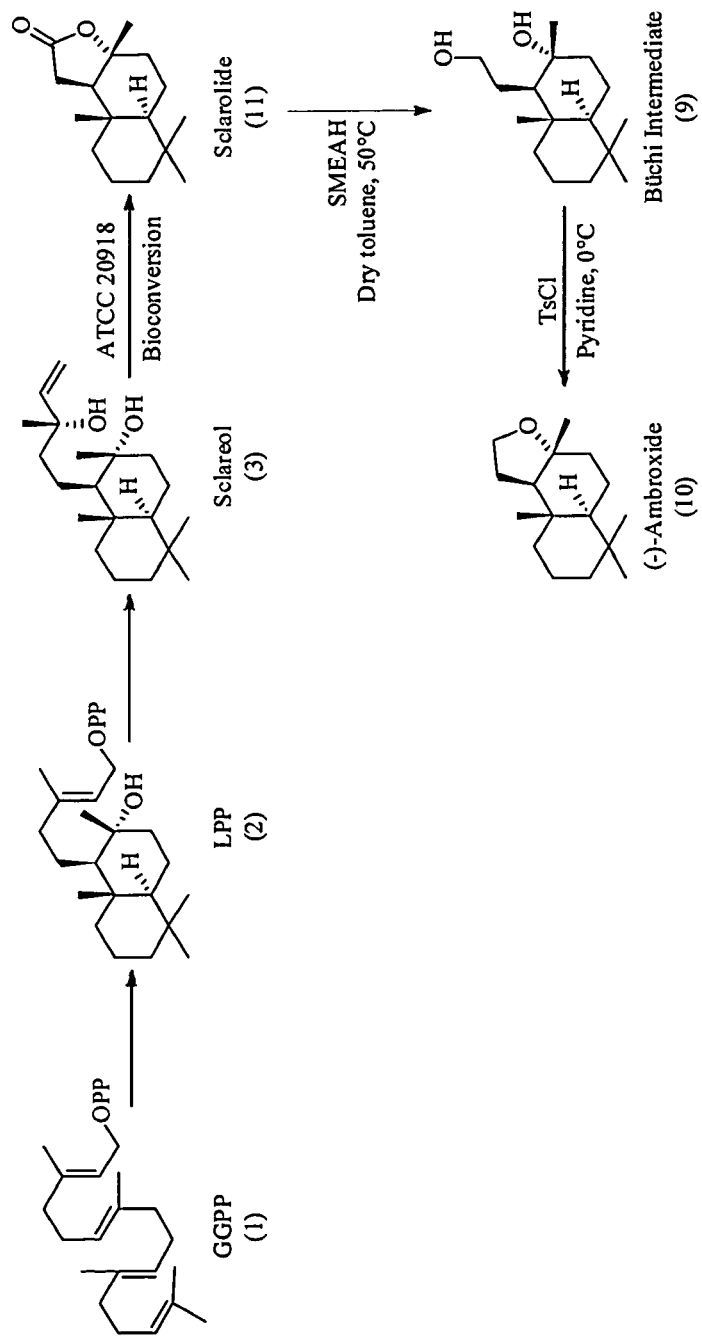

Sclareol can be converted to (−)-ambroxide through various chemical conversions (see FIGS. 2A-2C and Example 12). In one example, sclareol is subjected to oxidative degradation followed by reduction and cyclization thus forming (−)-ambroxide (e.g. see FIG. 2A, Scheme II; and Barrero et al. (1993) *Tetrahedron* 49(45): 10405-10412; Barrero et al., (2004) *Synthetic Communications* 34(19):3631-3643). In another example, sclareol is biochemically converted to sclareolide by the organism *Cryptococcus magnus* ATCC 20918. Subsequent reduction of sclareolide and cyclization results in the formation of (−)-ambroxide (see FIG. 2B, Scheme III). Alternatively, (−)-ambroxide is generated from geranylgeranyl diphosphate as shown in FIG. 2C, Scheme IV.

C. LABDENEDIOL DIPHOSPHATE (LPP) SYNTHASE AND SCLAREOL SYNTHASE POLYPEPTIDES AND ENCODING NUCLEIC ACID MOLECULES

Provided herein are labdenediol diphosphate (LPP) synthase polypeptides. Also provided herein are nucleic acid molecules that encode any of the LPP synthase polypeptides provided herein. The labdenediol diphosphate synthase polypeptides provided herein catalyze the formation of labdenediol diphosphate and/or other terpenes from any suitable acyclic pyrophosphate terpene precursor, including, but not limited to FPP, GPP and GGPP. Of interest herein is the production of LPP from GGPP. In some examples, the nucleic acid molecules that encode the LPP synthase polypeptides are those that are the same as those that are isolated from the tobacco plant *Nicotiana glutinosa*. In other examples, the nucleic acid molecules and encoded LPP synthase polypeptides are variants of those isolated from the tobacco plant *Nicotiana glutinosa*.

Also provided herein are modified labdenediol diphosphate synthase polypeptides and nucleic acid molecules that encode any of the modified LPP synthase polypeptides provided herein. The modifications can be made in any region of a labdenediol diphosphate synthase provided the resulting modified LPP synthase polypeptide at least retains labdenediol diphosphate synthase activity (i.e. the ability to catalyze the formation of labdenediol diphosphate synthase from an acyclic pyrophosphate terpene precursor, typically GGPP).

The modifications can include codon optimization of the nucleic acids and/or changes that results in a single amino acid modification in the encoded polypeptide, such as single amino acid replacements (substitutions), insertions or deletions, or multiple amino acid modifications, such as multiple amino acid replacements, insertions or deletions, including swaps of regions or domains of the polypeptide. In some examples, entire or partial domains or regions, such as any domain or region described herein below, are exchanged with corresponding domains or regions or portions thereof from another terpene synthase. Exemplary of modifications are amino acid replacements, including single or multiple amino acid replacements. For example, modified LPP synthase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the LPP synthase polypeptide not containing the modification.

Also provided herein are LPP synthase polypeptides that exhibit at least 60% amino acid sequence identity to a LPP synthase polypeptide set forth in any of SEQ ID NOS:2, 4, 6, 8, 10, 12 and 14. For example, the LPP synthase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a LPP synthase polypeptide set forth in any of SEQ ID NOS:2, 4, 6, 8, 10, 12 and 14, provided the resulting modified LPP synthase polypeptide at least retains labdenediol diphosphate synthase activity (i.e. the ability to catalyze the formation of labdenediol diphosphate synthase from an acyclic pyrophosphate terpene precursor, typically GGPP). Percent identity can be determined by one skilled in the art using standard alignment programs.

Provided herein are sclareol synthase polypeptides. Also provided herein are nucleic acid molecules that encode any of the sclareol synthase polypeptides provided herein. The sclareol synthase polypeptides provided herein catalyze the formation of sclareol from labdenediol diphosphate. Also provided herein are modified sclareol synthase polypeptides and nucleic acid molecules encoding the modified sclareol polypeptides. The modifications can include codon optimization of the nucleic acids and/or can be made in any region of a sclareol synthase polypeptide provided the resulting modified sclareol synthase polypeptide at least retains sclareol synthase activity (i.e., the ability to catalyze the formation of sclareol from labdenediol pyrophosphate).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another terpene synthase. Exemplary of modification are amino acid replacements, including single or multiple amino acid replacements. For example, modified sclareol synthase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the sclareol synthase polypeptide not containing the modification.

Also provided herein are sclareol synthase polypeptides that exhibit at least 60% amino acid sequence identity to a sclareol synthase polypeptide set forth in any of SEQ ID NOS:36, 38, 40 and 78. For example, the sclareol synthase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a sclareol synthase polypeptide set forth in any of SEQ ID NOS:36, 38, 40 and 78, provided the resulting modified sclareol synthase polypeptide at least retains sclareol synthase activity (i.e., the ability to catalyze the formation of sclareol from labdenediol pyrophosphate). Percent identity can be determined by one skilled in the art using standard alignment programs.

Also, in some examples, provided herein are catalytically active fragments of LPP or sclareol synthase polypeptides. In some examples, the active fragments of LPP or sclareol synthase polypeptides are modified as described above. Such fragments retain one or more properties of a full-length LPP or sclareol synthase polypeptide. Typically, the active fragments exhibit labdenediol diphosphate or sclareol synthase activity (i.e., catalyze the formation of labdenediol diphosphate and sclareol, respectively).

The LPP and/or sclareol synthase polypeptides provided herein can contain other modifications, for example, modifications not in the primary sequence of the polypeptide, including post-translational modifications. For example, modification described herein can be in a labdenediol diphosphate synthase or sclareol synthase that is a fusion polypeptide or chimeric polypeptide, including hybrids of different LPP or sclareol synthase polypeptides or different terpene synthase polypeptides (e.g. contain one or more domains or regions from another terpene synthase) and also synthetic LPP or sclareol synthase polypeptides prepared recombinantly or synthesized or constructed by other methods known in the art based upon the sequence of known polypeptides.

Provided herein are sclareol synthase fusion polypeptides having a sequence of amino acids set forth in any of SEQ ID NOS:90, 92 and 94. Also provided herein are sclareol synthase fusion polypeptides having a sequence of amino acids that exhibits at least 60% amino acid sequence identity to a sclareol synthase fusion polypeptide set forth in any of SEQ ID NOS:90, 92 and 94. For example, the sclareol synthase fusion polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a sclareol synthase polypeptide set forth in any of SEQ ID NOS: 90, 92 and 94, provided the resulting modified sclareol synthase fusion polypeptide at least retains sclareol synthase activity (i.e., the ability to catalyze the formation of sclareol from labdenediol pyrophosphate). Percent identity can be determined by one skilled in the art using standard alignment programs.

Provided herein are sclareol synthase chimeric polypeptides having a sequence of amino acids set forth in SEQ ID NO:86, or having a sequence of amino acids that exhibits at least 60% amino acid sequence identity to a sclareol synthase chimeric polypeptide set forth in SEQ ID NO:86. For example, the sclareol synthase chimeric polypeptide provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a sclareol synthase chimeric polypeptide set forth in SEQ ID NO:86, provided the resulting modified sclareol synthase fusion polypeptide at least retains sclareol synthase activity (i.e., the ability to catalyze the formation of sclareol from labdenediol pyrophosphate). Percent identity can be determined by one skilled in the art using standard alignment programs.

The LPP or sclareol synthase polypeptides provided herein can be used to catalyze production of labdenediol diphosphate and sclareol, respectively. Typically, the LPP synthase polypeptides provided herein catalyze the formation of labdenediol diphosphate from GGPP. Reactions can be performed in vivo, such as in a host cell into which the nucleic acid has been introduced. At least one of the polypeptides will be heterologous to the host. Reactions also can be performed in vitro by contacting the enzyme with the appropriate substrate under appropriate conditions.

In embodiments provided herein, the sclareol synthase polypeptides provided herein catalyze the formation of sclareol from labdenediol diphosphate. In some examples, provided herein are nucleic acid molecules encoding an LPP synthase and an sclareol synthase provided herein. In such examples, expression of the nucleic acid molecule in a suitable host, for example, a bacterial or yeast cell, results in expression of LPP synthase and sclareol synthase. Such cells can be used to produce the LPP and sclareol synthases and/or to perform reactions in vivo to produce LPP and/or sclareol and or both. For example sclareol can be generated in a yeast cell host from GGPP, particularly a yeast cell that overproduces the acyclic terpene precursor GGPP.

1. Labdenediol Diphosphate (LPP) Synthase Polypeptides

Provided herein are labdenediol diphosphate (LPP) synthase polypeptides. Also provided herein are nucleic acid molecules that encode any of the LPP synthase polypeptides provided herein. The labdenediol diphosphate synthase polypeptides provided herein catalyze the formation of labdenediol diphosphate and/or other terpenes from any suitable acyclic pyrophosphate terpene precursor, including, but not limited to FPP, GPP and GGPP. Typically, the LPP synthase polypeptides provided herein catalyze the formation of labdenediol diphosphate from GGPP.

For example, provided herein are LPP synthase polypeptides that have a sequence of amino acids set forth in SEQ ID NO:54. Also provided herein are variants of LPP synthase polypeptides that have a sequence of amino acids set forth in any of SEQ ID NOS:2, 4, 6, 8, 10, 12 and 14. In some examples, the labdenediol diphosphate synthase polypeptides contain a N-terminal 55 amino acid chloroplast transit sequence (set forth in SEQ ID NO:43 or 100). For example, the LPP synthase polypeptides set forth in SEQ ID NOS: 2, 4 and 6 contain a chloroplast transit sequence (amino acids 1-55) and an LPP synthase (amino acids 56-801). Exemplary of LPP synthase polypeptides provided herein are the LPP synthase polypeptides having a sequence of amino acids set forth in SEQ ID NO:10 and/or 14.

Also provided herein are LPP synthase polypeptides that exhibit at least 60% amino acid sequence identity to a LPP synthase polypeptide having a sequence of amino acids set forth in any of SEQ ID NOS: 2, 4, 6, 8, 10, 12, 14 and 54. For example, the LPP synthase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid sequence identity to a LPP synthase polypeptide set forth in any of SEQ ID NOS:2, 4, 6, 8, 10, 12, 14 and 54, provided the LPP synthase polypeptides exhibit labdenediol synthase activity (i.e., catalyze the formation of labdenediol diphosphate). Percent identity can be determined by one skilled in the art using standard alignment programs.

Also, in some examples, provided herein are active fragments of labdenediol diphosphate synthase polypeptides having a sequence of amino acids set forth in any of SEQ ID NOS:2, 4, 6, 8, 10, 12, 14 and 54. Such fragments retain one or more properties of a LPP synthase. Typically, the active fragments exhibit LPP synthase activity (i.e. the ability to catalyze the formation of labdenediol diphosphate from an acyclic pyrophosphate terpene precursor, such as GGPP). In particular examples, the active fragments are truncated at their N-terminus.

Also provided herein are nucleic acid molecules that have a sequence of nucleotides set forth in any of SEQ ID NOS:53, 1, 3, 5, 7, 9, 11 and 13, or degenerates thereof, that encode an LLP synthase polypeptide having a sequence of amino acids set forth in SEQ ID NOS:54, 2, 4, 6, 8, 10, 12 and 14, respectively. Also provided herein are nucleic acids encoding an LPP synthase polypeptide having at least 85% sequence identity to a sequence of nucleotides set forth in any of SEQ ID NOS:53, 1, 3, 5, 7, 9, 11 and 13. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in any of SEQ ID NOS:53, 1, 3, 5, 7, 9, 11 and 13, so long as the encoded LPP synthase polypeptides exhibit labdenediol synthase activity (i.e., catalyze the formation of labdenediol diphosphate). Also provided herein are degenerate sequences of any of those set forth in any of SEQ ID NOS:53, 1, 3, 5, 7, 9, 11 and 13, encoding an LLP synthase polypeptide having a sequence of amino acids set forth in SEQ ID NOS:54, 2, 4, 6, 8, 10, 12 and 14, respectively. Percent identity can be determined by one skilled in the art using standard alignment programs. In some examples, the nucleic acid molecules that encode the LPP synthase polypeptides are isolated from the tobacco plant *Nicotiana glutinosa*. In other examples, the nucleic acid molecules and encoded LPP synthase polypeptides are variants of those isolated from the tobacco plant *Nicotiana glutinosa*.

a. Modified Labdenediol Diphosphate Synthase Polypeptides

Provided herein are modified labdenediol diphosphate synthase polypeptides. Also provided herein are nucleic acid molecules that encode any of the modified LPP synthase polypeptides provided herein. The modifications can be made in any region of a labdenediol diphosphate synthase provided the resulting modified LPP synthase polypeptide at least retains labdenediol diphosphate synthase activity (i.e., the ability to catalyze the formation of labdenediol diphosphate from an acyclic pyrophosphate terpene precursor, typically GGPP).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another terpene synthase. Exemplary of modifications are amino acid replacements, including single or multiple amino acid replacements. For example, modified LPP synthase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the LPP synthase polypeptide not containing the modification.

The modifications described herein can be in any labdenediol diphosphate synthase polypeptide. Typically, the modifications are made in a labdenediol diphosphate synthase polypeptide provided herein. For example, the modifications described herein can be in a LPP synthase polypeptide as set forth in any of SEQ ID NOS:54, 2, 4, 6, 8, 10, 12 and 14 or any variant thereof, including any that have at least 60%, 70%, 75%, 80%, 85%, 90%, 91%, 92%, 93%, 94%, 95%, 96%, 97%, 98%, or 99% sequence identity to a LPP synthase polypeptide set forth in any of SEQ ID NOS:54, 2, 4, 6, 8, 10, 12 and 14.

In particular, the modified LPP synthase polypeptides provided herein contain amino acid replacements or substitutions, additions or deletions, truncations or combinations thereof with reference to the LPP synthase polypeptide set forth in SEQ ID NO:54. It is within the level of one of skill in the art to make such modifications in LPP synthase polypeptides, such as any set forth in SEQ ID NOS:2, 4, 6, 8, 10, 12 or 14 or any variant thereof. Based on this description, it is within the level of one of skill in the art to generate a LPP synthase containing any one or more of the described mutation, and test each for LPP synthase activity as described herein.

Also, in some examples, provided herein are modified active fragments of labdenediol diphosphate synthase polypeptides that contain any of the modifications provided herein. Such fragments retain one or more properties of a LPP synthase. Typically, the modified active fragments exhibit LPP synthase activity (i.e. the ability to catalyze the formation of labdenediol diphosphate from an acyclic pyrophosphate terpene precursor, such as GGPP).

Modifications in a labdenediol diphosphate synthase polypeptide also can be made to a labdenediol diphosphate synthase polypeptide that also contains other modifications, including modifications of the primary sequence and modifications not in the primary sequence of the polypeptide. For example, modification described herein can be in a labdenediol diphosphate synthase polypeptide that is a fusion polypeptide or chimeric polypeptide, including hybrids of different labdenediol diphosphate synthase polypeptides or different terpene synthase polypeptides (e.g. contain one or more domains or regions from another terpene synthase) and also synthetic labdenediol diphosphate synthase polypeptides prepared recombinantly or synthesized or constructed by other methods known in the art based upon the sequence of known polypeptides.

In some examples, the modifications are amino acid replacements. In further examples, the modified LPP synthase polypeptides provided herein contain one or more modifications in a structural domain such as the α, β1, γ or β2 domain. As described elsewhere herein, the modifications in a domain or structural domain can be by replacement of corresponding heterologous residues from another terpene synthase.

To retain LPP synthase activity, modifications typically are not made at those positions that are necessary for LPP synthase activity, i.e., in the active site DxDD (SEQ ID NO:103) motif. For example, generally modifications are not made at a position corresponding to position D380, D382 or D383, with reference to a sequence of amino acids set forth in SEQ ID NO:54.

Exemplary amino acid substitutions (or replacements) that can be included in the modified labdenediol diphosphate synthases provided herein include, but are not limited to, amino acid replacement corresponding to L31F, S72F, D151N, A242T, D272G, R342c, K441R, R478G, I661V, A674V, I719T, V751A, A772T, V783A, F797L or Q798H in a sequence of amino acids set forth in SEQ ID NO:54. It is understood that the replacements can be made in the corresponding position in another LPP synthase polypeptide by alignment therewith with the sequence set forth in SEQ ID NO:54 (see, e.g., FIGS. 6A-6J), whereby the corresponding position is the aligned position. In particular examples, the amino acid replacement(s) can be at the corresponding position in a LPP synthase polypeptide set forth in an of SEQ ID NOS:2, 4, 6, 8, 10, 12 or 14 or a variant thereof having at least 65%, 70%, 75%, 80%, 81%, 82%, 83%, 84%, 85%, 86%, 86%, 88%, 89%, 90%, 91%, 92%, 93%, 94%, 95%, 96%, 97%, 98%, 99% or more sequence identity thereto, so long as the resulting modified LPP synthase polypeptide exhibits at least one LPP synthase activity (i.e. the ability to catalyze the formation of labdenediol diphosphate from an acyclic pyrophosphate terpene precursor, such as GGPP).

In particular examples, provided herein is a modified LPP synthase polypeptide containing an amino acid replacement or replacements at a position or positions corresponding to 31, 72, 151, 242, 272, 342, 441, 478, 661, 674, 719, 751, 772, 783, 797 or 798 with reference to the amino acid positions set forth in SEQ ID NO:54. For example, the amino acid positions can be replacements at positions corresponding to replacement of Leucine (L) at position 31, S72, D151, A242, D272, R342, K441, R478, I661, A674, I719, V751, A772, V783, F797 or Q798 with reference to the amino acid positions set forth in SEQ ID NO:54. Exemplary amino acid replacements in the modified LPP synthase polypeptides provided herein include, but are not limited to, replacement with phenylalanine (F) at a position corresponding to position 31; F at a position corresponding to position 72; N at a position corresponding to position 151; T at a position corresponding to position 242; G at a position corresponding to position 272; C at a position corresponding to position 342; R at a position corresponding to position 441; G at a position corresponding to position 478; V at a position corresponding to position 661; V at a position corresponding to position 674; T at a position corresponding to position 719; A at a position corresponding to position 751; T at a position corresponding to position 772; A at a position corresponding to position 783; L at a position corresponding to position 797; and/or replacement with H at a position corresponding to position 798, each with reference to amino acid positions set forth in SEQ ID NO:54. In some examples, the modifications are conservative modifications, for example, a modification set forth in Table 2.

The modified labdenediol diphosphate synthase polypeptides can contain any one or more of the recited amino acid substitutions, in any combination, with or without additional modifications. Generally, multiple modifications provided herein can be combined by one of skill in the art so long as the modified polypeptide retains the ability to catalyze the formation of labdenediol diphosphate and/or other terpenes from any suitable acyclic pyrophosphate terpene precursor, including, but not limited to, FPP, GPP and GGPP. In some examples, the resulting modified LPP synthase polypeptide exhibits similar or increased labdenediol diphosphate production from GGPP compared to the unmodified LPP synthase polypeptide. In some instances, the resulting modified LPP synthase polypeptide exhibits decreased labdenediol diphosphate production from GGPP compared to the unmodified LPP synthase polypeptide.

Also provided herein are nucleic acid molecules that encode any of the modified labdenediol diphosphate synthase polypeptides provided herein. In particular examples, the nucleic acid sequence can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at kazusa.or.jp.codon (see Richmond (2000) *Genome Biology*, 1:241 for a description of the database). See also, Forsburg (2004) *Yeast*, 10:1045-1047; Brown et al. (1991) *Nucleic Acids Research*, 19:4298; Sharp et al. (1988) *Nucleic Acids Research*, 12:8207-8211; Sharp et al. (1991) *Yeast*, 657-78. In examples herein, nucleic acid sequences provided herein are codon optimized based on codon usage in *Saccharomyces cerevisiae*.

The modified polypeptides and encoding nucleic acid molecules provided herein can be produced by standard recombinant DNA techniques known to one of skill in the art. Any method known in the art to effect mutation of any one or more amino acids in a target protein can be employed. Methods include standard site-directed or random mutagenesis of encoding nucleic acid molecules, or solid phase polypeptide synthesis methods. For example, as described herein, nucleic acid molecules encoding a LPP synthase polypeptide can be subjected to mutagenesis, such as random mutagenesis of the encoding nucleic acid, by error-prone PCR, site-directed mutagenesis, overlap PCR, gene shuffling, or other recombinant methods. The nucleic acid encoding the polypeptides then can be introduced into a host cell to be expressed heterologously. Hence, also provided herein are nucleic acid molecules encoding any of the modified polypeptides provided herein. In some examples, the modified LPP synthase polypeptides are produced synthetically, such as using solid phase or solutions phase peptide synthesis.

b. Truncated LPP Synthase Polypeptides

Also provided herein are truncated labdenediol diphosphate synthase polypeptides. The truncated LPP synthase polypeptides can be truncated at the N-terminus or the C-terminus, so long as the truncated LPP synthase polypeptides retain catalytic activity of a LPP synthase. Typically, the truncated LPP synthase polypeptides exhibit LPP synthase activity (i.e. the ability to catalyze the formation of labdenediol diphosphate from an acyclic pyrophosphate terpene precursor, such as GGPP). In some examples, the LPP synthase polypeptides provided herein are truncated at the N-terminus. In other examples, the LPP synthase polypeptides provided herein are truncated at the C-terminus. In yet other examples, the LPP synthase polypeptides provided herein are truncated at the N-terminus and C-terminus.

In some examples, the LPP synthase polypeptides are truncated at the N-terminus, C-terminus or both termini of a LPP synthase polypeptide provided herein, such as truncation of a sequence of amino acids set forth in any of SEQ ID NOS:54, 2, 4, 6, 8, 10, 12 and 14. In other examples, any of the modified LPP synthases provided herein are truncated. In some examples, the LPP synthase polypeptides are truncated at their N-terminus. For example, any LPP synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the N-terminus, provided the LPP synthase polypeptide retains LPP activity. In other examples, any LPP synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the C-terminus, provided the LPP synthase polypeptide retains LPP activity.

c. LPP Synthase Polypeptides with Altered Activities and/or Properties

The modified labdenediol diphosphate synthase polypeptides provided herein can also exhibit changes in activities and/or properties. The modified labdenediol diphosphate synthase can exhibit, for example, increased catalytic activity, increased substrate (e.g. GGPP) binding, increased stability and/or increased expression in a host cell. Such altered activities and properties can result in increased labdenediol diphosphate production from GGPP. In other examples, the modified labdenediol diphosphate synthase polypeptides can catalyze the formation of other terpenes than labdenediol diphosphate from any suitable substrate, such as, for example, FPP, GPP or GGPP. For example, the modified labdenediol diphosphate synthases can produce one or more monoterpenes, sesquiterpenes or diterpenes other than labdenediol diphosphate. Typically, the modified labdenediol diphosphate synthase polypeptides produce more labdenediol diphosphate than any other terpene. This can result in increased production of sclareol, which in turn can lead to increased production of (−)-ambroxide.

d. Domain Swaps

Provided herein are modified labdenediol diphosphate synthase polypeptides that are chimeric polypeptides containing a swap (deletion and insertion) by deletion of amino acid residues of one or more domains or regions therein or portions thereof and insertion of a heterologous sequence of amino acids. In some examples, the heterologous sequence is a randomized sequence of amino acids. In other examples, the heterologous sequence is a contiguous sequence of amino acids for the corresponding domain or region or portion thereof from another terpene synthase polypeptide. The heterologous sequence that is replaced or inserted generally includes at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids. In examples where the heterologous sequence is from a corresponding domain or a portion thereof of another terpene synthase, the heterologous sequence generally includes at least 50%, 60%, 70%, 80%, 90%, 95% or more contiguous amino acids of the corresponding domain or region or portion. In such an example, adjacent residues to the heterologous corresponding domain or region or portion thereof also can be included in a modified LPP synthase polypeptide provided herein.

In one example of swap mutants provided herein, at least one domain or region or portion thereof of a LPP synthase polypeptide is replaced with a contiguous sequence of amino acids for the corresponding domain or region or portions thereof from another terpene synthase polypeptide. In some examples, 2, 3, 4, 5, 6, 7, 8, 9, 10 or more domains or regions or portions thereof are replaced with a contiguous sequence of amino acids for the corresponding domain or region or portions thereof from another terpene synthase polypeptide.

Any domain or region or portion thereof of a LPP synthase polypeptide can be replaced with a heterologous sequence of amino acids, such as heterologous sequence from the corresponding domain or region from another terpene. A domain or region can be a structural domain or a functional domain. One of skill in the art is familiar with domains or regions in terpene synthases. Functional domains include, for example, the catalytic domain or a portion thereof. A structural domain can include all or a portion of α, β1, β2 or γ domain.

One of skill in the art is familiar with various terpene synthases and can identify corresponding domains or regions or portions of amino acids thereof. Exemplary terpene synthases include, but are not limited to, *Arabidopsis thaliana* ent-copalyl diphosphate synthase (SEQ ID NO:83), *Pisum sativum* ent-copalyl diphosphate synthase (SEQ ID NO:107); *Cucurbita maxima* ent-copalyl diphosphate synthase 1 (SEQ ID NO:108); *Cucurbita maxima* ent-copalyl diphosphate synthase 2 (SEQ ID NO:109); *Lycopersicon esculentum* ent-copalyl diphosphate synthase (SEQ ID NO:110); *Stevia rebaudiana* ent-copalyl pyrophosphate synthase (SEQ ID NO:111); *Salvia miltiorrhiza* copalyl diphosphate synthase (SEQ ID NO:112); *Zea mays* ent-copalyl diphosphate synthases (SEQ ID NO:113 and 114); *Oryza sativa* ent-copalyl diphosphate synthases (SEQ ID NO:115 and 116); *Oryza sativa* syn-copalyl diphosphate synthase (SEQ ID NO:117); *Pinus taeda* abietadiene/levopimaradiene synthase (SEQ ID NO:124); *Picea abies* abietadiene/levopimaradiene synthase (SEQ ID NO:125); *Ginkgo biloba* levopimaradiene synthase (SEQ ID NO:126); *Pinus taeda* diterpene synthase (SEQ ID NO:127) and *Picea abies* isopimaradiene synthase (SEQ ID NO:128). In particular examples herein, modified LPP synthase polypeptide domain swap mutants provided herein contain heterologous sequences from a corresponding domain or region or portion thereof of a terpene synthase polypeptide that is a *Salvia sclarea* LPP synthase (SEQ ID NOS:57-59).

Typically, the resulting modified LPP synthase exhibits LPP synthase activity and the ability to produce labdenediol diphosphate from GGPP. For example, the modified LPP synthase polypeptides exhibit 50% to 5000%, such as 50% to 120%, 100% to 500% or 110% to 250% of the labdenediol diphosphate production from GGPP compared to the LPP synthase polypeptide not containing the modification (e.g. the amino acid replacement or swap of amino acid residues of a domain or region) and/or compared to wild type LPP synthase polypeptide set forth in SEQ ID NO:54. Typically, the modified LPP synthase polypeptides exhibit increased labdenediol diphosphate production from GGPP compared to the LPP synthase polypeptide not containing the modification, such as compared to wild type labdenediol diphosphate synthase set forth in SEQ ID NO:54. For example, the modified LPP synthase polypeptides can produce labdenediol diphosphate from GGPP in an amount that is at least or about 101%, 102%, 103%, 104%, 105%, 106%, 107%, 108%, 109%, 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of labdenediol diphosphate produced from GGPP by wild type LPP synthase not containing the modification under the same conditions. For example, the labdenediol diphosphate production is increased at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more.

In particular examples herein, modified labdenediol diphosphate synthase polypeptides provided herein are swap mutants whereby all or a portion of one or more structural domains is replaced with a corresponding structural domain of another terpene polypeptide. Table 3 below identifies structural domains with numbering based on LPP synthase numbering or the class II diterpene synthase ent-copalyl diphosphate synthase (CPS) numbering, which are common numbering schemes for all terpene synthases based on alignment of the synthase with the class II diterpene synthase ent-copalyl diphosphate synthase (CPS) or LPP synthase, respectively (see e.g. FIGS. 3A-3B). Hence, the corresponding domain can be identified in other terpene synthases.

TABLE 3

Structural Domains

| structure | ent-copalyl diphosphate synthase (CPS) (SEQ ID NO: 83) | NgLPP (SEQ ID NO: 2) |
|---|---|---|
| Helix A | 92-106 | 89-103 |
| Loop 1 | 107-116 | 104-113 |
| Helix B | 117-124 | 114-121 |
| Loop 2 | 125-136 | 122-138 |
| Helix C | 137-144 | 139-146 |
| Loop 3 | 145-159 | 147-161 |
| Helix D | 160-175 | 162-177 |
| Loop 4 | 176-180 | 178-182 |
| Helix E | 181-195 | 183-200 |
| Loop 5 | 196-209 | 201-211 |
| Helix F1 | 210-217 | 212-225 |
| Loop 6 | 218-220 | n.a. |
| Helix F2 | 221-223 | n.a. |
| Loop 7 | 224-237 | 226-239 |
| Helix G | 238-244 | 240-248 |
| Loop 8 | 245-250 | 249-252 |
| Helix H | 251-253 | 253-256 |
| Loop 9 | 254-272 | 257-275 |
| Helix I | 273-278 | 276-281 |
| Loop 10 | 279-289 | 282-292 |
| Helix J | 290-299 | 293-302 |
| Loop 11 | 300-303 | 303-306 |
| Helix K | 304-315 | 307-318 |
| Loop 12 | 316-326 | 319-328 |
| Helix L | 327-340 | 329-343 |
| Loop 13 | 341-347 | 344-349 |
| Helix M | 348-361 | 350-363 |
| Loop 14 | 362-377 | 364-380 |
| Helix N | 378-391 | 381-394 |
| Loop 15 | 392-419 | 395-422 |
| Helix O | 420-430 | 423-433 |
| Loop 16 | 431-438 | 434-441 |
| Helix P | 439-457 | 442-460 |
| Loop 17 | 458-469 | 461-472 |
| Helix Q | 470-479 | 473-482 |
| Loop 18 | 480-486 | 483-489 |
| Helix R | 487-495 | 490-498 |
| Loop 19 | 496-519 | 499-522 |
| Helix S | 520-558 | 523-551 |
| Loop 20 | 550-558 | 552-561 |
| Helix T | 559-572 | 562-575 |
| Loop 21 | 573-578 | 576-581 |
| Helix U | 579-598 | 582-600 |
| Loop 22 | 599-602 | 601-613 |
| Helix V | 603-618 | 614-623 |
| Loop 23 | 619-638 | 624-633 |
| Helix W | 639-661 | 634-654 |
| Loop 24 | 662-668 | 655-661 |
| Helix X | 669-685 | 662-675 |
| Loop 25 | 686-690 | 676-678 |

TABLE 3-continued

Structural Domains

| structure | ent-copalyl diphosphate synthase (CPS) (SEQ ID NO: 83) | NgLPP (SEQ ID NO: 2) |
|---|---|---|
| Helix Y | 691-702 | 679-686 |
| Loop 26 | 703-708 | 687-709 |
| Helix Z 1 | 709-711 | 710-730 |
| Loop 27 | 712-714 | n.a. |
| Helix Z 2 | 715-726 | n.a. |
| Loop 28 | 727-239 | 731-737 |
| Helix AA | 740-759 | 738-754 |
| Loop 29 | 760-763 | 755-764 |
| Helix AB | 764-784 | 765-782 |
| Loop 30 | 785-790 | 783-788 |
| Helix AC | 791-798 | 789-796 |
| Loop 31 | 799-802 | 797-801 |

Any methods known in the art for generating chimeric polypeptides can be used to replace all or a contiguous portion of a domain or a first terpene synthase with all or a contiguous portion of the corresponding domain of a second synthase (see, U.S. Pat. Nos. 5,824,774, 6,072,045, 7,186,891 and 8,106,260, and U.S. Pat. Pub. No. 20110081703). Also, gene shuffling methods can be employed to generate chimeric polypeptides and/or polypeptides with domain or region swaps.

For example, corresponding domains or regions of any two terpene synthases can be exchanged using any suitable recombinant method known in the art, or by in vitro synthesis. Exemplary of recombinant methods is a two stage overlapping PCR method, such as described herein. In such methods, primers that introduce mutations at a plurality of codon positions in the nucleic acids encoding the targeted domain or portion thereof in the first terpene synthase can be employed, wherein the mutations together form the heterologous region (i.e. the corresponding region from the second terpene synthase). Alternatively, for example, randomized amino acids can be used to replace specific domains or regions. It is understood that primer errors, PCR errors and/or other errors in the cloning or recombinant methods can result in errors such that the resulting swapped or replaced region or domain does not exhibit an amino acid sequence that is identical to the corresponding region from the second terpene synthase.

In an exemplary PCR-based method, the first stage PCR uses (i) a downstream primer that anneals downstream of the region that is being replaced with a mutagenic primer that includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene, and (ii) an upstream primer that anneals upstream of the region that is being replaced together with an opposite strand mutagenic primer that also includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene. If a replacement in which a domain or region of a first terpene synthase gene is replaced with the corresponding domain or region from a second terpene synthase is being performed, nucleotides in the mutagenic primers between the flanking regions from the first terpene synthase contain codons for the corresponding region of the second terpene synthase. In instances where the amino acids in a domain or region are to be randomized, nucleotides of the mutagenic primers between the flanking regions from the first terpene synthase contains random nucleotides. An overlapping PCR is then performed to join the two fragments, using the upstream and downstream oligo. The resulting PCR product then can be cloned into any suitable vector for expression of the modified terpene synthase.

Further, any of the modified labdenediol diphosphate synthase polypeptides containing swap mutations herein can contain one or more further amino acid replacements. Exemplary amino acid substitutions (or replacements) that can be included in the modified LPP synthase polypeptides include, but are not limited to, L31F, S72F, D151N, A242T, D272G, R342c, K441R, R478G, I661V, A674V, I719T, V751A, A772T, V783A, F797L or Q798H with reference to the positions set forth in SEQ ID NO:54.

e. Additional Variants

LPP synthase polypeptides provided herein can be modified by any method known to one of skill in the art for generating protein variants, including, but not limited to, DNA or gene shuffling, error prone PCR, overlap PCR or other recombinant methods. In one example, nucleic acid molecules encoding any LPP synthase polypeptide or variant LPP synthase polypeptide provided herein can be modified by gene shuffling. Gene shuffling involves one or more cycles of random fragmentation and reassembly of at least two nucleotide sequences, followed by screening to select nucleotide sequences encoding polypeptides with desired properties. The recombination can be performed in vitro (see Stemmer et al. (1994) *Proc Natl Acad Sci USA* 91:10747-10751; Stemmer et al. (1994) *Nature* 370:389-391; Cramieri Crameri et al. (1998) *Nature* 391:288-291; U.S. Pat. Nos. 5,605,793, 5,811,238, 5,830,721, 5,834,252 and 5,837,458) or in vivo (see, International Pat. Pub. No. WO199707205). The nucleic acid molecules encoding the polypeptides then can be introduced into a host cell to be expressed heterologously and tested for their LPP synthase activity by any method described in section D below.

2. Sclareol Synthase Polypeptides

Provided herein are sclareol synthase polypeptides. Also provided herein are nucleic acid molecules that encode any of the sclareol synthase polypeptides provided herein. The sclareol synthase polypeptides provided herein catalyze the formation of sclareol from labdenediol diphosphate.

For example, provided herein are sclareol synthase polypeptides that have a sequence of amino acids set forth in SEQ ID NO:31. Also provided herein are variants of sclareol synthase polypeptides that have a sequence of amino acids set forth in any of SEQ ID NOS:36, 38, 40 and 78. In some examples, the sclareol synthase polypeptides contain a N-terminal amino acid chloroplast transit sequence (set forth in SEQ ID NO:44 and 102). For example, the sclareol synthase polypeptide set forth in SEQ ID NO:36 contains a chloroplast transit sequence (amino acids 1-55) and a sclareol synthase (amino acids 56-792). Exemplary of a sclareol synthase polypeptide provided herein is a sclareol synthase polypeptide having a sequence of amino acids set forth in SEQ ID NO:40.

Also provided herein are sclareol synthase polypeptides that exhibit at least 60% amino acid sequence identity to a sclareol synthase polypeptide having a sequence of amino acids set forth in any of SEQ ID NOS:31, 36, 38, 40 and 78. For example, the sclareol synthase polypeptides provided herein can exhibit at least or at least about 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% or more amino acid sequence identity to a sclareol synthase polypeptide set forth in any of SEQ ID NOS:31, 36, 38, 40 and 78, provided the sclareol synthase polypeptides exhibit sclareol synthase activity (i.e., catalyze the formation of sclareol). Percent identity can be determined by one skilled in the art using standard alignment programs.

Also, in some examples, provided herein are active fragments of sclareol synthase polypeptides having a sequence of amino acids set forth in any of SEQ ID NOS:31, 36, 38, 40 and 78. Such fragments retain one or more properties of a sclareol synthase. Typically, the active fragments exhibit sclareol synthase activity (i.e. the ability to catalyze the formation of sclareol from labdenediol pyrophosphate). In particular examples, the active fragments are truncated at their N-terminus.

Also provided herein are nucleic acid molecules that have a sequence of nucleotides set forth in any of SEQ ID NOS:30, 35, 37, 39 and 77, or degenerates thereof, that encode a sclareol synthase polypeptide having a sequence of amino acids set forth in SEQ ID NOS:31, 36, 38, 40 and 78, respectively. Also provided herein are nucleic acids encoding a sclareol synthase polypeptide having at least 85% sequence identity to a sequence of nucleotides set forth in any of SEQ ID NOS:30, 35, 37, 39 and 77. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in any of SEQ ID NOS:30, 35, 37, 39 and 77, so long as the encoded sclareol synthase polypeptides exhibit sclareol synthase activity (i.e., catalyze the formation of sclareol). Also provided herein are degenerate sequences of any of those set forth in any of SEQ ID NOS:30, 35, 37, 39 and 77, encoding a sclareol synthase polypeptide having a sequence of amino acids set forth in SEQ ID NOS:31, 36, 38, 40 and 78, respectively. Percent identity can be determined by one skilled in the art using standard alignment programs. In some examples, the nucleic acid molecules that encode the sclareol synthase polypeptides are isolated from the tobacco plant *Nicotiana glutinosa*. In other examples, the nucleic acid molecules and encoded sclareol synthase polypeptides are variants of those isolated from the tobacco plant *Nicotiana glutinosa*.

a. Modified Sclareol Synthase Polypeptides

Provided herein are modified sclareol synthase polypeptides. Also provided herein are nucleic acid molecules that encode any of the modified sclareol synthase polypeptides provided herein. The modifications can be made in any region of a sclareol synthase provided the resulting modified sclareol synthase polypeptide at least retains sclareol synthase activity (i.e., the ability to catalyze the formation of sclareol from labdenediol diphosphate).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another terpene synthase. Exemplary of modifications are amino acid replacements, including single or multiple amino acid replacements. For example, modified sclareol synthase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the sclareol synthase polypeptide not containing the modification.

The modifications described herein can be in any sclareol synthase polypeptide. Typically, the modifications are made in a sclareol synthase polypeptide provided herein. For example, the modifications described herein can be in a sclareol synthase polypeptide as set forth in any of SEQ ID NOS: 31, 36, 38, 40 and 78 or any variant thereof, including any that have at least 60%, 70%, 80%, 90%, 91%, 92%, 93%, 94%, 95%, 96%, 97%, 98%, or 99% sequence identity to a sclareol synthase polypeptide set forth in any of SEQ ID NOS:31, 36, 38, 40 and 78.

In particular, the modified sclareol synthase polypeptides provided herein contain amino acid replacements or substitutions, additions or deletions, truncations or combinations thereof with reference to the sclareol synthase polypeptide set forth in SEQ ID NO:31. It is within the level of one of skill in the art to make such modifications in sclareol synthase polypeptides, such as any set forth in SEQ ID NOS:36, 38, 40 or 78 or any variant thereof. Based on this description, it is within the level of one of skill in the art to generate a sclareol synthase containing any one or more of the described mutation, and test each for sclareol synthase activity as described herein.

Also, in some examples, provided herein are modified active fragments of sclareol synthase polypeptides that contain any of the modifications provided herein. Such fragments retain one or more properties of a sclareol synthase. Typically, the modified active fragments exhibit sclareol synthase activity (i.e., the ability to catalyze the formation of sclareol from labdenediol diphosphate).

Modifications in a sclareol synthase polypeptide also can be made to a sclareol synthase polypeptide that also contains other modifications, including modifications of the primary sequence and modifications not in the primary sequence of the polypeptide. For example, modification described herein can be in a sclareol synthase polypeptide that is a fusion polypeptide or chimeric polypeptide, including hybrids of different sclareol synthase polypeptides or different terpene synthase polypeptides (e.g. contain one or more domains or regions from another terpene synthase) and also synthetic sclareol synthase polypeptides prepared recombinantly or synthesized or constructed by other methods known in the art based upon the sequence of known polypeptides.

In some examples, the modifications are amino acid replacements. In further examples, the modified sclareol synthase polypeptides provided herein contain one or more modifications in a structural domain such as the α, β1, γ or β2 domain As described elsewhere herein, the modifications in a domain or structural domain can be by replacement of corresponding heterologous residues from another terpene synthase.

To retain sclareol synthase activity, modifications typically are not made at those positions that are necessary for sclareol synthase activity, i.e., in the aspartate-rich region 1 DDxxD motif or the NSE/DTE motif. For example, generally modifications are not made at a position corresponding to position D540, D541, F542, F543, D544, N685, D686, I687, H688, S689, Y690, K691, R692, or E693 with reference to a sequence of amino acids set forth in SEQ ID NO:31.

Exemplary amino acid substitutions (or replacements) that can be included in the modified sclareol synthases provided herein include, but are not limited to, amino acid replacement corresponding to H31P, G52E, G59V, P65S, H110L, L240P, F289L, D299N, I586V, V702A or V725M in a sequence of amino acids set forth in SEQ ID NO:31. It is understood that the replacements can be made in the corresponding position in another sclareol synthase polypeptide by alignment therewith with the sequence set forth in SEQ ID NO:31 (see, e.g., FIGS. 6A-6J), whereby the corresponding position is the aligned position. In particular examples, the amino acid replacement(s) can be at the corresponding position in a sclareol synthase polypeptide set forth in any of SEQ ID NOS:36, 38, 40 or 78 or a variant thereof having at least 65%, 70%, 75%, 80%, 81%, 82%, 83%, 84%, 85%, 86%, 86%, 88%, 89%, 90%, 91%, 92%, 93%, 94%, 95%, 96%, 97%, 98%, 99% or more sequence identity thereto, so long as the resulting modified sclareol synthase polypeptide exhibits at least one sclareol synthase activity (i.e., the ability to catalyze the formation of sclareol from labdenediol diphosphate).

In particular examples, provided herein is a modified sclareol synthase polypeptide containing an amino acid replacement or replacements at a position or positions corresponding to 31, 52, 59, 65, 110, 240, 289, 299, 586, 702 or 725 with reference to the amino acid positions set forth in SEQ ID NO:31. For example, the amino acid positions can be replacements at positions corresponding to replacement of histidine (H) at position 31, G52, G59, P65, H110, L240, F289, D299, I586, V702 or V725 with reference to the amino acid positions set forth in SEQ ID NO:31. Exemplary amino acid replacements in the modified sclareol synthase polypeptides provided herein include, but are not limited to, replacement with proline (P) at a position corresponding to position 31; E at a position corresponding to position 52; V at a position corresponding to position 59; L at a position corresponding to position 110; P at a position corresponding to 240; L at a position corresponding to position 289; N at a position corresponding to position 299; V at a position corresponding to position 586; A at a position corresponding to position 702; and/or M at a position corresponding to position 725, each with reference to amino acid positions set forth in SEQ ID NO:31. In some examples, the modifications are conservative modifications, for example, a modification set forth in Table 2.

The modified sclareol synthase polypeptides can contain any one or more of the recited amino acid substitutions, in any combination, with or without additional modifications. Generally, multiple modifications provided herein can be combined by one of skill in the art so long as the modified polypeptide retains the ability to catalyze the formation of sclareol and/or other terpenes from labdenediol diphosphate or any suitable pyrophosphate terpene precursor. In some examples, the resulting modified sclareol synthase polypeptide exhibits similar or increased sclareol production from labdenediol diphosphate compared to the unmodified sclareol synthase polypeptide. In some instances, the resulting modified sclareol synthase polypeptide exhibits decreased sclareol production from labdenediol diphosphate compared to the unmodified sclareol synthase polypeptide.

Also provided herein are nucleic acid molecules that encode any of the modified sclareol synthase polypeptides provided herein. In particular examples, the nucleic acid sequence can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at kazusa.or.jp.codon (see Richmond (2000) *Genome Biology*, 1:241 for a description of the database). See also, Forsburg (2004) *Yeast*, 10:1045-1047; Brown et al. (1991) *Nucleic Acids Research*, 19:4298; Sharp et al. (1988) *Nucleic Acids Res.,* 12:8207-8211; Sharp et al. (1991) *Yeast,* 657-78. In examples herein, nucleic acid sequences provided herein are codon optimized based on codon usage in *Saccharomyces cerevisiae.*

The modified polypeptides and encoding nucleic acid molecules provided herein can be produced by standard recombinant DNA techniques known to one of skill in the art. Any method known in the art to effect mutation of any one or more amino acids in a target protein can be employed. Methods include standard site-directed or random mutagenesis of encoding nucleic acid molecules, or solid phase polypeptide synthesis methods. For example, as described herein, nucleic acid molecules encoding a sclareol synthase polypeptide can be subjected to mutagenesis, such as random mutagenesis of the encoding nucleic acid, by error-prone PCR, site-directed mutagenesis, overlap PCR, gene shuffling, or other recombinant methods. The nucleic acid encoding the polypeptides then can be introduced into a host cell to be expressed heterologously. Hence, also provided herein are nucleic acid molecules encoding any of the modified polypeptides provided herein. In some examples, the modified sclareol synthase polypeptides are produced synthetically, such as using solid phase or solutions phase peptide synthesis.

b. Truncated Sclareol Synthase Polypeptides

Also provided herein are truncated sclareol synthase polypeptides. The truncated sclareol synthase polypeptides can be truncated at the N-terminus or the C-terminus, so long as the truncated sclareol synthase polypeptides retain one or more properties of a sclareol synthase. Typically, the truncated sclareol synthase polypeptides exhibit sclareol synthase activity (i.e. the ability to catalyze the formation of sclareol from labdenediol diphosphate). In some examples, the sclareol synthase polypeptides provided herein are truncated at the N-terminus. In other examples, the sclareol synthase polypeptides provided herein are truncated at the C-terminus. In yet other examples, the sclareol synthase polypeptides provided herein are truncated at the N-terminus and C-terminus.

In some examples, the sclareol synthase polypeptides are truncated at the N-terminus, C-terminus or both termini of a sclareol synthase polypeptide provided herein, such as truncation of a sequence of amino acids set forth in any of SEQ ID NOS:31, 36, 38, 40 and 78. In other examples, any of the modified sclareol synthases provided herein are truncated. In some examples, the sclareol synthase polypeptides are truncated at their N-terminus. For example, any sclareol synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the N-terminus, provided the sclareol synthase polypeptide retains sclareol synthase activity. In other examples, any sclareol synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the C-terminus, provided the sclareol synthase polypeptide retains sclareol synthase activity.

c. Sclareol Synthase Polypeptides with Altered Activities and/or Properties

The modified sclareol synthase polypeptides provided herein can also exhibit changes in activities and/or properties. The modified sclareol synthase can exhibit, for example, increased catalytic activity, increased substrate (e.g. labdenediol. diphosphate) binding, increased stability and/or increased expression in a host cell. Such altered activities and properties can result in increased sclareol production from labdenediol diphosphate. In other examples, the modified sclareol synthase polypeptides can catalyze the formation of other terpenes than sclareol from any suitable substrate, such as, for example, FPP, GPP or GGPP. For example, the modified sclareol synthases can produce one or more monoterpenes, sesquiterpenes or diterpenes other than sclareol. Typically, the modified sclareol synthase polypeptides produce more sclareol than any other terpene. This can result in increased production of (−)-ambroxide.

d. Domain Swaps

Provided herein are modified sclareol synthase polypeptides that are chimeric polypeptides containing a swap (deletion and insertion) by deletion of amino acid residues of one of more domains or regions therein or portions thereof and insertion of a heterologous sequence of amino acids. In some examples, the heterologous sequence is a randomized sequence of amino acids. In other examples, the heterologous sequence is a contiguous sequence of amino acids for the corresponding domain or region or portion thereof from another terpene synthase polypeptide. The heterologous sequence that is replaced or inserted generally includes at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids. In examples where the heterologous sequence is from a corresponding domain or a portion thereof of another terpene synthase, the heterologous sequence generally includes at least 50%, 60%, 70%, 80%, 90%, 95% or more contiguous amino acids of the corresponding domain or region or portion. In such an example, adjacent residues to the heterologous corresponding domain or region or portion thereof also can be included in a modified sclareol synthase polypeptide provided herein.

In one example of swap mutants provided herein, at least one domain or region or portion thereof of a sclareol synthase polypeptide is replaced with a contiguous sequence of amino acids for the corresponding domain or region or portions thereof from another terpene synthase polypeptide. In some examples, 2, 3, 4, 5, 6, 7, 8, 9, 10 or more domains or regions or portions thereof are replaced with a contiguous sequence of amino acids for the corresponding domain or region or portions thereof from another terpene synthase polypeptide.

Any domain or region or portion thereof of a sclareol synthase polypeptide can be replaced with a heterologous sequence of amino acids, such as heterologous sequence from the corresponding domain or region from another terpene. A domain or region can be a structural domain or a functional domain. One of skill in the art is familiar with domains or regions in terpene synthases. Functional domains include, for example, the catalytic domain or a portion thereof. A structural domain can include all or a portion of $\alpha$, $\beta 1$, $\gamma$ or $\beta 2$ domain.

One of skill in the art is familiar with various terpene synthases and can identify corresponding domains or regions or portions of amino acids thereof. Exemplary terpene synthases include, but are not limited to, *Abies grandis* abietadiene synthase (SEQ ID NO:84); *Taxus brevifolia* taxadiene synthase (SEQ ID NO:118); *Helianthus annuus* kaurene synthase (SEQ ID NO:119); *Oryza sativa* ent-kaurene synthase (SEQ ID NO:120); *Oryza sativa* stemer-13-ene synthase (SEQ ID NO:121); *Oryza sativa* stemodene synthase (SEQ ID NO:122), *Stevia rebaudiana* copalyl pyrophosphate synthase (SEQ ID NO:123), *Nicotiana tabacum* abienol synthase (SEQ ID NO:129); *Pinus taeda* abietadiene/levopimaradiene synthase (SEQ ID NO:124); *Picea abies* abietadiene/levopimaradiene synthase (SEQ ID NO:125); *Ginkgo biloba* levopimaradiene synthase (SEQ ID NO:126); *Pinus taeda* diterpene synthase (SEQ ID NO:127) and *Picea abies* isopimaradiene synthase (SEQ ID NO:128). In particular examples herein, modified sclareol synthase polypeptide domain swap mutants provided herein contain heterologous sequences from a corresponding domain or region or portion thereof of a terpene synthase polypeptide that is a *Salvia sclarea* sclareol synthase (SEQ ID NOS:60-62).

Typically, the resulting modified sclareol synthase exhibits sclareol synthase activity and the ability to produce sclareol from labdenediol diphosphate. For example, the modified sclareol synthase polypeptides exhibit 50% to 5000%, such as 50% to 120%, 100% to 500% or 110% to 250% of the sclareol production from labdenediol diphosphate compared to the sclareol synthase polypeptide not containing the modification (e.g. the amino acid replacement or swap of amino acid residues of a domain or region) and/or compared to wild type sclareol synthase polypeptide set forth in SEQ ID NO:31. Typically, the modified sclareol synthase polypeptides exhibit increased sclareol production from labdenediol diphosphate compared to the sclareol synthase polypeptide not containing the modification, such as compared to wild type sclareol synthase set forth in SEQ ID NO:31. For example, the modified sclareol synthase polypeptides can produce sclareol from labdenediol diphosphate in an amount that is at least or about 101%, 102%, 103%, 104%, 105%, 106%, 107%, 108%, 109%, 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of sclareol produced from labdenediol diphosphate by wild type sclareol synthase not containing the modification under the same conditions. For example, the sclareol production is increased at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more.

In particular examples herein, modified sclareol synthase polypeptides provided herein are swap mutants whereby all or a portion of one or more structural domains is replaced with a corresponding structural domain of another terpene polypeptide. Table 4 below identifies structural domains with numbering based on sclareol synthase numbering or abietadiene numbering, which are common numbering schemes for all terpene synthases based on alignment of the synthase with abietadiene or sclareol synthase, respectively (see e.g. FIGS. 3C-3D). Hence, the corresponding domain can be identified in other terpene synthases.

TABLE 4

Structural domains

| structure | Abietadiene synthase (SEQ ID NO: 84) | Sclareol synthase (SEQ ID NO: 36) |
|---|---|---|
| Loop 1 | 110-111 | 40-41 |
| Helix A | 112-129 | 42-54 |
| Loop 2 | 130-138 | 55-65 |
| Helix B | 139-146 | 66-73 |
| Loop 3 | 146-160 | 74-87 |
| Helix C | 161-168 | 88-95 |
| Loop 4 | 169-183 | 96-112 |
| Helix D | 184-200 | 113-129 |
| Loop 5 | 201-204 | 130-133 |
| Helix E | 205-219 | 134-148 |
| Loop 6 | 220-233 | 149-161 |
| Helix F | 234-248 | 162-176 |
| Loop 7 | 249-256 | 177-184 |
| Helix G | 257-271 | 185-199 |
| Loop 8 | 272-274 | 200-202 |
| Helix H | 275-279 | 203-207 |
| Loop 9 | 280-297 | 208-225 |
| Helix I | 298-303 | 226-230 |
| Loop 10 | 304-314 | 231-242 |
| Helix J | 315-324 | 243-251 |
| Loop 11 | 325-328 | 252-257 |
| Helix K | 329-341 | 258-270 |
| Loop 12 | 342-351 | 271-280 |
| Helix L | 352-364 | 281-295 |
| Loop 13 | 365-372 | 296-301 |
| Helix M | 373-384 | 302-315 |
| Loop 14 | 385-402 | 316-326 |
| Helix N | 403-415 | 327-339 |
| Loop 15 | 416-422 | 340-346 |
| Helix O | 423-427 | 347-351 |
| Loop 16 | 428-445 | 352-368 |
| Helix P | 446-456 | 369-379 |
| Loop 17 | 457-465 | 380-389 |
| Helix Q | 466-481 | 390-406 |
| Loop 18 | 482-495 | 407-414 |
| Helix R | 496-505 | 415-424 |
| Loop 19 | 506-512 | 425-430 |
| Helix S | 513-523 | 431-441 |
| Loop 20 | 524-544 | 442-462 |
| Helix T | 545-573 | 463-491 |
| Loop 21 | 574-586 | 492-504 |
| Helix U | 587-595 | 505-513 |
| Loop 22 | 596-603 | 514-521 |
| Helix V | 604-625 | 522-543 |
| Loop 23 | 626-629 | 544-547 |
| Helix W | 630-642 | 548-560 |
| Loop 24 | 643-652 | 561-571 |
| Helix X | 653-677 | 572-596 |
| Loop 25 | 678-681 | 597-600 |
| Helix Y | 682-705 | 601-619 |
| Loop 26 | 706-710 | 620-630 |
| Helix Z | 711-721 | 631-641 |
| Loop 27 | 722-724 | 642-644 |
| Helix AA | 725-732 | 645-652 |
| Loop 28 | 733-740 | 653-660 |
| Helix AB | 741-745 | 661-664 |
| Loop 29 | 746-751 | 665-670 |
| Helix AC | 752-766 | 671-685 |
| Loop 30 | 767-769 | 686-688 |
| Helix AD | 770-773 | 689-692 |
| Loop 31 | 774-781 | 693-700 |
| Helix AE | 782-789 | 701-708 |
| Loop 32 | 790-794 | 709-713 |
| Helix AF | 795-819 | 714-738 |
| Loop 33 | 820-824 | 739-746 |
| Helix AG | 825-840 | 747-762 |
| Loop 34 | 841-849 | 763-774 |
| Helix AH | 850-863 | 775-782 |
| Loop 35 | 864-868 | 783-788 |

For example, provided herein is a variant sclareol synthase polypeptide set forth in SEQ ID NO:86 containing a swap at the N-terminus of sclareol synthase by replacement of nucleotides encoding residues 1-246 of *Nicotiana glutinosa* sclareol synthase with residues 61-77 of the sage sclareol synthase set forth in SEQ ID NO:60. Also provided herein is a variant sclareol synthase polypeptide having at least 60% sequence identity to the sclareol synthase polypeptide having a sequence of amino acids set forth in SEQ ID NO:86.

Any methods known in the art for generating chimeric polypeptides can be used to replace all or a contiguous portion of a domain or a first terpene synthase with all or a contiguous portion of the corresponding domain of a second synthase.

(see, U.S. Pat. Nos. 5,824,774, 6,072,045, 7,186,891 and 8,106,260, and U.S. Pat. Pub. No. 20110081703). Also, gene shuffling methods can be employed to generate chimeric polypeptides and/or polypeptides with domain or region swaps.

For example, corresponding domains or regions of any two terpene synthases can be exchanged using any suitable recombinant method known in the art, or by in vitro synthesis. Exemplary of recombinant methods is a two stage overlapping PCR method, such as described herein. In such methods, primers that introduce mutations at a plurality of codon positions in the nucleic acids encoding the targeted domain or portion thereof in the first terpene synthase can be employed, wherein the mutations together form the heterologous region (i.e. the corresponding region from the second terpene synthase). Alternatively, for example, randomized amino acids can be used to replace specific domains or regions. It is understood that primer errors, PCR errors and/or other errors in the cloning or recombinant methods can result in errors such that the resulting swapped or replaced region or domain does not exhibit an amino acid sequence that is identical to the corresponding region from the second terpene synthase.

In an exemplary PCR-based method, the first stage PCR uses (i) a downstream primer that anneals downstream of the region that is being replaced with a mutagenic primer that includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene, and (ii) an upstream primer that anneals upstream of the region that is being replaced together with an opposite strand mutagenic primer that also includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene. If a replacement in which a domain or region of a first terpene synthase gene is replaced with the corresponding domain or region from a second terpene synthase is being performed, nucleotides in the mutagenic primers between the flanking regions from the first terpene synthase contain codons for the corresponding region of the second terpene synthase. In instances where the amino acids in a domain or region are to be randomized, nucleotides of the mutagenic primers between the flanking regions from the first terpene synthase contains random nucleotides. An overlapping PCR is then performed to join the two fragments, using the upstream and downstream oligo. The resulting PCR product then can be cloned into any suitable vector for expression of the modified terpene synthase.

Further, any of the modified sclareol synthase polypeptides containing swap mutations herein can contain one or more further amino acid replacements. Exemplary amino acid substitutions (or replacements) that can be included in the modified sclareol synthase polypeptides include, but are not limited to, H31P, G52E, G59V, P65S, H110L, L240P, F289L, D299N, I586V, V702A or V725M with reference to the positions set forth in SEQ ID NO:31.

e. Additional Variants

Sclareol synthase polypeptides provided herein can be modified by any method known to one of skill in the art for generating protein variants, including, but not limited to, DNA or gene shuffling, error prone PCR, overlap PCR or other recombinant methods. In one example, nucleic acid molecules encoding any sclareol synthase polypeptide or variant sclareol synthase polypeptide provided herein can be modified by gene shuffling. Gene shuffling involves one or more cycles of random fragmentation and reassembly of at least two nucleotide sequences, followed by screening to select nucleotide sequences encoding polypeptides with desired properties. The recombination can be performed in vitro (see Stemmer et al. (1994) *Proc Natl Acad Sci USA* 91:10747-10751; Stemmer et al. (1994) *Nature* 370:389-391; Crameri et al. (1998) *Nature* 391:288-291; U.S. Pat. Nos. 5,605,793, 5,811,238, 5,830,721, 5,834,252 and 5,837,458) or in vivo (see, International Pat. Pub. No. WO199707205). The nucleic acid molecules encoding the polypeptides then can be introduced into a host cell to be expressed heterologously and tested for sclareol synthase activity by any method described in section D below.

3. Fusion or Chimeric LPP and Sclareol Synthase Polypeptides

Nucleic acid molecules provided herein include fusion or chimeric nucleic acid molecules that contain an LPP synthase and a sclareol synthase. For example, provided herein are nucleic acid molecules encoding a fusion polypeptide that is capable of catalyzing the formation of sclareol from GGPP that contains any LPP synthase and sclareol synthase provided herein. For example, provided herein are nucleic acid molecules encoding a fusion polypeptide that contains an LPP synthase set forth in any of SEQ ID NOS:54, 2, 4, 6, 8, 10, 12 or 14 and a sclareol synthase set forth in any of SEQ ID NOS:31, 36, 38, 40 or 78. Also provided herein are fusion polypeptides containing an LPP synthase set forth in any of SEQ ID NOS:54, 2, 4, 6, 8, 10, 12 or 14 and a sclareol synthase set forth in any of SEQ ID NOS:31, 36, 38, 40 or 78. Exemplary of such a fusion polypeptide is a fusion polypeptide set forth in SEQ ID NO:94 that contains an LPP synthase having a sequence of amino acids set forth in SEQ ID NO:130 and an sclareol synthase having a sequence of amino acids set forth in SEQ ID NO:131. The fusion polypeptides can be linked directly or via a linker. For example, provided herein are fusion polypeptides containing a green fluorescent protein (SEQ ID NO:98) or a cellulose binding domain, such as the cellulose binding domain from *Trichoderma harzianum* (SEQ ID NO:97) fused to a sclareol synthase polypeptide. Exemplary of such fusion polypeptides are the fusion polypeptides set forth in SEQ ID NOS:90 and 92, respectively.

In another example, provided herein is a nucleic acid molecule that encodes an LPP synthase and a sclareol synthase, such that, when expressed in a host cell, such as a bacterial or yeast host cell, an LPP synthase and an sclareol synthase are expressed. Exemplary of such nucleic acid molecules is the vector set forth in SEQ ID NO:74 and the nucleic acid set forth in SEQ ID NO:95. Further, when the host cell is capable of producing GGPP, the encoded synthase polypeptides catalyze the production of sclareol.

D. METHODS FOR PRODUCING MODIFIED LPP AND SCLAREOL SYNTHASES AND ENCODING NUCLEIC ACID MOLECULES

Provided are methods for producing modified terpene synthase polypeptides, including LPP synthase and sclareol synthase polypeptides. The methods can be used to generate terpene synthases with desired properties, including, but not limited to, increased terpene production upon reaction with an acyclic pyrophosphate terpene precursor, such as FPP, GPP or GGPP; altered product distribution; altered substrate specificity; and/or altered regioselectivity and/or stereoselectivity. Modified terpene synthases can be produced using any method known in the art and, optionally, screened for the desired properties. In particular examples, modified terpene synthases with desired properties are generated by mutation in accord with the methods exemplified herein. Thus, provided herein are modified terpene synthases and nucleic acid molecules encoding the modified terpene synthases that are produced using the methods described herein.

Exemplary of the methods provided herein are those in which modified terpene synthases are produced by replacing one or more endogenous domains or regions of a first terpene synthase with the corresponding domain(s) or regions(s) from a second terpene synthase (i.e. heterologous domains or regions). In further examples, two or more endogenous domains or regions of a first terpene synthase are replaced with the corresponding heterologous domain(s) or regions(s) from two or more other terpene synthases, such as a second, third, fourth, fifth, sixth, seventh, eighth, ninth, or tenth terpene synthase. Thus, the resulting modified terpene synthase can include heterologous domains or regions from 1, 2, 3, 4, 5, 6, 7, 8, 9 or more different terpene synthases. In further examples, the methods also or instead include replacing one or more domains or regions of a first terpene synthase with randomized amino acid residues.

Any terpene synthase can be used in the methods provided herein. The first terpene synthase (i.e. the terpene synthase to be modified) can be of the same or different class as the second (or third, fourth, fifth, etc.) terpene synthase (i.e. the terpene synthase(s) from which the heterologous domain(s) or region(s) is derived). For example, included among the methods provided herein are those in which the terpene synthase to be modified is a monoterpene, diterpene or sesquiterpene synthase, and the terpene synthase(s) from which the one or more heterologous domains or regions are derived is a monoterpene, diterpene or sesquiterpene synthase. In some examples, all of the terpene synthases used in the methods provided herein are diterpene synthases. Exemplary diterpene synthases include, but are not limited to, labdenediol diphosphate synthases, sclareol synthases, copalyl diphosphate synthases, ent-copalyl diphosphate synthases, abietadiene synthases, abienol synthases, kaurene synthases, taxadiene synthases, ent-kaurene synthases, stemer-13-ene synthases, abietadiene/levopimaradiene synthases, levopimaradiene synthases and isopimaradiene synthases. Exemplary terpene synthases that can be used in the methods herein, including exemplary amino acid and nucleic acid sequences thereof, include but are not limited to, any described, for example, in published International PCT application No. WO2012/058636.

In practicing the methods provided herein, all or a contiguous portion of an endogenous domain of a first terpene synthase can be replaced with all or a contiguous portion of the corresponding heterologous domain from a second terpene synthase. For example, 3, 4, 5, 6, 7, 8, 9, 10 or more contiguous amino acids from a domain or region in a first synthase can be replaced with 3, 4, 5, 6, 7, 8, 9, 10 or more contiguous amino acids from the corresponding region from a second terpene synthase. In some examples, one or more amino acid residues adjacent to the endogenous domain of the first terpene synthase also are replaced, and/or one or more amino acid residues adjacent to the heterologous domain also are used in the replacement. Further, the methods provided herein also include methods in which all or a contiguous portion of a first domain and all or a contiguous portion of a second adjacent domain are replaced with the corresponding domains (or portions thereof) from another terpene synthase.

Domains or regions that can be replaced include functional domains or structural domains. Exemplary α-helical domains that can be replaced in an LPP synthase using the methods described herein include, but are not limited to, the α domain, amino acids 537-801 of SEQ ID NO:54; the γ domain, amino acids 111-326 of SEQ ID NO:54; the β1 domain, amino acids 88-110 of SEQ ID NO:54; and the β2 domain, amino acids 327-536 of SEQ ID NO:54. Exemplary domains or regions that can be replaced in a LPP synthase using the methods described herein include, but are not limited to, structural domains or regions corresponding to Helix A, amino acids 89-103 of SEQ ID NO:54; Loop 1, amino acids 104-113 of SEQ ID NO:54; Helix B, amino acids 114-121 of SEQ ID NO:54; Loop 2, amino acids 122-138 of SEQ ID NO:54; Helix C, amino acids 139-146 of SEQ ID NO:54; Loop 3, amino acids 147-161 of SEQ ID NO:54; Helix D, amino acids 162-177 of SEQ ID NO:54; Loop 4, amino acids 178-182 of SEQ ID NO:54; Helix E, amino acids 183-200 of SEQ ID NO:54; Loop 5, amino acids 201-211 of SEQ ID NO:54; Helix F1, amino acids 212-225 of SEQ ID NO:54; Loop 7, amino acids 226-239 of SEQ ID NO:54; Helix G, amino acids 240-248 of SEQ ID NO:54; Loop 8, amino acids 249-252 of SEQ ID NO:54; Helix H, amino acids 253-256 of SEQ ID NO:54; Loop 9, amino acids 257-275 of SEQ ID NO:54; Helix I, amino acids 276-281 of SEQ ID NO:54; Loop 10, amino acids 282-292 of SEQ ID NO:54; Helix J, amino acids 293-302 of SEQ ID NO:54; Loop 11, amino acids 303-306 of SEQ ID NO:54; Helix K, amino acids 307-318 of SEQ ID NO:54; Loop 12, amino acids 319-328 of SEQ ID NO:54; Helix L, amino acids 329-343 of SEQ ID NO:54; Loop 13, amino acids 344-349 of SEQ ID NO:54; Helix M, amino acids 350-363 of SEQ ID NO:54; Loop 14, amino acids 364-380 of SEQ ID NO:54; Helix N, amino acids 381-394 of SEQ ID NO:54; Loop 15, amino acids 395-422 of SEQ ID NO:54; Helix O, amino acids 423-433 of SEQ ID NO:54; Loop 16, amino acids 434-441 of SEQ ID NO:54; Helix P, amino acids 442-460 of SEQ ID NO:54; Loop 17, amino acids 461-472 of SEQ ID NO:54; Helix Q, amino acids 473-482 of SEQ ID NO:54; Loop 18, amino acids 483-489 of SEQ ID NO:54; Helix R, amino acids 490-498 of SEQ ID NO:54; Loop 19, amino acids 499-522 of SEQ ID NO:54; Helix S, amino acids 523-551 of SEQ ID NO:54; Loop 20, amino acids 552-561 of SEQ ID NO:54; Helix T, amino acids 562-575 of SEQ ID NO:54; Loop 21, amino acids of 576-581 SEQ ID NO:54; Helix U, amino acids 582-600 of SEQ ID NO:54; Loop 22, amino acids 601-613 of SEQ ID NO:54; Helix V, amino acids 614-623 of SEQ ID NO:54; Loop 23, amino acids 624-633 of SEQ ID NO:54; Helix W, amino acids 634-654 of SEQ ID NO:54; Loop 24, amino acids 655-661 of SEQ ID NO:54; Helix X, amino acids 662-675 of SEQ ID NO:54; Loop 25, amino acids 676-678 of SEQ ID NO:54; Helix Y, amino acids 679-686 of SEQ ID NO:54; Loop 26, amino acids 687-709 of SEQ ID NO:54; Helix Z1, amino acids 710-730 of SEQ ID NO:54; Loop 28, amino acids 731-737 of SEQ ID NO:54; Helix AA, amino acids 738-754 of SEQ ID NO:54; Loop 29, amino acids 755-764 of SEQ ID NO:54; Helix AB, amino acids 765-782 of SEQ ID NO:54; Loop 30, amino acids 783-788 of SEQ ID NO:54; Helix AC, amino acids 789-796 of SEQ ID NO:54 and Loop 31, amino acids 797-801 of SEQ ID NO:54. Any one or more of these domains or regions, or a portion thereof, can be replaced with a corresponding domain from another terpene synthase using the methods provided herein. These domains are regions can be identified in any terpene synthase using methods well known in the art, such as, for example, by alignment using methods known to those of skill in the art (see, e.g., FIGS. 3A-3D). Such methods typically maximize matches, and include methods such as using manual alignments and by using the numerous alignment programs available (for example, BLASTP) and others known to those of skill in the art. By aligning the sequences of the LPP synthase set forth in SEQ ID NO:54, and any other terpene synthase, any of the domains or regions recited above can be identified in any terpene synthase.

Any one or more of these domains or regions, or a portion thereof, can be replaced with a corresponding domain from another terpene synthase using the methods provided herein. Exemplary α-helical domains that can be replaced in a sclareol synthase using the methods described herein include, but are not limited to, the α domain, amino acids 477-788 of SEQ ID NO:31; the γ domain, amino acids 63-278 of SEQ ID NO:31; the β1 domain, amino acids 40-62 of SEQ ID NO:31; and the β2 domain, amino acids 279-476 of SEQ ID NO:31. Exemplary domains or regions that can be replaced in a sclareol synthase using the methods described herein include, but are not limited to, structural domains or regions corresponding to Loop 1, amino acids 40-41 of SEQ ID NO:31; Helix A, amino acids 42-54 of SEQ ID NO:31; Loop 2, amino acids 55-65 of SEQ ID NO:31; Helix B, amino acids 66-73 of SEQ ID NO:31; Loop 3, amino acids 74-87 of SEQ ID NO:31; Helix C, amino acids 88-95 of SEQ ID NO:31; Loop 4, amino acids 96-112 of SEQ ID NO:31; Helix D, amino acids 113-129 of SEQ ID NO:31; Loop 5, amino acids 130-133 of SEQ ID NO:31; Helix E, amino acids 134-148 of SEQ ID NO:31; Loop 6, amino acids 149-161 of SEQ ID NO:31; Helix F, amino acids 162-176 of SEQ ID NO:31; Loop 7, amino acids 177-184 of SEQ ID NO:31; Helix G, amino acids 185-199 of SEQ ID NO:31; Loop 8, amino acids 200-202 of SEQ ID NO:31; Helix H, amino acids 203-207 of SEQ ID NO:31; Loop 9, amino acids 208-225 of SEQ ID NO:31; Helix I, amino acids 226-230 of SEQ ID NO:31; Loop 10, amino acids 231-242 of SEQ ID NO:31; Helix J, amino acids 243-251 of SEQ ID NO:31; Loop 11, amino acids 242-257 of SEQ ID NO:31; Helix K, amino acids 258-270 of SEQ ID NO:31; Loop 12, amino acids 271-280 of SEQ ID NO:31; Helix L, amino acids 281-295 of SEQ ID NO:31; Loop 13, amino acids 296-301 of SEQ ID NO:31; Helix M, amino acids 302-315 of SEQ ID NO:31; Loop 14, amino acids 316-326 of SEQ ID NO:31; Helix N, amino acids 327-339 of SEQ ID NO:31; Loop 15, amino acids 340-346 of SEQ ID NO:31; Helix O, amino acids 347-351 of SEQ ID NO:31; Loop 16, amino acids 352-368 of SEQ ID NO:31; Helix P, amino acids 369-379 of SEQ ID NO:31; Loop 17, amino acids 380-389 of SEQ ID NO:31; Helix Q, amino acids 390-406 of SEQ ID NO:31; Loop 18, amino acids 407-414 of SEQ ID NO:31; Helix R, amino acids 415-424 of SEQ ID NO:31, amino acids 425-430 of SEQ ID NO:31; Loop 19, amino acids 431-441 of SEQ ID NO:31; Helix S, amino acids 442-462 of SEQ ID NO:31; Loop 20, amino acids 463-491 of SEQ ID NO:31; Helix T, amino acids 492-501 of SEQ ID NO:31; Loop 21; Helix U, amino acids 505-513 of SEQ ID NO:31; Loop 22, amino acids 514-521 of SEQ ID NO:31; Helix V, amino acids 522-543 of SEQ ID NO:31; Loop 23, amino acids 544-547 of SEQ ID NO:31; Helix W, amino acids 548-560 of SEQ ID NO:31; Loop 24, amino acids 561-571 of SEQ ID NO:31; Helix X, amino acids 572-596 of SEQ ID NO:31; Loop 25, amino acids 579-600 of SEQ ID NO:31; Helix Y, amino acids 601-619 of SEQ ID NO:31; Loop 26, amino acids 620-630 of SEQ ID NO:31; Helix Z, amino acids 631-641 of SEQ ID NO:31; Loop 27, amino acids 642-644 of SEQ ID NO:31; Helix AA, amino acids 645-652 of SEQ ID NO:31; Loop 28, amino acids 653-660 of SEQ ID NO:31; Helix AB, amino acids 661-664 of SEQ ID NO:31; Loop 29, amino acids 665-670 of SEQ ID NO:31; Helix AC, amino acids 671-685 of SEQ ID NO:31; Loop 30, amino acids 686-688 of SEQ ID NO:31; Helix AD, amino acids 689-692 of SEQ ID NO:31; Loop 31, amino acids 693-700 of SEQ ID NO:31; Helix AE, amino acids 701-708 of SEQ ID NO:31; Loop 32, amino acids 709-713 of SEQ ID NO:31; Helix AF, amino acids 714-738 of SEQ ID NO:31; Loop 33, amino acids 739-746 of SEQ ID NO:31; Helix AG, amino acids 747-762 of SEQ ID NO:31; Loop 34, amino acids 763-774 of SEQ ID NO:31; Helix AH, amino acids 775-785 of SEQ ID NO:31; and Loop 35, amino acids 783-788 of SEQ ID NO:31. These domains are regions can be identified in any terpene synthase using methods well known in the art, such as, for example, by alignment using methods known to those of skill in the art (see, e.g., FIGS. 3A-3D). Such methods typically maximize matches, and include methods such as using manual alignments and by using the numerous alignment programs available (for example, BLASTP) and others known to those of skill in the art. By aligning the sequences of the sclareol synthase set forth in SEQ ID NO:31, and any other terpene synthase, any of the domains or regions recited above can be identified in any terpene synthase.

In the methods provided herein, all or a contiguous portion of an endogenous domain of a first terpene synthase can be replaced with all or a contiguous portion of the corresponding heterologous domain from a second terpene synthase using an suitable recombinant method known in the art as discussed above in Sections C.1.d. and C.2.d.

E. EXPRESSION OF LPP AND SCLAREOL SYNTHASE POLYPEPTIDES AND ENCODING NUCLEIC ACID MOLECULES

Terpene synthase polypeptides and active fragments thereof, including labdenediol diphosphate synthases and sclareol synthase polypeptides, can be obtained by methods well known in the art for recombinant protein generation and expression. Such LPP synthase polypeptides can be used to produce labdenediol diphosphate from any suitable acyclic pyrophosphate precursor, such as GGPP, in the host cell from which the synthase is expressed, or in vitro following purification of the synthase. Such sclareol synthase polypeptides can be used to produce sclareol from labdenediol diphosphate in the host cell from which the synthase is expressed, or in vitro following purification of the synthase. Such LPP and sclareol synthase polypeptides can be used to produce sclareol from any suitable acyclic pyrophosphate precursor, such as GGPP, in the host cell in which the synthases are expressed. Any method known to those of skill in the art for identification of nucleic acids that encode desired genes can be used to obtain the nucleic acid encoding a terpene synthase, such as a labdenediol synthase or sclareol synthase. For example, nucleic acid encoding unmodified or wild type labdenediol diphosphate synthase or sclareol synthase polypeptides can be obtained using well known methods from a plant source, such as tobacco. Modified labdenediol diphosphate synthase and sclareol synthase polypeptides then can be engineered using any method known in the art for introducing mutations into unmodified or wild type LPP and sclareol synthase polypeptides, including any method described herein, such as random mutagenesis of the encoding nucleic acid by error-prone PCR, site-directed mutagenesis, overlap PCR, or other recombinant methods. The nucleic acids encoding the polypeptides then can be introduced into a host cell to be expressed heterologously.

In some examples, the terpene synthases provided herein, including LPP and sclareol synthase polypeptides, are produced synthetically, such as using solid phase or solution phase peptide synthesis.

1. Isolation of Nucleic Acid Encoding LPP and Sclareol Synthases

Nucleic acids encoding terpene synthases, such as labdenediol diphosphate synthase and sclareol synthase, can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding a LPP or sclareol synthase polypeptide, including for example, polymerase chain reaction (PCR) methods. A nucleic acid containing material can be used as a starting material from which a LPP or sclareol synthase-encoding nucleic acid molecule can be isolated. For example, DNA and mRNA preparations from tobacco (*Nicotiana* sp.), including but not limited to *Nicotiana glutinosa* can be used to obtain LPP and sclareol synthase genes. Nucleic acid libraries also can be used as a source of starting material. Primers can be designed to amplify a terpene synthase-encoding molecule, such as a LPP or sclareol synthase-encoding molecule. For example, primers can be designed based on known nucleic acid sequences encoding a terpene synthase, such as a class I or class II diterpene synthase, such as those set forth in SEQ ID NOS:34-46. Nucleic acid molecules generated by amplification can be sequenced and confirmed to encode a diTPS polypeptide.

Additional nucleotide sequences can be joined to a LPP or sclareol synthase-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a LPP or sclareol synthase-encoding nucleic acid molecule. Still further, nucleic acid encoding other moieties or domains also can be included so that the resulting synthase is a fusion protein. For example, nucleic acids encoding other enzymes, such as GGPP synthase, LPP synthase or sclareol synthase, or protein purification tags, such as His or Flag tags.

2. Generation of Mutant or Modified Nucleic Acid

Nucleic acid encoding a modified terpene synthase, such as a modified LPP or sclareol synthase, can be prepared or generated using any method known in the art to effect mutation. Methods for modification include standard rational and/or random mutagenesis of encoding nucleic acid molecules (using e.g., error prone PCR, random site-directed saturation mutagenesis, DNA shuffling or rational site-directed mutagenesis, such as, for example, mutagenesis kits (e.g. QuikChange available from Stratagene)). In addition, routine recombinant DNA techniques can be utilized to generate nucleic acids encoding polypeptides that contain heterologous amino acid. For example, nucleic acid encoding chimeric polypeptides or polypeptides containing heterologous amino acid sequence, can be generated using a two-step PCR method, such as described above, and/or using restriction enzymes and cloning methodologies for routine subcloning of the desired chimeric polypeptide components.

Once generated, the nucleic acid molecules can be expressed in cells to generate modified terpene synthase polypeptides using any method known in the art. The modified terpene synthase polypeptides, such as modified LPP or sclareol synthase polypeptides, then can be assessed by screening for a desired property or activity, for example, for the ability to produce a terpene from a substrate. In particular examples, modified terpene synthases with desired properties are generated by mutation and screened for a property in accord with the examples exemplified herein. Typically, in instances where a modified LPP synthase is generated, the modified LPP synthase polypeptides produce LPP from GGPP. Typically, in instances where a modified sclareol synthase is generated, the modified sclareol synthase polypeptides produced sclareol from labdenediol diphosphate.

3. Vectors and Cells

Figure 5A:
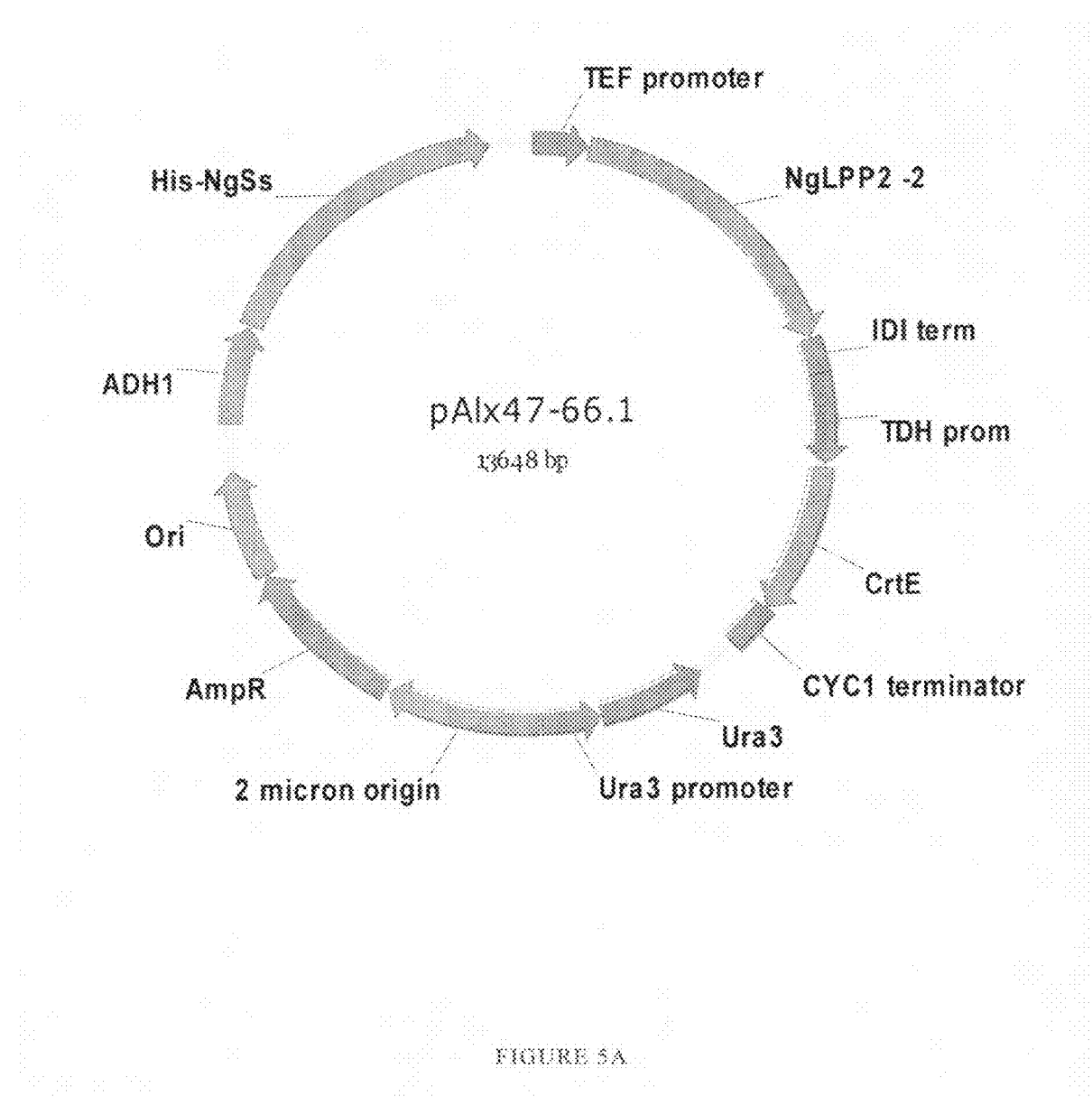
FIGS. 5A and 5B depict vector maps of the yeast expression vectors pALX47-66.1 and pALX40-170.2R, set forth in SEQ ID NOS:74 and 76, respectively, and described in Example 8.
Figure 5B:
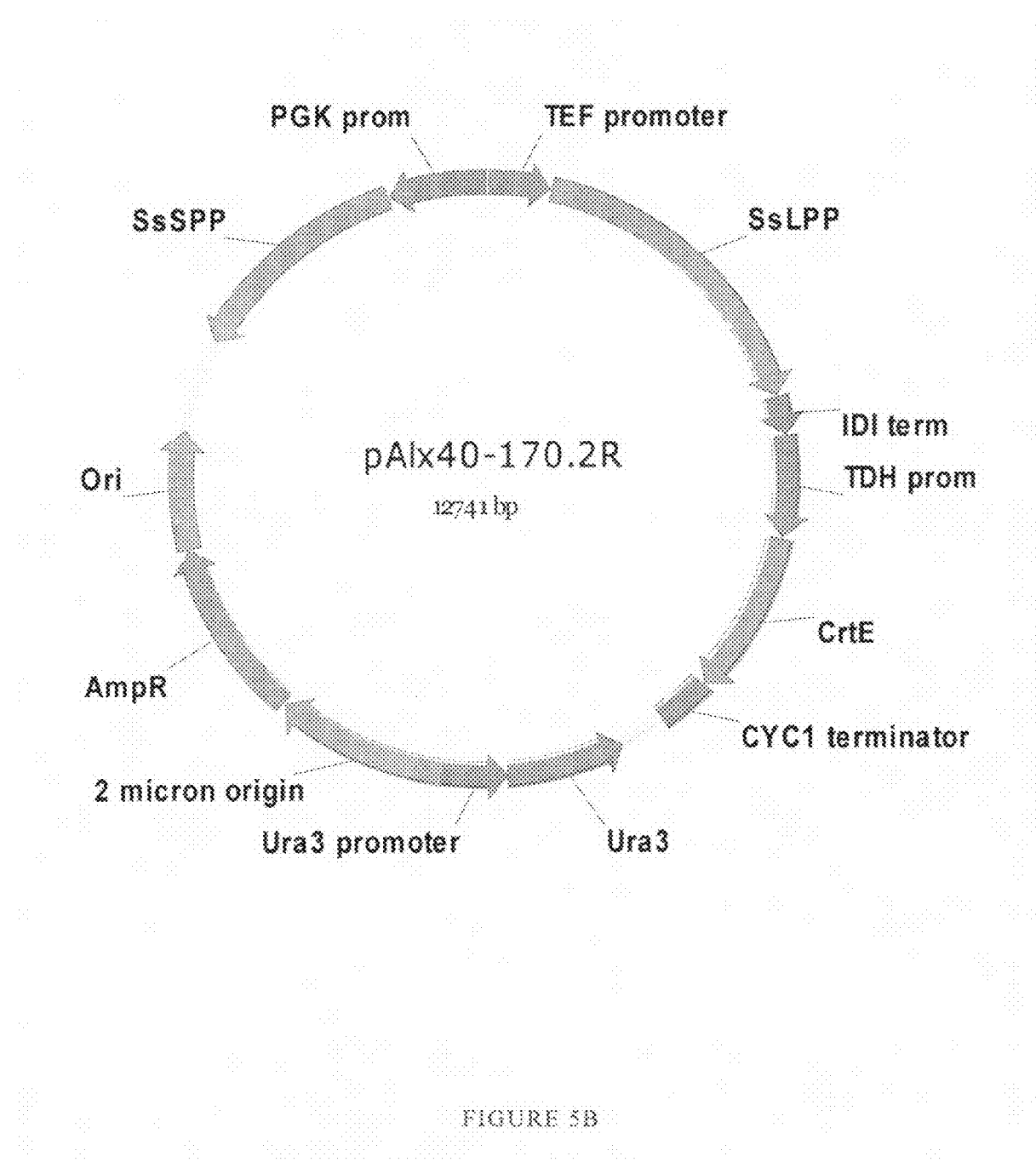

For recombinant expression of one or more of the terpene synthase polypeptides provided herein, including LPP and sclareol synthase polypeptides, the nucleic acid containing all or a portion of the nucleotide sequence encoding the synthase can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for a LPP or sclareol synthase gene, and/or their flanking regions. Thus, also provided herein are vectors that contain nucleic acid encoding any LPP and sclareol synthase polypeptide provided herein. Exemplary vectors are pALX47-66.1 and pALX40-170.2R set forth in SEQ ID NOS:74 and 76, respectively, and FIGS. 5A and 5B. These vectors contain the gene encoding the GGPP synthase crtE from *Xanthophyllomyces dendrorhous*. Both vectors also contain genes encoding a sclareol synthase and a labdenediol diphosphate synthase. The vectors are described in detail in Example 8 below. Cells, including prokaryotic and eukaryotic cells, containing the vectors also are provided. Such cells include bacterial cells, yeast cells, fungal cells, Archea, plant cells, insect cells and animal cells. In particular examples, the cells are yeast, such as *Saccharomyces cerevisiae*, that express an acyclic pyrophosphate terpene precursor, such as GGPP. The cells are used to produce a terpene synthase, such as a LPP synthase polypeptide or modified LPP synthase polypeptide, by growing the above-described cells under conditions whereby the encoded LPP synthase is expressed by the cell. In some instances, the expressed synthase is purified. In other instances, the expressed synthase, such as labdenediol diphosphate synthase, converts GGPP to one or moreterpenes (e.g. labdenediol diphosphate) in the host cell. In some examples, both an LPP and a sclareol synthase are expressed thereby converting GGPP to sclareol.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding a LPP or sclareol synthase polypeptide or modified LPP or sclareol synthase polypeptide, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a LPP or sclareol synthase protein. Promoters that can be used include but are not limited to prokaryotic, yeast, mammalian and plant promoters. The type of promoter depends upon the expression system used, described in more detail below.

In a specific embodiment, a vector is used that contains a promoter operably linked to nucleic acids encoding a LPP or sclareol synthase polypeptide or modified LPP or sclareol synthase polypeptide, or a domain, fragment, derivative or homolog, thereof, one or more origins of replication, and optionally, one or more selectable markers (e.g., an antibiotic resistance gene). Vectors and systems for expression of LPP and sclareol synthase polypeptides are described.

4. Expression Systems

Terpene synthase polypeptides, including LPP and sclareol synthase polypeptides (modified and unmodified) can be produced by any methods known in the art for protein production including in vitro and in vivo methods such as, for example, the introduction of nucleic acid molecules encoding the terpene synthase (e.g. LPP or sclareol synthase) into a host cell or host plant for in vivo production or expression from nucleic acid molecules encoding the terpene synthase (e.g. LPP or sclareol synthase) in vitro. Terpene synthases such as LPP and sclareol synthase and modified LPP and sclareol synthase polypeptides can be expressed in any organism suitable to produce the required amounts and forms of a synthase polypeptide. Expression hosts include prokaryotic and eukaryotic organisms such as E. coli, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Expression in eukaryotic hosts can include expression in yeasts such as those from the *Saccharomyces* genus (e.g. *Saccharomyces cerevisiae*) and *Pichia* genus (e.g. *Pichia pastoris*), insect cells such as *Drosophila* cells and *lepidopteran* cells, plants and plant cells such as citrus, tobacco, corn, rice, algae, and lemna. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Many expression vectors are available and known to those of skill in the art for the expression of a terpene synthase, such as LPP or sclareol synthase. Exemplary of expression vectors are those encoding a GGPP synthase, including the vectors pALX47-66.1 and pALX40-170.2R, set forth in SEQ ID NOS:74 and 76, respectively, and described elsewhere herein. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

Terpene synthases, including LPP or sclareol synthase and modified LPP or sclareol synthase polypeptides, also can be utilized or expressed as protein fusions. For example, a fusion can be generated to add additional functionality to a polypeptide. Examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association. In other examples, diterpene synthases such as LPP synthase or modified LPP synthase polypeptides can be fused to GGPP synthase (see, e.g., Brodelius et al. (2002) *Eur. J. Biochem.* 269:3570-3579).

Methods of production of terpene synthase polypeptides, including LPP and sclareol synthase polypeptides, can include co-expression of an acyclic pyrophosphate terpene precursor, such as GGPP, in the host cell. In some instances, the host cell naturally expresses GGPP. Such a cell can be modified to express greater quantities of GGPP (see e.g. U.S. Pat. Nos. 6,531,303, 6,689,593, 7,838,279 and 7,842,497). In other instances, a host cell that does not naturally produce GGPP is modified genetically to produce GGPP.

a. Prokaryotic Cells

Prokaryotes, especially *E. coli*, provide a system for producing large amounts of the LPP and sclareol synthase polypeptides provided herein. Transformation of *E. coli* is a simple and rapid technique well known to those of skill in the art. Exemplary expression vectors for transformation of *E. coli* cells, include, for example, the pGEM expression vectors, the pQE expression vectors, and the pET expression vectors (see, U.S. Pat. No. 4,952,496; available from Novagen, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator.

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad. Sci. USA* 80:21-25); see also "Useful Proteins from Recombinant Bacteria": in Scientific American 242:79-94 (1980)). Examples of inducible promoters include the lac promoter, the trp promoter, the hybrid tac promoter, the T7 and SP6 RNA promoters and the temperature regulated $\lambda P_L$ promoter.

Terpene synthases, including LPP and sclareol synthases can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression of LPP or sclareol synthases in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

b. Yeast Cells

Yeast systems, such as, but not limited to, those from the *Saccharomyces* genus (e.g. *Saccharomyces cerevisiae*), *Schizosaccharomyces pombe, Yarrowia lipolytica, Kluyveromyces lactis,* and *Pichia pastoris* can be used to express the terpene synthases, such as the LPP or sclareol synthase polypeptides and modified LPP and sclareol synthase polypeptides, provided herein. Yeast expression systems also can be used to produce terpenes whose reactions are catalyzed by the synthases. Yeast can be transformed with episomal replicating vectors or by stable chromosomal integration by homologous recombination. In some examples, inducible promoters are used to regulate gene expression. Exemplary promoter sequences for expression of LPP and sclareol synthase polypeptides in yeast include, among others, promoters for metallothionine, 3-phosphoglycerate kinase (Hitzeman et al. (1980) *J Biol. Chem.* 255:12073), or other glycolytic enzymes (Hess et al. (1968) *J Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene,* 107:285-195; and van den Berg et al. (1990) *Bio/Technology,* 8:135-139. Another alternative includes, but is not limited to, the glucose-repressible ADH2 promoter described by Russell et al. (*J. Biol. Chem.* 258: 2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* (Amp$^r$ gene and origin of replication) into the above-described yeast vectors.

Yeast expression vectors can include a selectable marker such as LEU2, TRP1, HIS3, and URA3 for selection and maintenance of the transformed DNA. Exemplary vectors include pALX47-66.1 and pALX40-170.R2, described elsewhere herein, that contain a URA3 marker. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally express the required proteins, including GGPP synthase (BST1; which can produce GGPP) for the mevalonate-dependent isoprenoid biosynthetic pathway. Thus, expression of the terpene synthases, including LPP and sclareol synthase polypeptides provided herein, in yeast cells can result in the production of diterpenes, such as labdenediol diphosphate from GGPP, and sclareol. Exemplary yeast cells for the expression of terpene synthases, including LPP and sclareol synthase polypeptides, include yeast modified to express increased levels of FPP and/or GGPP. For example, yeast cells can be modified to produce less squalene synthase or less active squalene synthase (e.g. erg9 mutants; see e.g. U.S. Pat. Nos. 6,531,303 and 6,689,593). This results in accumulation of FPP in the host cell at higher levels compared to wild type yeast cells, which in turn can result in increased yields of GGPP and diterpenes (e.g. labdenediol diphosphate and sclareol). In another example, yeast cells can be modified to produce more GGPP synthase by introduction of a GGPP synthase gene, such as BTS1 from *S. cerevisiae*, crtE from *Erwinia uredovora*, crtE from *Xanthophyllomyces dendrorhous*, al-3 from *Neuspora crassa* or ggs from *Giverella fujiuroi* (see U.S. Pat. No. 7,842,497). In some examples, the native GGPP gene in such yeast can be deleted. Other modifications that enable increased production of GGPP in yeast include, for example, but are not limited to, modifications that increase production of acetyl CoA, inactivate genes that encode enzymes that use FPP and GPP as substrate and overexpress of HMG-CoA reductases, as described in U.S. Pat. No. 7,842,497. Exemplary modified yeast cells include, but are not limited to, modified *Saccharomyces cerevisiae* strains CALI5-1 (ura3, leu2, his3, trp1, Δ erg9::HIS3, HMG2cat/TRP1::rDNA, dpp1, sue), ALX7-95 (ura3, his3, trp1, Δerg9::HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, and published U.S. Pat. Application Serial Nos. 20040249219 and 20110189717.

c. Plants and Plant Cells

Transgenic plant cells and plants can be used for the expression of terpene synthases, including LPP and sclareol synthase polypeptides provided herein. Expression constructs are typically transferred to plants using direct DNA transfer such as microprojectile bombardment and PEG-mediated transfer into protoplasts, and with agrobacterium-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Nicotiana, Solanum, Sorghum, Arabidopsis, Medicago* (alfalfa), *Gossypium* (cotton) and *Brassica* (rape). In some examples, the plant belongs to the species of *Nicotiana tabacum*, and is transformed with vectors that overexpress LPP synthase, sclareol synthase and geranylgeranyl diphosphate synthase, such as described in U.S. Pat. Pub. No. 20090123984 and U.S. Pat. No. 7,906,710.

d. Insects and Insect Cells

Insects and insect cells, particularly a baculovirus expression system, can be used for expressing terpene synthases, including LPP and sclareol synthase polypeptides provided herein (see, for example, Muneta et al. (2003) *J. Vet. Med. Sci.* 65(2):219-223). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

e. Mammalian Expression

Mammalian expression systems can be used to express terpene synthases, including LPP and sclareol synthase polypeptides provided herein and also can be used to produce terpenes whose reactions are catalyzed by the synthases. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_\epsilon$RI-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NS0 (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-42).

5. Purification

Methods for purification of terpene synthases, such as LPP and sclareol synthase polypeptides, from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

Terpene synthases, including LPP and sclareol synthases, can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or His$_6$ and affinity purified with myc antibody, glutathione resin, and Ni-resin, respectively, to a protein. Purity can be assessed by any method known in the art including gel electrophoresis and staining and spectrophotometric techniques.

6. Fusion Proteins

Fusion proteins containing a terpene synthase, including LPP and sclareol synthase polypeptides, and one or more other polypeptides also are provided. Linkage of a terpene synthase polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of a terpene synthase, such as a LPP or sclareol synthase polypeptide, to another polypeptide can be to the N- or C-terminus of the LPP or sclareol synthase polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). A LPP synthase polypeptide-encoding nucleic acid can be cloned into such an expression vector such that the fusion moiety is linked in-frame to the LPP synthase protein. A sclareol synthase polypeptide-encoding nucleic acid can be cloned into such an expression vector such that the fusion moiety is linked in-frame to the sclareol synthase protein. In some examples, a LPP synthase polypeptide-encoding nucleic acid can be cloned into such an expression vector such that the LPP synthase is linked in frame to a sclareol synthase polypeptide-encoding nucleic acid (as described for example in Example 8). The LPP and sclareol synthases can be linked directly, without a linker, or alternatively, linked indirectly in-frame with a linker (as described for example in Example 10).

F. METHODS FOR PRODUCING TERPENES CATALYZED BY LPP AND SCLAREOL SYNTHASES AND METHODS FOR DETECTING SUCH PRODUCTS AND THE ACTIVITY OF THE LPP AND SCLAREOL SYNTHASES

The LPP and sclareol synthases provided herein can be used to, and assessed for their ability to, produce terpenes, including monoterpenes, diterpenes and sesquiterpenes, from any suitable acyclic pyrophosphate terpene precursor, including, but not limited to, farnesyl diphosphate (FPP), geranyl diphosphate (GPP) or geranyl-geranyl diphosphate (GGPP). Typically, the LPP synthase polypeptides provided herein produce labdenediol diphosphate from GGPP and the sclareol synthase polypeptides provided herein produce sclareol from labdenediol diphosphate. In some examples, the LPP synthase polypeptides provided herein produce labdenediol diphosphate from GGPP under conditions such that the labdenediol diphosphate is converted to sclareol. Any method known to one of skill in the art can be used to produce terpenes, including labdenediol diphosphate and sclareol, catalyzed by the LPP and sclareol synthases provided herein. The ability of the LPP and sclareol synthases provided herein to catalyze the formation of labdenediol diphosphate and sclareol, respectively, from GGPP and LPP substrates can be assessed using these methods.

Other activities and properties of the terpene synthases, such as the LPP and sclareol synthases provided herein, also can be assessed using methods and assays well known in the art. In addition to assessing the activity of the synthases and their ability to catalyze the formation of terpenes, the kinetics of the reaction, modified regiochemistry or stereochemistry, altered substrate utilization and/or altered product distribution (as compared to another LPP or sclareol synthase) can be assessed using methods well known in the art. For example, the amount and type of terpenes produced from GGPP or labdenediol diphosphate by the LPP or sclareol synthase polypeptides can be assessed by gas chromatography methods (e.g. GC-MS), such as those described in Examples 4 and 7.

Provided below are methods for the production of labdenediol diphosphate, labdenediol, sclareol and (−)-ambroxide, where production of LPP and sclareol is catalyzed by the LPP and sclareol synthase polypeptides provided herein.

1. Labdenediol Diphosphate and Labdenediol

The labdenediol diphosphate synthase polypeptides provided herein can be used to catalyze the formation of labdenediol diphosphate from an acyclic pyrophosphate precursor, such as GGPP. In some examples, the LPP synthase polypeptides provided herein are expressed in cells that produce or overproduce GGPP, such that labdenediol diphosphate is produced as described elsewhere herein. In other examples, the labdenediol diphosphate synthase polypeptides provided herein are expressed and purified from any suitable host cell, such as described in Section E. The purified synthases are then combined in vitro with a GGPP to produce labdenediol diphosphate. Labdenediol diphosphate production is determined following conversion of labdenediol diphosphate to labdenediol, such as, by addition of an alkaline phosphatase.

In some examples, the labdenediol diphosphate synthase polypeptide provided herein is overexpressed and purified as described in Section E above. The labdenediol diphosphate synthase is then incubated with the substrate geranylgeranyl diphosphate and labdenediol diphosphate is produced. Treatment of the reaction mixture with alkaline phosphatase results in the formation of labdenediol. An organic solvent is added to partition the labdenediol into the organic phase for analysis. Production of labdenediol and quantification of the amount of product are then determined using any method provided herein, such as gas chromatography-mass spectroscopy (e.g. GC-MS) using an internal standard. Alternatively, the labdenediol diphosphate synthase is expressed in host cells that also produce GGPP, resulting in the production of labdenediol diphosphate. Labdenediol diphosphate is converted to labdenediol by addition of alkaline phosphatase to the cell culture medium. Labdenediol then can be extracted from the cell culture medium with an organic solvent and subsequently isolated or purified by any known method, such as column chromatography or HPLC, and the amount and purity of the recovered labdenediol are assessed.

Labdenediol diphosphate can readily undergo chemical or enzymatic modifications, depending on the conditions under which the reaction is carried out, resulting in the formation of labdenediol, sclareol and/or other terpenes. In some examples, the labdenediol diphosphate is converted to sclareol by addition of a sclareol synthase. In other examples, the labdenediol diphosphate is converted to sclareol under acidic conditions by acid rearrangement. For example, when the pH of the reaction medium or cell culture medium is 7 or below 7, the amount of sclareol produced is increased compared to other terpene products (see, e.g. International Pat. Pub. No. WO2009044336). In such examples, as the amount of sclareol increases, the amount of labdenediol decreases. Thus, in some examples provided herein, a labdenediol diphosphate synthase is reacted with GGPP in vitro, or in vivo in cells that produce GGPP, under acidic conditions and sclareol is isolated. In other examples, the reaction is carried out in the absence of $Mg^{2+}$, resulting in increased amounts of sclareol compared to other reaction products.

In yet other examples, the reaction products formed when a LPP synthase provided herein is reacted with GGPP, either in vitro, or in vivo in cells that produce GGPP, varies depending on the presence or absence of phosphatases. As indicated above, treatment with a phosphatase, such as alkaline phosphatase, results in the conversion of labdenediol diphosphate to labdenediol. In other examples, inhibition of phosphatases, for example, by addition of the inhibitor $Na_3VO_4$, results in suppression of phosphatase activity and an increased proportion of labdenediol diphosphate as compared to labdenediol.

2. Sclareol

The sclareol synthase polypeptides provided herein catalyze the formation of sclareol from labdenediol diphosphate. In some examples, the sclareol synthase polypeptides provided herein are expressed and purified from any suitable host cell, such as described in Section E. The purified synthases are then combined in vitro with labdenediol diphosphate to produce sclareol. In such examples, labdenediol diphosphate typically is generated by reaction of GGPP with a labdenediol diphosphate synthase, as described above. An organic solvent is added to partition the sclareol into the organic phase for analysis. Production of sclareol and quantification of the amount of product are then determined using any method provided herein, such as gas chromatography-mass spectroscopy (e.g. GC-MS) using an internal standard.

In some examples, sclareol is produced directly from geranylgeranyl diphosphate. In such examples, a labdenediol diphosphate synthase is incubated with the substrate GGPP generating labdenediol diphosphate, which is reacted with a sclareol synthase thereby producing sclareol. The two synthases can be added or present simultaneously or sequentially. Sclareol can be extracted from the cell culture medium with an organic solvent and subsequently isolated or purified by any known method, such as column chromatography or HPLC, and the amount and purity of the recovered sclareol are assessed. In some examples, the LPP synthase polypeptides and sclareol synthase polypeptides provided herein are expressed in cells that produce or overproduce GGPP, such that sclareol is produced directly from GGPP. Production of sclareol can be assessed as described above.

Alternatively, as described above, sclareol can be produced directly from labdenediol diphosphate under acidic conditions whereby labdenediol diphosphate undergoes rearrangement forming sclareol. The labdenediol diphosphate can be generated by any method known to one in the art. Typically, labdenediol diphosphate is generated by reaction of GGPP with a LPP synthase polypeptide provided herein. In such examples, use of an acidic medium promotes the formation of sclareol.

3. Production of Labdenediol Diphosphate and Sclareol a. Exemplary Cells

Labdenediol diphosphate and/or sclareol can be produced by expressing a labdenediol diphosphate synthase polypeptide and/or a sclareol synthase polypeptide provided herein in a cell line that produces GGPP as part of the mevalonate-dependent isoprenoid biosynthetic pathway (e.g. fungi, including yeast cells, and animal cells) or the mevalonate-independent isoprenoid biosynthetic pathway (e.g. bacteria and higher plants). In particular examples, labdenediol diphosphate is produced by expressing a labdenediol diphosphate synthase polypeptide provided herein in a cell line hat has been modified to overproduce GGPP. Labdenediol diphosphate can be converted to labdenediol or sclareol using any method described herein above. In other examples, sclareol is produced by expressing a labdenediol diphosphate synthase polypeptide provided herein and a sclareol synthase polypeptide provided herein in a cell line that has been modified to overproduce GGPP. Exemplary of such cells are modified yeast cells. For example, yeast cells that have been modified to produce less squalene synthase or less active squalene synthase (e.g. erg9 mutants; see eg. U.S. Pat. Nos. 6,531,303 and 6,689,593) are useful in the methods provided herein to produce labdenediol diphosphate. Reduced squalene synthase activity results in accumulation of FPP in the host cell at higher levels compared to wild type yeast cells, which in turn allows an increase in GGPP, thus allowing for increased yields of labdenediol diphosphate. Exemplary modified yeast cells include, but are not limited to, modified *Saccharomyces cerevisiae* strains CALI5-1 (ura3, leu2, his3, trp1, Δerg9::HIS3, HMG2cat/TRP1::rDNA, dpp1), ALX7-95 (ura3, his3, trp1, Δerg9::HIS3, HMG2cat/TRP1::rDNA, dpp1, sue), ALX11-30 (ura3, trp1, erg9$^{def}$25, HMG2cat/TRP1::rDNA, dpp1, sue), and those described in U.S. Pat. Nos. 7,838,279, 7,842,497, 6,531,303 and 6,689,593 and published U.S. Patent Appl. Nos. US20040249219 and 20110189717.

*Saccharomyces cerevisiae* strain CALI5-1 is a derivative of SW23B#74 (described in U.S. Pat. Nos. 6,531,303 and 6,689,593, and Takahashi et al. (2007) (*Biotechnol Bioeng.* 97(1): 170-181), which itself is derived from wild type strain ATCC 28383 (MATa). CALI5-1 was generated to have a decreased activity of the Dpp1 phosphatase (see e.g. U.S. Published Appl. No. US20040249219). *Saccharomyces cerevisiae* strain CALI5-1 contains, among other mutations, an erg9 mutation (the Δerg9::HIS3 allele) as well as a mutation supporting aerobic sterol uptake enhancement (sue). It also contains approximately 8 copies of the truncated HMG2 gene. The truncated form of HMG2 is driven by the GPD promoter and is therefore no longer under tight regulation, allowing for an increase in carbon flow to FPP. It also contains a deletion in the gene encoding diacylglycerol pyrophosphate (DGPP) phosphatase enzyme (dpp1), which limits dephosphorylation of FPP.

ALX7-95 and ALX11-30.1 are derivatives of CALI5-1. ALX7-95 was derived from CALI5-1 by correcting the Δleu2 deficiency of CALI5-1 with a functional leu gene so that leucine is not required to be supplemented to the media (see e.g. US2010/0151519). ALX11-30 was constructed from CALI5-1 in several steps, by 1) introducing a mutation into the ERG9 gene by error prone PCR and selecting for clones that produce a reporter protein in medium lacking ergosterol; 2) transforming such a clone with a complete HIS3 gene and selecting a transformant that grows in the absence of histidine; and 3) growing several generations of such a clone and selecting for a colony lacking the reporter protein (see, U.S. application Ser. No. 13/317,839).

b. Culture of Cells

In exemplary methods, a labdenediol diphosphate synthase provided herein is expressed in a host cell line that has been modified to overexpress geranylgeranyl diphosphate whereby upon expression of the labdenediol diphosphate synthase, geranylgeranyl diphosphate is converted to labdenediol diphosphate and/or sclareol. In other exemplary methods, a labdenediol diphosphate synthase and a sclareol synthase provided herein are expressed in a host cell line that has been modified to overexpress geranylgeranyl diphosphate whereby upon expression of both synthases, geranylgeranyl diphosphate is converted to sclareol. The LPP synthase and sclareol synthase can be expressed separately, or together, as a fusion protein described elsewhere herein. The LPP synthase and sclareol synthase can be expressed simultaneously or sequentially. The host cell is cultured using any suitable method well known in the art. In some examples, such as for high throughput screening of cell expressing various labdenediol diphosphate or sclareol synthases, the cells expressing the labdenediol diphosphate or sclareol synthase are cultured in individual wells of a 96-well plate. In other examples where the host cell is yeast, the cell expressing the labdenediol diphosphate synthase polypeptides and GGPP, or labdenediol diphosphate synthase polypeptide, sclareol synthase polypeptide and GGPP, is cultured using fermentation methods such as those described below.

A variety of fermentation methodologies can be utilized for the production of labdenediol diphosphate from yeast cells expressing the labdenediol diphosphate synthase polypeptides provided herein. For example, large scale production can be effected by either batch or continuous fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system, which is similar to a typical batch system with the exception that nutrients are added as the fermentation progresses. Fed-Batch systems are useful when catabolite repression tends to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as CO are generally measured and controlled in Fed-Batch fermentations.

Production of the labdenediol diphosphate and/or sclareol also can be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems aim to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art.

Following cell culture, the cell culture medium then can be harvested to obtain the produced labdenediol diphosphate as labdenediol after treatment with alkaline phosphatase, or sclareol.

c. Isolation and Assessment

The labdenediol and/or sclareol produced using the methods above with the labdenediol diphosphate synthase polypeptides and sclareol synthase polypeptides provided herein can be isolated and assessed by any method known in the art. In one example, the cell culture medium is extracted with an organic solvent to partition labdenediol, sclareol and any other terpene produced, into the organic layer. Labdenediol and/or sclareol production can be assessed and/or the labdenediol and/or sclareol isolated from other products using any method known in the art, such as, for example, gas chromatography or column chromatography. For example, the organic layer can be analyzed by gas chromatography.

The quantity of labdenediol and/or sclareol produced can be determined by any known standard chromatographic technique useful for separating and analyzing organic compounds. For example, labdenediol and/or sclareol production can be assayed by any known chromatographic technique useful for the detection and quantification of hydrocarbons, such as labdenediol and/or sclareol and other terpenes, including, but not limited to, gas chromatography mass spectrometry (GC-MS), gas chromatography using a flame ionization detector (GC-FID), capillary GC-MS, high performance liquid chromatography (HPLC) and column chromatography. Typically, these techniques are carried out in the presence of known internal standards which are used to quantify the amount of the terpene produced. For example, terpenes, including diterpenes, such as labdenediol and/or sclareol, can be identified by comparison of retention times and mass spectra to those of authentic standards in gas chromatography with mass spectrometry detection. Typical standards include, but are not limited to, sclareol and labdenediol. In other examples, quantification can be achieved by gas chromatography with flame ionization detection based upon calibration curves with known amounts of authentic standards and normalization to the peak area of an internal standard. These chromatographic techniques allow for the identification of any terpene present in the organic layer, including, for example, other terpenes produced by the labdenediol diphosphate synthase, including, for example, (+)-manoyl oxide, (+)-13-epi-manoyl oxide, geranylgeraniol and sclareol.

In some examples, kinetics of labdenediol and/or sclareol production can be determined by synthase assays in which radioactive isoprenoid substrates, such as $^3$H GGPP or $^{14}$C GGPP, are utilized with varying concentrations of synthase. The products are extracted into an organic layer and radioactivity is measured using a liquid scintillation counter. Kinetic constants are determined from direct fits of the Michaelis-Menton equation to the data.

4. Production of (−)-ambroxide

The labdenediol diphosphate synthase polypeptides and sclareol synthase polypeptides provided herein produce sclareol, which then can be converted to (−)-ambroxide. (−)-Ambroxide is used as a base note in the perfume industry as a substitute for ambergris. Conversion of sclareol to (−)-ambroxide can be carried out through chemical or biosynthetic means (see e.g. Barrero et al. (1993) *Tetrahedron* 49(45): 10405-10412; Barrero et al., (2004) *Synthetic Communications* 34(19):3631-3643; U.S. Pat. Nos. 4,701,543, 4,734,530, 4,814,469, 5,290,955 and 5,463,089; U.S. Pat. Publication No. 20060223883; International Pat. Publication No. WO2006010287; and Example 12 below). In one example, sclareol is converted to (−)-ambroxide by purely chemical methods involving oxidative degradation or ozonolysis of the side chain of sclareol followed by reduction and cyclization (see Example 12, Scheme II). In another example, sclareol is converted to sclareolide by the organism *Cryptococcus magnus*, ATCC 20918 (ATCC; deposited as *Cryptococcus albidus* by International Flavors & Fragrances, Inc.) as described in Example 9 and U.S. Pat. Nos. 4,970,163 and 5,212,078. Sclareolide is then converted to (−)-ambroxide following reduction and cyclization (see Example 12, Scheme III). (−)-Ambroxide can be purified from the reaction mixture by extraction with organic solvents, such as ethers and hydrocarbons, including for example, methyl tert-butyl ether, diethylether, n-hexane and toluene, column chromatography, or extraction with an organic solvent followed by column chromatography. (−)-Ambroxide formation can be confirmed and/or quantified by any of the chromatographic techniques described herein.

G. EXAMPLES

The following examples are included for illustrative purposes only and are not intended to limit the scope of the invention.

Example 1

Isolation of RNA and Generation of cDNA from *Nicotiana glutinosa*

RNA was extracted from the leaves of the tobacco plant *Nicotiana glutinosa*. *N. glutinosa* was purchased from a nursery in California, USA. Leaves, smaller than 1 cm, were cut from the plant, flash-frozen in liquid nitrogen, and ground to a fine powder using a mortar and pestle. Ground tissue was resuspended and thawed in TRIzol reagent (Invitrogen). Remaining insoluble material was pelleted by centrifugation at 12,000×g for 5 minutes at 4° C. The supernatant was extracted, chloroform was added (⅕ volume of TRIzol; e.g., 200 μL to 1 mL), and the mixture was vortexed. Following another centrifugation step, the aqueous phase was collected and transferred to a new tube. Isopropanol was added to precipitate the RNA, which was pelleted and washed with 70% ethanol. The resultant RNA was treated with DNase (New England BioLabs, Ipswich, Mass.) for 1 hour, and pure total RNA was obtained using the RNeasy mini kit (Qiagen, Valencia, Calif.).

Total RNA was reverse transcribed into cDNA using the DyNAmo cDNA synthesis kit (Finnzymes, New England BioLabs) and the Oligo(dT)$_{15}$ primer, following the manufacturer's instructions with the following modifications. The reverse transcriptase reaction was conducted at 37° C. for 10 minutes, then at 42° C. for 1 hour. Upon completion of the reaction, the reverse transcriptase was inactivated by heating at 70° C. for 10 minute and adding 1 mM EDTA.

Example 2

Isolation of a Class II Diterpene Synthase

The cDNA from the tobacco plant *N. glutinosa*, generated in Example 1 above, was used to isolate a class II diterpene synthase.

A. Primer Design and Amplification of a Class II Diterpene Synthase

To design a set of oligonucleotides to identify class II diterpene synthases from *N. glutinosa*, DNA sequences of several class II diterpene synthases were aligned to identify conserved regions among this class of synthases using ClustalW, a web-based program (see, e.g., ebi.ac.uk/Tools/msa/clustalw2/; Thompson et al. (1994) *Nucleic Acids Research* 11(22):4673-4680). Several conserved areas were selected and used to design oligonucleotides for degenerate polymerase chain reaction (PCR). One such degenerate oligonucleotide was designed from the sequence close to the 3' end of the sequences (30-101.4, set forth in SEQ ID NO:17). This oligonucleotide was used as a primer, along with the UPM primer (SEQ ID NO:18) provided in the SMARTer™ RACE PCR kit (Clontech), for PCR amplification. The PCR thermocycler conditions were as follows, using the Advantage 2 PCR kit (Clontech) with the addition of 0.2% DMSO:

1) 30 cycles of:
94° C. for 30 seconds
62° C. for 45 seconds
72° C. for 2 minutes The PCR products were evaluated on a 1.2% agarose gel and a 980 base pair PCR product was observed. The PCR product was cloned into a pGEM-T vector (Promega; SEQ ID NO:52) using the TA cloning method, and sequenced. The cDNA sequence is set forth in SEQ ID NO: 15, encoding a polypeptide whose amino acid sequence is set forth in SEQ ID NO:16.

The sequence of amino acids of the polypeptide (SEQ ID NO:16) was submitted for Basic Local Alignment Search Tool (BLASTX) analysis to identify enzymes with regions sharing homology with the generated fragment. The sequence shares 45% identity with the copal-8-ol diphosphate synthase sequence from *Cistus creticus* subsp. *creticus* (SEQ ID NO:45; NCBI Accession No. ADJ93862), thereby indicating that the encoded polypeptide is from a class II diterpene synthase.

B. cDNA Isolation by Rapid Amplification of cDNA Ends-Polymerase Chain Reaction (RACE-PCR)

Based on the PCR fragment set forth in SEQ ID NO:15, a set of oligonucleotide primers, 30-124.1 (SEQ ID NO:19) and 30-124.2 (SEQ ID NO:20), were designed to perform RACE-PCR. The two RACE-PCR-generated fragments were sequenced and two partial cDNA molecules were assembled using ContigExpress (Invitrogen). The 5' part of assembled sequence contained 558 base pairs (SEQ ID NO:48), which encodes an 186 amino acid protein (SEQ ID NO:49), and the 3' part of cDNA molecule contained 1599 base pairs (SEQ ID NO:50), which encodes a 532 amino acid protein (SEQ ID NO:51). The two sequences were submitted to a BlastX search. The 5' portion of the cDNA has 55% homology to copal-8-ol diphosphate synthase from *Cistus creticus* subsp. *Creticus* (SEQ ID NO:45; NCBI Accession No. ADJ93862), and the 3' portion of the cDNA has 50% homology to the same sequence.

Example 3

Isolation of Full-Length Class II Diterpene Synthases

In this example, full length cDNA molecule variants of the NgLPP synthase encoding fragments isolated in Example 2 were amplified and isolated. Based on the assembled diterpene synthase class II sequence assembled from two RACE-PCR products, oligonucleotide forward and reverse primers, designated 30-137.1 (SEQ ID NO:21) and 30-137.3 (SEQ ID NO:23), respectively, were designed to amplify the full-length cDNA molecule by PCR. The first 55 amino acids of the protein sequence (set forth in SEQ ID NO:43 and 100) were determined to be a chloroplast transit sequence, using the web-base prediction program ChloroP (cbs.dtu.dk/services/ChloroP/; Emanuelsson et al. (1999) *Protein Science* 8:978-984). To isolate nucleic acid encoding polypeptides corresponding to the mature protein lacking the chloroplast signaling sequence, a forward primer, designated 30-137.2 (SEQ ID NO:22), was designed to be used in combination with the reverse primer 30-137.3 (SEQ ID NO:23) for PCR amplification.

All resulting PCR products were cloned into pGEM-T vector and sequenced. The clones corresponding to the PCR products amplified using the 30-137.1 and 30-137.3 primers (SEQ ID NOS:21 and 23, respectively) were designated NgLPP2-1 (full-length sequence), and each of the unique sequence isolates was given a sequential isolate number. The web-based BlastX program (Altschul et al., (1990) *J. Mol. Biol.* 215:403-410) was then used to compare the sequence of the identified with sequences in the GenBank database. It shares 50% amino acid sequence identity with the *Cistus creticus* labdenediol diphosphate (LPP) synthase (SEQ ID NO:45; NCBI Accession No. ADJ93862) and 51% to 45% homology with copalyl synthases from various plant species. The product of this DNA sequence contains an arginine in close proximity of the $Mg^{2+}$ binding and active site, which is conserved among diterpene class II enzymes responsible for secondary metabolite production (Mann et al. (2010) *J. Biol. Chem.* 285(27):20558-20563), thus, the product of this DNA sequence is predicted as a class II diterpene synthase producing a secondary metabolite such as labdenediol diphosphate.

The sequences, lacking the chloroplast signaling sequence, obtained using the 30-137.2 and 30-137.3 primers (SEQ ID NOS:22 and 23, respectively), were designated NgLPP2-2, and, like the full-length sequences, each unique isolated product was given a sequential isolate number. Several nucleotide variants were identified for the full-length and truncated sequences, when all sequences were aligned using AlignX program (Invitrogen) and compared to consensus DNA and protein sequences (SEQ ID NOS:53 and 54, respectively). Several of the polymorphisms result in variations in the encoded amino acid sequence. The variants, and the corresponding amino acid substitutions for the sequences identified, as compared to the consensus sequence generated from multiple sequence alignment, are set forth in Table 5 below.

TABLE 5

Summary of identified LPP variants

| | Isolate No. | Nucleotide variation (amino acid change)* | cDNA SEQ ID NO | Protein SEQ ID NO |
|---|---|---|---|---|
| full-length cDNA sequence | NgLPP2-1-2 | C91T (L→F)<br>G2256A (silent)<br>G2314A (A→T)<br>T2348C (V→A)<br>G2394T (Q→H) | 1 | 2 |
| | NgLPP2-1-3 | G724A (A→T)<br>G792A (silent)<br>A815G (D→G)<br>A1322G (K→R) | 3 | 4 |
| | NgLPP2-1-4 | C215T (S→F)<br>G451A (D→N)<br>G792A (silent)<br>A1432G (R→G)<br>C2021T (A→V)<br>T2252C (V→A) | 5 | 6 |
| w/out chloroplast signal peptide (Δ1-55) | NgLPP2-2-1 | A291G (silent)<br>G792A (silent)<br>T2391A (F→L) | 7 | 8 |
| | NgLPP2-2-2 | A183T (silent)<br>T598C (silent)<br>A1965G (silent)<br>G2256A (silent)<br>G2314A (A→T)<br>T2348C (V→A)<br>G2394T (silent) | 9 | 10 |
| | NgLPP2-2-3 | C1024T (R→C)<br>A1981G (I→V)<br>C2156T (T→I) | 11 | 12 |
| | NgLPP2-2-4 | C2156T (T→I) | 13 | 14 |

*compared to the consensus DNA (SEQ ID NO: 53) and amino acid (SEQ ID NO: 54) sequences Example 4

Expression of NgLPP2 and Analysis of Enzyme Product

In this example, NgLPP2 variants 2-2-2 and 2-2-4, isolated in Example 3, were expressed, purified and subsequently tested to confirm labdenediol diphosphate (LPP) synthase activity.

A. Expression and Purification of NgLPP2-2-2 and NgLPP2-2-4

Among the variants identified in Example 3, two isozymes were most abundant: NgLPP2-2-2 and NgLPP2-2-4. These sequences were sub-cloned into a pET28 expression vector (Novagen) between the NdeI and NotI restriction sites, thereby fusing the coding sequence of an N-terminal hexa histidine to the coding sequences of the NgLPP synthases.

The resulting plasmids were transformed into T7 Express Iq E. coli cells (New England BioLabs), which were plated on Lysogeny broth (LB) agar plates containing 50 μg/mL kanamycin. The following day, for each vector, a single colony was selected from the LB plate and inoculated into 50 mL LB medium with 50 μg/mL kanamycin. The cultures were incubated overnight at 37° C. with constant shaking, and then diluted to an OD600 of 0.2 in 500 mL of LB with kanamycin (50 μg/mL). The diluted cultures were incubated at 37° C., while constantly shaking, until they reached an OD600 of 0.6. NgLPP2 protein expression was then induced by adding 500 μM IPTG.

The induction was conducted for 5.5 hours at room temperature, and the OD600 was checked every hour. The cells were harvested by centrifugation at 5,000×g in a Sorvall centrifuge for 10 minutes. The supernatants were removed and the pellets were frozen at −20° C. until further processing.

Protein was purified from each sample as described below. The pellet was thawed and resuspended in 20 mL of Bugbuster solution (Novagen) with 1 mM PMSF, and 1 unit of Benzonase® endonuclease (Merck KGaA) per mL of Bugbuster solution. The cell suspensions were incubated at room temperature, with constant shaking, for 15 minutes, and then cellular debris was pelleted by centrifugation at 15,000×g for 20 minutes. The supernatant was transferred into fresh tube and subjected to Ni-NTA column chromatography.

The Ni-NTA column (Qiagen) was equilibrated with lysis buffer (50 mM Tris-HCl [pH 8.0], 500 mM NaCl, 20 mM imidazole (pH 8.0), 10 mM beta-mercaptoethanol (BME), 10% v/v glycerol, 1% v/v Tween 20), followed by sample application. After the column was washed with 20 mL of lysis buffer, followed by 20 mL of washing buffer (50 mM Tris-HCl [pH 8.0], 500 mM NaCl, 20 mM imidazole pH 8.0, 10 mM BME, 10% v/v glycerol), the Ni-bound protein was eluted with elution buffer (washing buffer, but with 250 mM imidazole). The column eluate was collected in 3 mL fractions. Each fraction was analyzed by SDS-PAGE.

For both samples, there was a dominant band around 84 kDa, which is in close agreement with the predicted molecular weight of the His-tagged synthase (86 kDa). The fractions that contained the 84 kDa protein were dialyzed in dialysis buffer (50 mM Tris-HCl [pH 8.0], 100 mM NaCl, 10 mM BME), using a membrane with a 30 kDa cut off. The buffer was changed once, and then replaced with dialysis-glycerol buffer (50% glycerol with 50% dialysis buffer) to concentrate the sample and to add glycerol for storage purposes.

B. NgLPP2 Enzyme Activity

Labdenediol diphosphate synthase from S. sclarea, designated herein SsLPP synthase (nucleic acids set forth in SEQ ID NO:104; amino acids set forth in SEQ ID NO:58), and described in published International PCT application No. WO 2009101126, was synthesized and cloned into an NdeI/NotI-digested pET28 vector. This His-tagged LPP synthase was purified, as described in part A above, and used as a positive control for subsequent experiments.

Purified NgLPP2 and SsLPP synthase enzymes then were next tested to demonstrate production of labdenediol diphosphate (LPP) from geranylgeranyl diphosphate (GGPP). The LPP assay buffer was composed of 50 mM HEPES, 100 mM KCl, 1 mM MgCl$_2$ and 1 mM DTT with 100 μM GGPP. The reaction was incubated with purified enzyme at 28° C. overnight. The next morning, 10 units of alkaline phosphatase was added and the mixture was incubated for 1 hour at 37° C. The reaction product(s) was then extracted with hexane and analyzed by GC-MS (PerkinElmer). GC-MS analysis was performed with a Perkin Elmer TurboMass™ GC Mass Spectrometer, equipped with an AutoSystem XL autosampler. GC-MS was run from 50° C. to 275° C. with a ramping rate of 10° C./min, then held for 10 min at 275° C. Negative control samples that either did not contain alkaline phosphatase or contained heat inactivated LPP synthase also were extracted and tested.

The chromatogram revealed two peaks with retention times of 18.69 and 18.91 minutes for each of the NgLPP2-2-2, NgLPP2-2-4, and SsLPP samples, whereas no peak was detected from either of the negative control samples. The profiles of the MS spectra of the peaks at 18.69 and 18.91, for the two NgLPP synthases, were identical to those from the control SsLPP synthase, and were similar to that of a labdenediol standard.

Example 5

Isolation of a Class I Diterpene Synthase

In this example, cDNA from the tobacco plant *N. glutinosa*, generated in Example 1 above, was used to isolate a class I diterpene synthase.

A. Primer Design

The amino acid sequences for several class I diterpene synthases were aligned to identify areas of conservation. Two conserved motifs of interest were identified: DDFFDV (SEQ ID NO:41), a known active site for all class I diterpene synthases, and A(M/L)AFR (SEQ ID NO:42). Degenerate oligonucleotide sequences, to be used as primers, were deduced from these conserved amino acid motifs. The A(M/L)AFR motif was used to design degenerate forward primers and the DDFFDV motif was used to design degenerate reverse primers.

B. Amplification of a Class I Diterpene Synthase

Total RNA was extracted from *Nicotiana glutinosa* as described in Example 1. Polymerase chain reactions (PCR) were performed with the FailSafe™ PCR kit (Epicentre), according to the manufacturer's instructions, using buffer F, the cDNA from Example 1, and the primers designed in part A in all possible combinations of forward and reverse primers. Touchdown PCR cycling was implemented, to restrict amplification to only those sequences which exhibited very specific base pairing between the primer and the template. For each cycle of touchdown amplification, the annealing temperature was decreased by 0.5° C. The PCR thermocycler conditions were the following:

1) 12 cycles of:
94° C. for 30 seconds
54° C. for 45 seconds (Touchdown: decreased by 0.5° C. per cycle)
68° C. for 2 minutes
2) 28 cycles of:
94° C. for 30 seconds
47° C. for 45 seconds
68° C. for 2 minutes The PCR products were evaluated on a 1.2% agarose gel. A PCR product of approximately 630 base pairs was amplified using primers 27-75.8 and 30-9.8 (SEQ ID NOS:24 and 24, respectively). This 630 bp product was cloned into the pGEM-T vector (Promega; SEQ ID NO:52) using TA cloning, and sequenced.

Two partial cDNA clones were predicted as class I diterpene synthases, based on the encoded sequences. The one of two clones was designated NgSs3. The sequence of the cDNA clone designated NgSs3 is set forth in SEQ ID NO:26, with the encoded amino acid sequence set forth in SEQ ID NO:27. This sequence was submitted for Basic Local Alignment Search Tool (BLASTX) searches. The polypeptide encoded by NgSs3 shares 78% homology with the terpenoid cyclase of *Nicotiana tabacum* (SEQ ID NO:46; NCBI Accession No. AAS98912.1) and the terpene synthase of *Solanum lycopersicum* (SEQ ID NO:47; NCBI Accession No. ACO56896.1).

C. Full-Length cDNA Isolation by RACE-PCR

Based on the partial sequence information (part B above), primers for RACE-PCR were designed and RACE-PCR was performed to obtain the full-length cDNA of NgSs3. The primers used for RACE-PCR are listed in Table 6 below.

TABLE 6

Primers for RACE-PCR

| Gene ID | Primer name | SEQ ID NO | cDNA end to amplify |
|---------|-------------|-----------|---------------------|
| NgSs3   | 30-28.4     | 28        | 5'                  |
| NgSs3   | 30-28.1     | 29        | 3'                  |

The thermocycler conditions for RACE-PCR were as follows:
1) 94° C. for 3 minutes
2) 30 cycles of:
94° C. for 30 seconds
65° C. for 45 seconds
72° C. for 3 minutes
3) 72° C. for 7 minutes The RACE-PCR products were resolved by electrophoresis in a 1.2% agarose gel. The RACE-PCR products were approximately 1600 bp. The DNA fragments were excised from the gel and cloned into a pGEM-T vector (SEQ ID NO:52; Promega) using the TA cloning method and sequenced.

Each sequence was sequenced 2-3 times for each 3' and 5' RACE-PCR product to obtain a complete sequence, and the sequences were assembled using ContigExpress (Invitrogen). The assembled sequences were then subjected to search for homologous sequences in the GenBank database using the web-based BlastX program (Altschul et al., (1990) *J. Mol. Biol.* 215:403-410). The assembled NgSs3 sequence is composed of 2382 nucleotide base pairs (SEQ ID NO:30), which encodes a sequence of 793 amino acids (SEQ ID NO:31). The encoded protein sequence for NgSs3 shares 88% homology with terpenoid synthase of *N. tabacum* (SEQ ID NO:46), and 62% identity with the terpene synthase of *Solanum lycopersicum* (SEQ ID NO:47). It was predicted that NgSs3 encodes a class I diterpene synthase.

Example 6

Isolation of Full Length Class I Diterpene Synthases

In this example, variants of the NgSs synthase isolated in Example 5 were isolated. To clone full-length cDNA encoding the NgSs synthases, a set of forward and reverse oligonucleotide primers were designed based on the 5' and 3' ends of the sequences of cDNA molecules obtained by RACE-PCR. These primers were designated 30-87.13 S3F1 (forward primer; SEQ ID NO:32) and 30-87.15 S3R (reverse primer; SEQ ID NO:34).

Based on its the sequence, the first 38 amino acids of the NgSs3 amino acid sequence (SEQ ID NO:31), identified in Example 5 above, is a chloroplast transit peptide. The cleavage site for the chloroplast signal peptide was predicted using the web-based program, ChloroP (cbs.dtu.dk/services/ChloroP/; Emanuelsson et al. (1999) *Protein Science* 8:978-984). Subsequently, an alternative forward primer was designed to amplify a truncated S3 sclareol synthase encoding cDNA, lacking the DNA fragment encoding the N-terminal signal peptide. This alternative forward primer was designated 30-87.14 S3F2 (SEQ ID NO:33).

PCR was conducted using the reverse primer 30-87.15 S3R (SEQ ID NO:34) in combination with either the forward primer designed to amplify the full-length cDNA, 30-87.13 S3F1 (SEQ ID NO:32), or the forward primer designed to amplify the truncated sequence, 30-87.14 S3F2 (SEQ ID NO:33) using the following thermocycling conditions:

1) 94° C. for 3 minutes
2) 30 cycles of:
   94° C. for 30 seconds
   65° C. for 30 seconds
   72° C. for 2.5 minutes
3) 72° C. for 7 minutes Details of the PCR products and primers used are set forth in Table 7 below.

TABLE 7

Primers and PCR products

| Gene ID | Base pairs | Amino acids | Truncated amino acids | Forward Primer | Reverse Primer |
|---|---|---|---|---|---|
| S3F1 | 2391 | 796 | 0 | 30-87.13 S3F1 | 30-87.15 S3R |
| S3F2 | 2268 | 757 | 39 | 30-87.14 S3F2 | 30-87.15 S3R |

All PCR products were cloned into the pGEM-T vector and sequenced. Several sequence variants were observed from the sequencing analysis. The sequencing results are summarized in Table 8 below. The sequence variations set forth in Table 8 below are in comparison to the assembled RACE-PCR product, NgSs3, generated in Example 5 above. The N-terminal domain of the nucleic acid encoding the sclareol synthase S3F2-3 was codon optimized for expression in yeast. The codon optimized nucleic acid is set forth in SEQ ID NO:89.

TABLE 8

Sclareol Synthase Variants

| | Isolate No. | Nucleotide variation (amino acid change)* | cDNA SEQ ID NO | Protein SEQ ID NO |
|---|---|---|---|---|
| full-length cDNA sequence | S3F1-1 | A80T, AGA 81-83 deletion (K27N, D28del) A95C (H32P) G155A (G52E) A156G (silent) G176T (G59V) C867A (F289L) G895A (D299N) G1146A (silent) A1197T (silent) C1362T (silent) A1719G (silent) A1756G (I586V) T2112A (silent) G2173A (V725M) | 35 | 36 |
| | S3F1-4 | G155A (G52E) T2105C (V702A) T2112A (silent) G2173A (V725M) | 77 | 78 |
| w/out chloroplast signal peptide (Δaa1-38) | S3F2-1 | G155A (G52E) C193T (P65S) A329T (H110L) A777G (silent) G1555T (silent) T2112A (silent) G2173A (V725M) | 37 | 38 |

TABLE 8-continued

Sclareol Synthase Variants

| Isolate No. | Nucleotide variation (amino acid change)* | cDNA SEQ ID NO | Protein SEQ ID NO |
|---|---|---|---|
| S3F2-3 | G155A (G52E) C193T (P65S) A329T (H110L) T719C (L240P) T2112A (silent) G2173A (V725M) | 39 | 40 |

*compared to original RACE-PCR-identified sequence (NgSs3; SEQ ID NOS: 30 and 31)

Example 7

Expression of *Nicotiana glutinosa* Diterpene Synthase (NgSs) Gene and Enzyme Product Analysis In this example, NgSs *N. glutinosa* sclareol synthase S3F2-3, isolated in Example 6, was expressed, purified and subsequently tested to demonstrate sclareol synthase activity.

A. Expression and Purification of NgSs3 S3F2-3

The pGEM-T vector, containing the NgSs3 synthase, S3F2-3, was digested using FauI and XhoI restriction enzymes, and cloned into the pMAL-05E vector (New England BioLabs) that had been digested using NdeI and SalI. The pMAL-05E vector contains a maltose binding protein (MBP; 42.5 kDa) moiety so that the amino terminus of the recombinant NgSs synthase (MBP-NgSs) can be fused, which facilitates protein purification by amylose affinity chromatography. The resulting plasmid was designated pAlx 40-103.2 (SEQ ID NO:55). To serve as a positive control, a known sclareol synthase from *Salvia sclarea* (SsSs; nucleic acids set forth in SEQ ID NO:105; amino acids set forth in SEQ ID NO:60) was synthesized and cloned into the pMAL-5CE vector using the same method described above. This plasmid was designated pAlx 40-69.1 and the sequence is set forth in SEQ ID NO:56.

Each plasmid was transformed into BL-21 codon plus RIL competent *E. coli* cells (Agilent), which were plated on Lysogeny broth (LB) agar plates containing ampicillin (100 μg/mL) and chloramphenicol (30 μg/mL) and incubated overnight at 37° C. The following day, individual colonies were picked, inoculated into rich medium (10 g tryptone, 5 g yeast extract, 5 g NaCl, 2 g glucose, 100 mg ampicillin, and 30 mg chloramphenicol per liter ddH$_2$O), and cultured overnight at 37° C. with constant shaking. Saturated cultures were diluted next morning to OD600 ~0.2, and were then further incubated with constant shaking until the OD600 reached around 1.1. Isopropyl β-D-1-thiogalactopyranoside (IPTG) was then added to the cultures, to achieve a final concentration of 300 μM, to induce protein expression at room temperature for 4.5 hours.

Cells were harvested at 5,000×g for 10 minutes, resuspended in column buffer (20 mM Tris-HCl [pH 7.5], 200 mM NaCl, 1 mM EDTA), and were then frozen at −20° C. overnight. The following day, the cell suspension was thawed on ice and cell lysates were generated by French press. Each sample was passed through the French press once under approximately 1100 psi. The crude extracts were loaded onto a pre-equilibrated amylose column (New England BioLabs), followed by a wash of ten volumes of column buffer. The NgSs3 synthase was eluted from the column using four volumes of elution buffer (10 mM maltose in column buffer).

The eluate was collected in three mL fractions and the protein concentration of each fraction was quantified by Bradford assay (Thermo Scientific.).

Ten (10) microliters of protein from the crude extracts and eluate fractions were resolved by SDS-PAGE and stained with Coomassie blue. In the crude extract of the cells expressing the NgSs3, there a dominant band ran around 130 kDa, corresponding well with the predicted size of the MBP-NgSs3 chimeric protein. A similar band, running at approximately 98.5 kDa, was observed for the MBP-SsSs-containing extract. The affinity-purified protein, recovered from the amylose columns was relatively pure, primarily containing the 130 kDa and 98.5 kDa proteins mentioned above for the MBP-NgSs3- and MBP-SsSs-containing extracts, respectively. In the case of the MBP-NgSs3 extract, a secondary band was present at approximately 60 kDa which may have been a C-terminal truncated MBP-NgSs3 fusion protein.

B. Enzyme Activity Assay

The *N glutinosa* sclareol synthase (NgSs3) was further characterized by assaying its ability to convert labdenediol diphosphate (LPP) to sclareol. An LPP enzyme reaction mix was generated by mixing 100 μM geranylgeranyl diphosphate (GGPP), 1 mM dithiothreitol (DTT) in LPP assay buffer (described in Example 4B) containing 10 μl of LPP synthase, purified from *S. Sclarea* (see Example 4A) and incubated for 4 hours at 28° C. Five hundred (500) μL aliquots of the prepared LPP reaction mix were then incubated with twenty microliters of NgSs3 or SsSs3, affinity-purified enzyme or crude extracts thereof, or a negative control crude extract, overnight at 28° C.

The reaction product was extracted with ethyl acetate and analyzed by gas chromatography-mass spectrometry (GC-MS). GC-MS analysis was performed as described in Example 4B. The initial oven temperature was 80° C., which was increased to 275° C. with a ramping rate of 10° C./min. The identity of the product(s) was confirmed by concordance of the retention times and comparison of the spectra obtained from each of the samples with those obtained from known standards.

The crude extracts, containing either Ss sclareol synthase or Ng sclareol synthase, S3F2-3, produced a main product with a retention time of 17.95 and 17.94 min, respectably, which was similar to the retention time of the sclareol standard (17.96 min), while the sample treated with the negative control crude extract did not show any visible sclareol peak. The main product of the reaction using affinity-purified SsSs and NgSs3 and enzymes also generated sclareol peaks, on the chromatogram, at 17.94 min. The MS spectra, corresponding to the retention time of 17.95 min were identical throughout samples and for the sclareol standard, demonstrating that the NgSs3 enzyme is a sclareol synthase.

Example 8

Expression of NgLLP2 2-2 and NgSs S3F2-3 in *Saccharomyces cerevisiae*

In order to demonstrate sclareol production in *Saccharomyces cerevisiae*, NgLPP2 2-2 (SEQ ID NO:10) and NgSs S3F2-3 (SEQ ID NO:40) were cloned into a yeast expression vector containing a gene encoding the GGPP synthase crtE from *Xanthophyllomyces dendrorhous*. The resulting vector was transformed into *Saccharomyces cerevisiae* strain Alx11-30 resulting in the co-expression of LPP and sclareol synthase and GGPP and production of sclareol was determined.

A. Construction of the Yeast Expression Vector pAlx40-152.2

In this example, the gene encoding the GGPP synthase crtE of *Xanthophyllomyces dendrorhous* was cloned and inserted into a yeast expression vector. *X. dendrorhous* was cultured in yeast extract peptone dextrose medium for 16 hours at 30° C. Two (2) mL of culture was pelleted by centrifugation and flash-frozen in liquid nitrogen. The pellet was thawed with 0.5 mL of Trizol solution and 0.5 mL glass beads. The RNA was extracted, treated with DNase and purified as described in Example 1. cDNA synthesis was conducted using Proto-Script MML-V transcriptase (New England Biolabs) following the manufacturer's instruction. Briefly, an Eppendorf tube containing 6 μL of purified total RNA and 2 μL of oligo dT(23) was heated at 70° C. for 5 minutes, followed by the addition of 10 μL of MMLV reaction mix and 2 μL of MMLV enzyme mix. cDNA was synthesized by incubating the tube at 42° C. for 1 hour. MMLV reverse transcriptase was inactivated by heating to 80° C. for 5 minutes.

cDNA encoding CrtE was amplified from the cDNA pool by PCR using oligo 40-145.5 and 40-145.6 (SEQ ID NOS:63 and 64, respectively). PCR reaction parameters were as follows:
1) 96° C. for 1 min, followed by
2) 30 cycles of:
   96° C. for 30 sec
   55° C. for 30 sec
   72° C. for 2 min
3) 72° C. for 7 min PCR was performed using Expand long template PCR system (Roche). The products were resolved by electrophoresis on a 1.2% agarose gel. The resultant PCR product and the yeast expression vector pAlx27-126.2 (SEQ ID NO:65) were digested using KpnI and XbaI and two DNA fragments were ligated. The resultant crtE containing plasmid, pAlx40-152.2 (SEQ ID NO: 66), was sequenced to confirm that there were no mutations introduced during PCR.

B. Generation of a Vector Encoding Labdenediol Diphosphate Synthase and Sclareol Synthase NgLPP2 2-2 (SEQ ID NO:10) and NgSs S3F2-3 (SEQ ID NO:40) were cloned into the yeast expression vector, pAlx 40-152.2 (SEQ ID NO:66). In brief, NgLPP2 2-2 was amplified by PCR using primers 30-173.3 and 30-137.4 (SEQ ID NOS:67 and 68, respectively). PCR reaction parameters were as follows:
1) 94° C. for 1 min, followed by
2) 30 cycles of:
   96° C. for 30 sec
   55° C. for 30 sec
   72° C. for 3 min
3) 72° C. for 7 min The resulting PCR product and the vector pAlx40-3.1 (SEQ ID NO:69) were digested using KpnI and XbaI and the two DNA fragments were ligated. The resulting plasmid was sequenced to confirm there were no amino acid mutations introduced during PCR. The NgLPP2 2-2 expression cassette was then inserted to the crtE vector pAlx 40-152.2 (SEQ ID NO:66) generated in section A above as follows. The vector was digested using NotI then dephosphorylated and the NgLPP2 2-2 expression cassette was digested using NotI and PspOMI. The two DNA fragments were ligated and a plasmid containing the insert was selected. The resulting plasmid was designated pAlx40-160.4 (SEQ ID NO:70).

NgSs S3F2-3 was amplified by PCR using primers 40-92.1 and 40-92.2 (SEQ ID NOS:71 and 72, respectively) as described above for the NgLPP2 2-2 synthase. The resultant 2292 base pair PCR product was digested using KpnI and NheI. The vector pAlx46-116.2-6 (SEQ ID NO:73) containing an ADH1 promoter and ACT1 terminator was digested using KpnI and XbaI, and the resulting DNA fragments were ligated. The resultant plasmid was designated as pAlx 47-64.1. Various clones were sequenced and a clone free of mutations was selected for further cloning. The selected plasmid, pAlx 47-64.1, was digested using NotI and PspOMI and inserted into the vector pAlx40-160.4 (SEQ ID NO:70) containing the NgLPP2 2-2 synthase that was linearized using NotI. The resultant plasmid containing crtE, NgLPP2 2-2 and NgSs S3F2-3 was designated as pAlx47-66.1 (SEQ ID NO:74; see FIG. 5A).

C. Generation of a Control Plasmid Containing LPP and Sclareol Synthase from *Salvia sclarea*

A control plasmid encoding sage LPP (SsLPP) and sclareol (SsSs) synthases was constructed using the same vectors, except the cloning vector for SsSs, described above. SsSs was amplified and cloned into the vector designated pAlx 40-13.3 (SEQ ID NO: 75), which contains a PGK promoter and erg10 terminator. The final plasmid containing crtE, SsLPP and SsSs was designated as pAlx 40-170.2R (SEQ ID NO:76; see FIG. 5B).

D. Expression of Sclareol pAlx47-66.1 (SEQ ID NO:74) a encoding LPP synthase and sclareol synthase, and the positive control vector pAlx40-170.2 (SEQ ID NO:76) were transformed into the engineered *Saccharomyces cerevisiae* strain, Alx11-30 (ura3, trp1, erg9$^{def}$25, HMG2cat/TRP1::rDNA, dpp1, sue). The transformants were plated on synthetic drop out medium without tryptophan, histidine, uracil and leucine (SD-THUL) and several colonies were selected and inoculated into liquid SD-THUL medium. After incubation for two days at 30° C., each isolate was moved to fermentation medium and incubated for three days at 30° C. with constant shaking.

Sclareol was extracted from culture by adding an equal volume of acetone, then two volumes of hexane. Samples were analyzed using gas chromatography (Agilent). The GC parameters were as follows: initial starting temperature was 100° C.; which was then increased to 175° C. using a ramp rate of 50° C./min; which was then increased from 175° C. to 230° C. using a ramp rate of 10° C./min; which was then increased to 275° C. using a ramp rate of 50° C./min. The identity of the product(s) was confirmed by concordance of the retention times and comparison of the spectra obtained from each of the samples with those obtained from known standards.

A peak corresponding to sclareol was observed at the same retention time as for the positive control strain expressing sage LPP and sclareol synthase. The hexane layer was moved to new vial from the sample and analyzed again using GC-MS, as described in Example 4B. The results showed the two peaks had the same mass spectrometry pattern and both represented sclareol.

Example 9

Structure Analysis

In this example, the structures of the NgLPP2 1-2 synthase and the NgSs synthase were determined by modeling with known class II and class I terpene diterpene synthases.

A. *Nicotiana glutinosa* Labdenediol Diphosphate Synthase (NgLPP)

The web based modeling program Swiss-Model (swiss-model.expasy.org; Arnold et al. (2006) *Bioinformatics* 22:195-201; Kiefer et al. (2009) *Nucleic Acids Research* 37:D387-D392; Peitsch, M. C. (1995) *Bio/Technology* 13:658-660) was used to build a three-dimensional model structure of the *Nicotiana glutinosa* labdenediol diphosphate synthase NgLPP2 1-2 (SEQ ID NO:2) identified herein. Specifically, the structure model was built using automated mode with the crystal structure of the mature form of ent-copalyl diphosphate synthase from *Arabidopsis thaliana* (Köksal et al. (2011) *Nat. Chem. Biol.* 7(7):431-433; PDB Accession No. 3PYB; SEQ ID NO:82) as a template. The class II diterpene synthase ent-copalyl diphosphate synthase is a 802 amino acid precursor protein set forth in SEQ ID NO:83. The protein used for crystallization was 727 amino acids in length, containing a C-terminal hexa-his tag for purification (GSH-HHHHH; amino acids 720-727 of SEQ ID NO:82). The structure of NgLPP2 1-2 was compared to that of ent-copalyl diphosphate synthase to locate the active site and domain breaks using the Swiss-PdbViewer program (SPDBV; version 4.01; Guex et al. (1997) *Electrophoresis* 18:2714-2723; expasy.org/spdbv). The two structures were superimposed using 'iterative magic fit' by matching alpha carbons pairwise. The resulting root mean square (RMS) distance between the two structures was 0.23 Å. The ent-copalyl diphosphate synthase and NgLPP2 1-2 class II diterpene synthases share only 44% sequence identity on an amino acid level.

Modeling revealed the overall structure of NgLPP2 1-2 was nearly identical to that of class II diterpene synthases which contain three α helical domains, α, β and γ (see Table 9 below). The α domain of NgLPP2 1-2 was located between amino acids Arg537 to Gln801 and was less conserved as compared to the βγ domains, containing a larger loop from Asp624 to Thr633 and longer helices from His662 to Ala687 and Ala710 to Gln730. With the exception of the loop from Thr125 to Asp132 that is longer than the same loop in ent-copalyl diphosphate synthase, the βγ domains were very structurally similar. Similar to a structure previously reported in Wendt et al. (*Science* 277:1812-1815 (1997)), the γ domain (Ser111 to Tyr326) is located between the first and second a helices of the β domain (Thr88 to Ser110 and Pro327 to Gln536). As the template structure of ent-copalyl diphosphate synthase contained only the mature protein, the first 87 amino acids of NgLPP2 1-2 were not modeled. The structural helices and loops are set forth in Table 10 below.

The active site, DXDDTXM motif (SEQ ID NO:79) which is conserved among all class II diterpene synthases is located in the 13 domain at amino acids Asp380-Met386 superimposing to that of ent-copalyl diphosphate synthase by 0.04 Å. Since class II diterpene synthases do not need to bind metal ions, but directly initiate cyclization by protonation of double bond on isoprene, there is no DDXXD motif in the α domain. However, there is a motif similar to the DDXXD (SEQ ID NO:80) motif in the γ domain having the sequence DDLD (SEQ ID NO:106) between residues Asp272 and Asp275, although an EDXXD-like motif (SEQ ID NO:81; Cao et al. (2010) *Proteins* 78:2417-2432) in ent-copalyl diphosphate synthase was not conserved in NgLPP2 1-2. It was originally suspected that this EDXXD-like motif might possibly be involved in electrostatic interaction with $Mg^{2+}$, thus assisting cyclization of GGPP to copalyl diphosphate. However, the distance of the DDLD residues to the DXDDTXM motif is about 27 Å in NgLPP2 1-2 and the distance from the EDXXD motif to the DXDDTXM motif in ent-copalyl diphosphate synthase is 18 Å, which makes these residues unable to be involved in any catalytic activity in both cases.

TABLE 9

NgLPP2 1-2 Structural Domains

| Domain | ent-copalyl diphosphate synthase (SEQ ID NO: 83) | NgLPP2 1-2 (SEQ ID NO: 2) |
|---|---|---|
| α | A534-V802 | S537-Q801 |
| β1 | M84-I113 | T88-S110 |
| β2 | P325-Q533 | P327-Q536 |
| γ | T114-F324 | S111-Y326 |

TABLE 10

Structural domains and features

| structure | ent-copalyl diphosphate synthase (CPS) (SEQ ID NO: 83) | NgLPP (SEQ ID NO: 2) | Annotation/ Differences |
|---|---|---|---|
| Helix A | 92-106 | 89-103 | |
| Loop 1 | 107-116 | 104-113 | |
| Helix B | 117-124 | 114-121 | |
| Loop 2 | 125-136 | 122-138 | Bigger loop |
| Helix C | 137-144 | 139-146 | |
| Loop 3 | 145-159 | 147-161 | |
| Helix D | 160-175 | 162-177 | |
| Loop 4 | 176-180 | 178-182 | |
| Helix E | 181-195 | 183-200 | Longer helix |
| Loop 5 | 196-209 | 201-211 | Shorter loop |
| Helix F1 | 210-217 | 212-225 | Longer helix |
| Loop 6 | 218-220 | n.a. | |
| Helix F2 | 221-223 | n.a. | |
| Loop 7 | 224-237 | 226-239 | |
| Helix G | 238-244 | 240-248 | |
| Loop 8 | 245-250 | 249-252 | |
| Helix H | 251-253 | 253-256 | |
| Loop 9 | 254-272 | 257-275 | |
| Helix I | 273-278 | 276-281 | |
| Loop 10 | 279-289 | 282-292 | |
| Helix J | 290-299 | 293-302 | |
| Loop 11 | 300-303 | 303-306 | |
| Helix K | 304-315 | 307-318 | |
| Loop 12 | 316-326 | 319-328 | |
| Helix L | 327-340 | 329-343 | |
| Loop 13 | 341-347 | 344-349 | |
| Helix M | 348-361 | 350-363 | |
| Loop 14 | 362-377 | 364-380 | Active site |
| Helix N | 378-391 | 381-394 | Active site |
| Loop 15 | 392-419 | 395-422 | |
| Helix O | 420-430 | 423-433 | |
| Loop 16 | 431-438 | 434-441 | |
| Helix P | 439-457 | 442-460 | |
| Loop 17 | 458-469 | 461-472 | |
| Helix Q | 470-479 | 473-482 | |
| Loop 18 | 480-486 | 483-489 | |
| Helix R | 487-495 | 490-498 | |
| Loop 19 | 496-519 | 499-522 | |
| Helix S | 520-558 | 523-551 | |
| Loop 20 | 550-558 | 552-561 | |
| Helix T | 559-572 | 562-575 | |
| Loop 21 | 573-578 | 576-581 | |
| Helix U | 579-598 | 582-600 | |
| Loop 22 | 599-602 | 601-613 | |
| Helix V | 603-618 | 614-623 | |
| Loop 23 | 619-638 | 624-633 | CPS residues 621-637 missing in crystal structure |
| Helix W | 639-661 | 634-654 | |
| Loop 24 | 662-668 | 655-661 | |
| Helix X | 669-685 | 662-675 | |
| Loop 25 | 686-690 | 676-678 | |
| Helix Y | 691-702 | 679-686 | |
| Loop 26 | 703-708 | 687-709 | |
| Helix Z 1 | 709-711 | 710-730 | |
| Loop 27 | 712-714 | n.a. | |
| Helix Z 2 | 715-726 | n.a. | |
| Loop 28 | 727-239 | 731-737 | |
| Helix AA | 740-759 | 738-754 | |
| Loop 29 | 760-763 | 755-764 | |
| Helix AB | 764-784 | 765-782 | |
| Loop 30 | 785-790 | 783-788 | |
| Helix AC | 791-798 | 789-796 | |
| Loop 31 | 799-802 | 797-801 | |

B. *Nicotiana glutinosa* Sclareol Synthase (NgSs)

A three-dimensional model structure of the *Nicotiana glutinosa* sclareol synthase NgSs (SEQ ID NO:36) was built as described above using the crystal structure of abietadiene synthase from *Abies grandis* (AgAs; PDB accession number 3S9V) as a template. Abietadiene synthase is an 868 amino acid precursor protein set forth in SEQ ID NO:84 containing a 70 amino acid chloroplast transit peptide (amino acids 1-70 of SEQ ID NO:84). The protein used for crystallization contained amino acids 85-868 of SEQ ID NO:84 and was 785 amino acids in length (SEQ ID NO:85). The two structures were superimposed using 'iterative magic fit' by matching alpha carbons pairwise. The resulting RMS distance between the two proteins was 0.27 Å implying that these two proteins possess very similar structures although they only share 31% sequence identity on an amino acid level.

Modeling revealed the overall structure of NgSs was nearly identical to that of abietadiene synthase, containing three α helical domains, α, β and γ (see Table 11 below). The overall basic structure and size of the sclareol synthase identified herein is very similar to the abietadiene synthase although the N-terminus of sclareol synthase is approximately 70 amino acids shorter than that of abietadiene synthase. The β domain was interrupted by the γ domain between the first and the second a helices. The structural helices and loops are set forth in Table 12 below.

It is known that class I diterpene synthases initiate cyclization by ionization using three $Mg^{2+}$ bound in two aspartic acid motifs, DDXXD (SEQ ID NO:80) and (N/D)DXX(S/T)XXXE (NTE motif; SEQ ID NO:101) (see e.g. Zhou et al. (2012) *J. Biol. Chem.* 287:6840-6850, and Köksal et al. (2011) *Nature* 469:116-122). Both the DDXXD motif (539-DDFFD-543 of SEQ ID NO:36) and the NTE motif (684-NDIHSYKRE-692 of SEQ ID NO:26) of sclareol synthase are located in the α domain and superimposed to the same motifs of abietadiene synthase exhibiting RMS 0.03 and 0.04 Å respectively. Although, the threonine in the NTE motif was replaced by serine in the sclareol synthase sequence, the overall active site structure is nearly identical. The class II active site DXDDTXM (SEQ ID NO:79), which catalyzes protonation using general acid (e.g. the middle aspartic acid), presents in the β domain of abietadiene synthase (402-DID-DTAM-408 of SEQ ID NO:84). This active site may not be involved in catalytic activity since Asp404 forms a hydrogen bond with Asn451 (SEQ ID NO:84; Zhou et al. (2012) *J. Biol. Chem.* 287:6840-6850). When Asn 451 was mutated to alanine, the activity was reduced more than 100 times. This class II active site in abietadiene synthase was aligned to similar amino acid residues in β domain of sclareol synthase, but the two middle aspartic acids in the site were replaced to alanine and histidine (326-DIAHCAM-332 of SEQ ID NO:36) eliminating the possibility that these residues are involved in catalysis.

TABLE 11

Sclareol Synthase Structural Domains

| Domain | Abietadiene Synthase (SEQ ID NO: 84) | Sclareol Synthase (SEQ ID NO: 36) |
|---|---|---|
| α | S559-A868 | A477-N788 |
| β1 | A110-T135 | H40-L62 |
| β2 | P350-Q558 | P279-Q476 |
| γ | M136-Y349 | S63-Y278 |

TABLE 12

Structural domains and features

| structure | Abietadiene synthase (SEQ ID NO: 84) | Sclareol synthase (SEQ ID NO: 36) | Annotation/ Differences |
|---|---|---|---|
| Loop 1 | 110-111 | 40-41 | |
| Helix A | 112-129 | 42-54 | |
| Loop 2 | 130-138 | 55-65 | |
| Helix B | 139-146 | 66-73 | |
| Loop 3 | 146-160 | 74-87 | |
| Helix C | 161-168 | 88-95 | |
| Loop 4 | 169-183 | 96-112 | |
| Helix D | 184-200 | 113-129 | |
| Loop 5 | 201-204 | 130-133 | |
| Helix E | 205-219 | 134-148 | |
| Loop 6 | 220-233 | 149-161 | |
| Helix F | 234-248 | 162-176 | |
| Loop 7 | 249-256 | 177-184 | |
| Helix G | 257-271 | 185-199 | |
| Loop 8 | 272-274 | 200-202 | |
| Helix H | 275-279 | 203-207 | |
| Loop 9 | 280-297 | 208-225 | |
| Helix I | 298-303 | 226-230 | |
| Loop 10 | 304-314 | 231-242 | |
| Helix J | 315-324 | 243-251 | |
| Loop 11 | 325-328 | 252-257 | |
| Helix K | 329-341 | 258-270 | |
| Loop 12 | 342-351 | 271-280 | |
| Helix L | 352-364 | 281-295 | |
| Loop 13 | 365-372 | 296-301 | |
| Helix M | 373-384 | 302-315 | |
| Loop 14 | 385-402 | 316-326 | |
| Helix N | 403-415 | 327-339 | |
| Loop 15 | 416-422 | 340-346 | |
| Helix O | 423-427 | 347-351 | |
| Loop 16 | 428-445 | 352-368 | Short loop |
| Helix P | 446-456 | 369-379 | |
| Loop 17 | 457-465 | 380-389 | |
| Helix Q | 466-481 | 390-406 | |
| Loop 18 | 482-495 | 407-414 | |
| Helix R | 496-505 | 415-424 | |
| Loop 19 | 506-512 | 425-430 | |
| Helix S | 513-523 | 431-441 | |
| Loop 20 | 524-544 | 442-462 | |
| Helix T | 545-573 | 463-491 | |
| Loop 21 | 574-586 | 492-504 | |
| Helix U | 587-595 | 505-513 | |
| Loop 22 | 596-603 | 514-521 | |
| Helix V | 604-625 | 522-543 | DDXXD motif |
| Loop 23 | 626-629 | 544-547 | |
| Helix W | 630-642 | 548-560 | |
| Loop 24 | 643-652 | 561-571 | |
| Helix X | 653-677 | 572-596 | |
| Loop 25 | 678-681 | 597-600 | |
| Helix Y | 682-705 | 601-619 | Short helix |
| Loop 26 | 706-710 | 620-630 | Longer loop |
| Helix Z | 711-721 | 631-641 | |
| Loop 27 | 722-724 | 642-644 | |
| Helix AA | 725-732 | 645-652 | |
| Loop 28 | 733-740 | 653-660 | |
| Helix AB | 741-745 | 661-664 | |
| Loop 29 | 746-751 | 665-670 | |
| Helix AC | 752-766 | 671-685 | NTE motif |
| Loop 30 | 767-769 | 686-688 | NTE motif |
| Helix AD | 770-773 | 689-692 | |
| Loop 31 | 774-781 | 693-700 | |
| Helix AE | 782-789 | 701-708 | |
| Loop 32 | 790-794 | 709-713 | |
| Helix AF | 795-819 | 714-738 | |
| Loop 33 | 820-824 | 739-746 | |
| Helix AG | 825-840 | 747-762 | |
| Loop 34 | 841-849 | 763-774 | Longer loop |
| Helix AH | 850-863 | 775-782 | |
| Loop 35 | 864-868 | 783-788 | |

Example 10

Production of Sclareol Synthase Fusion Proteins

In this example, various sclareol synthase (NgSs) fusion proteins were generated. In one example, a fusion containing labdenediol diphosphate synthase fused to sclareol synthase was generated. In other examples, fusion proteins containing either the green fluorescent protein or the cellulose binding domain N-terminal linked sclareol synthase were generated to facilitate protein expression.

A. NgLPP-NgSs Fusion Protein

As an alternative to the vector of Example 8 containing the LPP and sclareol synthase polypeptides, a fusion protein containing at the N-terminus labdenediol diphosphate synthase fused to the sclareol synthase at the C-terminus was generated using standard molecular biology techniques. The two proteins were linked via a five amino acid GGSGG (SEQ ID NO:96) linker. The LPP synthase is set forth in SEQ ID NO:130 and the sclareol synthase is set forth in SEQ ID NO:131. The sequence of the DNA encoding the fusion protein is set forth in SEQ ID NO:95, and the sequence of the encoded polypeptide is set forth in SEQ ID NO:94.

B. Green Fluorescent Protein-NgSs Fusion Protein

A fusion protein containing green fluorescent protein linked to N-terminal to sclareol synthase was generated using standard molecular biology techniques. The encoding DNA sequence is set forth in SEQ ID NO:91, and the sequence of the encoded fusion protein is set forth in SEQ ID NO:90.

C. Cellulose Binding Domain-NgSs Fusion Protein

A fusion protein containing the cellulose binding domain from *Trichoderma harzianum* (SEQ ID NO:97) N-terminal to sclareol synthase was generated using standard molecular biology techniques. The sequence of the encoding DNA is set forth in SEQ ID NO:93, and the sequence of the encoded polypeptide is set forth in SEQ ID NO:92.

Example 11

Variant Sclareol Synthases

In this example, a variant sclareol synthase was generated containing a swap at the N-terminus of sclareol synthase by replacement of nucleotides encoding residues 1-246 of *Nicotiana glutinosa* sclareol synthase with residues 61-77 of the sage sclareol synthase set forth in SEQ ID NO:60. Thus, the variant sclareol synthase protein contained amino acids 61-77 from the sage sclareol synthase N-terminal lined to amino acids 247-755 of *Nicotiana glutinosa* sclareol synthase. The sequence of the encoding DNA is set forth in SEQ ID NO:87, and the sequence of the encoded polypeptide is set forth in SEQ ID NO:86.

Example 12

Production of Sclareol and (−)-ambroxide

In this example, sclareol and (−)-ambroxide, whose production is catalyzed by the enzymes provided herein, are produced.

A. Preparation of Sclareol

The mechanism of the biosynthetic production of sclareol from geranylgeranyl diphosphate (GGPP) is set forth in Scheme I below.

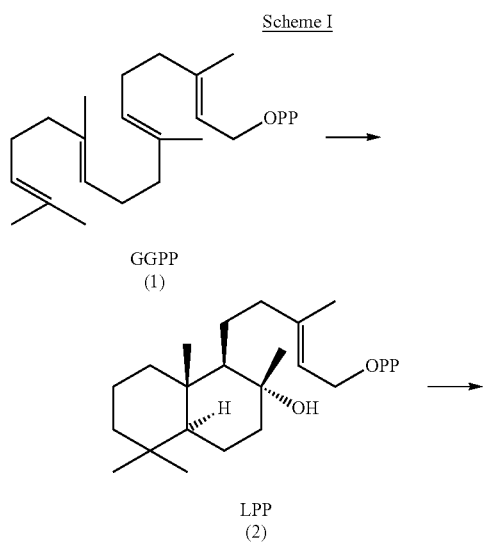

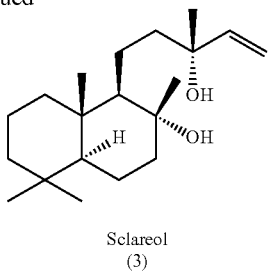

In Scheme I, the cyclization of GGPP (1) to form Sclareol (3) is carried out in two steps. In the first step, the terminal double bond of GGPP is protonated, leading to internal rearrangement and proton elimination, thereby yielding the diterpene phosphate intermediate, labdenediol diphosphate (LPP) (2). This reaction is catalyzed by a class II diterpene synthase, designated herein as LPP cyclase. In the second step, a class I diterpene synthase, designated herein as sclareol cyclase (or sclareol synthase (Ss)), catalyzes the ionization of the diphosphate ester functional group of LPP (2), followed by the reaction of the carbocation with an internal double bond, to generate the final product sclareol (3).

B. Production of (−)-Ambroxide

1. Preparation of (−)-Ambroxide from Sclareol

The preparation of (−)-ambroxide (1,5,5,9-tetramethyl-13-oxatricyclo[8.3.0.0$^{4,9}$]tridecane) from (−)-sclareol is known in the art, e.g. see Barrero et al. *Tetrahedron* 49(45): 10405-10412, 1993; Barrero et al., *Synthetic Communications* 34(19):3631-3643, 2004, which are incorporated herein by reference.

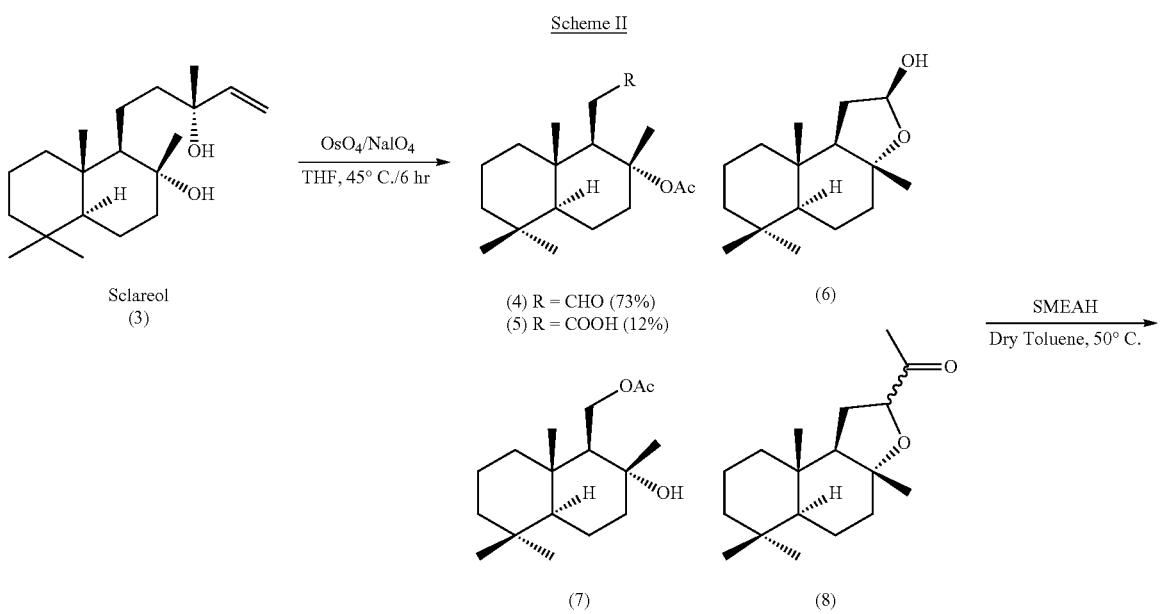

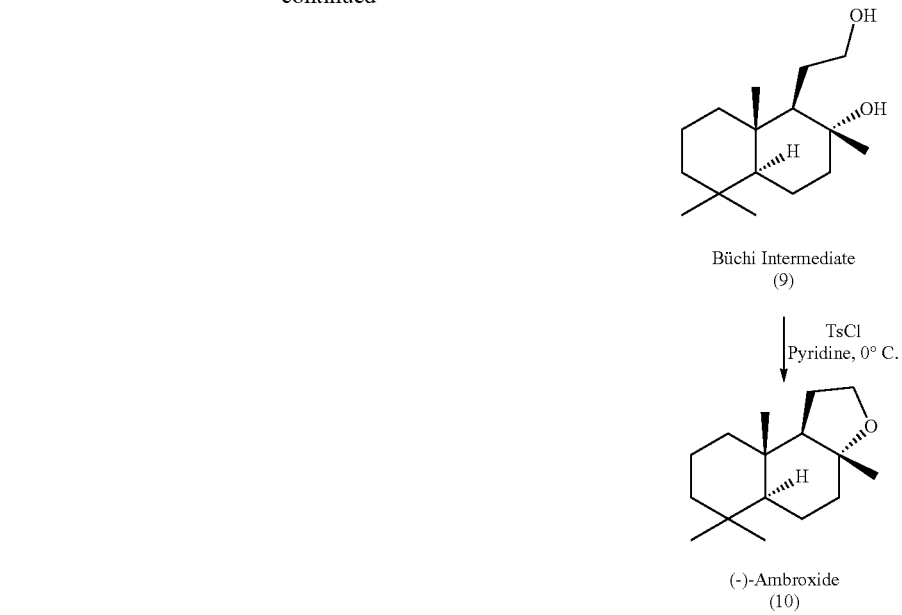

Büchi Intermediate
(9)

TsCl
Pyridine, 0° C.

(-)-Ambroxide
(10)

Scheme II describes an exemplary preparation of (−)-ambroxide (10) from (−)-sclareol starting material (3). Oxidative degradation of the side chain of compound (3) is carried out by treatment of (3) with osmium tetroxide-sodium periodate ($OsO_4/NaIO_4$) in tetrahydrofuran (THF) solution at 45° C. for 6 hours to form majority products acetoxyaldehyde (4) (approx. 73%), the acetoxyacid (5) (approx 12%), and the hemiacetal (6) (approx 5%) and minor products (7) and (8). As a less expensive alternative to $OsO_4$ treatment, ozonolysis of (3) can be used to obtain higher yields.

The mixture containing the major products of the oxidative degradation reaction, (4) and (5), is then reduced using a sodium bis(2-methoxyethoxy) aluminum hydride (SMEAH; $NaAlH_2(OC_2H_4OCH_3)_2$) solution in toluene at 50° C., generating a Büchi Intermediate (9), which is then cyclized into (−)-ambroxide (10) using tosyl chloride in the presence of a weak base, such as pyridine at 0° C. The overall yield for the reaction set forth in Scheme II is approximately 80%.

Scheme III

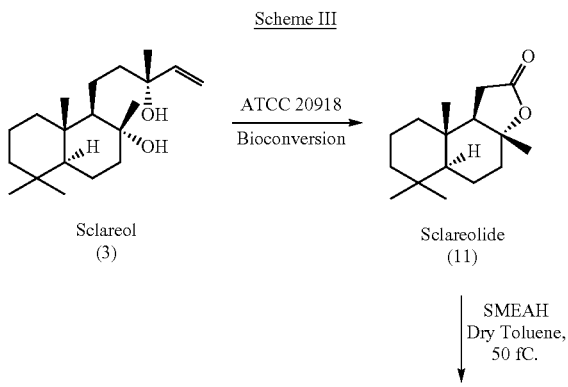

-continued

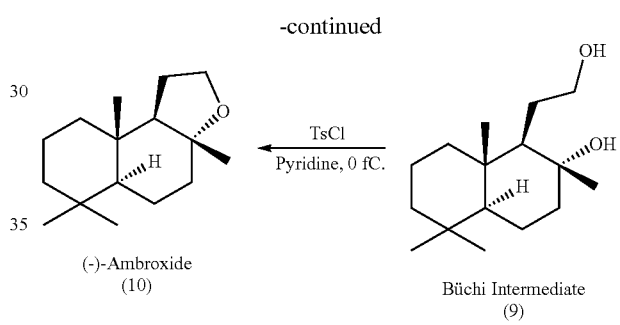

Scheme III describes an alternative preparation of (−)-ambroxide (10) from (−)-sclareol (3), whereby sclareol is converted to sclareolide (3a,6,6,9a-tetramethyl-1,4,5,5a,7,8,9,9b-octahydronaphtho[8,7-d]furan-2-one) (11), by way of a microbial method using the organism Cryptococcus magnus, ATCC 20918 (ATCC; deposited as Cryptococcus albidus by International Flavors & Fragrances, Inc.). Briefly ATCC 20918 is cultivated under fermentation conditions in an aqueous nutrient medium containing compound (3). This process has been previously described, e.g., in U.S. Pat. Nos. 4,970,163, 5,212,078. Compounds of structure (11) are then isolated and purified from the fermentation broths using conventional techniques, including filtration centrifugation, solvent extraction, crystallization, and the like. Purified compound (II) is then reduced by SMEAH in toluene at 50° C. to form a Büchi Intermediate (9). Using a strong base during this reduction reaction may increase the yield of (9). Finally, (9) is cyclized into (−)-ambroxide (10) using tosyl chloride in the presence pyridine at 0° C.

2. Preparation of (−)-Ambroxide from Geranylgeranyl Diphosphate (GGPP)

The production of (−)-ambroxide (10) from at starting compound of geranylgeranyl diphosphate (GGPP) (1) is accomplished by combining Schemes I and III to generate the reaction pathway set forth in Scheme IV below.

Scheme IV

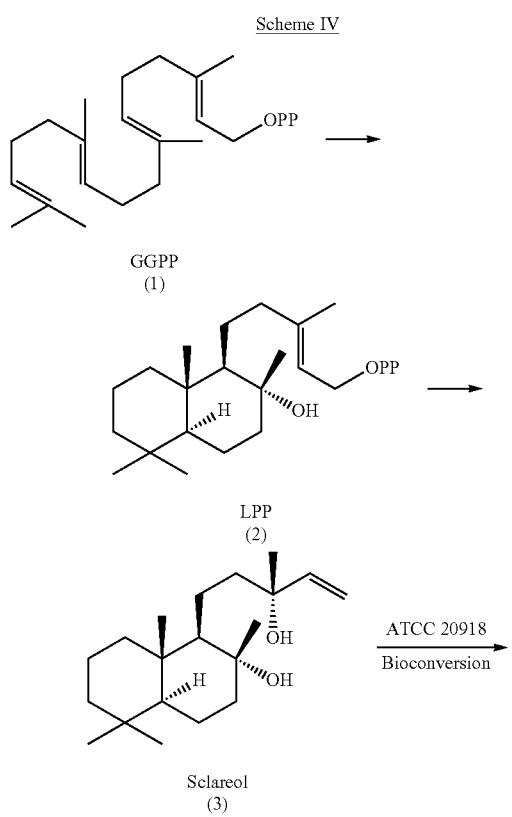

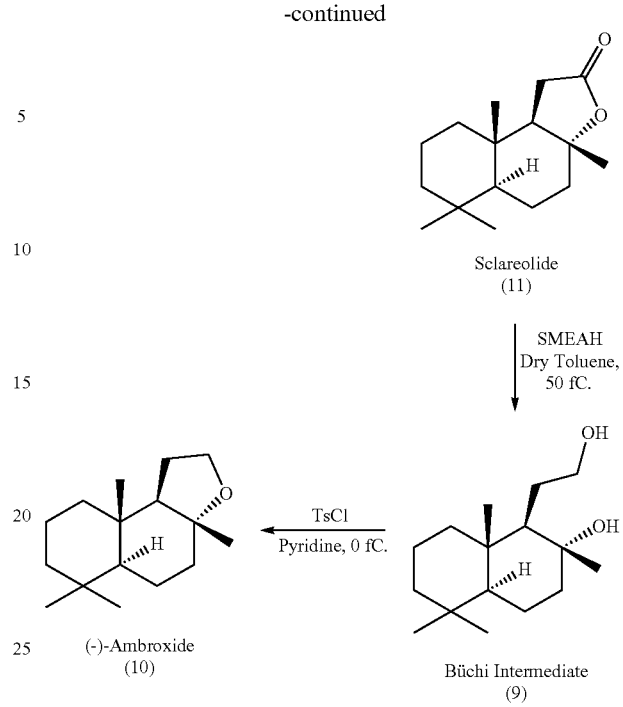

Since modifications will be apparent to those of skill in this art, it is intended that this invention be limited only by the scope of the appended claims.

The invention claimed is:

1. A host cell, comprising a cDNA molecule encoding a labdenediol diphosphate synthase polypeptide;
   wherein the cDNA molecule encoding the labdenediol diphosphate synthase is heterologous to the host cell and is operably linked to a heterologous promoter;
   wherein the labdenediol diphosphate synthase polypeptide comprises a sequence of amino acid residues that has at least 85% sequence identity to any of SEQ ID NOS: 2, 4, 6, 8, 10, 12, 14 and 54; and
   wherein the labdenediol diphosphate synthase polypeptide catalyzes production of a terpene from an acyclic pyrophosphate terpene precursor in the host cell.

2. The host cell of claim 1, wherein the cDNA molecule encoding the labdenediol diphosphate synthase polypeptide has a sequence set forth in any of SEQ ID NOS: 1, 3, 5, 7, 9, 11, 13 and 53.

3. The host cell of claim 1, wherein the acyclic pyrophosphate terpene precursor is geranylgeranyl diphosphate (GGPP) and the terpene product is labdenediol diphosphate.

4. The host cell of claim 3, wherein the host cell comprises heterologous nucleic acid encoding a GGPP synthase that catalyzes production of the GGPP.

5. The host cell of claim 1 that is a yeast cell.

6. The host cell of claim 1 wherein the labdenediol diphosphate synthase polypeptide comprises one or more heterologous domains or portions thereof from one or more different terpene synthases, wherein the domain is identified as Helix A; Loop 1; Helix B; Loop 2; Helix C; Loop 3; Helix D; Loop 4; Helix E; Loop 5; Helix F1; Loop 7; Helix G; Loop 8; Helix H; Loop 9; Helix I; Loop 10; Helix J; Loop 11; Helix K; Loop 12; Helix L; Loop 13; Helix M; Loop 14; Helix N; Loop 15; Helix O; Loop 16; Helix P; Loop 17; Helix Q; Loop 18; Helix R; Loop 19; Helix S; Loop 20; Helix T; Loop 21; Helix U; Loop 22; Helix V; Loop 23; Helix W; Loop 24; Helix X; Loop 25; Helix Y; Loop 26; Helix Z1; Loop 28; Helix AA; Loop 29; Helix AB; Loop 30; Helix AC or Loop 31.

7. A vector, comprising a cDNA molecule encoding a labdenediol diphosphate synthase polypeptide;
   wherein the cDNA molecule encoding the labdenediol diphosphate synthase is operably linked to a heterologous promoter;
   wherein the labdenediol diphosphate synthase polypeptide comprises a sequence of amino acid residues that has at least 85% sequence identity to the labdenediol diphosphate synthase polypeptide set forth in any of SEQ ID NOS: 2, 4, 6, 8, 10, 12, 14 or 54.

8. The vector of claim 7, wherein the vector is a prokaryotic vector, a viral vector or a eukaryotic vector.

9. The vector of claim 7, wherein the vector is a yeast vector.

10. A host cell, comprising the vector of claim 7.

11. A method for producing a labdenediol diphosphate synthase polypeptide, comprising:
    (a) culturing the host cell of claim 1 or claim 10 under conditions suitable for expression of the cDNA molecule encoding the labdenediol diphosphate synthase polypeptide; and
    (b) optionally isolating the labdenediol diphosphate synthase polypeptide.

* * * * *

SEQUENCE LISTING

<160> NUMBER OF SEQ ID NOS: 131

<210> SEQ ID NO 1
<211> LENGTH: 2406
<212> TYPE: DNA
<213> ORGANISM: Nicotiana glutinosa
<220> FEATURE:
<223> OTHER INFORMATION: NgLPP2-1-2

<400> SEQUENCE: 1

```
atgcaggtta aaattacgtc cagtcacagg cttttctgcc attttcatca actcaagagt      60
gctacatcgt tatctgcaca gaaaactgag tttagaaaat atggacccgg aaattcgttg     120
ttccaaactg aaggctcact tctatataaa ccagttcgtc tcaattgcgc acctattgat     180
gcaagttatc ttggttatct gaatgagttg gaatctaatt tctcaaacaa ccccgaagaa     240
aaggatattc aggtaagcag aacaatacag atcaaaaatt tgacagaaga aatcaaatgt     300
aagttgaatt cgatggagga tggaaggtca agtgtctcag cctatgacac agcttgggtt     360
tcctttattc caaatactac taataatgga aatgatcaaa ggcctatgtt tccatcttgt     420
cttcaatgga ttatagacaa tcaactttgc gatggttcat ggggagagga gagtgtattc     480
tgcatatatg atcgactctt gaacacacta gcatgtgttg ttgcattgac attatggaac     540
acatgccttc ctaagagaaa caaggtgtg atgtttatca aagaaaactt aattaagtta     600
gagacagggg aagttgaaca catgacttgt ggatttgaat ttgtgtttcc tgctctcctt     660
gagaaagctc aacaattaaa tattgacatt ccgtatgatg ctccagtctt aaaggatatt     720
tatgcaagga gagaagtaaa gtttacaaga attcctaaag agattgtcca tacgattccg     780
```

-continued

```
acaacagcat tgctttcatt agaaggatta agggacgacc tggattggca aagactttta    840
aattttcaaa tgcctgatgg ttcattctta tcagcccctg cttccactgc ctttgcattc    900
atgaaaacaa acgatgaaaa gtgtttggca tatcttcaaa atgttgttca aaagtctaat    960
ggaggagcgc gacactaccc actggacttg ttaaacacgac tttgggcaat tgatcgatta   1020
caacgccttg gaatatctta ttattttgcg gaagagttca aggaactttt gaatcatgtg   1080
ttcagatatt gggacgagga gaatggaatt ttcagtggaa ggaattcaaa cgtttgtgac   1140
gttgatgata catgcatggc tattaggttg cttaggttgc atgggtatga tgttagtcca   1200
gatgcgctaa acaatttcac agatggtgat caattctttt gccttagagg tgaagtggac   1260
gggtcaccaa cacatatgtt taatctttat agatgttccc aagttttatt cccaggagaa   1320
aagattcttg aagaggcaaa gaattttact tacaacttct tacagcaatg tcttgcaaac   1380
aatcgatgct tagacaaatg ggtcatagct aaggacattc ccggggagat aaggtatgca   1440
ctgaaatttc catggtatgc aagcttacct cgggtggaat ctaggctata catagaacag   1500
tacggcggag caaatgatat ttggattggc aagacattat acaggatgcc cgatgtcagc   1560
aacaatgttt atttacaagc tgcaaaatta gattacaaca gatgccaaag tcaacatcga   1620
tttgaatggc taattatgca acagtggttt gataagtgca actttcaaca atttggaata   1680
agcaaaaagt acctcctagt ttcttatttc ttagctgctg caagtatatt tgaagtcgaa   1740
aagtcaagag aacgacttgc gtgggctaaa tctcgtataa tatgtaagat gattacatct   1800
tactacaatg aagaagccac aacttggacc agtaggaatt cattgctaat ggaattcaag   1860
ggttctgatg atccaagcag aaaaaatggt aatgaaacaa aagagatcat agttctcaaa   1920
aatcttcgtc agttttttgca ccaactatca gaagaaactt ttgaagacct aggcaaagac   1980
atccatcacc aactacaaaa tgcatggaaa acgtggttgg cgttcttaag ggaggaaaaa   2040
aatacatgcc aagaagaagc agagttgcta gtgcgcacaa ttaatctctc cggcggccat   2100
atgatacatg atgagatact attcgatgcg gactacaaaa atctgtccaa ccttactaat   2160
aaagtttgct gcatgcttag tgagctccaa aatgacaagg tgactggcag ctcaaagaac   2220
actgacattg aactcaacat gcaagcactt gtaaaattag tgtttggtaa cacctcaagc   2280
aacatcaacc aagacattaa gcaaacattt tttacagttg ttaagacttt ctattacagt   2340
gcacatgcta gtgaggaaat aatcaacttt cacatatcca aggtgctttt tcatcaagtc   2400
cagtaa                                                              2406
```

<210> SEQ ID NO 2
<211> LENGTH: 801
<212> TYPE: PRT
<213> ORGANISM: Nicotiana glutinosa
<220> FEATURE:
<223> OTHER INFORMATION: NgLPP2-1-2

<400> SEQUENCE: 2

Met Gln Val Lys Ile Thr Ser Ser His Arg Leu Phe Cys His Phe His
1               5                   10                  15

Gln Leu Lys Ser Ala Thr Ser Leu Ser Ala Gln Lys Thr Glu Phe Arg
            20                  25                  30

Lys Tyr Gly Pro Gly Asn Ser Leu Phe Gln Thr Glu Gly Ser Leu Leu
        35                  40                  45

Tyr Lys Pro Val Arg Leu Asn Cys Ala Pro Ile Asp Ala Ser Tyr Leu
    50                  55                  60

```
Gly Tyr Leu Asn Glu Leu Glu Ser Asn Phe Ser Asn Asn Pro Glu Glu
 65                  70                  75                  80

Lys Asp Ile Gln Val Ser Arg Thr Ile Gln Ile Lys Asn Leu Thr Glu
                 85                  90                  95

Glu Ile Lys Cys Lys Leu Asn Ser Met Glu Asp Gly Arg Ser Ser Val
            100                 105                 110

Ser Ala Tyr Asp Thr Ala Trp Val Ser Phe Ile Pro Asn Thr Thr Asn
        115                 120                 125

Asn Gly Asn Asp Gln Arg Pro Met Phe Pro Ser Cys Leu Gln Trp Ile
    130                 135                 140

Ile Asp Asn Gln Leu Cys Asp Gly Ser Trp Gly Glu Ser Val Phe
145                 150                 155                 160

Cys Ile Tyr Asp Arg Leu Leu Asn Thr Leu Ala Cys Val Val Ala Leu
                165                 170                 175

Thr Leu Trp Asn Thr Cys Leu Pro Lys Arg Asn Lys Gly Val Met Phe
            180                 185                 190

Ile Lys Glu Asn Leu Ile Lys Leu Glu Thr Gly Glu Val Glu His Met
        195                 200                 205

Thr Cys Gly Phe Glu Phe Val Phe Pro Ala Leu Leu Glu Lys Ala Gln
    210                 215                 220

Gln Leu Asn Ile Asp Ile Pro Tyr Asp Ala Pro Val Leu Lys Asp Ile
225                 230                 235                 240

Tyr Ala Arg Arg Glu Val Lys Phe Thr Arg Ile Pro Lys Glu Ile Val
                245                 250                 255

His Thr Ile Pro Thr Thr Ala Leu Leu Ser Leu Glu Gly Leu Arg Asp
            260                 265                 270

Asp Leu Asp Trp Gln Arg Leu Leu Asn Phe Gln Met Pro Asp Gly Ser
        275                 280                 285

Phe Leu Ser Ala Pro Ala Ser Thr Ala Phe Ala Phe Met Lys Thr Asn
    290                 295                 300

Asp Glu Lys Cys Leu Ala Tyr Leu Gln Asn Val Val Gln Lys Ser Asn
305                 310                 315                 320

Gly Gly Ala Arg His Tyr Pro Leu Asp Leu Leu Thr Arg Leu Trp Ala
                325                 330                 335

Ile Asp Arg Leu Gln Arg Leu Gly Ile Ser Tyr Tyr Phe Ala Glu Glu
            340                 345                 350

Phe Lys Glu Leu Leu Asn His Val Phe Arg Tyr Trp Asp Glu Glu Asn
        355                 360                 365

Gly Ile Phe Ser Gly Arg Asn Ser Asn Val Cys Asp Val Asp Asp Thr
    370                 375                 380

Cys Met Ala Ile Arg Leu Leu Arg Leu His Gly Tyr Asp Val Ser Pro
385                 390                 395                 400

Asp Ala Leu Asn Asn Phe Thr Asp Gly Asp Gln Phe Phe Cys Leu Arg
                405                 410                 415

Gly Glu Val Asp Gly Ser Pro Thr His Met Phe Asn Leu Tyr Arg Cys
            420                 425                 430

Ser Gln Val Leu Phe Pro Gly Glu Lys Ile Leu Glu Glu Ala Lys Asn
        435                 440                 445

Phe Thr Tyr Asn Phe Leu Gln Gln Cys Leu Ala Asn Asn Arg Cys Leu
    450                 455                 460

Asp Lys Trp Val Ile Ala Lys Asp Ile Pro Gly Glu Ile Arg Tyr Ala
465                 470                 475                 480

Leu Lys Phe Pro Trp Tyr Ala Ser Leu Pro Arg Val Glu Ser Arg Leu
```

```
                485                490                495
Tyr Ile Glu Gln Tyr Gly Gly Ala Asn Asp Ile Trp Ile Gly Lys Thr
            500                505                510
Leu Tyr Arg Met Pro Asp Val Ser Asn Val Tyr Leu Gln Ala Ala
        515                520                525
Lys Leu Asp Tyr Asn Arg Cys Gln Ser Gln His Arg Phe Glu Trp Leu
    530                535                540
Ile Met Gln Gln Trp Phe Asp Lys Cys Asn Phe Gln Gln Phe Gly Ile
545                550                555                560
Ser Lys Lys Tyr Leu Leu Val Ser Tyr Phe Ala Ala Ala Ser Ile
                565                570                575
Phe Glu Val Glu Lys Ser Arg Glu Arg Leu Ala Trp Ala Lys Ser Arg
            580                585                590
Ile Ile Cys Lys Met Ile Thr Ser Tyr Tyr Asn Glu Glu Ala Thr Thr
        595                600                605
Trp Thr Ser Arg Asn Ser Leu Leu Met Glu Phe Lys Gly Ser Asp Asp
610                615                620
Pro Ser Arg Lys Asn Gly Asn Glu Thr Lys Glu Ile Val Leu Lys
625                630                635                640
Asn Leu Arg Gln Phe Leu His Gln Leu Ser Glu Thr Phe Glu Asp
                645                650                655
Leu Gly Lys Asp Ile His His Gln Leu Gln Asn Ala Trp Lys Thr Trp
            660                665                670
Leu Ala Phe Leu Arg Glu Glu Lys Asn Thr Cys Gln Glu Glu Ala Glu
        675                680                685
Leu Leu Val Arg Thr Ile Asn Leu Ser Gly Gly His Met Ile His Asp
    690                695                700
Glu Ile Leu Phe Asp Ala Asp Tyr Lys Asn Leu Ser Asn Leu Thr Asn
705                710                715                720
Lys Val Cys Cys Met Leu Ser Glu Leu Gln Asn Asp Lys Val Thr Gly
                725                730                735
Ser Ser Lys Asn Thr Asp Ile Glu Leu Asn Met Gln Ala Leu Val Lys
            740                745                750
Leu Val Phe Gly Asn Thr Ser Ser Asn Ile Asn Gln Asp Ile Lys Gln
        755                760                765
Thr Phe Phe Thr Val Val Lys Thr Phe Tyr Tyr Ser Ala His Ala Ser
    770                775                780
Glu Glu Ile Ile Asn Phe His Ile Ser Lys Val Leu Phe His Gln Val
785                790                795                800
Gln

<210> SEQ ID NO 3
<211> LENGTH: 2406
<212> TYPE: DNA
<213> ORGANISM: Nicotiana glutinosa
<220> FEATURE:
<223> OTHER INFORMATION: NgLPP2-1-3

<400> SEQUENCE: 3
atgcaggtta aaattacgtc cagtcacagg cttttctgcc attttcatca actcaagagt    60
gctacatcgt tatctgcaca gaaaactgag cttagaaaat atggacccgg aaattcgttg   120
ttccaaactg aaggctcact tctatataaa ccagttcgtc tcaattgcgc acctattgat   180
gcaagttatc ttggttatct gaatgagttg gaatctaatt tctcaaacaa ccccgaagaa   240
```

```
aaggatattc aggtaagcag aacaatacag atcaaaaatt tgacagaaga aatcaaatgt    300
aagttgaatt cgatggagga tggaaggtca agtgtctcag cctatgacac agcttgggtt    360
tcctttattc caaatactac taataatgga aatgatcaaa ggcctatgtt tccatcttgt    420
cttcaatgga ttatagacaa tcaactttgc gatggttcat ggggagagga gagtgtattc    480
tgcatatatg atcgactctt gaacacacta gcatgtgttg ttgcattgac attatggaac    540
acatgccttc ctaagagaaa caaggtgtg atgtttatca agaaaactt aattaagtta    600 gagacagggg aagttgaaca catgacttgt ggatttgaat ttgtgtttcc tgctctcctt    660
gagaaagctc aacaattaaa tattgacatt ccgtatgatg ctccagtctt aaaggatatt    720
tatacaagga gagaagtaaa gtttacaaga attcctaaag agattgtcca tacgattccg    780
acaacagcat tactttcatt agaaggatta aggggcgacc tggattggca agacttttta    840
aattttcaaa tgcctgatgg ttcattctta tcagccctg cttccactgc ctttgcattc    900
atgaaaacaa acgatgaaaa gtgtttggca tatcttcaaa atgttgttca aaagtctaat    960
ggaggagcgc gacactaccc actggacttg ttaacacgac tttgggcaat tgatcgatta    1020
caacgccttg gaatatctta ttattttgcg gaagagttca aggaactttt gaatcatgtg    1080
ttcagatatt gggacgagga aatggaatt ttcagtggaa ggaattcaaa cgtttgtgac    1140
gttgatgata catgcatggc tattaggttg cttaggttgc atgggtatga tgttagtcca    1200
gatgcgctaa acaatttcac agatggtgat caattcttt gccttagagg tgaagtggac    1260
gggtcaccaa cacatatgtt taatctttat agatgttccc aagtttatt cccaggagaa    1320 aggattcttg aagaggcaaa gaattttact tacaacttct tacagcaatg tcttgcaaac    1380
aatcgatgct tagacaaatg ggtcatagct aaggacattc ccggggagat aaggtatgca    1440
ctgaaatttc catggtatgc aagcttacct cgggtggaat ctaggctata catagaacag    1500
tacggcggag caaatgatat ttggattggc aagacattat acaggatgcc cgatgtcagc    1560
aacaatgttt atttacaagc tgcaaaatta gattacaaca gatgccaaag tcaacatcga    1620
tttgaatggc taattatgca acagtggttt gataagtgca actttcaaca atttggaata    1680
agcaaaaagt acctcctagt ttcttatttc ttagctgctg caagtatatt tgaagtcgaa    1740
aagtcaagag aacgacttgc gtgggctaaa tctcgtataa tatgtaagat gattacatct    1800
tactacaatg aagaagccac aacttggacc agtaggaatt cattgctaat ggaattcaag    1860
ggttctgatg atccaagcag aaaaaatggt aatgaaacaa aagagatcat agttctcaaa    1920
aatcttcgtc agttttttgca ccaactatca gaagaaactt ttgaagacct aggcaaagac    1980
atccatcacc aactacaaaa tgcatggaaa acgtggttgg cgttcttaag ggaggaaaaa    2040
aatacatgcc aagaagaagc agagttgcta gtgcgcacaa ttaatctctc cggcggccat    2100
atgatacatg atgagatact attcgatgcg gactacaaaa atctgtccaa ccttactaat    2160
aaagtttgct gcatgcttag tgagctccaa aatgacaagg tgactggcag ctcaaagaac    2220
actgacattg aactcaacat gcaagcactt gtaaagttag tgtttggtaa cacctcaagc    2280
aacatcaacc aagacattaa gcaaacattt tttgcagttg ttaagacttt ctattacagt    2340
gcacatgtta gtgaggaaat aatcaactttt cacatatcca aggtgctttt tcagcaagtc    2400
cagtaa                                                                2406
```

<210> SEQ ID NO 4
<211> LENGTH: 801
<212> TYPE: PRT
<213> ORGANISM: Nicotiana glutinosa
<220> FEATURE:
<223> OTHER INFORMATION: NgLPP2-1-3

<400> SEQUENCE: 4

```
Met Gln Val Lys Ile Thr Ser Ser His Arg Leu Phe Cys His Phe His
 1               5                  10                  15

Gln Leu Lys Ser Ala Thr Ser Leu Ser Ala Gln Lys Thr Glu Leu Arg
             20                  25                  30

Lys Tyr Gly Pro Gly Asn Ser Leu Phe Gln Thr Glu Gly Ser Leu Leu
         35                  40                  45

Tyr Lys Pro Val Arg Leu Asn Cys Ala Pro Ile Asp Ala Ser Tyr Leu
 50                  55                  60

Gly Tyr Leu Asn Glu Leu Glu Ser Asn Phe Ser Asn Asn Pro Glu Glu
 65                  70                  75                  80

Lys Asp Ile Gln Val Ser Arg Thr Ile Gln Ile Lys Asn Leu Thr Glu
                 85                  90                  95

Glu Ile Lys Cys Lys Leu Asn Ser Met Glu Asp Gly Arg Ser Ser Val
            100                 105                 110

Ser Ala Tyr Asp Thr Ala Trp Val Ser Phe Ile Pro Asn Thr Thr Asn
        115                 120                 125

Asn Gly Asn Asp Gln Arg Pro Met Phe Pro Ser Cys Leu Gln Trp Ile
130                 135                 140

Ile Asp Asn Gln Leu Cys Asp Gly Ser Trp Gly Glu Ser Val Phe
145                 150                 155                 160

Cys Ile Tyr Asp Arg Leu Leu Asn Thr Leu Ala Cys Val Val Ala Leu
                165                 170                 175

Thr Leu Trp Asn Thr Cys Leu Pro Lys Arg Asn Lys Gly Val Met Phe
            180                 185                 190

Ile Lys Glu Asn Leu Ile Lys Leu Glu Thr Gly Glu Val Glu His Met
        195                 200                 205

Thr Cys Gly Phe Glu Phe Val Phe Pro Ala Leu Leu Glu Lys Ala Gln
    210                 215                 220

Gln Leu Asn Ile Asp Ile Pro Tyr Asp Ala Pro Val Leu Lys Asp Ile
225                 230                 235                 240

Tyr Thr Arg Arg Glu Val Lys Phe Thr Arg Ile Pro Lys Glu Ile Val
                245                 250                 255

His Thr Ile Pro Thr Thr Ala Leu Leu Ser Leu Glu Gly Leu Arg Gly
            260                 265                 270

Asp Leu Asp Trp Gln Arg Leu Leu Asn Phe Gln Met Pro Asp Gly Ser
        275                 280                 285

Phe Leu Ser Ala Pro Ala Ser Thr Ala Phe Ala Phe Met Lys Thr Asn
290                 295                 300

Asp Glu Lys Cys Leu Ala Tyr Leu Gln Asn Val Val Gln Lys Ser Asn
305                 310                 315                 320

Gly Gly Ala Arg His Tyr Pro Leu Asp Leu Leu Thr Arg Leu Trp Ala
                325                 330                 335

Ile Asp Arg Leu Gln Arg Leu Gly Ile Ser Tyr Tyr Phe Ala Glu Glu
            340                 345                 350

Phe Lys Glu Leu Leu Asn His Val Phe Arg Tyr Trp Asp Glu Asn
        355                 360                 365

Gly Ile Phe Ser Gly Arg Asn Ser Asn Val Cys Asp Val Asp Asp Thr
    370                 375                 380

Cys Met Ala Ile Arg Leu Leu Arg Leu His Gly Tyr Asp Val Ser Pro
385                 390                 395                 400
```

```
Asp Ala Leu Asn Asn Phe Thr Asp Gly Asp Gln Phe Phe Cys Leu Arg
            405                 410                 415

Gly Glu Val Asp Gly Ser Pro Thr His Met Phe Asn Leu Tyr Arg Cys
        420                 425                 430

Ser Gln Val Leu Phe Pro Gly Glu Arg Ile Leu Glu Glu Ala Lys Asn
            435                 440                 445

Phe Thr Tyr Asn Phe Leu Gln Gln Cys Leu Ala Asn Asn Arg Cys Leu
    450                 455                 460

Asp Lys Trp Val Ile Ala Lys Asp Ile Pro Gly Glu Ile Arg Tyr Ala
465                 470                 475                 480

Leu Lys Phe Pro Trp Tyr Ala Ser Leu Pro Arg Val Glu Ser Arg Leu
                485                 490                 495

Tyr Ile Glu Gln Tyr Gly Gly Ala Asn Asp Ile Trp Ile Gly Lys Thr
            500                 505                 510

Leu Tyr Arg Met Pro Asp Val Ser Asn Asn Val Tyr Leu Gln Ala Ala
        515                 520                 525

Lys Leu Asp Tyr Asn Arg Cys Gln Ser Gln His Arg Phe Glu Trp Leu
    530                 535                 540

Ile Met Gln Gln Trp Phe Asp Lys Cys Asn Phe Gln Gln Phe Gly Ile
545                 550                 555                 560

Ser Lys Lys Tyr Leu Leu Val Ser Tyr Phe Leu Ala Ala Ala Ser Ile
                565                 570                 575

Phe Glu Val Glu Lys Ser Arg Glu Arg Leu Ala Trp Ala Lys Ser Arg
            580                 585                 590

Ile Ile Cys Lys Met Ile Thr Ser Tyr Tyr Asn Glu Glu Ala Thr Thr
        595                 600                 605

Trp Thr Ser Arg Asn Ser Leu Leu Met Glu Phe Lys Gly Ser Asp Asp
    610                 615                 620

Pro Ser Arg Lys Asn Gly Asn Glu Thr Lys Glu Ile Ile Val Leu Lys
625                 630                 635                 640

Asn Leu Arg Gln Phe Leu His Gln Leu Ser Glu Glu Thr Phe Glu Asp
                645                 650                 655

Leu Gly Lys Asp Ile His His Gln Leu Gln Asn Ala Trp Lys Thr Trp
            660                 665                 670

Leu Ala Phe Leu Arg Glu Glu Lys Asn Thr Cys Gln Glu Glu Ala Glu
        675                 680                 685

Leu Leu Val Arg Thr Ile Asn Leu Ser Gly Gly His Met Ile His Asp
    690                 695                 700

Glu Ile Leu Phe Asp Ala Asp Tyr Lys Asn Leu Ser Asn Leu Thr Asn
705                 710                 715                 720

Lys Val Cys Cys Met Leu Ser Glu Leu Gln Asn Asp Lys Val Thr Gly
                725                 730                 735

Ser Ser Lys Asn Thr Asp Ile Glu Leu Asn Met Gln Ala Leu Val Lys
            740                 745                 750

Leu Val Phe Gly Asn Thr Ser Ser Asn Ile Asn Gln Asp Ile Lys Gln
        755                 760                 765

Thr Phe Phe Ala Val Val Lys Thr Phe Tyr Tyr Ser Ala His Val Ser
    770                 775                 780

Glu Glu Ile Ile Asn Phe His Ile Ser Lys Val Leu Phe Gln Gln Val
785                 790                 795                 800

Gln
```

<210> SEQ ID NO 5
<211> LENGTH: 2406
<212> TYPE: DNA
<213> ORGANISM: Nicotiana glutinosa
<220> FEATURE:
<223> OTHER INFORMATION: NgLLP2-1-4

<400> SEQUENCE: 5

| | | | | | |
|---|---|---|---|---|---|
| atgcaggtta | aaattacgtc | cagtcacagg | cttttctgcc | attttcatca | actcaagagt | 60 |
| gctacatcgt | tatctgcaca | gaaaactgag | cttagaaaat | atggacccgg | aaattcgttg | 120 |
| ttccaaactg | aaggctcact | tctatataaa | ccagttcgtc | tcaattgcgc | acctattgat | 180 |
| gcaagttatc | ttggttatct | gaatgagttg | gaatttaatt | tctcaaacaa | ccccgaagaa | 240 |
| aaggatattc | aggtaagcag | aacaatacag | atcaaaaatt | tgacagaaga | atcaaatgt | 300 |
| aagttgaatt | cgatggagga | tggaaggtca | agtgtctcag | cctatgacac | agcttgggtt | 360 |
| tcctttattc | caaatactac | taataatgga | aatgatcaaa | ggcctatgtt | ccatcttgt | 420 |
| cttcaatgga | ttatagacaa | tcaactttgc | aatggttcat | gggagagga | gagtgtattc | 480 |
| tgcatatatg | atcgactctt | gaacacacta | gcatgtgttg | ttgcattgac | attatggaac | 540 |
| acatgccttc | ctaagagaaa | caaggtgtg | atgtttatca | agaaaaactt | aattaagtta | 600 |
| gagacagggg | aagttgaaca | catgacttgt | ggatttgaat | ttgtgtttcc | tgctctcctt | 660 |
| gagaaagctc | aacaattaaa | tattgacatt | ccgtatgatg | ctccagtctt | aaaggatatt | 720 |
| tatgcaagga | gagaagtaaa | gtttacaaga | attcctaaag | agattgtcca | tacgattccg | 780 |
| acaacagcat | tactttcatt | agaaggatta | agggacgacc | tggattggca | agacttta | 840 |
| aattttcaaa | tgcctgatgg | ttcattctta | tcagcccctg | cttccactgc | ctttgcattc | 900 |
| atgaaaacaa | acgatgaaaa | gtgtttggca | tatcttcaaa | atgttgttca | aaagtctaat | 960 |
| ggaggagcgc | gacactaccc | actggacttg | ttaacacgac | tttgggcaat | tgatcgatta | 1020 |
| caacgccttg | gaatatctta | ttattttgcg | gaagagttca | aggaactttt | gaatcatgtg | 1080 |
| ttcagatatt | gggacgagga | gaatggaatt | ttcagtggaa | ggaattcaaa | cgtttgtgac | 1140 |
| gttgatgata | catgcatggc | tattaggttg | cttaggttgc | atgggtatga | tgttagtcca | 1200 |
| gatgcgctaa | acaatttcac | agatggtgat | caattctttt | gccttagagg | tgaagtggac | 1260 |
| gggtcaccaa | cacatatgtt | taatctttat | agatgttccc | aagttttatt | cccaggagaa | 1320 |
| aagattcttg | aagaggcaaa | gaattttact | tacaacttct | tacagcaatg | tcttgcaaac | 1380 |
| aatcgatgct | tagacaaatg | ggtcatagct | aaggacattc | cggggagat | agggtatgca | 1440 |
| ctgaaatttc | catggtatgc | aagcttacct | cgggtggaat | ctaggctata | catagaacag | 1500 |
| tacggcggag | caaatgatat | ttggattggc | aagacattat | acaggatgcc | cgatgtcagc | 1560 |
| aacaatgttt | atttcaaagc | tgcaaaatta | gattacaaca | gatgccaaag | tcaacatcga | 1620 |
| tttgaatggc | taattatgca | acagtggttt | gataagtgca | actttcaaca | atttggaata | 1680 |
| agcaaaaagt | acctcctagt | ttcttatttc | ttagctgctg | caagtatatt | tgaagtcgaa | 1740 |
| aagtcaagag | aacgacttgc | gtgggctaaa | tctcgtataa | tatgtaagat | gattacatct | 1800 |
| tactacaatg | aagaagccac | aacttggacc | agtaggaatt | cattgctaat | ggaattcaag | 1860 |
| ggttctgatg | atccaagcag | aaaaaatggt | aatgaaacaa | aagagatcat | agttctcaaa | 1920 |
| atcttcgtc | agtttttgca | ccaactatca | gaagaaactt | tgaagacct | aggcaaagac | 1980 |
| atccatcacc | aactacaaaa | tgcatggaaa | acgtggttgg | tgttcttaag | ggaggaaaaa | 2040 |
| aatacatgcc | aagaagaagc | agagttgcta | gtgcgcacaa | ttaatctctc | cggcggccat | 2100 |

```
atgatacatg atgagatact attcgatgcg gactacaaaa atctgtccaa ccttactaat      2160
aaagtttgct gcatgcttag tgagctccaa aatgacaagg tgactggcag ctcaaagaac      2220
actgacattg aactcaacat gcaagcactt gcaaagttag tgtttggtaa cacctcaagc      2280
aacatcaacc aagacattaa gcaaacattt tttgcagttg ttaagacttt ctattacagt      2340
gcacatgtta gtgaggaaat aatcaacttt cacatatcca aggtgctttt tcagcaagtc      2400
cagtaa                                                                 2406
```

```
<210> SEQ ID NO 6
<211> LENGTH: 801
<212> TYPE: PRT
<213> ORGANISM: Nicotiana glutinosa
<220> FEATURE:
<223> OTHER INFORMATION: NgLPP2-1-4

<400> SEQUENCE: 6

Met Gln Val Lys Ile Thr Ser Ser His Arg Leu Phe Cys His Phe His
  1               5                  10                  15

Gln Leu Lys Ser Ala Thr Ser Leu Ser Ala Gln Lys Thr Glu Leu Arg
             20                  25                  30

Lys Tyr Gly Pro Gly Asn Ser Leu Phe Gln Thr Glu Gly Ser Leu Leu
         35                  40                  45

Tyr Lys Pro Val Arg Leu Asn Cys Ala Pro Ile Asp Ala Ser Tyr Leu
     50                  55                  60

Gly Tyr Leu Asn Glu Leu Glu Phe Asn Phe Ser Asn Asn Pro Glu Glu
 65                  70                  75                  80

Lys Asp Ile Gln Val Ser Arg Thr Ile Gln Ile Lys Asn Leu Thr Glu
                 85                  90                  95

Glu Ile Lys Cys Lys Leu Asn Ser Met Glu Asp Gly Arg Ser Ser Val
            100                 105                 110

Ser Ala Tyr Asp Thr Ala Trp Val Ser Phe Ile Pro Asn Thr Thr Asn
        115                 120                 125

Asn Gly Asn Asp Gln Arg Pro Met Phe Pro Ser Cys Leu Gln Trp Ile
    130                 135                 140

Ile Asp Asn Gln Leu Cys Asn Gly Ser Trp Gly Glu Glu Ser Val Phe
145                 150                 155                 160

Cys Ile Tyr Asp Arg Leu Leu Asn Thr Leu Ala Cys Val Val Ala Leu
                165                 170                 175

Thr Leu Trp Asn Thr Cys Leu Pro Lys Arg Asn Lys Gly Val Met Phe
            180                 185                 190

Ile Lys Glu Asn Leu Ile Lys Leu Glu Thr Gly Glu Val Glu His Met
        195                 200                 205

Thr Cys Gly Phe Glu Phe Val Phe Pro Ala Leu Leu Glu Lys Ala Gln
    210                 215                 220

Gln Leu Asn Ile Asp Ile Pro Tyr Asp Ala Pro Val Leu Lys Asp Ile
225                 230                 235                 240

Tyr Ala Arg Arg Glu Val Lys Phe Thr Arg Ile Pro Lys Glu Ile Val
                245                 250                 255

His Thr Ile Pro Thr Thr Ala Leu Leu Ser Leu Glu Gly Leu Arg Asp
            260                 265                 270

Asp Leu Asp Trp Gln Arg Leu Leu Asn Phe Gln Met Pro Asp Gly Ser
        275                 280                 285

Phe Leu Ser Ala Pro Ala Ser Thr Ala Phe Ala Phe Met Lys Thr Asn
    290                 295                 300
```

```
Asp Glu Lys Cys Leu Ala Tyr Leu Gln Asn Val Gln Lys Ser Asn
305                 310                 315                 320
Gly Gly Ala Arg His Tyr Pro Leu Asp Leu Thr Arg Leu Trp Ala
                325                 330                 335
Ile Asp Arg Leu Gln Arg Leu Gly Ile Ser Tyr Tyr Phe Ala Glu Glu
            340                 345                 350
Phe Lys Glu Leu Leu Asn His Val Phe Arg Tyr Trp Asp Glu Glu Asn
        355                 360                 365
Gly Ile Phe Ser Gly Arg Asn Ser Asn Val Cys Asp Val Asp Asp Thr
370                 375                 380
Cys Met Ala Ile Arg Leu Leu Arg Leu His Gly Tyr Asp Val Ser Pro
385                 390                 395                 400
Asp Ala Leu Asn Asn Phe Thr Asp Gly Asp Gln Phe Phe Cys Leu Arg
                405                 410                 415
Gly Glu Val Asp Gly Ser Pro Thr His Met Phe Asn Leu Tyr Arg Cys
            420                 425                 430
Ser Gln Val Leu Phe Pro Gly Glu Lys Ile Leu Glu Glu Ala Lys Asn
        435                 440                 445
Phe Thr Tyr Asn Phe Leu Gln Gln Cys Leu Ala Asn Asn Arg Cys Leu
450                 455                 460
Asp Lys Trp Val Ile Ala Lys Asp Ile Pro Gly Glu Ile Gly Tyr Ala
465                 470                 475                 480
Leu Lys Phe Pro Trp Tyr Ala Ser Leu Pro Arg Val Glu Ser Arg Leu
                485                 490                 495
Tyr Ile Glu Gln Tyr Gly Gly Ala Asn Asp Ile Trp Ile Gly Lys Thr
            500                 505                 510
Leu Tyr Arg Met Pro Asp Val Ser Asn Asn Val Tyr Leu Gln Ala Ala
        515                 520                 525
Lys Leu Asp Tyr Asn Arg Cys Gln Ser Gln His Arg Phe Glu Trp Leu
530                 535                 540
Ile Met Gln Gln Trp Phe Asp Lys Cys Asn Phe Gln Gln Phe Gly Ile
545                 550                 555                 560
Ser Lys Lys Tyr Leu Leu Val Ser Tyr Phe Leu Ala Ala Ala Ser Ile
                565                 570                 575
Phe Glu Val Glu Lys Ser Arg Glu Arg Leu Ala Trp Ala Lys Ser Arg
            580                 585                 590
Ile Ile Cys Lys Met Ile Thr Ser Tyr Tyr Asn Glu Ala Thr Thr
        595                 600                 605
Trp Thr Ser Arg Asn Ser Leu Leu Met Glu Phe Lys Gly Ser Asp Asp
610                 615                 620
Pro Ser Arg Lys Asn Gly Asn Glu Thr Lys Glu Ile Ile Val Leu Lys
625                 630                 635                 640
Asn Leu Arg Gln Phe Leu His Gln Leu Ser Glu Glu Thr Phe Glu Asp
                645                 650                 655
Leu Gly Lys Asp Ile His His Gln Leu Gln Asn Ala Trp Lys Thr Trp
            660                 665                 670
Leu Val Phe Leu Arg Glu Glu Lys Asn Thr Cys Gln Glu Glu Ala Glu
        675                 680                 685
Leu Leu Val Arg Thr Ile Asn Leu Ser Gly Gly His Met Ile His Asp
690                 695                 700
Glu Ile Leu Phe Asp Ala Asp Tyr Lys Asn Leu Ser Asn Leu Thr Asn
705                 710                 715                 720
Lys Val Cys Cys Met Leu Ser Glu Leu Gln Asn Asp Lys Val Thr Gly
```

|  |  | 725 |  |  |  | 730 |  |  |  | 735 |  |
|---|---|---|---|---|---|---|---|---|---|---|---|

Ser Ser Lys Asn Thr Asp Ile Glu Leu Asn Met Gln Ala Leu Ala Lys
        740                     745                 750

Leu Val Phe Gly Asn Thr Ser Ser Asn Ile Asn Gln Asp Ile Lys Gln
        755                     760                 765

Thr Phe Phe Ala Val Val Lys Thr Phe Tyr Tyr Ser Ala His Val Ser
    770                 775                 780

Glu Glu Ile Ile Asn Phe His Ile Ser Lys Val Leu Phe Gln Gln Val
785                 790                 795                 800

Gln

```
<210> SEQ ID NO 7
<211> LENGTH: 2229
<212> TYPE: DNA
<213> ORGANISM: Nicotiana glutinosa
<220> FEATURE:
<223> OTHER INFORMATION: NgLPP2-2-1

<400> SEQUENCE: 7
```

| | | |
|---|---|---|
| gatgcaagtt atcttggtta tctgaatgag ttggaatcta atttctcaaa caaccccgaa | 60 |
| gaaaaggata ttcaggtaag cagaacaata cagatcaaaa atttgacaga agagatcaaa | 120 |
| tgtaagttga attcgatgga ggatggaagg tcaagtgtct cagcctatga cacagcttgg | 180 |
| gtttcccttta ttccaaatac tactaataat ggaaatgatc aaaggcctat gtttccatct | 240 |
| tgtcttcaat ggattataga caatcaactt tgcgatggtt catggggaga ggagagtgta | 300 |
| ttctgcatat atgatcgact cttgaacaca ctagcatgtg ttgttgcatt gacattatgg | 360 |
| aacacatgcc ttcctaagag aaacaaaggt gtgatgttta tcaaagaaaa cttaattaag | 420 |
| ttagagacag gggaagttga acacatgact tgtggatttg aatttgtgtt tcctgctctc | 480 |
| cttgagaaag ctcaacaatt aaatattgac attccgtatg atgctccagt cttaaaggat | 540 |
| atttatgcaa ggagagaagt aaagtttaca agaattccta agagattgtt ccatacgatt | 600 |
| ccgacaacag cattactttc attagaagga ttaagggacg acctggattg caaagacctt | 660 |
| ttaaattttc aaatgcctga tggttcattc ttatcagccc ctgcttccac tgccttttgca | 720 |
| tcatgaaaa caaacgatga aaagtgtttg gcatatcttc aaaatgttgt tcaaaagtct | 780 |
| aatggaggag cgcgacacta cccactggac ttgttaacac gactttgggc aattgatcga | 840 |
| ttacaacgcc ttggaatatc ttattatttt gcggaagagt tcaaggaact tttgaatcat | 900 |
| gtgttcagat attgggacga ggagaatgga attttcagtg gaaggaattc aaacgtttgt | 960 |
| gacgttgatg atacatgcat ggctattagg ttgcttaggt tgcatgggta tgatgttagt | 1020 |
| ccagatgcgc taaacaattt cacagatggt gatcaattct tttgccttag aggtgaagtg | 1080 |
| gacgggtcac caacacatat gtttaatctt tatagatgtt cccaagtttt attcccagga | 1140 |
| gaaaagattc ttgaagaggc aaagaatttt acttacaact tcttacagca atgtcttgca | 1200 |
| aacaatcgat gcttagacaa atgggtcata gctaaggaca ttcccgggga gataaggtat | 1260 |
| gcactgaaat ttccatggta tgcaagctta cctcgggtgg aatctaggct atacatagaa | 1320 |
| cagtacggcg gagcaaatga tatttggatt ggcaagacat tatacaggat gcccgatgtc | 1380 |
| agcaacaatg tttatttaca agctgcaaaa ttagattaca acagatgcca aagtcaacat | 1440 |
| cgatttgaat ggctaattat gcaacagtgg tttgataagt gcaactttca acaatttgga | 1500 |
| ataagcaaaa agtacctcct agtttcttat ttccttagctg ctgcaagtat atttgaagtc | 1560 |
| gaaaagtcaa gagaacgact tgcgtgggct aaatctcgta taatatgtaa gatgattaca | 1620 |

```
tcttactaca atgaagaagc cacaacttgg accagtagga attcattgct aatggaattc    1680
aagggttctg atgatccaag cagaaaaaat ggtaatgaaa caaaagagat catagttctc    1740
aaaaatcttc gtcagttttt gcaccaacta tcagaagaaa cttttgaaga cctaggcaaa    1800
gacatccatc accaactaca aaatgcatgg aaaacgtggt tggcgttctt aagggaggaa    1860
aaaaatacat gccaagaaga agcagagttg ctagtgcgca caattaatct ctccggcggc    1920
catatgatac atgatgagat actattcgat gcggactaca aaaatctgtc caaccttact    1980
aataaagttt gctgcatgct tagtgagctc caaaatgaca aggtgactgg cagctcaaag    2040
aacactgaca ttgaactcaa catgcaagca cttgtaaagt tagtgtttgg taacacctca    2100
agcaacatca accaagacat taagcaaaca ttttttgcag ttgttaagac tttctattac    2160
agtgcacatg ttagtgagga aataatcaac tttcacatat ccaaggtgct tttacagcaa    2220
gtccagtaa                                                            2229
```

<210> SEQ ID NO 8
<211> LENGTH: 747
<212> TYPE: PRT
<213> ORGANISM: Nicotiana glutinosa
<220> FEATURE:
<223> OTHER INFORMATION: NgLLP2-2-1

<400> SEQUENCE: 8

```
Met Cys Ala Pro Ile Asp Ala Ser Tyr Leu Gly Tyr Leu Asn Glu Leu
 1               5                  10                  15

Glu Ser Asn Phe Ser Asn Asn Pro Glu Glu Lys Asp Ile Gln Val Ser
            20                  25                  30

Arg Thr Ile Gln Ile Lys Asn Leu Thr Glu Glu Ile Lys Cys Lys Leu
        35                  40                  45

Asn Ser Met Glu Asp Gly Arg Ser Ser Val Ser Ala Tyr Asp Thr Ala
    50                  55                  60

Trp Val Ser Phe Ile Pro Asn Thr Thr Asn Gly Asn Asp Gln Arg
65                  70                  75                  80

Pro Met Phe Pro Ser Cys Leu Gln Trp Ile Ile Asp Asn Gln Leu Cys
                85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
```

```
                    245                 250                 255
Tyr Leu Gln Asn Val Gln Lys Ser Asn Gly Gly Ala Arg His Tyr
                260                 265                 270
Pro Leu Asp Leu Leu Thr Arg Leu Trp Ala Ile Asp Arg Leu Gln Arg
                275                 280                 285
Leu Gly Ile Ser Tyr Tyr Phe Ala Glu Glu Phe Lys Glu Leu Leu Asn
            290                 295                 300
His Val Phe Arg Tyr Trp Asp Glu Glu Asn Gly Ile Phe Ser Gly Arg
305                 310                 315                 320
Asn Ser Asn Val Cys Asp Val Asp Thr Cys Met Ala Ile Arg Leu
                325                 330                 335
Leu Arg Leu His Gly Tyr Asp Val Ser Pro Asp Ala Leu Asn Asn Phe
                340                 345                 350
Thr Asp Gly Asp Gln Phe Phe Cys Leu Arg Gly Glu Val Asp Gly Ser
            355                 360                 365
Pro Thr His Met Phe Asn Leu Tyr Arg Cys Ser Gln Val Leu Phe Pro
        370                 375                 380
Gly Glu Lys Ile Leu Glu Glu Ala Lys Asn Phe Thr Tyr Asn Phe Leu
385                 390                 395                 400
Gln Gln Cys Leu Ala Asn Asn Arg Cys Leu Asp Lys Trp Val Ile Ala
                405                 410                 415
Lys Asp Ile Pro Gly Glu Ile Arg Tyr Ala Leu Lys Phe Pro Trp Tyr
            420                 425                 430
Ala Ser Leu Pro Arg Val Glu Ser Arg Leu Tyr Ile Glu Gln Tyr Gly
                435                 440                 445
Gly Ala Asn Asp Ile Trp Ile Gly Lys Thr Leu Tyr Arg Met Pro Asp
            450                 455                 460
Val Ser Asn Asn Val Tyr Leu Gln Ala Ala Lys Leu Asp Tyr Asn Arg
465                 470                 475                 480
Cys Gln Ser Gln His Arg Phe Glu Trp Leu Ile Met Gln Gln Trp Phe
                485                 490                 495
Asp Lys Cys Asn Phe Gln Gln Phe Gly Ile Ser Lys Lys Tyr Leu Leu
                500                 505                 510
Val Ser Tyr Phe Leu Ala Ala Ala Ser Ile Phe Glu Val Glu Lys Ser
            515                 520                 525
Arg Glu Arg Leu Ala Trp Ala Lys Ser Arg Ile Ile Cys Lys Met Ile
        530                 535                 540
Thr Ser Tyr Tyr Asn Glu Glu Ala Thr Trp Thr Ser Arg Asn Ser
545                 550                 555                 560
Leu Leu Met Glu Phe Lys Gly Ser Asp Asp Pro Ser Arg Lys Asn Gly
                565                 570                 575
Asn Glu Thr Lys Glu Ile Ile Val Leu Lys Asn Leu Arg Gln Phe Leu
                580                 585                 590
His Gln Leu Ser Glu Glu Thr Phe Glu Asp Leu Gly Lys Asp Ile His
            595                 600                 605
His Gln Leu Gln Asn Ala Trp Lys Thr Trp Leu Ala Phe Leu Arg Glu
        610                 615                 620
Glu Lys Asn Thr Cys Gln Glu Glu Ala Glu Leu Leu Val Arg Thr Ile
625                 630                 635                 640
Asn Leu Ser Gly Gly His Met Ile His Asp Glu Ile Leu Phe Asp Ala
                645                 650                 655
Asp Tyr Lys Asn Leu Ser Asn Leu Thr Asn Lys Val Cys Cys Met Leu
                660                 665                 670
```

```
Ser Glu Leu Gln Asn Asp Lys Val Thr Gly Ser Ser Lys Asn Thr Asp
            675                 680                 685

Ile Glu Leu Asn Met Gln Ala Leu Val Lys Leu Val Phe Gly Asn Thr
        690                 695                 700

Ser Ser Asn Ile Asn Gln Asp Ile Lys Gln Thr Phe Phe Ala Val Val
705                 710                 715                 720

Lys Thr Phe Tyr Tyr Ser Ala His Val Ser Glu Glu Ile Ile Asn Phe
                725                 730                 735

His Ile Ser Lys Val Leu Leu Gln Gln Val Gln
            740                 745

<210> SEQ ID NO 9
<211> LENGTH: 2244
<212> TYPE: DNA
<213> ORGANISM: Nicotiana glutinosa
<220> FEATURE:
<223> OTHER INFORMATION: NgLPP2-2-2

<400> SEQUENCE: 9
atgtgcgcac ctattgatgc tagttatctt ggttatctga atgagttgga atctaatttc      60
tcaaacaacc ccgaagaaaa ggatattcag gtaagcagaa caatacagat caaaaatttg     120
acagaagaaa tcaaatgtaa gttgaattcg atggaggatg aaggtcaag tgtctcagcc      180 tatgacacag cttgggtttc ctttattcca aatactacta ataatggaaa tgatcaaagg     240
cctatgtttc catcttgtct tcaatggatt atagacaatc aactttgcga tggttcatgg     300
ggagaggaga gtgtattctg catatatgat cgactcttga acacactagc atgtgttgtt     360
gcattgacat tatggaacac atgccttcct aagagaaaca aggtgtgat gtttatcaaa      420 gaaaacttaa ttaagctaga dacagggaa gttgaacaca tgacttgtgg atttgaattt     480
gtgtttcctg ctctccttga aaagctcaa caattaaata ttgacattcc gtatgatgct     540
ccagtcttaa aggatattta tgcaaggaga aagtaaagt ttacaagaat tcctaaagag      600
attgtccata cgattccgac aacagcattg ctttcattag aaggattaag ggacgacctg     660
gattggcaaa gacttttaaa ttttcaaatg cctgatggtt cattcttatc agccctgct       720 tccactgcct ttgcattcat gaaaacaaac gatgaaaagt gtttggcata tcttcaaat      780 gttgttcaaa agtctaatgg aggagcgcga cactacccac tggacttgtt aacacgactt     840
tgggcaattg atcgattaca acgccttgga atatcttatt attttgcgga agagttcaag     900
gaacttttga atcatgtgtt cagatattgg gacgaggaga atggaatttt cagtggaagg     960
aattcaaacg tttgtgacgt tgatgataca tgcatggcta ttaggttgct taggttgcat    1020
gggtatgatg ttagtccaga tgcgctaaac aatttcacag atggtgatca attcttttgc    1080
cttagaggtg aagtggacgg gtcaccaaca catatgttta atctttatag atgttcccaa    1140
gttttattcc caggagaaaa gattcttgaa gaggcaaaga attttactta caacttctta    1200
cagcaatgtc ttgcaaacaa tcgatgctta gacaaatggg tcatagctaa ggacattccc    1260
ggggagataa ggtatgcact gaaatttcca tggtatgcaa gcttacctcg ggtggaatct    1320
aggctataca tagaacagta cggcggagca aatgatattt ggattggcaa gacattatac    1380
aggatgcccg atgtcagcaa caatgtttat ttacaagctg caaaattaga ttacaacaga    1440
tgccaaagtc aacatcgatt tgaatggcta attatgcaac agtggtttga taagtgcaac    1500
tttcaacaat ttggaataag caaaaagtac ctcctagttt cttatttctt agctgctgca    1560
agtatatttg aagtcgaaaa gtcaagagaa cgacttgcgt gggctaaatc tcgtataata    1620
```

-continued

```
tgtaagatga ttacatctta ctacaatgaa gaagccacaa cttggaccag taggaattca   1680
ttgctaatgg aattcaaggg ttctgatgat ccaagcagaa aaaatggtaa tgaaacaaaa   1740
gagatcatag ttctcaaaaa tcttcgtcag tttttgcacc aactatcaga agaaactttt   1800
gaggacctag gcaaagacat ccatcaccaa ctacaaaatg catggaaaac gtggttggcg   1860
ttcttaaggg aggaaaaaaa tacatgccaa gaagaagcag agttgctagt gcgcacaatt   1920
aatctctccg gcggccatat gatacatgat gagatactat tcgatgcgga ctacaaaaat   1980
ctgtccaacc ttactaataa agtttgctgc atgcttagtg agctccaaaa tgacaaggtg   2040
actggcagct caaagaacac tgacattgaa ctcaacatgc aagcacttgt aaaattagtg   2100
tttggtaaca cctcaagcaa catcaaccaa gacattaagc aaacatttt tacagttgtt    2160 aagactttct attacagtgc acatgctagt gaggaaataa tcaactttca catatccaag   2220 gtgcttttc agcaagtcca gtaa                                           2244
```

<210> SEQ ID NO 10
<211> LENGTH: 747
<212> TYPE: PRT
<213> ORGANISM: Nicotiana glutinosa
<220> FEATURE:
<223> OTHER INFORMATION: NgLLP2-2-2

<400> SEQUENCE: 10

```
Met Cys Ala Pro Ile Asp Ala Ser Tyr Leu Gly Tyr Leu Asn Glu Leu
 1               5                  10                  15

Glu Ser Asn Phe Ser Asn Asn Pro Glu Glu Lys Asp Ile Gln Val Ser
            20                  25                  30

Arg Thr Ile Gln Ile Lys Asn Leu Thr Glu Glu Ile Lys Cys Lys Leu
        35                  40                  45

Asn Ser Met Glu Asp Gly Arg Ser Ser Val Ser Ala Tyr Asp Thr Ala
    50                  55                  60

Trp Val Ser Phe Ile Pro Asn Thr Thr Asn Gly Asn Asp Gln Arg
65                  70                  75                  80

Pro Met Phe Pro Ser Cys Leu Gln Trp Ile Ile Asp Asn Gln Leu Cys
                85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
```

245                 250                 255
Tyr Leu Gln Asn Val Val Gln Lys Ser Asn Gly Gly Ala Arg His Tyr
                260                 265                 270

Pro Leu Asp Leu Leu Thr Arg Leu Trp Ala Ile Asp Arg Leu Gln Arg
                275                 280                 285

Leu Gly Ile Ser Tyr Tyr Phe Ala Glu Glu Phe Lys Glu Leu Leu Asn
            290                 295                 300

His Val Phe Arg Tyr Trp Asp Glu Glu Asn Gly Ile Phe Ser Gly Arg
305                 310                 315                 320

Asn Ser Asn Val Cys Asp Val Asp Asp Thr Cys Met Ala Ile Arg Leu
                325                 330                 335

Leu Arg Leu His Gly Tyr Asp Val Ser Pro Asp Ala Leu Asn Asn Phe
                340                 345                 350

Thr Asp Gly Asp Gln Phe Phe Cys Leu Arg Gly Glu Val Asp Gly Ser
                355                 360                 365

Pro Thr His Met Phe Asn Leu Tyr Arg Cys Ser Gln Val Leu Phe Pro
            370                 375                 380

Gly Glu Lys Ile Leu Glu Glu Ala Lys Asn Phe Thr Tyr Asn Phe Leu
385                 390                 395                 400

Gln Gln Cys Leu Ala Asn Asn Arg Cys Leu Asp Lys Trp Val Ile Ala
                405                 410                 415

Lys Asp Ile Pro Gly Glu Ile Arg Tyr Ala Leu Lys Phe Pro Trp Tyr
                420                 425                 430

Ala Ser Leu Pro Arg Val Glu Ser Arg Leu Tyr Ile Glu Gln Tyr Gly
                435                 440                 445

Gly Ala Asn Asp Ile Trp Ile Gly Lys Thr Leu Tyr Arg Met Pro Asp
            450                 455                 460

Val Ser Asn Asn Val Tyr Leu Gln Ala Ala Lys Leu Asp Tyr Asn Arg
465                 470                 475                 480

Cys Gln Ser Gln His Arg Phe Glu Trp Leu Ile Met Gln Gln Trp Phe
                485                 490                 495

Asp Lys Cys Asn Phe Gln Gln Phe Gly Ile Ser Lys Lys Tyr Leu Leu
                500                 505                 510

Val Ser Tyr Phe Leu Ala Ala Ala Ser Ile Phe Glu Val Glu Lys Ser
            515                 520                 525

Arg Glu Arg Leu Ala Trp Ala Lys Ser Arg Ile Ile Cys Lys Met Ile
            530                 535                 540

Thr Ser Tyr Tyr Asn Glu Glu Ala Thr Trp Thr Ser Arg Asn Ser
545                 550                 555                 560

Leu Leu Met Glu Phe Lys Gly Ser Asp Asp Pro Ser Arg Lys Asn Gly
                565                 570                 575

Asn Glu Thr Lys Glu Ile Ile Val Leu Lys Asn Leu Arg Gln Phe Leu
                580                 585                 590

His Gln Leu Ser Glu Glu Thr Phe Glu Asp Leu Gly Lys Asp Ile His
                595                 600                 605

His Gln Leu Gln Asn Ala Trp Lys Thr Trp Leu Ala Phe Leu Arg Glu
            610                 615                 620

Glu Lys Asn Thr Cys Gln Glu Glu Ala Glu Leu Leu Val Arg Thr Ile
625                 630                 635                 640

Asn Leu Ser Gly Gly His Met Ile His Asp Glu Ile Leu Phe Asp Ala
                645                 650                 655

Asp Tyr Lys Asn Leu Ser Asn Leu Thr Asn Lys Val Cys Cys Met Leu
                660                 665                 670

```
Ser Glu Leu Gln Asn Asp Lys Val Thr Gly Ser Ser Lys Asn Thr Asp
        675                 680                 685

Ile Glu Leu Asn Met Gln Ala Leu Val Lys Leu Val Phe Gly Asn Thr
    690                 695                 700

Ser Ser Asn Ile Asn Gln Asp Ile Lys Gln Thr Phe Phe Thr Val Val
705                 710                 715                 720

Lys Thr Phe Tyr Tyr Ser Ala His Ala Ser Glu Glu Ile Ile Asn Phe
                725                 730                 735

His Ile Ser Lys Val Leu Phe Gln Gln Val Gln
        740                 745

<210> SEQ ID NO 11
<211> LENGTH: 2244
<212> TYPE: DNA
<213> ORGANISM: Nicotiana glutinosa
<220> FEATURE:
<223> OTHER INFORMATION: NgLLP2-2-3

<400> SEQUENCE: 11
atgtgcgcac ctattgatgc aagttatctt ggttatctga atgagttgga atctaatttc      60
tcaaacaacc ccgaagaaaa ggatattcag gtaagcagaa caatacagat caaaaatttg     120
acagaagaaa tcaaatgtaa gttgaattcg atggaggatg aaggtcaag tgtctcagcc      180 tatgacacag cttgggtttc ctttattcca aatactacta ataatggaaa tgatcaaagg     240
cctatgtttc catcttgtct tcaatggatt atagacaatc aactttgcga tggttcatgg     300
ggagaggaga gtgtattctg catatatgat cgactcttga acacactagc atgtgttgtt     360
gcattgacat tatggaacac atgccttcct aagagaaaca aggtgtgat gtttatcaaa      420 gaaaacttaa ttaagttaga gacagggga gttgaacaca tgacttgtgg atttgaattt     480
gtgtttcctg ctctccttga aaagctcaa caattaaata ttgacattcc gtatgatgct     540
ccagtcttaa aggatattta tgcaaggaga aagtaaagt ttacaagaat tcctaaagag     600
attgtccata cgattccgac aacagcattg ctttcattag aaggattaag ggacgacctg     660
gattggcaaa gacttttaaa ttttcaaatg cctgatggtt cattcttatc agcccctgct     720
tccactgcct ttgcattcat gaaaacaaac gatgaaaagt gtttggcata tcttcaaaat     780
gttgttcaaa agtctaatgg aggagcgcga cactacccac tggacttgtt aacacgactt     840
tgggcaattg atcgattaca atgccttgga atatcttatt attttgcgga agagttcaag     900
gaacttttga atcatgtgtt cagatattgg gacgaggaga atggaatttt cagtggaagg     960
aattcaaacg tttgtgacgt tgatgataca tgcatggcta ttaggttgct taggttgcat    1020
gggtatgatg ttagtccaga tgcgctaaac aatttcacag atggtgatca attcttttgc    1080
cttagaggtg aagtggacgg gtcaccaaca catatgttta tcttatag atgttcccaa      1140 gtttattcc caggagaaaa gattcttgaa gaggcaaaga ttttactta caacttctta     1200 cagcaatgtc ttgcaaacaa tcgatgctta gacaaatggg tcatagctaa ggacattccc    1260
ggggagataa ggtatgcact gaaatttcca tggtatgcaa gcttacctcg ggtggaatct    1320
aggctataca tagaacagta cggcggagca atgatatttt ggattggcaa gacattatac    1380
aggatgcccg atgtcagcaa caatgtttat tacaagctg caaaattaga ttacaacaga    1440
tgccaaagtc aacatcgatt tgaatggcta attatgcaac agtggttgga taagtgcaac    1500
tttcaacaat tggaataag caaaaagtac ctcctagttt cttatttctt agctgctgca    1560 agtatattg aagtcgaaaa gtcaagagaa cgacttgcgt gggctaaatc tcgtataata   1620
```

-continued

```
tgtaagatga ttacatctta ctacaatgaa gaagccacaa cttggaccag taggaattca    1680
ttgctaatgg aattcaaggg ttctgatgat ccaagcagaa aaatggtaa tgaaacaaaa    1740 gagatcatag ttctcaaaaa tcttcgtcag tttttgcacc aactatcaga agaaactttt    1800
gaagacctag gcaaagacgt ccatcaccaa ctacaaaatg catggaaaac gtggttggcg    1860
ttcttaaggg aggaaaaaaa tacatgccaa gaagaagcag agttgctagt gcgcacaatt    1920
aatctctccg gcggccatat gatacatgat gagatactat tcgatgcgga ctacaaaaat    1980
ctgtccaacc ttattaataa agtttgctgc atgcttagtg agctccaaaa tgacaaggtg    2040
actggcagct caaagaacac tgacattgaa ctcaacatgc aagcacttgt aaagttagtg    2100
tttggtaaca cctcaagcaa catcaaccaa gacattaagc aaacattttt tgcagttgtt    2160
aagactttct attacagtgc acatgttagt gaggaaataa tcaactttca catatccaag    2220 gtgcttttc agcaagtcca gtaa                                             2244
```

<210> SEQ ID NO 12
<211> LENGTH: 747
<212> TYPE: PRT
<213> ORGANISM: Nicotiana glutinosa
<220> FEATURE:
<223> OTHER INFORMATION: NgLLP2-2-3

<400> SEQUENCE: 12

```
Met Cys Ala Pro Ile Asp Ala Ser Tyr Leu Gly Tyr Leu Asn Glu Leu
  1               5                  10                  15

Glu Ser Asn Phe Ser Asn Asn Pro Glu Glu Lys Asp Ile Gln Val Ser
             20                  25                  30

Arg Thr Ile Gln Ile Lys Asn Leu Thr Glu Glu Ile Lys Cys Lys Leu
         35                  40                  45

Asn Ser Met Glu Asp Gly Arg Ser Ser Val Ser Ala Tyr Asp Thr Ala
     50                  55                  60

Trp Val Ser Phe Ile Pro Asn Thr Thr Asn Gly Asn Asp Gln Arg
 65                  70                  75                  80

Pro Met Phe Pro Ser Cys Leu Gln Trp Ile Ile Asp Asn Gln Leu Cys
                 85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
```

```
            245                 250                 255
Tyr Leu Gln Asn Val Val Gln Lys Ser Asn Gly Gly Ala Arg His Tyr
            260                 265                 270

Pro Leu Asp Leu Leu Thr Arg Leu Trp Ala Ile Asp Arg Leu Gln Cys
            275                 280                 285

Leu Gly Ile Ser Tyr Tyr Phe Ala Glu Glu Phe Lys Glu Leu Leu Asn
        290                 295                 300

His Val Phe Arg Tyr Trp Asp Glu Glu Asn Gly Ile Phe Ser Gly Arg
305                 310                 315                 320

Asn Ser Asn Val Cys Asp Val Asp Asp Thr Cys Met Ala Ile Arg Leu
                325                 330                 335

Leu Arg Leu His Gly Tyr Asp Val Ser Pro Asp Ala Leu Asn Asn Phe
                340                 345                 350

Thr Asp Gly Asp Gln Phe Phe Cys Leu Arg Gly Glu Val Asp Gly Ser
            355                 360                 365

Pro Thr His Met Phe Asn Leu Tyr Arg Cys Ser Gln Val Leu Phe Pro
        370                 375                 380

Gly Glu Lys Ile Leu Glu Glu Ala Lys Asn Phe Thr Tyr Asn Phe Leu
385                 390                 395                 400

Gln Gln Cys Leu Ala Asn Asn Arg Cys Leu Asp Lys Trp Val Ile Ala
                405                 410                 415

Lys Asp Ile Pro Gly Glu Ile Arg Tyr Ala Leu Lys Phe Pro Trp Tyr
                420                 425                 430

Ala Ser Leu Pro Arg Val Glu Ser Arg Leu Tyr Ile Glu Gln Tyr Gly
            435                 440                 445

Gly Ala Asn Asp Ile Trp Ile Gly Lys Thr Leu Tyr Arg Met Pro Asp
        450                 455                 460

Val Ser Asn Asn Val Tyr Leu Gln Ala Ala Lys Leu Asp Tyr Asn Arg
465                 470                 475                 480

Cys Gln Ser Gln His Arg Phe Glu Trp Leu Ile Met Gln Gln Trp Phe
                485                 490                 495

Asp Lys Cys Asn Phe Gln Gln Phe Gly Ile Ser Lys Lys Tyr Leu Leu
                500                 505                 510

Val Ser Tyr Phe Leu Ala Ala Ala Ser Ile Phe Glu Val Glu Lys Ser
            515                 520                 525

Arg Glu Arg Leu Ala Trp Ala Lys Ser Arg Ile Ile Cys Lys Met Ile
            530                 535                 540

Thr Ser Tyr Tyr Asn Glu Glu Ala Thr Thr Trp Thr Ser Arg Asn Ser
545                 550                 555                 560

Leu Leu Met Glu Phe Lys Gly Ser Asp Asp Pro Ser Arg Lys Asn Gly
                565                 570                 575

Asn Glu Thr Lys Glu Ile Ile Val Leu Lys Asn Leu Arg Gln Phe Leu
                580                 585                 590

His Gln Leu Ser Glu Glu Thr Phe Glu Asp Leu Gly Lys Asp Val His
            595                 600                 605

His Gln Leu Gln Asn Ala Trp Lys Thr Trp Leu Ala Phe Leu Arg Glu
            610                 615                 620

Glu Lys Asn Thr Cys Gln Glu Glu Ala Glu Leu Leu Val Arg Thr Ile
625                 630                 635                 640

Asn Leu Ser Gly Gly His Met Ile His Asp Glu Ile Leu Phe Asp Ala
                645                 650                 655

Asp Tyr Lys Asn Leu Ser Asn Leu Ile Asn Lys Val Cys Cys Met Leu
                660                 665                 670
```

```
Ser Glu Leu Gln Asn Asp Lys Val Thr Gly Ser Ser Lys Asn Thr Asp
            675                 680                 685

Ile Glu Leu Asn Met Gln Ala Leu Val Lys Leu Val Phe Gly Asn Thr
    690                 695                 700

Ser Ser Asn Ile Asn Gln Asp Ile Lys Gln Thr Phe Phe Ala Val Val
705                 710                 715                 720

Lys Thr Phe Tyr Tyr Ser Ala His Val Ser Glu Glu Ile Ile Asn Phe
                725                 730                 735

His Ile Ser Lys Val Leu Phe Gln Gln Val Gln
            740                 745

<210> SEQ ID NO 13
<211> LENGTH: 2244
<212> TYPE: DNA
<213> ORGANISM: Nicotiana glutinosa
<220> FEATURE:
<223> OTHER INFORMATION: NgLLP2-2-4

<400> SEQUENCE: 13
```

| | | | | | |
|---|---|---|---|---|---|
| atgtgcgcac | ctattgatgc | aagttatctt | ggttatctga | atgagttgga | atctaatttc | 60 |
| tcaaacaacc | ccgaagaaaa | ggatattcag | gtaagcagaa | caatacagat | caaaaatttg | 120 |
| acagaagaaa | tcaaatgtaa | gttgaattcg | atggaggatg | aaggtcaag | tgtctcagcc | 180 |
| tatgacacag | cttgggtttc | ctttattcca | aatactacta | ataatggaaa | tgatcaaagg | 240 |
| cctatgtttc | catcttgtct | tcaatggatt | atagacaatc | aactttgcga | tggttcatgg | 300 |
| ggagaggaga | gtgtattctg | catatatgat | cgactcttga | acacactagc | atgtgttgtt | 360 |
| gcattgacat | tatggaacac | atgccttcct | aagagaaaca | aggtgtgat | gtttatcaaa | 420 |
| gaaaacttaa | ttaagttaga | gacagggaa | gttgaacaca | tgacttgtgg | atttgaattt | 480 |
| gtgtttcctg | ctctccttga | gaaagctcaa | caattaaata | ttgacattcc | gtatgatgct | 540 |
| ccagtcttaa | aggatattta | tgcaaggaga | gaagtaaagt | ttacaagaat | tcctaaagag | 600 |
| attgtccata | cgattccgac | aacagcattg | ctttcattag | aaggattaag | ggacgacctg | 660 |
| gattggcaaa | gacttttaaa | ttttcaaatg | cctgatggtt | cattcttatc | agcccctgct | 720 |
| tccactgcct | ttgcattcat | gaaaacaaac | gatgaaaagt | gtttggcata | tcttcaaaat | 780 |
| gttgttcaaa | agtctaatgg | aggagcgcga | cactacccac | tggacttgtt | aacacgactt | 840 |
| tgggcaattg | atcgattaca | acgccttgga | atatcttatt | attttgcgga | agagttcaag | 900 |
| gaactttga | atcatgtgtt | cagatattgg | gacgaggaga | atggaatttt | cagtggaagg | 960 |
| aattcaaacg | tttgtgacgt | tgatgataca | tgcatggcta | ttaggttgct | taggttgcat | 1020 |
| gggtatgatg | ttagtccaga | tgcgctaaac | aatttcacag | atggtgatca | attcttttgc | 1080 |
| cttagaggtg | aagtggacgg | gtcaccaaca | catatgttta | atctttatag | atgttcccaa | 1140 |
| gtttattcc | aggagaaaa | gattcttgaa | gaggcaaaga | attttactta | caacttctta | 1200 |
| cagcaatgtc | ttgcaaacaa | tcgatgctta | gacaaatggg | tcatagctaa | ggacattccc | 1260 |
| ggggagataa | ggtatgcact | gaaatttcca | tggtatgcaa | gcttacctcg | ggtggaatct | 1320 |
| aggctataca | tagaacagta | cggcggagca | aatgatattt | ggattggcaa | gacattatac | 1380 |
| aggatgcccg | atgtcagcaa | caatgtttat | ttacaagctg | caaaattaga | ttacaacaga | 1440 |
| tgccaaagtc | aacatcgatt | tgaatggcta | attatgcaac | agtggtttga | taagtgcaac | 1500 |
| tttcaacaat | ttggaataag | caaaaagtac | ctcctagttt | cttatttctt | agctgctgca | 1560 |
| agtatatttg | aagtcgaaaa | gtcaagagaa | cgacttgcgt | gggctaaatc | tcgtataata | 1620 |

```
tgtaagatga ttacatctta ctacaatgaa gaagccacaa cttggaccag taggaattca    1680
ttgctaatgg aattcaaggg ttctgatgat ccaagcagaa aaatggtaa tgaaacaaaa     1740 gagatcatag ttctcaaaaa tcttcgtcag tttttgcacc aactatcaga agaaactttt    1800
gaagacctag gcaaagacat ccatcaccaa ctacaaaatg catggaaaac gtggttggcg    1860
ttcttaaggg aggaaaaaaa tacatgccaa gaagaagcag agttgctagt gcgcacaatt    1920
aatctctccg gcggccatat gatacatgat gagatactat tcgatgcgga ctacaaaaat    1980
ctgtccaacc ttattaataa agtttgctgc atgcttagtg agctccaaaa tgacaaggtg    2040
actggcagct caagaacac tgacattgaa ctcaacatgc aagcacttgt aaagttagtg      2100
tttggtaaca cctcaagcaa catcaaccaa gacattaagc aaacattttt tgcagttgtt    2160
aagactttct attacagtgc acatgttagt gaggaaataa tcaactttca catatccaag    2220 gtgcttttc agcaagtcca gtaa                                            2244
```

<210> SEQ ID NO 14
<211> LENGTH: 747
<212> TYPE: PRT
<213> ORGANISM: Nicotiana glutinosa
<220> FEATURE:
<223> OTHER INFORMATION: NgLLP2-2-4

<400> SEQUENCE: 14

```
Met Cys Ala Pro Ile Asp Ala Ser Tyr Leu Gly Tyr Leu Asn Glu Leu
  1               5                  10                  15

Glu Ser Asn Phe Ser Asn Asn Pro Glu Glu Lys Asp Ile Gln Val Ser
             20                  25                  30

Arg Thr Ile Gln Ile Lys Asn Leu Thr Glu Glu Ile Lys Cys Lys Leu
         35                  40                  45

Asn Ser Met Glu Asp Gly Arg Ser Ser Val Ser Ala Tyr Asp Thr Ala
     50                  55                  60

Trp Val Ser Phe Ile Pro Asn Thr Thr Asn Gly Asn Asp Gln Arg
 65                  70                  75                  80

Pro Met Phe Pro Ser Cys Leu Gln Trp Ile Ile Asp Asn Gln Leu Cys
                 85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
```

```
                    245                 250                 255
Tyr Leu Gln Asn Val Val Gln Lys Ser Asn Gly Gly Ala Arg His Tyr
            260                 265                 270

Pro Leu Asp Leu Leu Thr Arg Leu Trp Ala Ile Asp Arg Leu Gln Arg
        275                 280                 285

Leu Gly Ile Ser Tyr Tyr Phe Ala Glu Glu Phe Lys Glu Leu Leu Asn
    290                 295                 300

His Val Phe Arg Tyr Trp Asp Glu Glu Asn Gly Ile Phe Ser Gly Arg
305                 310                 315                 320

Asn Ser Asn Val Cys Asp Val Asp Thr Cys Met Ala Ile Arg Leu
            325                 330                 335

Leu Arg Leu His Gly Tyr Asp Val Ser Pro Asp Ala Leu Asn Asn Phe
            340                 345                 350

Thr Asp Gly Asp Gln Phe Phe Cys Leu Arg Gly Glu Val Asp Gly Ser
            355                 360                 365

Pro Thr His Met Phe Asn Leu Tyr Arg Cys Ser Gln Val Leu Phe Pro
        370                 375                 380

Gly Glu Lys Ile Leu Glu Glu Ala Lys Asn Phe Thr Tyr Asn Phe Leu
385                 390                 395                 400

Gln Gln Cys Leu Ala Asn Asn Arg Cys Leu Asp Lys Trp Val Ile Ala
                405                 410                 415

Lys Asp Ile Pro Gly Glu Ile Arg Tyr Ala Leu Lys Phe Pro Trp Tyr
            420                 425                 430

Ala Ser Leu Pro Arg Val Glu Ser Arg Leu Tyr Ile Glu Gln Tyr Gly
            435                 440                 445

Gly Ala Asn Asp Ile Trp Ile Gly Lys Thr Leu Tyr Arg Met Pro Asp
        450                 455                 460

Val Ser Asn Asn Val Tyr Leu Gln Ala Ala Lys Leu Asp Tyr Asn Arg
465                 470                 475                 480

Cys Gln Ser Gln His Arg Phe Glu Trp Leu Ile Met Gln Gln Trp Phe
                485                 490                 495

Asp Lys Cys Asn Phe Gln Gln Phe Gly Ile Ser Lys Lys Tyr Leu Leu
            500                 505                 510

Val Ser Tyr Phe Leu Ala Ala Ala Ser Ile Phe Glu Val Glu Lys Ser
        515                 520                 525

Arg Glu Arg Leu Ala Trp Ala Lys Ser Arg Ile Ile Cys Lys Met Ile
        530                 535                 540

Thr Ser Tyr Tyr Asn Glu Glu Ala Thr Trp Thr Ser Arg Asn Ser
545                 550                 555                 560

Leu Leu Met Glu Phe Lys Gly Ser Asp Asp Pro Ser Arg Lys Asn Gly
                565                 570                 575

Asn Glu Thr Lys Glu Ile Ile Val Leu Lys Asn Leu Arg Gln Phe Leu
            580                 585                 590

His Gln Leu Ser Glu Glu Thr Phe Glu Asp Leu Gly Lys Asp Ile His
        595                 600                 605

His Gln Leu Gln Asn Ala Trp Lys Thr Trp Leu Ala Phe Leu Arg Glu
        610                 615                 620

Glu Lys Asn Thr Cys Gln Glu Glu Ala Glu Leu Leu Val Arg Thr Ile
625                 630                 635                 640

Asn Leu Ser Gly Gly His Met Ile His Asp Glu Ile Leu Phe Asp Ala
                645                 650                 655

Asp Tyr Lys Asn Leu Ser Asn Leu Ile Asn Lys Val Cys Cys Met Leu
            660                 665                 670
```

```
Ser Glu Leu Gln Asn Asp Lys Val Thr Gly Ser Ser Lys Asn Thr Asp
        675                 680                 685

Ile Glu Leu Asn Met Gln Ala Leu Val Lys Leu Val Phe Gly Asn Thr
690                 695                 700

Ser Ser Asn Ile Asn Gln Asp Ile Lys Gln Thr Phe Phe Ala Val Val
705                 710                 715                 720

Lys Thr Phe Tyr Tyr Ser Ala His Val Ser Glu Glu Ile Ile Asn Phe
                725                 730                 735

His Ile Ser Lys Val Leu Phe Gln Gln Val Gln
                740                 745

<210> SEQ ID NO 15
<211> LENGTH: 879
<212> TYPE: DNA
<213> ORGANISM: Nicotiana glutinosa
<220> FEATURE:
<223> OTHER INFORMATION: NgLLP2 partial sequence

<400> SEQUENCE: 15
tggcagactc tttacaggat gcccgatgtc agcaacaatg tttatttaca agctgcaaaa      60
ttagattaca acagatgcca agtcaacat cgatttgaat ggctaattat gcaacagtgg     120
tttgataagt gcaactttca acaatttgga ataagcaaaa agtacctcct agtttcttat     180
ttcttagctg ctgcaagtat atttgaagtc gaaaagtcaa gagaacgact tgcgtgggct     240
aaatctcgta atatatgtaa gatgattaca tcttactaca atgaagaagc cacaacttgg     300
accagtagga attcattgct aatggaattc aagggttctg atgatccaag cagaaaaaat     360
ggtaatgaaa caaagagat catagttctc aaaatcttc gtcagttttt gcaccaacta     420
tcagaagaaa cttttgaaga cctaggcaaa gacatccatc accaactaca aaatgcatgg     480
aaaacgtggt tggcgttctt aagggaggaa aaaaatacat gccaagaaga agcagagttg     540
ctagtgcgca caattaatct ctccggcggc catatgatac atgatgagat actattcgat     600
gcggactaca aaaatctgtc caaccttatt aataaagttt gctgcatgct tagtgagctc     660
caaaatgaca aggtgactgg cagctcaaag aacactgaca ttgaactcaa catgcaagca     720
cttgtaaagt tagtgtttgg taacacctca agcaacatca accaagacat taagcaaaca     780 tttttttgcag ttgttaagac tttctattac agtgcacatg ttagtgagga ataatcaac     840 tttcacatat ccaaagtgct ttttcagcaa gtccagtaa                             879

<210> SEQ ID NO 16
<211> LENGTH: 292
<212> TYPE: PRT
<213> ORGANISM: Nicotiana glutinosa
<220> FEATURE:
<223> OTHER INFORMATION: NgLLP2 partial sequence

<400> SEQUENCE: 16

Trp Gln Thr Leu Tyr Arg Met Pro Asp Val Ser Asn Asn Val Tyr Leu
1                5                  10                  15

Gln Ala Ala Lys Leu Asp Tyr Asn Arg Cys Gln Ser Gln His Arg Phe
                20                  25                  30

Glu Trp Leu Ile Met Gln Gln Trp Phe Asp Lys Cys Asn Phe Gln Gln
            35                  40                  45

Phe Gly Ile Ser Lys Lys Tyr Leu Leu Val Ser Tyr Phe Leu Ala Ala
        50                  55                  60

Ala Ser Ile Phe Glu Val Glu Lys Ser Arg Glu Arg Leu Ala Trp Ala
```

-continued

```
                65                  70                  75                  80
Lys Ser Arg Ile Ile Cys Lys Met Ile Thr Ser Tyr Tyr Asn Glu Glu
                85                  90                  95

Ala Thr Thr Trp Thr Ser Arg Asn Ser Leu Leu Met Glu Phe Lys Gly
               100                 105                 110

Ser Asp Asp Pro Ser Arg Lys Asn Gly Asn Glu Thr Lys Glu Ile Ile
               115                 120                 125

Val Leu Lys Asn Leu Arg Gln Phe Leu His Gln Leu Ser Glu Glu Thr
130                 135                 140

Phe Glu Asp Leu Gly Lys Asp Ile His Gln Leu Gln Asn Ala Trp
145                 150                 155                 160

Lys Thr Trp Leu Ala Phe Leu Arg Glu Glu Lys Asn Thr Cys Gln Glu
                165                 170                 175

Glu Ala Glu Leu Leu Val Arg Thr Ile Asn Leu Ser Gly Gly His Met
               180                 185                 190

Ile His Asp Glu Ile Leu Phe Asp Ala Asp Tyr Lys Asn Leu Ser Asn
               195                 200                 205

Leu Ile Asn Lys Val Cys Cys Met Leu Ser Glu Leu Gln Asn Asp Lys
210                 215                 220

Val Thr Gly Ser Ser Lys Asn Thr Asp Ile Glu Leu Asn Met Gln Ala
225                 230                 235                 240

Leu Val Lys Leu Val Phe Gly Asn Thr Ser Ser Asn Ile Asn Gln Asp
                245                 250                 255

Ile Lys Gln Thr Phe Phe Ala Val Val Lys Thr Phe Tyr Tyr Ser Ala
                260                 265                 270

His Val Ser Glu Glu Ile Ile Asn Phe His Ile Ser Lys Val Leu Phe
               275                 280                 285

Gln Gln Val Gln
               290

<210> SEQ ID NO 17
<211> LENGTH: 29
<212> TYPE: DNA
<213> ORGANISM: Artificial Sequence
<220> FEATURE:
<223> OTHER INFORMATION: Primer 30-101.4

<400> SEQUENCE: 17
tggattggca agactctkta caggatgcc                                       29

<210> SEQ ID NO 18
<211> LENGTH: 45
<212> TYPE: DNA
<213> ORGANISM: Artificial Sequence
<220> FEATURE:
<223> OTHER INFORMATION: Primer UPM

<400> SEQUENCE: 18
ctaatacgac tcactatagg gcaagcagtg gtatcaacgc agagt                     45

<210> SEQ ID NO 19
<211> LENGTH: 30
<212> TYPE: DNA
<213> ORGANISM: Artificial Sequence
<220> FEATURE:
<223> OTHER INFORMATION: Primer 30-124.1

<400> SEQUENCE: 19
ttagccattc aaatcgatgt tgactttggc                                      30
```

```
<210> SEQ ID NO 20
<211> LENGTH: 30
<212> TYPE: DNA
<213> ORGANISM: Artificial Sequence
<220> FEATURE:
<223> OTHER INFORMATION: Primer 30-124.2

<400> SEQUENCE: 20
gcagctaaga aataagaaac taggaggtac                                    30

<210> SEQ ID NO 21
<211> LENGTH: 42
<212> TYPE: DNA
<213> ORGANISM: Artificial Sequence
<220> FEATURE:
<223> OTHER INFORMATION: Primer 30-137.1 NgL2-F1

<400> SEQUENCE: 21
ttcccgctac atatgcaggt taaaattacg tccagtcaca gg                      42

<210> SEQ ID NO 22
<211> LENGTH: 44
<212> TYPE: DNA
<213> ORGANISM: Artificial Sequence
<220> FEATURE:
<223> OTHER INFORMATION: Primer 30-137.2 NgL2 F2

<400> SEQUENCE: 22
ttcccgctac atatgtgcgc acctattgat gcaagttatc ttgg                    44

<210> SEQ ID NO 23
<211> LENGTH: 34
<212> TYPE: DNA
<213> ORGANISM: Artificial Sequence
<220> FEATURE:
<223> OTHER INFORMATION: Primer 30-137.3 NgLPP2-R

<400> SEQUENCE: 23
ttgcggccgc ttactggact tgctgaaaaa gcac                               34

<210> SEQ ID NO 24
<211> LENGTH: 20
<212> TYPE: DNA
<213> ORGANISM: Artificial Sequence
<220> FEATURE:
<223> OTHER INFORMATION: Primer 27-75.8
<220> FEATURE:
<221> NAME/KEY: variation
<222> LOCATION: 3, 6, 9, 15, 18
<223> OTHER INFORMATION: n = a, c, t or g

<400> SEQUENCE: 24
gcnmtngcnt tycgnctnct                                               20

<210> SEQ ID NO 25
<211> LENGTH: 17
<212> TYPE: DNA
<213> ORGANISM: Artificial Sequence
<220> FEATURE:
<223> OTHER INFORMATION: Primer 30-9.8

<400> SEQUENCE: 25
cartcraara artcrtc                                                  17

<210> SEQ ID NO 26
```

```
<211> LENGTH: 642
<212> TYPE: DNA
<213> ORGANISM: Nicotiana glutinosa
<220> FEATURE:
<223> OTHER INFORMATION: S3 degenerate PCR product

<400> SEQUENCE: 26
gcaatggctt tccggctgct gcggatgaat aactatgaag tttcctcaga agaacttgaa      60
ggatttgtcg accaagaaca tttccttaca acatcaggtg ggaaacttat tagtcacgtt    120
gcaattctcg aacttcaccg agcttcacag gtggatattc aagaagggaa agatctcatt    180
ttagataaaa taagtacttg gacaaggaat tttatggagc aagaactctt ggacaatcaa    240
atccttgata ggtcaaagaa ggagatggaa tttgctatga ggaaatttta tggcacattt    300
gatcgagtgg aaactagacg atacatcgag tcatacaaaa tggacagttt taagatctta    360
aaagcagcct acaggtcttc caacattaac aacatagact tgctaaagtt ctcagaacat    420
gattttaact tgtgccaagc ccgacacaaa gaagaacttc aacagattaa gaggtggttc    480
gcagattgca aactggaaca agtaggatca tcacaaaact acttatacac tagttacttc    540
ccaattgctg ccatactctt cgaacctgaa tatggtgatg ctcgtctagc atttgcaaag    600
tgtggcataa tcgcaacgac gatggacgac tttttcgact ga                       642

<210> SEQ ID NO 27
<211> LENGTH: 213
<212> TYPE: PRT
<213> ORGANISM: Nicotiana glutinosa
<220> FEATURE:
<223> OTHER INFORMATION: S3 degenerate PCR product

<400> SEQUENCE: 27

Ala Met Ala Phe Arg Leu Leu Arg Met Asn Asn Tyr Glu Val Ser Ser
 1               5                  10                  15

Glu Glu Leu Glu Gly Phe Val Asp Gln Glu His Phe Leu Thr Thr Ser
            20                  25                  30

Gly Gly Lys Leu Ile Ser His Val Ala Ile Leu Glu Leu His Arg Ala
        35                  40                  45

Ser Gln Val Asp Ile Gln Glu Gly Lys Asp Leu Ile Leu Asp Lys Ile
    50                  55                  60

Ser Thr Trp Thr Arg Asn Phe Met Glu Gln Glu Leu Leu Asp Asn Gln
65                  70                  75                  80

Ile Leu Asp Arg Ser Lys Lys Glu Met Glu Phe Ala Met Arg Lys Phe
                85                  90                  95

Tyr Gly Thr Phe Asp Arg Val Glu Thr Arg Arg Tyr Ile Glu Ser Tyr
            100                 105                 110

Lys Met Asp Ser Phe Lys Ile Leu Lys Ala Ala Tyr Arg Ser Ser Asn
        115                 120                 125

Ile Asn Asn Ile Asp Leu Leu Lys Phe Ser Glu His Asp Phe Asn Leu
    130                 135                 140

Cys Gln Ala Arg His Lys Glu Glu Leu Gln Gln Ile Lys Arg Trp Phe
145                 150                 155                 160

Ala Asp Cys Lys Leu Glu Gln Val Gly Ser Ser Gln Asn Tyr Leu Tyr
                165                 170                 175

Thr Ser Tyr Phe Pro Ile Ala Ala Ile Leu Phe Glu Pro Glu Tyr Gly
            180                 185                 190

Asp Ala Arg Leu Ala Phe Ala Lys Cys Gly Ile Ile Ala Thr Thr Met
        195                 200                 205
```

Asp Asp Phe Phe Asp
210

<210> SEQ ID NO 28
<211> LENGTH: 29
<212> TYPE: DNA
<213> ORGANISM: Artificial Sequence
<220> FEATURE:
<223> OTHER INFORMATION: Primer 30-28.1

<400> SEQUENCE: 28
gaggtggttc gcagattgca aactggaac                                29

<210> SEQ ID NO 29
<211> LENGTH: 29
<212> TYPE: DNA
<213> ORGANISM: Artificial Sequence
<220> FEATURE:
<223> OTHER INFORMATION: Primer 30-28.4

<400> SEQUENCE: 29
gtcgtccatc gtcgttgcga ttatgccac                                29

<210> SEQ ID NO 30
<211> LENGTH: 2382
<212> TYPE: DNA
<213> ORGANISM: Nicotiana glutinosa
<220> FEATURE:
<223> OTHER INFORMATION: S3 assembled

<400> SEQUENCE: 30

| | | | | | |
|---|---|---|---|---|---|
| atgatacttg | gactgagaag | cacaatcata | ccacttcctg | atcataagtt | gggaaatatc | 60 |
| aaattaggtt | cagtaaccaa | agattcaaat | ttccacagac | caagtagagt | aagatgcagc | 120 |
| cacagtactg | cttcatcact | ggaagaggcg | aagggaagaa | taagggaaac | atttggaaaa | 180 |
| aatgagctat | ctccttcttc | ctatgacaca | gcatgggtag | ctatggtccc | ttcaagatat | 240 |
| tctatgaacc | aaccatgttt | tcctcggtgc | ttggattgga | ttcttgaaaa | tcaaagagaa | 300 |
| gatggatctt | ggggcctaaa | tcctagccat | ccattgcttg | taaaagactc | cctttcttcc | 360 |
| actctagcat | gtttgcttgc | ccttcgcaaa | tggagaattg | gagataacca | agtccaaaga | 420 |
| ggccttggct | ttattgaaac | gcatggttgg | gcagttgata | acgtggatca | gatttcacct | 480 |
| ttaggatttg | atattatatt | tcccagcatg | atcaagtatg | cagagaaact | gaatttggat | 540 |
| ctacctttcg | atcctaacct | tgtaaatatg | atgctccgcg | aacgcgaatt | aacaattgaa | 600 |
| agagccctaa | agaatgaatt | cgaagggaat | atggcaaatg | ttgaatattt | tgctgaaggg | 660 |
| ctcggtgaat | tatgtcattg | gaaagagata | atgcttcatc | agagacgcaa | cggatcgctc | 720 |
| tttgactctc | cagcaactac | tgcagctgct | tgatttacc | atcagcacga | tgagaaatgc | 780 |
| tttgggtact | tgagctcaat | cttgaaactg | cacgagaatt | gggtccccac | tatttaccct | 840 |
| acaaaggtac | attcaaatct | cttcttcgtt | gatgcccttc | aaaatcttgg | agtagatcgg | 900 |
| tattttaaaa | cagaactcaa | aagtgtactc | gatgaaatat | acaggctttg | gctagaaaag | 960 |
| aatgaagaaa | ttttttcaga | cattgctcat | tgtgccatgg | cgtttcgact | tttgcggatg | 1020 |
| aataactatg | aagtttcctc | agaagaactt | gaaggatttg | tcgaccaaga | acatttcttt | 1080 |
| acaacatcag | gtgggaaact | tattagtcac | gttgcaattc | tcgaacttca | ccgagcttca | 1140 |
| caggtggata | ttcaagaagg | gaagatctc | attttagata | aaataagtac | ttggacaagg | 1200 |
| aattttatgg | agcaagaact | cttggacaat | caaatccttg | ataggtcaaa | gaaggagatg | 1260 |

-continued

```
gaatttgcta tgaggaaatt ttatggcaca tttgatcgag tggaaactag acgatacatc    1320
gagtcataca aaatggacag ttttaagatc ttaaaagcag cctacaggtc ttccaacatt    1380
aacaacatag acttgctaaa gttctcagaa catgatttta acttgtgcca agcccgacac    1440
aaagaagaac ttcaacagat taagaggtgg ttcgcagatt gcaaactgga caagtaggaa    1500
tcatcacaaa actacttata cactagttac ttcccaattg ctgccatact cttcgaacct    1560
gaatatggtg atgctcgtct agcatttgca aagtgtggca taatcgcaac gacggtggat    1620
gatttcttcg atggttttgc ttgcaatgaa gaactccaaa acatcatcga attagtagag    1680
aggtgggatg ataccccaac tgtcggattt cgttcagaaa gggttagaat tttcttttg     1740
gcactttaca aaatgataga ggaaattgcg gcaaaggcag aaactaagca aggtcgatgt    1800
gtcaaagatc tccttattaa cttgtggatt gatttattga aatgtatgct ggtggaattg    1860
gaccctttgga aaattaaatc aactacccca agcatagagg agtacttgtc tatcgcatgt   1920
gtaactacag gtgttaaatg tttaattctc atatcactac atcttcttgg accaaaactg    1980
tccaaggatg tcacagaaag ttctgaggtc agtgccttat ggaattgtac agctgttgtg    2040
gcccgattga ataatgatat acatagttac aagagagaac aagcagaaag ttcaacaaat    2100
atggtagcaa ttttaatatc acagagtcag agaactatct ctgaagaaga ggctataaga    2160
cagataaaag aagtgatgga agtaagaga agagagttgc tagggatggt tctacaaaat     2220
aaagaaagcc aattgccgca agtgtgcaaa gatcttttt ggacgacatt caaagcagct     2280
tattctatat atacacatgg cgatgagtat cgcttcccac aggaattgaa gaaccatata    2340
aacgatgtaa tttacaaacc actcaatcaa tattccccat aa                       2382
```

<210> SEQ ID NO 31
<211> LENGTH: 793
<212> TYPE: PRT
<213> ORGANISM: Nicotiana glutinosa
<220> FEATURE:
<223> OTHER INFORMATION: S3 assembled

<400> SEQUENCE: 31

```
Met Ile Leu Gly Leu Arg Ser Thr Ile Ile Pro Leu Pro Asp His Lys
  1               5                  10                  15

Leu Gly Asn Ile Lys Leu Gly Ser Val Thr Lys Asp Ser Asn Phe His
                 20                  25                  30

Arg Pro Ser Arg Val Arg Cys Ser His Ser Thr Ala Ser Ser Leu Glu
             35                  40                  45

Glu Ala Lys Gly Arg Ile Arg Glu Thr Phe Gly Lys Asn Glu Leu Ser
 50                  55                  60

Pro Ser Ser Tyr Asp Thr Ala Trp Val Ala Met Val Pro Ser Arg Tyr
 65                  70                  75                  80

Ser Met Asn Gln Pro Cys Phe Pro Arg Cys Leu Asp Trp Ile Leu Glu
                 85                  90                  95

Asn Gln Arg Glu Asp Gly Ser Trp Gly Leu Asn Pro Ser His Pro Leu
            100                 105                 110

Leu Val Lys Asp Ser Leu Ser Ser Thr Leu Ala Cys Leu Leu Ala Leu
            115                 120                 125

Arg Lys Trp Arg Ile Gly Asp Asn Gln Val Gln Arg Gly Leu Gly Phe
        130                 135                 140

Ile Glu Thr His Gly Trp Ala Val Asp Asn Val Asp Gln Ile Ser Pro
145                 150                 155                 160

Leu Gly Phe Asp Ile Ile Phe Pro Ser Met Ile Lys Tyr Ala Glu Lys
```

-continued

```
                165                 170                 175
Leu Asn Leu Asp Leu Pro Phe Asp Pro Asn Leu Val Asn Met Met Leu
            180                 185                 190
Arg Glu Arg Glu Leu Thr Ile Glu Arg Ala Leu Lys Asn Glu Phe Glu
            195                 200                 205
Gly Asn Met Ala Asn Val Glu Tyr Phe Ala Glu Gly Leu Gly Glu Leu
            210                 215                 220
Cys His Trp Lys Glu Ile Met Leu His Gln Arg Asn Gly Ser Leu
225                 230                 235                 240
Phe Asp Ser Pro Ala Thr Thr Ala Ala Leu Ile Tyr His Gln His
            245                 250                 255
Asp Glu Lys Cys Phe Gly Tyr Leu Ser Ser Ile Leu Lys Leu His Glu
            260                 265                 270
Asn Trp Val Pro Thr Ile Tyr Pro Thr Lys Val His Ser Asn Leu Phe
            275                 280                 285
Phe Val Asp Ala Leu Gln Asn Leu Gly Val Asp Arg Tyr Phe Lys Thr
            290                 295                 300
Glu Leu Lys Ser Val Leu Asp Glu Ile Tyr Arg Leu Trp Leu Glu Lys
305                 310                 315                 320
Asn Glu Glu Ile Phe Ser Asp Ile Ala His Cys Ala Met Ala Phe Arg
            325                 330                 335
Leu Leu Arg Met Asn Asn Tyr Glu Val Ser Ser Glu Glu Leu Glu Gly
            340                 345                 350
Phe Val Asp Gln Glu His Phe Phe Thr Thr Ser Gly Gly Lys Leu Ile
            355                 360                 365
Ser His Val Ala Ile Leu Glu Leu His Arg Ala Ser Gln Val Asp Ile
            370                 375                 380
Gln Glu Gly Lys Asp Leu Ile Leu Asp Lys Ile Ser Thr Trp Thr Arg
385                 390                 395                 400
Asn Phe Met Glu Gln Glu Leu Leu Asp Asn Gln Ile Leu Asp Arg Ser
            405                 410                 415
Lys Lys Glu Met Glu Phe Ala Met Arg Lys Phe Tyr Gly Thr Phe Asp
            420                 425                 430
Arg Val Glu Thr Arg Arg Tyr Ile Glu Ser Tyr Lys Met Asp Ser Phe
            435                 440                 445
Lys Ile Leu Lys Ala Ala Tyr Arg Ser Ser Asn Ile Asn Asn Ile Asp
450                 455                 460
Leu Leu Lys Phe Ser Glu His Asp Phe Asn Leu Cys Gln Ala Arg His
            470                 475                 480
Lys Glu Glu Leu Gln Gln Ile Lys Arg Trp Phe Ala Asp Cys Lys Leu
            485                 490                 495
Glu Gln Val Gly Ser Ser Gln Asn Tyr Leu Tyr Thr Ser Tyr Phe Pro
            500                 505                 510
Ile Ala Ala Ile Leu Phe Glu Pro Glu Tyr Gly Asp Ala Arg Leu Ala
            515                 520                 525
Phe Ala Lys Cys Gly Ile Ile Ala Thr Thr Val Asp Asp Phe Phe Asp
            530                 535                 540
Gly Phe Ala Cys Asn Glu Glu Leu Gln Asn Ile Ile Glu Leu Val Glu
545                 550                 555                 560
Arg Trp Asp Gly Tyr Pro Thr Val Gly Phe Arg Ser Glu Arg Val Arg
            565                 570                 575
Ile Phe Phe Leu Ala Leu Tyr Lys Met Ile Glu Glu Ile Ala Ala Lys
            580                 585                 590
```

```
Ala Glu Thr Lys Gln Gly Arg Cys Val Lys Asp Leu Leu Ile Asn Leu
        595                 600                 605
Trp Ile Asp Leu Leu Lys Cys Met Leu Val Glu Leu Asp Leu Trp Lys
        610                 615                 620
Ile Lys Ser Thr Thr Pro Ser Ile Glu Glu Tyr Leu Ser Ile Ala Cys
625                 630                 635                 640
Val Thr Thr Gly Val Lys Cys Leu Ile Leu Ile Ser Leu His Leu Leu
                645                 650                 655
Gly Pro Lys Leu Ser Lys Asp Val Thr Glu Ser Ser Glu Val Ser Ala
                660                 665                 670
Leu Trp Asn Cys Thr Ala Val Val Ala Arg Leu Asn Asn Asp Ile His
        675                 680                 685
Ser Tyr Lys Arg Glu Gln Ala Glu Ser Ser Thr Asn Met Val Ala Ile
        690                 695                 700
Leu Ile Ser Gln Ser Gln Arg Thr Ile Ser Glu Glu Ala Ile Arg
705                 710                 715                 720
Gln Ile Lys Glu Val Met Glu Ser Lys Arg Arg Glu Leu Leu Gly Met
                725                 730                 735
Val Leu Gln Asn Lys Glu Ser Gln Leu Pro Gln Val Cys Lys Asp Leu
        740                 745                 750
Phe Trp Thr Thr Phe Lys Ala Ala Tyr Ser Ile Tyr Thr His Gly Asp
        755                 760                 765
Glu Tyr Arg Phe Pro Gln Glu Leu Lys Asn His Ile Asn Asp Val Ile
        770                 775                 780
Tyr Lys Pro Leu Asn Gln Tyr Ser Pro
785                 790

<210> SEQ ID NO 32
<211> LENGTH: 31
<212> TYPE: DNA
<213> ORGANISM: Artificial Sequence
<220> FEATURE:
<223> OTHER INFORMATION: Primer 30-87.13 S3 F1

<400> SEQUENCE: 32
ttccatggat gatacttgga ctgagaagca c                              31

<210> SEQ ID NO 33
<211> LENGTH: 36
<212> TYPE: DNA
<213> ORGANISM: Artificial Sequence
<220> FEATURE:
<223> OTHER INFORMATION: Primer 30-87.14 S3 F2

<400> SEQUENCE: 33
ttccatggat gagccacagt actgcttcat cactgg                         36

<210> SEQ ID NO 34
<211> LENGTH: 34
<212> TYPE: DNA
<213> ORGANISM: Artificial Sequence
<220> FEATURE:
<223> OTHER INFORMATION: Primer 30-87.15 S3 R

<400> SEQUENCE: 34
ttgcggccgc ttatggggaa tattgattga gtgg                           34

<210> SEQ ID NO 35
<211> LENGTH: 2379
```

<212> TYPE: DNA
<213> ORGANISM: Nicotiana glutinosa
<220> FEATURE:
<223> OTHER INFORMATION: NgSPP S3F1-1

<400> SEQUENCE: 35

| | | | | | |
|---|---|---|---|---|---|
| atgatacttg | gactgagaag | cacaatcata | ccacttcctg | atcataagtt | gggaaatatc | 60 |
| aaattaggtt | cagtaaccaa | ttcaaatttc | cccagaccaa | gtagagtaag | atgcagccac | 120 |
| agtactgctt | catcactgga | agaggcgaag | gagagaataa | gggaaacatt | tgtaaaaaat | 180 |
| gagctatctc | cttcttccta | tgacacagca | tgggtagcta | tggtcccttc | aagatattct | 240 |
| atgaaccaac | catgttttcc | tcggtgcttg | gattggattc | ttgaaaatca | aagagaagat | 300 |
| ggatcttggg | gcctaaatcc | tagccatcca | ttgcttgtaa | aagactccct | tcttccact | 360 |
| ctagcatgtt | tgcttgccct | tcgcaaatgg | agaattggag | ataaccaagt | ccaaagaggc | 420 |
| cttggcttta | ttgaaacgca | tggttgggca | gttgataacg | tggatcagat | tcacccttta | 480 |
| ggatttgata | ttatatttcc | cagcatgatc | aagtatgcag | agaaactgaa | tttggatcta | 540 |
| cctttcgatc | ctaaccttgt | aaatatgatg | ctccgcgaac | gcgaattaac | aattgaaaga | 600 |
| gccctaaaga | atgaattcga | agggaatatg | gcaaatgttg | aatattttgc | tgaagggctc | 660 |
| ggtgaattat | gtcattggaa | agagataatg | cttcatcaga | gacgcaacgg | atcgctcttt | 720 |
| gactctccag | caactactgc | agctgctttg | atttaccatc | agcacgatga | gaaatgcttt | 780 |
| gggtacttga | gctcaatctt | gaaactgcac | gagaattggg | tccccactat | ttaccctaca | 840 |
| aagtacatt | caaatctctt | cttagttgat | gcccttcaaa | atcttggagt | aaatcggtat | 900 |
| tttaaaacag | aactcaaaag | tgtactcgat | gaaatataca | ggctttggct | agaaaagaat | 960 |
| gaagaaattt | tttcagacat | tgctcattgt | gccatggcgt | ttcgactttt | gcggatgaat | 1020 |
| aactatgaag | tttcctcaga | agaacttgaa | ggatttgtcg | accaagaaca | tttctttaca | 1080 |
| acatcaggtg | ggaaacttat | tagtcacgtt | gcaattctcg | aacttcaccg | agcttcacag | 1140 |
| gtagatattc | aagaagggaa | agatctcatt | ttagataaaa | taagtacttg | gactaggaat | 1200 |
| tttatggagc | aagaactctt | ggacaatcaa | atccttgata | ggtcaaagaa | ggagatggaa | 1260 |
| tttgctatga | ggaaatttta | tggcacattt | gatcgagtgg | aaactagacg | atacatcgag | 1320 |
| tcatacaaaa | tggacagttt | taagatctta | aaagcagctt | acaggtcttc | caacattaac | 1380 |
| aacatagact | tgctaaagtt | ctcagaacat | gattttaact | tgtgccaagc | ccgacacaaa | 1440 |
| gaagaacttc | aacagattaa | gaggtggttc | gcagattgca | aactggaaca | agtaggatca | 1500 |
| tcacaaaact | acttatacac | tagttacttc | ccaattgctg | ccatactctt | cgaacctgaa | 1560 |
| tatggtgatg | ctcgtctagc | atttgcaaag | tgtggcataa | tcgcaacgac | ggtggatgat | 1620 |
| ttcttcgatg | gttttgcttg | caatgaagaa | ctccaaaaca | tcatcgaatt | agtagagagg | 1680 |
| tgggatggat | acccaactgt | cggatttcgt | tcagagaggg | ttagaatttt | cttttttggca | 1740 |
| ctttacaaaa | tggtagagga | aattgcggca | aaggcagaaa | ctaagcaagg | tcgatgtgtc | 1800 |
| aaagatctcc | ttattaactt | gtggattgat | ttattgaaat | gtatgctggt | ggaattggac | 1860 |
| ctttggaaaa | ttaaatcaac | taccccaagc | atagaggagt | acttgtctat | cgcatgtgta | 1920 |
| actacaggtg | ttaaatgttt | aattctcata | tcactacatc | ttcttggacc | aaaactgtcc | 1980 |
| aaggatgtca | cagaaagttc | tgaggtcagt | gccttatgga | attgtacagc | tgttgtggcc | 2040 |
| cgattgaata | atgatataca | tagttacaag | agagaacaag | cagaaagttc | aacaaatatg | 2100 |
| gtagcaatat | taatatcaca | gagtcagaga | actatctctg | aagaagaggc | tataagacag | 2160 |

```
ataaaagaaa tgatggaaag taagagaaga gagttgctag ggatggttct acaaaataaa      2220
gaaagccaat tgccgcaagt gtgcaaagat cttttttgga cgacattcaa agcagcttat      2280
tctatatata cacatggcga tgagtatcgc ttcccacagg aattgaagaa ccatataaac      2340
gatgtaattt acaaaccact caatcaatat tccccataa                             2379
```

<210> SEQ ID NO 36
<211> LENGTH: 792
<212> TYPE: PRT
<213> ORGANISM: Nicotiana glutinosa
<220> FEATURE:
<223> OTHER INFORMATION: NgSPP S3F1-1

<400> SEQUENCE: 36

```
Met Ile Leu Gly Leu Arg Ser Thr Ile Ile Pro Leu Pro Asp His Lys
1               5                   10                  15

Leu Gly Asn Ile Lys Leu Gly Ser Val Thr Asn Ser Asn Phe Pro Arg
            20                  25                  30

Pro Ser Arg Val Arg Cys Ser His Ser Thr Ala Ser Ser Leu Glu Glu
        35                  40                  45

Ala Lys Glu Arg Ile Arg Glu Thr Phe Val Lys Asn Glu Leu Ser Pro
    50                  55                  60

Ser Ser Tyr Asp Thr Ala Trp Val Ala Met Val Pro Ser Arg Tyr Ser
65                  70                  75                  80

Met Asn Gln Pro Cys Phe Pro Arg Cys Leu Asp Trp Ile Leu Glu Asn
                85                  90                  95

Gln Arg Glu Asp Gly Ser Trp Gly Leu Asn Pro Ser His Pro Leu Leu
            100                 105                 110

Val Lys Asp Ser Leu Ser Ser Thr Leu Ala Cys Leu Leu Ala Leu Arg
        115                 120                 125

Lys Trp Arg Ile Gly Asp Asn Gln Val Gln Arg Gly Leu Gly Phe Ile
    130                 135                 140

Glu Thr His Gly Trp Ala Val Asp Asn Val Asp Gln Ile Ser Pro Leu
145                 150                 155                 160

Gly Phe Asp Ile Ile Phe Pro Ser Met Ile Lys Tyr Ala Glu Lys Leu
                165                 170                 175

Asn Leu Asp Leu Pro Phe Asp Pro Asn Leu Val Asn Met Met Leu Arg
            180                 185                 190

Glu Arg Glu Leu Thr Ile Glu Arg Ala Leu Lys Asn Glu Phe Glu Gly
        195                 200                 205

Asn Met Ala Asn Val Glu Tyr Phe Ala Glu Gly Leu Gly Glu Leu Cys
    210                 215                 220

His Trp Lys Glu Ile Met Leu His Gln Arg Arg Asn Gly Ser Leu Phe
225                 230                 235                 240

Asp Ser Pro Ala Thr Thr Ala Ala Ala Leu Ile Tyr His Gln His Asp
                245                 250                 255

Glu Lys Cys Phe Gly Tyr Leu Ser Ser Ile Leu Lys Leu His Glu Asn
            260                 265                 270

Trp Val Pro Thr Ile Tyr Pro Thr Lys Val His Ser Asn Leu Phe Leu
        275                 280                 285

Val Asp Ala Leu Gln Asn Leu Gly Val Asn Arg Tyr Phe Lys Thr Glu
    290                 295                 300

Leu Lys Ser Val Leu Asp Glu Ile Tyr Arg Leu Trp Leu Glu Lys Asn
305                 310                 315                 320

Glu Glu Ile Phe Ser Asp Ile Ala His Cys Ala Met Ala Phe Arg Leu
```

```
                    325                 330                 335
Leu Arg Met Asn Asn Tyr Glu Val Ser Ser Glu Glu Leu Glu Gly Phe
                340                 345                 350

Val Asp Gln Glu His Phe Phe Thr Thr Ser Gly Gly Lys Leu Ile Ser
                355                 360                 365

His Val Ala Ile Leu Glu Leu His Arg Ala Ser Gln Val Asp Ile Gln
            370                 375                 380

Glu Gly Lys Asp Leu Ile Leu Asp Lys Ile Ser Thr Trp Thr Arg Asn
385                 390                 395                 400

Phe Met Glu Gln Glu Leu Leu Asp Asn Gln Ile Leu Asp Arg Ser Lys
                405                 410                 415

Lys Glu Met Glu Phe Ala Met Arg Lys Phe Tyr Gly Thr Phe Asp Arg
                420                 425                 430

Val Glu Thr Arg Arg Tyr Ile Glu Ser Tyr Lys Met Asp Ser Phe Lys
            435                 440                 445

Ile Leu Lys Ala Ala Tyr Arg Ser Ser Asn Ile Asn Asn Ile Asp Leu
        450                 455                 460

Leu Lys Phe Ser Glu His Asp Phe Asn Leu Cys Gln Ala Arg His Lys
465                 470                 475                 480

Glu Glu Leu Gln Gln Ile Lys Arg Trp Phe Ala Asp Cys Lys Leu Glu
                485                 490                 495

Gln Val Gly Ser Ser Gln Asn Tyr Leu Tyr Thr Ser Tyr Phe Pro Ile
            500                 505                 510

Ala Ala Ile Leu Phe Glu Pro Glu Tyr Gly Asp Ala Arg Leu Ala Phe
        515                 520                 525

Ala Lys Cys Gly Ile Ile Ala Thr Thr Val Asp Asp Phe Phe Asp Gly
530                 535                 540

Phe Ala Cys Asn Glu Glu Leu Gln Asn Ile Ile Glu Leu Val Glu Arg
545                 550                 555                 560

Trp Asp Gly Tyr Pro Thr Val Gly Phe Arg Ser Glu Arg Val Arg Ile
                565                 570                 575

Phe Phe Leu Ala Leu Tyr Lys Met Val Glu Glu Ile Ala Ala Lys Ala
            580                 585                 590

Glu Thr Lys Gln Gly Arg Cys Val Lys Asp Leu Leu Ile Asn Leu Trp
        595                 600                 605

Ile Asp Leu Leu Lys Cys Met Leu Val Glu Leu Asp Leu Trp Lys Ile
        610                 615                 620

Lys Ser Thr Thr Pro Ser Ile Glu Glu Tyr Leu Ser Ile Ala Cys Val
625                 630                 635                 640

Thr Thr Gly Val Lys Cys Leu Ile Leu Ile Ser Leu His Leu Leu Gly
                645                 650                 655

Pro Lys Leu Ser Lys Asp Val Thr Glu Ser Ser Glu Val Ser Ala Leu
            660                 665                 670

Trp Asn Cys Thr Ala Val Val Ala Arg Leu Asn Asn Asp Ile His Ser
        675                 680                 685

Tyr Lys Arg Glu Gln Ala Glu Ser Ser Thr Asn Met Val Ala Ile Leu
    690                 695                 700

Ile Ser Gln Ser Gln Arg Thr Ile Ser Glu Glu Ala Ile Arg Gln
705                 710                 715                 720

Ile Lys Glu Met Met Glu Ser Lys Arg Arg Glu Leu Leu Gly Met Val
                725                 730                 735

Leu Gln Asn Lys Glu Ser Gln Leu Pro Gln Val Cys Lys Asp Leu Phe
            740                 745                 750
```

```
Trp Thr Thr Phe Lys Ala Ala Tyr Ser Ile Tyr Thr His Gly Asp Glu
        755                 760                 765

Tyr Arg Phe Pro Gln Glu Leu Lys Asn His Ile Asn Asp Val Ile Tyr
        770                 775                 780

Lys Pro Leu Asn Gln Tyr Ser Pro
785                 790

<210> SEQ ID NO 37
<211> LENGTH: 2268
<212> TYPE: DNA
<213> ORGANISM: Nicotiana glutinosa
<220> FEATURE:
<223> OTHER INFORMATION: NgSPP S3F2-1

<400> SEQUENCE: 37
atgagccaca gtactgcttc atcactggaa gaggcgaagg aaagaataag ggaaacattt      60
ggaaaaaatg agctatcttc ttcttcctat gacacagcat gggtagctat ggtcccttca     120
agatattcta tgaaccaacc atgttttcct cggtgcttgg attggattct tgaaaatcaa     180
agagaagatg gatcttgggg cctaaatcct agccttccat tgcttgtaaa agactccctt     240
tcttccactc tagcatgttt gcttgcccct cgcaaatgga gaattggaga taaccaagtc     300
caaagaggcc ttggctttat tgaaacgcat ggttgggcag ttgataacgt ggatcagatt     360
tcacctttag gatttgatat tatatttccc agcatgatca gtatgcagaa gaaactgaat     420
ttggatctac ctttcgatcc taaccttgta aatatgatgc tccgcgaacg cgaattaaca     480
attgaaagag ccctaaagaa tgaattcgaa gggaatatgg caaatgttga atattttgct     540
gaagggctcg gtgaattatg tcattggaaa gagataatgc ttcatcagag acgcaacgga     600
tcgctctttg actctccagc aactactgca gctgctttga tttaccatca gcacgatgag     660
aagtgctttg ggtacttgag ctcaatcttg aaactgcacg agaattgggt ccccactatt     720
taccctacaa aggtacattc aaatctcttc ttcgttgatg cccttcaaaa tcttggagta     780
gatcggtatt ttaaaacaga actcaaaagt gtactcgatg aaatatacag gctttggcta     840
gaaaagaatg aagaaatttt ttcagacatt gctcattgtg ccatggcgtt tcgacttttg     900
cggatgaata actatgaagt ttcctcagaa gaacttgaag gatttgtcga ccaagaacat     960
ttctttacaa catcaggtgg gaaacttatt agtcacgttg caattctcga acttcaccga    1020
gcttcacagg tggatattca agaagggaaa gatctcattt tagataaaat aagtacttgg    1080
acaaggaatt ttatggagca agaactcttg acaatcaaa tccttgatag gtcaaagaag    1140
gagatggaat tgctatgag gaaatttat ggcacatttg atcgagtgga aactagacga    1200
tacatcgagt catacaaaat ggacagtttt aagatcttaa aagcagccta caggtcttcc    1260
aacattaaca acatagactt gctaaagttc tcagaacatg atttaactt gtgccaagcc    1320 cgacacaaag aagaacttca acagattaag aggtggttcg cagattgcaa actgaacaa    1380 gtaggatcat cacaaaacta cttatacact agttacttcc caattgctgc catactcttc    1440
gaacctgaat atggtgatgc tcgtctagca tttgcaaagt gtggcataat cgcaacgacg    1500
gtggatgatt tcttcgatgg ttttgcttgc aatgaagaac tccaaaacat catcgaatta    1560
gtagagaggt gggatggata cccaactgtc ggatttcgtt cagaaagggt tagaattttc    1620
tttttggcac tttacaaaat gatagaggaa attgcggcaa aggcagaaac taagcaaggt    1680
cgatgtgtca agatctcct tattaacttg tggattgatt tattgaaatg tatgctggtg    1740
gaattggacc tttggaaaat taaatcaact accccaagca tagaggagta cttgtctatc    1800
```

```
gcatgtgtaa ctacaggtgt taaatgttta attctcatat cactacatct tcttggacca   1860
aaactgtcca aggatgtcac agaaagttct gaggtcagtg ccttatggaa ttgtacagct   1920
gttgtggccc gattgaataa tgatatacat agttacaaga gagaacaagc agaaagttca   1980
acaaatatgg tagcaatatt aatatcacag agtcagagaa ctatctctga agaagaggct   2040
ataagacaga taaagaaat gatggaaagt aagagaagag agttgctagg gatggttcta    2100
caaaataaag aaagccaatt gccgcaagtg tgcaaagatc ttttttggac gacattcaaa   2160
gcagcttatt ctatatatac acatggcgat gagtatcgct tcccacagga attgaagaac   2220
catataaacg atgtaattta caaccactc aatcaatatt ccccataa                 2268
```

<210> SEQ ID NO 38
<211> LENGTH: 755
<212> TYPE: PRT
<213> ORGANISM: Nicotiana glutinosa
<220> FEATURE:
<223> OTHER INFORMATION: NgSPP S3F2-1

<400> SEQUENCE: 38

```
Met Ser His Ser Thr Ala Ser Ser Leu Glu Glu Ala Lys Glu Arg Ile
1               5                   10                  15

Arg Glu Thr Phe Gly Lys Asn Glu Leu Ser Ser Ser Tyr Asp Thr
            20                  25                  30

Ala Trp Val Ala Met Val Pro Ser Arg Tyr Ser Met Asn Gln Pro Cys
        35                  40                  45

Phe Pro Arg Cys Leu Asp Trp Ile Leu Glu Asn Gln Arg Glu Asp Gly
    50                  55                  60

Ser Trp Gly Leu Asn Pro Ser Leu Pro Leu Leu Val Lys Asp Ser Leu
65                  70                  75                  80

Ser Ser Thr Leu Ala Cys Leu Leu Ala Leu Arg Lys Trp Arg Ile Gly
                85                  90                  95

Asp Asn Gln Val Gln Arg Gly Leu Gly Phe Ile Glu Thr His Gly Trp
            100                 105                 110

Ala Val Asp Asn Val Asp Gln Ile Ser Pro Leu Gly Phe Asp Ile Ile
        115                 120                 125

Phe Pro Ser Met Ile Lys Tyr Ala Glu Lys Leu Asn Leu Asp Leu Pro
    130                 135                 140

Phe Asp Pro Asn Leu Val Asn Met Met Leu Arg Glu Arg Glu Leu Thr
145                 150                 155                 160

Ile Glu Arg Ala Leu Lys Asn Glu Phe Glu Gly Asn Met Ala Asn Val
                165                 170                 175

Glu Tyr Phe Ala Glu Gly Leu Gly Glu Leu Cys His Trp Lys Glu Ile
            180                 185                 190

Met Leu His Gln Arg Arg Asn Gly Ser Leu Phe Asp Ser Pro Ala Thr
        195                 200                 205

Thr Ala Ala Leu Ile Tyr His Gln His Asp Glu Lys Cys Phe Gly
    210                 215                 220

Tyr Leu Ser Ser Ile Leu Lys Leu His Glu Asn Trp Val Pro Thr Ile
225                 230                 235                 240

Tyr Pro Thr Lys Val His Ser Asn Leu Phe Phe Val Asp Ala Leu Gln
                245                 250                 255

Asn Leu Gly Val Asp Arg Tyr Phe Lys Thr Glu Leu Lys Ser Val Leu
            260                 265                 270

Asp Glu Ile Tyr Arg Leu Trp Leu Glu Lys Asn Glu Glu Ile Phe Ser
```

```
                275                 280                 285
Asp Ile Ala His Cys Ala Met Ala Phe Arg Leu Leu Arg Met Asn Asn
290                 295                 300

Tyr Glu Val Ser Ser Glu Leu Glu Gly Phe Val Asp Gln Glu His
305                 310                 315                 320

Phe Phe Thr Thr Ser Gly Gly Lys Leu Ile Ser His Val Ala Ile Leu
                325                 330                 335

Glu Leu His Arg Ala Ser Gln Val Asp Ile Gln Glu Gly Lys Asp Leu
                340                 345                 350

Ile Leu Asp Lys Ile Ser Thr Trp Thr Arg Asn Phe Met Glu Gln Glu
                355                 360                 365

Leu Leu Asp Asn Gln Ile Leu Asp Arg Ser Lys Lys Glu Met Glu Phe
370                 375                 380

Ala Met Arg Lys Phe Tyr Gly Thr Phe Asp Arg Val Glu Thr Arg Arg
385                 390                 395                 400

Tyr Ile Glu Ser Tyr Lys Met Asp Ser Phe Lys Ile Leu Lys Ala Ala
                405                 410                 415

Tyr Arg Ser Ser Asn Ile Asn Asn Ile Asp Leu Leu Lys Phe Ser Glu
                420                 425                 430

His Asp Phe Asn Leu Cys Gln Ala Arg His Lys Glu Glu Leu Gln Gln
                435                 440                 445

Ile Lys Arg Trp Phe Ala Asp Cys Lys Leu Glu Gln Val Gly Ser Ser
                450                 455                 460

Gln Asn Tyr Leu Tyr Thr Ser Tyr Phe Pro Ile Ala Ala Ile Leu Phe
465                 470                 475                 480

Glu Pro Glu Tyr Gly Asp Ala Arg Leu Ala Phe Ala Lys Cys Gly Ile
                485                 490                 495

Ile Ala Thr Thr Val Asp Asp Phe Phe Asp Gly Phe Ala Cys Asn Glu
                500                 505                 510

Glu Leu Gln Asn Ile Ile Glu Leu Val Glu Arg Trp Asp Gly Tyr Pro
                515                 520                 525

Thr Val Gly Phe Arg Ser Glu Arg Val Arg Ile Phe Phe Leu Ala Leu
                530                 535                 540

Tyr Lys Met Ile Glu Glu Ile Ala Ala Lys Ala Glu Thr Lys Gln Gly
545                 550                 555                 560

Arg Cys Val Lys Asp Leu Leu Ile Asn Leu Trp Ile Asp Leu Leu Lys
                565                 570                 575

Cys Met Leu Val Glu Leu Asp Leu Trp Lys Ile Lys Ser Thr Thr Pro
                580                 585                 590

Ser Ile Glu Glu Tyr Leu Ser Ile Ala Cys Val Thr Thr Gly Val Lys
                595                 600                 605

Cys Leu Ile Leu Ile Ser His Leu Leu Gly Pro Lys Leu Ser Lys
610                 615                 620

Asp Val Thr Glu Ser Ser Glu Val Ser Ala Leu Trp Asn Cys Thr Ala
625                 630                 635                 640

Val Val Ala Arg Leu Asn Asn Asp Ile His Ser Tyr Lys Arg Glu Gln
                645                 650                 655

Ala Glu Ser Ser Thr Asn Met Val Ala Ile Leu Ile Ser Gln Ser Gln
                660                 665                 670

Arg Thr Ile Ser Glu Glu Glu Ala Ile Arg Gln Ile Lys Glu Met Met
                675                 680                 685

Glu Ser Lys Arg Arg Glu Leu Leu Gly Met Val Leu Gln Asn Lys Glu
690                 695                 700
```

| Ser | Gln | Leu | Pro | Gln | Val | Cys | Lys | Asp | Leu | Phe | Trp | Thr | Thr | Phe | Lys |
| 705 |     |     |     | 710 |     |     |     |     | 715 |     |     |     |     | 720 |     |

| Ala | Ala | Tyr | Ser | Ile | Tyr | Thr | His | Gly | Asp | Glu | Tyr | Arg | Phe | Pro | Gln |
|     |     |     | 725 |     |     |     |     | 730 |     |     |     |     | 735 |     |     |

| Glu | Leu | Lys | Asn | His | Ile | Asn | Asp | Val | Ile | Tyr | Lys | Pro | Leu | Asn | Gln |
|     |     |     | 740 |     |     |     |     | 745 |     |     |     |     | 750 |     |     |

Tyr Ser Pro
        755

<210> SEQ ID NO 39
<211> LENGTH: 2268
<212> TYPE: DNA
<213> ORGANISM: Nicotiana glutinosa
<220> FEATURE:
<223> OTHER INFORMATION: NgSPP S3F2-3

<400> SEQUENCE: 39

```
atgagccaca gtactgcttc atcactggaa gaggcgaagg aaagaataag ggaaacattt      60
ggaaaaaatg agctatcttc ttcttcctat gacacagcat gggtagctat ggtcccttca     120
agatattcta tgaaccaacc atgttttcct cggtgcttgg attggattct tgaaaatcaa     180
agagaagatg gatcttgggg cctaaatcct agccttccat tgcttgtaaa agactccctt     240
tcttccactc tagcatgttt gcttgcccct cgcaaatgga gaattggaga taaccaagtc     300
caaagaggcc ttggctttat tgaaacgcat ggttgggcag ttgataacgt ggatcagatt     360
tcacctttag gatttgatat tatatttccc agcatgatca agtatgcaga gaaactgaat     420
ttggatctac ctttcgatcc taaccttgta aatatgatgc tccgcgaacg cgaattaaca     480
attgaaagag ccctaaagaa tgaattcgaa gggaatatgg caaatgttga atattttgct     540
gaagggctcg gtgaattatg tcattggaaa gagataatgc ttcatcagag acgcaacgga     600
tcgccctttg actctccagc aactactgca gctgctttga tttaccatca gcacgatgag     660
aagtgctttg ggtacttgag ctcaatcttg aaactgcacg agaattgggt ccccactatt     720
taccctacaa aggtacattc aaatctcttc ttcgttgatg cccttcaaaa tcttggagta     780
gatcggtatt ttaaaacaga actcaaaagt gtactcgatg aaatatacag gctttggcta     840
gaaaagaatg aagaaatttt ttcagacatt gctcattgtg ccatggcgtt tcgactttg      900
cggatgaata actatgaagt ttcctcagaa gaacttgaag gatttgtcga ccaagaacat     960
ttctttacaa catcaggtgg gaaacttatt agtcacgttg caattctcga acttcaccga    1020
gcttcacagg tggatattca agaagggaaa gatctcattt tagataaaat aagtacttgg    1080
acaaggaatt ttatggagca agaactcttg gacaatcaaa tccttgatag gtcaaagaag    1140
gagatggaat tgctatgag  gaaatttat  ggcacatttg atcgagtgga aactagacga    1200
tacatcgagt catacaaaat ggacagtttt aagatcttaa aagcagccta caggtcttcc    1260
aacattaaca acatagactt gctaaagttc tcagaacatg atttttaactt gtgccaagcc    1320
cgacacaaag aagaacttca acagattaag aggtggttcg cagattgcaa actggaacaa    1380
gtaggatcat cacaaaacta cttatacact agttacttcc caattgctgc catactcttc    1440
gaacctgaat atggtgatgc tcgtctagca tttgcaaagt gtggcataat cgcaacgacg    1500
gtggatgatt tcttcgatgg ttttgcttgc aatgaagaac tccaaaacat catcgaatta    1560
gtagagaggt gggatggata cccaactgtc ggatttcgtt cagaaagggt tagaattttc    1620
ttttggcac  tttacaaaat gatagaggaa attgcggcaa aggcagaaac taagcaaggt    1680
```

```
cgatgtgtca aagatctcct tattaacttg tggattgatt tattgaaatg tatgctggtg    1740
gaattggacc tttggaaaat taaatcaact accccaagca tagaggagta cttgtctatc    1800
gcatgtgtaa ctacaggtgt taaatgttta attctcatat cactacatct tcttggacca    1860
aaactgtcca aggatgtcac agaaagttct gaggtcagtg ccttatggaa ttgtacagct    1920
gttgtggccc gattgaataa tgatatacat agttacaaga gagaacaagc agaaagttca    1980
acaaatatgg tagcaatatt aatatcacag agtcagagaa ctatctctga agaaggct      2040 ataagacaga taaagaaat gatggaaagt aagagaagag agttgctagg gatggttcta     2100
caaaataaag aaagccaatt gccgcaagtg tgcaaagatc ttttttggac gacattcaaa    2160
gcagcttatt ctatatatac acatggcgat gagtatcgct tcccacagga attgaagaac    2220
catataaacg atgtaattta caaaccactc aatcaatatt ccccataa                 2268
```

<210> SEQ ID NO 40
<211> LENGTH: 755
<212> TYPE: PRT
<213> ORGANISM: Nicotiana glutinosa
<220> FEATURE:
<223> OTHER INFORMATION: NgSPP S3F2-3

<400> SEQUENCE: 40

```
Met Ser His Ser Thr Ala Ser Ser Leu Glu Glu Ala Lys Glu Arg Ile
 1               5                  10                  15

Arg Glu Thr Phe Gly Lys Asn Glu Leu Ser Ser Ser Tyr Asp Thr
                20                  25                  30

Ala Trp Val Ala Met Val Pro Ser Arg Tyr Ser Met Asn Gln Pro Cys
            35                  40                  45

Phe Pro Arg Cys Leu Asp Trp Ile Leu Glu Asn Gln Arg Glu Asp Gly
        50                  55                  60

Ser Trp Gly Leu Asn Pro Ser Leu Pro Leu Leu Val Lys Asp Ser Leu
65                  70                  75                  80

Ser Ser Thr Leu Ala Cys Leu Leu Ala Leu Arg Lys Trp Arg Ile Gly
                85                  90                  95

Asp Asn Gln Val Gln Arg Gly Leu Gly Phe Ile Glu Thr His Gly Trp
            100                 105                 110

Ala Val Asp Asn Val Asp Gln Ile Ser Pro Leu Gly Phe Asp Ile Ile
        115                 120                 125

Phe Pro Ser Met Ile Lys Tyr Ala Glu Lys Leu Asn Leu Asp Leu Pro
    130                 135                 140

Phe Asp Pro Asn Leu Val Asn Met Met Leu Arg Glu Arg Glu Leu Thr
145                 150                 155                 160

Ile Glu Arg Ala Leu Lys Asn Glu Phe Glu Gly Asn Met Ala Asn Val
                165                 170                 175

Glu Tyr Phe Ala Glu Gly Leu Gly Glu Leu Cys His Trp Lys Glu Ile
            180                 185                 190

Met Leu His Gln Arg Arg Asn Gly Ser Pro Phe Asp Ser Pro Ala Thr
        195                 200                 205

Thr Ala Ala Ala Leu Ile Tyr His Gln His Asp Glu Lys Cys Phe Gly
    210                 215                 220

Tyr Leu Ser Ser Ile Leu Lys Leu His Glu Asn Trp Val Pro Thr Ile
225                 230                 235                 240

Tyr Pro Thr Lys Val His Ser Asn Leu Phe Phe Val Asp Ala Leu Gln
                245                 250                 255

Asn Leu Gly Val Asp Arg Tyr Phe Lys Thr Glu Leu Lys Ser Val Leu
```

```
                260                 265                 270
Asp Glu Ile Tyr Arg Leu Trp Leu Glu Lys Asn Glu Glu Ile Phe Ser
            275                 280                 285

Asp Ile Ala His Cys Ala Met Ala Phe Arg Leu Leu Arg Met Asn Asn
        290                 295                 300

Tyr Glu Val Ser Ser Glu Leu Glu Gly Phe Val Asp Gln Glu His
305                 310                 315                 320

Phe Phe Thr Thr Ser Gly Gly Lys Leu Ile Ser His Val Ala Ile Leu
                325                 330                 335

Glu Leu His Arg Ala Ser Gln Val Asp Ile Gln Glu Gly Lys Asp Leu
            340                 345                 350

Ile Leu Asp Lys Ile Ser Thr Trp Thr Arg Asn Phe Met Glu Gln Glu
        355                 360                 365

Leu Leu Asp Asn Gln Ile Leu Asp Arg Ser Lys Lys Glu Met Glu Phe
    370                 375                 380

Ala Met Arg Lys Phe Tyr Gly Thr Phe Asp Arg Val Glu Thr Arg Arg
385                 390                 395                 400

Tyr Ile Glu Ser Tyr Lys Met Asp Ser Phe Lys Ile Leu Lys Ala Ala
                405                 410                 415

Tyr Arg Ser Ser Asn Ile Asn Asn Ile Asp Leu Leu Lys Phe Ser Glu
            420                 425                 430

His Asp Phe Asn Leu Cys Gln Ala Arg His Lys Glu Glu Leu Gln Gln
        435                 440                 445

Ile Lys Arg Trp Phe Ala Asp Cys Lys Leu Glu Gln Val Gly Ser Ser
    450                 455                 460

Gln Asn Tyr Leu Tyr Thr Ser Tyr Phe Pro Ile Ala Ala Ile Leu Phe
465                 470                 475                 480

Glu Pro Glu Tyr Gly Asp Ala Arg Leu Ala Phe Ala Lys Cys Gly Ile
                485                 490                 495

Ile Ala Thr Thr Val Asp Asp Phe Phe Asp Gly Phe Ala Cys Asn Glu
            500                 505                 510

Glu Leu Gln Asn Ile Ile Glu Leu Val Glu Arg Trp Asp Gly Tyr Pro
        515                 520                 525

Thr Val Gly Phe Arg Ser Glu Arg Val Arg Ile Phe Phe Leu Ala Leu
    530                 535                 540

Tyr Lys Met Ile Glu Glu Ile Ala Ala Lys Ala Glu Thr Lys Gln Gly
545                 550                 555                 560

Arg Cys Val Lys Asp Leu Leu Ile Asn Leu Trp Ile Asp Leu Leu Lys
                565                 570                 575

Cys Met Leu Val Glu Leu Asp Leu Trp Lys Ile Lys Ser Thr Thr Pro
            580                 585                 590

Ser Ile Glu Glu Tyr Leu Ser Ile Ala Cys Val Thr Thr Gly Val Lys
        595                 600                 605

Cys Leu Ile Leu Ile Ser Leu His Leu Gly Pro Lys Leu Ser Lys
    610                 615                 620

Asp Val Thr Glu Ser Ser Glu Val Ser Ala Leu Trp Asn Cys Thr Ala
625                 630                 635                 640

Val Val Ala Arg Leu Asn Asn Asp Ile His Ser Tyr Lys Arg Glu Gln
                645                 650                 655

Ala Glu Ser Ser Thr Asn Met Val Ala Ile Leu Ile Ser Gln Ser Gln
            660                 665                 670

Arg Thr Ile Ser Glu Glu Glu Ala Ile Arg Gln Ile Lys Glu Met Met
        675                 680                 685
```

```
Glu Ser Lys Arg Arg Glu Leu Leu Gly Met Val Leu Gln Asn Lys Glu
        690                 695                 700

Ser Gln Leu Pro Gln Val Cys Lys Asp Leu Phe Trp Thr Thr Phe Lys
705                 710                 715                 720

Ala Ala Tyr Ser Ile Tyr Thr His Gly Asp Glu Tyr Arg Phe Pro Gln
                725                 730                 735

Glu Leu Lys Asn His Ile Asn Asp Val Ile Tyr Lys Pro Leu Asn Gln
            740                 745                 750

Tyr Ser Pro
        755

<210> SEQ ID NO 41
<211> LENGTH: 6
<212> TYPE: PRT
<213> ORGANISM: Artificial Sequence
<220> FEATURE:
<223> OTHER INFORMATION: Class I Synthase motif

<400> SEQUENCE: 41

Asp Asp Phe Phe Asp Val
1               5

<210> SEQ ID NO 42
<211> LENGTH: 5
<212> TYPE: PRT
<213> ORGANISM: Artificial Sequence
<220> FEATURE:
<223> OTHER INFORMATION: Class I Synthase motif
<220> FEATURE:
<221> NAME/KEY: VARIANT
<222> LOCATION: 2
<223> OTHER INFORMATION: Xaa = Met or Leu

<400> SEQUENCE: 42

Ala Xaa Ala Phe Arg
1               5

<210> SEQ ID NO 43
<211> LENGTH: 55
<212> TYPE: PRT
<213> ORGANISM: Artificial Sequence
<220> FEATURE:
<223> OTHER INFORMATION: Chloroplast transit sequence

<400> SEQUENCE: 43

Met Gln Val Lys Ile Thr Ser Ser His Arg Leu Phe Cys His Phe His
1               5                   10                  15

Gln Leu Lys Ser Ala Thr Ser Leu Ser Ala Gln Lys Thr Glu Phe Arg
            20                  25                  30

Lys Tyr Gly Pro Gly Asn Ser Leu Phe Gln Thr Glu Gly Ser Leu Leu
        35                  40                  45

Tyr Lys Pro Val Arg Leu Asn
    50                  55

<210> SEQ ID NO 44
<211> LENGTH: 38
<212> TYPE: PRT
<213> ORGANISM: Artificial Sequence
<220> FEATURE:
<223> OTHER INFORMATION: Chloroplast transit sequence

<400> SEQUENCE: 44

Met Ile Leu Gly Leu Arg Ser Thr Ile Ile Pro Leu Pro Asp His Lys
```

```
            1               5                    10                  15
Leu Gly Asn Ile Lys Leu Gly Ser Val Thr Lys Asp Ser Asn Phe His
                    20                  25                  30

Arg Pro Ser Arg Val Arg
            35

<210> SEQ ID NO 45
<211> LENGTH: 808
<212> TYPE: PRT
<213> ORGANISM: Cistus creticus
<220> FEATURE:
<223> OTHER INFORMATION: Copal-8-ol diphosphate synthase
<300> PUBLICATION INFORMATION:
<308> DATABASE ACCESSION NUMBER: Genbank ADJ93862
<309> DATABASE ENTRY DATE: 2010-06-30

<400> SEQUENCE: 45

Met Ala Phe Thr Phe Thr Ser Ala His Leu Phe Leu Pro Val Thr Glu
 1               5                  10                  15

Asn His Ser Val His Val Asn Tyr Ser Ile Pro Pro Gly Asn Trp Arg
                20                  25                  30

Leu Trp Ser Thr Ala Lys Gly Gly Ser Asn Lys Leu Asp Ile Arg Arg
            35                  40                  45

Leu Arg Cys Ser Ala Arg Arg Thr Pro Glu Pro Leu Ala Gln Gly Ser
    50                  55                  60

Asn Gly Gly Arg Asp Gly Val Glu Ala Ile Gln Arg Leu Gln Thr Ile
65                  70                  75                  80

Ala Asp Asp Lys Ile Asp Gly Ala Asn Glu Leu Gly Ile Val Val
                85                  90                  95

Trp Asp Leu Ile Arg Asp Gly Val Asp Ala Val Lys Ser Met Phe Asp
            100                 105                 110

Ser Met Gly Asp Gly Asp Ile Ser Ile Ser Ala Tyr Asp Thr Ala Trp
        115                 120                 125

Val Ala Leu Val Lys Asp Val Asn Gly Ser Gly Gly Pro Gln Phe Pro
    130                 135                 140

Ser Ser Leu Gln Trp Ile Val Asp Asn Gln Leu Pro Asp Gly Ser Trp
145                 150                 155                 160

Gly Asp Ser Glu Val Phe Ser Ala Tyr Asp Arg Leu Leu Lys Thr Leu
                165                 170                 175

Ala Cys Val Val Ala Leu Lys Ser Trp Asn Ile Arg Pro Asp Lys Cys
            180                 185                 190

Gln Lys Gly Leu Lys Phe Phe Arg Asp Asn Ile Ser Lys Leu Glu Lys
        195                 200                 205

Glu Asn Val Glu Ala Ser Ala Gln Met Leu Ser Gly Phe Glu Val Val
    210                 215                 220

Phe Leu Ser Leu Ile Glu Val Ala Arg Arg Leu Asp Ile Gln Ile Pro
225                 230                 235                 240

Leu His Ser Pro Val Phe Glu Asp Leu Ile Ala Arg Arg Asn Leu Lys
                245                 250                 255

Phe Ala Lys Ile Pro Leu Asp Leu Met His Asn Val Pro Thr Ser Leu
            260                 265                 270

Leu Asn Ser Leu Glu Gly Met Thr Gly Val Glu Leu Asp Trp Glu Lys
        275                 280                 285

Leu Leu Lys Leu Gln Ser Gln Asp Gly Ser Phe Ile Thr Ser Pro Ser
    290                 295                 300

Ser Thr Ala Phe Ala Leu Met Gln Thr Asn Asp Thr Lys Cys Leu Gly
```

```
            305                 310                 315                 320
Tyr Leu Lys Phe Val Val Gln Lys Phe Asn Gly Gly Ala Pro Gly Gln
                    325                 330                 335
Tyr Pro Val Glu Ile Phe Glu Arg Ile Trp Val Val Asp Arg Leu Gln
                    340                 345                 350
Arg Leu Gly Ile Ser Arg Tyr Phe Gln Leu Glu Ile Lys Glu Cys Cys
                    355                 360                 365
Leu Asp Tyr Ala Phe Lys His Trp Thr Gln Tyr Gly Ser Ser Trp Ala
        370                 375                 380
Arg Asn Thr Pro Val Tyr Asp Leu Asp Asp Thr Cys Met Ala Phe Arg
385                 390                 395                 400
Ile Leu Arg Leu His Gly Tyr Asp Val Ser Ala Glu Ala Phe Arg His
                    405                 410                 415
Phe Glu Lys Asn Gly Val Phe Phe Cys Phe Gly Trp Glu Thr Thr Gln
                    420                 425                 430
Ser Val Thr Val Asn Phe Asn Leu Tyr Arg Ala Thr Gln Val Ala Phe
                    435                 440                 445
Pro Gly Glu Asn Ile Leu Lys Glu Ala Lys Gln Phe Ser Phe Asn Phe
        450                 455                 460
Leu Met Lys Lys Gln Ala Ala Arg Glu Phe Gln Asp Lys Trp Val Ile
465                 470                 475                 480
Leu Lys Asp Phe Pro Gly Glu Leu Lys Tyr Ala Leu Glu Phe Pro Trp
                    485                 490                 495
Tyr Ala Ser Leu Pro Arg Val Glu Thr Arg Phe Tyr Val Glu Gln Tyr
                    500                 505                 510
Gly Gly Asp Asn Asp Val Trp Ile Gly Lys Thr Leu Tyr Arg Met Pro
                    515                 520                 525
Tyr Ile Asn Asn Asn Val Tyr Leu Glu Leu Ala Lys Leu Asp Phe Asn
                    530                 535                 540
Asn Cys Gln Ala Leu His Arg Lys Glu Trp Glu Thr Met Gln Lys Trp
545                 550                 555                 560
Phe Met Glu Ser Lys Leu Asp Glu Phe Gly Val Ser Ser Lys Thr Leu
                    565                 570                 575
Leu Glu Ser Tyr Phe Leu Ala Ala Ala Ser Ile Phe Glu Pro Glu Arg
                    580                 585                 590
Ser Thr Glu Arg Leu Ala Trp Ala Lys Thr Ala Phe Leu Met Glu Thr
                    595                 600                 605
Ile Gly Ser Tyr Phe Asp Asp Glu Met Asn Ser Lys Asp Leu Arg Lys
        610                 615                 620
Ala Phe Val Gln Glu Phe Lys Asn Ile Tyr Glu Arg Arg Met Glu Ala
625                 630                 635                 640
Lys Gly Thr Lys Trp Asn Leu Ile Ile Ile Leu Leu Thr Thr Leu Asn
                    645                 650                 655
His Leu Thr Glu Val Cys Gly Arg Asp Ile Asn Ser Tyr Leu Cys His
                    660                 665                 670
Ser Trp Glu Lys Trp Met Met Met Trp Glu Pro Glu Gly Asp Arg Tyr
                    675                 680                 685
Lys Gly Ala Ala Glu Leu Leu Ser Asn Ser Ile Asn Leu Ser Ser Gly
                    690                 695                 700
Arg Leu Phe Ser Asn Asp Thr Leu Ser His Pro Asn Tyr Glu Lys Leu
705                 710                 715                 720
Val Thr Leu Ser Asn Lys Leu Cys His Gln Leu Gly Asn Ser Arg Arg
                    725                 730                 735
```

-continued

```
Gly Asn His Asn Glu Asp Ser Asp Ile Lys Asp Thr Lys Ile Glu Ile
            740                 745                 750

Ala Met Gln Glu Leu Val Gln Leu Val His Gln Asn Ser Ser Asp Asp
            755                 760                 765

Ile Ser Met Asp Leu Lys Gln Thr Phe Phe Ala Val Val Arg Ser Phe
770                 775                 780

Tyr Tyr Ala Ala His Cys Asp Arg Gly Thr Ile Asn Ser His Ile Val
785                 790                 795                 800

Lys Val Leu Phe Glu Ser Val Val
            805

<210> SEQ ID NO 46
<211> LENGTH: 759
<212> TYPE: PRT
<213> ORGANISM: Nicotiana tabacum
<220> FEATURE:
<223> OTHER INFORMATION: Terpenoid cyclase
<300> PUBLICATION INFORMATION:
<308> DATABASE ACCESSION NUMBER: Genbank AAS98912
<309> DATABASE ENTRY DATE: 2005-02-01

<400> SEQUENCE: 46

Met Glu Glu Ala Lys Glu Arg Ile Arg Glu Thr Phe Gly Lys Ile Glu
1               5                   10                  15

Leu Ser Pro Ser Ser Tyr Asp Thr Ala Trp Val Ala Met Val Pro Ser
            20                  25                  30

Arg Tyr Ser Met Asn Gln Pro Cys Phe Pro Gln Cys Leu Asp Trp Ile
        35                  40                  45

Leu Glu Asn Gln Arg Glu Asp Gly Ser Trp Gly Leu Asn Pro Ser His
    50                  55                  60

Pro Leu Leu Val Lys Asp Ser Leu Ser Ser Thr Leu Ala Ser Leu Leu
65                  70                  75                  80

Ala Leu Arg Lys Trp Arg Ile Gly Asp Asn Gln Val Gln Arg Gly Leu
                85                  90                  95

Gly Phe Ile Glu Thr His Gly Trp Ala Val Asp Asn Lys Asp Gln Ile
            100                 105                 110

Ser Pro Leu Gly Phe Glu Ile Ile Phe Pro Cys Met Thr Asn Tyr Ala
        115                 120                 125

Glu Lys Leu Asn Leu Asp Leu Pro Leu Asp Pro Asn Leu Val Asn Met
    130                 135                 140

Met Leu Cys Glu Arg Glu Leu Thr Ile Glu Arg Ala Leu Lys Asn Glu
145                 150                 155                 160

Phe Glu Gly Asn Met Ala Asn Val Glu Tyr Phe Ala Glu Gly Leu Gly
                165                 170                 175

Glu Ser Cys His Trp Lys Glu Met Met Leu Arg Gln Arg His Asn Gly
            180                 185                 190

Ser Leu Phe Asp Ser Pro Ala Thr Thr Ala Ala Leu Ile Tyr His
        195                 200                 205

Gln Tyr Asp Glu Lys Cys Phe Gly Tyr Leu Asn Ser Ile Leu Lys Leu
    210                 215                 220

His Asp Asn Trp Val His Thr Ile Cys Pro Thr Lys Ile His Ser Asn
225                 230                 235                 240

Leu Phe Leu Val Asp Ala Leu Gln Asn Leu Gly Val Asp Arg Tyr Phe
                245                 250                 255

Lys Thr Glu Val Lys Arg Val Leu Asp Glu Ile Tyr Arg Leu Trp Leu
            260                 265                 270
```

-continued

```
Glu Lys Asn Glu Glu Ile Phe Ser Asp Val Ala His Cys Ala Met Ala
        275                 280                 285

Phe Arg Leu Leu Arg Met Asn Asn Tyr Glu Val Ser Ser Glu Glu Leu
290                 295                 300

Glu Gly Phe Val Asp Gln Glu His Phe Phe Thr Thr Ser Ser Gly Lys
305                 310                 315                 320

Leu Met Asn His Val Ala Ile Leu Glu Leu His Arg Ala Ser Gln Val
                325                 330                 335

Ala Ile His Glu Arg Lys Asp His Ile Leu Asp Lys Ile Ser Thr Trp
                340                 345                 350

Thr Arg Asn Phe Met Glu Gln Lys Leu Leu Asp Lys His Ile Pro Asp
                355                 360                 365

Arg Ser Lys Lys Glu Met Glu Phe Ala Met Arg Lys Phe Tyr Gly Thr
        370                 375                 380

Phe Asp Arg Val Glu Thr Arg Tyr Ile Glu Ser Tyr Lys Met Asp
385                 390                 395                 400

Ser Phe Lys Ile Leu Lys Ala Ala Tyr Arg Ser Ser Gly Ile Asn Asn
                405                 410                 415

Ile Asp Leu Leu Lys Phe Ser Glu His Asp Phe Asn Leu Cys Gln Thr
                420                 425                 430

Arg His Lys Glu Glu Leu Gln Gln Met Lys Arg Trp Phe Thr Asp Cys
        435                 440                 445

Lys Leu Glu Gln Val Gly Leu Ser Gln Gln Tyr Leu Tyr Thr Ser Tyr
        450                 455                 460

Phe Ile Ile Ala Ala Ile Leu Phe Glu Pro Glu Tyr Ala Asp Ala Arg
465                 470                 475                 480

Leu Ala Tyr Ala Lys Tyr Ala Ile Ile Thr Ala Val Asp Asp Phe
                485                 490                 495

Phe Asp Cys Phe Ile Cys Lys Glu Glu Leu Gln Asn Ile Ile Glu Leu
                500                 505                 510

Val Glu Arg Trp Glu Gly Tyr Ser Thr Val Gly Phe Arg Ser Glu Arg
        515                 520                 525

Val Arg Ile Phe Phe Leu Ala Leu Tyr Lys Met Val Glu Glu Ile Ala
        530                 535                 540

Ala Lys Ala Glu Thr Lys Gln Gly Arg Cys Val Lys Asp His Leu Ile
545                 550                 555                 560

Asn Leu Trp Ile Asp Met Leu Lys Cys Met Leu Val Glu Leu Asp Leu
                565                 570                 575

Trp Lys Ile Lys Ser Thr Thr Pro Ser Ile Glu Glu Tyr Leu Ser Val
                580                 585                 590

Ala Cys Val Thr Ile Gly Val Pro Cys Phe Val Leu Thr Ser Leu Tyr
                595                 600                 605

Leu Leu Gly Pro Lys Leu Ser Lys Asp Val Ile Glu Ser Ser Glu Val
        610                 615                 620

Ser Ala Leu Cys Asn Cys Thr Ala Ala Val Ala Arg Leu Ile Asn Asp
625                 630                 635                 640

Ile His Ser Tyr Lys Arg Glu Gln Ala Glu Ser Ser Thr Asn Met Val
                645                 650                 655

Ser Ile Leu Ile Thr Gln Ser Gln Gly Thr Ile Ser Glu Glu Glu Ala
                660                 665                 670

Ile Arg Gln Ile Lys Glu Met Met Glu Ser Lys Arg Arg Glu Leu Leu
                675                 680                 685
```

```
Gly Met Val Leu Gln Asn Lys Glu Ser Gln Leu Pro Gln Val Cys Lys
            690                 695                 700
Asp Leu Phe Trp Thr Thr Ile Asn Ala Ala Tyr Ser Ile His Thr
705                 710                 715                 720
His Gly Arg Trp Val Ser Leu Pro Arg Gly Ile Gln Glu Pro Tyr Gln
                725                 730                 735
Arg Cys Asn Leu Gln Thr Thr Gln Ser Ile Phe Pro Ile Ile Cys Leu
            740                 745                 750
Lys Ser Phe Thr Ile Cys Tyr
            755
```

<210> SEQ ID NO 47
<211> LENGTH: 778
<212> TYPE: PRT
<213> ORGANISM: Artificial Sequence
<220> FEATURE:
<223> OTHER INFORMATION: Terpene synthase
<300> PUBLICATION INFORMATION:
<308> DATABASE ACCESSION NUMBER: Genbank ACO56896
<309> DATABASE ENTRY DATE: 2009-07-08

<400> SEQUENCE: 47

```
Met Ile Val Gly Tyr Arg Ser Thr Ile Ile Thr Leu Ser His Pro Lys
1               5                   10                  15
Leu Gly Asn Gly Lys Thr Ile Ser Ser Asn Ala Ile Phe Gln Arg Ser
            20                  25                  30
Cys Arg Val Arg Cys Ser His Ser Thr Thr Ser Ser Met Asn Gly Phe
        35                  40                  45
Glu Asp Ala Arg Asp Arg Ile Arg Glu Ser Phe Gly Lys Leu Glu Leu
50                  55                  60
Ser Pro Ser Ser Tyr Asp Thr Ala Trp Val Ala Met Val Pro Ser Arg
65                  70                  75                  80
His Ser Leu Asn Glu Pro Cys Phe Pro Gln Cys Leu Asp Trp Ile Ile
                85                  90                  95
Glu Asn Gln Arg Glu Asp Gly Ser Trp Gly Leu Asn Pro Thr His Pro
            100                 105                 110
Leu Leu Leu Lys Asp Ser Leu Ser Ser Thr Leu Ala Cys Leu Leu Ala
        115                 120                 125
Leu Thr Lys Trp Arg Val Gly Asp Glu Gln Ile Lys Arg Gly Leu Gly
130                 135                 140
Phe Ile Glu Thr Tyr Gly Trp Ala Val Asp Asn Lys Asp Gln Ile Ser
145                 150                 155                 160
Pro Leu Gly Phe Glu Val Ile Phe Ser Ser Met Ile Lys Ser Ala Glu
                165                 170                 175
Lys Leu Asp Leu Asn Leu Pro Leu Asn Leu His Leu Val Asn Leu Val
            180                 185                 190
Lys Cys Lys Arg Asp Ser Thr Ile Lys Arg Asn Val Glu Tyr Met Gly
        195                 200                 205
Glu Gly Val Gly Glu Leu Cys Asp Trp Lys Glu Met Ile Lys Leu His
210                 215                 220
Gln Arg Gln Asn Gly Ser Leu Phe Asp Ser Pro Ala Thr Thr Ala Ala
225                 230                 235                 240
Ala Leu Ile Tyr His Gln His Asp Gln Lys Cys Tyr Gln Tyr Leu Asn
                245                 250                 255
Ser Ile Phe Gln Gln His Lys Asn Trp Val Pro Thr Met Tyr Pro Thr
            260                 265                 270
```

```
Lys Val His Ser Leu Leu Cys Leu Val Asp Thr Leu Gln Asn Leu Gly
            275                 280                 285

Val His Arg His Phe Lys Ser Glu Ile Lys Lys Ala Leu Asp Glu Ile
    290                 295                 300

Tyr Arg Leu Trp Gln Gln Lys Asn Glu Gln Ile Phe Ser Asn Val Thr
305                 310                 315                 320

His Cys Ala Met Ala Phe Arg Leu Leu Arg Met Ser Tyr Tyr Asp Val
                325                 330                 335

Ser Ser Asp Glu Leu Ala Glu Phe Val Asp Glu His Phe Phe Ala
            340                 345                 350

Thr Asn Gly Lys Tyr Lys Ser His Val Glu Ile Leu Glu Leu His Lys
            355                 360                 365

Ala Ser Gln Leu Ala Ile Asp His Glu Lys Asp Asp Ile Leu Asp Lys
370                 375                 380

Ile Asn Asn Trp Thr Arg Ala Phe Met Glu Gln Lys Leu Leu Asn Asn
385                 390                 395                 400

Gly Phe Ile Asp Arg Met Ser Lys Lys Glu Val Glu Leu Ala Leu Arg
                405                 410                 415

Lys Phe Tyr Thr Thr Ser His Leu Ala Glu Asn Arg Arg Tyr Ile Lys
                420                 425                 430

Ser Tyr Glu Glu Asn Asn Phe Lys Ile Leu Lys Ala Ala Tyr Arg Ser
            435                 440                 445

Pro Asn Ile Asn Asn Lys Asp Leu Leu Ala Phe Ser Ile His Asp Phe
            450                 455                 460

Glu Leu Cys Gln Ala Gln His Arg Glu Leu Gln Gln Leu Lys Arg
465                 470                 475                 480

Trp Phe Glu Asp Tyr Arg Leu Asp Gln Leu Gly Leu Ala Glu Arg Tyr
                485                 490                 495

Ile His Ala Ser Tyr Leu Phe Gly Val Thr Val Ile Pro Glu Pro Glu
            500                 505                 510

Leu Ser Asp Ala Arg Leu Met Tyr Ala Lys Tyr Val Met Leu Leu Thr
            515                 520                 525

Ile Val Asp Asp His Phe Glu Ser Phe Ala Ser Lys Asp Glu Cys Phe
530                 535                 540

Asn Ile Ile Glu Leu Val Glu Arg Trp Asp Asp Tyr Ala Ser Val Gly
545                 550                 555                 560

Tyr Lys Ser Glu Lys Val Lys Val Phe Phe Ser Val Phe Tyr Lys Ser
                565                 570                 575

Ile Glu Glu Leu Ala Thr Ile Ala Glu Ile Lys Gln Gly Arg Ser Val
            580                 585                 590

Lys Asn His Leu Ile Asn Leu Trp Leu Glu Leu Met Lys Leu Met Leu
            595                 600                 605

Met Glu Arg Val Glu Trp Cys Ser Gly Lys Thr Ile Pro Ser Ile Glu
            610                 615                 620

Glu Tyr Leu Tyr Val Thr Ser Ile Thr Phe Cys Ala Lys Leu Ile Pro
625                 630                 635                 640

Leu Ser Thr Gln Tyr Phe Leu Gly Ile Lys Ile Ser Lys Asp Leu Leu
                645                 650                 655

Glu Ser Asp Glu Ile Cys Gly Leu Trp Asn Cys Ser Gly Arg Val Met
            660                 665                 670

Arg Ile Leu Asn Asp Leu Gln Asp Ser Lys Arg Glu Gln Lys Glu Val
            675                 680                 685

Ser Ile Asn Leu Val Thr Leu Leu Met Lys Ser Met Ser Glu Glu Glu
```

```
                    690              695              700
Ala Ile Met Lys Ile Lys Glu Ile Leu Glu Met Asn Arg Arg Glu Leu
705                 710                  715                  720

Leu Lys Met Val Leu Val Gln Lys Lys Gly Ser Gln Leu Pro Gln Leu
                    725                  730                  735

Cys Lys Asp Ile Phe Trp Arg Thr Ser Lys Trp Ala His Phe Thr Tyr
                740                  745                  750

Ser Gln Thr Asp Gly Tyr Arg Ile Ala Glu Glu Met Lys Asn His Ile
            755                  760                  765

Asp Glu Val Phe Tyr Lys Pro Leu Asn His
            770                  775

<210> SEQ ID NO 48
<211> LENGTH: 558
<212> TYPE: DNA
<213> ORGANISM: Artificial Sequence
<220> FEATURE:
<223> OTHER INFORMATION: 5' LPP partial sequence
<220> FEATURE:
<221> NAME/KEY: variation
<222> LOCATION: 505
<223> OTHER INFORMATION: n = a, c, g or t

<400> SEQUENCE: 48
atgcaggtta aaattacgtc cagtcacagg cttttctgcc attttcatca actcaagagt     60
gctacatcgt tatctgcaca gaaaactgag cttagaaaat atggacccgg aaattcgttg    120
ttccaaactg aaggctcact tctatataaa ccagttcgtc tcaattgcgc acctattgat    180
gcaagttatc ttggttatct gaatgagttg gaatctaatt tctcaaacaa ccccgaagaa    240
aaggatattc aggtaagcag aacaatacag atcaaaaatt tgacagaaga atcaaatgt    300 aagttgaatt cgatggagga tggaaggtca agtgtctcag cctatgacac agcttgggtt    360 tccttattc caaatactac taataatgga aatgatcaaa ggcctatgtt tccatcttgt    420
cttcaatgga ttatagacaa tcaactttgc gatggttcat ggggagagga gagtgtattc    480
tgcatatatg atcgactctt gaacncacta gcatgtgttg ttgcattgac attatggaac    540
acatgccttc ctaagaga                                                 558

<210> SEQ ID NO 49
<211> LENGTH: 186
<212> TYPE: PRT
<213> ORGANISM: Artificial Sequence
<220> FEATURE:
<223> OTHER INFORMATION: 5' LPP partial sequence
<220> FEATURE:
<221> NAME/KEY: VARIANT
<222> LOCATION: 169
<223> OTHER INFORMATION: Xaa = unknown

<400> SEQUENCE: 49

Met Gln Val Lys Ile Thr Ser Ser His Arg Leu Phe Cys His Phe His
1               5                   10                  15

Gln Leu Lys Ser Ala Thr Ser Leu Ser Ala Gln Lys Thr Glu Leu Arg
                20                  25                  30

Lys Tyr Gly Pro Gly Asn Ser Leu Phe Gln Thr Glu Gly Ser Leu Leu
            35                  40                  45

Tyr Lys Pro Val Arg Leu Asn Cys Ala Pro Ile Asp Ala Ser Tyr Leu
        50                  55                  60

Gly Tyr Leu Asn Glu Leu Glu Ser Asn Phe Ser Asn Asn Pro Glu Glu
65              70                  75                  80
```

```
Lys Asp Ile Gln Val Ser Arg Thr Ile Gln Ile Lys Asn Leu Thr Glu
                85                  90                  95

Glu Ile Lys Cys Lys Leu Asn Ser Met Glu Asp Gly Arg Ser Ser Val
            100                 105                 110

Ser Ala Tyr Asp Thr Ala Trp Val Ser Phe Ile Pro Asn Thr Thr Asn
        115                 120                 125

Asn Gly Asn Asp Gln Arg Pro Met Phe Pro Ser Cys Leu Gln Trp Ile
    130                 135                 140

Ile Asp Asn Gln Leu Cys Asp Gly Ser Trp Gly Glu Glu Ser Val Phe
145                 150                 155                 160

Cys Ile Tyr Asp Arg Leu Leu Asn Xaa Leu Ala Cys Val Val Ala Leu
                165                 170                 175

Thr Leu Trp Asn Thr Cys Leu Pro Lys Arg
                180                 185

<210> SEQ ID NO 50
<211> LENGTH: 1599
<212> TYPE: DNA
<213> ORGANISM: Artificial Sequence
<220> FEATURE:
<223> OTHER INFORMATION: 3' LPP partial sequence
<220> FEATURE:
<221> NAME/KEY: variation
<222> LOCATION: 1575
<223> OTHER INFORMATION: n = a, c, t or g

<400> SEQUENCE: 50
ggacgacctg gattggcaag gacttttaaa ttttcaaaat gctggatggt tcattcttat      60
cagcccctgc tttccactgc ctttgcattc atagaaaaca aaacgatgaa agtgtttgg     120 catatcttcc aaaatgttgt tcaaaagtct aatggaggag cgcgacacta cccactggac    180
ttgttaacac gactttgggc aattgatcga ttacaacgcc ttggaatatc ttattatttt    240
gcggaagagt tcaaggaact tttgaatcat gtgttcagat attgggacga ggagaatgga    300
attttcagtg aaggaattc aaacgtttgt gacgttgatg atacatgcat ggctattagg     360
ttgcttaggt tgcatgggta tgatgttagt ccagatgcgc taaacaattt cacagatggt    420
gatcaattct tttgccttag aggtgaagtg gacgggtcac caacacatat gtttaatctt    480
tatagatgtt cccaagtttt attcccagga gaaaagattc ttgaagaggc aaagaatttt    540
acttacaact tcttacagca atgtcttgca acaatcgat gcttagacaa atgggtcata     600
gctaaggaca ttcccgggga gataaggtat gcactgaaat ttccatggta tgcaagctta    660
cctcgggtgg aatctaggct atacatagaa cagtacggcg gagcaaatga tatttggatt    720
ggcaagacgt tatacaggat gcccgatgtc agcaacaatg tttatttaca agctgcaaaa    780
ttagattaca acagatgcca aagtcaacat cgatttgaat ggctaattat gcaacagtgg    840
tttgataagt gcaactttca acaatttgga ataagcaaaa agtacctcct agtttcttat    900
ttcttagctg ctgcaagtat atttgaagtc gaaaagtcaa gagaacgact tgcgtgggct    960
aaatctcgta atatgtaa gatgattaca tcttactaca tgaagaagc cacaacttgg     1020 accagtagga attcattgct aatggaattc aagggttctg atgatccaag cagaaaaaat   1080
ggtaatgaaa caaaagagat catagttctc aaaaatcttc gtcagttttt gcaccaacta   1140
tcagaagaaa ctttttgaaga cctaggcaaa gacatccatc accaactaca aaatgcatgg   1200
aaaacgtggt tggcgttctt aagggaggaa aaaaatacat gccaagaaga agcagagttg   1260
ctagtgcgca caattaatct ctccggcggc catatgatac atgatgagat actattcgat   1320
```

-continued

```
gcggactaca aaaatctgtc caaccttatt aataaagttt gctgcatgct tagtgagctc    1380
caaaatgaca aggtgactgg cagctcaaag aacactgaca ttgaactcaa catgcaagca    1440
cttgtaaagt tagtgtttgg taacacctca agcaacatca accaagacat taagcaaaca    1500
ttttttgcag ttgttaagac tttctattac agtgcacatg ttagtgagga aataatcaac    1560
tttcacatat ccaangtgct ttttcagcaa gtccagtaa                           1599
```

<210> SEQ ID NO 51
<211> LENGTH: 532
<212> TYPE: PRT
<213> ORGANISM: Artificial Sequence
<220> FEATURE:
<223> OTHER INFORMATION: 3' LPP partial sequence
<220> FEATURE:
<221> NAME/KEY: VARIANT
<222> LOCATION: 525
<223> OTHER INFORMATION: Xaa = unknown

<400> SEQUENCE: 51

```
Gly Arg Pro Gly Leu Ala Arg Thr Phe Lys Phe Ser Lys Cys Trp Met
  1               5                  10                  15

Val His Ser Tyr Gln Pro Leu Leu Ser Thr Ala Phe Ala Phe Ile Glu
             20                  25                  30

Asn Lys Thr Met Lys Ser Val Trp His Ile Phe Gln Asn Val Val Gln
         35                  40                  45

Lys Ser Asn Gly Gly Ala Arg His Tyr Pro Leu Asp Leu Leu Thr Arg
     50                  55                  60

Leu Trp Ala Ile Asp Arg Leu Gln Arg Leu Gly Ile Ser Tyr Tyr Phe
 65                  70                  75                  80

Ala Glu Glu Phe Lys Glu Leu Leu Asn His Val Phe Arg Tyr Trp Asp
                 85                  90                  95

Glu Glu Asn Gly Ile Phe Ser Gly Arg Asn Ser Asn Val Cys Asp Val
            100                 105                 110

Asp Asp Thr Cys Met Ala Ile Arg Leu Leu Arg Leu His Gly Tyr Asp
        115                 120                 125

Val Ser Pro Asp Ala Leu Asn Asn Phe Thr Asp Gly Asp Gln Phe Phe
    130                 135                 140

Cys Leu Arg Gly Glu Val Asp Gly Ser Pro Thr His Met Phe Asn Leu
145                 150                 155                 160

Tyr Arg Cys Ser Gln Val Leu Phe Pro Gly Glu Lys Ile Leu Glu Glu
                165                 170                 175

Ala Lys Asn Phe Thr Tyr Asn Phe Leu Gln Gln Cys Leu Ala Asn Asn
            180                 185                 190

Arg Cys Leu Asp Lys Trp Val Ile Ala Lys Asp Ile Pro Gly Glu Ile
        195                 200                 205

Arg Tyr Ala Leu Lys Phe Pro Trp Tyr Ala Ser Leu Pro Arg Val Glu
    210                 215                 220

Ser Arg Leu Tyr Ile Glu Gln Tyr Gly Gly Ala Asn Asp Ile Trp Ile
225                 230                 235                 240

Gly Lys Thr Leu Tyr Arg Met Pro Asp Val Ser Asn Asn Val Tyr Leu
                245                 250                 255

Gln Ala Ala Lys Leu Asp Tyr Asn Arg Cys Gln Ser Gln His Arg Phe
            260                 265                 270

Glu Trp Leu Ile Met Gln Gln Trp Phe Asp Lys Cys Asn Phe Gln Gln
        275                 280                 285
```

```
Phe Gly Ile Ser Lys Lys Tyr Leu Leu Val Ser Tyr Phe Leu Ala Ala
    290                 295                 300

Ala Ser Ile Phe Glu Val Glu Lys Ser Arg Glu Arg Leu Ala Trp Ala
305                 310                 315                 320

Lys Ser Arg Ile Ile Cys Lys Met Ile Thr Ser Tyr Tyr Asn Glu Glu
                325                 330                 335

Ala Thr Thr Trp Thr Ser Arg Asn Ser Leu Leu Met Glu Phe Lys Gly
                340                 345                 350

Ser Asp Asp Pro Ser Arg Lys Asn Gly Asn Glu Thr Lys Glu Ile Ile
                355                 360                 365

Val Leu Lys Asn Leu Arg Gln Phe Leu His Gln Leu Ser Glu Glu Thr
    370                 375                 380

Phe Glu Asp Leu Gly Lys Asp Ile His His Gln Leu Gln Asn Ala Trp
385                 390                 395                 400

Lys Thr Trp Leu Ala Phe Leu Arg Glu Glu Lys Asn Thr Cys Gln Glu
                405                 410                 415

Glu Ala Glu Leu Leu Val Arg Thr Ile Asn Leu Ser Gly Gly His Met
                420                 425                 430

Ile His Asp Glu Ile Leu Phe Asp Ala Asp Tyr Lys Asn Leu Ser Asn
    435                 440                 445

Leu Ile Asn Lys Val Cys Cys Met Leu Ser Glu Leu Gln Asn Asp Lys
    450                 455                 460

Val Thr Gly Ser Ser Lys Asn Thr Asp Ile Glu Leu Asn Met Gln Ala
465                 470                 475                 480

Leu Val Lys Leu Val Phe Gly Asn Thr Ser Ser Asn Ile Asn Gln Asp
                485                 490                 495

Ile Lys Gln Thr Phe Phe Ala Val Val Lys Thr Phe Tyr Tyr Ser Ala
                500                 505                 510

His Val Ser Glu Glu Ile Ile Asn Phe His Ile Ser Xaa Val Leu Phe
            515                 520                 525

Gln Gln Val Gln
    530

<210> SEQ ID NO 52
<211> LENGTH: 3000
<212> TYPE: DNA
<213> ORGANISM: Artificial Sequence
<220> FEATURE:
<223> OTHER INFORMATION: pGEMT vector

<400> SEQUENCE: 52
gggcgaattg ggcccgacgt cgcatgctcc cggccgccat ggccgcggga tatcactagt      60
gcggccgcct gcaggtcgac catatgggag agctcccaac gcgttggatg catagcttga     120
gtattctata gtgtcaccta aatagcttgg cgtaatcatg gtcatagctg tttcctgtgt     180
gaaattgtta tccgctcaca attccacaca catacgagc cggaagcata agtgtaaag      240 cctggggtgc ctaatgagtg agctaactca cattaattgc gttgcgctca ctgcccgctt     300
tccagtcggg aaacctgtcg tgccagctgc attaatgaat cggccaacgc gcggggagag     360
gcggtttgcg tattgggcgc tcttccgctt cctcgctcac tgactcgctg cgctcggtcg     420
ttcggctgcg gcgagcggta tcagctcact caaaggcggt aatacggtta tccacagaat     480
caggggataa cgcaggaaag aacatgtgag caaaaggcca gcaaaaggcc aggaaccgta     540
aaaaggccgc gttgctggcg ttttccata ggctccgccc ccctgacgag catcacaaaa      600
atcgacgctc aagtcagagg tggcgaaacc cgacaggact ataaagatac caggcgtttc     660
```

```
ccctggaag ctccctcgtg cgctctcctg ttccgaccct gccgcttacc ggatacctgt    720
ccgcctttct cccttcggga agcgtggcgc tttctcatag ctcacgctgt aggtatctca    780
gttcggtgta ggtcgttcgc tccaagctgg gctgtgtgca cgaaccccc gttcagcccg    840
accgctgcgc cttatccggt aactatcgtc ttgagtccaa cccggtaaga cacgacttat    900
cgccactggc agcagccact ggtaacagga ttagcagagc gaggtatgta ggcggtgcta    960
cagagttctt gaagtggtgg cctaactacg gctacactag aagaacagta tttggtatct   1020
gcgctctgct gaagccagtt accttcggaa aaagagttgg tagctcttga tccggcaaac   1080
aaaccaccgc tggtagcggt ggttttttg tttgcaagca gcagattacg cgcagaaaaa   1140
aaggatctca agaagatcct ttgatctttt ctacgggtc tgacgctcag tggaacgaaa   1200
actcacgtta agggattttg gtcatgagat tatcaaaaag gatcttcacc tagatccttt   1260
taaattaaaa atgaagtttt aaatcaatct aaagtatata tgagtaaact tggtctgaca   1320
gttaccaatg cttaatcagt gaggcaccta tctcagcgat ctgtctattt cgttcatcca   1380
tagttgcctg actccccgtc gtgtagataa ctacgatacg ggagggctta ccatctggcc   1440
ccagtgctgc aatgataccg cgagacccac gctcaccggc tccagattta tcagcaataa   1500
accagccagc cggaagggcc gagcgcagaa gtggtcctgc aactttatcc gcctccatcc   1560
agtctattaa ttgttgccgg gaagctagag taagtagttc gccagttaat agtttgcgca   1620
acgttgttgc cattgctaca ggcatcgtgg tgtcacgctc gtcgtttggt atggcttcat   1680
tcagctccgg ttcccaacga tcaaggcgag ttacatgatc ccccatgttg tgcaaaaaag   1740
cggttagctc cttcggtcct ccgatcgttg tcagaagtaa gttggccgca gtgttatcac   1800
tcatggttat ggcagcactg cataattctc ttactgtcat gccatccgta agatgctttt   1860
ctgtgactgg tgagtactca accaagtcat tctgagaata gtgtatgcgg cgaccgagtt   1920
gctcttgccc ggcgtcaata cgggataata ccgcgccaca tagcagaact ttaaaagtgc   1980
tcatcattgg aaaacgttct cggggcgaaa actctcaag gatcttaccg ctgttgagat   2040
ccagttcgat gtaacccact cgtgcaccca actgatcttc agcatctttt actttcacca   2100
gcgtttctgg gtgagcaaaa acaggaaggc aaaatgccgc aaaaaaggga ataagggcga   2160
cacggaaatg ttgaatactc atactcttcc tttttcaata ttattgaagc atttatcagg   2220
gttattgtct catgagcgga tacatatttg aatgtattta gaaaaataaa caaatagggg   2280
ttccgcgcac atttccccga aaagtgccac ctgatgcggt gtgaaatacc gcacagatgc   2340
gtaaggagaa ataccgcat caggaaattg taagcgttaa tattttgtta aaattcgcgt   2400
taaattttg ttaaatcagc tcatttttta accataggc cgaaatcggc aaaatccctt   2460
ataaatcaaa agaatagacc gagatagggt tgagtgttgt tccagtttgg aacaagagtc   2520
cactattaaa gaacgtggac tccaacgtca agggcgaaa aaccgtctat cagggcgatg   2580
gcccactacg tgaaccatca ccctaatcaa gttttttggg gtcgaggtgc cgtaaagcac   2640
taaatcggaa ccctaaaggg agcccccgat ttagagcttg acggggaaag ccggcgaacg   2700
tggcgagaaa ggaagggaag aaagcgaaag gagcgggcgc tagggcgctg gcaagtgtag   2760
cggtcacgct gcgcgtaacc accacacccg ccgcgcttaa tgcgccgcta cagggcgcgt   2820
ccattcgcca ttcaggctgc gcaactgttg ggaagggcga tcggtgcggg cctcttcgct   2880
attacgccag ctggcgaaag ggggatgtgc tgcaaggcga ttaagttggg taacgccagg   2940
gttttcccag tcacgacgtt gtaaaacgac ggccagtgaa ttgtaatacg actcactata   3000
```

<210> SEQ ID NO 53
<211> LENGTH: 2406
<212> TYPE: DNA
<213> ORGANISM: Artificial Sequence
<220> FEATURE:
<223> OTHER INFORMATION: LPP Synthase consensus sequence

<400> SEQUENCE: 53

| | |
|---|---|
| atgcaggtta aaattacgtc cagtcacagg cttttctgcc attttcatca actcaagagt | 60 |
| gctacatcgt tatctgcaca gaaaactgag tttagaaaat atggacccgg aaattcgttg | 120 |
| ttccaaactg aaggctcact tctatataaa ccagttcgtc tcaattgcgc acctattgat | 180 |
| gcaagttatc ttggttatct gaatgagttg gaatctaatt tctcaaacaa ccccgaagaa | 240 |
| aaggatattc aggtaagcag aacaatacag atcaaaaatt tgacagaaga atcaaatgt | 300 |
| aagttgaatt cgatggagga tggaaggtca agtgtctcag cctatgacac agcttgggtt | 360 |
| tcctttattc caaatactac taataatgga aatgatcaaa ggcctatgtt tccatcttgt | 420 |
| cttcaatgga ttatagacaa tcaactttgc gatggttcat gggagagga gagtgtattc | 480 |
| tgcatatatg atcgactctt gaacacacta gcatgtgttg ttgcattgac attatggaac | 540 |
| acatgccttc ctaagagaaa caaggtgtg atgtttatca agaaaaactt aattaagtta | 600 |
| gagacagggg aagttgaaca catgacttgt ggatttgaat tgtgtttcc tgctctcctt | 660 |
| gagaaagctc aacaattaaa tattgacatt ccgtatgatg ctccagtctt aaaggatatt | 720 |
| tatgcaagga gaagtaaa gtttacaaga attcctaaag agattgtcca tacgattccg | 780 |
| acaacagcat tgctttcatt agaaggatta agggacgacc tggattggca aagacttta | 840 |
| aattttcaaa tgcctgatgg ttcattctta tcagcccctg cttccactgc ctttgcattc | 900 |
| atgaaaacaa acgatgaaaa gtgtttggca tatcttcaaa atgttgttca aaagtctaat | 960 |
| ggaggagcgc gacactaccc actggacttg ttaacacgac tttgggcaat tgatcgatta | 1020 |
| caacgccttg gaatatctta ttattttgcg gaagagttca aggaactttt gaatcatgtg | 1080 |
| ttcagatatt gggacgagga gaatggaatt ttcagtggaa ggaattcaaa cgtttgtgac | 1140 |
| gttgatgata catgcatggc tattaggttg cttaggttgc atgggtatga tgttagtcca | 1200 |
| gatgcgctaa acaatttcac agatggtgat caattctttt gccttagagg tgaagtggac | 1260 |
| gggtcaccaa cacatatgtt taatctttat agatgttccc aagttttatt cccaggagaa | 1320 |
| aagattcttg aagaggcaaa gaattttact tacaacttct tacagcaatg tcttgcaaac | 1380 |
| aatcgatgct tagacaaatg ggtcatagct aaggacattc ccggggagat aaggtatgca | 1440 |
| ctgaaatttc catggtatgc aagcttacct cgggtggaat ctaggctata catagaacag | 1500 |
| tacggcggag caaatgatat ttggattggc aagacattat acaggatgcc cgatgtcagc | 1560 |
| aacaatgttt atttacaagc tgcaaaatta gattacaaca gatgccaaag tcaacatcga | 1620 |
| tttgaatggc taattatgca acagtggttt gataagtgca actttcaaca atttggaata | 1680 |
| agcaaaaagt acctcctagt ttcttatttc ttagctgctg caagtatatt tgaagtcgaa | 1740 |
| aagtcaagag aacgacttgc gtgggctaaa tctcgtataa tatgtaagat gattacatct | 1800 |
| tactacaatg aagaagccac aacttggacc agtaggaatt cattgctaat ggaattcaag | 1860 |
| ggttctgatg atccaagcag aaaaaatggt aatgaaacaa aagagatcat agttctcaaa | 1920 |
| aatcttcgtc agttttttgca ccaactatca gaagaaactt tgaagaccct aggcaaagac | 1980 |
| atccatcacc aactacaaaa tgcatggaaa acgtggttgg cgttcttaag ggaggaaaaa | 2040 |
| aatacatgcc aagaagaagc agagttgcta gtgcgcacaa ttaatctctc cggcggccat | 2100 |

```
atgatacatg atgagatact attcgatgcg gactacaaaa atctgtccaa ccttactaat    2160
aaagtttgct gcatgcttag tgagctccaa aatgacaagg tgactggcag ctcaaagaac    2220
actgacattg aactcaacat gcaagcactt gtaaagttag tgtttggtaa cacctcaagc    2280
aacatcaacc aagacattaa gcaaacattt tttgcagttg ttaagacttt ctattacagt    2340
gcacatgtta gtgaggaaat aatcaacttt cacatatcca aggtgctttt tcagcaagtc    2400
cagtaa                                                               2406
```

```
<210> SEQ ID NO 54
<211> LENGTH: 801
<212> TYPE: PRT
<213> ORGANISM: Artificial Sequence
<220> FEATURE:
<223> OTHER INFORMATION: LPP Synthase consensus sequence

<400> SEQUENCE: 54
```

Met Gln Val Lys Ile Thr Ser Ser His Arg Leu Phe Cys His Phe His
1               5                   10                  15

Gln Leu Lys Ser Ala Thr Ser Leu Ser Ala Gln Lys Thr Glu Leu Arg
            20                  25                  30

Lys Tyr Gly Pro Gly Asn Ser Leu Phe Gln Thr Glu Gly Ser Leu Leu
        35                  40                  45

Tyr Lys Pro Val Arg Leu Asn Cys Ala Pro Ile Asp Ala Ser Tyr Leu
    50                  55                  60

Gly Tyr Leu Asn Glu Leu Glu Ser Asn Phe Ser Asn Asn Pro Glu Glu
65                  70                  75                  80

Lys Asp Ile Gln Val Ser Arg Thr Ile Gln Ile Lys Asn Leu Thr Glu
                85                  90                  95

Glu Ile Lys Cys Lys Leu Asn Ser Met Glu Asp Gly Arg Ser Ser Val
            100                 105                 110

Ser Ala Tyr Asp Thr Ala Trp Val Ser Phe Ile Pro Asn Thr Thr Asn
        115                 120                 125

Asn Gly Asn Asp Gln Arg Pro Met Phe Pro Ser Cys Leu Gln Trp Ile
    130                 135                 140

Ile Asp Asn Gln Leu Cys Asp Gly Ser Trp Gly Glu Glu Ser Val Phe
145                 150                 155                 160

Cys Ile Tyr Asp Arg Leu Leu Asn Thr Leu Ala Cys Val Val Ala Leu
                165                 170                 175

Thr Leu Trp Asn Thr Cys Leu Pro Lys Arg Asn Lys Gly Val Met Phe
            180                 185                 190

Ile Lys Glu Asn Leu Ile Lys Leu Glu Thr Gly Glu Val Glu His Met
        195                 200                 205

Thr Cys Gly Phe Glu Phe Val Phe Pro Ala Leu Leu Glu Lys Ala Gln
    210                 215                 220

Gln Leu Asn Ile Asp Ile Pro Tyr Asp Ala Pro Val Leu Lys Asp Ile
225                 230                 235                 240

Tyr Ala Arg Arg Glu Val Lys Phe Thr Arg Ile Pro Lys Glu Ile Val
                245                 250                 255

His Thr Ile Pro Thr Thr Ala Leu Leu Ser Leu Glu Gly Leu Arg Asp
            260                 265                 270

Asp Leu Asp Trp Gln Arg Leu Leu Asn Phe Gln Met Pro Asp Gly Ser
        275                 280                 285

Phe Leu Ser Ala Pro Ala Ser Thr Ala Phe Ala Phe Met Lys Thr Asn
    290                 295                 300

```
Asp Glu Lys Cys Leu Ala Tyr Leu Gln Asn Val Val Gln Lys Ser Asn
305                 310                 315                 320

Gly Gly Ala Arg His Tyr Pro Leu Asp Leu Leu Thr Arg Leu Trp Ala
                325                 330                 335

Ile Asp Arg Leu Gln Arg Leu Gly Ile Ser Tyr Tyr Phe Ala Glu Glu
            340                 345                 350

Phe Lys Glu Leu Leu Asn His Val Phe Arg Tyr Trp Asp Glu Glu Asn
        355                 360                 365

Gly Ile Phe Ser Gly Arg Asn Ser Asn Val Cys Asp Val Asp Asp Thr
    370                 375                 380

Cys Met Ala Ile Arg Leu Leu Arg Leu His Gly Tyr Asp Val Ser Pro
385                 390                 395                 400

Asp Ala Leu Asn Asn Phe Thr Asp Gly Asp Gln Phe Phe Cys Leu Arg
                405                 410                 415

Gly Glu Val Asp Gly Ser Pro Thr His Met Phe Asn Leu Tyr Arg Cys
            420                 425                 430

Ser Gln Val Leu Phe Pro Gly Glu Lys Ile Leu Glu Glu Ala Lys Asn
        435                 440                 445

Phe Thr Tyr Asn Phe Leu Gln Gln Cys Leu Ala Asn Asn Arg Cys Leu
    450                 455                 460

Asp Lys Trp Val Ile Ala Lys Asp Ile Pro Gly Glu Ile Arg Tyr Ala
465                 470                 475                 480

Leu Lys Phe Pro Trp Tyr Ala Ser Leu Pro Arg Val Glu Ser Arg Leu
                485                 490                 495

Tyr Ile Glu Gln Tyr Gly Gly Ala Asn Asp Ile Trp Ile Gly Lys Thr
            500                 505                 510

Leu Tyr Arg Met Pro Asp Val Ser Asn Asn Val Tyr Leu Gln Ala Ala
        515                 520                 525

Lys Leu Asp Tyr Asn Arg Cys Gln Ser Gln His Arg Phe Glu Trp Leu
    530                 535                 540

Ile Met Gln Gln Trp Phe Asp Lys Cys Asn Phe Gln Gln Phe Gly Ile
545                 550                 555                 560

Ser Lys Lys Tyr Leu Leu Val Ser Tyr Phe Leu Ala Ala Ala Ser Ile
                565                 570                 575

Phe Glu Val Glu Lys Ser Arg Glu Arg Leu Ala Trp Ala Lys Ser Arg
            580                 585                 590

Ile Ile Cys Lys Met Ile Thr Ser Tyr Tyr Asn Glu Glu Ala Thr Thr
        595                 600                 605

Trp Thr Ser Arg Asn Ser Leu Leu Met Glu Phe Lys Gly Ser Asp Asp
    610                 615                 620

Pro Ser Arg Lys Asn Gly Asn Glu Thr Lys Glu Ile Ile Val Leu Lys
625                 630                 635                 640

Asn Leu Arg Gln Phe Leu His Gln Leu Ser Glu Glu Thr Phe Glu Asp
                645                 650                 655

Leu Gly Lys Asp Ile His His Gln Leu Gln Asn Ala Trp Lys Thr Trp
            660                 665                 670

Leu Ala Phe Leu Arg Glu Glu Lys Asn Thr Cys Gln Glu Glu Ala Glu
        675                 680                 685

Leu Leu Val Arg Thr Ile Asn Leu Ser Gly Gly His Met Ile His Asp
    690                 695                 700

Glu Ile Leu Phe Asp Ala Asp Tyr Lys Asn Leu Ser Asn Leu Thr Asn
705                 710                 715                 720
```

-continued

```
Lys Val Cys Cys Met Leu Ser Glu Leu Gln Asn Asp Lys Val Thr Gly
            725                 730                 735

Ser Ser Lys Asn Thr Asp Ile Glu Leu Asn Met Gln Ala Leu Val Lys
        740                 745                 750

Leu Val Phe Gly Asn Thr Ser Ser Asn Ile Asn Gln Asp Ile Lys Gln
            755                 760                 765

Thr Phe Phe Ala Val Val Lys Thr Phe Tyr Tyr Ser Ala His Val Ser
    770                 775                 780

Glu Glu Ile Ile Asn Phe His Ile Ser Lys Val Leu Phe Gln Gln Val
785                 790                 795                 800

Gln

<210> SEQ ID NO 55
<211> LENGTH: 7924
<212> TYPE: DNA
<213> ORGANISM: Artificial Sequence
<220> FEATURE:
<223> OTHER INFORMATION: pALX40-103.2 vector

<400> SEQUENCE: 55
tcgacggatc cgaattccct gcaggtaatt aaataagctt caaataaaac gaaaggctca      60
gtcgaaagac tgggcctttc gttttatctg ttgtttgtcg gtgaacgctc tcctgagtag     120
gacaaatccg ccgggagcgg atttgaacgt tgcgaagcaa cggcccggag ggtggcgggc     180
aggacgcccg ccataaactg ccaggcatca aattaagcag aaggccatcc tgacggatgg     240
ccttttttgcg tttctacaaa ctctttcggt ccgttgttta ttttctaaa tacattcaaa     300
tatgtatccg ctcatgagac aataaccctg ataaatgctt caataatatt gaaaaaggaa     360
gagtatgagt attcaacatt tccgtgtcgc ccttattccc ttttttgcgg cattttgcct     420
tcctgttttt gctcacccag aaacgctggt gaaagtaaaa gatgctgaag atcagttggg     480
tgcacgagtg ggttacatcg aactggatct caacagcggt aagatccttg agagttttcg     540
ccccgaagaa cgtttcccaa tgatgagcac ttttaaagtt ctgctatgtg gcgcggtatt     600
atcccgtgtt gacgccgggc aagagcaact cggtcgccgc atacactatt ctcagaatga     660
cttggttgag tactcaccag tcacagaaaa gcatcttacg gatggcatga cagtaagaga     720
attatgcagt gctgccataa ccatgagtga taacactgcg gccaacttac ttctgacaac     780
gatcggagga ccgaaggagc taaccgcttt tttgcacaac atgggggatc atgtaactcg     840
ccttgatcgt tgggaaccgg agctgaatga agccatacca aacgacgagc gtgacaccac     900
gatgcctgta gcaatggcaa caacgttgcg caaactatta actggcgaac tacttactct     960
agcttcccgg caacaattaa tagactggat ggaggcggat aaagttgcag gaccacttct    1020
gcgctcggcc cttccggctg gctggtttat tgctgataaa tctggagccg gtgagcgtgg    1080
gtctcgcggt atcattgcag cactggggcc agatggtaag ccctcccgta tcgtagttat    1140
ctacacgacg gggagtcagg caactatgga tgaacgaaat agacagatcg ctgagatagg    1200
tgcctcactg attaagcatt ggtaactgtc agaccaagtt tactcatata ctttagat     1260
tgatttcctt aggactgagc gtcaaccccg tagaaaagat caaaggatct tcttgagatc    1320
cttttttttct gcgcgtaatc tgctgcttgc aaacaaaaaa accaccgcta ccagcggtgg    1380
tttgtttgcc ggatcaagag ctaccaactc tttttccgaa ggtaactggc ttcagcagag    1440
cgcagatacc aaatactgtc cttctagtgt agccgtagtt aggccaccac ttcaagaact    1500
ctgtagcacc gcctacatac ctcgctctgc taatcctgtt accagtggct gctgccagtg    1560
```

```
gcgataagtc gtgtcttacc gggttggact caagacgata gttaccggat aaggcgcagc    1620
ggtcgggctg aacgggggt  tcgtgcacac agcccagctt ggagcgaacg acctacaccg    1680
aactgagata cctacagcgt gagctatgag aaagcgccac gcttcccgaa gggagaaagg    1740
cggacaggta tccggtaagc ggcagggtcg aacaggaga  gcgcacgagg gagcttccag    1800
ggggaaacgc ctggtatctt tatagtcctg tcgggtttcg ccacctctga cttgagcgtc    1860 gattttgtg  atgctcgtca ggggggcgga gcctatggaa aaacgccagc aacgcggcct    1920
ttttacggtt cctggccttt tgctggcctt ttgctcacat gttctttcct gcgttatccc    1980
ctgattctgt ggataaccgt attaccgcct ttgagtgagc tgataccgct cgccgcagcc    2040
gaacgaccga gcgcagcgag tcagtgagcg aggaagcgga agagcgcctg atgcggtatt    2100
ttctccttac gcatctgtgc ggtatttcac accgcatata aggtgcactg tgactgggtc    2160
atggctgcgc cccgacaccc gccaacaccc gctgacgcgc cctgacgggc ttgtctgctc    2220
ccggcatccg cttacagaca agctgtgacc gtctccggga gctgcatgtg tcagaggttt    2280
tcaccgtcat caccgaaacg cgcgaggcag ctgcggtaaa gctcatcagc gtggtcgtgc    2340
agcgattcac agatgtctgc ctgttcatcc gcgtccagct cgttgagttt ctccagaagc    2400
gttaatgtct ggcttctgat aaagcgggcc atgttaaggg cggttttttc ctgtttggtc    2460
actgatgcct ccgtgtaagg gggatttctg ttcatggggg taatgatacc gatgaaacga    2520
gagaggatgc tcacgatacg ggttactgat gatgaacatg cccggttact ggaacgttgt    2580
gagggtaaac aactggcggt atggatgcgg cgggaccaga gaaaaatcac tcagggtcaa    2640
tgccagcgct tcgttaatac agatgtaggt gttccacagg gtagccagca gcatcctgcg    2700
atgcagatcc ggaacataat ggtgcagggc gctgacttcc gcgtttccag actttacgaa    2760
acacggaaac cgaagaccat tcatgttgtt gctcaggtcg cagacgtttt gcagcagcag    2820
tcgcttcacg ttcgctcgcg tatcggtgat tcattctgct aaccagtaag gcaaccccgc    2880
cagcctagcc gggtcctcaa cgacaggagc acgatcatgc gcacccgtgg ccaggaccca    2940
acgctgcccg aaattccgac accatcgaat ggtgcaaaac ctttcgcggt atggcatgat    3000
agcgcccgga agagagtcaa ttcagggtgg tgaatgtgaa accagtaacg ttatacgatg    3060
tcgcagagta tgccggtgtc tcttatcaga ccgtttcccg cgtggtgaac caggccagcc    3120
acgtttctgc gaaaacgcgg gaaaagtgg  aagcggcgat ggcggagctg aattacattc    3180
ccaaccgcgt ggcacaacaa ctggcgggca aacagtcgtt gctgattggc gttgccacct    3240
ccagtctggc cctgcacgcg ccgtcgcaaa ttgtcgcggc gattaaatct cgcgccgatc    3300
aactgggtgc cagcgtggtg gtgtcgatgg tagaacgaag cggcgtcgaa gcctgtaaag    3360
cggcggtgca caatcttctc gcgcaacgcg tcagtgggct gatcattaac tatccgctgg    3420
atgaccagga tgccattgct gtggaagctg cctgcactaa tgttccggcg ttatttcttg    3480
atgtctctga ccagacaccc atcaacagta ttattttctc ccatgaagac ggtacgcgac    3540
tgggcgtgga gcatctggtc gcattgggtc accagcaaat cgcgctgtta gcgggcccat    3600
taagttctgt ctcggcgcgt ctgcgtctgg ctggctggca taaatatctc actcgcaatc    3660
aaattcagcc gatagcggaa cggaaggcg  actggagtgc catgtccggt tttcaacaaa    3720
ccatgcaaat gctgaatgag ggcatcgttc ccactgcgat gctggttgcc aacgatcaga    3780
tggcgctggg cgcaatgcgc gccattaccg agtccgggct gcgcgttggt gcggatattt    3840
cggtagtggg atacgacgat accgaagaca gctcatgtta tatcccgccg ttaaccacca    3900
tcaaacagga ttttcgcctg ctggggcaaa ccagcgtgga ccgcttgctg caactctctc    3960
```

```
agggccaggc ggtgaagggc aatcagctgt tgcccgtctc actggtgaaa agaaaaacca   4020
ccctggcgcc caatacgcaa accgcctctc cccgcgcgtt ggccgattca ttaatgcagc   4080
tggcacgaca ggtttcccga ctggaaagcg ggcagtgagc gcaacgcaat taatgtaagt   4140
tagctcactc attaggcaca attctcatgt ttgacagctt atcatcgact gcacggtgca   4200
ccaatgcttc tggcgtcagg cagccatcgg aagctgtggt atggctgtgc aggtcgtaaa   4260
tcactgcata attcgtgtcg ctcaaggcgc actcccgttc tggataatgt ttttgcgcc    4320
gacatcataa cggttctggc aaatattctg aaatgagctg ttgacaatta atcatcggct   4380
cgtataatgt gtggaattgt gagcggataa caatttcaca caggaaacag ccagtccgtt   4440
taggtgtttt cacgagcaat tgaccaacaa ggaccataga ttatgaaaat cgaagaaggt   4500
aaactggtaa tctggattaa cggcgataaa ggctataacg gtctcgctga agtcggtaag   4560
aaattcgaga agataccgg aattaaagtc accgttgagc atccggataa actggaagag    4620
aaattcccac aggttgcggc aactggcgat ggccctgaca ttatcttctg ggcacacgac   4680
cgctttggtg gctacgctca atctggcctg ttggctgaaa tcaccccgga caaagcgttc   4740
caggacaagc tgtatccgtt tacctgggat gccgtacgtt acaacggcaa gctgattgct   4800
tacccgatcg ctgttgaagc gttatcgctg atttataaca aagatctgct gccgaacccg   4860
ccaaaaacct gggaagagat cccggcgctg gataaagaac tgaaagcgaa aggtaagagc   4920
gcgctgatgt tcaacctgca agaaccgtac ttcacctggc cgctgattgc tgctgacggg   4980
ggttatgcgt tcaagtatga aaacggcaag tacgacatta agacgtggg cgtggataac    5040
gctggcgcga aagcgggtct gaccttcctg gttgacctga ttaaaaacaa acacatgaat   5100
gcagacaccg attactccat cgcagaagct gcctttaata aaggcgaaac agcgatgacc   5160
atcaacggcc cgtgggcatg gtccaacatc gacaccagca agtgaattta tggtgtaacg   5220
gtactgccga ccttcaaggg tcaaccatcc aaaccgttcg ttggcgtgct gagcgcaggt   5280
attaacgccg ccagtccgaa caaagagctg gcaaagagt tcctcgaaaa ctatctgctg    5340
actgatgaag gtctggaagc ggttaataaa gacaaaccgc tgggtgccgt agcgctgaag   5400
tcttacgagg aagagttggt gaaagatccg cgtattgccg ccactatgga aaacgcccag   5460
aaaggtgaaa tcatgccgaa catcccgcag atgtccgctt tctggtatgc cgtgcgtact   5520
gcggtgatca acgccgccag cggtcgtcag actgtcgatg aagccctgaa agacgcgcag   5580
actaattcga gctcgaacaa caacaacaat aacaataaca caacctcgg ggatgacgat    5640
gacaaggtac cgcatatgag ccacagtact gcttcatcac tggaagaggc gaaggaagaa   5700
ataagggaaa catttggaaa aaatgagcta tctccttctt cctatgacac agcatgggta   5760
gctatggtcc cttcaagata ttctatgaac caaccatgtt ttcctcggtg cttggattgg   5820
attcttgaaa atcaaagaga agatggatct tggggcctaa atcctagcca tccattgctt   5880
gtaaaagact ccctttcttc cactctagca tgtttgcttg cccttcgcaa atggagaatt   5940
ggagataacc aagtccaaag aggccttggc tttattgaaa cgcatggttg ggcagttgat   6000
aacgtggatc agatttcacc tttaggattt gatattatat ttcccagcat gatcaagtat   6060
gcagagaaac tgaatttgga tctacctttc gatcctaacc ttgtaaatat gatgctccgc   6120
gaacgcgaat taacaattga agagccctat aagaatgaat tcgaagggaa tatggcaaat   6180
gttgaatatt ttgctgaagg gctcggtgaa ttatgtcatt ggaaagagat aatgcttcat   6240
cagagacgca acggatcgcc ctttgactct ccagcaacta ctgcagctgc tttgatttac   6300
```

| | |
|---|---|
| catcagcacg atgagaaatg ctttgggtac ttgagctcaa tcttgaaact gcacgagaat | 6360 |
| tgggtcccca ctatttaccc tacaaaggta cattcaaatc tcttcttcgt tgatgccctt | 6420 |
| caaaatcttg gagtagatcg gtattttaaa acagaactca aaagtgtact cgatgaaata | 6480 |
| tacaggcttt ggctagaaaa gaatgaagaa atttttcag acattgctca ttgtgccatg | 6540 |
| gcgtttcgac ttttgcggat gaataactat gaagtttcct cagaagaact gaaggatt | 6600 |
| gtcgaccaag aacatttctt tacaacatca ggtgggaaac ttattagtca cgttgcaatt | 6660 |
| ctcgaacttc accgagcttc acaggtggat attcaagaag ggaaagatct catttagat | 6720 |
| aaaataagta cttggacaag gaatttatg gagcaagaac tcttggacaa tcaaatcctt | 6780 |
| gataggtcaa agaaggagat ggaattgct atgaggaaat ttatggcac atttgatcga | 6840 |
| gtggaaacta gacgatacat cgagtcatac aaaatggaca gttttaagat cttaaaagca | 6900 |
| gcctacaggt cttccaacat taacaacata gacttgctaa agttctcaga acatgattt | 6960 |
| aacttgtgcc aagcccgaca caagaagaa cttcaacaga ttaagaggtg gttcgcagat | 7020 |
| tgcaaactgg aacaagtagg atcatcacaa aactacttat acactagtta cttcccaatt | 7080 |
| gctgccatac tcttcgaacc tgaatatggt gatgctcgtc tagcatttgc aaagtgtggc | 7140 |
| ataatcgcaa cgacggtgga tgatttcttc gatggttttg cttgcaatga agaactccaa | 7200 |
| aacatcatcg aattagtaga gaggtgggat ggatacccaa ctgtcggatt tcgttcagaa | 7260 |
| agggttagaa ttttctttt ggcactttac aaaatgatag aggaaattgc ggcaaaggca | 7320 |
| gaaactaagc aaggtcgatg tgtcaaagat ctccttatta acttgtggat tgatttattg | 7380 |
| aaatgtatgc tggtggaatt ggacctttgg aaaattaaat caactacccc aagcatagag | 7440 |
| gagtacttgt ctatcgcatg tgtaactaca ggtgttaaat gtttaattct catatcacta | 7500 |
| catcttcttg gaccaaaact gtccaaggat gtcacagaaa gttctgaggt cagtgcctta | 7560 |
| tggaattgta cagctgttgt ggcccgattg aataatgata tacatagtta caagagagaa | 7620 |
| caagcagaaa gttcaacaaa tatggtagca atattaatat cacagagtca gagaactatc | 7680 |
| tctgaagaag aggctataag acagataaaa gaaatgatgg aaagtaagag aagagagttg | 7740 |
| ctagggatgg ttctacaaaa taagaaagc caattgccgc aagtgtgcaa agatctttt | 7800 |
| tggacgacat tcaaagcagc ttattctata tatacacatg gcgatgagta tcgcttccca | 7860 |
| caggaattga agaaccatat aaacgatgta atttacaaac cactcaatca atattcccca | 7920 |
| taac | 7924 |

<210> SEQ ID NO 56
<211> LENGTH: 7378
<212> TYPE: DNA
<213> ORGANISM: Artificial Sequence
<220> FEATURE:
<223> OTHER INFORMATION: pALX40-69.1 vector

<400> SEQUENCE: 56

| | |
|---|---|
| gatccgaatt ccctgcaggt aattaaataa gcttcaaata aaacgaaagg ctcagtcgaa | 60 |
| agactgggcc tttcgtttta tctgttgttt gtcggtgaac gctctcctga gtaggacaaa | 120 |
| tccgccggga gcggatttga acgttgcgaa gcaacggccc ggagggtggc gggcaggacg | 180 |
| cccgccataa actgccaggc atcaaattaa gcagaaggcc atcctgacgg atggcctttt | 240 |
| tgcgtttcta caaactcttt cggtccgttg tttattttc taaatacatt caaatatgta | 300 |
| tccgctcatg agacaataac cctgataaat gcttcaataa tattgaaaaa ggaagagtat | 360 |
| gagtattcaa catttccgtg tcgcccttat tccctttt gcggcatttt gccttcctgt | 420 |

```
ttttgctcac ccagaaacgc tggtgaaagt aaaagatgct gaagatcagt tgggtgcacg    480
agtgggttac atcgaactgg atctcaacag cggtaagatc cttgagagtt ttcgccccga    540
agaacgtttc ccaatgatga gcacttttaa agttctgcta tgtggcgcgg tattatcccg    600
tgttgacgcc gggcaagagc aactcggtcg ccgcatacac tattctcaga atgacttggt    660
tgagtactca ccagtcacag aaaagcatct tacggatggc atgacagtaa gagaattatg    720
cagtgctgcc ataaccatga gtgataacac tgccggccaac ttacttctga caacgatcgg    780
aggaccgaag gagctaaccg cttttttgca acatggggg gatcatgtaa ctcgccttga    840
tcgttgggaa ccgagctga atgaagccat accaaacgac gagcgtgaca ccacgatgcc    900
tgtagcaatg gcaacaacgt tgcgcaaact attaactggc gaactactta ctctagcttc    960
ccggcaacaa ttaatagact ggatggaggc ggataaagtt gcaggaccac ttctgcgctc   1020
ggcccttccg gctggctggt ttattgctga taaatctgga gccggtgagc gtgggtctcg   1080
cggtatcatt gcagcactgg ggccagatgg taagccctcc cgtatcgtag ttatctacac   1140
gacggggagt caggcaacta tggatgaacg aaatagacag atcgctgaga taggtgcctc   1200
actgattaag cattggtaac tgtcagacca gtttactca tatatacttt agattgattt   1260
ccttaggact gagcgtcaac cccgtagaaa agatcaaagg atcttcttga tccttttt    1320 ttctgcgcgt aatctgctgc ttgcaaacaa aaaaaccacc gctaccagcg gtggtttgtt   1380
tgccggatca agagctacca actcttttt cgaaggtaac tggcttcagc agagcgcaga   1440
taccaaatac tgtccttcta gtgtagccgt agttaggcca ccacttcaag aactctgtag   1500
caccgcctac atacctcgct ctgctaatcc tgttaccagt ggctgctgcc agtggcgata   1560
agtcgtgtct taccgggttg gactcaagac gatagttacc ggataagcg cagcggtcgg   1620 gctgaacggg gggttcgtgc acacagccca gcttggagcg aacgacctac accgaactga   1680
gatacctaca gcgtgagcta tgagaaagcg ccacgcttcc cgaagggaga aaggcggaca   1740
ggtatccggt aagcggcagg gtcggaacag gagagcgcac gagggagctt ccaggggaa   1800 acgcctggta tctttatagt cctgtcgggt ttcgccacct ctgacttgag cgtcgatttt   1860
tgtgatgctc gtcaggggg cggagcctat ggaaaaacgc cagcaacgcg ccttttttac   1920
ggttcctggc cttttgctgg ccttttgctc acatgttctt tcctgcgtta tcccctgatt   1980
ctgtggataa ccgtattacc gcctttgagt gagctgatac cgctcgccgc agccgaacga   2040
ccgagcgcag cgagtcagtg agcgaggaag cggaagagcg cctgatgcgg tatttctcc    2100 ttacgcatct gtgcggtatt tcacaccgca tataaggtgc actgtgactg gtcatggct    2160 gcgccccgac acccgccaac acccgctgac gcgccctgac gggcttgtct gctcccggca   2220
tccgcttaca gacaagctgt gaccgtctcc gggagctgca tgtgtcagag gttttcaccg   2280
tcatcaccga aacgcgcgag gcagctgcgg taaagctcat cagcgtggtc gtgcagcgat   2340
tcacagatgt ctgcctgttc atccgcgtcc agctcgttga gtttctccag aagcgttaat   2400
gtctggcttc tgataaagcg ggccatgtta agggcggttt tttcctgttt ggtcactgat   2460
gcctccgtgt aagggggatt tctgttcatg gggtaatga taccgatgaa acgagagagg   2520
atgctcacga tacgggttac tgatgatgaa catgcccggt tactggaacg ttgtgagggt   2580
aaacaactgg cggtatggat gcggcggac cagagaaaaa tcactcaggg tcaatgccag   2640
cgcttcgtta atacagatgt aggtgttcca cagggtagcc agcagcatcc tgcgatgcag   2700
atccggaaca taatggtgca gggcgctgac ttccgcgttt ccagacttta cgaaacacgg   2760
```

```
aaaccgaaga ccattcatgt tgttgctcag gtcgcagacg ttttgcagca gcagtcgctt    2820
cacgttcgct cgcgtatcgg tgattcattc tgctaaccag taaggcaacc ccgccagcct    2880
agccgggtcc tcaacgacag gagcacgatc atgcgcaccc gtggccagga cccaacgctg    2940
cccgaaattc cgacaccatc gaatggtgca aaacctttcg cggtatggca tgatagcgcc    3000
cggaagagag tcaattcagg gtggtgaatg tgaaaccagt aacgttatac gatgtcgcag    3060
agtatgccgg tgtctcttat cagaccgttt cccgcgtggt gaaccaggcc agccacgttt    3120
ctgcgaaaac gcgggaaaaa gtggaagcgg cgatggcgga gctgaattac attcccaacc    3180
gcgtggcaca acaactggcg ggcaaacagt cgttgctgat ggcgttgcc acctccagtc     3240 tggccctgca cgcgccgtcg caaattgtcg cggcgattaa atctcgcgcc gatcaactgg    3300
gtgccagcgt ggtggtgtcg atggtagaac gaagcggcgt cgaagcctgt aaagcggcgg    3360
tgcacaatct tctcgcgcaa cgcgtcagtg ggctgatcat taactatccg ctggatgacc    3420
aggatgccat tgctgtggaa gctgcctgca ctaatgttcc ggcgttattt cttgatgtct    3480
ctgaccagac acccatcaac agtattattt tctcccatga agacggtacg cgactgggcg    3540
tggagcatct ggtcgcattg ggtcaccagc aaatcgcgct gttagcgggc ccattaagtt    3600
ctgtctcggc gcgtctgcgt ctggctggct ggcataaata tctcactcgc aatcaaattc    3660
agccgatagc ggaacgggaa ggcgactgga gtgccatgtc cggttttcaa caaaccatgc    3720
aaatgctgaa tgagggcatc gttcccactg cgatgctggt tgccaacgat cagatggcgc    3780
tgggcgcaat gcgcgccatt accgagtccg ggctgcgcgt tggtgcggat atttcggtag    3840
tgggatacga cgataccgaa gacagctcat gttatatccc gccgttaacc accatcaaac    3900
aggattttcg cctgctgggg caaccagcg tggaccgctt gctgcaactc tctcagggcc     3960
aggcggtgaa gggcaatcag ctgttgcccg tctcactggt gaaagaaaa accaccctgg     4020 cgcccaatac gcaaaccgcc tctccccgcg cgttggccga ttcattaatg cagctggcac    4080
gacaggtttc ccgactggaa agcgggcagt gagcgcaacg caattaatgt aagttagctc    4140
actcattagg cacaattctc atgtttgaca gcttatcatc gactgcacgg tgcaccaatg    4200
cttctggcgt caggcagcca tcggaagctg tggtatggct gtgcaggtcg taaatcactg    4260
cataattcgt gtcgctcaag gcgcactccc gttctggata atgttttttg cgccgacatc    4320
ataacggttc tggcaaatat tctgaaatga gctgttgaca attaatcatc ggctcgtata    4380
atgtgtggaa ttgtgagcgg ataacaattt cacacaggaa acagccagtc cgtttaggtg    4440
ttttcacgag caattgacca acaaggacca tagattatga aatcgaaga aggtaaactg     4500 gtaatctgga ttaacggcga taaaggctat aacggtctcg ctgaagtcgg taagaaattc    4560
gagaaagata ccggaattaa agtcaccgtt gagcatccgg ataaactgga agagaaattc    4620
ccacaggttg cggcaactgg cgatggccct gacattatct tctgggcaca cgaccgcttt    4680
ggtggctacg ctcaatctgg cctgttggct gaaatcaccc cggacaaagc gttccaggac    4740
aagctgtatc cgtttacctg ggatgccgta cgttacaacg gcaagctgat tgcttacccg    4800
atcgctgttg aagcgttatc gctgatttat aacaaagatc tgctgccgaa cccgccaaaa    4860
acctgggaag agatcccggc gctggataaa gaactgaaag cgaaaggtaa gagcgcgctg    4920
atgttcaacc tgcaagaacc gtacttcacc tggccgctga ttgctgctga cggggttat    4980 gcgttcaagt atgaaaacgg caagtacgac attaagacg tgggcgtgga taacgctggc     5040
gcgaaagcgg gtctgacctt cctggttgac ctgattaaaa acaaacacat gaatgcagac    5100
accgattact ccatcgcaga agctgccttt aataaaggcg aaacagcgat gaccatcaac    5160
```

```
ggcccgtggg catggtccaa catcgacacc agcaaagtga attatggtgt aacggtactg    5220
ccgaccttca agggtcaacc atccaaaccg ttcgttggcg tgctgagcgc aggtattaac    5280
gccgccagtc cgaacaaaga gctggcaaaa gagttcctcg aaaactatct gctgactgat    5340
gaaggtctgg aagcggttaa taaagacaaa ccgctgggtg ccgtagcgct gaagtcttac    5400
gaggaagagt tggtgaaaga tccgcgtatt gccgccacta tggaaaacgc ccagaaaggt    5460
gaaatcatgc cgaacatccc gcagatgtcc gctttctggt atgccgtgcg tactgcggtg    5520
atcaacgccg ccagcggtcg tcagactgtc gatgaagccc tgaaagacgc gcagactaat    5580
tcgagctcga acaacaacaa caataacaat aacaacaacc tcggggatga cgatgacaag    5640
gtaccgcata tgtcgctcgc cttcaacgtc ggagttacgc ctttctccgg ccaaagagtt    5700
gggagcagga agaaaaaatt tccagtccaa ggatttcctg tgaccacccc caataggtca    5760
cgtctcatcg ttaactgcag ccttactaca atagatttca tggcgaaaat gaaagagaat    5820
ttcaagaggg aagacgataa atttccaacg acaacgactc ttcgatccga agatataccc    5880
tctaatttgt gtataatcga caccccttcaa aggttggggg tcgatcaatt cttccaatat    5940
gaaatcaaca ctattctaga taacacattc aggttgtggc aagaaaaaca caaagttata    6000
tatggcaatg ttactactca tgcaatggca tttaggcttt tgcgagtgaa aggatacgaa    6060
gtttcatcag aggagttggc tccatatggt aaccaagagg ctgttagcca gcaaacaaat    6120
gacctgccga tgattattga gctttataga gcagcaaatg agagaatata tgaagaagag    6180
aggagtcttg aaaaaattct tgcttggact accatctttc tcaataagca agtgcaagat    6240
aactcaattc ccgacaaaaa actgcacaaa ctggtggaat tctacttgag gaattacaaa    6300
ggcataacca taagattggg agctagacga aacctcgagc tatatgacat gacctactat    6360
caagctctga atctacaaa caggttctct aatttatgca acgaagattt tctagttttc    6420
gcaaagcaag atttcgatat acatgaagcc cagaaccaga aaggacttca acaactgcaa    6480
aggtggtatg cagattgtag gttggacacc ttaaactttg aagagatgt agttattatt    6540 gctaattatt tggcttcatt aattattggt gatcatgcgt ttgactatgt tcgtctcgca    6600
tttgccaaaa catctgtgct tgtaacaatt atggatgatt ttttcgactg tcatggctct    6660
agtcaagagt gtgacaagat cattgaatta gtaaaagaat ggaaggagaa tccggatgca    6720
gagtacggat ctgaggagct tgagatcctt tttatggcgt tgtacaatac agtaaatgag    6780
ttggcggaga gggctcgtgt tgaacagggg cgtagtgtca agagtttct agtcaaactg    6840 tgggttgaaa tactctcagc tttcaagata gaattagata catggagcaa tggcacgcag    6900
caaagcttcg atgaatacat ttcttcgtcg tggttgtcga acggttcccg gctgacaggt    6960
ctcctgacga tgcaattcgt cggagtaaaa ttgtccgatg aaatgcttat gagtgaagag    7020
tgcactgatt tggctaggca tgtctgtatg gtcggccggc tgctcaacga cgtgtgcagt    7080
tctgagaggg agcgcgagga aaatattgca ggaaaaagtt atagcattct actagcaact    7140
gagaaagatg gaagaaaagt tagtgaagat gaagccattg cagagatcaa tgaaatggtt    7200
gaatatcact ggagaaaagt gttgcagatt gtgtataaaa aagaaagcat tttgccaaga    7260
agatgcaaag atgtattttt ggagatggct aagggtacgt tttatgctta tgggatcaac    7320
gatgaattga cttctcctca gcaatccaag gaagatatga aatcctttgt cttttgag     7378
```

<210> SEQ ID NO 57
<211> LENGTH: 785
<212> TYPE: PRT

<213> ORGANISM: Salvia sclarea
<220> FEATURE:
<223> OTHER INFORMATION: SsTps1
<300> PUBLICATION INFORMATION:
<310> PATENT DOCUMENT NUMBER: WO2009044336

<400> SEQUENCE: 57

```
Met Thr Ser Val Asn Leu Ser Arg Ala Pro Ala Ile Ile Arg Arg
 1               5                  10                  15

Arg Leu Gln Leu Gln Pro Glu Phe His Ala Glu Cys Ser Trp Leu Lys
                 20                  25                  30

Ser Ser Ser Lys His Ala Pro Leu Thr Leu Ser Cys Gln Ile Arg Pro
             35                  40                  45

Lys Gln Leu Ser Gln Ile Ala Glu Leu Arg Val Thr Ser Leu Asp Ala
 50                  55                  60

Ser Gln Ala Ser Glu Lys Asp Ile Ser Leu Val Gln Thr Pro His Lys
 65                  70                  75                  80

Val Glu Val Asn Glu Lys Ile Glu Glu Ser Ile Glu Tyr Val Gln Asn
                 85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His His Gln Leu Ala Asp
130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Asp Leu Pro
210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
370                 375                 380
```

```
Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
            405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
            435                 440                 445

Glu Met Leu Val Lys Asp Arg Leu Gln Glu Arg Trp Val Ile Ser Asp
            450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
            485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
            515                 520                 525

Gln Thr Gln His Gln Leu Glu Trp Ile His Met Gln Glu Trp Tyr Asp
            530                 535                 540

Arg Cys Ser Leu Ser Glu Phe Gly Ile Ser Lys Arg Glu Leu Leu Arg
545                 550                 555                 560

Ser Tyr Phe Leu Ala Ala Thr Ile Phe Glu Pro Glu Arg Thr Gln
            565                 570                 575

Glu Arg Leu Leu Trp Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
            595                 600                 605

Asn Gly Leu Asp Glu Ile Ile Ser Ser Ala Asn Glu Asp Gln Gly Leu
            610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
            645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
            675                 680                 685

Asn Asn Glu Tyr Thr Ala Leu Ser Thr Leu Thr Asn Lys Ile Cys Asn
            690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
            725                 730                 735

Leu Val Leu Gln Glu Asn Gly Gly Ala Val Asp Arg Asn Ile Arg His
            740                 745                 750

Thr Phe Leu Ser Val Ser Lys Thr Phe Tyr Tyr Asp Ala Tyr His Asp
            755                 760                 765

Asp Glu Thr Thr Asp Leu His Ile Phe Lys Val Leu Phe Arg Pro Val
            770                 775                 780

Val
785
```

<210> SEQ ID NO 58
<211> LENGTH: 785
<212> TYPE: PRT
<213> ORGANISM: Salvia sclarea
<220> FEATURE:
<223> OTHER INFORMATION: SsLPPs3
<300> PUBLICATION INFORMATION:
<310> PATENT DOCUMENT NUMBER: WO2009044336

<400> SEQUENCE: 58

```
Met Thr Ser Val Asn Leu Ser Arg Ala Pro Ala Ile Thr Arg Arg
  1               5                  10                  15

Arg Leu Gln Leu Gln Pro Glu Phe His Ala Glu Cys Ser Trp Leu Lys
                 20                  25                  30

Ser Ser Ser Lys His Ala Pro Leu Thr Leu Ser Cys Gln Ile Arg Pro
             35                  40                  45

Lys Gln Leu Ser Gln Ile Ala Glu Leu Arg Val Thr Ser Leu Asp Ala
         50                  55                  60

Ser Gln Ala Ser Glu Lys Asp Ile Ser Leu Val Gln Thr Pro His Lys
 65                  70                  75                  80

Val Glu Val Asn Glu Lys Ile Glu Glu Ser Ile Glu Tyr Val Gln Asn
                     85                  90                  95

Leu Leu Met Thr Ser Gly Asp Gly Arg Ile Ser Val Ser Pro Tyr Asp
                100                 105                 110

Thr Ala Val Ile Ala Leu Ile Lys Asp Leu Lys Gly Arg Asp Ala Pro
            115                 120                 125

Gln Phe Pro Ser Cys Leu Glu Trp Ile Ala His His Gln Leu Ala Asp
        130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Asp Leu Pro
    210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
```

-continued

```
            355                 360                 365
Lys Phe Ser Asp Ile Asp Asp Thr Ser Met Gly Val Arg Leu Leu Lys
    370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
        435                 440                 445

Glu Met Leu Val Lys Asp Arg Leu Gln Glu Arg Trp Val Ile Ser Asp
    450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile His Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
        595                 600                 605

Asn Gly Leu Asp Glu Ile Ile Ser Ser Ala Asn Glu Asp Gln Gly Leu
    610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
        675                 680                 685

Asn Asn Glu Tyr Thr Ala Leu Ser Thr Leu Thr Asn Lys Ile Cys Asn
    690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
            740                 745                 750

Thr Phe Leu Ser Val Ser Lys Thr Phe Tyr Tyr Asp Ala Tyr His Asp
        755                 760                 765

Asp Glu Thr Thr Asp Leu His Ile Phe Lys Val Leu Phe Arg Pro Val
    770                 775                 780
```

Val
785

<210> SEQ ID NO 59
<211> LENGTH: 784
<212> TYPE: PRT
<213> ORGANISM: Salvia sclarea
<220> FEATURE:
<223> OTHER INFORMATION: SsLPPs9
<300> PUBLICATION INFORMATION:
<310> PATENT DOCUMENT NUMBER: WO2009044336

<400> SEQUENCE: 59

```
Met Thr Ser Val Asn Leu Ser Arg Ala Pro Ala Ile Ile Arg Arg
 1               5                  10                  15

Arg Leu Gln Leu Gln Pro Glu Phe His Ala Glu Cys Ser Trp Leu Lys
                 20                  25                  30

Ser Ser Ser Lys His Ala Pro Phe Thr Leu Ser Cys Gln Ile Arg Pro
             35                  40                  45

Lys Gln Leu Ser Gln Ile Ala Glu Leu Arg Val Thr Ser Leu Asp Ala
         50                  55                  60

Ser Gln Ala Ser Glu Lys Asp Ile Ser Leu Val Gln Thr Pro His Lys
 65                  70                  75                  80

Val Glu Val Asn Glu Lys Ile Glu Glu Ser Ile Glu Tyr Val Gln Asn
                 85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His Gln Leu Ala Asp
130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu Gln Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Gly Leu Pro
    210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335
```

```
Gly Ile Ser Arg Phe Phe Gln His Glu Ile Lys Tyr Phe Leu Asp His
            340                 345                 350

Ile Glu Ser Val Trp Glu Thr Gly Val Phe Ser Gly Arg Tyr Thr
        355                 360                 365

Lys Phe Ser Asp Ile Asp Asp Thr Ser Met Gly Val Arg Leu Leu Lys
    370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
        435                 440                 445

Glu Met Leu Val Lys Asp Arg Leu Gln Glu Arg Trp Val Ile Ser Asp
    450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile Gln Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
        580                 585                 590

Ser Phe Val Asn Ile Ser Gly Thr Thr Leu Ser Leu Asp Tyr Asn Phe
    595                 600                 605

Asn Gly Leu Asp Glu Ile Ile Ser Ala Asn Glu Asp Gln Gly Leu Ala
610                 615                 620

Gly Thr Leu Leu Ala Thr Phe His Gln Leu Leu Asp Gly Phe Asp Ile
625                 630                 635                 640

Tyr Thr Leu His Gln Leu Lys His Val Trp Ser Gln Trp Phe Met Lys
                645                 650                 655

Val Gln Gln Gly Glu Gly Ser Gly Gly Glu Asp Ala Val Leu Leu Ala
            660                 665                 670

Asn Thr Leu Asn Ile Cys Ala Gly Leu Asn Glu Asp Val Leu Ser Asn
        675                 680                 685

Asn Glu Tyr Thr Ala Leu Ser Thr Leu Thr Asn Lys Ile Cys Asn Arg
    690                 695                 700

Leu Ala Gln Ile Gln Asp Asn Lys Ile Leu Gln Val Val Asp Gly Ser
705                 710                 715                 720

Ile Lys Asp Lys Glu Leu Glu Gln Asp Met Gln Ala Leu Val Lys Leu
                725                 730                 735

Val Leu Gln Glu Asn Gly Gly Ala Val Asp Arg Asn Ile Arg His Thr
            740                 745                 750

Phe Leu Ser Val Ser Lys Thr Phe Tyr Tyr Asp Ala Tyr His Asp Asp
```

```
            755                 760                 765
Glu Thr Thr Asp Leu His Ile Phe Lys Val Leu Phe Arg Pro Val Val
    770                 775                 780

<210> SEQ ID NO 60
<211> LENGTH: 575
<212> TYPE: PRT
<213> ORGANISM: Salvia sclarea
<220> FEATURE:
<223> OTHER INFORMATION: SsTps1132 SPP
<300> PUBLICATION INFORMATION:
<310> PATENT DOCUMENT NUMBER: WO2009095366

<400> SEQUENCE: 60

Met Ser Leu Ala Phe Asn Val Gly Val Thr Pro Phe Ser Gly Gln Arg
  1               5                  10                  15

Val Gly Ser Arg Lys Glu Lys Phe Pro Val Gln Gly Phe Pro Val Thr
             20                  25                  30

Thr Pro Asn Arg Ser Arg Leu Ile Val Asn Cys Ser Leu Thr Thr Ile
         35                  40                  45

Asp Phe Met Ala Lys Met Lys Glu Asn Phe Lys Arg Glu Asp Asp Lys
     50                  55                  60

Phe Pro Thr Thr Thr Thr Leu Arg Ser Glu Asp Ile Pro Ser Asn Leu
 65                  70                  75                  80

Cys Ile Ile Asp Thr Leu Gln Arg Leu Gly Val Asp Gln Phe Phe Gln
                 85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
    130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
            260                 265                 270

Leu Gln Gln Leu Gln Arg Trp Tyr Ala Asp Cys Arg Leu Asp Thr Leu
        275                 280                 285

Asn Phe Gly Arg Asp Val Val Ile Ile Ala Asn Tyr Leu Ala Ser Leu
    290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335
```

```
Ser Ser Gln Glu Cys Asp Lys Ile Ile Glu Leu Val Lys Glu Trp Lys
            340                 345                 350

Glu Asn Pro Asp Ala Glu Tyr Gly Ser Glu Leu Glu Ile Leu Phe
            355                 360                 365

Met Ala Leu Tyr Asn Thr Val Asn Glu Leu Ala Glu Arg Ala Arg Val
370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Trp Leu Ser Asn Gly
            420                 425                 430

Ser Arg Leu Thr Gly Leu Leu Thr Met Gln Phe Val Gly Val Lys Leu
            435                 440                 445

Ser Asp Glu Met Leu Met Ser Glu Cys Thr Asp Leu Ala Arg His
            450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
            500                 505                 510

Ile Asn Glu Met Val Glu Tyr His Trp Arg Lys Val Leu Gln Ile Val
            515                 520                 525

Tyr Lys Lys Glu Ser Ile Leu Pro Arg Arg Cys Lys Asp Val Phe Leu
530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
            565                 570                 575

<210> SEQ ID NO 61
<211> LENGTH: 525
<212> TYPE: PRT
<213> ORGANISM: Salvia sclarea
<220> FEATURE:
<223> OTHER INFORMATION: SsTps1132-2-5 SPP
<300> PUBLICATION INFORMATION:
<310> PATENT DOCUMENT NUMBER: WO200905366

<400> SEQUENCE: 61

Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
            20                  25                  30

Ile Asp Thr Leu Gln Arg Leu Gly Val Asp Gln Phe Phe Gln Tyr Glu
        35                  40                  45

Ile Asn Thr Ile Leu Asp Asn Thr Phe Arg Leu Trp Gln Glu Lys His
    50                  55                  60

Lys Val Ile Tyr Gly Asn Val Thr Thr His Ala Met Ala Phe Arg Leu
65              70                  75                  80

Leu Arg Val Lys Gly Tyr Glu Val Ser Ser Glu Glu Leu Ala Pro Tyr
                85                  90                  95

Gly Asn Gln Glu Ala Val Ser Gln Thr Asn Asp Leu Pro Met Ile
            100                 105                 110
```

```
Ile Glu Leu Tyr Arg Ala Ala Asn Glu Arg Ile Tyr Glu Glu Arg
            115                 120                 125
Ser Leu Glu Lys Ile Leu Ala Trp Thr Thr Ile Phe Leu Asn Lys Gln
130                 135                 140
Val Gln Asp Asn Ser Ile Pro Asp Lys Lys Leu His Lys Leu Val Glu
145                 150                 155                 160
Phe Tyr Leu Arg Asn Tyr Lys Gly Ile Thr Ile Arg Leu Gly Ala Arg
                165                 170                 175
Arg Asn Leu Glu Leu Tyr Asp Met Thr Tyr Tyr Gln Ala Leu Lys Ser
            180                 185                 190
Thr Asn Arg Phe Ser Asn Leu Cys Asn Glu Asp Phe Leu Val Phe Ala
        195                 200                 205
Lys Gln Asp Phe Asp Ile His Glu Ala Gln Asn Gln Lys Gly Leu Gln
210                 215                 220
Gln Leu Gln Arg Trp Tyr Ala Asp Cys Arg Leu Asp Thr Leu Asn Phe
225                 230                 235                 240
Gly Arg Asp Val Val Ile Ile Ala Asn Tyr Leu Ala Ser Leu Ile Ile
                245                 250                 255
Gly Asp His Ala Phe Asp Tyr Val Arg Leu Ala Phe Ala Lys Thr Ser
            260                 265                 270
Val Leu Val Thr Ile Met Asp Asp Phe Phe Asp Cys His Gly Ser Ser
        275                 280                 285
Gln Glu Cys Asp Lys Ile Ile Glu Leu Val Lys Glu Trp Lys Glu Asn
290                 295                 300
Pro Asp Ala Glu Tyr Gly Ser Glu Glu Leu Glu Ile Leu Phe Met Ala
305                 310                 315                 320
Leu Tyr Asn Thr Val Asn Glu Leu Ala Glu Arg Ala Arg Val Glu Gln
                325                 330                 335
Gly Arg Ser Val Lys Glu Phe Leu Val Lys Leu Trp Val Glu Ile Leu
            340                 345                 350
Ser Ala Phe Lys Ile Glu Leu Asp Thr Trp Ser Asn Gly Thr Gln Gln
        355                 360                 365
Ser Phe Asp Glu Tyr Ile Ser Ser Ser Trp Leu Ser Asn Gly Ser Arg
370                 375                 380
Leu Thr Gly Leu Leu Thr Met Gln Phe Val Gly Val Lys Leu Ser Asp
385                 390                 395                 400
Glu Met Leu Met Ser Glu Glu Cys Thr Asp Leu Ala Arg His Val Cys
                405                 410                 415
Met Val Gly Arg Leu Leu Asn Asp Val Cys Ser Ser Glu Arg Glu Arg
            420                 425                 430
Glu Glu Asn Ile Ala Gly Lys Ser Tyr Ser Ile Leu Leu Ala Thr Glu
        435                 440                 445
Lys Asp Gly Arg Lys Val Ser Glu Asp Glu Ala Ile Ala Glu Ile Asn
450                 455                 460
Glu Met Val Glu Tyr His Trp Arg Lys Val Leu Gln Ile Val Tyr Lys
465                 470                 475                 480
Lys Glu Ser Ile Leu Pro Arg Arg Cys Lys Asp Val Phe Leu Glu Met
                485                 490                 495
Ala Lys Gly Thr Phe Tyr Ala Tyr Gly Ile Asn Asp Glu Leu Thr Ser
            500                 505                 510
Pro Gln Gln Ser Lys Glu Asp Met Lys Ser Phe Val Phe
        515                 520                 525
```

```
<210> SEQ ID NO 62
<211> LENGTH: 795
<212> TYPE: PRT
<213> ORGANISM: Salvia sclarea
<220> FEATURE:
<223> OTHER INFORMATION: SsTps1137
<300> PUBLICATION INFORMATION:
<310> PATENT DOCUMENT NUMBER: WO200905366

<400> SEQUENCE: 62
```

| | | | | | | | | | | | | | | |
|---|---|---|---|---|---|---|---|---|---|---|---|---|---|---|
| Met | Ser | Leu | Pro | Leu | Ser | Thr | Cys | Asn | Gly | Ser | His | Phe | Arg | Arg | Tyr |
| 1 | | | | 5 | | | | | 10 | | | | | 15 | |
| Arg | Leu | Ser | Pro | Ala | Ser | Ala | Ser | Met | Glu | Thr | Gly | Leu | Gln | Thr | Ala |
| | | | 20 | | | | | 25 | | | | | 30 | | |
| Thr | Ser | Ala | Lys | Ile | Ala | Ser | Met | Pro | Ala | Cys | Phe | Glu | Glu | Thr | Arg |
| | | 35 | | | | | 40 | | | | | 45 | | | |
| Gly | Arg | Ile | Ala | Lys | Leu | Phe | His | Lys | Asp | Glu | Leu | Ser | Val | Ser | Thr |
| | 50 | | | | | 55 | | | | | 60 | | | | |
| Tyr | Asp | Thr | Ala | Trp | Val | Ala | Met | Val | Pro | Ser | Pro | Thr | Ser | Leu | Glu |
| 65 | | | | | 70 | | | | | 75 | | | | | 80 |
| Glu | Pro | Cys | Phe | Pro | Asp | Cys | Leu | Asn | Trp | Leu | Leu | Glu | Asn | Gln | Cys |
| | | | | 85 | | | | | 90 | | | | | 95 | |
| His | Asp | Gly | Ser | Trp | Ala | Arg | Pro | His | His | Ser | Leu | Leu | Met | Lys |
| | | | 100 | | | | | 105 | | | | | 110 | | |
| Asp | Val | Leu | Ser | Ser | Thr | Leu | Ala | Cys | Ile | Leu | Ala | Leu | Lys | Lys | Trp |
| | | | 115 | | | | | 120 | | | | | 125 | | |
| Gly | Val | Gly | Glu | Lys | Gln | Ile | Asn | Arg | Gly | Leu | His | Phe | Met | Glu | Leu |
| | | 130 | | | | | 135 | | | | | 140 | | | |
| Asn | Phe | Ala | Ser | Ala | Thr | Glu | Lys | Cys | Gln | Ile | Thr | Pro | Met | Gly | Phe |
| 145 | | | | | 150 | | | | | 155 | | | | | 160 |
| Asp | Ile | Val | Phe | Pro | Ala | Met | Leu | Asp | Tyr | Ala | Arg | Asp | Phe | Ser | Leu |
| | | | | 165 | | | | | 170 | | | | | 175 | |
| Asp | Met | His | Leu | Glu | Pro | Thr | Thr | Leu | Asn | Asp | Leu | Ile | His | Lys | Arg |
| | | | 180 | | | | | 185 | | | | | 190 | | |
| Asp | Leu | Glu | Leu | Lys | Ser | Lys | Pro | Asp | Phe | Ser | Ser | Asp | Gly | Glu | Ala |
| | | | 195 | | | | | 200 | | | | | 205 | | |
| Tyr | Trp | Ala | Tyr | Ile | Ala | Glu | Gly | Met | Gly | Asn | Leu | Arg | Asn | Trp | Glu |
| | 210 | | | | | 215 | | | | | 220 | | | | |
| Ser | Val | Met | Lys | Tyr | Gln | Arg | Arg | Asn | Gly | Ser | Leu | Phe | Asn | Cys | Pro |
| 225 | | | | | 230 | | | | | 235 | | | | | 240 |
| Ser | Thr | Thr | Ala | Ala | Ala | Phe | Val | Ala | Leu | Gly | Asn | Ser | Asp | Cys | Leu |
| | | | | 245 | | | | | 250 | | | | | 255 | |
| Asn | Tyr | Leu | His | Ser | Ala | Leu | Lys | Lys | Phe | Gly | Asn | Ala | Val | Pro | Ala |
| | | | 260 | | | | | 265 | | | | | 270 | | |
| Val | Tyr | Pro | Leu | Asp | Ile | Tyr | Ser | His | Leu | Cys | Ile | Val | Asp | Asn | Leu |
| | | | 275 | | | | | 280 | | | | | 285 | | |
| Glu | Arg | Leu | Gly | Ile | Ser | Arg | Tyr | Phe | Leu | Thr | Glu | Ile | Gln | Ser | Val |
| | | 290 | | | | | 295 | | | | | 300 | | | |
| Leu | Asp | Glu | Thr | His | Arg | Cys | Trp | Met | Gln | Gly | Asn | Glu | Glu | Ile | Phe |
| 305 | | | | | 310 | | | | | 315 | | | | | 320 |
| Met | Asp | Ala | Ser | Thr | Cys | Ala | Leu | Ala | Phe | Arg | Ile | Leu | Arg | Leu | Asn |
| | | | | 325 | | | | | 330 | | | | | 335 | |
| Gly | Tyr | Asp | Val | Thr | Ser | Asp | Pro | Val | Thr | Lys | Ile | Gln | His | Glu | Cys |
| | | | 340 | | | | | 345 | | | | | 350 | | |
| Phe | Ser | Ser | Ser | Phe | His | Gly | Asn | Val | Met | Asp | Ile | Asn | Thr | Thr | Leu |
| | | | 355 | | | | | 360 | | | | | 365 | | |

```
Glu Leu Tyr Arg Ala Ser Glu Leu Ile Leu Tyr Pro Asp Glu Arg Asp
    370                 375                 380
Leu Val Arg Gln Asn Leu Arg Leu Lys Gln Ile Leu Glu Gln Glu Leu
385                 390                 395                 400
Ser Asn Gly Phe Ile Gln Ser Cys Gln Leu Gly Arg Ser Val Asn Ala
                405                 410                 415
Glu Val Asn Gln Ala Ile Glu Tyr Pro Phe Tyr Ala Ile Met Asp Arg
            420                 425                 430
Val Ala Lys Arg Lys Asn Ile Glu Asn Tyr Asn Phe Asp Asn Thr Arg
        435                 440                 445
Ile Leu Lys Thr Ser Tyr Cys Ser Pro Asn Phe Gly Asn Lys Asp Phe
    450                 455                 460
Leu Phe Leu Ser Val Glu Asp Phe Asn Leu Cys Gln Ala Thr His Arg
465                 470                 475                 480
Glu Glu Leu Arg Glu Leu Glu Arg Trp Val Glu Asn Arg Leu Asp
                485                 490                 495
Glu Leu Gln Phe Ala Arg Ser Lys Ser Ala Tyr Cys Tyr Phe Ser Ala
            500                 505                 510
Ala Ala Thr Phe Ser Ala Pro Glu Leu Arg Asp Ala Arg Met Ser Trp
        515                 520                 525
Ala Lys Gly Gly Val Leu Thr Thr Val Ile Asp Asp Phe Phe Asp Val
    530                 535                 540
Gly Gly Ser Met Glu Glu Leu Lys Asn Leu Ile His Leu Val Glu Lys
545                 550                 555                 560
Trp Asp Val Asp Val Ser Thr Glu Cys Ser Ser His Asn Val Gln Ile
                565                 570                 575
Ile Phe Ser Ala Leu Lys Ser Thr Ile Arg Glu Ile Gly Tyr Lys Gly
            580                 585                 590
Leu Lys Leu Gln Gly Arg Cys Ile Thr Asn His Ile Ile Gly Ile Trp
        595                 600                 605
Leu Asp Leu Leu Asn Ser Met Met Lys Glu Thr Glu Trp Ala Arg Asp
    610                 615                 620
Asn Tyr Val Pro Thr Ile Asp Glu Tyr Met Ser Asn Ala Tyr Val Ser
625                 630                 635                 640
Phe Ala Leu Gly Pro Ile Val Leu Pro Thr Leu Tyr Leu Val Gly Pro
                645                 650                 655
Lys Leu Ser Glu Glu Met Ala Asn His Pro Glu Tyr Tyr Lys Leu Phe
            660                 665                 670
Lys Leu Met Ser Thr Cys Gly Arg Leu Leu Asn Asp Ile Arg Gly Tyr
        675                 680                 685
Glu Arg Glu Leu Lys Asp Gly Lys Leu Asn Ala Leu Ser Leu Tyr Met
    690                 695                 700
Ala Asn His Gly Gly Glu Val Ser Lys Glu Ala Ile Ser Glu Ile
705                 710                 715                 720
Lys Ser Trp Ile Glu Ser Ser Arg Arg Glu Leu Leu Arg Leu Val Leu
                725                 730                 735
Glu Gly Lys Lys Ser Val Leu Pro Lys Pro Cys Lys Glu Leu Phe Trp
            740                 745                 750
His Met Cys Ser Val Val His Leu Phe Tyr Ser Lys Asp Asp Gly Phe
        755                 760                 765
Thr Ser Gln Asp Leu Ile Gln Val Val Asn Ala Ile Ile His Lys Pro
    770                 775                 780
```

```
Ile Val Leu Lys Glu Gln Thr Gly Ala Arg Ile
785                 790                 795
```

<210> SEQ ID NO 63
<211> LENGTH: 45
<212> TYPE: DNA
<213> ORGANISM: Artificial Sequence
<220> FEATURE:
<223> OTHER INFORMATION: 40-145.5 primer

<400> SEQUENCE: 63

```
ctcggtacca tttaaaaaaa tggattacgc gaacatcctc acagc            45
```

<210> SEQ ID NO 64
<211> LENGTH: 40
<212> TYPE: DNA
<213> ORGANISM: Artificial Sequence
<220> FEATURE:
<223> OTHER INFORMATION: 40-145.6 primer

<400> SEQUENCE: 64

```
ccgtctagat cacagaggga tatcggctag cttttttcagg                 40
```

<210> SEQ ID NO 65
<211> LENGTH: 7880
<212> TYPE: DNA
<213> ORGANISM: Artificial Sequence
<220> FEATURE:
<223> OTHER INFORMATION: pALX24-126.2 vector

<400> SEQUENCE: 65

```
aacacgcttt ttcagttcga gtttatcatt atcaatactg ccatttcaaa gaatacgtaa     60
ataattaata gtagtgattt tcctaacttt atttagtcaa aaattagcc ttttaattct    120
gctgtaaccc gtacatgccc aaaataggggg gcgggttaca cagaatatat aacatcgtag    180
gtgtctgggt gaacagttta ttcctggcat ccactaaata taatggagcc cgcttttttaa    240
gctggcatcc agaaaaaaaa agaatcccag caccaaaata ttgttttctt caccaaccat    300
cagttcatag gtccattctc ttagcgcaac tacagagaac aggggcacaa acaggcaaaa    360
aacgggcaca acctcaatgg agtgatgcaa cctgcctgga gtaaatgatg acacaaggca    420
attgacccac gcatgtatct atctcatttt cttacacctt ctattacctt ctgctctctc    480
tgatttggaa aaagctgaaa aaaaaggttg aaaccagttc cctgaaatta ttcccctact    540
tgactaataa gtatataaag acggtaggta ttgattgtaa ttctgtaaat ctatttctta    600
aacttcttaa attctacttt tatagttagt ctttttttta gttttaaaac accagaact    660
tagtttcgaa taaacacaca taaacaaacc caggtaccac ggctttaaaa aaatgtcatc    720
tggtgaaact tttagaccaa ctgctgattt tcatccatct ttgtggagaa atcattttt    780
gcaaggtgca tcagatttta agactgttga tcatacagct acaaatgaaa gacatgaagc    840
tttgaaggaa gaagttagaa gaatgattac tgatgcagaa gatcaaccaa ttcaaaaatt    900
gagattgatt gatgaagttc aaagattggg tgttgcttac ttttttgaaa agaaattga    960
agatgctatt caacaattgt gtccaattca tattgattct gataaagctg atttgcatac   1020
tgtttctttg catttcagat tgttgagaca acaaggtatt aagatttctt gtgatgtttt   1080
cgaacaattt aaggatgatg aaggtagatt caaaagttct ttgattaatg atgttcaagg   1140
catgttgtct ttgtatgaag ctgcttatat ggctgtagga ggtgaacata ttttggatga   1200
agctattgca tttactacta ctcatttgca atcattggtt gcacaagatc atgttactcc   1260
```

```
aagattggct gaacaaatta accatgcttt gtatagacca ttgagaaaaa ctttgccaag    1320
attggaagca agatacatta tgtcaagaat tgattctact tctgatgatt tggttaacaa    1380
gactttgtta aatttcgcta agttggattt caatattttg ttggatttgc ataaagaaga    1440
attgaacgaa ttgactaaat ggtggcaaga tttggatttt actactaaat tgccatatgc    1500
tagagataga ttggttgaat tgtacttttg ggatttgggt acttattttg aaccacaata    1560
cgcttttggt agaaaaatca tgactaaatt gaactacatt ttgtccatta ttgatgatac    1620
ctacgatgct tacggtactt tggaagaatt gtctttgttc accgaagctg ttgctcgttg    1680
gaacattgaa gctgttgaca tgttgccaga ttatatgaag ttaatctaca gaactttgtt    1740
ggatacattc aacgaaatag aagaggatat ggctaaacaa ggtagatctc attgtgtaag    1800
atacgctaaa gaagaaattc aaaaggttat tggtgcttat tacgttcaag ctaagtggtt    1860
ttctgaaggt tatgtcccta ctattgaaga atacatgcca attgctttga cttcttgcgc    1920
ttacagattt gttattacca attctttttt gggtatgggt gatttcgcta caaaggaagt    1980
attcgaatgg atttctggta atccaaaagt tgttaaatct gcttctgtta tttgtagatt    2040
gatggacgat atgcaaggac acgaatttga acaaaaaaga ggtcacgttg catctgcaat    2100
tgaatgctat actaaacaac atggtgtttc caaggaagag gctatcaaga tgttcgagga    2160
agaggttgct aacgcttgga aggatatcaa tgaagaatta atgatgaaac caccagttgt    2220
tgctagacca ttgttaggta ctattttgaa tttggctaga gctatcgatt ttatctataa    2280
agaagatgac ggttacactc attcttattt gattaaggaa caaatagcat ctgttttggg    2340
tgatcatgtt ccatttttaat ctagaaactg cgtgcacttc gtggccgagg agcaggactg    2400
acacgtccga cggcggccca cgggtcccag gcctcggaga tccgtccccc ttttcctttg    2460
tcgatatcat gtaattagtt atgtcacgct tacattcacg ccctccccc acatccgctc    2520 taaccgaaaa ggaaggagtt agacaacctg aagtctaggt ccctattat ttttttatag    2580 ttatgttagt attaagaacg ttatttatat ttcaaatttt tcttttttt ctgtacagac    2640 gcgtgtacgc atgtaacatt atactgaaaa ccttgcttga aaggttttg ggacgctcga    2700 aggctttaat ttgcaagctg aattgtaccg ggcccggatc ctctaggctt ggcactggcc    2760
gtcgttttac aacgtcgtga ctgggaaaac cctggcgtta cccaacttaa tcgccttgca    2820
gcacatcccc ctttcgccag ctggcgtaat agcgaagagg cccgcaccga tcgcccttcc    2880
caacagttgc gcagcctgaa tggcgaatgg cgcctgatgc ggtattttct ccttacgcat    2940
ctgtgcggta tttcacaccg catagggtaa taactgatat aattaaattg aagctctaat    3000
ttgtgagttt agtatacatg catttactta taatacagtt tttagtttt gctggccgca    3060 tcttctcaaa tatgcttccc agcctgcttt tctgtaacgt tcaccctcta ccttagcatc    3120
ccttcccttt gcaaatagtc ctcttccaac aataataatg tcagatcctg tagagaccac    3180
atcatccacg gttctatact gttgacccaa tgcgtctccc ttgtcatcta aacccacacc    3240
gggtgtcata atcaaccaat cgtaaccttc atctcttcca cccatgtctc tttgagcaat    3300
aaagccgata acaaaatctt tgtcgctctt cgcaatgtca acagtaccct tagtatattc    3360
tccagtagat agggagccct tgcatgacaa ttctgctaac atcaaaaggc ctctaggttc    3420
ctttgttact tcttctgccg cctgcttcaa accgctaaca atacctgggc ccaccacacc    3480
gtgtgcattc gtaatgtctg cccattctgc tattctgtat acaccgcag agtactgcaa    3540 tttgactgta ttaccaatgt cagcaaattt tctgtcttcg aagagtaaaa aattgtactt    3600
ggcggataat gcctttagcg gcttaactgt gccctccatg gaaaaatcag tcaagatatc    3660
```

```
cacatgtgtt tttagtaaac aaattttggg acctaatgct tcaactaact ccagtaattc   3720
cttggtggta cgaacatcca atgaagcaca caagtttgtt tgcttttcgt gcatgatatt   3780
aaatagcttg gcagcaacag gactaggatg agtagcagca cgttccttat atgtagcttt   3840
cgacatgatt tatcttcgtt tcggttttttg ttctgtgcag ttgggttaag aatactgggc   3900
aatttcatgt ttcttcaaca ctacatatgc gtatatatac caatctaagt ctgtgctcct   3960
tccttcgttc ttccttctgt tcggagatta ccgaatcaaa aaaatttcaa ggaaaccgaa   4020
atcaaaaaaa agaataaaaa aaaaatgatg aattgaaaag cacttgttac ccatcattga   4080
attttgaaca tccgaacctg ggagttttcc ctgaaacaga tagtatattt gaacctgtat   4140
aataatatat agtctagcgc tttacggaag acaatgtatg tatttcggtt cctggagaaa   4200
ctattgcatc tattgcatag gtaatcttgc acgtcgcatc cccggttcat tttctgcgtt   4260
tccatcttgc acttcaatag catatctttg ttaacgaagc atctgtgctt cattttgtaa   4320
aacaaaaatg caacgcgaga gcgctaattt ttcaaacaaa gaatctgagc tgcattttta   4380
cagaacagaa atgcaacgcg aaagcgctat tttaccaacg aagaatctgt gcttcatttt   4440
tgtaaaacaa aaatgcaacg cgagagcgct aattttttcaa acaaagaatc tgagctgcat   4500
ttttacagaa cagaaatgca acgcgagagc gctattttac caacaaagaa tctatacttc   4560 tttttttgttc tacaaaaatg catcccgaga gcgcttattt tctaacaaag catcttagat   4620
tacttttttt ctcctttgtg cgctctataa tgcagtctct tgataacttt ttgcactgta   4680
ggtccgttaa ggttagaaga aggctacttt ggtgtctatt ttctcttcca taaaaaaagc   4740
ctgactccac ttcccgcgtt tactgattac tagcgaagct gcgggtgcat tttttcaaga   4800
taaaggcatc cccgattata ttctataccg atgtggattg cgcatacttt gtgaacagaa   4860
agtgatagcg ttgatgattc ttcattggtc agaaaattat gaacggtttc ttctattttg   4920
tctctatata ctacgtatag gaaatgttta cattttcgta ttgttttcga ttcactctat   4980
gaatagttct tactacaatt tttttgtcta aagagtaata ctagagataa acataaaaaa   5040
tgtagaggtc gagtttagat gcaagttcaa ggagcgaaag gtggatgggt aggttatata   5100
gggatatagc acagagatat atagcaaaga gatacttttg agcaatgttt gtggaagcgg   5160
tattcgcaat attttagtag ctcgttacag tccggtgcgt ttttggtttt ttgaaagtgc   5220
gtcttcagag cgcttttggt tttcaaaagc gctctgaagt tcctatactt tctagctaga   5280
gaataggaac ttcggaatag gaacttcaaa gcgtttccga aaacgagcgc ttccgaaaat   5340
gcaacgcgag ctgcgcacat acagctcact gttcacgtcg cacctatatc tgcgtgttgc   5400
ctgtatatat atatacatga gaagaacggc atagtgcgtg tttatgctta aatgcgttat   5460
ggtgcactct cagtacaatc tgctctgatg ccgcatagtt aagccagccc cgacacccgc   5520
caacacccgc tgacgcgccc tgacgggctt gtctgctccc ggcatccgct tacagacaag   5580
ctgtgaccgt ctccgggagc tgcatgtgtc agaggttttc accgtcatca ccgaaacgcg   5640
cgagacgaaa gggcctcgtg atacgcctat ttttataggt taatgtcatg ataataatgg   5700
tttcttagac gtcaggtggc acttttcggg gaaatgtgcg cggaacccct atttgtttat   5760
ttttctaaat acattcaaat atgtatccgc tcatgagaca ataaccctga taaatgcttc   5820
aataatattg aaaaggaag agtatgagta ttcaacattt ccgtgtcgcc cttattccct   5880
tttttgcggc attttgcctt cctgtttttg ctcacccaga aacgctggtg aaagtaaaag   5940
atgctgaaga tcagttgggt gcacgagtgg gttacatcga actggatctc aacagcggta   6000
```

```
agatccttga gagttttcgc cccgaagaac gttttccaat gatgagcact tttaaagttc    6060
tgctatgtgg cgcggtatta tcccgtattg acgccgggca agagcaactc ggtcgccgca    6120
tacactattc tcagaatgac ttggttgagt actcaccagt cacagaaaag catcttacgg    6180
atggcatgac agtaagagaa ttatgcagtg ctgccataac catgagtgat aacactgcgg    6240
ccaacttact tctgacaacg atcggaggac cgaaggagct aaccgctttt ttgcacaaca    6300
tgggggatca tgtaactcgc cttgatcgtt gggaaccgga gctgaatgaa gccataccaa    6360
acgacgagcg tgacaccacg atgcctgtag caatggcaac aacgttgcgc aaactattaa    6420
ctggcgaact acttactcta gcttcccggc aacaattaat agactggatg gaggcggata    6480
aagttgcagg accacttctg cgctcggccc ttccggctgg ctggtttatt gctgataaat    6540
ctggagccgg tgagcgtggg tctcgcggta tcattgcagc actggggcca gatggtaagc    6600
cctcccgtat cgtagttatc tacacgacgg ggagtcaggc aactatggat gaacgaaata    6660
gacagatcgc tgagataggt gcctcactga ttaagcattg gtaactgtca gaccaagttt    6720
actcatatat actttagatt gatttaaaac ttcatttttta atttaaaagg atctaggtga    6780 agatccttttt tgataatctc atgaccaaaa tcccttaacg tgagttttcg ttccactgag    6840
cgtcagaccc cgtagaaaag atcaaaggat cttcttgaga tcctttttttt ctgcgcgtaa    6900 tctgctgctt gcaaacaaaa aaaccaccgc taccagcggt ggtttgtttg ccggatcaag    6960
agctaccaac tcttttttccg aaggtaactg gcttcagcag agcgcagata ccaaatactg    7020
ttcttctagt gtagccgtag ttaggccacc acttcaagaa ctctgtagca ccgcctacat    7080
accacgctct gctaatcctg ttaccagtgg ctgctgccag tggcgataag tcgtgtctta    7140
ccgggttgga ctcaagacga tagttaccgg ataaggcgca gcggtcgggc tgaacggggg    7200
gttcgtgcac acagcccagc ttggagcgaa cgacctacac cgaactgaga tacctacagc    7260
gtgagctatg agaaagcgcc acgcttcccg aagggagaaa ggcggacagg tatccggtaa    7320
gcggcagggt cggaacagga gagcgcacga gggagcttcc agggggaaac gcctggtatc    7380
tttatagtcc tgtcgggttt cgccacctct gacttgagcg tcgatttttg tgatgctcgt    7440
caggggggcg gagcctatgg aaaaacgcca gcaacgcggc ctttttacgg ttcctggcct    7500
tttgctggcc ttttgctcac atgttctttc ctgcgttatc ccctgattct gtggataacc    7560
gtattaccgc ctttgagtga gctgataccg ctcgccgcag ccgaacgacc gagcgcagcg    7620
agtcagtgag cgaggaagcg gaagagcgcc caatacgcaa accgcctctc cccgcgcgtt    7680
ggccgattca ttaatgcagc tggcacgaca ggtttcccga ctggaaagcg ggcagtgacg    7740
caacgcaatt aatgtgagtt agctcactca ttaggcaccc caggctttac actttatgct    7800
tccggctcgt atgttgtgtg gaattgtgag cggataacaa tttcacacag gaaacagcta    7860
tgacatgatt acgcggccgc                                                7880
```

<210> SEQ ID NO 66
<211> LENGTH: 7360
<212> TYPE: DNA
<213> ORGANISM: Artificial Sequence
<220> FEATURE:
<223> OTHER INFORMATION: pALX40-152.2 crtE vector

<400> SEQUENCE: 66

```
ctagaaactg cgtgcacttc gtggccgagg agcaggactg acacgtccga cggcggccca      60
cgggtcccag gcctcggaga tccgtccccc ttttcctttg tcgatatcat gtaattagtt     120
atgtcacgct tacattcacg ccctcccccc acatccgctc taaccgaaaa ggaaggagtt     180
```

```
agacaacctg aagtctaggt ccctatttat ttttttatag ttatgttagt attaagaacg    240
ttatttatat ttcaaatttt tcttttttt  ctgtacagac gcgtgtacgc atgtaacatt    300
atactgaaaa ccttgcttga aaggttttg  ggacgctcga aggctttaat ttgcaagctg    360
aattgtaccg ggcccggatc ctctaggctt ggcactggcc gtcgttttac aacgtcgtga    420
ctgggaaaac cctggcgtta cccaacttaa tcgccttgca gcacatcccc ctttcgccag    480
ctggcgtaat agcgaagagg cccgcaccga tcgcccttcc caacagttgc gcagcctgaa    540
tggcgaatgg cgcctgatgc ggtattttct ccttacgcat ctgtgcggta tttcacaccg    600
catagggtaa taactgatat aattaaattg aagctctaat ttgtgagttt agtatacatg    660
catttactta taatacagtt ttttagtttt gctggccgca tcttctcaaa tatgcttccc    720
agcctgcttt tctgtaacgt tcaccctcta ccttagcatc ccttcccttt gcaaatagtc    780
ctcttccaac aataataatg tcagatcctg tagagaccac atcatccacg gttctatact    840
gttgacccaa tgcgtctccc ttgtcatcta aacccacacc gggtgtcata atcaaccaat    900
cgtaaccttc atctcttcca cccatgtctc tttgagcaat aaagccgata acaaaatctt    960
tgtcgctctt cgcaatgtca acagtaccct tagtatattc tccagtagat agggagccct   1020
tgcatgacaa ttctgctaac atcaaaaggc ctctaggttc ctttgttact tcttctgccg   1080
cctgcttcaa accgctaaca atacctgggc ccaccacacc gtgtgcattc gtaatgtctg   1140
cccattctgc tattctgtat acacccgcag agtactgcaa tttgactgta ttaccaatgt   1200
cagcaaattt tctgtcttcg aagagtaaaa aattgtactt ggcggataat gcctttagcg   1260
gcttaactgt gccctccatg gaaaaatcag tcaagatatc cacatgtgtt tttagtaaac   1320
aaattttggg acctaatgct tcaactaact ccagtaattc cttggtggta cgaacatcca   1380
atgaagcaca caagtttgtt tgcttttcgt gcatgatatt aaatagcttg gcagcaacag   1440
gactaggatg agtagcagca cgttccttat atgtagcttt cgacatgatt tatcttcgtt   1500 tcggttttg  ttctgtgcag ttgggttaag aatactgggc aatttcatgt ttcttcaaca   1560
ctacatatgc gtatatatac caatctaagt ctgtgctcct tccttcgttc ttccttctgt   1620
tcggagatta ccgaatcaaa aaaatttcaa ggaaaccgaa atcaaaaaaa agaataaaaa   1680
aaaaatgatg aattgaaaag cacttgttac ccatcattga attttgaaca tccgaacctg   1740
ggagttttcc ctgaaacaga tagtatattt gaacctgtat aataatatat agtctagcgc   1800
tttacggaag acaatgtatg tatttcggtt cctggagaaa ctattgcatc tattgcatag   1860
gtaatcttgc acgtcgcatc cccggttcat tttctgcgtt tccatcttgc acttcaatag   1920
catatctttg ttaacgaagc atctgtgctt cattttgtaa aacaaaaatg caacgcgaga   1980
gcgctaattt ttcaaacaaa gaatctgagc tgcatttta  cagaacagaa atgcaacgcg   2040
aaagcgctat tttaccaacg aagaatctgt gcttcatttt tgtaaaacaa aaatgcaacg   2100
cgagagcgct aattttcaa  acaaagaatc tgagctgcat ttttacgaa  cagaaatgca   2160 acgcgagagc gctattttac caacaaagaa tctatacttc ttttttgttc tacaaaaatg   2220
catcccgaga cgctatttt  tctaacaaag catcttagat tactttttt  ctcctttgtg   2280 cgctctataa tgcagtctct tgataacttt ttgcactgta ggtccgttaa ggttagaaga   2340
aggctacttt ggtgtctatt ttctcttcca taaaaaaagc ctgactccac ttcccgcgtt   2400
tactgattac tagcgaagct gcgggtgcat ttttcaaga  taaaggcatc ccgattata    2460 ttctataccg atgtggattg cgcatacttt gtgaacagaa agtgatagcg ttgatgattc   2520
```

```
ttcattggtc agaaaattat gaacggtttc ttctattttg tctctatata ctacgtatag    2580
gaaatgttta cattttcgta ttgttttcga ttcactctat gaatagttct tactacaatt    2640
tttttgtcta aagagtaata ctagagataa acataaaaaa tgtagaggtc gagtttagat    2700
gcaagttcaa ggagcgaaag gtggatgggt aggttatata gggatatagc acagagatat    2760
atagcaaaga gatactttg agcaatgttt gtggaagcgg tattcgcaat attttagtag     2820
ctcgttacag tccggtgcgt ttttggtttt ttgaaagtgc gtcttcagag cgcttttggt    2880
tttcaaaagc gctctgaagt tcctatactt tctagctaga gaataggaac ttcggaatag    2940
gaacttcaaa gcgtttccga aaacgagcgc ttccgaaaat gcaacgcgag ctgcgcacat    3000
acagctcact gttcacgtcg cacctatatc tgcgtgttgc ctgtatatat atatacatga    3060
gaagaacggc atagtgcgtg tttatgctta aatgcgttat ggtgcactct cagtacaatc    3120
tgctctgatg ccgcatagtt aagccagccc cgacacccgc caacacccgc tgacgcgccc    3180
tgacgggctt gtctgctccc ggcatccgct tacagacaag ctgtgaccgt ctccgggagc    3240
tgcatgtgtc agaggttttc accgtcatca ccgaaacgcg cgagacgaaa gggcctcgtg    3300
atacgcctat ttttataggt taatgtcatg ataataatgg tttcttagac gtcaggtggc    3360
acttttcggg gaaatgtgcg cggaacccct atttgtttat ttttctaaat acattcaaat    3420
atgtatccgc tcatgagaca ataaccctga taaatgcttc aataatattg aaaaaggaag    3480
agtatgagta ttcaacattt ccgtgtcgcc cttattccct tttttgcggc attttgcctt    3540
cctgttttg ctcacccaga aacgctggtg aaagtaaaag atgctgaaga tcagttgggt      3600
gcacgagtgg gttacatcga actggatctc aacagcggta agatccttga gttttcgc       3660
cccgaagaac gttttccaat gatgagcact tttaaagttc tgctatgtgg cgcggtatta    3720
tcccgtattg acgccgggca agagcaactc ggtcgccgca tacactattc tcagaatgac    3780
ttggttgagt actcaccagt cacagaaaag catcttacgg atggcatgac agtaagagaa    3840
ttatgcagtg ctgccataac catgagtgat aacactgcgg ccaacttact tctgacaacg    3900
atcggaggac cgaaggagct aaccgctttt ttgcacaaca tgggggatca tgtaactcgc    3960
cttgatcgtt gggaaccgga gctgaatgaa gccataccaa acgacgagcg tgacaccacg    4020
atgcctgtag caatggcaac aacgttgcgc aaactattaa ctggcgaact acttactcta    4080
gcttcccggc aacaattaat agactggatg gaggcggata agttgcagg accacttctg     4140
cgctcggccc ttccggctgg ctggtttatt gctgataaat ctggagccgg tgagcgtggg    4200
tctcgcggta tcattgcagc actggggcca gatggtaagc cctcccgtat cgtagttatc    4260
tacacgacgg ggagtcaggc aactatggat gaacgaaata gacagatcgc tgagataggt    4320
gcctcactga ttaagcattg gtaactgtca gaccaagttt actcatatat actttagatt    4380
gatttaaaac ttcattttta atttaaaagg atctaggtga agatccttt tgataatctc     4440
atgaccaaaa tcccttaacg tgagttttcg ttccactgag cgtcagaccc cgtagaaaag    4500
atcaaaggat cttcttgaga tcctttttt ctgcgcgtaa tctgctgctt gcaaacaaaa     4560
aaaccaccgc taccagcggt ggtttgtttg ccggatcaag agctaccaac tcttttccg     4620
aaggtaactg gcttcagcag agcgcagata ccaaatactg ttcttctagt gtagccgtag    4680
ttaggccacc acttcaagaa ctctgtagca ccgcctacat accacgctct gctaatcctg    4740
ttaccagtgg ctgctgccag tggcgataag tcgtgtctta ccgggttgga ctcaagacga    4800
tagttaccgg ataaggcgca gcggtcgggc tgaacggggg gttcgtgcac acagcccagc    4860
ttggagcgaa cgacctacac cgaactgaga tacctacagc gtgagctatg agaaagcgcc    4920
```

```
acgcttcccg aagggagaaa ggcggacagg tatccggtaa gcggcagggt cggaacagga    4980
gagcgcacga gggagcttcc aggggggaaac gcctggtatc tttatagtcc tgtcgggttt    5040
cgccacctct gacttgagcg tcgattttg tgatgctcgt caggggggcg gagcctatgg     5100
aaaaacgcca gcaacgcggc cttttttacgg ttcctggcct tttgctggcc ttttgctcac   5160
atgttctttc ctgcgttatc ccctgattct gtggataacc gtattaccgc ctttgagtga    5220
gctgataccg ctcgccgcag ccgaacgacc gagcgcagcg agtcagtgag cgaggaagcg    5280
gaagagcgcc caatacgcaa accgcctctc cccgcgcgtt ggccgattca ttaatgcagc    5340
tggcacgaca ggtttcccga ctggaaagcg ggcagtgacg caacgcaatt aatgtgagtt    5400
agctcactca ttaggcaccc caggctttac actttatgct tccggctcgt atgttgtgtg    5460
gaattgtgag cggataacaa tttcacacag gaaacagcta tgacatgatt acgcggccgc    5520
aacacgcttt ttcagttcga gtttatcatt atcaatactg ccatttcaaa gaatacgtaa    5580
ataattaata gtagtgattt tcctaacttt atttagtcaa aaaattagcc ttttaattct    5640
gctgtaaccc gtacatgccc aaaatagggg gcgggttaca cagaatatat aacatcgtag    5700
gtgtctgggt gaacagttta ttcctggcat ccactaaata taatgagcc cgcttttttaa    5760 gctggcatcc agaaaaaaaa agaatcccag caccaaaata ttgtttcttt caccaaccat    5820
cagttcatag gtccattctc ttagcgcaac tacagagaac aggggcacaa acaggcaaaa    5880
aacgggcaca acctcaatgg agtgatgcaa cctgcctgga gtaaatgatg acacaaggca    5940
attgacccac gcatgtatct atctcatttt cttacacctt ctattacctt ctgctctctc    6000
tgatttggaa aaagctgaaa aaaaaggttg aaaccagttc cctgaaatta ttccccctact   6060 tgactaataa gtatataaag acggtaggta ttgattgtaa ttctgtaaat ctatttctta    6120
aacttcttaa attctacttt tatagttagt ctttttttta gttttaaaac accaagaact    6180
tagtttcgaa taaacacaca taaacaaacc caggtaccat ttaaaaaaat ggattacgcg    6240
aacatcctca cagcaattcc actcgagttt actcctcagg atgatatcgt gctccttgaa    6300
ccgtatcact acctaggaaa gaaccctgga aagaaaattc gatcacaact catcgaggct    6360
ttcaactatt ggttggatgt caagaaggag gatctcgagg tcatccagaa cgttgttggc    6420
atgctacata ccgctagctt attaatggac gatgtggagg attcatcggt cctcaggcgt    6480
gggtcgcctg tggcccatct aatttacggg attccgcaga caataaacac tgcaaactac    6540
gtctactttc tggcttatca agagatcttc aagcttcgcc caacaccgat acccatgcct    6600
gtaattcctc cttcatctgc ttcgcttcaa tcatccgtct cctctgcatc ctcctcctcc    6660
tcggcctcgt ctgaaaacgg gggcacgtca actcctaatt cgcagattcc gttctcgaaa    6720
gatacgtatc ttgataaagt gatcacagac gagatgcttt ccctccatag agggcaaggc    6780
ctggagctat tctggagaga tagtctgacg tgtcctagcg aagaggaata tgtgaaaatg    6840
gttcttggaa agacgggagg tttgttccgt atagcggtca gattgatgat ggcaaagtca    6900
gaatgtgaca tagactttgt ccagcttgtc aacttgatct caatatactt ccagatcagg    6960
gatgactata tgaaccttca gtcttctgag tatgcccata ataagaattt tgcagaggac    7020
ctcacagaag ggaaattcag ttttcccact atccactcga ttcatgccaa ccctcatcg     7080 agactcgtca tcaatacgtt gcagaagaaa tcgacctctc ctgagatcct tcaccactgt    7140
gtaaactaca tgcgcacaga aacccactca ttcgaatata tccaggaagt cctcaacacc    7200
ttgtcaggtg cactcgagag agaactagga aggcttcaag gagagttcgc agaagctaac    7260
```

```
tcaaggatgg atcttggaga cgtagattcg gaaggaagaa cggggaagaa cgtcaaattg    7320
gaagcgatcc tgaaaaagct agccgatatc cctctgtgat                          7360

<210> SEQ ID NO 67
<211> LENGTH: 51
<212> TYPE: DNA
<213> ORGANISM: Artificial Sequence
<220> FEATURE:
<223> OTHER INFORMATION: 30-173.3 primer

<400> SEQUENCE: 67
ctcggtacca tttaaaaaaa tgtgcgcacc tattgatgca agttatcttg g              51

<210> SEQ ID NO 68
<211> LENGTH: 38
<212> TYPE: DNA
<213> ORGANISM: Artificial Sequence
<220> FEATURE:
<223> OTHER INFORMATION: 30-173.4 primer

<400> SEQUENCE: 68
ctctctagat tactggactt gctgtaaaag caccttgg                             38

<210> SEQ ID NO 69
<211> LENGTH: 7540
<212> TYPE: DNA
<213> ORGANISM: Artificial Sequence
<220> FEATURE:
<223> OTHER INFORMATION: pALX40-3.1 vector

<400> SEQUENCE: 69
atagcttcaa aatgtttcta ctccttttttt actcttccag attttctcgg actccgcgca    60
tcgccgtacc acttcaaaac acccaagcac agcatactaa atttccctc tttcttcctc    120 tagggtgtcg ttaattaccc gtactaaagg tttggaaaag aaaaaagaga ccgcctcgtt    180
tcttttcctt cgtcgaaaaa ggcaataaaa attttatca cgtttctttt tcttgaaaat    240
tttttttttt gatttttttc tctttcgatg acctcccatt gatatttaag ttaataaacg    300
gtcttcaatt tctcaagttt cagtttcatt tttcttgttc tattacaact ttttttactt    360
cttgctcatt agaaagaaag catagcaatc taatctaagt tttggtacca cggctttaaa    420
aaaatggccc cagctatagt gatgagtaac tacgaagagg aggagattgt tcgccctgtt    480
gcagattttt ctccaagtct ttggggtgat cgtttccatt cattctcagt tgacaatcag    540
gttgcggaaa agtatgctca agagattgaa actttgaagg aacaaacaag tactatgttg    600
tctgctgctt gtggaacaac attgactgag aaattgaatt tgatagatat tattgagcgc    660
cttggaatag cttatcattt cgagaaacaa atagaagata tgttggatca catttacaga    720
gctgatcctt attttgaggc tcatgaatac aatgatttaa acacttcatc cgttcaattt    780
cgactactca gacaacatgg ttacaacgtc tctccaaata tatttagcag attccaagat    840
gcaaatggca aattcaagga gtctcttaga agcgacatca ggggcctact gaacttatac    900
gaagcttcac atgtaaggac tcataaagag atattttgg aagaagcact tgtttttttct    960 gttggtcatc ttgaatctgc agctccacat ttgaagtcac ctctgagtaa gcaagtgaca    1020
catgccctcg aacaatctct ccataagagc attccaagag tcgagatacg gtacttcatc    1080
tccatctacg aagaggagga atttaagaat gatttgttgc ttcgatttgc taaattggat    1140
tacaacttac ttcagatgtt gcacaagcat gaactcagtg aagtatcaag gtggtggaaa    1200
gatttggatt tcgtgacaac acttccatat gctagggaca gagcagttga gtgctacttt    1260
```

```
tggacgatgg gggtgtatgc tgaacctcaa tactcccagg ctcgtgtcat gcttgctaag   1320
actatagcaa tgatttccat agtagatgac acattcgatg cttatggcat cgtaaaagaa   1380
cttgaagtct acacagatgc catacagagg tgggatatta gtcaaattga tcgactcccg   1440
gaatatatga aaatcagtta taaggctctt ttggatctct atgacgatta tgaaaaggag   1500
ttgtcaaagg atggtagatc cgatgttgtc cactatgcaa agaaagaat gaaggagatt    1560 gtgagaaact attttattga agcaaaatgg tttattgagg gatatatgcc atctgtttcc   1620
gagtacctta gcaatgcact agctactagc acatattact tgctaactac gacatcctac   1680
ttgggaatga aatcagcaac caaggaacat tttgaatggt tggctacgaa ccctaaaatt   1740
ctggaagcta atgctacatt atgccgagtt gttgatgaca tagccacgta tgaggttgag   1800
aagggtaggg gtcaaattgc aacaggaatt gagtgttata tgagggatta cggtgtatcc   1860
acagaagtag caatggagaa attccaagaa atggctgaca tagcatggaa ggatgtaaat   1920
gaagaaattc ttcgaccaac acctgtctct tcagaaattc ttactcgtat tctcaacctc   1980
gctcgaatta tagatgtcac ttacaagcat aatcaagatg gatacactca tcctgaaaaa   2040
gtactaaaac ctcacatcat cgccttggtg gtggattcta ttgatattct cgagcaccac   2100
caccaccacc actaatctag acaacgcgtc aataatatag gctacataaa aatcataata   2160
actttgttat catagcaaaa tgtgatataa acgtttcat ttcacctgaa aaatagtaaa    2220
aataggcgac aaaaatcctt agtaatatgt aaactttatt ttctttattt atttacagaa   2280
ctctgaatat acattgattg ttcacatttt ttttttctct tctcaatttc ccttgattat   2340
attcaaaagg ttattggcct cttgaatgtt tcccactgat ggtcgacgtg ggcccggatc   2400
ctctaggctt ggcactggcc gtcgttttac aacgtcgtga ctgggaaaac cctggcgtta   2460
cccaacttaa tcgccttgca gcacatcccc ctttcgccag ctggcgtaat agcgaagagg   2520
cccgcaccga tcgcccttcc caacagttgc gcagcctgaa tggcgaatgg cgcctgatgc   2580
ggtattttct ccttacgcat ctgtgcggta tttcacaccg catagggtaa taactgatat   2640
aattaaattg aagctctaat ttgtgagttt agtatacatg catttactta taatacagtt   2700
ttttagtttt gctggccgca tcttctcaaa tatgcttccc agcctgcttt tctgtaacgt   2760
tcaccctcta ccttagcatc ccttcccttt gcaaatagtc ctcttccaac aataataatg   2820
tcagatcctg tagagaccac atcatccacg gttctatact gttgacccaa tgcgtctccc   2880
ttgtcatcta aacccacacc gggtgtcata atcaaccaat cgtaaccttc atctcttcca   2940
cccatgtctc tttgagcaat aaagccgata acaaatcttt gtcgctctt cgcaatgtca    3000 acagtaccct tagtatattc tccagtagat agggagccct tgcatgacaa ttctgctaac   3060
atcaaaaggc ctctaggttc ctttgttact tcttctgccg cctgcttcaa accgctaaca   3120
atacctgggc ccaccacacc gtgtgcattc gtaatgtctg cccattctgc tattctgtat   3180
acacccgcag agtactgcaa tttgactgta ttaccaatgt cagcaaattt tctgtcttcg   3240
aagagtaaaa aattgtactt ggcggataat gcctttagcg gcttaactgt gccctccatg   3300
gaaaaatcag tcaagatatc cacatgtgtt tttagtaaac aaattttggg acctaatgct   3360
tcaactaact ccagtaattc cttggtggta cgaacatcca atgaagcaca caagtttgtt   3420
tgcttttcgt gcatgatatt aaatagcttg gcagcaacag gactaggatg agtagcagca   3480
cgttccttat atgtagcttt cgacatgatt tatcttcgtt tcggttttg ttctgtgcag    3540 ttgggttaag aatactgggc aatttcatgt ttcttcaaca ctacatatgc gtatatatac   3600
```

```
caatctaagt ctgtgctcct tccttcgttc ttccttctgt tcggagatta ccgaatcaaa   3660
aaaatttcaa ggaaaccgaa atcaaaaaaa agaataaaaa aaaatgatg aattgaaaag    3720
cacttgttac ccatcattga attttgaaca tccgaacctg ggagttttcc ctgaaacaga   3780
tagtatattt gaacctgtat aataatatat agtctagcgc tttacggaag acaatgtatg   3840
tatttcggtt cctggagaaa ctattgcatc tattgcatag gtaatcttgc acgtcgcatc   3900
cccggttcat tttctgcgtt tccatcttgc acttcaatag catatctttg ttaacgaagc   3960
atctgtgctt cattttgtaa aacaaaaatg caacgcgaga gcgctaattt ttcaaacaaa   4020
gaatctgagc tgcattttta cagaacagaa atgcaacgcg aaagcgctat tttaccaacg   4080
aagaatctgt gcttcatttt tgtaaaacaa aaatgcaacg cgagagcgct aattttttcaa  4140
acaaagaatc tgagctgcat ttttacgaaa cagaaatgca acgcgagagc gctatttac    4200
caacaaagaa tctatacttc ttttttgttc tacaaaaatg catcccgaga gcgctatttt   4260
tctaacaaag catcttagat tactttttt ctcctttgtg cgctctataa tgcagtctct    4320
tgataacttt ttgcactgta ggtccgttaa ggttagaaga aggctacttt ggtgtctatt   4380
ttctcttcca taaaaaaagc ctgactccac ttcccgcgtt tactgattac tagcgaagct   4440
gcgggtgcat tttttcaaga taaaggcatc cccgattata ttctataccg atgtggattg   4500
cgcatacttt gtgaacagaa agtgatagcg ttgatgattc ttcattggtc agaaaattat   4560
gaacggtttc ttctattttg tctctatata ctacgtatag gaaatgttta cattttcgta   4620
ttgttttcga ttcactctat gaatagttct tactacaatt ttttgtcta aagagtaata    4680
ctagagataa acataaaaaa tgtagaggtc gagtttagat gcaagttcaa ggagcgaaag   4740
gtggatgggt aggttatata gggatatagc acagagatat atagcaaaga gatactttg    4800
agcaatgttt gtggaagcgg tattcgcaat attttagtag ctcgttacag tccggtgcgt   4860
ttttggtttt ttgaaagtgc gtcttcagag cgcttttggt tttcaaaagc gctctgaagt   4920
tcctatactt tctagctaga gaataggaac ttcggaatag gaacttcaaa gcgtttccga   4980
aaacgagcgc ttccgaaaat gcaacgcgag ctgcgcacat acagctcact gttcacgtcg   5040
cacctatatc tgcgtgttgc ctgtatatat atatacatga aagaacggc atagtgcgtg    5100
tttatgctta aatgcgttat ggtgcactct cagtacaatc tgctctgatg ccgcatagtt   5160
aagccagccc cgacacccgc caacacccgc tgacgcgccc tgacgggctt gtctgctccc   5220
ggcatccgct tacagacaag ctgtgaccgt ctccgggagc tgcatgtgtc agaggttttc   5280
accgtcatca ccgaaacgcg cgagacgaaa gggcctcgtg atacgcctat tttataggt    5340
taatgtcatg ataataatgg tttcttagac gtcaggtggc acttttcggg gaaatgtgcg   5400
cggaaccct atttgtttat ttttctaaat acattcaaat atgtatccgc tcatgagaca    5460
ataaccctga taaatgcttc aataatattg aaaaggaag agtatgagta ttcaacattt    5520
ccgtgtcgcc cttattccct tttttgcgg attttgcctt cctgttttg ctcacccaga     5580
aacgctggtg aaagtaaaag atgctgaaga tcagttgggt gcacgagtgg gttacatcga   5640
actggatctc aacagcggta agatccttga gagttttcgc cccgaagaac gttttccaat   5700
gatgagcact tttaaagttc tgctatgtgg cgcggtatta cccgtattg acgccgggca    5760
agagcaactc ggtcgccgca tacactattc tcagaatgac ttggttgagt actcaccagt   5820
cacagaaaag catcttacgg atggcatgac agtaagagaa ttatgcagtg ctgccataac   5880
catgagtgat aacactgcgg ccaacttact tctgacaacg atcggaggac cgaaggagct   5940
aaccgctttt ttgcacaaca tgggggatca tgtaactcgc cttgatcgtt gggaaccgga   6000
```

```
gctgaatgaa gccataccaa acgacgagcg tgacaccacg atgcctgtag caatggcaac    6060
aacgttgcgc aaactattaa ctggcgaact acttactcta gcttcccggc aacaattaat    6120
agactggatg gaggcggata aagttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcattttta    6420
atttaaaagg atctaggtga agatccttt tgataatctc atgaccaaaa tcccttaacg     6480
tgagttttcg ttccactgag cgtcagaccc cgtagaaaag atcaaaggat cttcttgaga    6540 tcctttttt ctgcgcgtaa tctgctgctt gcaaacaaaa aaaccaccgc taccagcggt      6600
ggtttgtttg ccggatcaag agctaccaac tcttttccg aaggtaactg gcttcagcag      6660
agcgcagata ccaaatactg ttcttctagt gtagccgtag ttaggccacc acttcaagaa    6720
ctctgtagca ccgcctacat accacgctct gctaatcctg ttaccagtgg ctgctgccag    6780
tggcgataag tcgtgtctta ccgggttgga ctcaagacga tagttaccgg ataaggcgca    6840
gcggtcgggc tgaacggggg gttcgtgcac acagcccagc ttggagcgaa cgacctacac    6900
cgaactgaga tacctacagc gtgagctatg agaaagcgcc acgcttcccg aagggagaaa    6960
ggcggacagg tatccggtaa gcggcagggt cggaacagga gagcgcacga gggagcttcc    7020 aggggaaac gcctggtatc tttatagtcc tgtcgggttt cgccacctct gacttgagcg      7080
tcgatttttg tgatgctcgt caggggggcg gagcctatgg aaaaacgcca gcaacgcggc    7140
ctttttacgg ttcctggcct tttgctggcc ttttgctcac atgttctttc ctgcgttatc    7200
ccctgattct gtggataacc gtattaccgc ctttgagtga gctgataccg ctcgccgcag    7260
ccgaacgacc gagcgcagcg agtcagtgag cgaggaagcg gaagagcgcc caatacgcaa    7320
accgcctctc cccgcgcgtt ggccgattca ttaatgcagc tggcacgaca ggtttcccga    7380
ctggaaagcg ggcagtgacg caacgcaatt aatgtgagtt agctcactca ttaggcaccc    7440
caggctttac actttatgct tccggctcgt atgttgtgtg gaattgtgag cggataacaa    7500
tttcacacag gaaacagcta tgacatgatt acgcggccgc                          7540
```

<210> SEQ ID NO 70  
<211> LENGTH: 10304  
<212> TYPE: DNA  
<213> ORGANISM: Artificial Sequence  
<220> FEATURE:  
<223> OTHER INFORMATION: pALX40-160.4 vector

<400> SEQUENCE: 70

```
ggccgcaaca cgcttttca gttcgagttt atcattatca atactgccat tcaaagaat       60 acgtaaataa ttaatagtag tgattttcct aactttattt agtcaaaaaa ttagccttt     120 aattctgctg taacccgtac atgcccaaaa taggggggcgg gttacacaga atatataaca   180
tcgtaggtgt ctgggtgaac agtttattcc tggcatccac taaatataat ggagcccgct    240
ttttaagctg catccagaa aaaaaagaa tcccagcacc aaaatattgt ttcttcacc        300 aaccatcagt tcataggtcc attctcttag cgcaactaca gagaacaggg gcacaaacag    360
gcaaaaaacg ggcacaacct caatggagtg atgcaacctg cctggagtaa atgatgacac    420
aaggcaattg acccacgcat gtatctatct cattttctta caccttctat taccttctgc    480
```

```
tctctctgat ttggaaaaag ctgaaaaaaa aggttgaaac cagttccctg aaattattcc       540
cctacttgac taataagtat ataaagacgg taggtattga ttgtaattct gtaaatctat       600
ttcttaaact tcttaaattc tacttttata gttagtcttt tttttagttt taaaacacca       660
agaacttagt ttcgaataaa cacacataaa caaacccagg taccatttaa aaaaatggat       720
tacgcgaaca tcctcacagc aattccactc gagtttactc ctcaggatga tatcgtgctc       780
cttgaaccgt atcactacct aggaaagaac cctggaaaag aaattcgatc acaactcatc       840
gaggctttca actattggtt ggatgtcaag aaggaggatc tcgaggtcat ccagaacgtt       900
gttggcatgc tacataccgc tagcttatta atggacgatg tggaggattc atcggtcctc       960
aggcgtgggt cgcctgtggc ccatctaatt tacgggattc cgcagacaat aaacactgca      1020
aactacgtct actttctggc ttatcaagag atcttcaagc ttcgcccaac accgataccc      1080
atgcctgtaa ttcctccttc atctgcttcg cttcaatcat ccgtctcctc tgcatcctcc      1140
tcctcctcgg cctcgtctga aacgggggc acgtcaactc ctaattcgca gattccgttc       1200
tcgaaagata cgtatcttga taaagtgatc acagacgaga tgctttccct ccatagaggg      1260
caaggcctgg agctattctg agagatagt ctgacgtgtc ctagcgaaga ggaatatgtg       1320
aaaatggttc ttggaaagac gggaggtttg ttccgtatag cggtcagatt gatgatggca      1380
aagtcagaat gtgacataga cttttgtccag cttgtcaact tgatctcaat atacttccag      1440
atcagggatg actatatgaa ccttcagtct tctgagtatg cccataataa gaattttgca      1500
gaggacctca cagaagggaa attcagtttt cccactatcc actcgattca tgccaacccc      1560
tcatcgagac tcgtcatcaa tacgttgcag aagaaatcga cctctcctga gatccttcac      1620
cactgtgtaa actacatgcg cacagaaacc cactcattcg aatatactca ggaagtcctc      1680
aacaccttgt caggtgcact cgagagagaa ctaggaaggc ttcaaggaga gttcgcagaa      1740
gctaactcaa ggatggatct tggagacgta gattcggaag gaagaacggg aagaacgtc       1800 aaattggaag cgatcctgaa aaagctagcc gatatccctc tgtgatctag aaactgcgtg      1860
cacttcgtgg ccgaggagca ggactgacac gtccgacggc ggcccacggg tcccaggcct      1920
cggagatccg tccccctttt cctttgtcga tatcatgtaa ttagttatgt cacgcttaca      1980
ttcacgccct ccccccacat ccgctctaac cgaaaaggaa ggagttagac aacctgaagt      2040
ctaggtccct atttattttt ttatagttat gttagtatta agaacgttat ttatatttca      2100
aattttcttt ttttttctgt acagacgcgt gtacgcatgt aacattatac tgaaaacctt      2160
gcttgagaag gttttgggac gctcgaaggc tttaatttgc aagctgaatt gtaccgggcc      2220
cggatcctct aggcttggca ctggccgtcg ttttacaacg tcgtgactgg gaaaaccctg      2280
gcgttaccca acttaatcgc cttgcagcac atcccccttt cgccagctgg cgtaatagcg      2340
aagaggcccg caccgatcgc ccttcccaac agttgcgcag cctgaatggc gaatggcgcc      2400
tgatgcggta ttttctcctt acgcatctgt gcggtatttc acaccgcata gggtaataac      2460
tgatataatt aaattgaagc tctaatttgt gagtttagta tacatgcatt tacttataat      2520
acagtttttt agttttgctg gccgcatctt ctcaaatatg cttcccagcc tgcttttctg      2580
taacgttcac cctctacctt agcatccctt ccctttgcaa atagtcctct tccaacaata      2640
ataatgtcag atcctgtaga gaccacatca tccacggttc tatactgttg acccaatgcg      2700
tctcccttgt catctaaacc cacaccgggt gtcataatca accatcgta accttcatct       2760 cttccaccca tgtctctttg agcaataaag ccgataacaa aatctttgtc gctcttcgca      2820
atgtcaacag taccctagt atattctcca gtagataggg agcccttgca tgacaattct      2880
```

```
gctaacatca aaaggcctct aggttccttt gttacttctt ctgccgcctg cttcaaaccg    2940
ctaacaatac ctgggcccac cacaccgtgt gcattcgtaa tgtctgccca ttctgctatt    3000
ctgtatacac ccgcagagta ctgcaatttg actgtattac caatgtcagc aaattttctg    3060
tcttcgaaga gtaaaaaatt gtacttggcg gataatgcct ttagcggctt aactgtgccc    3120
tccatggaaa aatcagtcaa gatatccaca tgtgttttta gtaaacaaat tttgggacct    3180
aatgcttcaa ctaactccag taattccttg gtggtacgaa catccaatga agcacacaag    3240
tttgtttgct tttcgtgcat gatattaaat agcttggcag caacaggact aggatgagta    3300
gcagcacgtt ccttatatgt agcttttcgac atgatttatc ttcgtttcgg ttttttgttct   3360 gtgcagttgg gttaagaata ctgggcaatt tcatgtttct tcaacactac atatgcgtat    3420
atataccaat ctaagtctgt gctccttcct tcgttcttcc ttctgttcgg agattaccga    3480
atcaaaaaaa tttcaaggaa accgaaatca aaaaaaagaa taaaaaaaaa atgatgaatt    3540
gaaaagcact tgttacccat cattgaattt tgaacatccg aacctgggag ttttccctga    3600
aacagatagt atatttgaac ctgtataata atatatagtc tagcgcttta cggaagacaa    3660
tgtatgtatt tcggttcctg gagaaactat tgcatctatt gcataggtaa tcttgcacgt    3720
cgcatccccg gttcatttc tgcgtttcca tcttgcactt caatagcata tctttgttaa    3780
cgaagcatct gtgcttcatt ttgtaaaaca aaaatgcaac gcgagagcgc taatttttca    3840
aacaaagaat ctgagctgca ttttacaga acagaaatgc aacgcgaaag cgctattta    3900 ccaacgaaga atctgtgctt cattttgta aacaaaaat gcaacgcgag agcgctaatt    3960
tttcaaacaa agaatctgag ctgcattttt acagaacaga atgcaacgc gagagcgcta   4020 ttttaccaac aaagaatcta acttctttt tgttctaca aaatgcatc ccgagagcgc     4080 tatttttcta acaaagcatc ttagattact tttttctcc tttgtgcgct ctataatgca    4140
gtctcttgat aacttttgc actgtaggtc cgttaaggtt agaagaaggc tactttggtg    4200
tctattttct cttccataaa aaaagcctga ctccacttcc cgcgtttact gattactagc    4260
gaagctgcgg gtgcatttt tcaagataa ggcatcccg attatattct ataccgatgt     4320
ggattgcgca tactttgtga acagaaagtg atagcgttga tgattcttca ttggtcagaa   4380
aattatgaac ggtttcttct attttgtctc tatatactac gtataggaaa tgtttacatt   4440
ttcgtattgt tttcgattca ctctatgaat agttcttact acaatttttt tgtctaaaga    4500
gtaatactag agataaacat aaaaaatgta gaggtcgagt ttagatgcaa gttcaaggag    4560
cgaaaggtgg atgggtaggt tatatagggg tatagcacag agatatatag caaagagata    4620
cttttgagca atgtttgtgg aagcggtatt cgcaatattt tagtagctcg ttacagtccg    4680
gtgcgttttt ggttttttga aagtgcgtct tcagagcgct tttggttttc aaaagcgctc    4740
tgaagttcct atactttcta gctagagaat aggaacttcg gaataggaac ttcaaagcgt    4800
ttccgaaaac gagcgcttcc gaaaatgcaa cgcgagctgc gcacatacag ctcactgttc    4860
acgtcgcacc tatatctgcg tgttgcctgt atatatatat acatgagaag aacggcatag    4920
tgcgtgttta tgcttaaatg cgttatggtg cactctcagt acaatctgct ctgatgccgc    4980
atagttaagc cagccccgac acccgccaac acccgctgac gcgccctgac gggcttgtct    5040
gctcccggca tccgcttaca gacaagctgt gaccgtctcc gggagctgca tgtgtcagag    5100
gttttcaccg tcatcaccga aacgcgcgag acgaaagggc ctcgtgatac gcctattttt    5160
ataggttaat gtcatgataa taatggtttc ttagacgtca ggtggcactt ttcggggaaa    5220
```

```
tgtgcgcgga accccctattt gtttattttt ctaaatacat tcaaatatgt atccgctcat   5280
gagacaataa ccctgataaa tgcttcaata atattgaaaa aggaagagta tgagtattca   5340
acatttccgt gtcgcccta ttcccttttt tgcggcattt tgccttcctg tttttgctca    5400
cccagaaacg ctggtgaaag taaaagatgc tgaagatcag ttgggtgcac gagtgggtta   5460
catcgaactg gatctcaaca gcggtaagat ccttgagagt tttcgccccg aagaacgttt   5520
tccaatgatg agcacttta aagttctgct atgtggcgcg gtattatccc gtattgacgc    5580
cgggcaagag caactcggtc gccgcataca ctattctcag aatgacttgg ttgagtactc   5640
accagtcaca gaaaagcatc ttacggatgg catgacagta agagaattat gcagtgctgc   5700
cataaccatg agtgataaca ctgcggccaa cttacttctg acaacgatcg gaggaccgaa   5760
ggagctaacc gcttttttgc acaacatggg ggatcatgta actcgccttg atcgttggga   5820
accggagctg aatgaagcca taccaaacga cgagcgtgac accacgatgc ctgtagcaat   5880
ggcaacaacg ttgcgcaaac tattaactgg cgaactactt actctagctt cccggcaaca   5940
attaatagac tggatggagg cggataaagt tgcaggacca cttctgcgct cggcccttcc   6000
ggctggctgg tttattgctg ataaatctgg agccggtgag cgtgggtctc gcggtatcat   6060
tgcagcactg gggccagatg gtaagccctc ccgtatcgta gttatctaca cgacggggag   6120
tcaggcaact atggatgaac gaaatagaca gatcgctgag ataggtgcct cactgattaa   6180
gcattggtaa ctgtcagacc aagtttactc atatatactt tagattgatt taaaacttca   6240
tttttaattt aaaaggatct aggtgaagat cctttttgat aatctcatga ccaaaatccc   6300
ttaacgtgag ttttcgttcc actgagcgtc agacccegta gaaaagatca aaggatcttc   6360
ttgagatcct ttttttctgc gcgtaatctg ctgcttgcaa acaaaaaaac caccgctacc   6420
agcggtggtt tgtttgccgg atcaagagct accaactctt tttccgaagg taactggctt   6480
cagcagagcg cagataccaa atactgttct tctagtgtag ccgtagttag gccaccactt   6540
caagaactct gtagcaccgc ctacatacca gctctgctaa tcctgttac cagtggctgc    6600
tgccagtggc gataagtcgt gtcttaccgg gttggactca agacgatagt taccggataa   6660
ggcgcagcgg tcgggctgaa cggggggttc gtgcacacag cccagcttgg agcgaacgac   6720
ctacaccgaa ctgagatacc tacagcgtga gctatgagaa agcgccacgc ttcccgaagg   6780
gagaaaggcg gacaggtatc cggtaagcgg cagggtcgga acaggagagc gcacgaggga   6840
gcttccaggg ggaaacgcct ggtatcttta tagtcctgtc gggtttcgcc acctctgact   6900
tgagcgtcga tttttgtgat gctcgtcagg ggggcggagc ctatggaaaa acgccagcaa   6960
cgcggccttt ttacggttcc tggccttttg ctggcctttt gctcacatgt tctttcctgc   7020
gttatcccct gattctgtgg ataaccgtat taccgccttt gagtgagctg ataccgctcg   7080
ccgcagccga acgaccgagc gcagcgagtc agtgagcgag gaagcggaag agcgcccaat   7140
acgcaaaccg cctctccccg cgcgttggcc gattcattaa tgcagctggc acgacaggtt   7200
tcccgactgg aaagcgggca gtgacgcaac gcaattaatg tgagttagct cactcattag   7260
gcaccccagg ctttacactt tatgcttccg gctcgtatgt tgtgtggaat tgtgagcgga   7320
taacaatttc acacaggaaa cagctatgac atgattacgc ggccgcatag cttcaaaatg   7380
tttctactcc ttttttactc ttccagattt tctcggactc cgcgcatcgc cgtaccactt   7440
caaaacaccc aagcacagca tactaaattt cccctctttc ttcctctagg gtgtcgttaa   7500
ttacccgtac taaaggtttg gaaaagaaaa aagagaccgc ctcgtttctt ttcttcgtc    7560
gaaaaaggca ataaaaattt ttatcacgtt tcttttttctt gaaaattttt tttttgatt   7620
```

```
tttttctctt tcgatgacct cccattgata tttaagttaa taaacggtct tcaatttctc    7680
aagtttcagt ttcattttc ttgttctatt acaactttt ttacttcttg ctcattagaa     7740
agaaagcata gcaatctaat ctaagttttg gtaccattta aaaaaatgtg cgcacctatt    7800
gatgcaagtt atcttggtta tctgaatgag ttggaatcta atttctcaaa caaccccgaa    7860
gaaaaggata ttcaggtaag cagaacaata cagatcaaaa atttgacaga agaaatcaaa    7920
tgtaagttga attcgatgga ggatggaagg tcaagtgtct cagcctatga cacagcttgg    7980
gtttccttta ttccaaatac tactaataat ggaaatgatc aaaggcctat gtttccatct    8040
tgtcttcaat ggattataga caatcaactt tgcgatggtt catggggaga ggagagtgta    8100
ttctgcatat atgatcgact cttgaacaca ctagcatgtg ttgttgcatt gacattatgg    8160
aacacatgcc ttcctaagag aaacaaaggt gtgatgttta tcaaagaaaa cttaattaag    8220
ctagagacag gggaagttga acacatgact tgtggatttg aatttgtgtt tcctgctctc    8280
cttgagaaag ctcaacaatt aaatattgac attccgtatg atgctccagt cttaaaggat    8340
atttatgcaa ggagagaagt aaagtttaca agaattccta agagagattgt ccatacgatt    8400 ccgacaacag cattgctttc attagaagga ttaagggacg acctggattg gcaaagactt    8460
ttaaattttc aaatgcctga tggttcattc ttatcagccc ctgcttccac tgcctttgca    8520
ttcatgaaaa caaacgatga aaagtgtttg gcatatcttc aaaatgttgt tcaaaagtct    8580
aatggaggag cgcgacacta cccactggac ttgttaacac gactttgggc aattgatcga    8640
ttacaacgcc ttggaatatc ttattatttt gcggaagagt tcaaggaact tttgaatcat    8700
gtgttcagat attgggacga ggagaatgga attttcagtg gaaggaattc aaacgtttgt    8760
gacgttgatg atacatgcat ggctattagg ttgcttaggt tgcatgggta tgatgttagt    8820
ccagatgcgc taaacaattt cacagatggt gatcaattct tttgccttag aggtgaagtg    8880
gacgggtcac caacacatat gtttaatctt tatagatgtt cccaagtttt attcccagga    8940
gaaaagattc ttgaagaggc aaagaatttt acttacaact tcttacagca atgtcttgca    9000
aacaatcgat gcttagacaa atgggtcata gctaaggaca ttcccgggga gataaggtat    9060
gcactgaaat ttcatggta tgcaagctta cctcgggtgg aatctaggct atacatagaa    9120
cagtacggcg gagcaaatga tatttggatt ggcaagacat tatacaggat gcccgatgtc    9180
agcaacaatg tttatttaca agctgcaaaa ttagattaca acagatgcca aagtcaacat    9240
cgatttgaat ggctaattat gcaacagtgg tttgataagt gcaactttca acaatttgga    9300
ataagcaaaa agtacctcct agtttcttat ttccttagctg ctgcaagtat atttgaagtc    9360
gaaaagtcaa gagaacgact tgcgtgggct aaatctcgta taatatgtaa gatgattaca    9420
tcttactaca atgaagaagc cacaacttgg accagtagga attcattgct aatggaattc    9480
aagggttctg atgatccaag cagaaaaaat ggtaatgaaa caaagagat catagttctc    9540 aaaaatcttc gtcagttttt gcaccaacta tcagaagaaa cttttgagga cctaggcaaa    9600
gacatccatc accaactaca aaatgcatgg aaaacgtggt tggcgttctt aagggaggaa    9660
aaaaatacat gccaagaaga agcagagttg ctagtgcgca caattaatct ctccggcggc    9720
catatgatac atgatgagat actattcgat gcggactaca aaaatctgtc caaccttact    9780
aataaagttt gctgcatgct tagtgagctc caaaatgaca aggtgactgg cagctcaaag    9840
aacactgaca ttgaactcaa catgcaagca cttgtaaaat tagtgtttgg taacacctca    9900
agcaacatca accaagacat taagcaaaca ttttttacag ttgttaagac tttctattac    9960
```

| | |
|---|---|
| agtgcacatg ctagtgagga aataatcaac tttcacatat ccaaggtgct tttacagcaa | 10020 |
| gtccagtaat ctagacaacg cgtcaataat ataggctaca taaaaatcat aataactttg | 10080 |
| ttatcatagc aaaatgtgat ataaaacgtt tcatttcacc tgaaaaatag taaaaatagg | 10140 |
| cgacaaaaat ccttagtaat atgtaaactt tattttcttt atttatttac agaactctga | 10200 |
| atatacattg attgttcaca ttttttttt ctcttctcaa tttcccttga ttatattcaa | 10260 |
| aaggttattg gcctcttgaa tgtttcccac tgatggtcga cgtg | 10304 |

<210> SEQ ID NO 71
<211> LENGTH: 70
<212> TYPE: DNA
<213> ORGANISM: Artificial Sequence
<220> FEATURE:
<223> OTHER INFORMATION: 40-92.1 primer

<400> SEQUENCE: 71

| | |
|---|---|
| ctcggtacca tttaaaaaaa ttcacatcat catcaccatc atatggagcc acagtactgc | 60 |
| ttcatcactg | 70 |

<210> SEQ ID NO 72
<211> LENGTH: 33
<212> TYPE: DNA
<213> ORGANISM: Artificial Sequence
<220> FEATURE:
<223> OTHER INFORMATION: 40-92.2 primer

<400> SEQUENCE: 72

| | |
|---|---|
| cctgctagct tatggggaat attgattgag tgg | 33 |

<210> SEQ ID NO 73
<211> LENGTH: 7497
<212> TYPE: DNA
<213> ORGANISM: Artificial Sequence
<220> FEATURE:
<223> OTHER INFORMATION: pALX46-116.2-6 vector

<400> SEQUENCE: 73

| | |
|---|---|
| ctagaatctc tgcttttgtg cgcgtatgtt tatgtatgta cctctctctc tatttctatt | 60 |
| tttaaaccac cctctcaata aaataaaaat aataaagtat ttttaaggaa aagacgtgtt | 120 |
| taagcactga cttatctac ttttgtacg ttttcattga tataatgtgt tttgtctctc | 180 |
| cctttctac gaaaatttca aaaattgacc aaaaaaagga atatatatac gaaaaactat | 240 |
| tatatttata tcatagtg ttgataaaaa atgtttatcc attggaccgt gtatcagggc | 300 |
| ccggatcctc taggcttggc actggccgtc gttttacaac gtcgtgactg ggaaaaccct | 360 |
| ggcgttaccc aacttaatcg ccttgcagca catccccctt tcgccagctg gcgtaatagc | 420 |
| gaagaggccc gcaccgatcg cccttcccaa cagttgcgca gcctgaatgg cgaatggcgc | 480 |
| ctgatgcggt attttctcct tacgcatctg tgcggtattt cacaccgcat agggtaataa | 540 |
| ctgatataat taaattgaag ctctaatttg tgagtttagt atacatgcat ttacttataa | 600 |
| tacagttttt tagttttgct ggccgcatct tctcaaatat gcttcccagc ctgcttttct | 660 |
| gtaacgttca ccctctacct tagcatccct tcccttgca aatagtcctc ttccaacaat | 720 |
| aataatgtca gatcctgtag agaccacatc atccacggtt ctatactgtt gacccaatgc | 780 |
| gtctcccttg tcatctaaac ccacaccggg tgtcataatc aaccaatcgt aaccttcatc | 840 |
| tcttccaccc atgtctcttt gagcaataaa gccgataaca aaatctttgt cgctcttcgc | 900 |
| aatgtcaaca gtacccttag tatattctcc agtagatagg gagcccttgc atgacaattc | 960 |

```
tgctaacatc aaaaggcctc taggttcctt tgttacttct tctgccgcct gcttcaaacc    1020
gctaacaata cctgggccca ccacaccgtg tgcattcgta atgtctgccc attctgctat    1080
tctgtataca cccgcagagt actgcaattt gactgtatta ccaatgtcag caaattttct    1140
gtcttcgaag agtaaaaaat tgtacttggc ggataatgcc tttagcggct taactgtgcc    1200
ctccatggaa aaatcagtca agatatccac atgtgttttt agtaaacaaa ttttgggacc    1260
taatgcttca actaactcca gtaattcctt ggtggtacga acatccaatg aagcacacaa    1320
gtttgtttgc ttttcgtgca tgatattaaa tagcttggca gcaacaggac taggatgagt    1380
agcagcacgt tccttatatg tagctttcga catgatttat cttcgtttcg gtttttgttc    1440
tgtgcagttg ggttaagaat actgggcaat tcatgtttc ttcaacacta ccgatgcgta    1500
tatataccaa tctaagtctg tgctccttcc ttcgttcttc cttctgttcg agattaccg    1560 aatcaaaaaa atttcaaaga aaccgaaatc aaaaaaaaga ataaaaaaaa aatgatgaat    1620
tgaaaagctc ttgttaccca tcattgaatt ttgaacatcc gaacctggga gttttccctg    1680
aaacagatag tatatttgaa cctgtataat aatatatagt ctagcgcttt acggaagaca    1740
atgtatgtat ttcggttcct ggagaaacta ttgcatctat tgcataggta atcttgcacg    1800
tcgcatcccc ggttcatttt ctgcgtttcc atcttgcact tcaatagcat atctttgtta    1860
acgaagcatc tgtgcttcat tttgtagaac aaaaatgcaa cgcgagagcg ctaatttttc    1920
aaacaaagaa tctgagctgc attttacag aacagaaatg caacgcgaaa gcgctatttt    1980
accaacgaag aatctgtgct tcattttgt aaaacaaaaa tgcaacgcga gagcgctaat    2040
ttttcaaaca aagaatctga gctgcatttt tacagaacag aaatgcaacg cgagagcgct    2100
attttaccaa caagaatct atacttcttt tttgttctac aaaaatgcat cccgagagcg    2160
ctatttttct aacaaagcat cttagattac ttttttttctc ctttgtgcgc tctataatgc    2220
agtctcttga taacttttttg cactgtaggt ccgttaaggt tagaagaagg ctactttggt    2280 gtctatttc tcttccataa aaaaagcctg actccacttc ccgcgtttac tgattactag    2340
cgaagctgcg ggtgcatttt ttcaagataa aggcatcccc gattatattc tataccgatg    2400
tggattgcgc atactttgtg aacagaaagt gatagcgttg atgattcttc attggtcaga    2460
aaattatgaa cggtttcttc tattttgtct ctatatacta cgtataggaa atgtttacat    2520
tttcgtattg ttttcgattc actctatgaa tagttcttac tacaatttt ttgtctaaag    2580 agtaatacta gagataaaca taaaaaatgt agaggtcgag tttagatgca agttcaagga    2640
gcgaaaggtg gatgggtagg ttatataggg atatagcaca gagatatata gcaaagagat    2700
acttttgagc aatgtttgtg gaagcggtat tcgcaatatt ttagtagctc gttacagtcc    2760
ggtgcgtttt tggttttttg aaagtgcgtc ttcagagcgc ttttggtttt caaaagcgct    2820
ctgaagttcc tatactttct agctagagaa taggaacttc ggaataggaa cttcaaagcg    2880
tttccgaaaa cgagcgcttc cgaaaatgca acgcgagctg cgcacataca gctcactgtt    2940
cacgtcgcac ctatatctgc gtgttgcctg tatatatata tacatgagaa gaacggcata    3000
gtgcgtgttt atgcttaaat gcgttatggt gcactctcag tacaatctgc tctgatgccg    3060
catagttaag ccagccccga cacccgccaa cacccgctga cgcgccctga cgggcttgtc    3120
tgctcccggc atccgcttac agacaagctg tgaccgtctc cgggagctgc atgtgtcaga    3180
ggttttcacc gtcatcaccg aaacgcgcga gacgaaaggg cctcgtgata cgcctatttt    3240
tataggttaa tgtcatgata ataatggttt cttagacgtc aggtggcact tttcggggaa    3300
```

```
atgtgcgcgg aaccccctatt tgtttatttt tctaaataca ttcaaatatg tatccgctca   3360
tgagacaata accctgataa atgcttcaat aatattgaaa aaggaagagt atgagtattc   3420
aacatttccg tgtcgccctt attccctttt ttgcggcatt ttgccttcct gttttttgctc  3480
acccagaaac gctggtgaaa gtaaaagatg ctgaagatca gttgggtgca cgagtgggtt   3540
acatcgaact ggatctcaac agcggtaaga tccttgagag ttttcgcccc gaagaacgtt   3600
ttccaatgat gagcactttt aaagttctgc tatgtggcgc ggtattatcc cgtattgacg   3660
ccgggcaaga gcaactcggt cgccgcatac actattctca gaatgacttg gttgagtact   3720
caccagtcac agaaaagcat cttacggatg gcatgacagt aagagaatta tgcagtgctg   3780
ccataaccat gagtgataac actgcggcca acttacttct gacaacgatc ggaggaccga   3840
aggagctaac cgcttttttg cacaacatgg ggatcatgt aactcgcctt gatcgttggg    3900
aaccggagct gaatgaagcc ataccaaacg acgagcgtga ccacgatg cctgtagcaa     3960
tggcaacaac gttgcgcaaa ctattaactg gcgaactact tactctagct tcccggcaac   4020
aattaataga ctggatggag gcggataaag ttgcaggacc acttctgcgc tcggcccttc   4080
cggctggctg gtttattgct gataaatctg gagccggtga gcgtgggtct cgcggtatca   4140
ttgcagcact ggggccagat ggtaagccct cccgtatcgt agttatctac acgacgggga   4200
gtcaggcaac tatggatgaa cgaaatagac agatcgctga gataggtgcc tcactgatta   4260
agcattggta actgtcagac caagtttact catatatact ttagattgat ttaaaacttc   4320
attttttaatt taaaaggatc taggtgaaga tccttttga taatctcatg accaaaatcc   4380
cttaacgtga gttttcgttc cactgagcgt cagaccccgt agaaaagatc aaaggatctt   4440
cttgagatcc ttttttttctg cgcgtaatct gctgcttgca acaaaaaaa ccaccgctac   4500
cagcggtggt ttgtttgccg gatcaagagc taccaactct ttttccgaag gtaactggct   4560
tcagcagagc gcagatacca aatactgttc ttctagtgta gccgtagtta ggccaccact   4620
tcaagaactc tgtagcaccg cctacatacc acgctctgct aatcctgtta ccagtggctg   4680
ctgccagtgg cgataagtcg tgtcttaccg ggttggactc aagacgatag ttaccggata   4740
aggcgcagcg gtcgggctga acggggggtt cgtgcacaca gcccagcttg gagcgaacga   4800
cctacaccga actgagatac ctacagcgtg agctatgaga aagcgccacg cttcccgaag   4860
ggagaaaggc ggacaggtat ccggtaagcg gcagggtcgg aacaggagag cgcacgaggg   4920
agcttccagg gggaaacgcc tggtatcttt atagtcctgt cgggtttcgc cacctctgac   4980
ttgagcgtcg atttttgtga tgctcgtcag ggggcggag cctatggaaa aacgccagca    5040
acgcggcctt tttacggttc ctggccttt gctggccttt tgctcacatg ttcttcctg    5100
cgttatcccc tgattctgtg gataaccgta ttaccgcctt tgagtgagct gataccgctc   5160
gccgcagccg aacgaccgag cgcagcgagt cagtgagcga ggaagcggaa gagcgcccaa   5220
tacgcaaacc gcctctcccc gcgcgttggc cgattcatta atgcagctgg cacgacaggt   5280
ttcccgactg gaaagcgggc agtgacgcaa cgcaattaat gtgagttagc tcactcatta   5340
ggcaccccag gctttacact ttatgcttcc ggctcgtatg ttgtgtggaa ttgtgagcgg   5400
ataacaattt cacacaggaa acagctatga catgattacg cggccgcgtg aatatttcg    5460
gatatccttt tgttgttcc gggtgtacaa tatggacttc ctcttttctg gcaaccaaac    5520
ccatacatcg ggattcctat aataccttcg ttggtctccc taacatgtag gtggcggagg   5580
ggagatatac aatagaacag ataccagaca agacataatg ggctaaacaa gactacacca   5640
attacactgc ctcattgatg gtggtacata acgaactaat actgtagccc tagacttgat   5700
```

| | | |
|---|---|---|
| agccatcatc atatcgaagt ttcactaccc tttttccatt tgccatctat tgaagtaata | 5760 |
| ataggcgcat gcaacttctt ttcttttttt ttcttttctc tctccccgt tgttgtctca | 5820 |
| ccatatccgc aatgacaaaa aaatgatgga agacactaaa ggaaaaaatt aacgacaaag | 5880 |
| acagcaccaa cagatgtcgt tgttccagag ctgatgaggg gtatctcgaa gcacacgaaa | 5940 |
| cttttccctt ccttcattca cgcacactac tctctaatga gcaacggtat acggccttcc | 6000 |
| ttccagttac ttgaatttga aataaaaaaa agtttgctgt cttgctatca agtataaata | 6060 |
| gacctgcaat tattaatctt ttgtttcctc gtcattgttc tcgttccctt tcttccttgt | 6120 |
| ttcttttct gcacaatatt tcaagctata ccaagcatac aatcaactcc aagctgaatt | 6180 |
| cgagctcggt accattaaa aaaatgtcac atcatcatca ccatcatatg gacaaggtag | 6240 |
| gaaatttgaa agcttgcctg tgtgatgaca cgagaggact cttagctttg tacgaagcat | 6300 |
| cctatttatc catggaaggg gaaagcatac tggatttggc caaagatttc tcactgaatc | 6360 |
| atcttgctcg agggctcgac aaaatcaagg agccgagcct agctgagcaa gtgaggcatg | 6420 |
| ctttggaggt tccactgcac tggagagtgg agaggctaga agccatatgg ttcgtgcaag | 6480 |
| cgtatgagag tagaactgac gcgaaccctg tccttgtgga gctcgctaaa ttggatttca | 6540 |
| acgtgctaca ggcgacgtac caggaagagc ttaagctcat ttcaaggtgg tataaagaaa | 6600 |
| ctggcctggc agaaaagtta gggtttgcgc ggcaccgatg ggcagagagt ttcttgtggt | 6660 |
| ctttgggatt tgttccagag caccattttg cagaatcaag ggagattttg aacaaggttg | 6720 |
| cggcgttcgt caccatacta gatgacatat atgatgtata tggaacattt gaagaactcc | 6780 |
| agttgttcac ccagacaatc gaaaggtggg atattaattc gatcgacaac cttccagagt | 6840 |
| atatgcagat ttgtttccta ggtctcttca acttggtgaa tgaattggct tatcgtatta | 6900 |
| tgagggatca agggctgaac gttatctcaa acatgaggag aatgtgggtt gatttgtgta | 6960 |
| gagcttacta cttggaagtg atatggtttc acagtggata tatcccaacc acaaatgaat | 7020 |
| acctcaatac agcttgggtt tccatttctg gtcctttgct tctcttttat gtctacttct | 7080 |
| caacaattcc tataaacaag gaggaattgc agagtttaga gcaacatccc ggtatcattc | 7140 |
| gcgagccatc catgattctt cgtcttgcag atgatttggg aacatcatcc gacgaaatca | 7200 |
| aacgagggga tgtcccgaaa tcaatccaat gcttcatgaa agaaacaggg tgctctgagg | 7260 |
| tggacgctcg cgagcacgtg aagcagttga ttgaggcggc gttgaagcga atgaataagg | 7320 |
| agatactgat ggagaagccg ttgaagagtt ttgggcacac tgccatgaat cttggacgaa | 7380 |
| tctcactctg catgtatcaa catggagatg gtttcggcaa tattaatccg catgccgaaa | 7440 |
| ccaagaaaca tttggtctcg atcctcgtta accctctgcc ctgactcgag aagcttt | 7497 |

<210> SEQ ID NO 74
<211> LENGTH: 13648
<212> TYPE: DNA
<213> ORGANISM: Artificial Sequence
<220> FEATURE:
<223> OTHER INFORMATION: pALX47-66.1 vector

<400> SEQUENCE: 74

| | | |
|---|---|---|
| ggccgcatag cttcaaaatg tttctactcc ttttttactc ttccagattt tctcggactc | 60 |
| cgcgcatcgc cgtaccactt caaaacaccc aagcacagca tactaaattt cccctctttc | 120 |
| ttcctctagg gtgtcgttaa ttacccgtac taaaggtttg gaaagaaaaa aagagaccgc | 180 |
| ctcgtttctt tttcttcgtc gaaaaaggca ataaaaattt ttatcacgtt tctttttctt | 240 |

```
gaaaattttt ttttttgatt tttttctctt tcgatgacct cccattgata tttaagttaa      300
taaacggtct tcaatttctc aagtttcagt ttcattttc ttgttctatt acaacttttt        360
ttacttcttg ctcattagaa agaaagcata gcaatctaat ctaagttttg gtaccattta      420
aaaaaatgtg cgcacctatt gatgcaagtt atcttggtta tctgaatgag ttggaatcta      480
atttctcaaa caaccccgaa gaaaaggata ttcaggtaag cagaacaata cagatcaaaa      540
atttgacaga agaaatcaaa tgtaagttga attcgatgga ggatggaagg tcaagtgtct      600
cagcctatga cacagcttgg gtttcctta ttccaaatac tactaataat ggaaatgatc        660
aaaggcctat gtttccatct tgtcttcaat ggattataga caatcaactt tgcgatggtt      720
catggggaga ggagagtgta ttctgcatat atgatcgact cttgaacaca ctagcatgtg      780
ttgttgcatt gacattatgg aacacatgcc ttcctaagag aaacaaaggt gtgatgttta      840
tcaaagaaaa cttaattaag ctagagacag gggaagttga acacatgact tgtggatttg      900
aatttgtgtt tcctgctctc cttgagaaag ctcaacaatt aaatattgac attccgtatg      960
atgctccagt cttaaaggat atttatgcaa ggagagaagt aaagtttaca agaattccta     1020
aagagattgt ccatacgatt ccgacaacag cattgctttc attagaagga ttaagggacg     1080
acctggattg gcaaagactt ttaaattttc aaatgcctga tggttcattc ttatcagccc     1140
ctgcttccac tgcctttgca ttcatgaaaa caaacgatga aaagtgtttg gcatatcttc     1200
aaaatgttgt tcaaaagtct aatggaggag cgcgacacta cccactggac ttgttaacac     1260
gactttgggc aattgatcga ttacaacgcc ttggaatatc ttattatttt gcggaagagt     1320
tcaaggaact tttgaatcat gtgttcagat attgggacga ggagaatgga attttcagtg     1380
gaaggaattc aaacgtttgt gacgttgatg atacatgcat ggctattagg ttgcttaggt     1440
tgcatgggta tgatgttagt ccagatgcgc taaacaattt cacagatggt gatcaattct     1500
tttgccttag aggtgaagtg gacgggtcac caacacatat gtttaatctt tatagatgtt     1560
cccaagtttt attcccagga gaaaagattc ttgaagaggc aaagaatttt acttacaact     1620
tcttacagca atgtcttgca aacaatcgat gcttagacaa atgggtcata gctaaggaca     1680
ttcccgggga gataaggtat gcactgaaat ttccatggta tgcaagctta cctcgggtgg     1740
aatctaggct atacatagaa cagtacggcg gagcaaatga tatttggatt ggcaagacat     1800
tatacaggat gcccgatgtc agcaacaatg tttatttaca agctgcaaaa ttagattaca     1860
acagatgcca aagtcaacat cgatttgaat ggctaattat gcaacagtgg tttgataagt     1920 gcaacttca acaatttgga ataagcaaaa agtacctcct agtttcttat tcttagctg      1980 ctgcaagtat atttgaagtc gaaaagtcaa gagaacgact tgcgtgggct aaatctcgta     2040
taatatgtaa gatgattaca tcttactaca atgaagaagc cacaacttgg accagtagga     2100
attcattgct aatggaattc aagggttctg atgatccaag cagaaaaaat ggtaatgaaa     2160
caaaagagat catagttctc aaaaatcttc gtcagttttt gcaccaacta tcagaagaaa     2220
cttttgagga cctaggcaaa gacatccatc accaactaca aaatgcatgg aaaacgtggt     2280
tggcgttctt aagggaggaa aaaaatacat gccaagaaga agcagagttg ctagtgcgca     2340
caattaatct ctccggcggc catatgatac atgatgagat actattcgat gcggactaca     2400
aaaatctgtc caaccttact aataaagttt gctgcatgct tagtgagctc caaaatgaca     2460
aggtgactgg cagctcaaag aacactgaca ttgaactcaa catgcaagca cttgtaaaat     2520
tagtgtttgg taacacctca gcaacatca accaagacat taagcaaaca ttttttacag     2580
ttgttaagac tttctattac agtgcacatg ctagtgagga ataatcaac tttcacatat       2640
```

```
ccaaggtgct tttacagcaa gtccagtaat ctagacaacg cgtcaataat ataggctaca    2700
taaaaatcat aataactttg ttatcatagc aaaatgtgat ataaaacgtt tcatttcacc    2760
tgaaaaatag taaaaatagg cgacaaaaat ccttagtaat atgtaaactt tattttcttt    2820
atttatttac agaactctga atatacattg attgttcaca ttttttttt ctcttctcaa     2880 tttcccttga ttatattcaa aaggttattg gcctcttgaa tgtttcccac tgatggtcga    2940
cgtgggccgc aacacgcttt ttcagttcga gtttatcatt atcaatactg ccatttcaaa    3000
gaatacgtaa ataattaata gtagtgattt tcctaacttt atttagtcaa aaaattagcc    3060
ttttaattct gctgtaaccc gtacatgccc aaaataggg gcgggttaca cagaatatat    3120
aacatcgtag gtgtctgggt gaacagttta ttcctggcat ccactaaata taatggagcc    3180 cgcttttaa gctggcatcc agaaaaaaaa agaatcccag caccaaaata ttgttttctt     3240
caccaaccat cagttcatag gtccattctc ttagcgcaac tacagagaac aggggcacaa    3300
acaggcaaaa aacgggcaca acctcaatgg agtgatgcaa cctgcctgga gtaaatgatg    3360
acacaaggca attgacccac gcatgtatct atctcatttt cttacacctt ctattacctt    3420
ctgctctctc tgatttggaa aaagctgaaa aaaaaggttg aaaccagttc cctgaaatta    3480
ttcccctact tgactaataa gtatataaag acggtaggta ttgattgtaa ttctgtaaat    3540
ctatttctta aacttcttaa attctacttt tatagttagt cttttttta gttttaaaac     3600 accaagaact tagtttcgaa taaacacaca taaacaaacc caggtaccat ttaaaaaaat    3660
ggattacgcg aacatcctca cagcaattcc actcgagttt actcctcagg atgatatcgt    3720
gctccttgaa ccgtatcact acctaggaaa gaaccctgga aagaaattc gatcacaact      3780 catcgaggct ttcaactatt ggttggatgt caagaaggag gatctcgagg tcatccagaa    3840
cgttgttggc atgctacata ccgctagctt attaatggac gatgtggagg attcatcggt    3900
cctcaggcgt gggtcgcctg tggcccatct aatttacggg attccgcaga caataaacac    3960
tgcaaactac gtctactttc tggcttatca agagatcttc aagcttcgcc caacaccgat    4020
acccatgcct gtaattcctc cttcatctgc ttcgcttcaa tcatccgtct cctctgcatc    4080
ctcctcctcc tcggcctcgt ctgaaaacgg gggcacgtca actcctaatt cgcagattcc    4140
gttctcgaaa gatacgtatc ttgataaagt gatcacagac gagatgcttt ccctccatag    4200
agggcaaggc ctggagctat tctggagaga tagtctgacg tgtcctagcg aagaggaata    4260
tgtgaaaatg gttcttggaa agacgggagg tttgttccgt atagcggtca gattgatgat    4320
ggcaaagtca gaatgtgaca tagactttgt ccagcttgtc aacttgatct caatatactt    4380
ccagatcagg gatgactata tgaaccttca gtcttctgag tatgcccata ataagaattt    4440
tgcagaggac ctcacagaag ggaaattcag ttttcccact atccactcga ttcatgccaa    4500
cccctcatcg agactcgtca tcaatacgtt gcagaagaaa tcgacctctc ctgagatcct    4560
tcaccactgt gtaaactaca tgcgcacaga aacccactca ttcgaatata ctcaggaagt    4620
cctcaacacc ttgtcaggtg cactcgagag agaactagga aggcttcaag gagagttcgc    4680
agaagctaac tcaaggatgg atcttggaga cgtagattcg gaaggaagaa cggggaagaa    4740
cgtcaaattg gaagcgatcc tgaaaaagct agccgatatc cctctgtgat ctagaaactg    4800
cgtgcacttc gtggccgagg agcaggactg acacgtccga cggcggccca cgggtcccag    4860
gcctcggaga tccgtccccc ttttcctttg tcgatatcat gtaattagtt atgtcacgct    4920
tacattcacg ccctcccccc acatccgctc taaccgaaaa ggaaggagtt agacaacctg    4980
```

```
aagtctaggt ccctatttat tttttttatag ttatgttagt attaagaacg ttatttatat    5040
ttcaaatttt tcttttttttt ctgtacagac gcgtgtacgc atgtaacatt atactgaaaa    5100
ccttgcttga aaggttttg ggacgctcga aggctttaat ttgcaagctg aattgtaccg     5160
ggcccggatc tctaggctt ggcactggcc gtcgttttac aacgtcgtga ctgggaaaac      5220
cctggcgtta cccaacttaa tcgccttgca gcacatcccc ctttcgccag ctggcgtaat    5280
agcgaagagg cccgcaccga tcgcccttcc caacagttgc gcagcctgaa tggcgaatgg    5340
cgcctgatgc ggtatttttct ccttacgcat ctgtgcggta tttcacaccg catagggtaa  5400
taactgatat aattaaattg aagctctaat ttgtgagttt agtatacatg catttactta    5460
taatacagtt ttttagttttt gctggccgca tcttctcaaa tatgcttccc agcctgcttt   5520
tctgtaacgt tcaccctcta ccttagcatc ccttcccttt gcaaatagtc ctcttccaac    5580
aataataatg tcagatcctg tagagaccac atcatccacg ttctatact gttgacccaa    5640 tgcgtctccc ttgtcatcta aacccacacc gggtgtcata atcaaccaat cgtaaccttc   5700
atctcttcca cccatgtctc tttgagcaat aaagccgata acaaaatctt tgtcgctctt    5760
cgcaatgtca acagtaccct tagtatattc tccagtagat agggagccct tgcatgacaa   5820
ttctgctaac atcaaaaggc ctctaggttc ctttgttact tcttctgccg cctgcttcaa    5880
accgctaaca ataccgggc ccaccacacc gtgtgcattc gtaatgtctg cccattctgc    5940
tattctgtat acacccgcag agtactgcaa tttgactgta ttaccaatgt cagcaaattt    6000
tctgtcttcg aagagtaaaa aattgtactt ggcggataat gcctttagcg cttaactgt    6060 gccctccatg gaaaaatcag tcaagatatc cacatgtgtt tttagtaaac aaattttggg    6120
acctaatgct tcaactaact ccagtaattc cttggtggta cgaacatcca atgaagcaca    6180
caagtttgtt tgcttttcgt gcatgatatt aaatagcttg gcagcaacag gactaggatg    6240
agtagcagca cgttccttat atgtagcttt cgacatgatt tatcttcgtt tcggttttg    6300 ttctgtgcag ttgggttaag aatactgggc aatttcatgt ttcttcaaca ctacatatgc   6360
gtatatatac caatctaagt ctgtgctcct tccttcgttc ttccttctgt tcggagatta   6420
ccgaatcaaa aaaatttcaa ggaaaccgaa atcaaaaaaa agaataaaaa aaaaatgatg   6480
aattgaaaag cacttgttac ccatcattga attttgaaca tccgaacctg ggagttttcc   6540
ctgaaacaga tagtatattt gaacctgtat aataatatat agtctagcgc tttacggaag   6600
acaatgtatg tatttcggtt cctggagaaa ctattgcatc tattgcatag gtaatcttgc    6660
acgtcgcatc cccggttcat tttctgcgtt tccatcttgc acttcaatag catatctttg   6720
ttaacgaagc atctgtgctt catttttgtaa aacaaaaatg caacgcgaga gcgctaattt   6780
ttcaaacaaa gaatctgagc tgcatttttta cagaacagaa atgcaacgcg aaagcgctat   6840
tttaccaacg aagaatctgt gcttcatttt tgtaaaacaa aaatgcaacg cgagagcgct   6900
aatttttcaa acaaagaatc tgagctgcat tttacagaa cagaaatgca acgcgagagc   6960
gctattttac caacaaagaa tctatacttc ttttttgttc tacaaaaatg catcccgaga   7020
gcgctatttt tctaacaaag catcttagat tactttttttt ctcctttgtg cgctctataa   7080
tgcagtctct tgataacttt ttgcactgta ggtccgttaa ggttagaaga aggctacttt   7140
ggtgtctatt ttctcttcca taaaaaaagc ctgactccac ttcccgcgtt tactgattac   7200
tagcgaagct gcgggtgcat ttttttcaaga taaaggcatc cccgattata ttctataccg  7260
atgtggattg cgcatacttt gtgaacgaaa agtgatagcg ttgatgattc ttcattggtc   7320
agaaaattat gaacggtttc ttctatttttg tctctatata ctacgtatag gaaatgttta   7380
```

```
cattttcgta ttgttttcga ttcactctat gaatagttct tactacaatt tttttgtcta    7440
aagagtaata ctagagataa acataaaaaa tgtagaggtc gagtttagat gcaagttcaa    7500
ggagcgaaag gtggatgggt aggttatata gggatatagc acagagatat atagcaaaga    7560
gatacttttg agcaatgttt gtggaagcgg tattcgcaat attttagtag ctcgttacag    7620
tccggtgcgt ttttggtttt ttgaaagtgc gtcttcagag cgcttttggt tttcaaaagc    7680
gctctgaagt tcctatactt tctagctaga gaataggaac ttcggaatag gaacttcaaa    7740
gcgtttccga aaacgagcgc ttccgaaaat gcaacgcgag ctgcgcacat acagctcact    7800
gttcacgtcg cacctatatc tgcgtgttgc ctgtatatat atatacatga gaagaacggc    7860
atagtgcgtg tttatgctta aatgcgttat ggtgcactct cagtacaatc tgctctgatg    7920
ccgcatagtt aagccagccc cgacacccgc caacacccgc tgacgcgccc tgacgggctt    7980
gtctgctccc ggcatccgct tacagacaag ctgtgaccgt ctccgggagc tgcatgtgtc    8040
agaggttttc accgtcatca ccgaaacgcg cgagacgaaa gggcctcgtg atacgcctat    8100
ttttataggt taatgtcatg ataataatgg tttcttagac gtcaggtggc acttttcggg    8160
gaaatgtgcg cggaacccct atttgtttat ttttctaaat acattcaaat atgtatccgc    8220
tcatgagaca ataaccctga taaatgcttc aataatattg aaaaaggaag agtatgagta    8280
ttcaacattt ccgtgtcgcc cttattccct tttttgcggc attttgcctt cctgtttttg    8340
ctcacccaga aacgctggtg aaagtaaaag atgctgaaga tcagttgggt gcacgagtgg    8400
gttacatcga actggatctc aacagcggta agatccttga gttttcgc cccgaagaac     8460 gttttccaat gatgagcact tttaaagttc tgctatgtgg cgcggtatta tcccgtattg    8520
acgccgggca agagcaactc ggtcgccgca tacactattc tcagaatgac ttggttgagt    8580
actcaccagt cacagaaaag catcttacgg atggcatgac agtaagagaa ttatgcagtg    8640
ctgccataac catgagtgat aacactgcgg ccaacttact tctgacaacg atcggaggac    8700
cgaaggagct aaccgctttt ttgcacaaca tgggggatca tgtaactcgc cttgatcgtt    8760
gggaaccgga gctgaatgaa gccataccaa acgacgagcg tgacaccacg atgcctgtag    8820
caatggcaac aacgttgcgc aaactattaa ctggcgaact acttactcta gcttcccggc    8880
aacaattaat agactggatg gaggcggata aagttgcagg accacttctg cgctcggccc    8940
ttccggctgg ctggtttatt gctgataaat ctggagccgg tgagcgtggg tctcgcggta    9000
tcattgcagc actggggcca gatggtaagc cctcccgtat cgtagttatc tacacgacgg    9060
ggagtcaggc aactatggat gaacgaaata gacagatcgc tgagataggt gcctcactga    9120
ttaagcattg gtaactgtca gaccaagttt actcatatat actttagatt gatttaaaac    9180 ttcatttta atttaaaagg atctaggtga agatccttt tgataatctc atgaccaaaa      9240
tcccttaacg tgagttttcg ttccactgag cgtcagaccc cgtagaaaag atcaaggat     9300 cttcttgaga tccttttttt ctgcgcgtaa tctgctgctt gcaaacaaaa aaaccaccgc    9360
taccagcggt ggtttgtttg ccggatcaag agctaccaac tctttttccg aaggtaactg    9420
gcttcagcag agcgcagata ccaaatactg ttcttctagt gtagccgtag ttaggccacc    9480
acttcaagaa ctctgtagca ccgcctacat accacgctct gctaatcctg ttaccagtgg    9540
ctgctgccag tggcgataag tcgtgtctta ccgggttgga ctcaagacga tagttaccgg    9600
ataaggcgca gcggtcgggc tgaacggggg gttcgtgcac acagcccagc ttggagcgaa    9660
cgacctacac cgaactgaga tacctacagc gtgagctatg agaaagcgcc acgcttcccg    9720
```

```
aagggagaaa ggcggacagg tatccggtaa gcggcagggt cggaacagga gagcgcacga    9780
gggagcttcc aggggggaaac gcctggtatc tttatagtcc tgtcgggttt cgccacctct    9840
gacttgagcg tcgattttttg tgatgctcgt caggggggcg gagcctatgg aaaaacgcca    9900
gcaacgcggc cttttttacgg ttcctggcct tttgctggcc ttttgctcac atgttctttc    9960
ctgcgttatc ccctgattct gtggataacc gtattaccgc ctttgagtga gctgataccg    10020
ctcgccgcag ccgaacgacc gagcgcagcg agtcagtgag cgaggaagcg gaagagcgcc    10080
caatacgcaa accgcctctc cccgcgcgtt ggccgattca ttaatgcagc tggcacgaca    10140
ggtttcccga ctggaaagcg ggcagtgacg caacgcaatt aatgtgagtt agctcactca    10200
ttaggcaccc caggctttac actttatgct tccggctcgt atgttgtgtg aattgtgag    10260 cggataacaa tttcacacag gaaacagcta tgacatgatt acgcggccgc gtggaatatt    10320
tcggatatcc ttttgttgtt ccgggtgta caatatggac ttcctctttt ctggcaacca    10380
aacccataca tcgggattcc tataatacct tcgttggtct ccctaacatg taggtggcgg    10440
aggggagata tacaatagaa cagataccag acaagacata atgggctaaa caagactaca    10500
ccaattacac tgcctcattg atggtggtac ataacgaact aatactgtag ccctagactt    10560
gatagccatc atcatatcga agtttcacta cccttttttcc atttgccatc tattgaagta    10620
ataataggcg catgcaactt cttttcttttt ttttttctttt ctctctcccc cgttgttgtc    10680
tcaccatatc cgcaatgaca aaaaaatgat ggaagacact aaaggaaaaa attaacgaca    10740
aagacagcac caacagatgt cgttgttcca gagctgatga ggggtatctc gaagcacacg    10800 aaacttttttc cttccttcat tcacgcacac tactctctaa tgagcaacgg tatacggcct    10860
tccttccagt tacttgaatt tgaaataaaa aaagtttgc tgtcttgcta tcaagtataa    10920
atagacctgc aattattaat cttttgtttc ctcgtcattg ttctcgttcc ctttcttcct    10980
tgtttctttt tctgcacaat atttcaagct ataccaagca tacaatcaac tccaagctga    11040
attcgagctc ggtaccattt aaaaaaatgt cacatcatca tcaccatcat atgagccaca    11100
gtactgcttc atcactggaa gaggcgaagg aaagaataag ggaaacattt ggaaaaaatg    11160
agctatctcc ttcttcctat gacacagcat gggtagctat ggtcccttca agatattcta    11220
tgaaccaacc atgttttcct cggtgcttgg attggattct tgaaaatcaa agagaagatg    11280
gatcttgggg cctaaatcct agccatccat tgcttgtaaa agactccctt tcttccactc    11340
tagcatgttt gcttgccctt cgcaaatgga gaattggaga taaccaagtc aaagaggcc    11400 ttggctttat tgaaacgcat ggttgggcag ttgataacgt ggatcagatt tcacctttag    11460
gatttgatat tatatttccc agcatgatca agtatgcaga gaaactgaat ttggatctac    11520
ctttcgatcc taaccttgta aatatgatgc tccgcgaacg cgaattaaca attgaaagag    11580
ccctaaagaa tgaattcgaa gggaatatgg caaatgttga atattttgct gaagggctcg    11640
gtgaattatg tcattggaaa gagataatgc ttcatcagag acgcaacgga tcgcccttg    11700 actctccagc aactactgca gctgctttga tttaccatca gcacgatgag aaatgctttg    11760
ggtacttgag ctcaatcttg aaactgcacg agaattgggt ccccactatt taccctacaa    11820
aggtacattc aaatctcttc ttcgttgatg cccttcaaaa tcttggagta gatcggtatt    11880
ttaaaacaga actcaaaagt gtactcgatg aaatatacag gctttggcta gaaaagaatg    11940
aagaaatttt ttcagacatt gctcattgtg ccatggcgtt tcgactttg cggatgaata    12000 actatgaagt ttcctcagaa gaacttgaag gatttgtcga ccaagaacat ttctttacaa    12060
catcaggtgg gaaacttatt agtcacgttg caattctcga acttcaccga gcttcacagg    12120
```

```
tggatattca agaagggaaa gatctcattt tagataaaat aagtacttgg acaaggaatt    12180
ttatggagca agaactcttg gacaatcaaa tccttgatag gtcaaagaag gagatggaat    12240
ttgctatgag gaaattttat ggcacatttg atcgagtgga aactagacga tacatcgagt    12300
catacaaaat ggacagtttt aagatcttaa aagcagccta caggtcttcc aacattaaca    12360
acatagactt gctaaagttc tcagaacatg attttaactt gtgccaagcc cgacacaaag    12420
aagaacttca acagattaag aggtggttcg cagattgcaa actggaacaa gtaggatcat    12480
cacaaaacta cttatacact agttacttcc caattgctgc catactcttc gaacctgaat    12540
atggtgatgc tcgtctagca tttgcaaagt gtggcataat cgcaacgacg gtggatgatt    12600
tcttcgatgg ttttgcttgc aatgaagaac tccaaaacat catcgaatta gtagagaggt    12660
gggatggata cccaactgtc ggatttcgtt cagaaagggt tagaattttc ttttgcac     12720 tttacaaaat gatagaggaa attgcggcaa aggcagaaac taagcaaggt cgatgtgtca    12780
aagatctcct tattaacttg tggattgatt tattgaaatg tatgctggtg gaattggacc    12840
tttggaaaat taaatcaact accccaagca tagaggagta cttgtctatc gcatgtgtaa    12900
ctacaggtgt taaatgttta attctctatat cactacatct tcttggacca aaactgtcca    12960
aggatgtcac agaaagttct gaggtcagtg ccttatggaa ttgtacagct gttgtggccc    13020
gattgaataa tgatatacat agttacaaga gagaacaagc agaaagttca acaaatatgg    13080
tagcaatatt aatatcacag agtcagagaa ctatctctga agaagaggct ataagacaga    13140
taaaagaaat gatggaaagt aagagaagag agttgctagg gatggttcta caaaataaag    13200
aaagccaatt gccgcaagtg tgcaaagatc ttttttggac gacattcaaa gcagcttatt    13260
ctatatatac acatggcgat gagtatcgct tcccacagga attgaagaac catataaacg    13320
atgtaattta caaaccactc aatcaatatt ccccataagc tagattacgt tctgcgattt    13380
tctcatgatc tttttcataa aatacataaa tatataaatg gctttatgta acaggcat     13440 aatttaaagt tttatttgcg attcatcgtt tttcaggtac tcaaacgctg aggtgtgcct    13500
tttgacttac ttttccgcct tggcaagctg gccgggtgat acttgcacaa gttccactaa    13560
ttactgacat ttgtggtatt aactcgtttg actgctctac aattgtagga tgttaatcaa    13620
tgtcttggct gccttcattc tcttcagg                                       13648
```

<210> SEQ ID NO 75
<211> LENGTH: 7760
<212> TYPE: DNA
<213> ORGANISM: Artificial Sequence
<220> FEATURE:
<223> OTHER INFORMATION: pALX40-13.3 vector

<400> SEQUENCE: 75

```
atgtcatctg gtgaaacttt tagaccaact gctgattttc atccatcttt gtggagaaat      60
cattttttgc aaggtgcatc agattttaag actgttgatc atacagctac aaatgaaaga    120
catgaagctt tgaaggaaga agttagaaga atgattactg atgcagaaga tcaaccaatt    180
caaaaattga gattgattga tgaagttcaa agattgggtg ttgcttacca ttttgaaaaa    240
gaaattgaag atgctattca acaattgtgt ccaattcata ttgattctga taagctgat     300 ttgcatactg tttctttgca tttcagattg ttgagacaac aaggtattaa gatttcttgt    360
gatgttttcg aacaatttaa ggatgatgaa ggtagattca aaagttcttt gattaatgat    420
gttcaaggca tgttgtcttt gtatgaagct gcttatatgg ctgttagagg tgaacatatt    480
```

```
ttggatgaag ctattgcatt tactactact catttgcaat cattggttgc acaagatcat    540
gttactccaa gattggctga acaaattaac catgctttgt atagaccatt gagaaaaact    600
ttgccaagat tggaagcaag atacattatg tcaagaattg attctacttc tgatgatttg    660
gttaacaaga ctttgttaaa tttcgctaag ttggatttca atattttgtt ggatttgcat    720
aaagaagaat tgaacgaatt gactaaatgg tggcaagatt tggattttac tactaaattg    780
ccatatgcta gagatagatt ggttgaattg tacttttggg atttgggtac ttattttgaa    840
ccacaatacg cttttggtag aaaaatcatg actaaattga actacatttt gtccattatt    900
gatgatacct acgatgctta cggtactttg gaagaattgt ctttgttcac cgaagctgtt    960
gctcgttgga acattgaagc tgttgacatg ttgccagatt atatgaagtt aatctacaga   1020
actttgttgg atacattcaa cgaaatagaa gaggatatgg ctaaacaagg tagatctcat   1080
tgtgtaagat acgctaaaga agaaattcaa aaggttattg gtgcttatta cgttcaagct   1140
aagtggtttt ctgaaggtta tgtccctact attgaagaat acatgccaat tgctttgact   1200
tcttgcgctt acagatttgt tattaccaat tcttttttgg gtatgggtga tttcgctaca   1260
aaggaagtat tcgaatggat ttctggtaat ccaaaagttg ttaaatctgc ttctgttatt   1320
tgtagattga tggacgatat gcaaggacac gaatttgaac aaaaaagagg tcacgttgca   1380
tctgcaattg aatgctatac taaacaacat ggtgtttcca aggaagaggc tatcaagatg   1440
ttcgaggaag aggttgctaa cgcttggaag gatatcaatg aagaattaat gatgaaacca   1500
ccagttgttg ctagaccatt gttaggtact attttgaatt tggctagagc tatcgatttt   1560
atctataaag aagatgacgg ttacactcat tcttatttga ttaaggaaca aatagcatct   1620
gttttgggtg atcatgttcc attttaatct agattacgtt ctgcgatttt ctcatgatct   1680
ttttcataaa atacataaat atataaatgg ctttatgtat aacaggcata atttaaagtt   1740
ttatttgcga ttcatcgttt ttcaggtact caaacgctga ggtgtgcctt tgacttact    1800
tttccgcctt ggcaagctgg ccgggtgata cttgcacaag ttccactaat tactgacatt   1860
tgtggtatta actcgtttga ctgctctaca attgtaggat gttaatcaat gtcttggctg   1920
ccttcattct cttcagggc ccggatcctc taggcttggc actggccgtc gttttacaac    1980
gtcgtgactg ggaaaaccct ggcgttaccc aacttaatcg ccttgcagca catccccctt   2040
tcgccagctg gcgtaatagc gaagaggccc gcaccgatcg cccttcccaa cagttgcgca   2100
gcctgaatgg cgaatggcgc ctgatgcggt attttctcct tacgcatctg tgcggtattt   2160
cacaccgcat agggtaataa ctgatataat taaattgaag ctctaatttg tgagtttagt   2220
atacatgcat ttacttataa tacagttttt tagttttgct ggccgcatct tctcaaatat   2280
gcttcccagc ctgctttct gtaacgttca ccctctacct tagcatccct ccctttgca     2340
aatagtcctc ttccaacaat aataatgtca gatcctgtag agaccacatc atccacggtt   2400
ctatactgtt gacccaatgc gtctcccttg tcatctaaac ccacaccggg tgtcataatc   2460
aaccaatcgt aaccttcatc tcttccaccc atgtctcttt gagcaataaa gccgataaca   2520
aaatctttgt cgctcttcgc aatgtcaaca gtaccctag tatattctcc agtagatagg    2580
gagcccttgc atgacaattc tgctaacatc aaaaggcctc taggttcctt tgttacttct   2640
tctgccgcct gcttcaaacc gctaacaata cctggtccca ccacaccgtg tgcattcgta   2700
atgtctgccc attctgctat tctgtataca cccgcagagt actgcaattt gactgtatta   2760
ccaatgtcag caaattttct gtcttcgaag agtaaaaaat tgtacttggc ggataatgcc   2820
tttagcggct taactgtgcc ctccatggaa aaatcagtca agatatccac atgtgttttt   2880
```

```
agtaaacaaa ttttgggacc taatgcttca actaactcca gtaattcctt ggtggtacga    2940
acatccaatg aagcacacaa gtttgtttgc ttttcgtgca tgatattaaa tagcttggca    3000
gcaacaggac taggatgagt agcagcacgt tccttatatg tagctttcga catgatttat    3060
cttcgtttcg gttttgttc tgtgcagttg ggttaagaat actgggcaat ttcatgtttc    3120
ttcaacacta catttgcgta tataccaa tctaagtctg tgctccttcc ttcgttcttc    3180
cttctgttcg gagattaccg aatcaaaaaa atttcaagga aaccgaaatc aaaaaaaaga    3240
ataaaaaaaa aatgatgaat tgaaaagcac ttgttaccca tcattgaatt ttgaacatcc    3300
gaacctggga gttttccctg aaacagatag tatatttgaa cctgtataat aatatatagt    3360
ctagcgcttt acggaagaca atgtatgtat ttcggttcct ggagaaacta ttgcatctat    3420
tgcataggta atcttgcacg tcgcatcccc ggttcatttt ctgcgtttcc atcttgcact    3480
tcaatagcat atctttgtta acgaagcatc tgtgcttcat tttgtaaaac aaaaatgcaa    3540
cgcgagagcg ctaattttc aaacaaagaa tctgagctgc atttttacag aacagaaatg    3600
caacgcgaaa gcgctatttt accaacgaag aatctgtgct tcatttttgt aaaacaaaaa    3660
tgcaacgcga gagcgctaat tttcaaaaca aagaatctga gctgcatttt tacagaacag    3720
aaatgcaacg cgagagcgct atttaccaa caaagaatct atacttcttt tttgttctac    3780
aaaaatgcat cccgagagcg ctattttct aacaaagcat cttagattac tttttttctc    3840
ctttgtgcgc tctataatgc agtctcttga taacttttg cactgtaggt ccgttaaggt    3900
tagaagaagg ctactttggt gtctattttc tcttccataa aaaaagcctg actccacttc    3960
ccgcgtttac tgattactag cgaagctgcg ggtgcatttt ttcaagataa aggcatcccc    4020
gattatattc tataccgatg tggattgcgc atactttgtg aacagaaagt gatagcgttg    4080
atgattcttc attggtcaga aaattatgaa cggtttcttc tattttgtct ctatatacta    4140
cgtataggaa atgtttacat tttcgtattg ttttcgattc actctatgaa tagttcttac    4200 tacaatttt ttgtctaaag agtaaactta gagataaca taaaaaatgt agaggtcgag    4260
tttagatgca agttcaagga gcgaaaggtg gatgggtagg ttatataggg atatagcaca    4320
gagatatata gcaaagagat acttttgagc aatgtttgtg gaagcggtat tcgcaatatt    4380
ttagtagctc gttacagtcc ggtgcgtttt tggttttttg aaagtgcgtc ttcagagcgc    4440
ttttggtttt caaaagcgct ctgaagttcc tatactttct agctagagaa taggaacttc    4500
ggaataggaa cttcaaagcg tttccgaaaa cgagcgcttc cgaaaatgca acgcgagctg    4560
cgcacataca gctcactgtt cacgtcgcac ctatatctgc gtgttgcctg tatatatata    4620
tacatgagaa gaacggcata gtgcgtgttt atgcttaaat gcgttatggt gcactctcag    4680
tacaatctgc tctgatgccg catagttaag ccagccccga cacccgccaa cacccgctga    4740
cgcgccctga cgggcttgtc tgctcccggc atccgcttac agacaagctg tgaccgtctc    4800
cgggagctga atgtgtcaga ggttttcacc gtcatcaccg aaacgcgcga gacgaaaggg    4860
cctcgtgata cgcctatttt tataggttaa tgtcatgata ataatggttt cttagacgtc    4920
aggtggcact tttcggggaa atgtgcgcgg aaccccctat tgtttatttt tctaaataca    4980
ttcaaatatg tatccgctca tgagacaata accctgataa atgcttcaat aatattgaaa    5040
aaggaagagt atgagtattc aacatttccg tgtcgccctt attccctttt tgcggcatt    5100 ttgccttcct gttttgctc acccagaaac gctggtgaaa gtaaaagatg ctgaagatca    5160
gttgggtgca cgagtgggtt acatcgaact ggatctcaac agcggtaaga tccttgagag    5220
```

```
ttttcgcccc gaagaacgtt ttccaatgat gagcactttt aaagttctgc tatgtggcgc    5280
ggtattatcc cgtattgacg ccgggcaaga gcaactcggt cgccgcatac actattctca    5340
gaatgacttg gttgagtact caccagtcac agaaaagcat cttacggatg gcatgacagt    5400
aagagaatta tgcagtgctg ccataaccat gagtgataac actgcggcca acttacttct    5460
gacaacgatc ggaggaccga aggagctaac cgcttttttg cacaacatgg ggatcatgt     5520 aactcgcctt gatcgttggg aaccggagct gaatgaagcc ataccaaacg acgagcgtga    5580
caccacgatg cctgtagcaa tggcaacaac gttgcgcaaa ctattaactg gcgaactact    5640
tactctagct tcccggcaac aattaataga ctggatggag gcggataaag ttgcaggacc    5700
acttctgcgc tcggcccttc cggctggctg gtttattgct gataaatctg gagccggtga    5760
gcgtgggtct cgcggtatca ttgcagcact ggggccagat ggtaagccct cccgtatcgt    5820
agttatctac acgacgggga gtcaggcaac tatgatgaa cgaaatagac agatcgctga     5880
gataggtgcc tcactgatta agcattggta actgtcagac caagtttact catatatact    5940
ttagattgat ttaaaacttc attttaatt taaaaggatc taggtgaaga tcctttttga     6000
taatctcatg accaaaatcc cttaacgtga gttttcgttc cactgagcgt cagacccgt     6060 agaaaagatc aaaggatctt cttgagatcc ttttttctg cgcgtaatct gctgcttgca     6120 aacaaaaaa ccaccgctac cagcggtggt ttgtttgccg gatcaagagc taccaactct     6180
ttttccgaag gtaactggct tcagcagagc gcagatacca atactgttc ttctagtgta     6240 gccgtagtta ggccaccact tcaagaactc tgtagcaccg cctacatacc acgctctgct    6300
aatcctgtta ccagtggctg ctgccagtgg cgataagtcg tgtcttaccg ggttggactc    6360
aagacgatag ttaccggata aggcgcagcg gtcgggctga acggggggtt cgtgcacaca    6420
gcccagcttg gagcgaacga cctacaccga actgagatac ctacagcgtg agctatgaga    6480
aagcgccacg cttcccgaag ggagaaaggc ggacaggtat ccggtaagcg cagggtcgg    6540 aacaggagag cgcacgaggg agcttccagg gggaaacgcc tggtatcttt atagtcctgt    6600
cgggtttcgc cacctctgac ttgagcgtcg atttttgtga tgctcgtcag ggggacggag    6660
cctatggaaa aacgccagca acgcggcctt tttacggttc ctggccttt gctggccttt     6720 tgctcacatg ttcttcctg cgttatcccc tgattctgtg ataaccgta ttaccgcctt       6780 tgagtgagct gataccgctc gccgcagccg aacgaccgag cgcagcgagt cagtgagcga    6840
ggaagcggaa gagcgcccaa tacgcaaacc gcctctcccc gcgcgttggc cgattcatta    6900
atgcagctgg cacgacaggt ttcccgactg gaaagcgggc agtgacgcaa cgcaattaat    6960
gtgagttagc tcactcatta ggcaccccag gctttacact ttatgcttcc ggctcgtatg    7020
ttgtgtggaa ttgtgagcgg ataacaattt cacacaggaa acagctatga catgattacg    7080
aattgggcgg ccgcttgggc gcgaatcctt tattttggct tcaccctcat actattatca    7140
gggccagaaa aaggaagtgt ttccctcctt cttgaattga tgttaccctc ataaagcacg    7200
tggcctctta tcgagaaaga aattaccgtc gctcgtgatt tgtttgcaaa aagaacaaaa    7260
ctgaaaaaac ccagacacgc tcgacttcct gtcttcctat tgattgcagc ttccaatttc    7320
gtcacacaac aaggtcctag cgacggctca caggttttgt aacaagcaat cgaaggttct    7380
ggaatggcgg gaaagggttt agtaccacat gctatgatgc ccactgtgat ctccagagca    7440
aagttcgttc gatcgtactg ttactctctc tctttcaaac agaattgtcc gaatcgtgtg    7500
acaacaacag cctgttctca cacactcttt tcttctaacc aaggggggtgg tttagtttag    7560 tagaacctcg tgaaacttac atttacatat atataaactt gcataaattg gtcaatgcaa    7620
```

```
gaaatacata tttggtcttt tctaattcgt agttttttcaa gttcttagat gctttctttt    7680
tctctttttt acagatcatc aaggaagtaa ttatctactt tttacaacaa atataaaaca    7740
ggtaccacgg ctttaaaaaa                                                 7760
```

<210> SEQ ID NO 76
<211> LENGTH: 12741
<212> TYPE: DNA
<213> ORGANISM: Artificial Sequence
<220> FEATURE:
<223> OTHER INFORMATION: pALX40-170.2R vector

<400> SEQUENCE: 76

```
ggccgcatag cttcaaaatg tttctactcc ttttttactc ttccagattt tctcggactc      60
cgcgcatcgc cgtaccactt caaaacaccc aagcacagca tactaaattt cccctctttc     120
ttcctctagg gtgtcgttaa ttacccgtac taaaggtttg gaaagaaaa aagagaccgc      180 ctcgtttctt tttcttcgtc gaaaaggca ataaaaattt ttatcacgtt tcttttttctt    240 gaaaattttt ttttttgatt ttttctctt tcgatgacct cccattgata tttaagttaa    300
taaacggtct tcaatttctc aagtttcagt ttcattttc ttgttctatt acaactttt     360 ttacttcttg ctcattagaa agaaagcata gcaatctaat ctaagttttg gtaccattta    420
aaaaaatggc gtcgcaagcg agtgaaaaag acatttccct tgttcaaact ccgcataagg    480
ttgaggttaa tgaaaagatc gaggagtcaa tcgagtacgt ccaaaatctg ttgatgacgt    540
cgggcgacgg gcgaataagc gtgtcaccct atgacacggc agtgatcgcc ctgatcaagg    600
acttgaaagg gcgcgacgcc ccgcagtttc cgtcatgtct cgagtggatc gcgcaccacc    660
aactggctga tggctcatgg ggcgacgaat tcttctgtat ttatgatcgg attctaaata    720
cattggcatg tgtcgtagcc ttgaaatcat ggaaccttca ctctgatatt attgaaaaag    780
gagtgacgta catcaaggag aatgtgcata aacttaaagg tgcaaatgtt gagcacagga    840
cagcggggtt cgaacttgtg gttcctactt ttatgcaaat ggccacagat ttgggcatcc    900
aagatctgcc ctatgatcat ccctctcatca aggagattgc tgacacaaaa caacaaagat    960
tgaaagagat acccaaggat ttggtttacc aaatgccaac gaatttactg tacagtttag   1020
aagggttagg agatttggag tgggaaaggc tactgaaact gcagtcgggc aatggctcct   1080
tcctcacttc gccgtcgtcc accgccgccg tcttgatgca taccaaagat gaaaatgtt    1140 tgaaatacat cgaaaacgcc ctcaagaatt gcgacggagg agcaccacat acttatccag   1200
tcgatatctt ctcaagactt tgggcaatcg ataggctaca acgcctagga atttctcgtt   1260
tcttccagca cgagatcaag tatttcttag atcacatcga aagcgtttgg gaggagaccg   1320
gagttttcag tggaagatat acgaaattta gcgatattga tgcacgtcc atgggcgtta    1380 ggcttctcaa aatgcacgga tacgacgtcg atccaaatgt actaaaacat ttcaagcaac   1440
aagatggtaa atttcctgc tacattggtc aatcggtcga gtctgcatct ccaatgtaca    1500
atctttatag ggctgctcaa ctaagatttc caggagaaga agttcttgaa gaagccacta   1560
aatttgcctt taacttcttg caagaaatgc tagtcaaaga tcgacttcaa gaaagatggg   1620
tgatatccga ccacttattt gatgagataa agctggggtt gaagatgcca tggtacgcca   1680
ctctaccccg agtcgaggct gcatattatc tagaccatta tgctggttct ggtgatgtat   1740
ggattggcaa gagtttctac aggatgccag aaatcagcaa tgatacatac aaggagcttg   1800
cgatattgga tttcaacaga tgccaaacac aacatcagtt ggagtggatc cacatgcagg   1860
```

```
aatggtacga cagatgcagc cttagcgaat tcgggataag caaaagagag ttgcttcgct    1920
cttactttct ggccgcagca accatattcg aaccggagag aactcaagag aggcttctgt    1980
gggccaaaac cagaattctt tctaagatga tcacttcatt tgtcaacatt agtggaacaa    2040
cactatcttt ggactacaat ttcaatggcc tcgatgaaat aattagtagt gccaatgaag    2100
atcaaggact ggctgggact ctgctggcaa ccttccatca acttctagac ggattcgata    2160
tatacactct ccatcaactc aaacatgttt ggagccaatg gttcatgaaa gtgcagcaag    2220
gagagggaag cggcgggaa gacgcggtgc tcctagcgaa cacgctcaac atctgcgccg    2280
gcctcaacga agacgtgttg tccaacaatg aatacacggc tctgtccacc ctcacaaata    2340
aaatctgcaa tcgcctcgcc caaattcaag acaataagat tctccaagtt gtggatggga    2400
gcataaagga taaggagcta aacaggata tgcaggcgtt ggtgaagtta gtgcttcaag    2460
aaaatggcgg cgccgtagac agaaacatca gacacacgtt tttgtcggtt ccaagactt    2520 tctactacga tgcctaccac gacgatgaga cgaccgatct tcatatcttc aaagtactct    2580
ttcgaccggt tgtatgaact agacaacgcg tcaataatat aggctacata aaaatcataa    2640
taactttgtt atcatagcaa aatgtgatat aaaacgtttc atttcacctg aaaaatagta    2700
aaaataggcg acaaaaatcc ttagtaatat gtaaacttta ttttctttat ttatttacag    2760
aactctgaat atacattgat tgttcacatt ttttttttct cttctcaatt tcccttgatt    2820
atattcaaaa ggttattggc ctcttgaatg tttcccactg atggtcgacg tgggccgcaa    2880
cacgcttttt cagttcgagt ttatcattat caatactgcc atttcaaaga atacgtaaat    2940
aattaatagt agtgattttc ctaactttat ttagtcaaaa aattagcctt ttaattctgc    3000
tgtaacccgt acatgcccaa aatagggggc gggttacaca gaatatataa catcgtaggt    3060
gtctgggtga acagtttatt cctggcatcc actaaatata atggagcccg cttttttaagc    3120 tggcatccag aaaaaaaaag aatcccagca ccaaatatt gttttcttca ccaaccatca    3180
gttcataggt ccattctctt agcgcaacta cagagaacag gggcacaaac aggcaaaaaa    3240
cgggcacaac ctcaatggag tgatgcaacc tgcctggagt aaatgatgac acaaggcaat    3300
tgacccacgc atgtatctat ctcatttct tacaccttct attaccttct gctctctctg    3360
atttggaaaa agctgaaaaa aaaggttgaa accagttccc tgaaattatt ccctacttg    3420 actaataagt atataaagac ggtaggtatt gattgtaatt ctgtaaatct atttcttaaa    3480
cttcttaaat tctactttta tagttagtct tttttttagt tttaaaacac caagaactta    3540
gtttcgaata aacacacata aacaaaccca ggtaccattt aaaaaaatgg attacgcgaa    3600
catcctcaca gcaattccac tcgagtttac tcctcaggat gatatcgtgc tccttgaacc    3660
gtatcactac ctaggaaaga accctggaaa agaaattcga tcacaactca tcgaggcttt    3720
caactattgg ttggatgtca agaaggagga tctcgaggtc atccagaacg ttgttggcat    3780
gctacatacc gctagcttat taatggacga tgtggaggat tcatcggtcc tcaggcgtgg    3840
gtcgcctgtg gcccatctaa tttacgggat tccgcagaca ataaacactg caaactacgt    3900
ctactttctg gcttatcaag agatcttcaa gcttcgccca acaccgatac ccatgcctgt    3960
aattcctcct tcatctgctt cgcttcaatc atccgtctcc tctgcatcct cctcctcctc    4020
ggcctcgtct gaaaacgggg gcacgtcaac tcctaattcg cagattccgt tctcgaaaga    4080
tacgtatctt gataaagtga tcacagacga gatgctttcc ctccatagag ggcaaggcct    4140
ggagctattc tggagagata gtctgacgtg tcctagcgaa gaggaatatg tgaaaatggt    4200
tcttggaaag acgggaggtt tgttccgtat agcggtcaga ttgatgatgg caaagtcaga    4260
```

```
atgtgacata gactttgtcc agcttgtcaa cttgatctca atatacttcc agatcaggga    4320
tgactatatg aaccttcagt cttctgagta tgcccataat aagaattttg cagaggacct    4380
cacagaaggg aaattcagtt ttcccactat ccactcgatt catgccaacc cctcatcgag    4440
actcgtcatc aatacgttgc agaagaaatc gacctctcct gagatccttc accactgtgt    4500
aaactacatg cgcacagaaa cccactcatt cgaatatact caggaagtcc tcaacacctt    4560
gtcaggtgca ctcgagagag aactaggaag cttcaagga gagttcgcag aagctaactc    4620
aaggatggat cttggagacg tagattcgga aggaagaacg gggaagaacg tcaaattgga    4680
agcgatcctg aaaaagctag ccgatatccc tctgtgatct agaaactgcg tgcacttcgt    4740
ggccgaggag caggactgac acgtccgacg gcggcccacg ggtcccaggc ctcggagatc    4800
cgtccccctt ttcctttgtc gatatcatgt aattagttat gtcacgctta cattcacgcc    4860
ctccccccac atccgctcta accgaaaagg aaggagttag acaacctgaa gtctaggtcc    4920
ctatttattt ttttatagtt atgttagtat taagaacgtt attatatttt caaatttttc    4980
ttttttttct gtacagacgc gtgtacgcat gtaacattat actgaaaacc ttgcttgaga    5040
aggttttggg acgctcgaag gctttaattt gcaagctgaa ttgtaccggg cccggatcct    5100
ctaggcttgg cactggccgt cgttttacaa cgtcgtgact gggaaaaccc tggcgttacc    5160
caacttaatc gccttgcagc acatccccct ttcgccagct ggcgtaatag cgaagaggcc    5220
cgcaccgatc gcccttccca acagttgcgc agcctgaatg gcgaatggcg cctgatgcgg    5280
tattttctcc ttacgcatct gtgcggtatt tcacaccgca tagggtaata actgatataa    5340
ttaaattgaa gctctaattt gtgagtttag tatacatgca tttacttata atacagtttt    5400
ttagttttgc tggccgcatc ttctcaaata tgcttcccag cctgcttttc tgtaacgttc    5460
accctctacc ttagcatccc ttccctttgc aaatagtcct cttccaacaa taataatgtc    5520
agatcctgta gagaccacat catccacggt tctatactgt tgacccaatg cgtctccctt    5580
gtcatctaaa cccacaccgg gtgtcataat caaccaatcg taaccttcat ctcttccacc    5640
catgtctctt tgagcaataa agccgataac aaaatctttg tcgctcttcg caatgtcaac    5700
agtaccctta gtatattctc cagtagatag ggagcccttg catgacaatt ctgctaacat    5760
caaaaggcct ctaggttcct tgttacttc ttctgccgcc tgcttcaaac cgctaacaat    5820
acctgggccc accacaccgt gtgcattcgt aatgtctgcc cattctgcta ttctgtatac    5880
acccgcagag tactgcaatt tgactgtatt accaatgtca gcaaattttc tgtcttcgaa    5940
gagtaaaaaa ttgtacttgg cggataatgc ctttagcggc ttaactgtgc cctccatgga    6000
aaaatcagtc aagatatcca catgtgtttt tagtaaacaa attttgggac ctaatgcttc    6060
aactaactcc agtaattcct tggtggtacg aacatccaat gaagcacaca gtttgtttg    6120
cttttcgtgc atgatattaa atagcttggc agcaacagga ctaggatgag tagcagcacg    6180
ttccttatat gtagctttcg acatgattta tcttcgtttc ggttttgtt ctgtgcagtt    6240
gggttaagaa tactgggcaa tttcatgttt cttcaacact acatatgcgt atatatacca    6300
atctaagtct gtgctccttc cttcgttctt ccttctgttc ggagattacc gaatcaaaaa    6360
aatttcaagg aaaccgaaat caaaaaaaag aataaaaaaa aatgatgaa ttgaaaagca    6420
cttgttaccc atcattgaat tttgaacatc cgaacctggg agttttccct gaaacagata    6480
gtatatttga acctgtataa taatatatag tctagcgctt tacggaagac aatgtatgta    6540
tttcggttcc tggagaaact attgcatcta ttgcataggt aatcttgcac gtcgcatccc    6600
```

-continued

```
cggttcattt tctgcgtttc catcttgcac ttcaatagca tatctttgtt aacgaagcat    6660
ctgtgcttca ttttgtaaaa caaaaatgca acgcgagagc gctaattttt caaacaaaga    6720
atctgagctg catttttaca gaacagaaat gcaacgcgaa agcgctattt taccaacgaa    6780
gaatctgtgc ttcatttttg taaaacaaaa atgcaacgcg agagcgctaa ttttcaaac     6840 aaagaatctg agctgcattt ttacagaaca gaaatgcaac gcgagagcgc tattttacca    6900
acaaagaatc tatacttctt ttttgttcta caaaaatgca cccgagagc gctattttc      6960 taacaaagca tcttagatta ctttttttct cctttgtgcg ctctataatg cagtctcttg    7020
ataacttttt gcactgtagg tccgttaagg ttagaagaag gctactttgg tgtctatttt    7080
ctcttccata aaaaagcct gactccactt cccgcgttta ctgattacta gcgaagctgc     7140
gggtgcattt tttcaagata aaggcatccc cgattatatt ctataccgat gtggattgcg    7200
catactttgt gaacagaaag tgatagcgtt gatgattctt cattggtcag aaaattatga    7260
acggtttctt ctattttgtc tctatatact acgtatagga aatgtttaca ttttcgtatt    7320
gttttcgatt cactctatga atagttctta ctacaatttt tttgtctaaa gagtaatact    7380
agagataaac ataaaaatg tagaggtcga gtttagatgc aagttcaagg agcgaaaggt     7440
ggatgggtag gttatatagg gatatagcac agagatatat agcaaagaga ctttttgag    7500 caatgtttgt ggaagcggta ttcgcaatat tttagtagct cgttacagtc cggtgcgttt    7560 ttggttttt gaaagtgcgt cttcagagcg cttttggttt tcaaaagcgc tctgaagttc     7620
ctatactttc tagctagaga ataggaactt cggaatagga acttcaaagc gtttccgaaa    7680
acgagcgctt ccgaaaatgc aacgcgagct gcgcacatac agctcactgt tcacgtcgca    7740
cctatatctg cgtgttgcct gtatatatat atacatgaga gaacggcat agtgcgtgtt    7800 tatgcttaaa tgcgttatgg tgcactctca gtacaatctg ctctgatgcc gcatagttaa    7860
gccagccccg acaccgcca acacccgctg acgcgccctg acgggcttgt ctgctcccgg     7920
catccgctta cagacaagct gtgaccgtct ccgggagctg catgtgtcag aggttttcac    7980
cgtcatcacc gaaacgcgcg agacgaaagg gcctcgtgat acgcctattt ttataggtta    8040
atgtcatgat aataatggtt tcttagacgt caggtggcac ttttcgggga atgtgcgcg    8100 gaaccctat ttgtttattt ttctaaatac attcaaatat gtatccgctc atgagacaat     8160
aaccctgata aatgcttcaa taatattgaa aaaggaagag tatgagtatt caacatttcc    8220
gtgtcgccct tattccttt tttgcggcat tttgccttcc tgttttgct cacccagaaa      8280 cgctggtgaa agtaaaagat gctgaagatc agttgggtgc acgagtgggt tacatcgaac    8340
tggatctcaa cagcggtaag atccttgaga ttttcgccc cgaagaacgt tttccaatga    8400
tgagcacttt taaagttctg ctatgtggcg cggtattatc ccgtattgac gccgggcaag    8460
agcaactcgg tcgccgcata cactattctc agaatgactt ggttgagtac tcaccagtca    8520
cagaaaagca tcttacggat ggcatgacag taagagaatt atgcagtgct gccataacca    8580
tgagtgataa cactgcggcc aacttacttc tgacaacgat cggaggaccg aaggagctaa    8640 ccgcttttt gcacaacatg gggatcatg taactcgcct gatcgttgg gaaccggagc       8700 tgaatgaagc cataccaaac gacgagcgtg acaccacgat gcctgtagca atggcaacaa    8760
cgttgcgcaa actattaact ggcgaactac ttactctagc ttcccggcaa caattaatag    8820
actggatgga ggcggataaa gttgcaggac cacttctgcg ctcggccctt ccggctggct    8880
ggtttattgc tgataaatct ggagccggtg agcgtgggtc tcgcggtatc attgcagcac    8940
tggggccaga tggtaagccc tcccgtatcg tagttatcta cacgacgggg agtcaggcaa    9000
```

```
ctatggatga acgaaataga cagatcgctg agataggtgc ctcactgatt aagcattggt   9060
aactgtcaga ccaagtttac tcatatatac tttagattga tttaaaactt catttttaat   9120
ttaaaaggat ctaggtgaag atcctttttg ataatctcat gaccaaaatc ccttaacgtg   9180
agttttcgtt ccactgagcg tcagacccg tagaaaagat caaaggatct tcttgagatc    9240
ctttttttct gcgcgtaatc tgctgcttgc aaacaaaaaa accaccgcta ccagcggtgg   9300
tttgtttgcc ggatcaagag ctaccaactc tttttccgaa ggtaactggc ttcagcagag   9360
cgcagatacc aaatactgtt cttctagtgt agccgtagtt aggccaccac ttcaagaact   9420
ctgtagcacc gcctacatac cacgctctgc taatcctgtt accagtggct gctgccagtg   9480
gcgataagtc gtgtcttacc gggttggact caagacgata gttaccggat aaggcgcagc   9540
ggtcgggctg aacggggggt tcgtgcacac agcccagctt ggagcgaacg acctacaccg   9600
aactgagata cctacagcgt gagctatgag aaagcgccac gcttcccgaa gggagaaagg   9660
cggacaggta tccggtaagc ggcagggtcg gaacaggaga gcgcacgagg gagcttccag   9720
ggggaaacgc ctggtatctt tatagtcctg tcgggtttcg ccacctctga cttgagcgtc   9780
gatttttgtg atgctcgtca ggggggcgga gcctatggaa aaacgccagc aacgcggcct   9840
ttttacggtt cctggccttt tgctggcctt ttgctcacat gttctttcct gcgttatccc   9900
ctgattctgt ggataaccgt attaccgcct ttgagtgagc tgataccgct cgccgcagcc   9960
gaacgaccga gcgcagcgag tcagtgagcg aggaagcgga agagcgccca atacgcaaac  10020
cgcctctccc cgcgcgttgg ccgattcatt aatgcagctg gcacgacagg tttcccgact  10080
ggaaagcggg cagtgacgca acgcaattaa tgtgagttag ctcactcatt aggcaccca   10140 ggctttacac tttatgcttc cggctcgtat gttgtgtgga attgtgagcg ataacaatt   10200 tcacacagga aacagctatg acatgattac gcggcccctg aagagaatga aggcagccaa  10260
gacattgatt aacatcctac aattgtagag cagtcaaacg agttaatacc acaaatgtca  10320
gtaattagtg gaacttgtgc aagtatcacc cggccagctt gccaaggcgg aaaagtaagt  10380
caaaaggcac acctcagcgt ttgagtacct gaaaaacgat gaatcgcaaa taaaacttta  10440
aattatgcct gttatacata aagccattta tatatttatg tattttatga aaaagatcat  10500
gagaaaatcg cagaacgtaa tctagttcaa aagacaaagg atttcatatc ttccttggat  10560
tgctgaggag aagtcaattc atcgttgatc ccataagcat aaaacgtacc cttagccatc  10620
tccaaaaata catctttgca tcttcttggc aaaatgcttt ctttttata cacaatctgc   10680 aacacttttc tccagtgata ttcaaccatt tcattgatct ctgcaatggc ttcatcttca  10740
ctaacttttc ttccatcttt ctcagttgct agtagaatgc tataacttt tcctgcaata   10800 ttttcctcgc gctccctctc agaactgcac acgtcgttga gcagccggcc gaccatacag  10860
acatgcctag ccaaatcagt gcactcttca ctcataagca tttcatcgga caattttact  10920
ccgacgaatt gcatcgtcag gagacctgtc agccgggaac cgttcgacaa ccacgacgaa  10980
gaaatgtatt catcgaagct ttgctgcgtg ccattgctcc atgtatctaa ttctatcttg  11040
aaagctgaga gtatttcaac ccacagtttg actagaaact ctttgacact acgcccctgt  11100
tcaacacgag ccctctccgc caactcattt actgtattgt acaacgccat aaaaaggatc  11160
tcaagctcct cagatccgta ctctgcatcc ggattctcct tccattcttt tactaattca  11220
atgatcttgt cacactcttg actagagcca tgacagtcga aaaaatcatc cataattgtt  11280
acaagcacag atgttttggc aaatgcgaga cgaacatagt caaacgcatg atcaccaata  11340
```

| attaatgaag ccaaataatt agcaataata actacatctc ttccaaagtt taaggtgtcc | 11400 |
| aacctacaat ctgcatacca cctttgcagt tgttgaagtc ctttctggtt ctgggcttca | 11460 |
| tgtatatcga atcttgctt tgcgaaaact agaaaatctt cgttgcataa attagagaac | 11520 |
| ctgtttgtag atttcagagc ttgatagtag gtcatgtcat atagctcgag gtttcgtcta | 11580 |
| gctcccaatc ttatggttat gcctttgtaa ttcctcaagt agaattccac cagtttgtgc | 11640 |
| agttttttgt cgggaattga gttatcttgc acttgcttat tgagaaagat ggtagtccaa | 11700 |
| gcaagaattt tttcaagact cctctcttct tcatatattc tctcatttgc tgctctataa | 11760 |
| agctcaataa tcatcggcag gtcatttgtt tgctggctaa cagcctcttg gttaccatat | 11820 |
| ggagccaact cctctgatga aacttcgtat cctttcactc gcaaaagcct aaatgccatt | 11880 |
| gcatgagtag taacattgcc atatataact ttgtgttttt cttgccacaa cctgaatgtg | 11940 |
| ttatctagaa tagtgttgat ttcatattgg aagaattgat cgaccccaa cctttgaagg | 12000 |
| gtgtcgatta tacacaaatt agagggtata tcttcggatc gaagagtcgt tgtcgttgga | 12060 |
| aatttatcgt cttccatttt tttaaatggt acctgtttta tatttgttgt aaaaagtaga | 12120 |
| taattacttc cttgatgatc tgtaaaaaag agaaaaagaa agcatctaag aacttgaaaa | 12180 |
| actacgaatt agaaaagacc aaatatgtat ttcttgcatt gaccaattta tgcaagttta | 12240 |
| tatatatgta aatgtaagtt tcacgaggtt ctactaaact aaaccacccc cttggttaga | 12300 |
| agaaaagagt gtgtgagaac aggctgttgt tgtcacacga ttcggacaat tctgtttgaa | 12360 |
| agagagagag taacagtacg atcgaacgaa cttgctctg gagatcacag tgggcatcat | 12420 |
| agcatgtggt actaaaccct tcccgccat tccagaacct tcgattgctt gttacaaaac | 12480 |
| ctgtgagccg tcgctaggac cttgttgtgt gacgaaattg gaagctgcaa tcaataggaa | 12540 |
| gacaggaagt cgagcgtgtc tgggtttttt cagttttgtt cttttgcaa acaaatcacg | 12600 |
| agcgacggta atttctttct cgataagagg ccacgtgctt tatgagggta acatcaattc | 12660 |
| aagaaggagg gaaacacttc cttttctgg ccctgataat agtatgaggg tgaagccaaa | 12720 |
| ataaaggatt cgcgcccaag c | 12741 |

<210> SEQ ID NO 77
<211> LENGTH: 2382
<212> TYPE: DNA
<213> ORGANISM: Nicotiana glutinosa
<220> FEATURE:
<223> OTHER INFORMATION: NgSPP S3F1-4

<400> SEQUENCE: 77

| atgatacttg gactgagaag cacaatcata ccacttcctg atcataagtt gggaaatatc | 60 |
| aaattaggtt cagtaaccaa agattcaaat ttccacagac caagtagagt aagatgcagc | 120 |
| cacagtactg cttcatcact ggaagaggcg aaggaaagaa taagggaaac atttggaaaa | 180 |
| aatgagctat ctccttcttc ctatgacaca gcatgggtag ctatggtccc ttcaagatat | 240 |
| tctatgaacc aaccatgttt tcctcggtgc ttggattgga ttcttgaaaa tcaaagagaa | 300 |
| gatggatctt ggggcctaaa tcctagccat ccattgcttg taaaagactc cctttcttcc | 360 |
| actctagcat gtttgcttgc ccttcgcaaa tggagaattg gagataacca agtccaagaa | 420 |
| ggccttggct ttattgaaac gcatggttgg gcagttgata acgtggatca gatttcacct | 480 |
| ttaggatttg atattatatt tcccagcatg atcaagtatg cagagaaact gaatttggat | 540 |
| ctaccttcg atcctaacct tgtaaatatg atgctccgcg aacgcgaatt aacaattgaa | 600 |
| agagccctaa agaatgaatt cgaagggaat atggcaaatg ttgaatattt tgctgaaggg | 660 |

-continued

```
ctcggtgaat tatgtcattg gaaagagata atgcttcatc agagacgcaa cggatcgctc      720
tttgactctc cagcaactac tgcagctgct ttgatttacc atcagcacga tgagaaatgc      780
tttgggtact tgagctcaat cttgaaactg cacgagaatt gggtccccac tatttaccct      840
acaaaggtac attcaaatct cttcttcgtt gatgcccttc aaaatcttgg agtagatcgg      900
tattttaaaa cagaactcaa aagtgtactc gatgaaatat acaggctttg gctagaaaag      960
aatgaagaaa ttttttcaga cattgctcat tgtgccatgg cgtttcgact tttgcggatg     1020
aataactatg aagtttcctc agaagaactt gaaggatttg tcgaccaaga cattctcttt     1080
acaacatcag gtgggaaact tattagtcac gttgcaattc tcgaacttca ccgagcttca     1140
caggtggata ttcaagaagg gaaagatctc attttagata aaataagtac ttggacaagg     1200
aattttatgg agcaagaact cttggacaat caaatccttg ataggtcaaa gaaggagatg     1260
gaatttgcta tgaggaaatt ttatggcaca tttgatcgag tggaaactag acgatacatc     1320
gagtcataca aaatggacag ttttaagatc ttaaaagcag cctacaggtc ttccaacatt     1380
aacaacatag acttgctaaa gttctcagaa catgatttta acttgtgcca agcccgacac     1440
aaagaagaac ttcaacagat taagaggtgg ttcgcagatt gcaaactgga caagtagga      1500
tcatcacaaa actacttata cactagttac ttcccaattg ctgccatact cttcgaacct     1560
gaatatggtg atgctcgtct agcatttgca aagtgtggca taatcgcaac gacggtggat     1620
gatttcttcg atggttttgc ttgcaatgaa gaactccaaa acatcatcga attagtagag     1680
aggtgggatg ataccccaac tgtcggattt cgttcagaaa gggttagaat tttcttttg      1740
gcactttaca aaatgataga ggaaattgcg gcaaaggcag aaactaagca aggtcgatgt     1800
gtcaaagatc tccttattaa cttgtggatt gatttattga aatgtatgct ggtggaattg     1860
gacctttgga aaattaaatc aactacccca agcatagagg agtacttgtc tatcgcatgt     1920
gtaactacag gtgttaaatg tttaattctc atatcactac atcttcttgg accaaaactg     1980
tccaaggatg tcacagaaag ttctgaggtc agtgccttat ggaattgtac agctgttgtg     2040
gcccgattga ataatgatat acatagttac aagagagaac aagcagaaag ttcaacaaat     2100
atggcagcaa tattaatatc acagagtcag agaactatct ctgaagaaga ggctataaga     2160
cagataaaag aaatgatgga agtaagaga  agagagttgc tagggatggt tctacaaaat      2220
aaagaaagcc aattgccgca agtgtgcaaa gatctttttt ggacgacatt caaagcagct     2280
tattctatat atacacatgg cgatgagtat cgcttcccac aggaattgaa gaaccatata     2340
aacgatgtaa tttacaaacc actcaatcaa tattccccat aa                        2382
```

```
<210> SEQ ID NO 78
<211> LENGTH: 793
<212> TYPE: PRT
<213> ORGANISM: Nicotiana glutinosa
<220> FEATURE:
<223> OTHER INFORMATION: NgSPP S3F1-4

<400> SEQUENCE: 78
```

```
Met Ile Leu Gly Leu Arg Ser Thr Ile Ile Pro Leu Pro Asp His Lys
 1               5                  10                  15

Leu Gly Asn Ile Lys Leu Gly Ser Val Thr Lys Asp Ser Asn Phe His
            20                  25                  30

Arg Pro Ser Arg Val Arg Cys Ser His Ser Thr Ala Ser Ser Leu Glu
        35                  40                  45

Glu Ala Lys Glu Arg Ile Arg Glu Thr Phe Gly Lys Asn Glu Leu Ser
```

```
                50                  55                  60
Pro Ser Ser Tyr Asp Thr Ala Trp Val Ala Met Val Pro Ser Arg Tyr
 65                  70                  75                  80

Ser Met Asn Gln Pro Cys Phe Pro Arg Cys Leu Asp Trp Ile Leu Glu
                     85                  90                  95

Asn Gln Arg Glu Asp Gly Ser Trp Gly Leu Asn Pro Ser His Pro Leu
                100                 105                 110

Leu Val Lys Asp Ser Leu Ser Ser Thr Leu Ala Cys Leu Leu Ala Leu
                115                 120                 125

Arg Lys Trp Arg Ile Gly Asp Asn Gln Val Gln Arg Gly Leu Gly Phe
                130                 135                 140

Ile Glu Thr His Gly Trp Ala Val Asp Asn Val Asp Gln Ile Ser Pro
145                 150                 155                 160

Leu Gly Phe Asp Ile Ile Phe Pro Ser Met Ile Lys Tyr Ala Glu Lys
                165                 170                 175

Leu Asn Leu Asp Leu Pro Phe Asp Pro Asn Leu Val Asn Met Met Leu
                180                 185                 190

Arg Glu Arg Glu Leu Thr Ile Glu Arg Ala Leu Lys Asn Glu Phe Glu
                195                 200                 205

Gly Asn Met Ala Asn Val Glu Tyr Phe Ala Glu Gly Leu Gly Glu Leu
                210                 215                 220

Cys His Trp Lys Glu Ile Met Leu His Gln Arg Arg Asn Gly Ser Leu
225                 230                 235                 240

Phe Asp Ser Pro Ala Thr Thr Ala Ala Ala Leu Ile Tyr His Gln His
                245                 250                 255

Asp Glu Lys Cys Phe Gly Tyr Leu Ser Ser Ile Leu Lys Leu His Glu
                260                 265                 270

Asn Trp Val Pro Thr Ile Tyr Pro Thr Lys Val His Ser Asn Leu Phe
                275                 280                 285

Phe Val Asp Ala Leu Gln Asn Leu Gly Val Asp Arg Tyr Phe Lys Thr
                290                 295                 300

Glu Leu Lys Ser Val Leu Asp Glu Ile Tyr Arg Leu Trp Leu Glu Lys
305                 310                 315                 320

Asn Glu Glu Ile Phe Ser Asp Ile Ala His Cys Ala Met Ala Phe Arg
                325                 330                 335

Leu Leu Arg Met Asn Asn Tyr Glu Val Ser Ser Glu Glu Leu Glu Gly
                340                 345                 350

Phe Val Asp Gln Glu His Phe Phe Thr Thr Ser Gly Gly Lys Leu Ile
                355                 360                 365

Ser His Val Ala Ile Leu Glu Leu His Arg Ala Ser Gln Val Asp Ile
370                 375                 380

Gln Glu Gly Lys Asp Leu Ile Leu Asp Lys Ile Ser Thr Trp Thr Arg
385                 390                 395                 400

Asn Phe Met Glu Gln Glu Leu Leu Asp Asn Gln Ile Leu Asp Arg Ser
                405                 410                 415

Lys Lys Glu Met Glu Phe Ala Met Arg Lys Phe Tyr Gly Thr Phe Asp
                420                 425                 430

Arg Val Glu Thr Arg Arg Tyr Ile Glu Ser Tyr Lys Met Asp Ser Phe
                435                 440                 445

Lys Ile Leu Lys Ala Ala Tyr Arg Ser Ser Asn Ile Asn Asn Ile Asp
                450                 455                 460

Leu Leu Lys Phe Ser Glu His Asp Phe Asn Leu Cys Gln Ala Arg His
465                 470                 475                 480
```

```
Lys Glu Glu Leu Gln Gln Ile Lys Arg Trp Phe Ala Asp Cys Lys Leu
                485                 490                 495

Glu Gln Val Gly Ser Ser Gln Asn Tyr Leu Tyr Thr Ser Tyr Phe Pro
            500                 505                 510

Ile Ala Ala Ile Leu Phe Glu Pro Glu Tyr Gly Asp Ala Arg Leu Ala
            515                 520                 525

Phe Ala Lys Cys Gly Ile Ile Ala Thr Thr Val Asp Asp Phe Phe Asp
            530                 535                 540

Gly Phe Ala Cys Asn Glu Glu Leu Gln Asn Ile Ile Glu Leu Val Glu
545                 550                 555                 560

Arg Trp Asp Gly Tyr Pro Thr Val Gly Phe Arg Ser Glu Arg Val Arg
                565                 570                 575

Ile Phe Phe Leu Ala Leu Tyr Lys Met Ile Glu Glu Ile Ala Ala Lys
                580                 585                 590

Ala Glu Thr Lys Gln Gly Arg Cys Val Lys Asp Leu Leu Ile Asn Leu
                595                 600                 605

Trp Ile Asp Leu Leu Lys Cys Met Leu Val Glu Leu Asp Leu Trp Lys
                610                 615                 620

Ile Lys Ser Thr Thr Pro Ser Ile Glu Glu Tyr Leu Ser Ile Ala Cys
625                 630                 635                 640

Val Thr Thr Gly Val Lys Cys Leu Ile Leu Ile Ser Leu His Leu Leu
                645                 650                 655

Gly Pro Lys Leu Ser Lys Asp Val Thr Glu Ser Ser Glu Val Ser Ala
                660                 665                 670

Leu Trp Asn Cys Thr Ala Val Val Ala Arg Leu Asn Asn Asp Ile His
                675                 680                 685

Ser Tyr Lys Arg Glu Gln Ala Glu Ser Ser Thr Asn Met Ala Ala Ile
                690                 695                 700

Leu Ile Ser Gln Ser Gln Arg Thr Ile Ser Glu Glu Ala Ile Arg
705                 710                 715                 720

Gln Ile Lys Glu Met Met Glu Ser Lys Arg Arg Glu Leu Leu Gly Met
                725                 730                 735

Val Leu Gln Asn Lys Glu Ser Gln Leu Pro Gln Val Cys Lys Asp Leu
                740                 745                 750

Phe Trp Thr Thr Phe Lys Ala Ala Tyr Ser Ile Tyr Thr His Gly Asp
                755                 760                 765

Glu Tyr Arg Phe Pro Gln Glu Leu Lys Asn His Ile Asn Asp Val Ile
                770                 775                 780

Tyr Lys Pro Leu Asn Gln Tyr Ser Pro
785                 790

<210> SEQ ID NO 79
<211> LENGTH: 7
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 2, 6
<223> OTHER INFORMATION: Xaa = any amino acid

<400> SEQUENCE: 79

Asp Xaa Asp Asp Thr Xaa Met
1               5
```

```
<210> SEQ ID NO 80
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (3)...(4)
<223> OTHER INFORMATION: Xaa = Any amino acid

<400> SEQUENCE: 80

Asp Asp Xaa Xaa Asp
 1               5

<210> SEQ ID NO 81
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (3)...(4)
<223> OTHER INFORMATION: Xaa = any amino acid

<400> SEQUENCE: 81

Glu Asp Xaa Xaa Asp
 1               5

<210> SEQ ID NO 82
<211> LENGTH: 727
<212> TYPE: PRT
<213> ORGANISM: Artificial Sequence
<220> FEATURE:
<223> OTHER INFORMATION: ent-copalyl diphosphate synthase
<300> PUBLICATION INFORMATION:
<308> DATABASE ACCESSION NUMBER: Genbank 3PYB
<309> DATABASE ENTRY DATE: 2011-05-25

<400> SEQUENCE: 82

Met Ile Ser Val Gly Ser Asn Ser Asn Ala Phe Lys Glu Ala Val Lys
 1               5                  10                  15

Ser Val Lys Thr Ile Leu Arg Asn Leu Thr Asp Gly Glu Ile Thr Ile
             20                  25                  30

Ser Ala Tyr Asp Thr Ala Trp Val Ala Leu Ile Asp Ala Gly Asp Lys
         35                  40                  45

Thr Pro Ala Phe Pro Ser Ala Val Lys Trp Ile Ala Glu Asn Gln Leu
     50                  55                  60

Ser Asp Gly Ser Trp Gly Asp Ala Tyr Leu Phe Ser Tyr His Asp Arg
 65                  70                  75                  80

Leu Ile Asn Thr Leu Ala Cys Val Val Ala Leu Arg Ser Trp Asn Leu
                 85                  90                  95

Phe Pro His Gln Cys Asn Lys Gly Ile Thr Phe Phe Arg Glu Asn Ile
            100                 105                 110

Gly Lys Leu Glu Asp Glu Asn Asp Glu His Met Pro Ile Gly Phe Glu
        115                 120                 125

Val Ala Phe Pro Ser Leu Leu Glu Ile Ala Arg Gly Ile Asn Ile Asp
    130                 135                 140

Val Pro Tyr Asp Ser Pro Val Leu Lys Asp Ile Tyr Ala Lys Lys Glu
145                 150                 155                 160

Leu Lys Leu Thr Arg Ile Pro Lys Glu Ile Met His Lys Ile Pro Thr
                165                 170                 175
```

-continued

Thr Leu Leu His Ser Leu Glu Gly Met Arg Asp Leu Asp Trp Glu Lys
            180                 185                 190

Leu Leu Lys Leu Gln Ser Gln Asp Gly Ser Phe Leu Phe Ser Pro Ser
        195                 200                 205

Ser Thr Ala Phe Ala Phe Met Gln Thr Arg Asp Ser Asn Cys Leu Glu
    210                 215                 220

Tyr Leu Arg Asn Ala Val Lys Arg Phe Asn Gly Val Pro Asn Val
225                 230                 235                 240

Phe Pro Val Asp Leu Phe Glu His Ile Trp Ile Val Asp Arg Leu Gln
                245                 250                 255

Arg Leu Gly Ile Ser Arg Tyr Phe Glu Glu Ile Lys Glu Cys Leu
            260                 265                 270

Asp Tyr Val His Arg Tyr Trp Thr Asp Asn Gly Ile Cys Trp Ala Arg
        275                 280                 285

Cys Ser His Val Gln Asp Ile Asp Asp Thr Ala Met Ala Phe Arg Leu
    290                 295                 300

Leu Arg Gln His Gly Tyr Gln Val Ser Ala Asp Val Phe Lys Asn Phe
305                 310                 315                 320

Glu Lys Glu Gly Glu Phe Phe Cys Phe Val Gly Gln Ser Asn Gln Ala
                325                 330                 335

Val Thr Gly Met Phe Asn Leu Tyr Arg Ala Ser Gln Leu Ala Phe Pro
            340                 345                 350

Arg Glu Glu Ile Leu Lys Asn Ala Lys Glu Phe Ser Tyr Asn Tyr Leu
        355                 360                 365

Leu Glu Lys Arg Glu Arg Glu Glu Leu Ile Asp Lys Trp Ile Ile Met
370                 375                 380

Lys Asp Leu Pro Gly Glu Ile Gly Phe Ala Leu Glu Ile Pro Trp Tyr
385                 390                 395                 400

Ala Ser Leu Pro Arg Val Glu Thr Arg Phe Tyr Ile Asp Gln Tyr Gly
                405                 410                 415

Gly Glu Asn Asp Val Trp Ile Gly Lys Thr Leu Tyr Arg Met Pro Tyr
            420                 425                 430

Val Asn Asn Asn Gly Tyr Leu Glu Leu Ala Lys Gln Asp Tyr Asn Asn
        435                 440                 445

Cys Gln Ala Gln His Gln Leu Glu Trp Asp Ile Phe Gln Lys Trp Tyr
    450                 455                 460

Glu Glu Asn Arg Leu Ser Glu Trp Gly Val Arg Arg Ser Glu Leu Leu
465                 470                 475                 480

Glu Cys Tyr Tyr Leu Ala Ala Ala Thr Ile Phe Glu Ser Glu Arg Ser
                485                 490                 495

His Glu Arg Met Val Trp Ala Lys Ser Ser Val Leu Val Lys Ala Ile
            500                 505                 510

Ser Ser Ser Phe Gly Glu Ser Ser Asp Ser Arg Arg Ser Phe Ser Asp
        515                 520                 525

Gln Phe His Glu Tyr Ile Ala Asn Ala Arg Arg Ser Asp His His Phe
    530                 535                 540

Asn Asp Arg Asn Met Arg Leu Asp Arg Pro Gly Ser Val Gln Ala Ser
545                 550                 555                 560

Arg Leu Ala Gly Val Leu Ile Gly Thr Leu Asn Gln Met Ser Phe Asp
                565                 570                 575

Leu Phe Met Ser His Gly Arg Asp Val Asn Asn Leu Leu Tyr Leu Ser
            580                 585                 590

Trp Gly Asp Trp Met Glu Lys Trp Lys Leu Tyr Gly Asp Glu Gly Glu

```
                    595                 600                 605
Gly Glu Leu Met Val Lys Met Ile Ile Leu Met Lys Asn Asn Asp Leu
    610                 615                 620

Thr Asn Phe Phe Thr His Thr His Phe Val Arg Leu Ala Glu Ile Ile
625                 630                 635                 640

Asn Arg Ile Cys Leu Pro Arg Gln Tyr Leu Lys Ala Arg Arg Asn Asp
                645                 650                 655

Glu Lys Glu Lys Thr Ile Lys Ser Met Glu Lys Glu Met Gly Lys Met
                660                 665                 670

Val Glu Leu Ala Leu Ser Glu Ser Asp Thr Phe Arg Asp Val Ser Ile
            675                 680                 685

Thr Phe Leu Asp Val Ala Lys Ala Phe Tyr Tyr Phe Ala Leu Cys Gly
690                 695                 700

Asp His Leu Gln Thr His Ile Ser Lys Val Leu Phe Gln Lys Val Gly
705                 710                 715                 720

Ser His His His His His His
                725

<210> SEQ ID NO 83
<211> LENGTH: 802
<212> TYPE: PRT
<213> ORGANISM: Arabidopsis thaliana
<220> FEATURE:
<223> OTHER INFORMATION: ent-copalyl diphosphate synthase
<300> PUBLICATION INFORMATION:
<308> DATABASE ACCESSION NUMBER: Genbank NP_192187
<309> DATABASE ENTRY DATE: 1996-11-01

<400> SEQUENCE: 83

Met Ser Leu Gln Tyr His Val Leu Asn Ser Ile Pro Ser Thr Thr Phe
 1               5                  10                  15

Leu Ser Ser Thr Lys Thr Thr Ile Ser Ser Ser Phe Leu Thr Ile Ser
                20                  25                  30

Gly Ser Pro Leu Asn Val Ala Arg Asp Lys Ser Arg Ser Gly Ser Ile
            35                  40                  45

His Cys Ser Lys Leu Arg Thr Gln Glu Tyr Ile Asn Ser Gln Glu Val
50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Ala Phe Lys Glu
                85                  90                  95

Ala Val Lys Ser Val Lys Thr Ile Leu Arg Asn Leu Thr Asp Gly Glu
                100                 105                 110

Ile Thr Ile Ser Ala Tyr Asp Thr Ala Trp Val Ala Leu Ile Asp Ala
            115                 120                 125

Gly Asp Lys Thr Pro Ala Phe Pro Ser Ala Val Lys Trp Ile Ala Glu
        130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
                180                 185                 190

Glu Asn Ile Gly Lys Leu Glu Asp Glu Asn Asp Glu His Met Pro Ile
            195                 200                 205

Gly Phe Glu Val Ala Phe Pro Ser Leu Leu Glu Ile Ala Arg Gly Ile
```

```
            210                 215                 220
Asn Ile Asp Val Pro Tyr Asp Ser Pro Val Leu Lys Asp Ile Tyr Ala
225                 230                 235                 240
Lys Lys Glu Leu Lys Leu Thr Arg Ile Pro Lys Glu Ile Met His Lys
                    245                 250                 255
Ile Pro Thr Thr Leu Leu His Ser Leu Glu Gly Met Arg Asp Leu Asp
                260                 265                 270
Trp Glu Lys Leu Leu Lys Leu Gln Ser Gln Asp Gly Ser Phe Leu Phe
                275                 280                 285
Ser Pro Ser Ser Thr Ala Phe Ala Phe Met Gln Thr Arg Asp Ser Asn
            290                 295                 300
Cys Leu Glu Tyr Leu Arg Asn Ala Val Lys Arg Phe Asn Gly Gly Val
305                 310                 315                 320
Pro Asn Val Phe Pro Val Asp Leu Phe Glu His Ile Trp Ile Val Asp
                325                 330                 335
Arg Leu Gln Arg Leu Gly Ile Ser Arg Tyr Phe Glu Glu Glu Ile Lys
                340                 345                 350
Glu Cys Leu Asp Tyr Val His Arg Tyr Trp Thr Asp Asn Gly Ile Cys
            355                 360                 365
Trp Ala Arg Cys Ser His Val Gln Asp Ile Asp Asp Thr Ala Met Ala
        370                 375                 380
Phe Arg Leu Leu Arg Gln His Gly Tyr Gln Val Ser Ala Asp Val Phe
385                 390                 395                 400
Lys Asn Phe Glu Lys Glu Gly Glu Phe Phe Cys Phe Val Gly Gln Ser
                405                 410                 415
Asn Gln Ala Val Thr Gly Met Phe Asn Leu Tyr Arg Ala Ser Gln Leu
            420                 425                 430
Ala Phe Pro Arg Glu Glu Ile Leu Lys Asn Ala Lys Glu Phe Ser Tyr
            435                 440                 445
Asn Tyr Leu Leu Glu Lys Arg Glu Arg Glu Glu Leu Ile Asp Lys Trp
            450                 455                 460
Ile Ile Met Lys Asp Leu Pro Gly Glu Ile Gly Phe Ala Leu Glu Ile
465                 470                 475                 480
Pro Trp Tyr Ala Ser Leu Pro Arg Val Glu Thr Arg Phe Tyr Ile Asp
                485                 490                 495
Gln Tyr Gly Gly Glu Asn Asp Val Trp Ile Gly Lys Thr Leu Tyr Arg
                500                 505                 510
Met Pro Tyr Val Asn Asn Gly Tyr Leu Glu Leu Ala Lys Gln Asp
            515                 520                 525
Tyr Asn Asn Cys Gln Ala Gln His Gln Leu Glu Trp Asp Ile Phe Gln
530                 535                 540
Lys Trp Tyr Glu Glu Asn Arg Leu Ser Glu Trp Gly Val Arg Arg Ser
545                 550                 555                 560
Glu Leu Leu Glu Cys Tyr Tyr Leu Ala Ala Ala Thr Ile Phe Glu Ser
                565                 570                 575
Glu Arg Ser His Glu Arg Met Val Trp Ala Lys Ser Ser Val Leu Val
            580                 585                 590
Lys Ala Ile Ser Ser Ser Phe Gly Glu Ser Ser Asp Ser Arg Arg Ser
            595                 600                 605
Phe Ser Asp Gln Phe His Glu Tyr Ile Ala Asn Ala Arg Arg Ser Asp
            610                 615                 620
His His Phe Asn Asp Arg Asn Met Arg Leu Asp Arg Pro Gly Ser Val
625                 630                 635                 640
```

Gln Ala Ser Arg Leu Ala Gly Val Leu Ile Gly Thr Leu Asn Gln Met
            645                 650                 655

Ser Phe Asp Leu Phe Met Ser His Gly Arg Asp Val Asn Asn Leu Leu
            660                 665                 670

Tyr Leu Ser Trp Gly Asp Trp Met Glu Lys Trp Lys Leu Tyr Gly Asp
            675                 680                 685

Glu Gly Glu Gly Glu Leu Met Val Lys Met Ile Ile Leu Met Lys Asn
690                 695                 700

Asn Asp Leu Thr Asn Phe Phe Thr His Thr His Phe Val Arg Leu Ala
705                 710                 715                 720

Glu Ile Ile Asn Arg Ile Cys Leu Pro Arg Gln Tyr Leu Lys Ala Arg
            725                 730                 735

Arg Asn Asp Glu Lys Glu Lys Thr Ile Lys Ser Met Glu Lys Glu Met
            740                 745                 750

Gly Lys Met Val Glu Leu Ala Leu Ser Glu Ser Asp Thr Phe Arg Asp
            755                 760                 765

Val Ser Ile Thr Phe Leu Asp Val Ala Lys Ala Phe Tyr Tyr Phe Ala
            770                 775                 780

Leu Cys Gly Asp His Leu Gln Thr His Ile Ser Lys Val Leu Phe Gln
785                 790                 795                 800

Lys Val

<210> SEQ ID NO 84
<211> LENGTH: 868
<212> TYPE: PRT
<213> ORGANISM: Artificial Sequence
<220> FEATURE:
<223> OTHER INFORMATION: abietadiene synthase
<300> PUBLICATION INFORMATION:
<308> DATABASE ACCESSION NUMBER: Genbank Q38710
<309> DATABASE ENTRY DATE: 2005-04-12

<400> SEQUENCE: 84

Met Ala Met Pro Ser Ser Leu Ser Ser Gln Ile Pro Thr Ala Ala
1               5                   10                  15

His His Leu Thr Ala Asn Ala Gln Ser Ile Pro His Phe Ser Thr Thr
            20                  25                  30

Leu Asn Ala Gly Ser Ser Ala Ser Lys Arg Arg Ser Leu Tyr Leu Arg
        35                  40                  45

Trp Gly Lys Gly Ser Asn Lys Ile Ile Ala Cys Val Gly Glu Gly Gly
    50                  55                  60

Ala Thr Ser Val Pro Tyr Gln Ser Ala Glu Lys Asn Asp Ser Leu Ser
65                  70                  75                  80

Ser Ser Thr Leu Val Lys Arg Glu Phe Pro Pro Gly Phe Trp Lys Asp
            85                  90                  95

Asp Leu Ile Asp Ser Leu Thr Ser Ser His Lys Val Ala Ala Ser Asp
            100                 105                 110

Glu Lys Arg Ile Glu Thr Leu Ile Ser Glu Ile Lys Asn Met Phe Arg
            115                 120                 125

Cys Met Gly Tyr Gly Glu Thr Asn Pro Ser Ala Tyr Asp Thr Ala Trp
        130                 135                 140

Val Ala Arg Ile Pro Ala Val Asp Gly Ser Asp Asn Pro His Phe Pro
145                 150                 155                 160

Glu Thr Val Glu Trp Ile Leu Gln Asn Gln Leu Lys Asp Gly Ser Trp
            165                 170                 175

```
Gly Glu Gly Phe Tyr Phe Leu Ala Tyr Asp Arg Ile Leu Ala Thr Leu
            180                 185                 190

Ala Cys Ile Ile Thr Leu Thr Leu Trp Arg Thr Gly Glu Thr Gln Val
        195                 200                 205

Gln Lys Gly Ile Glu Phe Phe Arg Thr Gln Ala Gly Lys Met Glu Asp
    210                 215                 220

Glu Ala Asp Ser His Arg Pro Ser Gly Phe Glu Ile Val Phe Pro Ala
225                 230                 235                 240

Met Leu Lys Glu Ala Lys Ile Leu Gly Leu Asp Leu Pro Tyr Asp Leu
                245                 250                 255

Pro Phe Leu Lys Gln Ile Ile Glu Lys Arg Glu Ala Lys Leu Lys Arg
            260                 265                 270

Ile Pro Thr Asp Val Leu Tyr Ala Leu Pro Thr Thr Leu Leu Tyr Ser
        275                 280                 285

Leu Glu Gly Leu Gln Glu Ile Val Asp Trp Gln Lys Ile Met Lys Leu
    290                 295                 300

Gln Ser Lys Asp Gly Ser Phe Leu Ser Ser Pro Ala Ser Thr Ala Ala
305                 310                 315                 320

Val Phe Met Arg Thr Gly Asn Lys Lys Cys Leu Asp Phe Leu Asn Phe
                325                 330                 335

Val Leu Lys Lys Phe Gly Asn His Val Pro Cys His Tyr Pro Leu Asp
            340                 345                 350

Leu Phe Glu Arg Leu Trp Ala Val Asp Thr Val Glu Arg Leu Gly Ile
        355                 360                 365

Asp Arg His Phe Lys Glu Glu Ile Lys Glu Ala Leu Asp Tyr Val Tyr
    370                 375                 380

Ser His Trp Asp Glu Arg Gly Ile Gly Trp Ala Arg Glu Asn Pro Val
385                 390                 395                 400

Pro Asp Ile Asp Asp Thr Ala Met Gly Leu Arg Ile Leu Arg Leu His
                405                 410                 415

Gly Tyr Asn Val Ser Ser Asp Val Leu Lys Thr Phe Arg Asp Glu Asn
            420                 425                 430

Gly Glu Phe Phe Cys Phe Leu Gly Gln Thr Gln Arg Gly Val Thr Asp
        435                 440                 445

Met Leu Asn Val Asn Arg Cys Ser His Val Ser Phe Pro Gly Glu Thr
    450                 455                 460

Ile Met Glu Glu Ala Lys Leu Cys Thr Glu Arg Tyr Leu Arg Asn Ala
465                 470                 475                 480

Leu Glu Asn Val Asp Ala Phe Asp Lys Trp Ala Phe Lys Lys Asn Ile
                485                 490                 495

Arg Gly Glu Val Glu Tyr Ala Leu Lys Tyr Pro Trp His Lys Ser Met
            500                 505                 510

Pro Arg Leu Glu Ala Arg Ser Tyr Ile Glu Asn Tyr Gly Pro Asp Asp
        515                 520                 525

Val Trp Leu Gly Lys Thr Val Tyr Met Met Pro Tyr Ile Ser Asn Glu
    530                 535                 540

Lys Tyr Leu Glu Leu Ala Lys Leu Asp Phe Asn Lys Val Gln Ser Ile
545                 550                 555                 560

His Gln Thr Glu Leu Gln Asp Leu Arg Arg Trp Trp Lys Ser Ser Gly
                565                 570                 575

Phe Thr Asp Leu Asn Phe Thr Arg Glu Arg Val Thr Glu Ile Tyr Phe
            580                 585                 590

Ser Pro Ala Ser Phe Ile Phe Glu Pro Glu Phe Ser Lys Cys Arg Glu
```

```
                    595                 600                 605
Val Tyr Thr Lys Thr Ser Asn Phe Thr Val Ile Leu Asp Asp Leu Tyr
610                 615                 620

Asp Ala His Gly Ser Leu Asp Leu Lys Leu Phe Thr Glu Ser Val
625                 630                 635                 640

Lys Arg Trp Asp Leu Ser Leu Val Asp Gln Met Pro Gln Gln Met Lys
                    645                 650                 655

Ile Cys Phe Val Gly Phe Tyr Asn Thr Phe Asn Asp Ile Ala Lys Glu
                660                 665                 670

Gly Arg Glu Arg Gln Gly Arg Asp Val Leu Gly Tyr Ile Gln Asn Val
                675                 680                 685

Trp Lys Val Gln Leu Glu Ala Tyr Thr Lys Glu Ala Glu Trp Ser Glu
690                 695                 700

Ala Lys Tyr Val Pro Ser Phe Asn Glu Tyr Ile Glu Asn Ala Ser Val
705                 710                 715                 720

Ser Ile Ala Leu Gly Thr Val Val Leu Ile Ser Ala Leu Phe Thr Gly
                    725                 730                 735

Glu Val Leu Thr Asp Glu Val Leu Ser Lys Ile Asp Arg Glu Ser Arg
                740                 745                 750

Phe Leu Gln Leu Met Gly Leu Thr Gly Arg Leu Val Asn Asp Thr Lys
                755                 760                 765

Thr Tyr Gln Ala Glu Arg Gly Gln Gly Glu Val Ala Ser Ala Ile Gln
770                 775                 780

Cys Tyr Met Lys Asp His Pro Lys Ile Ser Glu Glu Ala Leu Gln
785                 790                 795                 800

His Val Tyr Ser Val Met Glu Asn Ala Leu Glu Glu Leu Asn Arg Glu
                    805                 810                 815

Phe Val Asn Asn Lys Ile Pro Asp Ile Tyr Lys Arg Leu Val Phe Glu
                820                 825                 830

Thr Ala Arg Ile Met Gln Leu Phe Tyr Met Gln Gly Asp Gly Leu Thr
                835                 840                 845

Leu Ser His Asp Met Glu Ile Lys Glu His Val Lys Asn Cys Leu Phe
850                 855                 860

Gln Pro Val Ala
865

<210> SEQ ID NO 85
<211> LENGTH: 785
<212> TYPE: PRT
<213> ORGANISM: Abies grandis
<220> FEATURE:
<223> OTHER INFORMATION: abietadiene synthase
<300> PUBLICATION INFORMATION:
<308> DATABASE ACCESSION NUMBER: Genbank 3S9V
<309> DATABASE ENTRY DATE: 2011-06-02

<400> SEQUENCE: 85

Met Val Lys Arg Glu Phe Pro Pro Gly Phe Trp Lys Asp Asp Leu Ile
1               5                   10                  15

Asp Ser Leu Thr Ser Ser His Lys Val Ala Ala Ser Asp Glu Lys Arg
                20                  25                  30

Ile Glu Thr Leu Ile Ser Glu Ile Lys Asn Met Phe Arg Cys Met Gly
                35                  40                  45

Tyr Gly Glu Thr Asn Pro Ser Ala Tyr Asp Thr Ala Trp Val Ala Arg
            50                  55                  60

Ile Pro Ala Val Asp Gly Ser Asp Asn Pro His Phe Pro Glu Thr Val
```

```
             65                  70                  75                  80
Glu Trp Ile Leu Gln Asn Gln Leu Lys Asp Gly Ser Trp Gly Glu Gly
                 85                  90                  95
Phe Tyr Phe Leu Ala Tyr Asp Arg Ile Leu Ala Thr Leu Ala Cys Ile
                100                 105                 110
Ile Thr Leu Thr Leu Trp Arg Thr Gly Glu Thr Gln Val Gln Lys Gly
                115                 120                 125
Ile Glu Phe Phe Arg Thr Gln Ala Gly Lys Met Glu Asp Glu Ala Asp
                130                 135                 140
Ser His Arg Pro Ser Gly Phe Glu Ile Val Phe Pro Ala Met Leu Lys
145                 150                 155                 160
Glu Ala Lys Ile Leu Gly Leu Asp Leu Pro Tyr Asp Leu Pro Phe Leu
                165                 170                 175
Lys Gln Ile Ile Glu Lys Arg Glu Ala Lys Leu Lys Arg Ile Pro Thr
                180                 185                 190
Asp Val Leu Tyr Ala Leu Pro Thr Thr Leu Leu Tyr Ser Leu Glu Gly
                195                 200                 205
Leu Gln Glu Ile Val Asp Trp Gln Lys Ile Met Lys Leu Gln Ser Lys
        210                 215                 220
Asp Gly Ser Phe Leu Ser Ser Pro Ala Ser Thr Ala Ala Val Phe Met
225                 230                 235                 240
Arg Thr Gly Asn Lys Lys Cys Leu Asp Phe Leu Asn Phe Val Leu Lys
                245                 250                 255
Lys Phe Gly Asn His Val Pro Cys His Tyr Pro Leu Asp Leu Phe Glu
                260                 265                 270
Arg Leu Trp Ala Val Asp Thr Val Glu Arg Leu Gly Ile Asp Arg His
                275                 280                 285
Phe Lys Glu Glu Ile Lys Glu Ala Leu Asp Tyr Val Tyr Ser His Trp
                290                 295                 300
Asp Glu Arg Gly Ile Gly Trp Ala Arg Glu Asn Pro Val Pro Asp Ile
305                 310                 315                 320
Asp Asp Thr Ala Met Gly Leu Arg Ile Leu Arg Leu His Gly Tyr Asn
                325                 330                 335
Val Ser Ser Asp Val Leu Lys Thr Phe Arg Asp Glu Asn Gly Glu Phe
                340                 345                 350
Phe Cys Phe Leu Gly Gln Thr Gln Arg Gly Val Thr Asp Met Leu Asn
                355                 360                 365
Val Asn Arg Cys Ser His Val Ser Phe Pro Gly Glu Thr Ile Met Glu
                370                 375                 380
Glu Ala Lys Leu Cys Thr Glu Arg Tyr Leu Arg Asn Ala Leu Glu Asn
385                 390                 395                 400
Val Asp Ala Phe Asp Lys Trp Ala Phe Lys Lys Asn Ile Arg Gly Glu
                405                 410                 415
Val Glu Tyr Ala Leu Lys Tyr Pro Trp His Lys Ser Met Pro Arg Leu
                420                 425                 430
Glu Ala Arg Ser Tyr Ile Glu Asn Tyr Gly Pro Asp Asp Val Trp Leu
                435                 440                 445
Gly Lys Thr Val Tyr Met Met Pro Tyr Ile Ser Asn Glu Lys Tyr Leu
                450                 455                 460
Glu Leu Ala Lys Leu Asp Phe Asn Lys Val Gln Ser Ile His Gln Thr
465                 470                 475                 480
Glu Leu Gln Asp Leu Arg Arg Trp Trp Lys Ser Ser Gly Phe Thr Asp
                485                 490                 495
```

```
Leu Asn Phe Thr Arg Glu Arg Val Thr Glu Ile Tyr Phe Ser Pro Ala
            500                 505                 510

Ser Phe Ile Phe Glu Pro Glu Phe Ser Lys Cys Arg Glu Val Tyr Thr
            515                 520                 525

Lys Thr Ser Asn Phe Thr Val Ile Leu Asp Asp Leu Tyr Asp Ala His
530                 535                 540

Gly Ser Leu Asp Asp Leu Lys Leu Phe Thr Glu Ser Val Lys Arg Trp
545                 550                 555                 560

Asp Leu Ser Leu Val Asp Gln Met Pro Gln Gln Met Lys Ile Cys Phe
                565                 570                 575

Val Gly Phe Tyr Asn Thr Phe Asn Asp Ile Ala Lys Glu Gly Arg Glu
            580                 585                 590

Arg Gln Gly Arg Asp Val Leu Gly Tyr Ile Gln Asn Val Trp Lys Val
            595                 600                 605

Gln Leu Glu Ala Tyr Thr Lys Glu Ala Glu Trp Ser Glu Ala Lys Tyr
            610                 615                 620

Val Pro Ser Phe Asn Glu Tyr Ile Glu Asn Ala Ser Val Ser Ile Ala
625                 630                 635                 640

Leu Gly Thr Val Val Leu Ile Ser Ala Leu Phe Thr Gly Glu Val Leu
                645                 650                 655

Thr Asp Glu Val Leu Ser Lys Ile Asp Arg Glu Ser Arg Phe Leu Gln
            660                 665                 670

Leu Met Gly Leu Thr Gly Arg Leu Val Asn Asp Thr Lys Thr Tyr Gln
            675                 680                 685

Ala Glu Arg Gly Gln Gly Glu Val Ala Ser Ala Ile Gln Cys Tyr Met
            690                 695                 700

Lys Asp His Pro Lys Ile Ser Glu Glu Ala Leu Gln His Val Tyr
705                 710                 715                 720

Ser Val Met Glu Asn Ala Leu Glu Glu Leu Asn Arg Glu Phe Val Asn
            725                 730                 735

Asn Lys Ile Pro Asp Ile Tyr Lys Arg Leu Val Phe Glu Thr Ala Arg
            740                 745                 750

Ile Met Gln Leu Phe Tyr Met Gln Gly Asp Gly Leu Thr Leu Ser His
            755                 760                 765

Asp Met Glu Ile Lys Glu His Val Lys Asn Cys Leu Phe Gln Pro Val
    770                 775                 780

Ala
785

<210> SEQ ID NO 86
<211> LENGTH: 527
<212> TYPE: PRT
<213> ORGANISM: Artificial Sequence
<220> FEATURE:
<223> OTHER INFORMATION: SsSs-NgSs fusion; N-terminal domain swap

<400> SEQUENCE: 86

Met Glu Asp Asp Lys Phe Pro Thr Thr Thr Thr Leu Arg Ser Glu Asp
1               5                   10                  15

Ile Pro Ser Asn Leu Phe Phe Val Asp Ala Leu Gln Asn Leu Gly Val
            20                  25                  30

Asp Arg Tyr Phe Lys Thr Glu Leu Lys Ser Val Leu Asp Glu Ile Tyr
        35                  40                  45

Arg Leu Trp Leu Glu Lys Asn Glu Glu Ile Phe Ser Asp Ile Ala His
    50                  55                  60
```

```
Cys Ala Met Ala Phe Arg Leu Leu Arg Met Asn Asn Tyr Glu Val Ser
 65                  70                  75                  80

Ser Glu Glu Leu Glu Gly Phe Val Asp Gln Glu His Phe Phe Thr Thr
                 85                  90                  95

Ser Gly Gly Lys Leu Ile Ser His Val Ala Ile Leu Glu Leu His Arg
            100                 105                 110

Ala Ser Gln Val Asp Ile Gln Glu Gly Lys Asp Leu Ile Leu Asp Lys
        115                 120                 125

Ile Ser Thr Trp Thr Arg Asn Phe Met Glu Gln Glu Leu Leu Asp Asn
130                 135                 140

Gln Ile Leu Asp Arg Ser Lys Lys Glu Met Glu Phe Ala Met Arg Lys
145                 150                 155                 160

Phe Tyr Gly Thr Phe Asp Arg Val Glu Thr Arg Arg Tyr Ile Glu Ser
                165                 170                 175

Tyr Lys Met Asp Ser Phe Lys Ile Leu Lys Ala Ala Tyr Arg Ser Ser
            180                 185                 190

Asn Ile Asn Asn Ile Asp Leu Leu Lys Phe Ser Glu His Asp Phe Asn
        195                 200                 205

Leu Cys Gln Ala Arg His Lys Glu Glu Leu Gln Gln Ile Lys Arg Trp
210                 215                 220

Phe Ala Asp Cys Lys Leu Glu Gln Val Gly Ser Ser Gln Asn Tyr Leu
225                 230                 235                 240

Tyr Thr Ser Tyr Phe Pro Ile Ala Ala Ile Leu Phe Glu Pro Glu Tyr
                245                 250                 255

Gly Asp Ala Arg Leu Ala Phe Ala Lys Cys Gly Ile Ile Ala Thr Thr
            260                 265                 270

Val Asp Asp Phe Phe Asp Gly Phe Ala Cys Asn Glu Glu Leu Gln Asn
        275                 280                 285

Ile Ile Glu Leu Val Glu Arg Trp Asp Gly Tyr Pro Thr Val Gly Phe
290                 295                 300

Arg Ser Glu Arg Val Arg Ile Phe Phe Leu Ala Leu Tyr Lys Met Ile
305                 310                 315                 320

Glu Glu Ile Ala Ala Lys Ala Glu Thr Lys Gln Gly Arg Cys Val Lys
                325                 330                 335

Asp Leu Leu Ile Asn Leu Trp Ile Asp Leu Leu Lys Cys Met Leu Val
            340                 345                 350

Glu Leu Asp Leu Trp Lys Ile Lys Ser Thr Thr Pro Ser Ile Glu Glu
        355                 360                 365

Tyr Leu Ser Ile Ala Cys Val Thr Thr Gly Val Lys Cys Leu Ile Leu
370                 375                 380

Ile Ser Leu His Leu Leu Gly Pro Lys Leu Ser Lys Asp Val Thr Glu
385                 390                 395                 400

Ser Ser Glu Val Ser Ala Leu Trp Asn Cys Thr Ala Val Val Ala Arg
                405                 410                 415

Leu Asn Asn Asp Ile His Ser Tyr Lys Arg Glu Gln Ala Glu Ser Ser
            420                 425                 430

Thr Asn Met Val Ala Ile Leu Ile Ser Gln Ser Gln Arg Thr Ile Ser
        435                 440                 445

Glu Glu Glu Ala Ile Arg Gln Ile Lys Glu Met Met Glu Ser Lys Arg
    450                 455                 460

Arg Glu Leu Leu Gly Met Val Leu Gln Asn Lys Glu Ser Gln Leu Pro
465                 470                 475                 480
```

Gln Val Cys Lys Asp Leu Phe Trp Thr Thr Phe Lys Ala Ala Tyr Ser
            485                 490                 495

Ile Tyr Thr His Gly Asp Glu Tyr Arg Phe Pro Gln Glu Leu Lys Asn
        500                 505                 510

His Ile Asn Asp Val Ile Tyr Lys Pro Leu Asn Gln Tyr Ser Pro
    515                 520                 525

<210> SEQ ID NO 87
<211> LENGTH: 1584
<212> TYPE: DNA
<213> ORGANISM: Artificial Sequence
<220> FEATURE:
<223> OTHER INFORMATION: SsSs-NgSs fusion; N-terminal domain swap

<400> SEQUENCE: 87

```
atggaagacg ataaatttcc aacgacaacg actcttcgat ccgaagatat accctcaaat      60
ctcttcttcg ttgatgccct tcaaaatctt ggagtagatc ggtattttaa aacagaactc     120
aaaagtgtac tcgatgaaat atacaggctt tggctagaaa agaatgaaga aatttttttca   180
gacattgctc attgtgccat ggcgtttcga cttttgcgga tgaataacta tgaagtttcc    240
tcagaagaac ttgaaggatt tgtcgaccaa gaacatttct ttacaacatc aggtgggaaa    300
cttattagtc acgttgcaat tctcgaactt caccgagctt cacaggtgga tattcaagaa    360
gggaaagatc tcattttaga taaaataagt acttggacaa ggaattttat ggagcaagaa    420
ctcttggaca atcaaatcct tgataggtca agaaggaga tggaatttgc tatgaggaaa     480
ttttatggca catttgatcg agtggaaact agacgataca tcgagtcata caaaatggac    540
agttttaaga tcttaaaagc agcctacagg tcttccaaca ttaacaacat agacttgcta    600
aagttctcag aacatgattt taacttgtgc caagcccgac acaaagaaga acttcaacag    660
attaagaggt ggttcgcaga ttgcaaactg gaacaagtag gatcatcaca aaactactta    720
tacactagtt acttcccaat tgctgccata ctcttcgaac tgaatatggg tgatgctcgt    780
ctagcatttg caaagtgtgg cataatcgca acgacggtgg atgatttctt cgatggtttt    840
gcttgcaatg aagaactcca aaacatcatc gaattagtag agaggtggga tggataccca    900
actgtcggat ttcgttcaga aagggttaga attttctttt tggcacttta caaaatgata    960
gaggaaattg cggcaaaggc agaaactaag caaggtcgat gtgtcaaaga tctccttatt   1020
aacttgtgga ttgatttatt gaatgtatg ctggtgaat tggacctttg gaaaattaaa     1080
tcaactaccc caagcataga ggagtacttg tctatcgcat gtgtaactac aggtgttaaa   1140
tgtttaattc tcatatcact acatcttctt ggaccaaaac tgtccaagga tgtcacagaa   1200
agttctgagg tcagtgcctt atggaattgt acagctgttg tggcccgatt gaataatgat   1260
atacatagtt acaagagaga acaagcagaa agttcaacaa atatggtagc aatattaata   1320
tcacagagtc agagaactat ctctgaagaa gaggctataa gacagataaa agaaatgatg   1380
gaaagtaaga gaagagagtt gctagggatg gttctacaaa ataaagaaag ccaattgccg   1440
caagtgtgca agatcttttt ttggacgaca ttcaaagcag cttattctat atatacacat   1500
ggcgatgagt atcgcttccc acaggaattg aagaaccata taacgatgt aatttacaaa    1560
ccactcaatc aatattcccc ataa                                          1584
```

<210> SEQ ID NO 88
<211> LENGTH: 755
<212> TYPE: PRT
<213> ORGANISM: Artificial Sequence
<220> FEATURE:

<223> OTHER INFORMATION: Codon optimized N-terminal NgSs domain

<400> SEQUENCE: 88

```
Met Ser His Ser Thr Ala Ser Ser Leu Glu Glu Ala Lys Glu Arg Ile
 1               5                  10                  15

Arg Glu Thr Phe Gly Lys Asn Glu Leu Ser Pro Ser Ser Tyr Asp Thr
            20                  25                  30

Ala Trp Val Ala Met Val Pro Ser Arg Tyr Ser Met Asn Gln Pro Cys
        35                  40                  45

Phe Pro Arg Cys Leu Asp Trp Ile Leu Glu Asn Gln Arg Glu Asp Gly
    50                  55                  60

Ser Trp Gly Leu Asn Pro Ser His Pro Leu Leu Val Lys Asp Ser Leu
65                  70                  75                  80

Ser Ser Thr Leu Ala Cys Leu Leu Ala Leu Arg Lys Trp Arg Ile Gly
                85                  90                  95

Asp Asn Gln Val Gln Arg Gly Leu Gly Phe Ile Glu Thr His Gly Trp
            100                 105                 110

Ala Val Asp Asn Val Asp Gln Ile Ser Pro Leu Gly Phe Asp Ile Ile
        115                 120                 125

Phe Pro Ser Met Ile Lys Tyr Ala Glu Lys Leu Asn Leu Asp Leu Pro
    130                 135                 140

Phe Asp Pro Asn Leu Val Asn Met Met Leu Arg Glu Arg Glu Leu Thr
145                 150                 155                 160

Ile Glu Arg Ala Leu Lys Asn Glu Phe Glu Gly Asn Met Ala Asn Val
                165                 170                 175

Glu Tyr Phe Ala Glu Gly Leu Gly Glu Leu Cys His Trp Lys Glu Ile
            180                 185                 190

Met Leu His Gln Arg Arg Asn Gly Ser Pro Phe Asp Ser Pro Ala Thr
        195                 200                 205

Thr Ala Ala Ala Leu Ile Tyr His Gln His Asp Glu Lys Cys Phe Gly
    210                 215                 220

Tyr Leu Ser Ser Ile Leu Lys Leu His Glu Asn Trp Val Pro Thr Ile
225                 230                 235                 240

Tyr Pro Thr Lys Val His Ser Asn Leu Phe Phe Val Asp Ala Leu Gln
                245                 250                 255

Asn Leu Gly Val Asp Arg Tyr Phe Lys Thr Glu Leu Lys Ser Val Leu
            260                 265                 270

Asp Glu Ile Tyr Arg Leu Trp Leu Glu Lys Asn Glu Glu Ile Phe Ser
        275                 280                 285

Asp Ile Ala His Cys Ala Met Ala Phe Arg Leu Leu Arg Met Asn Asn
    290                 295                 300

Tyr Glu Val Ser Ser Glu Glu Leu Glu Gly Phe Val Asp Gln Glu His
305                 310                 315                 320

Phe Phe Thr Thr Ser Gly Gly Lys Leu Ile Ser His Val Ala Ile Leu
                325                 330                 335

Glu Leu His Arg Ala Ser Gln Val Asp Ile Gln Glu Gly Lys Asp Leu
            340                 345                 350

Ile Leu Asp Lys Ile Ser Thr Trp Thr Arg Asn Phe Met Glu Gln Glu
        355                 360                 365

Leu Leu Asp Asn Gln Ile Leu Asp Arg Ser Lys Lys Glu Met Glu Phe
    370                 375                 380

Ala Met Arg Lys Phe Tyr Gly Thr Phe Asp Arg Val Glu Thr Arg Arg
385                 390                 395                 400
```

Tyr Ile Glu Ser Tyr Lys Met Asp Ser Phe Lys Ile Leu Lys Ala Ala
            405                 410                 415

Tyr Arg Ser Ser Asn Ile Asn Asn Ile Asp Leu Leu Lys Phe Ser Glu
            420                 425                 430

His Asp Phe Asn Leu Cys Gln Ala Arg His Lys Glu Glu Leu Gln Gln
            435                 440                 445

Ile Lys Arg Trp Phe Ala Asp Cys Lys Leu Glu Gln Val Gly Ser Ser
450                 455                 460

Gln Asn Tyr Leu Tyr Thr Ser Tyr Phe Pro Ile Ala Ala Ile Leu Phe
465                 470                 475                 480

Glu Pro Glu Tyr Gly Asp Ala Arg Leu Ala Phe Ala Lys Cys Gly Ile
            485                 490                 495

Ile Ala Thr Thr Val Asp Asp Phe Phe Asp Gly Phe Ala Cys Asn Glu
            500                 505                 510

Glu Leu Gln Asn Ile Ile Glu Leu Val Glu Arg Trp Asp Gly Tyr Pro
            515                 520                 525

Thr Val Gly Phe Arg Ser Glu Arg Val Arg Ile Phe Phe Leu Ala Leu
            530                 535                 540

Tyr Lys Met Ile Glu Glu Ile Ala Ala Lys Ala Glu Thr Lys Gln Gly
545                 550                 555                 560

Arg Cys Val Lys Asp Leu Leu Ile Asn Leu Trp Ile Asp Leu Leu Lys
            565                 570                 575

Cys Met Leu Val Glu Leu Asp Leu Trp Lys Ile Lys Ser Thr Thr Pro
            580                 585                 590

Ser Ile Glu Glu Tyr Leu Ser Ile Ala Cys Val Thr Thr Gly Val Lys
            595                 600                 605

Cys Leu Ile Leu Ile Ser Leu His Leu Leu Gly Pro Lys Leu Ser Lys
            610                 615                 620

Asp Val Thr Glu Ser Ser Glu Val Ser Ala Leu Trp Asn Cys Thr Ala
625                 630                 635                 640

Val Val Ala Arg Leu Asn Asn Asp Ile His Ser Tyr Lys Arg Glu Gln
            645                 650                 655

Ala Glu Ser Ser Thr Asn Met Val Ala Ile Leu Ile Ser Gln Ser Gln
            660                 665                 670

Arg Thr Ile Ser Glu Glu Ala Ile Arg Gln Ile Lys Glu Met Met
            675                 680                 685

Glu Ser Lys Arg Arg Glu Leu Leu Gly Met Val Leu Gln Asn Lys Glu
            690                 695                 700

Ser Gln Leu Pro Gln Val Cys Lys Asp Leu Phe Trp Thr Thr Phe Lys
705                 710                 715                 720

Ala Ala Tyr Ser Ile Tyr Thr His Gly Asp Glu Tyr Arg Phe Pro Gln
            725                 730                 735

Glu Leu Lys Asn His Ile Asn Asp Val Ile Tyr Lys Pro Leu Asn Gln
            740                 745                 750

Tyr Ser Pro
        755

<210> SEQ ID NO 89
<211> LENGTH: 2268
<212> TYPE: DNA
<213> ORGANISM: Artificial Sequence
<220> FEATURE:
<223> OTHER INFORMATION: Codon optimized N-terminal NgSs domain

<400> SEQUENCE: 89

| | |
|---|---|
| atgtcacact ccactgcttc atcacttgaa gaggcgaagg aaagaattag ggaaacattt | 60 |
| ggtaaaaatg agctatctcc ttctagttat gatactgctt gggtagctat ggtgccttct | 120 |
| agatattcta tgaaccaacc atgttttcct cgatgcttgg attggatttt agaaaatcaa | 180 |
| agagaagatg gttcttgggg cctaaatcct agtcatccat tgttagtaaa agacagttta | 240 |
| tctagtactt tagcttgttt gttagcctta cgaaaatgga gaattggtga taaccaagta | 300 |
| caaagaggat tgggatttat tgaaacccat ggttgggcag ttgataacgt tgatcagatt | 360 |
| tcaccactag gttttgatat tatatttccc agtatgatta agtatgctga gaaacttaat | 420 |
| ttggatctac catttgatcc taacttggta aatatgatgc tacgagaacg agaattgaca | 480 |
| attgaaagag ccctaaagaa tgaattcgaa ggcaatatgg caaatgttga atattttgct | 540 |
| gaaggccttg gtgaattgtg tcattggaaa gagataatgc tacatcagag acgaaacggt | 600 |
| agtccctttg actctccagc aactactgca gctgctttga tttaccatca gcacgatgag | 660 |
| aaatgctttg ggtacttgag ctcaatcttg aaactgcacg agaattgggt ccccactatt | 720 |
| taccctacaa aggtacattc aaatctcttc ttcgttgatg cccttcaaaa tcttggagta | 780 |
| gatcggtatt ttaaaacaga actcaaaagt gtactcgatg aaatatacag gctttggcta | 840 |
| gaaaagaatg aagaaatttt ttcagacatt gctcattgtg ccatggcgtt tcgacttttg | 900 |
| cggatgaata actatgaagt ttcctcagaa gaacttgaag gatttgtcga ccaagaacat | 960 |
| ttctttacaa catcaggtgg gaaacttatt agtcacgttg caattctcga acttcaccga | 1020 |
| gcttcacagg tggatattca agaagggaaa gatctcattt tagataaaat aagtacttgg | 1080 |
| acaaggaatt ttatggagca agaactcttg gacaatcaaa tccttgatag gtcaaagaag | 1140 |
| gagatggaat ttgctatgag gaaatttttat ggcacatttg atcgagtgga aactagacga | 1200 |
| tacatcgagt catacaaaat ggacagtttt aagatcttaa aagcagccta caggtcttcc | 1260 |
| aacattaaca acatagactt gctaaagttc tcagaacatg attttaactt gtgccaagcc | 1320 |
| cgacacaaag aagaacttca acagattaag aggtggttcg cagattgcaa actgaacaa | 1380 |
| gtaggatcat cacaaaacta cttatacact agttacttcc caattgctgc catactcttc | 1440 |
| gaacctgaat atggtgatgc tcgtctagca tttgcaaagt gtggcataat cgcaacgacg | 1500 |
| gtggatgatt tcttcgatgg ttttgcttgc aatgaagaac tccaaaacat catcgaatta | 1560 |
| gtagagaggg gggatggata cccaactgtc ggatttcgtt cagaaagggt tagaattttc | 1620 |
| ttttttggcac tttacaaaat gatagaggaa attgcggcaa aggcagaaac taagcaaggt | 1680 |
| cgatgtgtca agatctcct tattaacttg tggattgatt tattgaaatg tatgctggtg | 1740 |
| gaattggacc tttggaaaat taaatcaact accccaagca tagaggagta cttgtctatc | 1800 |
| gcatgtgtaa ctacaggtgt taaatgttta attctcatat cactacatct tcttggacca | 1860 |
| aaactgtcca aggatgtcac agaaagttct gaggtcagtg ccttatggaa ttgtacagct | 1920 |
| gttgtggccc gattgaataa tgatatacat agttacaaga gagaacaagc agaaagttca | 1980 |
| acaaatatgg tagcaatatt aatatcacag agtcagagaa ctatctctga gaagaggct | 2040 |
| ataagacaga taaaagaaat gatggaaagt aagagaagag agttgctagg gatggttcta | 2100 |
| caaaataaag aaagccaatt gccgcaagtg tgcaaagatc tttttttggac gacattcaaa | 2160 |
| gcagcttatt ctatatatac acatggcgat gagtatcgct tcccacagga attgaagaac | 2220 |
| catataaacg atgtaattta caaaccactc aatcaatatt ccccataa | 2268 |

<210> SEQ ID NO 90
<211> LENGTH: 999

```
<212> TYPE: PRT
<213> ORGANISM: Artificial Sequence
<220> FEATURE:
<223> OTHER INFORMATION: GFP-NgSs fusion

<400> SEQUENCE: 90
```

| | | | | | | | | | | | | | | |
|---|---|---|---|---|---|---|---|---|---|---|---|---|---|---|
| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |
| Glu | Leu | Asp | Gly | Asp | Val | Asn | Gly | His | Lys | Phe | Ser | Val | Ser | Gly | Glu |
| | | | 20 | | | | | 25 | | | | | 30 | | |
| Gly | Glu | Gly | Asp | Ala | Thr | Tyr | Gly | Lys | Leu | Thr | Leu | Lys | Phe | Ile | Cys |
| | | 35 | | | | | 40 | | | | | 45 | | | |
| Thr | Thr | Gly | Lys | Leu | Pro | Val | Pro | Trp | Pro | Thr | Leu | Val | Thr | Thr | Phe |
| 50 | | | | | 55 | | | | | 60 | | | | | |
| Gly | Tyr | Gly | Val | Gln | Cys | Phe | Ala | Arg | Tyr | Pro | Asp | His | Met | Lys | Gln |
| 65 | | | | 70 | | | | | 75 | | | | | 80 | |
| His | Asp | Phe | Phe | Lys | Ser | Ala | Met | Pro | Glu | Gly | Tyr | Val | Gln | Glu | Arg |
| | | | 85 | | | | | 90 | | | | | 95 | | |
| Thr | Ile | Phe | Phe | Lys | Asp | Asp | Gly | Asn | Tyr | Lys | Thr | Arg | Ala | Glu | Val |
| | | | 100 | | | | | 105 | | | | | 110 | | |
| Lys | Phe | Glu | Gly | Asp | Thr | Leu | Val | Asn | Arg | Ile | Glu | Leu | Lys | Gly | Ile |
| | | | | 115 | | | | | 120 | | | | | 125 | |
| Asp | Phe | Lys | Glu | Asp | Gly | Asn | Ile | Leu | Gly | His | Lys | Leu | Glu | Tyr | Asn |
| | | 130 | | | | | 135 | | | | | 140 | | | |
| Tyr | Asn | Ser | His | Asn | Val | Tyr | Ile | Met | Ala | Asp | Lys | Gln | Lys | Asn | Gly |
| 145 | | | | | 150 | | | | | 155 | | | | | 160 |
| Ile | Lys | Val | Asn | Phe | Lys | Ile | Arg | His | Asn | Ile | Glu | Asp | Gly | Ser | Val |
| | | | | 165 | | | | | 170 | | | | | 175 | |
| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |
| Val | Leu | Leu | Pro | Asp | Asn | His | Tyr | Leu | Ser | Thr | Gln | Ser | Ala | Leu | Ser |
| | | | | 195 | | | | | 200 | | | | | 205 | |
| Lys | Asp | Pro | Asn | Glu | Lys | Arg | Asp | His | Met | Val | Leu | Leu | Glu | Phe | Val |
| | | | 210 | | | | | 215 | | | | | 220 | | |
| Thr | Ala | Ala | Gly | Ile | Thr | His | Gly | Met | Asp | Glu | Leu | Tyr | Lys | Thr | Ala |
| 225 | | | | | 230 | | | | | 235 | | | | | 240 |
| Gly | Ser | Gly | His | Met | Ser | His | Ser | Thr | Ala | Ser | Ser | Leu | Glu | Glu | Ala |
| | | | | 245 | | | | | 250 | | | | | 255 | |
| Lys | Glu | Arg | Ile | Arg | Glu | Thr | Phe | Gly | Lys | Asn | Glu | Leu | Ser | Pro | Ser |
| | | | 260 | | | | | 265 | | | | | 270 | | |
| Ser | Tyr | Asp | Thr | Ala | Trp | Val | Ala | Met | Val | Pro | Ser | Arg | Tyr | Ser | Met |
| | | | 275 | | | | | 280 | | | | | 285 | | |
| Asn | Gln | Pro | Cys | Phe | Pro | Arg | Cys | Leu | Asp | Trp | Ile | Leu | Glu | Asn | Gln |
| | | 290 | | | | | 295 | | | | | 300 | | | |
| Arg | Glu | Asp | Gly | Ser | Trp | Gly | Leu | Asn | Pro | Ser | His | Pro | Leu | Leu | Val |
| 305 | | | | | 310 | | | | | 315 | | | | | 320 |
| Lys | Asp | Ser | Leu | Ser | Ser | Thr | Leu | Ala | Cys | Leu | Leu | Ala | Leu | Arg | Lys |
| | | | | 325 | | | | | 330 | | | | | 335 | |
| Trp | Arg | Ile | Gly | Asp | Asn | Gln | Val | Gln | Arg | Gly | Leu | Gly | Phe | Ile | Glu |
| | | | 340 | | | | | 345 | | | | | 350 | | |
| Thr | His | Gly | Trp | Ala | Val | Asp | Asn | Val | Asp | Gln | Ile | Ser | Pro | Leu | Gly |
| | | 355 | | | | | 360 | | | | | 365 | | | |
| Phe | Asp | Ile | Ile | Phe | Pro | Ser | Met | Ile | Lys | Tyr | Ala | Glu | Lys | Leu | Asn |
| 370 | | | | | 375 | | | | | 380 | | | | | |

```
Leu Asp Leu Pro Phe Asp Pro Asn Leu Val Asn Met Met Leu Arg Glu
385                 390                 395                 400

Arg Glu Leu Thr Ile Glu Arg Ala Leu Lys Asn Glu Phe Glu Gly Asn
            405                 410                 415

Met Ala Asn Val Glu Tyr Phe Ala Glu Gly Leu Gly Glu Leu Cys His
            420                 425                 430

Trp Lys Glu Ile Met Leu His Gln Arg Arg Asn Gly Ser Pro Phe Asp
            435                 440                 445

Ser Pro Ala Thr Thr Ala Ala Leu Ile Tyr His Gln His Asp Glu
    450                 455                 460

Lys Cys Phe Gly Tyr Leu Ser Ser Ile Leu Lys Leu His Glu Asn Trp
465                 470                 475                 480

Val Pro Thr Ile Tyr Pro Thr Lys Val His Ser Asn Leu Phe Phe Val
            485                 490                 495

Asp Ala Leu Gln Asn Leu Gly Val Asp Arg Tyr Phe Lys Thr Glu Leu
            500                 505                 510

Lys Ser Val Leu Asp Glu Ile Tyr Arg Leu Trp Leu Glu Lys Asn Glu
            515                 520                 525

Glu Ile Phe Ser Asp Ile Ala His Cys Ala Met Ala Phe Arg Leu Leu
            530                 535                 540

Arg Met Asn Asn Tyr Glu Val Ser Ser Glu Glu Leu Glu Gly Phe Val
545                 550                 555                 560

Asp Gln Glu His Phe Phe Thr Thr Ser Gly Lys Leu Ile Ser His
                565                 570                 575

Val Ala Ile Leu Glu Leu His Arg Ala Ser Gln Val Asp Ile Gln Glu
            580                 585                 590

Gly Lys Asp Leu Ile Leu Asp Lys Ile Ser Thr Trp Thr Arg Asn Phe
            595                 600                 605

Met Glu Gln Glu Leu Leu Asp Asn Gln Ile Leu Asp Arg Ser Lys Lys
610                 615                 620

Glu Met Glu Phe Ala Met Arg Lys Phe Tyr Gly Thr Phe Asp Arg Val
625                 630                 635                 640

Glu Thr Arg Arg Tyr Ile Glu Ser Tyr Lys Met Asp Ser Phe Lys Ile
            645                 650                 655

Leu Lys Ala Ala Tyr Arg Ser Ser Asn Ile Asn Asn Ile Asp Leu Leu
            660                 665                 670

Lys Phe Ser Glu His Asp Phe Asn Leu Cys Gln Ala Arg His Lys Glu
            675                 680                 685

Glu Leu Gln Gln Ile Lys Arg Trp Phe Ala Asp Cys Lys Leu Glu Gln
            690                 695                 700

Val Gly Ser Ser Gln Asn Tyr Leu Tyr Thr Ser Tyr Phe Pro Ile Ala
705                 710                 715                 720

Ala Ile Leu Phe Glu Pro Glu Tyr Gly Asp Ala Arg Leu Ala Phe Ala
            725                 730                 735

Lys Cys Gly Ile Ile Ala Thr Val Asp Asp Phe Phe Asp Gly Phe
            740                 745                 750

Ala Cys Asn Glu Glu Leu Gln Asn Ile Ile Glu Leu Val Glu Arg Trp
            755                 760                 765

Asp Gly Tyr Pro Thr Val Gly Phe Arg Ser Glu Arg Val Arg Ile Phe
            770                 775                 780

Phe Leu Ala Leu Tyr Lys Met Ile Glu Glu Ile Ala Ala Lys Ala Glu
785                 790                 795                 800

Thr Lys Gln Gly Arg Cys Val Lys Asp Leu Leu Ile Asn Leu Trp Ile
```

Asp Leu Leu Lys Cys Met Leu Val Glu Leu Asp Leu Trp Lys Ile Lys
            820                 825                 830

Ser Thr Thr Pro Ser Ile Glu Glu Tyr Leu Ser Ile Ala Cys Val Thr
        835                 840                 845

Thr Gly Val Lys Cys Leu Ile Leu Ile Ser Leu His Leu Leu Gly Pro
    850                 855                 860

Lys Leu Ser Lys Asp Val Thr Glu Ser Ser Glu Val Ser Ala Leu Trp
865                 870                 875                 880

Asn Cys Thr Ala Val Val Ala Arg Leu Asn Asn Asp Ile His Ser Tyr
                885                 890                 895

Lys Arg Glu Gln Ala Glu Ser Ser Thr Asn Met Val Ala Ile Leu Ile
            900                 905                 910

Ser Gln Ser Gln Arg Thr Ile Ser Glu Glu Ala Ile Arg Gln Ile
        915                 920                 925

Lys Glu Met Met Glu Ser Lys Arg Arg Glu Leu Leu Gly Met Val Leu
    930                 935                 940

Gln Asn Lys Glu Ser Gln Leu Pro Gln Val Cys Lys Asp Leu Phe Trp
945                 950                 955                 960

Thr Thr Phe Lys Ala Ala Tyr Ser Ile Tyr Thr His Gly Asp Glu Tyr
                965                 970                 975

Arg Phe Pro Gln Glu Leu Lys Asn His Ile Asn Asp Val Ile Tyr Lys
            980                 985                 990

Pro Leu Asn Gln Tyr Ser Pro
        995

<210> SEQ ID NO 91
<211> LENGTH: 3000
<212> TYPE: DNA
<213> ORGANISM: Artificial Sequence
<220> FEATURE:
<223> OTHER INFORMATION: GFP-NgSs fusion

<400> SEQUENCE: 91
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tcggttatgg tgttcaatgc tttgcgagat acccagatca tatgaaacag     240
catgactttt tcaagagtgc catgcccgaa ggttatgtac aggaaagaac tatattttc     300 aaagatgacg ggaactacaa gacacgtgct gaagtcaagt ttgaaggtga taccttgtt     360 aatagaatcg agttaaaagg tattgatttt aagaagatgg aaacattct tggacacaaa     420 ttggaataca actataactc acacaatgta tacatcatgg cagacaaaca aagaatgga     480 atcaaagtta acttcaaaat tagacacaac attgaagatg gaagcgttca actagcagac     540
cattatcaac aaaatactcc aattggcgat ggccctgtcc ttttaccaga caaccattac     600
ctgtccacac aatctgccct ttcgaaagat cccaacgaaa agagagacca catggtcctt     660
cttgagtttg taacagctgc tgggattaca catggcatgg atgaactata caagacggct     720
ggtagtggtc atatgagcca gtactgctt catcactgg aagaggcgaa ggaaagaata     780
agggaaacat ttggaaaaaa tgagctatct ccttcttcct atgacacagc atgggtagct     840
atggtccctt caagatattc tatgaaccaa ccatgttttc ctcggtgctt ggattggatt     900
cttgaaaatc aaagagaaga tggatcttgg ggcctaaatc ctagccatcc attgcttgta     960

```
aaagactccc tttcttccac tctagcatgt ttgcttgccc ttcgcaaatg gagaattgga    1020
gataaccaag tccaaagagg ccttggcttt attgaaacgc atggttgggc agttgataac    1080
gtggatcaga tttcaccttt aggatttgat attatatttc ccagcatgat caagtatgca    1140
gagaaactga atttggatct acctttcgat cctaaccttg taaatatgat gctccgcgaa    1200
cgcgaattaa caattgaaag agccctaaag aatgaattcg aagggaatat ggcaaatgtt    1260
gaatattttg ctgaagggct cggtgaatta tgtcattgga agagataat gcttcatcag     1320 agacgcaacg gatcgccctt tgactctcca gcaactactg cagctgcttt gatttaccat    1380
cagcacgatg agaaatgctt tgggtacttg agctcaatct tgaaactgca cgagaattgg    1440
gtccccacta tttaccctac aaaggtacat tcaaatctct tcttcgttga tgcccttcaa    1500
aatcttggag tagatcggta ttttaaaaca gaactcaaaa gtgtactcga tgaaatatac    1560
aggctttggc tagaaaagaa tgaagaaatt ttttcagaca ttgctcattg tgccatggcg    1620
tttcgacttt tgcggatgaa taactatgaa gtttcctcag aagaacttga aggatttgtc    1680
gaccaagaac atttctttac aacatcaggt gggaaactta ttagtcacgt tgcaattctc    1740
gaacttcacc gagcttcaca ggtggatatt caagaaggga aagatctcat tttagataaa    1800
ataagtactt ggacaaggaa ttttatggag caagaactct ggacaatca aatccttgat     1860 aggtcaaaga aggagatgga atttgctatg aggaattttt atggcacatt tgatcgagtg    1920
gaaactagac gatacatcga gtcatacaaa atggacagtt ttaagatctt aaaagcagcc    1980
tacaggtctt ccaacattaa caacatagac ttgctaaagt tctcagaaca tgattttaac    2040
ttgtgccaag cccgacacaa agaagaactt caacagatta gaggtggtt cgcagattgc     2100 aaactggaac aagtaggatc atcacaaaac tacttataca ctagttactt cccaattgct    2160
gccatactct tcgaacctga atatggtgat gctcgtctag catttgcaaa gtgtggcata    2220
atcgcaacga cggtggatga tttcttcgat ggttttgctt gcaatgaaga actccaaaac    2280
atcatcgaat tagtagagag gtgggatgga tacccaactg tcggatttcg ttcagaaagg    2340
gttagaattt tctttttggc actttacaaa atgatagagg aaattgcggc aaaggcagaa    2400
actaagcaag gtcgatgtgt caaagatctc cttattaact tgtggattga tttattgaaa    2460
tgtatgctgg tggaattgga cctttggaaa attaaatcaa ctaccccaag catgaggag     2520 tacttgtcta tcgcatgtgt aactacaggt gttaaatgtt taattctcat atcactacat    2580
cttcttggac caaaactgtc caaggatgtc acagaaagtt ctgaggtcag tgccttatgg    2640
aattgtacag ctgttgtggc ccgattgaat aatgatatac atagttacaa gagagaacaa    2700
gcagaaagtt caacaaatat ggtagcaata ttaatatcac agagtcagag aactatctct    2760
gaagaagagg ctataagaca gataaaagaa atgatggaaa gtaagagaag agagttgcta    2820
gggatggttc tacaaaataa agaaagccaa ttgccgcaag tgtgcaaaga tcttttttgg    2880
acgacattca aagcagctta ttctatatat acacatggcg atgagtatcg cttcccacag    2940
gaattgaaga accatataaa cgatgtaatt tacaaaccac tcaatcaata ttccccataa    3000
```

<210> SEQ ID NO 92
<211> LENGTH: 827
<212> TYPE: PRT
<213> ORGANISM: Artificial Sequence
<220> FEATURE:
<223> OTHER INFORMATION: CBP-NgSs fusion

<400> SEQUENCE: 92

```
Met Gln Gln Thr Val Trp Gly Gln Cys Gly Gly Gln Gly Trp Ser Gly
  1               5                  10                  15

Pro Thr Ser Cys Val Ala Gly Ser Ala Cys Ser Thr Leu Asn Pro Tyr
             20                  25                  30

Tyr Ala Gln Cys Ile Pro Gly Ala Thr Thr Met Ser Thr Thr Thr Lys
             35                  40                  45

Pro Thr Ser Val Ser Ala Ser Thr Thr Arg Ala Ser Ala Thr Ser Ser
     50                  55                  60

Ala Thr Pro Pro Thr Ser Ser His Met Ser His Ser Thr Ala Ser Ser
 65                  70                  75                  80

Leu Glu Glu Ala Lys Glu Arg Ile Arg Glu Thr Phe Gly Lys Asn Glu
                 85                  90                  95

Leu Ser Pro Ser Ser Tyr Asp Thr Ala Trp Val Ala Met Val Pro Ser
            100                 105                 110

Arg Tyr Ser Met Asn Gln Pro Cys Phe Pro Arg Cys Leu Asp Trp Ile
            115                 120                 125

Leu Glu Asn Gln Arg Glu Asp Gly Ser Trp Gly Leu Asn Pro Ser His
            130                 135                 140

Pro Leu Leu Val Lys Asp Ser Leu Ser Ser Thr Leu Ala Cys Leu Leu
145                 150                 155                 160

Ala Leu Arg Lys Trp Arg Ile Gly Asp Asn Gln Val Gln Arg Gly Leu
                165                 170                 175

Gly Phe Ile Glu Thr His Gly Trp Ala Val Asp Asn Val Asp Gln Ile
            180                 185                 190

Ser Pro Leu Gly Phe Asp Ile Ile Phe Pro Ser Met Ile Lys Tyr Ala
            195                 200                 205

Glu Lys Leu Asn Leu Asp Leu Pro Phe Asp Pro Asn Leu Val Asn Met
            210                 215                 220

Met Leu Arg Glu Arg Glu Leu Thr Ile Glu Arg Ala Leu Lys Asn Glu
225                 230                 235                 240

Phe Glu Gly Asn Met Ala Asn Val Glu Tyr Phe Ala Glu Gly Leu Gly
                245                 250                 255

Glu Leu Cys His Trp Lys Glu Ile Met Leu His Gln Arg Arg Asn Gly
            260                 265                 270

Ser Pro Phe Asp Ser Pro Ala Thr Thr Ala Ala Leu Ile Tyr His
            275                 280                 285

Gln His Asp Glu Lys Cys Phe Gly Tyr Leu Ser Ser Ile Leu Lys Leu
            290                 295                 300

His Glu Asn Trp Val Pro Thr Ile Tyr Pro Thr Lys Val His Ser Asn
305                 310                 315                 320

Leu Phe Phe Val Asp Ala Leu Gln Asn Leu Gly Val Asp Arg Tyr Phe
            325                 330                 335

Lys Thr Glu Leu Lys Ser Val Leu Asp Glu Ile Tyr Arg Leu Trp Leu
            340                 345                 350

Glu Lys Asn Glu Glu Ile Phe Ser Asp Ile Ala His Cys Ala Met Ala
            355                 360                 365

Phe Arg Leu Leu Arg Met Asn Asn Tyr Glu Val Ser Ser Glu Glu Leu
370                 375                 380

Glu Gly Phe Val Asp Gln Glu His Phe Phe Thr Thr Ser Gly Gly Lys
385                 390                 395                 400

Leu Ile Ser His Val Ala Ile Leu Glu Leu His Arg Ala Ser Gln Val
            405                 410                 415

Asp Ile Gln Glu Gly Lys Asp Leu Ile Leu Asp Lys Ile Ser Thr Trp
```

```
            420             425             430
Thr Arg Asn Phe Met Glu Gln Glu Leu Leu Asp Asn Gln Ile Leu Asp
            435             440             445
Arg Ser Lys Lys Glu Met Glu Phe Ala Met Arg Lys Phe Tyr Gly Thr
            450             455             460
Phe Asp Arg Val Glu Thr Arg Arg Tyr Ile Glu Ser Tyr Lys Met Asp
465             470             475             480
Ser Phe Lys Ile Leu Lys Ala Ala Tyr Arg Ser Ser Asn Ile Asn Asn
            485             490             495
Ile Asp Leu Leu Lys Phe Ser Glu His Asp Phe Asn Leu Cys Gln Ala
            500             505             510
Arg His Lys Glu Glu Leu Gln Gln Ile Lys Arg Trp Phe Ala Asp Cys
            515             520             525
Lys Leu Glu Gln Val Gly Ser Ser Gln Asn Tyr Leu Tyr Thr Ser Tyr
            530             535             540
Phe Pro Ile Ala Ala Ile Leu Phe Glu Pro Glu Tyr Gly Asp Ala Arg
545             550             555             560
Leu Ala Phe Ala Lys Cys Gly Ile Ile Ala Thr Thr Val Asp Asp Phe
            565             570             575
Phe Asp Gly Phe Ala Cys Asn Glu Glu Leu Gln Asn Ile Ile Glu Leu
            580             585             590
Val Glu Arg Trp Asp Gly Tyr Pro Thr Val Gly Phe Arg Ser Glu Arg
            595             600             605
Val Arg Ile Phe Phe Leu Ala Leu Tyr Lys Met Ile Glu Glu Ile Ala
            610             615             620
Ala Lys Ala Glu Thr Lys Gln Gly Arg Cys Val Lys Asp Leu Leu Ile
625             630             635             640
Asn Leu Trp Ile Asp Leu Leu Lys Cys Met Leu Val Glu Leu Asp Leu
            645             650             655
Trp Lys Ile Lys Ser Thr Thr Pro Ser Ile Glu Glu Tyr Leu Ser Ile
            660             665             670
Ala Cys Val Thr Thr Gly Val Lys Cys Leu Ile Leu Ile Ser Leu His
            675             680             685
Leu Leu Gly Pro Lys Leu Ser Lys Asp Val Thr Glu Ser Ser Glu Val
            690             695             700
Ser Ala Leu Trp Asn Cys Thr Ala Val Ala Arg Leu Asn Asn Asp
705             710             715             720
Ile His Ser Tyr Lys Arg Glu Gln Ala Glu Ser Ser Thr Asn Met Val
            725             730             735
Ala Ile Leu Ile Ser Gln Ser Gln Arg Thr Ile Ser Glu Glu Glu Ala
            740             745             750
Ile Arg Gln Ile Lys Glu Met Met Glu Ser Lys Arg Arg Glu Leu Leu
            755             760             765
Gly Met Val Leu Gln Asn Lys Glu Ser Gln Leu Pro Gln Val Cys Lys
            770             775             780
Asp Leu Phe Trp Thr Thr Phe Lys Ala Ala Tyr Ser Ile Tyr Thr His
785             790             795             800
Gly Asp Glu Tyr Arg Phe Pro Gln Glu Leu Lys Asn His Ile Asn Asp
            805             810             815
Val Ile Tyr Lys Pro Leu Asn Gln Tyr Ser Pro
            820             825

<210> SEQ ID NO 93
```

<211> LENGTH: 2484
<212> TYPE: DNA
<213> ORGANISM: Artificial Sequence
<220> FEATURE:
<223> OTHER INFORMATION: CBP-NgSs fusion

<400> SEQUENCE: 93

| | | | | | |
|---|---|---|---|---|---|
| atgcagcaaa | ctgtttgggg | gcaatgcgga | ggtcaaggat | ggagcggccc | gactagttgc | 60 |
| gttgctggat | ctgcttgttc | tactctcaac | ccctactacg | ctcaatgcat | tcctggagcc | 120 |
| actaccatgt | ctaccacaac | caagccgacc | tccgtttcag | catcaacgac | cagggcgagt | 180 |
| gcaacatcgt | ccgctactcc | gccaactagc | tctcatatgt | cccactccac | cgcttcatct | 240 |
| ttggaagaag | ctaaagaaag | aatcagagaa | accttcggta | agaacgaatt | gtctccatct | 300 |
| tcttatgata | ctgcttgggt | tgctatggtt | ccatctagat | actctatgaa | tcaaccatgt | 360 |
| ttcccaagat | gcttggattg | gatcttggaa | aatcaaagag | aagatggttc | ttggggtttg | 420 |
| aatccatctc | atccattatt | ggtcaaggat | tccttgtcat | ctactttggc | ttgtttgttg | 480 |
| gctttgagaa | agtggagaat | cggtgataat | caagtccaaa | gaggtttggg | tttcatcgaa | 540 |
| actcatggtt | gggctgttga | taacgttgac | caaatttctc | cattgggttt | cgatatcatc | 600 |
| ttcccatcca | tgattaagta | cgccgaaaag | ttgaatttgg | atttgccatt | cgatccaaac | 660 |
| ttggtcaata | tgatgttgag | agaaagagaa | ttgaccatcg | aaagagcctt | gaaaaacgaa | 720 |
| ttcgaaggta | acatggctaa | cgttaatac | tttgctgaag | gttaggtga | attgtgccac | 780 |
| tggaaagaaa | tcatgttgca | ccaaagaaga | aacggttctc | catttgattc | tccagctact | 840 |
| acagctgctg | ctttgatcta | tcatcaacat | gacgaaaagt | gcttcggtta | cttgtcctct | 900 |
| attttgaagt | tgcacgaaaa | ctgggttcca | actatctatc | caactaaggt | tcactccaac | 960 |
| ttgttttcg | ttgatgcctt | gcaaaacttg | ggtgttgaca | gatactttaa | gaccgaattg | 1020 |
| aagtccgttt | tggacgaaat | ctacagattg | tggttggaaa | agaacgaaga | aatcttctcc | 1080 |
| gatattgctc | attgtgctat | ggccttcaga | ttattgagaa | tgaacaacta | cgaagtttcc | 1140 |
| tccgaagaat | tggaaggttt | tgttgatcaa | gaacacttct | tcactacctc | tggtggtaag | 1200 |
| ttgatttccc | catgttgctat | cttggaattg | catagagctt | cccaagttga | tatccaagaa | 1260 |
| ggtaaggatt | tgattttgga | caagatttct | acctggacca | gaaacttcat | ggaacaagaa | 1320 |
| ttattggaca | atcaaatctt | ggacagatcc | aagaaagaaa | tggaattcgc | catgagaaag | 1380 |
| ttctacggta | ctttcgatag | agtcgaaacc | agaagatata | ttgaatccta | caagatggac | 1440 |
| tccttcaaga | ttttgaaagc | tgcctacaga | tcctccaaca | tcaacaacat | tgatttgttg | 1500 |
| aagttctccg | aacacgactt | caacttgtgt | caagcaagac | acaaagaaga | attgcaacaa | 1560 |
| atcaagagat | ggttcgctga | ttgcaagttg | aacaagtag | ttcttctca | aaactacttg | 1620 |
| tacacctcct | actttccaat | tgctgccatt | tgtttgaac | cagaatatgg | tgatgctaga | 1680 |
| ttggcttttg | ctaagtgcgg | tattattgct | actaccgttg | atgatttttt | cgacggtttt | 1740 |
| gcttgcaacg | aagaattaca | aaacatcatc | gaattggtcg | aaagatggga | tggttatcca | 1800 |
| actgttggtt | tcagatcaga | aagagtcaga | attttcttct | tggccttgta | caaaatgatt | 1860 |
| gaagaaattg | ctgctaaggc | cgaaactaag | caagtagat | gtgtaaaaga | cttgttgatt | 1920 |
| aacttgtgga | tcgacttatt | gaagtgcatg | ttggttgaat | tggacttgtg | aagattaag | 1980 |
| tctaccaccc | catctatcga | agaatacttg | tctattgctt | gtgttaccac | cggtgttaag | 2040 |
| tgcttgattt | tgatctccctt | gcatttgtta | ggtccaaagt | tgtctaagga | cgttaccgaa | 2100 |
| tcttctgaag | tttcagcttt | gtggaactgt | actgctgttg | ttgcaagatt | gaacaacgat | 2160 |

```
atccactctt acaagagaga acaagctgaa tcttctacca acatggtcgc cattttgatc    2220
agtcaatctc aaagaactat ctctgaagaa gaagccatca gacaaatcaa agaaatgatg    2280
gaatccaaga gaagagaatt attaggtatg gtcttgcaaa acaagaatc ccaattgcca     2340 caagtctgca aagatttgtt ctggactact tttaaggctg cctactctat ctatacccat    2400
ggtgatgaat acagattccc acaagaattg aagaaccaca tcaacgacgt tatctacaag    2460
ccattgaatc aatactcccc ataa                                           2484
```

<210> SEQ ID NO 94
<211> LENGTH: 1507
<212> TYPE: PRT
<213> ORGANISM: Nicotiana glutinosa
<220> FEATURE:
<223> OTHER INFORMATION: NgLPP-NgSs fusion

<400> SEQUENCE: 94

```
Met Cys Ala Pro Ile Asp Ala Ser Tyr Leu Gly Tyr Leu Asn Glu Leu
 1               5                  10                  15

Glu Ser Asn Phe Ser Asn Asn Pro Glu Glu Lys Asp Ile Gln Val Ser
                20                  25                  30

Arg Thr Ile Gln Ile Lys Asn Leu Thr Glu Glu Ile Lys Cys Lys Leu
            35                  40                  45

Asn Ser Met Glu Asp Gly Arg Ser Ser Val Ser Ala Tyr Asp Thr Ala
        50                  55                  60

Trp Val Ser Phe Ile Pro Asn Thr Thr Asn Asn Gly Asn Asp Gln Arg
 65                  70                  75                  80

Pro Met Phe Pro Ser Cys Leu Gln Trp Ile Ile Asp Asn Gln Leu Cys
                 85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
                245                 250                 255

Tyr Leu Gln Asn Val Val Gln Lys Ser Asn Gly Gly Ala Arg His Tyr
            260                 265                 270

Pro Leu Asp Leu Leu Thr Arg Leu Trp Ala Ile Asp Arg Leu Gln Arg
        275                 280                 285

Leu Gly Ile Ser Tyr Tyr Phe Ala Glu Glu Phe Lys Glu Leu Leu Asn
    290                 295                 300
```

```
His Val Phe Arg Tyr Trp Asp Glu Glu Asn Gly Ile Phe Ser Gly Arg
305                 310                 315                 320

Asn Ser Asn Val Cys Asp Val Asp Thr Cys Met Ala Ile Arg Leu
            325                 330                 335

Leu Arg Leu His Gly Tyr Asp Val Ser Pro Asp Ala Leu Asn Asn Phe
            340                 345                 350

Thr Asp Gly Asp Gln Phe Phe Cys Leu Arg Gly Glu Val Asp Gly Ser
            355                 360                 365

Pro Thr His Met Phe Asn Leu Tyr Arg Cys Ser Gln Val Leu Phe Pro
            370                 375                 380

Gly Glu Lys Ile Leu Glu Ala Lys Asn Phe Thr Tyr Asn Phe Leu
385                 390                 395                 400

Gln Gln Cys Leu Ala Asn Asn Arg Cys Leu Asp Lys Trp Val Ile Ala
                405                 410                 415

Lys Asp Ile Pro Gly Glu Ile Arg Tyr Ala Leu Lys Phe Pro Trp Tyr
            420                 425                 430

Ala Ser Leu Pro Arg Val Glu Ser Arg Leu Tyr Ile Glu Gln Tyr Gly
            435                 440                 445

Gly Ala Asn Asp Ile Trp Ile Gly Lys Thr Leu Tyr Arg Met Pro Asp
450                 455                 460

Val Ser Asn Asn Val Tyr Leu Gln Ala Ala Lys Leu Asp Tyr Asn Arg
465                 470                 475                 480

Cys Gln Ser Gln His Arg Phe Glu Trp Leu Ile Met Gln Trp Phe
                485                 490                 495

Asp Lys Cys Asn Phe Gln Gln Phe Gly Ile Ser Lys Lys Tyr Leu Leu
            500                 505                 510

Val Ser Tyr Phe Leu Ala Ala Ala Ser Ile Phe Glu Val Glu Lys Ser
            515                 520                 525

Arg Glu Arg Leu Ala Trp Ala Lys Ser Arg Ile Ile Cys Lys Met Ile
530                 535                 540

Thr Ser Tyr Tyr Asn Glu Glu Ala Thr Thr Trp Thr Ser Arg Asn Ser
545                 550                 555                 560

Leu Leu Met Glu Phe Lys Gly Ser Asp Pro Ser Arg Lys Asn Gly
                565                 570                 575

Asn Glu Thr Lys Glu Ile Ile Val Leu Lys Asn Leu Arg Gln Phe Leu
            580                 585                 590

His Gln Leu Ser Glu Glu Thr Phe Glu Asp Leu Gly Lys Asp Ile His
            595                 600                 605

His Gln Leu Gln Asn Ala Trp Lys Thr Trp Leu Ala Phe Leu Arg Glu
            610                 615                 620

Glu Lys Asn Thr Cys Gln Glu Glu Ala Glu Leu Leu Val Arg Thr Ile
625                 630                 635                 640

Asn Leu Ser Gly Gly His Met Ile His Asp Glu Ile Leu Phe Asp Ala
                645                 650                 655

Asp Tyr Lys Asn Leu Ser Asn Leu Thr Asn Lys Val Cys Cys Met Leu
            660                 665                 670

Ser Glu Leu Gln Asn Asp Lys Val Thr Gly Ser Ser Lys Asn Thr Asp
            675                 680                 685

Ile Glu Leu Asn Met Gln Ala Leu Val Lys Leu Val Phe Gly Asn Thr
            690                 695                 700

Ser Ser Asn Ile Asn Gln Asp Ile Lys Gln Thr Phe Phe Thr Val Val
705                 710                 715                 720
```

```
Lys Thr Phe Tyr Tyr Ser Ala His Ala Ser Glu Glu Ile Ile Asn Phe
                725                 730                 735

His Ile Ser Lys Val Leu Leu Gln Gln Val Gln Gly Gly Ser Gly Gly
                740                 745                 750

Met Ser His Ser Thr Ala Ser Ser Leu Glu Glu Ala Lys Glu Arg Ile
                755                 760                 765

Arg Glu Thr Phe Gly Lys Asn Glu Leu Ser Pro Ser Ser Tyr Asp Thr
                770                 775                 780

Ala Trp Val Ala Met Val Pro Ser Arg Tyr Ser Met Asn Gln Pro Cys
785                 790                 795                 800

Phe Pro Arg Cys Leu Asp Trp Ile Leu Glu Asn Gln Arg Glu Asp Gly
                805                 810                 815

Ser Trp Gly Leu Asn Pro Ser His Pro Leu Leu Val Lys Asp Ser Leu
                820                 825                 830

Ser Ser Thr Leu Ala Cys Leu Leu Ala Leu Arg Lys Trp Arg Ile Gly
                835                 840                 845

Asp Asn Gln Val Gln Arg Gly Leu Gly Phe Ile Glu Thr His Gly Trp
                850                 855                 860

Ala Val Asp Asn Val Asp Gln Ile Ser Pro Leu Gly Phe Asp Ile Ile
865                 870                 875                 880

Phe Pro Ser Met Ile Lys Tyr Ala Glu Lys Leu Asn Leu Asp Leu Pro
                885                 890                 895

Phe Asp Pro Asn Leu Val Asn Met Met Leu Arg Glu Arg Glu Leu Thr
                900                 905                 910

Ile Glu Arg Ala Leu Lys Asn Glu Phe Glu Gly Asn Met Ala Asn Val
                915                 920                 925

Glu Tyr Phe Ala Glu Gly Leu Gly Glu Leu Cys His Trp Lys Glu Ile
                930                 935                 940

Met Leu His Gln Arg Arg Asn Gly Ser Pro Phe Asp Ser Pro Ala Thr
945                 950                 955                 960

Thr Ala Ala Ala Leu Ile Tyr His Gln His Asp Glu Lys Cys Phe Gly
                965                 970                 975

Tyr Leu Ser Ser Ile Leu Lys Leu His Glu Asn Trp Val Pro Thr Ile
                980                 985                 990

Tyr Pro Thr Lys Val His Ser Asn Leu Phe Phe Val Asp Ala Leu Gln
                995                 1000                1005

Asn Leu Gly Val Asp Arg Tyr Phe Lys Thr Glu Leu Lys Ser Val Leu
                1010                1015                1020

Asp Glu Ile Tyr Arg Leu Trp Leu Glu Lys Asn Glu Glu Ile Phe Ser
1025                1030                1035                1040

Asp Ile Ala His Cys Ala Met Ala Phe Arg Leu Leu Arg Met Asn Asn
                1045                1050                1055

Tyr Glu Val Ser Ser Glu Glu Leu Glu Gly Phe Val Asp Gln Glu His
                1060                1065                1070

Phe Phe Thr Thr Ser Gly Gly Lys Leu Ile Ser His Val Ala Ile Leu
                1075                1080                1085

Glu Leu His Arg Ala Ser Gln Val Asp Ile Gln Glu Gly Lys Asp Leu
                1090                1095                1100

Ile Leu Asp Lys Ile Ser Thr Trp Thr Arg Asn Phe Met Glu Gln Glu
1105                1110                1115                1120

Leu Leu Asp Asn Gln Ile Leu Asp Arg Ser Lys Lys Glu Met Glu Phe
                1125                1130                1135

Ala Met Arg Lys Phe Tyr Gly Thr Phe Asp Arg Val Glu Thr Arg Arg
```

1140            1145            1150
Tyr Ile Glu Ser Tyr Lys Met Asp Ser Phe Lys Ile Leu Lys Ala Ala
            1155            1160            1165
Tyr Arg Ser Ser Asn Ile Asn Asn Ile Asp Leu Leu Lys Phe Ser Glu
    1170            1175            1180
His Asp Phe Asn Leu Cys Gln Ala Arg His Lys Glu Glu Leu Gln Gln
1185            1190            1195            1200
Ile Lys Arg Trp Phe Ala Asp Cys Lys Leu Glu Gln Val Gly Ser Ser
                1205            1210            1215
Gln Asn Tyr Leu Tyr Thr Ser Tyr Phe Pro Ile Ala Ala Ile Leu Phe
            1220            1225            1230
Glu Pro Glu Tyr Gly Asp Ala Arg Leu Ala Phe Ala Lys Cys Gly Ile
        1235            1240            1245
Ile Ala Thr Thr Val Asp Phe Phe Asp Gly Phe Ala Cys Asn Glu
    1250            1255            1260
Glu Leu Gln Asn Ile Ile Glu Leu Val Glu Arg Trp Asp Gly Tyr Pro
1265            1270            1275            1280
Thr Val Gly Phe Arg Ser Glu Arg Val Arg Ile Phe Phe Leu Ala Leu
                1285            1290            1295
Tyr Lys Met Ile Glu Glu Ile Ala Ala Lys Ala Glu Thr Lys Gln Gly
            1300            1305            1310
Arg Cys Val Lys Asp Leu Leu Ile Asn Leu Trp Ile Asp Leu Leu Lys
        1315            1320            1325
Cys Met Leu Val Glu Leu Asp Leu Trp Lys Ile Lys Ser Thr Thr Pro
    1330            1335            1340
Ser Ile Glu Glu Tyr Leu Ser Ile Ala Cys Val Thr Thr Gly Val Lys
1345            1350            1355            1360
Cys Leu Ile Leu Ile Ser Leu His Leu Leu Gly Pro Lys Leu Ser Lys
                1365            1370            1375
Asp Val Thr Glu Ser Ser Glu Val Ser Ala Leu Trp Asn Cys Thr Ala
            1380            1385            1390
Val Val Ala Arg Leu Asn Asn Asp Ile His Ser Tyr Lys Arg Glu Gln
        1395            1400            1405
Ala Glu Ser Ser Thr Asn Met Val Ala Ile Leu Ile Ser Gln Ser Gln
    1410            1415            1420
Arg Thr Ile Ser Glu Glu Ala Ile Arg Gln Ile Lys Glu Met Met
1425            1430            1435            1440
Glu Ser Lys Arg Arg Glu Leu Leu Gly Met Val Leu Gln Asn Lys Glu
                1445            1450            1455
Ser Gln Leu Pro Gln Val Cys Lys Asp Leu Phe Trp Thr Thr Phe Lys
            1460            1465            1470
Ala Ala Tyr Ser Ile Tyr Thr His Gly Asp Glu Tyr Arg Phe Pro Gln
        1475            1480            1485
Glu Leu Lys Asn His Ile Asn Asp Val Ile Tyr Lys Pro Leu Asn Gln
    1490            1495            1500
Tyr Ser Pro
1505

<210> SEQ ID NO 95
<211> LENGTH: 3081
<212> TYPE: DNA
<213> ORGANISM: Artificial Sequence
<220> FEATURE:
<223> OTHER INFORMATION: NgLPP-NgSs fusion

```
<400> SEQUENCE: 95
atgtgcgcac ctattgatgc aagttatctt ggttatctga atgagttgga atctaatttc      60
tcaaacaacc ccgaagaaaa ggatattcag gtaagcagaa caatacagat caaaaatttg     120
acagaagaaa tcaaatgtaa gttgaattcg atggaggatg aaggtcaag tgtctcagcc      180 tatgacacag cttgggtttc ctttattcca aatactacta ataatggaaa tgatcaaagg     240
cctatgtttc catcttgtct tcaatggatt atagacaatc aacttttgcga tggttcatgg    300 ggagaggaga gtgtattctg catatatgat cgactcttga acacactagc atgtgttgtt    360
gcattgacat tatggaacac atgccttcct aagagaaaca aaggtgtgat gtttatcaaa     420
gaaaacttaa ttaagctaga gacaggggaa gttgaacaca tgacttgtgg atttgaattt    480
gtgtttcctg ctctccttga gaaagctcaa caattaaata ttgacattcc gtatgatgct     540
ccagtcttaa aggatattta tgcaaggaga gaagtaaagt ttacaagaat tcctaaagag    600
attgtccata cgattccgac aacagcattg ctttcattag aaggattaag ggacgacctg    660
gattggcaaa gactttaaaa ttttcaaatg cctgatggtt cattcttatc agcccctgct    720
tccactgcct ttgcattcat gaaaacaaac gatgaaaagt gtttggcata tcttcaaaat    780
gttgttcaaa agtctaatgg aggagcgcga cactacccac tggacttgtt aacacgactt    840
tgggcaattg atcgattaca acgccttgga atatcttatt attttgcgga agagttcaag    900
gaacttttga atcatgtgtt cagatattgg gacgaggaga atggaatttt cagtggaagg     960
aattcaaacg tttgtgacgt tgatgataca tgcatggcta ttaggttgct taggttgcat   1020
gggtatgatg ttagtccaga tgcgctaaac aatttcacag atggtgatca attcttttgc    1080
cttagaggtg aagtggacgg gtcaccaaca catatgttta atctttatag atgttcccaa    1140
gttttattcc caggagaaaa gattcttgaa gaggcaaaga atttttactta caacttctta   1200 cagcaatgtc ttgcaaacaa tcgatgctta gacaaatggg tcatagctaa ggacattccc    1260
ggggagataa ggtatgcact gaaatttcca tggtatgcaa gcttacctcg ggtggaatct    1320
aggctataca tagaacagta cggcggagca atgatatttt ggattggcaa gacattatac    1380
aggatgcccg atgtcagcaa caatgtttat ttacaagctg caaaattaga ttacaacaga    1440
tgccaaagtc aacatcgatt tgaatggcta attatgcaac agtggtttga taagtgcaac    1500
tttcaacaat ttggaataag caaaaagtac ctccctagttt cttatttctt agctgctgca   1560
agtatatttg aagtcgaaaa gtcaagagaa cgacttgcgt gggctaaatc tcgtataata    1620
tgtaagatga ttacatctta ctacaatgaa gaagccacaa cttggaccag taggaattca    1680
ttgctaatgg aattcaaggg ttctgatgat ccaagcagaa aaaatggtaa tgaaacaaaa    1740
gagatcatag ttctcaaaaa tcttcgtcag ttttttgcacc aactatcaga gaaactttt     1800 gaggacctag gcaaagacat ccatcaccaa ctacaaaatg catggaaaac gtggttggcg    1860
ttcttaaggg aggaaaaaaa tacatgccaa gaagaagcag agttgctagt gcgcacaatt    1920
aatctctccg gcggccatat gatacatgat gagatactat tcgatgcgga ctacaaaaat    1980
ctgtccaacc ttactaataa agtttgctgc atgcttagtg agctccaaaa tgacaaggtg    2040
actggcagct caaagaacac tgacattgaa ctcaacatgc aagcacttgt aaaattagtg    2100
tttggtaaca ccctcaagca catcaaccaa gacattaagc aaacattttt tacagttgtt   2160
aagactttct attacagtgc acatgctagt gaggaaataa tcaactttca catatccaag   2220
gtgcttttac agcaagtcca gggtggttct ggtggtatga gccacagtac tgcttcatca    2280
ctggaagagg cgaaggaaag aataagggaa acatttggaa aaaatgagct atctccttct   2340
```

```
tcctatgaca cagcatgggt agctatggtc ccttcaagat attctatgaa ccaaccatgt   2400
tttcctcggt gcttggattg gattcttgaa aatcaaagag aagatggatc ttggggccta   2460
aatcctagcc atccattgct tgtaaaagac tcccttcctt ccactctagc atgtttgctt   2520
gcccttcgca aatggagaat tggagataac caagtccaaa gaggccttgg ctttattgaa   2580
acgcatggtt gggcagttga taacgtggat cagatttcac ctttaggatt tgatattata   2640
tttcccagca tgatcaagta tgcagagaaa ctgaatttgg atctacccttt cgatcctaac   2700 cttgtaaata tgatgctccg cgaacgcgaa ttaacaattg aaagagccct aaagaatgaa   2760
ttcgaaggga atatgcaaa tgttgaatat tttgctgaag ggctcggtga attatgtcat   2820
tggaaagaga taatgcttca tcagagacgc aacggatcgc cctttgactc tccagcaact   2880
actgcagctg ctttgattta ccatcagcac gatgagaaat gctttgggta cttgagctca   2940
atcttgaaac tgcacgagaa ttgggtcccc actatttacc ctacaaaggt acattcaaat   3000
ctcttcttcg ttgatgccct tcaaaatctt ggagtagatc ggtattttaa aacagaactc   3060
aaaagtgtac tcgatgaaat a                                            3081
```

<210> SEQ ID NO 96
<211> LENGTH: 5
<212> TYPE: PRT
<213> ORGANISM: Artificial Sequence
<220> FEATURE:
<223> OTHER INFORMATION: Linker

<400> SEQUENCE: 96

Gly Gly Ser Gly Gly
1               5

<210> SEQ ID NO 97
<211> LENGTH: 72
<212> TYPE: PRT
<213> ORGANISM: Trichoderma harzianum
<220> FEATURE:
<223> OTHER INFORMATION: Cellulose binding domain

<400> SEQUENCE: 97

Met Gln Gln Thr Val Trp Gly Gln Cys Gly Gly Gln Gly Trp Ser Gly
1               5                   10                  15

Pro Thr Ser Cys Val Ala Gly Ser Ala Cys Ser Thr Leu Asn Pro Tyr
                20                  25                  30

Tyr Ala Gln Cys Ile Pro Gly Ala Thr Thr Met Ser Thr Thr Thr Lys
            35                  40                  45

Pro Thr Ser Val Ser Ala Ser Thr Thr Arg Ala Ser Ala Thr Ser Ser
        50                  55                  60

Ala Thr Pro Pro Thr Ser Ser His
65                  70

<210> SEQ ID NO 98
<211> LENGTH: 235
<212> TYPE: PRT
<213> ORGANISM: Artificial Sequence
<220> FEATURE:
<223> OTHER INFORMATION: Green fluorescent protein

<400> SEQUENCE: 98

Gly Glu Glu Leu Phe Thr Gly Val Val Pro Ile Leu Val Glu Leu Asp
1               5                   10                  15

Gly Asp Val Asn Gly His Lys Phe Ser Val Ser Gly Glu Gly Glu Gly

```
                    20                  25                  30

Asp Ala Thr Tyr Gly Lys Leu Thr Leu Lys Phe Ile Cys Thr Thr Gly
                35                  40                  45

Lys Leu Pro Val Pro Trp Pro Thr Leu Val Thr Thr Phe Gly Tyr Gly
 50                  55                  60

Val Gln Cys Phe Ala Arg Tyr Pro Asp His Met Lys Gln His Asp Phe
 65                  70                  75                  80

Phe Lys Ser Ala Met Pro Glu Gly Tyr Val Gln Glu Arg Thr Ile Phe
                85                  90                  95

Phe Lys Asp Asp Gly Asn Tyr Lys Thr Arg Ala Glu Val Lys Phe Glu
                100                 105                 110

Gly Asp Thr Leu Val Asn Arg Ile Glu Leu Lys Gly Ile Asp Phe Lys
                115                 120                 125

Glu Asp Gly Asn Ile Leu Gly His Lys Leu Glu Tyr Asn Tyr Asn Ser
                130                 135                 140

His Asn Val Tyr Ile Met Ala Asp Lys Gln Lys Asn Gly Ile Lys Val
145                 150                 155                 160

Asn Phe Lys Ile Arg His Asn Ile Glu Asp Gly Ser Val Gln Leu Ala
                165                 170                 175

Asp His Tyr Gln Gln Asn Thr Pro Ile Gly Asp Gly Pro Val Leu Leu
                180                 185                 190

Pro Asp Asn His Tyr Leu Ser Thr Gln Ser Ala Leu Ser Lys Asp Pro
                195                 200                 205

Asn Glu Lys Arg Asp His Met Val Leu Leu Glu Phe Val Thr Ala Ala
                210                 215                 220

Gly Ile Thr His Gly Met Asp Glu Leu Tyr Lys
225                 230                 235

<210> SEQ ID NO 99
<211> LENGTH: 9
<212> TYPE: PRT
<213> ORGANISM: Artificial Sequence
<220> FEATURE:
<223> OTHER INFORMATION: NTE motif
<220> FEATURE:
<221> NAME/KEY: VARIANT
<222> LOCATION: 1
<223> OTHER INFORMATION: Xaa = Asp or Asn
<220> FEATURE:
<221> NAME/KEY: VARIANT
<222> LOCATION: (2)...(4)
<223> OTHER INFORMATION: Xaa = any amino acid
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: (6)...(8)
<223> OTHER INFORMATION: Xaa = any amino acid

<400> SEQUENCE: 99

Xaa Xaa Xaa Xaa Xaa Xaa Xaa Xaa Glu
 1               5

<210> SEQ ID NO 100
<211> LENGTH: 55
<212> TYPE: PRT
<213> ORGANISM: Artificial Sequence
<220> FEATURE:
<223> OTHER INFORMATION: chloroplast transit sequence

<400> SEQUENCE: 100
```

```
Met Gln Val Lys Ile Thr Ser Ser His Arg Leu Phe Cys His Phe His
1               5                   10                  15

Gln Leu Lys Ser Ala Thr Ser Leu Ser Ala Gln Lys Thr Glu Leu Arg
            20                  25                  30

Lys Tyr Gly Pro Gly Asn Ser Leu Phe Gln Thr Glu Gly Ser Leu Leu
        35                  40                  45

Tyr Lys Pro Val Arg Leu Asn
    50              55

<210> SEQ ID NO 101
<211> LENGTH: 9
<212> TYPE: PRT
<213> ORGANISM: Artificial Sequence
<220> FEATURE:
<223> OTHER INFORMATION: NTE motif
<220> FEATURE:
<221> NAME/KEY: VARIANT
<222> LOCATION: 1
<223> OTHER INFORMATION: Xaa = Asp or Asn
<220> FEATURE:
<221> NAME/KEY: VARIANT
<222> LOCATION: (3)...(4)
<223> OTHER INFORMATION: Xaa = any amino acid
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: (6)...(8)
<223> OTHER INFORMATION: Xaa = any amino acid

<400> SEQUENCE: 101

Xaa Asp Xaa Xaa Xaa Xaa Xaa Xaa Glu
1               5

<210> SEQ ID NO 102
<211> LENGTH: 37
<212> TYPE: PRT
<213> ORGANISM: Artificial Sequence
<220> FEATURE:
<223> OTHER INFORMATION: chloroplast transit sequence

<400> SEQUENCE: 102

Met Ile Leu Gly Leu Arg Ser Thr Ile Ile Pro Leu Pro Asp His Lys
1               5                   10                  15

Leu Gly Asn Ile Lys Leu Gly Ser Val Thr Asn Ser Asn Phe Pro Arg
            20                  25                  30

Pro Ser Arg Val Arg
        35

<210> SEQ ID NO 103
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 2
<223> OTHER INFORMATION: Xaa = any amino acid

<400> SEQUENCE: 103

Asp Xaa Asp Asp
1
```

<210> SEQ ID NO 104
<211> LENGTH: 2358
<212> TYPE: DNA
<213> ORGANISM: Salvia sclarea
<220> FEATURE:
<223> OTHER INFORMATION: SsLPPs3
<300> PUBLICATION INFORMATION:
<310> PATENT DOCUMENT NUMBER: WO2009101126

<400> SEQUENCE: 104

| | |
|---|---:|
| atgacttctg taaatttgag cagagcacca gcagcgatta cccggcgcag gctgcagcta | 60 |
| cagccggaat tcatgccga gtgttcatgg ctgaaaagca gcagcaaaca cgcgcccttg | 120 |
| accttgagtt gccaaatccg tcctaagcaa ctctcccaaa tagctgaatt gagagtaaca | 180 |
| agcctggatg cgtcgcaagc gagtgaaaaa gacatttccc ttgttcaaac tccgcataag | 240 |
| gttgaggtta atgaaaagat cgaggagtca atcgagtacg tccaaaatct gttgatgacg | 300 |
| tcgggcgacg ggcgaataag cgtgtcaccc tatgacacgg cagtgatcgc cctgatcaag | 360 |
| gacttgaaag gcgcgacgc cccgcagttt ccgtcatgtc tcgagtggat cgcgcaccac | 420 |
| caactggctg atggctcatg gggcgacgaa ttcttctgta tttatgatcg gattctaaat | 480 |
| acattggcat gtgtcgtagc cttgaaatca tggaaccttc actctgatat tattgaaaaa | 540 |
| ggagtgacgt acatcaagga gaatgtgcat aaacttaaag gtgcaaatgt tgagcacagg | 600 |
| acagcggggt tcgaacttgt ggttcctact tttatgcaaa tggccacaga tttgggcatc | 660 |
| caagatctgc cctatgatca tcccctcatc aaggagattg ctgacacaaa caacaaaga | 720 |
| ttgaaagaga tacccaagga tttggtttac caaatgccaa cgaatttact gtacagttta | 780 |
| gaagggttag agatttgga gtgggaaagg ctactgaaac tgcagtcggg caatggctcc | 840 |
| ttcctcactt cgccgtcgtc caccgccgcc gtcttgatgc ataccaaaga tgaaaaatgt | 900 |
| ttgaaataca tcgaaaacgc cctcaagaat tgcgacggag gagcaccaca tacttatcca | 960 |
| gtcgatatct tctcaagact tgggcaatc gataggctac aacgcctagg aatttctcgt | 1020 |
| ttcttccagc acgagatcaa gtatttctta gatcacatcg aaagcgtttg ggaggagacc | 1080 |
| ggagttttca gtggaagata tacgaaattt agcgatattg atgacacgtc catgggcgtt | 1140 |
| aggcttctca aaatgcacgg atacgacgtc gatccaaatg tactaaaaca tttcaagcaa | 1200 |
| caagatggta aattttcctg ctacattggt caatcggtcg agtctgcatc tccaatgtac | 1260 |
| aatctttata gggctgctca actaagattt ccaggagaag aagttcttga agaagccact | 1320 |
| aaatttgcct ttaacttctt gcaagaaatg ctagtcaaag atcgacttca gaaagatgg | 1380 |
| gtgatatccg accacttatt tgatgagata aagctggggt tgaagatgcc atggtacgcc | 1440 |
| actctacccc gagtcgaggc tgcatattat ctagaccatt atgctggttc tggtgatgta | 1500 |
| tggattggca gagtttcta caggatgcca gaaatcagca atgatacata caggagctt | 1560 |
| gcgatattgg atttcaacag atgccaaaca caacatcagt tggagtggat ccacatgcag | 1620 |
| gaatggtacg acagatgcag ccttagcgaa ttcgggataa gcaaaagaga gttgcttcgc | 1680 |
| tcttactttc tggccgcagc aaccatattc gaaccggaga gaactcaaga gaggcttctg | 1740 |
| tgggccaaaa ccagaattct ttctaagatg atcacttcat tgtcaacat tagtggaaca | 1800 |
| acactatctt tggactacaa tttcaatggc ctcgatgaaa taattagtag tgccaatgaa | 1860 |
| gatcaaggac tggctgggac tctgctggca accttccatc aacttctaga cggattcgat | 1920 |
| atatacactc tccatcaact caaacatgtt tggagccaat ggttcatgaa agtgcagcaa | 1980 |
| ggagagggaa gcggcgggga agacgcggtg ctcctagcga acacgctcaa catctgcgcc | 2040 |

| | | | | |
|---|---|---|---|---|
| ggcctcaacg | aagacgtgtt | gtccaacaat | gaatacacgg | ctctgtccac | cctcacaaat | 2100 |
| aaaatctgca | atcgcctcgc | ccaaattcaa | gacaataaga | ttctccaagt | tgtggatggg | 2160 |
| agcataaagg | ataaggagct | agaacaggat | atgcaggcgt | tggtgaagtt | agtgcttcaa | 2220 |
| gaaaatggcg | gcgccgtaga | cagaaacatc | agacacacgt | ttttgtcggt | ttccaagact | 2280 |
| ttctactacg | atgcctacca | cgacgatgag | acgaccgatc | ttcatatctt | caaagtactc | 2340 |
| tttcgaccgg | ttgtatga | | | | 2358 |

<210> SEQ ID NO 105
<211> LENGTH: 1728
<212> TYPE: DNA
<213> ORGANISM: Salvia sclarea
<220> FEATURE:
<223> OTHER INFORMATION: SsTPS1132 SPP
<300> PUBLICATION INFORMATION:
<310> PATENT DOCUMENT NUMBER: WO2009101126

<400> SEQUENCE: 105

| | | | | | |
|---|---|---|---|---|---|
| atgtcgctcg | ccttcaacgt | cggagttacg | cctttctccg | gccaaagagt | tgggagcagg | 60 |
| aaagaaaaat | ttccagtcca | aggatttcct | gtgaccaccc | ccaataggtc | acgtctcatc | 120 |
| gttaactgca | gccttactac | aatagatttc | atggcgaaaa | tgaaagagaa | ttcaagagg | 180 |
| gaagacgata | aatttccaac | gacaacgact | cttcgatccg | aagatatacc | ctctaatttg | 240 |
| tgtataatcg | acacccttca | aaggttgggg | gtcgatcaat | tcttccaata | tgaaatcaac | 300 |
| actattctag | ataacacatt | caggttgtgg | caagaaaaac | acaaagttat | atatggcaat | 360 |
| gttactactc | atgcaatggc | atttaggctt | ttgcgagtga | aggatacgga | agtttcatca | 420 |
| gaggagttgg | ctccatatgg | taaccaagag | gctgttagcc | agcaaacaaa | tgacctgccg | 480 |
| atgattattg | agctttatag | agcagcaaat | gagagaatat | atgaagaaga | gaggagtctt | 540 |
| gaaaaaattc | ttgcttggac | taccatcttt | ctcaataagc | aagtgcaaga | taactcaatt | 600 |
| cccgacaaaa | aactgcacaa | actggtggaa | ttctacttga | ggaattacaa | aggcataacc | 660 |
| ataagattgg | gagctagacg | aaacctcgag | ctatatgaca | tgacctacta | tcaagctctg | 720 |
| aaatctacaa | acaggttctc | taatttatgc | aacgaagatt | ttctagtttt | cgcaaagcaa | 780 |
| gatttcgata | tacatgaagc | ccagaaccag | aaaggacttc | aacaactgca | aaggtggtat | 840 |
| gcagattgta | ggttggacac | cttaaacttt | ggaagagatg | tagttattat | tgctaattat | 900 |
| ttggcttcat | taattattgg | tgatcatgcg | tttgactatg | ttcgtctcgc | atttgccaaa | 960 |
| acatctgtgc | ttgtaacaat | tatggatgat | ttttcgact | gtcatggctc | tagtcaagag | 1020 |
| tgtgacaaga | tcattgaatt | agtaaaagaa | tggaaggaga | atccggatgc | agagtacgga | 1080 |
| tctgaggagc | ttgagatcct | ttttatggcg | ttgtacaata | cagtaaatga | gttggcggag | 1140 |
| agggctcgtg | ttgaacaggg | gcgtagtgtc | aaagagtttc | tagtcaaact | gtgggttgaa | 1200 |
| atactctcag | ctttcaagat | agaattagat | acatggagca | atggcacgca | gcaaagcttc | 1260 |
| gatgaataca | tttcttcgtc | gtggttgtcg | aacggttccc | ggctgacagg | tctcctgacg | 1320 |
| atgcaattcg | tcggagtaaa | attgtccgat | gaaatgctta | tgagtgaaga | gtgcactgat | 1380 |
| ttggctaggc | atgtctgtat | ggtcggccgg | ctgctcaacg | acgtgtgcag | ttctgagagg | 1440 |
| gagcgcgagg | aaaatattgc | aggaaaaagt | tatagcattc | tactagcaac | tgagaaagat | 1500 |
| ggaagaaaag | ttagtgaaga | tgaagccatt | gcagagatca | atgaaatggt | tgaatatcac | 1560 |
| tggagaaaag | tgttgcagat | tgtgtataaa | aagaaagca | ttttgccaag | aagatgcaaa | 1620 |
| gatgtatttt | tggagatggc | taagggtacg | ttttatgctt | atgggatcaa | cgatgaattg | 1680 | acttctcctc agcaatccaa ggaagatatg aaatcctttg tcttttga         1728

<210> SEQ ID NO 106
<211> LENGTH: 4
<212> TYPE: PRT
<213> ORGANISM: Artificial Sequence
<220> FEATURE:
<223> OTHER INFORMATION: motif

<400> SEQUENCE: 106

Asp Asp Leu Asp
1

<210> SEQ ID NO 107
<211> LENGTH: 801
<212> TYPE: PRT
<213> ORGANISM: Artificial Sequence
<220> FEATURE:
<223> OTHER INFORMATION: ent-copalyl diphosphate synthase
<300> PUBLICATION INFORMATION:
<308> DATABASE ACCESSION NUMBER: Genbank AAB58822
<309> DATABASE ENTRY DATE: 1997-06-05

<400> SEQUENCE: 107

Met Phe Thr His Phe Ser Thr His Phe His Leu Pro Ser Ser Ser Ser
1               5                   10                  15

Leu Phe Phe Leu His Pro Phe Tyr Lys Ser Ser Ser Leu Gly Ala Val
            20                  25                  30

Ser Phe Val Ala Lys Asp Lys Glu Lys Arg Cys Arg Ala Ile Ser Lys
        35                  40                  45

Ser Arg Thr Gln Glu Tyr Glu Gly Val Phe Gln Thr Asn Val Ala Thr
    50                  55                  60

Leu Lys Leu Ser Glu Ile Asn Val Glu Asp Val Ile Val Ile Asp Asp
65                  70                  75                  80

Glu Glu Glu Gln Asp Ile Arg Val Gly Leu Val Asn Lys Ile Lys Ser
                85                  90                  95

Ile Leu Ser Ser Leu Glu Asp Gly Glu Ile Thr Ile Ser Ala Tyr Asp
            100                 105                 110

Thr Ala Trp Val Ala Leu Val Glu Asp Val Asn Ala Ile Ser Thr Pro
        115                 120                 125

Gln Phe Pro Ser Ser Leu Glu Trp Ile Ala Lys Asn Gln Leu Gln Asp
    130                 135                 140

Gly Ser Trp Gly Asp Ser Arg Leu Phe Ser Ala His Asp Arg Ile Ile
145                 150                 155                 160

Asn Thr Leu Ala Cys Val Ile Ala Leu Arg Ser Trp Asn Met His Ser
                165                 170                 175

Glu Lys Cys Asp Lys Gly Met Ile Phe Phe Arg Glu Asn Leu Ser Lys
            180                 185                 190

Leu Glu Asn Glu Asn Glu Glu His Met Pro Ile Gly Phe Glu Val Ala
        195                 200                 205

Phe Pro Ser Leu Leu Glu Gly Ala Arg Gly Ile Lys Pro Leu Met Cys
    210                 215                 220

Pro Asn Asp Ser Pro Ile Leu Lys Asn Ile Phe Glu Lys Arg Asp Glu
225                 230                 235                 240

Lys Leu Thr Arg Ile Pro Lys Glu Ile Met His Lys Val Pro Thr Thr
                245                 250                 255

Leu Leu His Ser Leu Glu Gly Met Ser Gly Leu Asp Trp Lys Gln Leu
            260                 265                 270

```
Leu Lys Leu Gln Ser Gln Asp Gly Ser Phe Leu Phe Ser Pro Ser Ser
            275                 280                 285

Thr Ala Phe Ala Leu Met Gln Thr Lys Asp Gly Asn Cys Leu Lys Tyr
        290                 295                 300

Leu Asn Asn Val Val Lys Lys Phe Asn Gly Gly Val Pro Asn Val Tyr
305                 310                 315                 320

Pro Val Asp Leu Phe Glu His Ile Trp Val Asp Arg Leu Glu Arg
                325                 330                 335

Leu Gly Ile Ser Arg Phe Phe Arg His Glu Ile Lys Asp Cys Met Asn
                340                 345                 350

Tyr Val Ser Lys Ile Trp Ser Glu Lys Gly Ile Cys Trp Ala Arg Asn
                355                 360                 365

Ser Asn Val Gln Asp Ile Asp Asp Thr Ala Met Ala Phe Arg Leu Leu
            370                 375                 380

Arg Leu His Gly His Gln Val Ser Ala His Val Phe Lys His Phe Glu
385                 390                 395                 400

Arg Asn Gly Glu Phe Phe Cys Phe Ala Gly Gln Cys Thr Gln Ala Val
                    405                 410                 415

Thr Gly Met Tyr Asn Leu Phe Arg Ala Ser Gln Val Leu Phe Pro Gly
                420                 425                 430

Glu Lys Ile Leu Glu His Ala Lys His Phe Ser Ala Lys Val Leu Lys
            435                 440                 445

Glu Lys Arg Glu Ala Asn Glu Leu Ile Asp Lys Trp Ile Ile Met Lys
            450                 455                 460

Asn Leu Pro Glu Glu Val Gly Tyr Ala Leu Asp Met Pro Trp Tyr Ala
465                 470                 475                 480

Asn Leu Asp Arg Ile Glu Thr Arg Phe Tyr Ile Asp Gln Tyr Gly Ala
                485                 490                 495

Glu Ser Asp Val Trp Ile Gly Lys Thr Leu Tyr Arg Met Ala Tyr Val
                500                 505                 510

Asn Asn Asn Asn Tyr Leu Glu Leu Ala Lys Leu Asp Tyr Asn Asn Cys
            515                 520                 525

Gln Ala Gln His Leu Ile Glu Trp Asn Val Ile Gln Thr Trp Tyr Leu
            530                 535                 540

Glu Ser Arg Leu Gly Glu Phe Gly Leu Ser Lys Arg Asp Leu Leu Leu
545                 550                 555                 560

Ala Tyr Phe Leu Ala Thr Gly Ser Ile Phe Glu Pro Glu Arg Ser His
                565                 570                 575

Glu Arg Leu Ala Trp Ala Lys Thr Thr Ala Leu Leu Glu Thr Ile Lys
                580                 585                 590

Cys Tyr Val Arg Asn Glu Asp Leu Arg Lys Asp Phe Ala Lys Lys Phe
                595                 600                 605

Asn Asp His Ile Asp Val Arg Asp Tyr Ser Ile Ala Arg Arg Met Lys
            610                 615                 620

Arg Asn Lys Thr Glu His Glu Leu Val Glu Ser Leu Phe Ala Thr Ile
625                 630                 635                 640

Gly Glu Ile Ser Trp Asp Val Arg Leu Ser Tyr Gly His Glu Ile Gly
                645                 650                 655

Tyr Asp Met His Gln Cys Trp Lys Lys Trp Leu Ser Ser Trp Gln Ser
                660                 665                 670

Glu Gly Asp Lys Cys Glu Gly Glu Ala Glu Leu Leu Ile Gln Ile Ile
                675                 680                 685
```

```
Asn Leu Cys Ser Asn His Trp Ile Ser Glu Gly Pro Ser Met Gln Ser
    690             695                 700

Thr Ile Gln His Leu Leu Gln Leu Thr Asn Ser Ile Cys His Lys Leu
705             710                 715                 720

Ser Cys Tyr Gln Lys Asp Lys Glu Leu Lys Gly Ile Ser Cys Gln Glu
                725                 730                 735

Asn Ile Thr Asn Ser Glu Val Glu Ser Lys Met Gln Glu Leu Val Gln
            740                 745                 750

Met Val Phe Gln Lys Cys Pro Asn Asp Ile Asp Phe Asn Val Lys Asn
                755                 760                 765

Thr Phe Phe Thr Ile Ala Lys Ser Phe Tyr Tyr Ala Ala Phe Cys Asp
770             775                 780

Ser Arg Thr Ile Asn Phe His Ile Ala Lys Val Leu Phe Glu Lys Val
785             790                 795                 800

Val
```

<210> SEQ ID NO 108
<211> LENGTH: 823
<212> TYPE: PRT
<213> ORGANISM: Cucurbita maxima
<220> FEATURE:
<223> OTHER INFORMATION: ent-copalyl diphosphate synthase 1
<300> PUBLICATION INFORMATION:
<308> DATABASE ACCESSION NUMBER: Genbank AAD04292
<309> DATABASE ENTRY DATE: 1999-01-13

<400> SEQUENCE: 108

```
Met Lys Ala Leu Ser Leu Ser Arg Pro Phe Pro Cys Ser Ser Asp Ala
 1               5                  10                  15

Thr Lys Leu Ser Ser Arg Pro Pro Pro Pro Val Gly Ser Cys
            20                  25                  30

Ser Phe Lys Val Glu Ser Ile Arg Ser Ser Arg Ile Ile Lys Cys Asn
            35                  40                  45

Ala Ile Ser Lys Pro Pro Thr Gln Glu Tyr Ser Asp Val Leu Gln Ser
 50                  55                  60

Gly Val Pro Val Ile Lys Trp Gln Gln Phe Val Glu Asp Asp Ile Glu
 65              70                  75                  80

Ser Glu Thr Thr Ala His Val Leu Ile Ser Lys Glu Ile Glu Glu Arg
                85                  90                  95

Val Asn Arg Ile Lys Ser Met Leu Ser Ser Met Asp Asp Gly Asp Ile
            100                 105                 110

Ser Ile Ser Ala Tyr Asp Thr Ala Trp Val Ala Leu Ile Pro Arg Val
            115                 120                 125

Leu Asp Gly Val Lys Thr Pro Leu Phe Pro Ser Ser Leu Glu Trp Ile
130                 135                 140

Ala Gln Asn Gln Leu Pro Asp Gly Ser Trp Gly Asp Ser Gly Ile Phe
145                 150                 155                 160

Ser Ala His Asp Arg Ile Leu Ser Thr Leu Ala Cys Val Leu Ala Leu
                165                 170                 175

Asn Ser Trp Lys Leu His Pro Asp Lys Ser Glu Lys Gly Met Val Phe
            180                 185                 190

Leu Asn Lys Asn Ile Ser Lys Leu Glu Asp Glu Asn Ala Glu His Met
            195                 200                 205

Leu Ile Gly Phe Glu Val Ala Phe Pro Ser Leu Met Glu Phe Ala Lys
210                 215                 220

Arg Leu Asn Leu Gln Val Pro Thr Asp Ser Pro Val Leu Gln Glu Ile
```

```
             225                 230                 235                 240
Asn His Arg Arg Ser Ile Lys Leu Thr Arg Ile Pro Lys Glu Ile Met
                245                 250                 255

His Lys Val Pro Thr Thr Leu Leu His Ser Leu Glu Gly Met Glu Gly
            260                 265                 270

Met Glu Gly Leu Asp Trp Gly Met Leu Leu Lys Leu Gln Ala Pro Asp
            275                 280                 285

Gly Ser Phe Leu Lys Ser Pro Ala Ser Thr Ala Phe Ala Phe Met Lys
        290                 295                 300

Thr Asn Asn Ser Asn Cys Phe Lys Tyr Leu Glu Ser Val Val Ser Arg
305                 310                 315                 320

Phe Asn Gly Gly Val Pro Asn Val Tyr Pro Val Asp Leu Phe Glu His
                325                 330                 335

Ile Trp Ala Val Asp Arg Leu Gln Arg Leu Gly Val Ser Arg Phe Phe
            340                 345                 350

His Pro Glu Ile Val Glu Ser Val Asp Tyr Leu Arg Arg His Trp Thr
        355                 360                 365

Asp Lys Gly Ile Cys Trp Ala Arg Asp Val Glu Phe Tyr Asp Ile Asp
370                 375                 380

Asp Thr Ala Met Gly Phe Lys Leu Leu Arg Leu Phe Gly His Glu Val
385                 390                 395                 400

Ser Ala Glu Val Phe Lys Asn Phe Glu Lys Asp Gly Glu Phe Val Cys
                405                 410                 415

Ile Ala Gly Gln Ser Thr Gln Ala Val Thr Gly Met Phe Asn Leu Tyr
            420                 425                 430

Arg Ala Ser Asp Gln Val Met Phe Pro Gly Glu Lys Ile Leu Glu Asp
        435                 440                 445

Ala Lys Gln Phe Ser Tyr Lys Phe Leu Arg Glu Lys Gln Ala Ala Asp
        450                 455                 460

Glu Leu Leu Asp Lys Trp Ile Ile Thr Lys Asp Leu Pro Gly Glu Val
465                 470                 475                 480

Gly Tyr Ala Leu Asp Val Pro Trp Phe Ala Ser Leu Pro Arg Val Glu
                485                 490                 495

Thr Arg Tyr Phe Ile Glu Gln Tyr Gly Gly Glu Asn Asp Ile Trp Ile
            500                 505                 510

Gly Lys Thr Leu Tyr Arg Met Phe Lys Val Asn Asn Asp Thr Tyr Leu
        515                 520                 525

Glu Leu Ala Lys Leu Asp Tyr Asn Lys Cys Gln Leu Leu His Gln Asn
    530                 535                 540

Glu Trp Val Asp Ile Gln Lys Trp Tyr Thr Glu Asn Asn Leu Arg Asp
545                 550                 555                 560

Tyr Gly Met Arg Arg Thr Ser Leu Leu Phe Ser Tyr Phe Gly Ala Ala
                565                 570                 575

Cys Ser Ile Phe Glu Pro Glu Arg Ala Lys Glu Arg Leu Ala Trp Thr
            580                 585                 590

Lys Thr Ala Ala Leu Val Gly Ala Ile Glu Ser His Phe Lys Asp Ala
        595                 600                 605

Asn Ala Asp Gln Arg Arg Ala Phe Ile Gln Phe Ile Asn Phe Asp
    610                 615                 620

Ala Ile Asp Gln Ala Tyr Asp Thr Asn Ala Trp Arg Ala Gly Asn Val
625                 630                 635                 640

Gln Gln Lys Gly Gly Gly Gln Gly Leu Val Gly Ile Leu Leu Arg Thr
                645                 650                 655
```

```
Leu Thr Ser Ile Ser Leu Asp Ile Leu Val Ser His Gly Phe Asp Ile
                660                 665                 670

Thr His His Leu His Gln Ala Trp Glu Lys Trp Leu Phe Lys Trp Gln
            675                 680                 685

Glu Asp Gly Asp Val His Lys Glu Ala Glu Leu Leu Val Gly Thr
        690                 695                 700

Ile Ile Leu Asn Ser Gly Cys Ser Thr Leu Glu Asp Leu Leu Ser Asn
705                 710                 715                 720

Pro Gln Tyr Gln Lys Leu Ser Tyr Leu Thr Asn Lys Val Cys His Gln
                725                 730                 735

Leu Gly His Phe Lys Lys His Lys Val Thr Asn Gly Gly Ile Tyr Lys
            740                 745                 750

Glu Lys Thr Glu Asn Lys Met Pro Pro Glu Ile Glu Glu Asp Met Arg
        755                 760                 765

Lys Leu Leu Gln Met Val Ile Gln Asn Ser Ser Asp Gly Asn Asp Ile
    770                 775                 780

Asp Ser Pro Ile Lys Asn Thr Phe Leu Thr Val Ala Lys Ser Ser Tyr
785                 790                 795                 800

Tyr Ala Ala Tyr Phe Asp Pro Trp Thr Ile Asn Tyr His Ile Ala Lys
                805                 810                 815

Val Leu Phe Glu Arg Val Phe
            820

<210> SEQ ID NO 109
<211> LENGTH: 827
<212> TYPE: PRT
<213> ORGANISM: Cucurbita maxima
<220> FEATURE:
<223> OTHER INFORMATION: ent-copalyl diphosphate synthase 2
<300> PUBLICATION INFORMATION:
<308> DATABASE ACCESSION NUMBER: Genbank AAD04293
<309> DATABASE ENTRY DATE: 1999-01-13

<400> SEQUENCE: 109

Met Ser Ser Ser Ser Leu Ser Leu Ser Arg His Cys Leu Ser Ser
1               5                   10                  15

Ser Phe Ser Phe Arg Leu Pro Asn Leu Phe Pro Pro Ala Pro Gly
            20                  25                  30

Gly Cys Ser Leu Arg Val Lys Asp Lys Gly Ala Val Leu Glu Ser Ser
        35                  40                  45

Ile Arg Cys Ile Ile Lys Cys Asn Ala Ile Ser Lys Pro Pro Thr Gln
    50                  55                  60

Asp Tyr Ser Asp Val Leu Gln Ser Gly Val Pro Leu Leu Lys Trp Gln
65                  70                  75                  80

Gln Phe Val Glu Glu Gly Ile Glu Ser Glu Thr Ala Ala Gln Val Ser
                85                  90                  95

Val Trp Glu Glu Ile Glu Glu Arg Val Lys Trp Ile Lys Ser Met Leu
            100                 105                 110

Ser Ser Met Asp Asp Gly Asp Ile Ser Ile Ser Ala Tyr Asp Thr Ala
        115                 120                 125

Trp Val Ala Leu Ile Pro Lys Val Thr Glu Glu Gly Val Lys Ser Pro
    130                 135                 140

Gln Phe Pro Ser Ser Leu Glu Trp Ile Ala Asn Asn Gln Leu Pro Asp
145                 150                 155                 160

Gly Ser Trp Gly Asp Ala Gln Ile Phe Ser Pro His Asp Arg Ile Ile
                165                 170                 175
```

```
Asn Thr Leu Ala Ser Leu Val Ala Leu Lys Ser Trp Asn Leu His Pro
            180                 185                 190

Gln Asn Thr Arg Lys Gly Val Ala Phe Phe Asn Gln Asn Ile Trp Lys
        195                 200                 205

Leu Glu Glu Glu Asn Ala Glu His Met Pro Ile Gly Phe Glu Ile Ala
    210                 215                 220

Phe Pro Ser Leu Leu Glu Phe Ala Lys Lys Leu Lys Leu Gly Ile Arg
225                 230                 235                 240

Ser Asp Ser Pro Ala Leu Gln Gln Ile Asn Ala Arg Arg Leu Lys
                245                 250                 255

Leu Ala Arg Ile Pro Lys Asp Ile Met His Lys Leu Pro Thr Thr Leu
            260                 265                 270

Leu His Ser Leu Glu Gly Met Ser Gly Leu Asp Trp Glu Lys Leu Leu
        275                 280                 285

Lys Leu Gln Ser Gln Asp Gly Ser Phe Leu Ser Ser Pro Ala Ser Thr
    290                 295                 300

Ala Phe Ala Leu Met His Thr Asn His Pro Asn Cys Phe Lys Tyr Leu
305                 310                 315                 320

Glu Ala Ser Val His Arg Phe Asn Gly Gly Val Pro Asn Val Tyr Pro
                325                 330                 335

Val Asp Leu Phe Glu His Ile Trp Ala Val Asp Arg Leu Gln Arg Leu
            340                 345                 350

Gly Ile Ser Arg Phe Phe His Pro His Ile Val Glu Cys Val Asn Asn
        355                 360                 365

Val Arg Thr His Trp Ser Glu Lys Gly Ile Cys Trp Ala Arg Asn Ser
    370                 375                 380

Glu Phe Arg Asp Ile Asp Asp Thr Ala Met Gly Phe Arg Leu Leu Arg
385                 390                 395                 400

Leu Tyr Gly His Asp Val Ser Ala Glu Val Phe Lys His Phe Glu Lys
                405                 410                 415

Asp Gly Glu Phe Val Cys Ile Ala Gly Gln Ser Thr Gln Ala Val Thr
            420                 425                 430

Gly Met Leu Asn Leu Tyr Arg Ala Ser Asp Gln Val Met Phe Pro Gly
        435                 440                 445

Glu Lys Ile Leu Glu Asp Ala Lys Gln Phe Ala Ser Lys Phe Leu Arg
    450                 455                 460

Gln Lys Gln Ala Ala Asn Gln Leu Leu Asp Lys Trp Ile Ile Ala Lys
465                 470                 475                 480

Asp Leu Pro Gly Glu Val Gly Tyr Ala Leu Asp Val Pro Trp Phe Ala
                485                 490                 495

Ser Leu Pro Arg Val Glu Thr Arg Leu Tyr Ile Gln His Tyr Gly Gly
            500                 505                 510

Lys Asn Asp Val Trp Ile Gly Lys Thr Leu Tyr Arg Met Phe Lys Val
        515                 520                 525

Asn Asn Asp Thr Tyr Leu Glu Leu Ala Lys Leu Asp Tyr Asn Asn Cys
    530                 535                 540

Gln Arg Leu His Gln Ile Glu Trp Val Asp Ile Gln Lys Trp Tyr Thr
545                 550                 555                 560

Glu Ser Lys Leu Arg Asp Tyr Gly Met Arg Arg Ser Ser Ile Leu Phe
                565                 570                 575

Ser Tyr Phe Gly Ala Val Cys Ser Ile Phe Glu Pro Glu Arg Ala Lys
            580                 585                 590
```

-continued

```
Glu Arg Leu Ala Trp Thr Lys Thr Ala Ala Leu Val His Thr Ile Ala
            595                 600                 605

Ser His Tyr Lys Asp Ala Asn Ala His Gln Arg Ala Phe Leu Gln
    610                 615                 620

Gln Phe Thr Asn Phe His Ala Ala Gln Pro Tyr Asp Asn Asn Ala Trp
625                 630                 635                 640

Arg Ser Gly Asn Met Gln Gln Lys Gly Gly Glu Gly Leu Val Gly Ile
                645                 650                 655

Leu Leu Arg Thr Leu Thr Asn Ile Ser Leu Asp Ile Leu Leu Ser His
            660                 665                 670

Gly Val Asp Ile Thr His His Leu His Gln Ala Trp Gln Lys Trp Val
    675                 680                 685

Phe Lys Trp Gln Glu Asp Gly Asp Val His Lys Glu Glu Ala Glu Leu
690                 695                 700

Leu Val Gln Thr Ile Ile Leu Asn Ser Gly Cys Ser Thr Leu Glu Asp
705                 710                 715                 720

Leu Leu Ser Asn Ser Gln Phe Gln Lys Leu Ser Asn Leu Thr Asn Lys
                725                 730                 735

Val Cys His Gln Leu Ala His Phe Lys Lys His Lys Val Asn Asn Gly
            740                 745                 750

Asn Leu Tyr Lys Glu Lys Thr Asp Asn Lys Met Pro Pro Glu Ile Glu
    755                 760                 765

Glu Asp Ile Arg Lys Leu Val Gln Leu Val Ile Gln Lys Ser Ser Asp
770                 775                 780

Gly Asn Asp Ile Asp Ser Pro Ile Lys Gln Thr Phe Leu Thr Val Ala
785                 790                 795                 800

Lys Ser Val Tyr Tyr Ala Ala Tyr Phe Asp Ala Trp Thr Ile Asn Tyr
                805                 810                 815

His Ile Ala Lys Val Leu Phe Glu Arg Val Phe
            820                 825

<210> SEQ ID NO 110
<211> LENGTH: 800
<212> TYPE: PRT
<213> ORGANISM: Lycopersicon esculentum
<220> FEATURE:
<223> OTHER INFORMATION: ent-copalyl diphosphate synthase
<300> PUBLICATION INFORMATION:
<308> DATABASE ACCESSION NUMBER: Genbank BAA84918
<309> DATABASE ENTRY DATE: 2006-10-21

<400> SEQUENCE: 110

Met Ser Ile Ser Ala Ser Phe Leu Arg Phe Ser Leu Thr Ala His Tyr
1               5                   10                  15

Gln Pro Ser Pro Ser Ser Pro Pro Asn Gln Pro Phe Lys Phe Leu
            20                  25                  30

Lys Ser Asn Arg Glu His Val Glu Phe Asn Arg Ile Leu Gln Cys His
        35                  40                  45

Ala Val Ser Arg Arg Thr Lys Asp Tyr Lys Glu Val Gln Ser Gly
    50                  55                  60

Ser Leu Pro Val Ile Lys Trp Asp Asp Ile Ala Glu Glu Val Asp Glu
65              70                  75                  80

Glu Thr His Thr Leu Glu Val Tyr Asp Pro Ser Ser Asn Glu Asp His
                85                  90                  95

Ile Asp Ala Ile Arg Ser Met Leu Gly Ser Met Gly Asp Gly Glu Ile
            100                 105                 110
```

```
Ser Val Ser Ala Tyr Asp Thr Ala Trp Val Ala Met Lys Asp Val
            115                 120                 125
Lys Gly Thr Glu Thr Pro Gln Phe Pro Ser Ser Leu Glu Trp Ile Ala
130                 135                 140
Asn Asn Gln Leu Ala Asp Gly Ser Trp Gly Asp Asn Ser Ile Phe Leu
145                 150                 155                 160
Val Tyr Asp Arg Val Ile Asn Thr Leu Ala Cys Val Ile Ala Leu Lys
                165                 170                 175
Ser Trp Asn Leu His Pro Asp Lys Ile Leu Leu Gly Met Ser Phe Met
                180                 185                 190
Arg Glu Asn Leu Ser Arg Ile Gly Asp Glu Asn Ala Glu His Met Pro
                195                 200                 205
Ile Gly Phe Glu Val Ala Phe Pro Ser Leu Ile Glu Ile Ala Lys Lys
            210                 215                 220
Leu Gly Leu Asp Phe Pro Tyr Asp Ser Pro Val Leu Gln Asp Ile Tyr
225                 230                 235                 240
Ala Ser Arg Gln Leu Lys Leu Thr Arg Ile Pro Lys Asp Ile Met His
                245                 250                 255
Lys Val Pro Thr Thr Leu Leu His Ser Leu Glu Gly Met Thr Asp Leu
            260                 265                 270
Asp Trp Gln Lys Leu Leu Gln Phe Gln Cys Thr Asp Gly Ser Phe Leu
        275                 280                 285
Phe Ser Pro Ser Ser Thr Ala Tyr Ala Leu Met Gln Thr Gln Asp His
    290                 295                 300
Asn Cys Leu Asn Tyr Leu Lys Asn Ala Val His Lys Phe Asn Gly Gly
305                 310                 315                 320
Val Pro Asn Val Tyr Pro Val Asp Leu Phe Glu His Ile Trp Thr Val
                325                 330                 335
Asp Arg Leu Gln Arg Leu Gly Ile Ser Arg Tyr Phe Glu Leu Lys Ile
                340                 345                 350
Lys Lys Cys Ile Asp Tyr Phe Ser Lys Tyr Trp Thr Asn Lys Gly Ile
            355                 360                 365
Cys Trp Ala Arg Asn Ser Pro Val Gln Asp Ile Asp Asp Thr Ala Met
        370                 375                 380
Ala Phe Arg Leu Leu Arg Leu His Gly Tyr Ala Val Ser Ala Asp Val
385                 390                 395                 400
Phe Lys His Phe Glu Ser Lys Gly Glu Phe Phe Cys Phe Val Gly Gln
                405                 410                 415
Ser Asn Gln Ala Val Thr Gly Met Tyr Asn Leu Tyr Arg Ala Ser His
                420                 425                 430
Val Met Phe Ser Gly Glu Lys Ile Leu Glu Asn Ala Lys Ile Ser Thr
            435                 440                 445
Ser Asn Tyr Leu Arg Glu Lys Arg Ala Gln Asn Gln Leu Leu Asp Lys
    450                 455                 460
Trp Ile Ile Thr Lys Asp Leu Pro Gly Glu Val Gly Tyr Ala Leu Asp
465                 470                 475                 480
Val Pro Trp Tyr Ala Ser Leu Pro Arg Leu Glu Thr Arg Phe Phe Leu
                485                 490                 495
Glu His Tyr Gly Gly Glu Asp Asp Val Trp Ile Gly Lys Thr Leu Tyr
                500                 505                 510
Arg Met Pro Leu Val Asn Asn Ser Leu Tyr Leu Glu Leu Ala Lys Ser
            515                 520                 525
Asp Tyr Asn Asn Cys Gln Ala Leu His Gln Phe Glu Trp Arg Arg Ile
```

```
            530                 535                 540
Arg Lys Trp Tyr Tyr Glu Cys Gly Leu Arg Glu Phe Gly Leu Ser Glu
545                 550                 555                 560

Lys Arg Leu Leu Val Thr Tyr Leu Gly Ser Ala Ser Ile Phe Glu
                565                 570                 575

Ala Gln Arg Ser Thr Glu Arg Met Ala Trp Val Lys Thr Ala Ala Leu
                580                 585                 590

Met Asp Cys Val Arg Ser Cys Phe Gly Ser Pro Gln Val Ser Ala Ala
            595                 600                 605

Ala Phe Leu Cys Glu Phe Ala His Tyr Ser Ser Thr Ala Leu Asn Ser
        610                 615                 620

Arg Tyr Asn Thr Glu Asp Arg Leu Val Gly Val Ile Leu Gly Thr Leu
625                 630                 635                 640

Asn His Leu Ser Leu Ser Ala Leu Leu Thr His Gly Arg Asp Ile His
                645                 650                 655

His Tyr Leu Arg His Ala Trp Glu Asn Trp Leu Leu Thr Val Gly Glu
                660                 665                 670

Gly Glu Gly Glu Gly Glu Gly Ala Glu Leu Ile Ile Arg Thr Leu
            675                 680                 685

Asn Leu Cys Ser Val His Trp Ile Ser Glu Ile Leu Leu Ser His
        690                 695                 700

Pro Thr Tyr Gln Lys Leu Leu Glu Ile Thr Asn Arg Val Ser His Arg
705                 710                 715                 720

Leu Arg Leu Tyr Lys Gly His Ser Glu Lys Gln Val Gly Met Leu Thr
                725                 730                 735

Phe Ser Glu Glu Ile Glu Gly Asp Met Gln Gln Leu Ala Glu Leu Val
                740                 745                 750

Leu Ser His Ser Asp Ala Ser Glu Leu Asp Ala Asn Ile Lys Asp Thr
            755                 760                 765

Phe Leu Thr Val Ala Lys Ser Phe Tyr Tyr Ser Ala Tyr Cys Asp Asp
        770                 775                 780

Arg Thr Ile Asn Phe His Ile Ala Lys Val Leu Phe Glu Arg Val Val
785                 790                 795                 800

<210> SEQ ID NO 111
<211> LENGTH: 787
<212> TYPE: PRT
<213> ORGANISM: Stevia rebaudiana
<220> FEATURE:
<223> OTHER INFORMATION: ent-copalyl pyrophosphate synthase
<300> PUBLICATION INFORMATION:
<308> DATABASE ACCESSION NUMBER: Genbank AAB87091
<309> DATABASE ENTRY DATE: 2000-03-22

<400> SEQUENCE: 111

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
                20                  25                  30

Ser Thr Gly Ile Val Ala Leu Arg Asp Ile Asn Phe Arg Cys Lys Ala
            35                  40                  45

Val Ser Lys Glu Tyr Ser Asp Leu Leu Gln Lys Asp Glu Ala Ser Phe
        50                  55                  60

Thr Lys Trp Asp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
```

-continued

```
                85                  90                  95
Ala Met Phe Gly Ser Met Asn Asp Gly Glu Ile Asn Val Ser Ala Tyr
            100                 105                 110
Asp Thr Ala Trp Val Ala Leu Val Gln Asp Val Asp Gly Ser Gly Ser
            115                 120                 125
Pro Gln Phe Pro Ser Ser Leu Glu Trp Ile Ala Asn Asn Gln Leu Ser
            130                 135                 140
Asp Gly Ser Trp Gly Asp His Leu Leu Phe Ser Ala His Asp Arg Ile
145                 150                 155                 160
Ile Asn Thr Leu Ala Cys Val Ile Ala Leu Thr Ser Trp Asn Val His
                165                 170                 175
Pro Ser Lys Cys Glu Lys Gly Leu Asn Phe Leu Arg Glu Asn Ile Cys
                180                 185                 190
Lys Leu Glu Asp Glu Asn Ala Glu His Met Pro Ile Gly Phe Glu Val
                195                 200                 205
Thr Phe Pro Ser Leu Ile Asp Ile Ala Lys Lys Leu Asn Ile Glu Val
            210                 215                 220
Pro Glu Asp Thr Pro Ala Leu Lys Glu Ile Tyr Ala Arg Arg Asp Ile
225                 230                 235                 240
Lys Leu Thr Lys Ile Pro Met Glu Val Leu His Lys Val Pro Thr Thr
                245                 250                 255
Leu Leu His Ser Leu Glu Gly Met Pro Asp Leu Glu Trp Glu Lys Leu
            260                 265                 270
Leu Lys Leu Gln Cys Lys Asp Gly Ser Phe Leu Phe Ser Pro Ser Ser
            275                 280                 285
Thr Ala Phe Ala Leu Met Gln Thr Lys Asp Glu Lys Cys Leu Gln Tyr
            290                 295                 300
Leu Thr Asn Ile Val Thr Lys Phe Asn Gly Gly Val Pro Asn Val Tyr
305                 310                 315                 320
Pro Val Asp Leu Phe Glu His Ile Trp Val Val Asp Arg Leu Gln Arg
                325                 330                 335
Leu Gly Ile Ala Arg Tyr Phe Lys Ser Glu Ile Lys Asp Cys Val Glu
                340                 345                 350
Tyr Ile Asn Lys Tyr Trp Thr Lys Asn Gly Ile Cys Trp Ala Arg Asn
                355                 360                 365
Thr His Val Gln Asp Ile Asp Asp Thr Ala Met Gly Phe Arg Val Leu
            370                 375                 380
Arg Ala His Gly Tyr Asp Val Thr Pro Asp Val Phe Arg Gln Phe Glu
385                 390                 395                 400
Lys Asp Gly Lys Phe Val Cys Phe Ala Gly Gln Ser Thr Gln Ala Val
                405                 410                 415
Thr Gly Met Phe Asn Val Tyr Arg Ala Ser Gln Met Leu Phe Pro Gly
                420                 425                 430
Glu Arg Ile Leu Glu Asp Ala Lys Lys Phe Ser Tyr Asn Tyr Leu Lys
                435                 440                 445
Glu Lys Gln Ser Thr Asn Glu Leu Leu Asp Lys Trp Ile Ile Ala Lys
            450                 455                 460
Asp Leu Pro Gly Glu Val Gly Tyr Ala Leu Asp Ile Pro Trp Tyr Ala
465                 470                 475                 480
Ser Leu Pro Arg Leu Glu Thr Arg Tyr Tyr Leu Glu Gln Tyr Gly Gly
                485                 490                 495
Glu Asp Asp Val Trp Ile Gly Lys Thr Leu Tyr Arg Met Gly Tyr Val
                500                 505                 510
```

```
Ser Asn Asn Thr Tyr Leu Glu Met Ala Lys Leu Asp Tyr Asn Asn Tyr
        515                 520                 525

Val Ala Val Leu Gln Leu Glu Trp Tyr Thr Ile Gln Gln Trp Tyr Val
        530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ala Ser Ile Phe Glu Pro Arg Ser
                565                 570                 575

Lys Glu Arg Ile Ala Trp Ala Lys Thr Thr Ile Leu Val Asp Lys Ile
                580                 585                 590

Thr Ser Ile Phe Asp Ser Ser Gln Ser Ser Lys Glu Asp Ile Thr Ala
            595                 600                 605

Phe Ile Asp Lys Phe Arg Asn Lys Ser Ser Lys Lys His Ser Ile
        610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
                660                 665                 670

Gly Val Asp Val Thr Ala Glu Leu Met Val Gln Met Ile Asn Met Thr
            675                 680                 685

Ala Gly Arg Trp Val Ser Lys Glu Leu Leu Thr His Pro Gln Tyr Gln
        690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                725                 730                 735

Leu Val Gln Leu Val Phe Ser Asp Thr Pro Asp Asp Leu Asp Gln Asp
                740                 745                 750

Met Lys Gln Thr Phe Leu Thr Val Met Lys Thr Phe Tyr Tyr Lys Ala
            755                 760                 765

Trp Cys Asp Pro Asn Thr Ile Asn Asp His Ile Ser Lys Val Phe Glu
        770                 775                 780

Ile Val Ile
785

<210> SEQ ID NO 112
<211> LENGTH: 793
<212> TYPE: PRT
<213> ORGANISM: Salvia miltiorrhiza
<220> FEATURE:
<223> OTHER INFORMATION: copalyl diphosphate synthase
<300> PUBLICATION INFORMATION:
<308> DATABASE ACCESSION NUMBER: Genbank ABV57835
<309> DATABASE ENTRY DATE: 2010-12-03

<400> SEQUENCE: 112

Met Ala Ser Leu Ser Ser Thr Ile Leu Ser Arg Ser Pro Ala Ala Arg
 1               5                   10                  15

Arg Arg Ile Thr Pro Ala Ser Ala Lys Leu His Arg Pro Glu Cys Phe
                20                  25                  30

Ala Thr Ser Ala Trp Met Gly Ser Ser Lys Asn Leu Ser Leu Ser
            35                  40                  45

Tyr Gln Leu Asn His Lys Lys Ile Ser Val Ala Thr Val Asp Ala Pro
        50                  55                  60
```

```
Gln Val His Asp His Asp Gly Thr Thr Val His Gln Gly His Asp Ala
 65                  70                  75                  80

Val Lys Asn Ile Glu Asp Pro Ile Glu Tyr Ile Arg Thr Leu Leu Arg
             85                  90                  95

Thr Thr Gly Asp Gly Arg Ile Ser Val Ser Pro Tyr Asp Thr Ala Trp
            100                 105                 110

Val Ala Met Ile Lys Asp Val Glu Gly Arg Asp Gly Pro Gln Phe Pro
            115                 120                 125

Ser Ser Leu Glu Trp Ile Val Gln Asn Gln Leu Glu Asp Gly Ser Trp
            130                 135                 140

Gly Asp Gln Lys Leu Phe Cys Val Tyr Asp Arg Leu Val Asn Thr Ile
145                 150                 155                 160

Ala Cys Val Val Ala Leu Arg Ser Trp Asn Val His Ala His Lys Val
                165                 170                 175

Lys Arg Gly Val Thr Tyr Ile Lys Glu Asn Val Asp Lys Leu Met Glu
            180                 185                 190

Gly Asn Glu Glu His Met Thr Cys Gly Phe Glu Val Val Phe Pro Ala
            195                 200                 205

Leu Leu Gln Lys Ala Lys Ser Leu Gly Ile Glu Asp Leu Pro Tyr Asp
            210                 215                 220

Ser Pro Ala Val Gln Glu Val Tyr His Val Arg Glu Gln Lys Leu Lys
225                 230                 235                 240

Arg Ile Pro Leu Glu Ile Met His Lys Ile Pro Thr Ser Leu Leu Phe
                245                 250                 255

Ser Leu Glu Gly Leu Glu Asn Leu Asp Trp Asp Lys Leu Leu Lys Leu
            260                 265                 270

Gln Ser Ala Asp Gly Ser Phe Leu Thr Ser Pro Ser Ser Thr Ala Phe
            275                 280                 285

Ala Phe Met Gln Thr Lys Asp Glu Lys Cys Tyr Gln Phe Ile Lys Asn
            290                 295                 300

Thr Ile Asp Thr Phe Asn Gly Gly Ala Pro His Thr Tyr Pro Val Asp
305                 310                 315                 320

Val Phe Gly Arg Leu Trp Ala Ile Asp Arg Leu Gln Arg Leu Gly Ile
                325                 330                 335

Ser Arg Phe Phe Glu Pro Glu Ile Ala Asp Cys Leu Ser His Ile His
            340                 345                 350

Lys Phe Trp Thr Asp Lys Gly Val Phe Ser Gly Arg Glu Ser Glu Phe
            355                 360                 365

Cys Asp Ile Asp Asp Thr Ser Met Gly Met Arg Leu Met Arg Met His
            370                 375                 380

Gly Tyr Asp Val Asp Pro Asn Val Leu Arg Asn Phe Lys Gln Lys Asp
385                 390                 395                 400

Gly Lys Phe Ser Cys Tyr Gly Gly Gln Met Ile Glu Ser Pro Ser Pro
            405                 410                 415

Ile Tyr Asn Leu Tyr Arg Ala Ser Gln Leu Arg Phe Pro Gly Glu Glu
            420                 425                 430

Ile Leu Glu Asp Ala Lys Arg Phe Ala Tyr Asp Phe Leu Lys Glu Lys
            435                 440                 445

Leu Ala Asn Asn Gln Ile Leu Asp Lys Trp Val Ile Ser Lys His Leu
            450                 455                 460

Pro Asp Glu Ile Lys Leu Gly Leu Glu Met Pro Trp Leu Ala Thr Leu
465                 470                 475                 480
```

Pro Arg Val Glu Ala Lys Tyr Tyr Ile Gln Tyr Tyr Ala Gly Ser Gly
             485                 490                 495

Asp Val Trp Ile Gly Lys Thr Leu Tyr Arg Met Pro Glu Ile Ser Asn
            500                 505                 510

Asp Thr Tyr His Asp Leu Ala Lys Thr Asp Phe Lys Arg Cys Gln Ala
        515                 520                 525

Lys His Gln Phe Glu Trp Leu Tyr Met Gln Glu Trp Tyr Glu Ser Cys
    530                 535                 540

Gly Ile Glu Glu Phe Gly Ile Ser Arg Lys Asp Leu Leu Leu Ser Tyr
545                 550                 555                 560

Phe Leu Ala Thr Ala Ser Ile Phe Glu Leu Glu Arg Thr Asn Glu Arg
                565                 570                 575

Ile Ala Trp Ala Lys Ser Gln Ile Ile Ala Lys Met Ile Thr Ser Phe
            580                 585                 590

Phe Asn Lys Glu Thr Thr Ser Glu Glu Asp Lys Arg Ala Leu Leu Asn
        595                 600                 605

Glu Leu Gly Asn Ile Asn Gly Leu Asn Asp Thr Asn Gly Ala Gly Arg
    610                 615                 620

Glu Gly Gly Ala Gly Ser Ile Ala Leu Ala Thr Leu Thr Gln Phe Leu
625                 630                 635                 640

Glu Gly Phe Asp Arg Tyr Thr Arg His Gln Leu Lys Asn Ala Trp Ser
                645                 650                 655

Val Trp Leu Thr Gln Leu Gln His Gly Glu Ala Asp Asp Ala Glu Leu
            660                 665                 670

Leu Thr Asn Thr Leu Asn Ile Cys Ala Gly His Ile Ala Phe Arg Glu
        675                 680                 685

Glu Ile Leu Ala His Asn Glu Tyr Lys Ala Leu Ser Asn Leu Thr Ser
    690                 695                 700

Lys Ile Cys Arg Gln Leu Ser Phe Ile Gln Ser Glu Lys Glu Met Gly
705                 710                 715                 720

Val Glu Gly Glu Ile Ala Ala Lys Ser Ser Ile Lys Asn Lys Glu Leu
                725                 730                 735

Glu Glu Asp Met Gln Met Leu Val Lys Leu Val Leu Glu Lys Tyr Gly
            740                 745                 750

Gly Ile Asp Arg Asn Ile Lys Lys Ala Phe Leu Ala Val Ala Lys Thr
        755                 760                 765

Tyr Tyr Tyr Arg Ala Tyr His Ala Ala Asp Thr Ile Asp Thr His Met
    770                 775                 780

Phe Lys Val Leu Phe Glu Pro Val Ala
785                 790

<210> SEQ ID NO 113
<211> LENGTH: 823
<212> TYPE: PRT
<213> ORGANISM: Zea mays
<220> FEATURE:
<223> OTHER INFORMATION: ent-copalyl diphosphate synthase
<300> PUBLICATION INFORMATION:
<308> DATABASE ACCESSION NUMBER: Genbank AAA73960
<309> DATABASE ENTRY DATE: 1995-08-03

<400> SEQUENCE: 113

Met Pro Tyr Pro His Pro Tyr Pro Trp Gln Ser Ser Arg Arg Arg Arg
1               5                   10                  15

Arg Arg Arg Gly Arg Asp Gly Ala Pro Arg Gln Pro Gln Ala Arg Arg
            20                  25                  30

-continued

Val Val Glu Arg Ala Ala Ala Gly Pro Gly His Ala Thr Thr Gln
         35                  40                  45

Gln Pro Asp Asn Val Ser Ser Ala Lys Val Phe Gln Thr Ser Arg Val
 50                  55                  60

Glu Thr Glu Ser Lys Leu Arg Asn Gly Arg Lys Pro Gln Asp Leu Glu
 65                  70                  75                  80

Asp Glu His Gln Ala Glu Ala Glu Leu Gln Pro Leu Ile Asp Gln
                 85                  90                  95

Val Arg Ala Met Leu Arg Ser Met Asn Asp Gly Asp Thr Ser Ala Ser
                100                 105                 110

Ala Tyr Asp Thr Ala Trp Val Ala Met Val Pro Lys Val Gly Gly Asp
                115                 120                 125

Gly Gly Ala Gln Pro Gln Phe Pro Ala Thr Val Arg Trp Ile Val Asp
    130                 135                 140

His Gln Leu Pro Asp Gly Ser Trp Gly Asp Ser Ala Leu Phe Ser Ala
145                 150                 155                 160

Tyr Asp Arg Met Ile Asn Thr Leu Ala Cys Val Val Ala Leu Thr Lys
                165                 170                 175

Trp Ser Leu Glu Pro Ala Arg Cys Glu Ala Gly Leu Ser Phe Leu His
                180                 185                 190

Glu Asn Met Trp Arg Leu Ala Glu Glu Glu Ala Glu Ser Met Pro Ile
                195                 200                 205

Gly Phe Glu Ile Ala Phe Pro Ser Leu Ile Gln Thr Ala Arg Asp Leu
    210                 215                 220

Gly Val Val Asp Phe Pro Tyr Gly His Pro Ala Leu Gln Ser Ile Tyr
225                 230                 235                 240

Ala Asn Arg Glu Val Lys Leu Lys Arg Ile Pro Arg Asp Met Met His
                245                 250                 255

Arg Val Pro Thr Ser Ile Leu His Ser Leu Glu Gly Met Pro Asp Leu
                260                 265                 270

Asp Trp Pro Arg Leu Leu Asn Leu Gln Ser Cys Asp Gly Ser Phe Leu
                275                 280                 285

Phe Ser Pro Ser Ala Thr Ala Tyr Ala Leu Met Gln Thr Gly Asp Lys
    290                 295                 300

Lys Cys Phe Glu Tyr Ile Asp Arg Ile Val Lys Lys Phe Asn Gly Gly
305                 310                 315                 320

Val Pro Asn Val Tyr Pro Val Asp Leu Phe Glu His Ile Trp Val Val
                325                 330                 335

Asp Arg Leu Glu Arg Leu Gly Ile Ser Arg Tyr Phe Gln Arg Glu Ile
                340                 345                 350

Glu Gln Cys Met Asp Tyr Val Asn Arg His Trp Thr Glu Asp Gly Ile
                355                 360                 365

Cys Trp Ala Arg Lys Ser Asn Val Lys Asp Val Asp Asp Thr Ala Met
    370                 375                 380

Ala Phe Arg Leu Leu Arg Leu His Gly Tyr Asn Val Ser Pro Ser Val
385                 390                 395                 400

Phe Lys Asn Phe Glu Lys Asp Gly Glu Phe Phe Cys Phe Val Gly Gln
                405                 410                 415

Ser Thr Gln Ala Val Thr Gly Met Tyr Asn Leu Asn Arg Ala Ser Gln
                420                 425                 430

Ile Ser Phe Gln Gly Glu Asp Val Leu His Arg Ala Arg Val Phe Ser
                435                 440                 445

Tyr Glu Phe Leu Arg Gln Arg Glu Glu Gln Gly Met Ile Arg Asp Lys

```
                450              455              460
Trp Ile Val Ala Lys Asp Leu Pro Gly Glu Val Gln Tyr Thr Leu Asp
465                 470                 475                 480

Phe Pro Trp Tyr Ala Ser Leu Pro Arg Val Glu Ala Arg Thr Tyr Leu
                485                 490                 495

Asp Gln Tyr Gly Gly Lys Asp Val Trp Ile Gly Lys Thr Leu Tyr
            500                 505                 510

Arg Met Pro Leu Val Asn Asn Asp Thr Tyr Leu Glu Leu Ala Ile Arg
            515                 520                 525

Asp Phe Asn His Cys Gln Ala Leu His Gln Leu Glu Cys Asn Gly Leu
530                 535                 540

Gln Thr Trp Tyr Lys Asp Asn Cys Leu Asp Ala Phe Gly Val Glu Pro
545                 550                 555                 560

Gln Asp Val Leu Arg Ser Tyr Phe Leu Ala Ala Cys Ile Phe Glu
                565                 570                 575

Pro Ser Arg Ala Ala Glu Arg Leu Ala Trp Ala Arg Thr Ser Met Ile
            580                 585                 590

Ala Asn Ala Ile Ser Thr His Leu Arg Asp Ile Ser Glu Asp Lys Lys
            595                 600                 605

Arg Leu Glu Cys Phe Val His Cys Leu Tyr Glu Glu Asn Asp Val Ser
610                 615                 620

Trp Leu Lys Arg Asn Pro Asn Asp Val Ile Leu Glu Arg Ala Leu Arg
625                 630                 635                 640

Arg Leu Ile Asn Leu Leu Ala Gln Glu Ala Leu Pro Ile His Glu Gly
                645                 650                 655

Gln Arg Phe Ile His Ser Leu Leu Ser Leu Ala Trp Thr Glu Trp Met
                660                 665                 670

Leu Gln Lys Ala Asn Lys Glu Gln Asn Lys Tyr His Lys Cys Ser Gly
            675                 680                 685

Ile Glu Pro Gln Tyr Met Val His Asp Arg Gln Thr Tyr Leu Leu Leu
            690                 695                 700

Val Gln Val Ile Glu Ile Cys Ala Gly Arg Ile Gly Glu Ala Val Ser
705                 710                 715                 720

Met Ile Asn Asn Lys Asp Asn Asp Trp Phe Ile Gln Leu Thr Cys Ala
                725                 730                 735

Thr Cys Asp Ser Leu Asn His Arg Met Leu Leu Ser Gln Asp Thr Met
            740                 745                 750

Lys Asn Glu Ala Arg Ile Asn Trp Ile Glu Lys Glu Ile Glu Leu Asn
            755                 760                 765

Met Gln Glu Leu Ala Gln Ser Leu Leu Leu Arg Cys Asp Glu Lys Thr
770                 775                 780

Ser Asn Lys Lys Thr Lys Lys Thr Leu Trp Asp Val Leu Arg Ser Leu
785                 790                 795                 800

Tyr Tyr Ala Thr His Ser Pro Gln His Met Ile Asp Arg His Val Ser
                805                 810                 815

Arg Val Ile Phe Glu Pro Val
            820

<210> SEQ ID NO 114
<211> LENGTH: 827
<212> TYPE: PRT
<213> ORGANISM: Zea mays
<220> FEATURE:
<223> OTHER INFORMATION: ent-copalyl diphosphate synthase
<300> PUBLICATION INFORMATION:
```

-continued

<308> DATABASE ACCESSION NUMBER: Genbank NP_001105257
<309> DATABASE ENTRY DATE: 2004-10-11

<400> SEQUENCE: 114

```
Met Val Leu Ser Ser Cys Thr Thr Val Pro His Leu Ser Ser Leu
  1               5                  10                  15

Ala Val Val Gln Leu Gly Pro Trp Ser Ser Arg Ile Lys Lys Lys Thr
                 20                  25                  30

Asp Thr Val Ala Val Pro Ala Ala Gly Arg Trp Arg Arg Ala Leu
             35                  40                  45

Ala Arg Ala Gln His Thr Ser Glu Ser Ala Ala Val Ala Lys Gly Ser
 50                  55                  60

Ser Leu Thr Pro Ile Val Arg Thr Asp Ala Glu Ser Arg Arg Thr Arg
 65                  70                  75                  80

Trp Pro Thr Asp Asp Asp Ala Glu Pro Leu Val Asp Glu Ile Arg
                 85                  90                  95

Ala Met Leu Thr Ser Met Ser Asp Gly Asp Ile Ser Val Ser Ala Tyr
                100                 105                 110

Asp Thr Ala Trp Val Gly Leu Val Pro Arg Leu Asp Gly Gly Glu Gly
             115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
                180                 185                 190

Lys Leu Ala Thr Glu Asp Glu Ser Met Pro Ile Gly Phe Glu Leu
                195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
                260                 265                 270

Leu Leu Lys Leu Gln Ser Ser Asp Gly Ser Phe Leu Phe Ser Pro Ala
            275                 280                 285

Ala Thr Ala Tyr Ala Leu Met Asn Thr Gly Asp Asp Arg Cys Phe Ser
    290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

Arg Leu Gly Ile Ser Arg Tyr Phe Gln Lys Glu Ile Glu Gln Cys Met
            340                 345                 350

Asp Tyr Val Asn Arg His Trp Thr Glu Asp Gly Ile Cys Trp Ala Arg
    355                 360                 365

Asn Ser Asp Val Lys Glu Val Asp Asp Thr Ala Met Ala Phe Arg Leu
370                 375                 380

Leu Arg Leu His Gly Tyr Ser Val Ser Pro Asp Val Phe Lys Asn Phe
385                 390                 395                 400
```

```
Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
            435                 440                 445

Arg Arg Lys Glu Ala Glu Gly Ala Leu Arg Asp Lys Trp Ile Ile Ser
450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
            515                 520                 525

Cys Gln Ala Leu His Gln Leu Glu Trp Gln Gly Leu Lys Arg Trp Tyr
            530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ala Ser Val Tyr Glu Pro Cys Arg Ala
                565                 570                 575

Ala Glu Arg Leu Ala Trp Ala Arg Ala Ala Ile Leu Ala Asn Ala Val
            580                 585                 590

Ser Thr His Leu Arg Asn Ser Pro Ser Phe Arg Glu Arg Leu Glu His
            595                 600                 605

Ser Leu Arg Cys Arg Pro Ser Glu Glu Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
            675                 680                 685

Val Glu Gln Glu Gly Ser Arg Met Val His Asp Lys Gln Thr Cys Leu
            690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
            755                 760                 765

Ile Arg Glu Phe Val Gln Tyr Leu Leu Arg Leu Gly Glu Lys Lys Thr
770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815
```

Arg Val Ile Phe Glu Pro Val Ser Ala Ala Lys
            820                 825

<210> SEQ ID NO 115
<211> LENGTH: 867
<212> TYPE: PRT
<213> ORGANISM: Oryza sativa
<220> FEATURE:
<223> OTHER INFORMATION: ent-copalyl diphosphate synthase
<300> PUBLICATION INFORMATION:
<308> DATABASE ACCESSION NUMBER: Genbank Q6ET36
<309> DATABASE ENTRY DATE: 2004-08-16

<400> SEQUENCE: 115

Met Ile His Leu His Ser Pro Pro Thr Ala Pro Ala Ala Phe Gly Gly
 1               5                  10                  15

Ala Gly Ser Ala Asp Trp Arg Arg Arg Arg Trp Ser Trp Ser Ser
            20                  25                  30

Ser Ser Arg Ala Pro Val Ala Lys Gly Gly His Leu Arg Pro Cys Val
            35                  40                  45

Trp Arg Arg Gly Gly Asp Gly Gly Gly Glu Asp His His Ala Asp
        50                  55                  60

Gly Gly Gly Gly Gly Gly Ala Ala Trp Arg Ala Arg Ala Thr
65                  70                  75                  80

Thr Ala Gly Val Ser Ser Ser Ser Thr Ala Lys Gly Leu Gln Ala
                85                  90                  95

Asn Ile Ile Glu His Glu Thr Pro Arg Ile Thr Lys Trp Pro Asn Glu
            100                 105                 110

Ser Arg Asp Leu Asp Asp His Gln Gln Asn Asn Glu Ala Asp Glu Glu
            115                 120                 125

Ala Asp Asp Glu Leu Gln Pro Leu Val Glu Gln Val Arg Ser Met Leu
        130                 135                 140

Ser Ser Met Glu Asp Gly Ala Ile Thr Ala Ser Ala Tyr Asp Thr Ala
145                 150                 155                 160

Trp Val Ala Leu Val Pro Arg Leu Asp Gly Glu Gly Gly Thr Gln Phe
                165                 170                 175

Pro Ala Ala Val Arg Trp Ile Val Gly Ser Gln Leu Ala Asp Gly Ser
            180                 185                 190

Trp Gly Asp Glu Ala Leu Phe Ser Ala Tyr Asp Arg Val Ile Asn Thr
        195                 200                 205

Leu Ala Cys Val Val Ala Leu Thr Arg Trp Ser Leu His His Asp Gln
    210                 215                 220

Cys Lys Gln Gly Leu Gln Phe Leu Asn Leu Asn Leu Trp Arg Leu Ala
225                 230                 235                 240

Glu Glu Glu Pro Asp Thr Met Pro Ile Gly Phe Glu Ile Ala Phe Pro
                245                 250                 255

Ser Leu Val Glu Ala Ala Arg Gly Leu Gly Ile Asp Phe Pro Tyr Asp
            260                 265                 270

His Pro Ala Leu Lys Gly Ile Tyr Ala Asn Arg Glu Leu Lys Leu Lys
        275                 280                 285

Arg Ile Pro Lys Asp Met Met His Ile Val Pro Thr Ser Ile Leu His
    290                 295                 300

Ser Leu Glu Gly Met Pro Gly Leu Asp Trp Gln Arg Leu Leu Lys Leu
305                 310                 315                 320

Gln Cys Ser Asp Gly Ser Phe Leu Phe Ser Pro Ser Ala Thr Ala Tyr
                325                 330                 335

```
Ala Leu Met Gln Thr Gly Asp Lys Lys Cys Phe Ala Tyr Ile Asp Arg
            340                 345                 350

Ile Ile Lys Lys Phe Asp Gly Val Pro Asn Val Tyr Pro Val Asp
        355                 360                 365

Leu Phe Glu His Ile Trp Val Val Asp Arg Leu Glu Arg Leu Gly Ile
    370                 375                 380

Ser Arg Tyr Phe Gln Arg Glu Ile Glu Gln Asn Met Asp Tyr Val Asn
385                 390                 395                 400

Arg His Trp Thr Glu Asp Gly Ile Cys Trp Ala Arg Asn Ser Asn Val
                405                 410                 415

Lys Glu Val Asp Asp Thr Ala Met Ala Phe Arg Leu Leu Arg Leu His
            420                 425                 430

Gly Tyr Asn Val Ser Pro Ser Val Phe Lys Asn Phe Glu Lys Asp Gly
        435                 440                 445

Glu Phe Phe Cys Phe Val Gly Gln Ser Thr Gln Ala Val Thr Gly Met
    450                 455                 460

Tyr Asn Leu Asn Arg Ala Ser Gln Ile Ser Phe Pro Gly Glu Asp Ile
465                 470                 475                 480

Leu Gln Arg Ala Arg Asn Phe Ser Tyr Glu Phe Leu Arg Glu Arg Glu
                485                 490                 495

Ala Gln Gly Thr Leu His Asp Lys Trp Ile Ile Ser Lys Asp Leu Pro
            500                 505                 510

Gly Glu Val Gln Tyr Thr Leu Asp Phe Pro Trp Tyr Ala Ser Leu Pro
        515                 520                 525

Arg Val Glu Ala Arg Thr Tyr Ile Gly Gln Tyr Gly Gly Asn Asp Asp
530                 535                 540

Val Trp Ile Gly Lys Thr Leu Tyr Arg Met Pro Ile Val Asn Asn Ala
545                 550                 555                 560

Thr Tyr Leu Glu Leu Ala Lys Gln Asp Phe Asn Arg Cys Gln Ala Leu
                565                 570                 575

His Gln His Glu Leu Gln Gly Leu Gln Lys Trp Phe Ile Glu Asn Gly
            580                 585                 590

Leu Glu Ala Phe Gly Met Thr Pro Glu Asp Val Leu Arg Ala Tyr Phe
        595                 600                 605

Leu Ala Ala Ala Cys Ile Phe Glu Pro Asn Arg Ala Ser Glu Arg Leu
    610                 615                 620

Ala Trp Ala Arg Val Ser Val Leu Ala Asn Thr Ile Ser Arg His Phe
625                 630                 635                 640

Tyr Ser Asp Met Ser Ser Met Lys Arg Met Glu Arg Phe Met Trp Ser
                645                 650                 655

Ser Leu Tyr Glu Glu Asn Gly Asn Val Leu Gly Leu Glu Gly Tyr Ala
            660                 665                 670

Lys Asp Gly Ile Leu Ala Arg Thr Leu Cys Gln Leu Ile Asp Leu Leu
        675                 680                 685

Ser Gln Glu Thr Pro Pro Val Arg Glu Gly Gln Lys Cys Ile His Asn
    690                 695                 700

Leu Ile Arg Cys Ala Trp Ile Glu Trp Met Met Gln Gln Ile Asn Met
705                 710                 715                 720

Lys Asp Gly Arg Tyr Asp Lys Gly Arg Val Met His Pro Gly Ser Cys
                725                 730                 735

Thr Val His Asn Lys Glu Thr Cys Leu Leu Ile Ala Gln Ile Val Glu
            740                 745                 750

Ile Cys Ala Gly Arg Ile Glu Glu Ala Ala Ser Met Ile Asn Asn Thr
```

```
                755                 760                 765
Glu Gly Ser Trp Phe Ile Gln Leu Ala Ser Ser Ile Cys Asp Ser Leu
770                 775                 780

His Ala Lys Met Leu Leu Ser Gln Asp Thr Lys Lys Asn Glu Thr Thr
785                 790                 795                 800

Ile Asn Gln Ile Asp Lys Glu Ile Glu Leu Gly Met Gln Glu Leu Ala
                805                 810                 815

Gln Tyr Leu Leu Pro Arg Val Asp Asp Arg Ile Asn Asn Lys Thr
                820                 825                 830

Lys Gln Thr Phe Leu Ser Ile Val Lys Ser Cys Tyr Tyr Ala Ala Asn
                835                 840                 845

Cys Ser Pro His Met Leu Asp Gln His Ile Ser Glu Val Ile Phe Glu
850                 855                 860

Gln Val Ile
865

<210> SEQ ID NO 116
<211> LENGTH: 800
<212> TYPE: PRT
<213> ORGANISM: Oryza sativa
<220> FEATURE:
<223> OTHER INFORMATION: ent-copalyl diphosphate synthase
<300> PUBLICATION INFORMATION:
<308> DATABASE ACCESSION NUMBER: Genbank Q6Z5I0
<309> DATABASE ENTRY DATE: 2004-07-05

<400> SEQUENCE: 116

Met Gln Met Gln Val Leu Thr Ala Ala Ser Ser Leu Pro Arg Ala Thr
1               5                   10                  15

Leu Leu Arg Pro Ala Ala Ala Glu Pro Trp Arg Gln Ser Phe Leu Gln
                20                  25                  30

Leu Gln Ala Arg Pro Ile Gln Arg Pro Gly Ile Met Leu His Cys Lys
            35                  40                  45

Ala Gln Leu Gln Gly Gln Glu Thr Arg Glu Arg Gln Leu Asp Asp
    50                  55                  60

Asp Glu His Ala Arg Pro Pro Gln Gly Gly Asp Asp Val Ala Ala
65                  70                  75                  80

Ser Thr Ser Glu Leu Pro Tyr Met Ile Glu Ser Ile Lys Ser Lys Leu
                85                  90                  95

Arg Ala Ala Arg Asn Ser Leu Gly Glu Thr Thr Val Ser Ala Tyr Asp
                100                 105                 110

Thr Ala Trp Ile Ala Leu Val Asn Arg Leu Asp Gly Gly Gly Glu Arg
            115                 120                 125

Ser Pro Gln Phe Pro Glu Ala Ile Asp Trp Ile Ala Arg Asn Gln Leu
    130                 135                 140

Pro Asp Gly Ser Trp Gly Asp Ala Gly Met Phe Ile Val Gln Asp Arg
145                 150                 155                 160

Leu Ile Asn Thr Leu Gly Cys Val Val Ala Leu Ala Thr Trp Gly Val
                165                 170                 175

His Glu Glu Gln Arg Ala Arg Gly Leu Ala Tyr Ile Gln Asp Asn Leu
                180                 185                 190

Trp Arg Leu Gly Glu Asp Asp Glu Glu Trp Met Met Val Gly Phe Glu
            195                 200                 205

Ile Thr Phe Pro Val Leu Leu Glu Lys Ala Lys Asn Leu Gly Leu Asp
    210                 215                 220

Ile Asn Tyr Asp Asp Pro Ala Leu Gln Asp Ile Tyr Ala Lys Arg Gln
```

```
            225                 230                 235                 240
Leu Lys Leu Ala Lys Ile Pro Arg Glu Ala Leu His Ala Arg Pro Thr
            245                 250                 255

Thr Leu Leu His Ser Leu Glu Gly Met Glu Asn Leu Asp Trp Glu Arg
            260                 265                 270

Leu Leu Gln Phe Lys Cys Pro Ala Gly Ser Leu His Ser Ser Pro Ala
            275                 280                 285

Ala Ser Ala Tyr Ala Leu Ser Glu Thr Gly Asp Lys Glu Leu Leu Glu
            290                 295                 300

Tyr Leu Glu Thr Ala Ile Asn Asn Phe Asp Gly Gly Ala Pro Cys Thr
305                 310                 315                 320

Tyr Pro Val Asp Asn Phe Asp Arg Leu Trp Ser Val Asp Arg Leu Arg
            325                 330                 335

Arg Leu Gly Ile Ser Arg Tyr Phe Thr Ser Glu Ile Glu Glu Tyr Leu
            340                 345                 350

Glu Tyr Ala Tyr Arg His Leu Ser Pro Asp Gly Met Ser Tyr Gly Gly
            355                 360                 365

Leu Cys Pro Val Lys Asp Ile Asp Asp Thr Ala Met Ala Phe Arg Leu
370                 375                 380

Leu Arg Leu His Gly Tyr Asn Val Ser Ser Val Phe Asn His Phe
385                 390                 395                 400

Glu Lys Asp Gly Glu Tyr Phe Cys Phe Ala Gly Gln Ser Ser Gln Ser
            405                 410                 415

Leu Thr Ala Met Tyr Asn Ser Tyr Arg Ala Ser Gln Ile Val Phe Pro
            420                 425                 430

Gly Asp Asp Gly Leu Glu Gln Leu Arg Ala Tyr Cys Arg Ala Phe
            435                 440                 445

Leu Glu Glu Arg Arg Ala Thr Gly Asn Leu Met Asp Lys Trp Val Ile
450                 455                 460

Ala Asn Gly Leu Pro Ser Glu Val Glu Tyr Ala Leu Asp Phe Pro Trp
465                 470                 475                 480

Lys Ala Ser Leu Pro Arg Val Glu Thr Arg Val Tyr Leu Glu Gln Tyr
            485                 490                 495

Gly Ala Ser Glu Asp Ala Trp Ile Gly Lys Gly Leu Tyr Arg Met Thr
            500                 505                 510

Leu Val Asn Asn Asp Leu Tyr Leu Glu Ala Ala Lys Ala Asp Phe Thr
            515                 520                 525

Asn Phe Gln Arg Leu Ser Arg Leu Glu Trp Leu Ser Leu Lys Arg Trp
            530                 535                 540

Tyr Ile Arg Asn Asn Leu Gln Ala His Gly Val Thr Glu Gln Ser Val
545                 550                 555                 560

Leu Arg Ala Tyr Phe Leu Ala Ala Ala Asn Ile Phe Glu Pro Asn Arg
            565                 570                 575

Ala Ala Glu Arg Leu Gly Trp Ala Arg Thr Ala Ile Leu Ala Glu Ala
            580                 585                 590

Ile Ala Ser His Leu Arg Gln Tyr Ser Ala Asn Gly Ala Ala Asp Gly
            595                 600                 605

Met Thr Glu Arg Leu Ile Ser Gly Leu Ala Ser His Asp Trp Asp Trp
            610                 615                 620

Arg Glu Ser Lys Asp Ser Ala Ala Arg Ser Leu Leu Tyr Ala Leu Asp
625                 630                 635                 640

Glu Leu Ile Asp Leu His Ala Phe Gly Asn Ala Ser Asp Ser Leu Arg
            645                 650                 655
```

-continued

Glu Ala Trp Lys Gln Trp Leu Met Ser Trp Thr Asn Glu Ser Gln Gly
            660                 665                 670

Ser Thr Gly Gly Asp Thr Ala Leu Leu Val Arg Thr Ile Glu Ile
        675                 680                 685

Cys Ser Gly Arg His Gly Ser Ala Glu Gln Ser Leu Lys Asn Ser Ala
        690                 695                 700

Asp Tyr Ala Arg Leu Glu Gln Ile Ala Ser Ser Met Cys Ser Lys Leu
705                 710                 715                 720

Ala Thr Lys Ile Leu Ala Gln Asn Gly Gly Ser Met Asp Asn Val Glu
            725                 730                 735

Gly Ile Asp Gln Glu Val Asp Val Glu Met Lys Glu Leu Ile Gln Arg
            740                 745                 750

Val Tyr Gly Ser Ser Ser Asn Asp Val Ser Ser Val Thr Arg Gln Thr
            755                 760                 765

Phe Leu Asp Val Val Lys Ser Phe Cys Tyr Val Ala His Cys Ser Pro
        770                 775                 780

Glu Thr Ile Asp Gly His Ile Ser Lys Val Leu Phe Glu Asp Val Asn
785                 790                 795                 800

<210> SEQ ID NO 117
<211> LENGTH: 767
<212> TYPE: PRT
<213> ORGANISM: Oryza sativa
<220> FEATURE:
<223> OTHER INFORMATION: syn-copalyl diphosphate synthase
<300> PUBLICATION INFORMATION:
<308> DATABASE ACCESSION NUMBER: Genbank Q0JF02
<309> DATABASE ENTRY DATE: 2006-10-03

<400> SEQUENCE: 117

Met Pro Val Phe Thr Ala Ser Phe Gln Cys Val Thr Leu Phe Gly Gln
1               5                   10                  15

Pro Ala Ser Ala Ala Asp Ala Gln Pro Leu Leu Gln Gly Gln Arg Pro
            20                  25                  30

Phe Leu His Leu His Ala Arg Arg Arg Pro Cys Gly Pro Met Leu
        35                  40                  45

Ile Ser Lys Ser Pro Pro Tyr Pro Ala Ser Glu Glu Thr Arg Glu Trp
    50                  55                  60

Glu Ala Asp Gly Gln His Glu His Thr Asp Glu Leu Arg Glu Thr Thr
65                  70                  75                  80

Thr Thr Met Ile Asp Gly Ile Arg Thr Ala Leu Arg Ser Ile Gly Glu
                85                  90                  95

Gly Glu Ile Ser Ile Ser Ala Tyr Asp Thr Ser Leu Val Ala Leu Leu
            100                 105                 110

Lys Arg Leu Asp Gly Gly Asp Gly Pro Gln Phe Pro Ser Thr Ile Asp
        115                 120                 125

Trp Ile Val Gln Asn Gln Leu Pro Asp Gly Ser Trp Gly Asp Ala Ser
    130                 135                 140

Phe Phe Met Met Gly Asp Arg Ile Met Ser Thr Leu Ala Cys Val Val
145                 150                 155                 160

Ala Leu Lys Ser Trp Asn Ile His Thr Asp Lys Cys Glu Arg Gly Leu
                165                 170                 175

Leu Phe Ile Gln Glu Asn Met Trp Arg Leu Ala His Glu Glu Glu Asp
            180                 185                 190

Trp Met Leu Val Gly Phe Glu Ile Ala Leu Pro Ser Leu Leu Asp Met
        195                 200                 205

```
Ala Lys Asp Leu Asp Leu Asp Ile Pro Tyr Asp Glu Pro Ala Leu Lys
    210                 215                 220
Ala Ile Tyr Ala Glu Arg Glu Arg Lys Leu Ala Lys Ile Pro Arg Asp
225                 230                 235                 240
Val Leu His Ser Met Pro Thr Thr Leu Leu His Ser Leu Glu Gly Met
                245                 250                 255
Val Asp Leu Asp Trp Glu Lys Leu Leu Lys Leu Arg Cys Leu Asp Gly
            260                 265                 270
Ser Phe His Cys Ser Pro Ala Ser Thr Ala Thr Ala Phe Gln Gln Thr
        275                 280                 285
Gly Asp Gln Lys Cys Phe Glu Tyr Leu Asp Gly Ile Val Lys Lys Phe
290                 295                 300
Asn Gly Gly Val Pro Cys Ile Tyr Pro Leu Asp Val Tyr Glu Arg Leu
305                 310                 315                 320
Trp Ala Val Asp Arg Leu Thr Arg Leu Gly Ile Ser Arg His Phe Thr
                325                 330                 335
Ser Glu Ile Glu Asp Cys Leu Asp Tyr Ile Phe Arg Asn Trp Thr Pro
            340                 345                 350
Asp Gly Leu Ala His Thr Lys Asn Cys Pro Val Lys Asp Ile Asp Asp
        355                 360                 365
Thr Ala Met Gly Phe Arg Leu Leu Arg Leu Tyr Gly Tyr Gln Val Asp
370                 375                 380
Pro Cys Val Leu Lys Lys Phe Glu Lys Asp Gly Lys Phe Phe Cys Leu
385                 390                 395                 400
His Gly Glu Ser Asn Pro Ser Ser Val Thr Pro Met Tyr Asn Thr Tyr
                405                 410                 415
Arg Ala Ser Gln Leu Lys Phe Pro Gly Asp Asp Gly Val Leu Gly Arg
            420                 425                 430
Ala Glu Val Phe Cys Arg Ser Phe Leu Gln Asp Arg Arg Gly Ser Asn
        435                 440                 445
Arg Met Lys Asp Lys Trp Ala Ile Ala Lys Asp Ile Pro Gly Glu Val
450                 455                 460
Glu Tyr Ala Met Asp Tyr Pro Trp Lys Ala Ser Leu Pro Arg Ile Glu
465                 470                 475                 480
Thr Arg Leu Tyr Leu Asp Gln Tyr Gly Gly Ser Gly Asp Val Trp Ile
                485                 490                 495
Gly Lys Val Leu His Arg Met Thr Leu Phe Cys Asn Asp Leu Tyr Leu
            500                 505                 510
Lys Ala Ala Lys Ala Asp Phe Ser Asn Phe Gln Lys Glu Cys Arg Val
        515                 520                 525
Glu Leu Asn Gly Leu Arg Arg Trp Tyr Leu Arg Ser Asn Leu Glu Lys
530                 535                 540
Phe Gly Gly Thr Asp Pro Gln Thr Thr Leu Met Thr Ser Tyr Phe Leu
545                 550                 555                 560
Ala Ser Ala Asn Ile Phe Glu Ala Asn Arg Ala Ala Glu Arg Leu Gly
                565                 570                 575
Trp Ala Arg Val Ala Leu Leu Ala Asp Ala Val Ser Ser His Phe Arg
            580                 585                 590
Arg Ile Gly Gly Pro Lys Asn Ser Thr Ser Asn Leu Glu Glu Leu Ile
        595                 600                 605
Ser Leu Val Pro Phe Asp Asp Ala Tyr Ser Gly Ser Leu Arg Glu Ala
610                 615                 620
```

Trp Lys Gln Trp Leu Met Ala Trp Thr Ala Lys Glu Ser Ser Gln Glu
625                 630                 635                 640

Ser Ile Glu Gly Asp Thr Ala Ile Leu Leu Val Arg Ala Ile Glu Ile
            645                 650                 655

Phe Gly Gly Arg His Val Leu Thr Gly Gln Arg Pro Asp Leu Trp Glu
            660                 665                 670

Tyr Ser Gln Leu Glu Gln Leu Thr Ser Ser Ile Cys Cys Lys Leu Ser
            675                 680                 685

Arg Arg Val Leu Ala Gln Glu Asn Gly Glu Ser Thr Glu Lys Val Glu
            690                 695                 700

Glu Ile Asp Gln Gln Val Asp Leu Glu Met Gln Glu Leu Thr Arg Arg
705                 710                 715                 720

Val Leu Gln Gly Cys Ser Ala Ile Asn Arg Leu Thr Arg Glu Thr Phe
                725                 730                 735

Leu His Val Val Lys Ser Phe Cys Tyr Val Ala Tyr Cys Ser Pro Glu
            740                 745                 750

Thr Ile Asp Ser His Ile Asp Lys Val Ile Phe Gln Asp Val Ile
            755                 760                 765

<210> SEQ ID NO 118
<211> LENGTH: 862
<212> TYPE: PRT
<213> ORGANISM: Taxus brevifolia
<220> FEATURE:
<223> OTHER INFORMATION: taxadiene synthase
<300> PUBLICATION INFORMATION:
<308> DATABASE ACCESSION NUMBER: AAC49310
<309> DATABASE ENTRY DATE: 1996-06-05

<400> SEQUENCE: 118

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

```
Gln Val Gln Gln Gly Ala Glu Phe Ile Ala Glu Asn Leu Arg Leu Leu
210             215                 220

Asn Glu Glu Asp Glu Leu Ser Pro Asp Phe Gln Ile Ile Phe Pro Ala
225             230                 235                 240

Leu Leu Gln Lys Ala Lys Ala Leu Gly Ile Asn Leu Pro Tyr Asp Leu
            245                 250                 255

Pro Phe Ile Lys Tyr Leu Ser Thr Thr Arg Glu Ala Arg Leu Thr Asp
            260                 265                 270

Val Ser Ala Ala Asp Asn Ile Pro Ala Asn Met Leu Asn Ala Leu
            275                 280                 285

Glu Gly Leu Glu Glu Val Ile Asp Trp Asn Lys Ile Met Arg Phe Gln
290             295                 300

Ser Lys Asp Gly Ser Phe Leu Ser Ser Pro Ala Ser Thr Ala Cys Val
305             310                 315                 320

Leu Met Asn Thr Gly Asp Glu Lys Cys Phe Thr Phe Leu Asn Asn Leu
            325                 330                 335

Leu Asp Lys Phe Gly Gly Cys Val Pro Cys Met Tyr Ser Ile Asp Leu
            340                 345                 350

Leu Glu Arg Leu Ser Leu Val Asp Asn Ile Glu His Leu Gly Ile Gly
            355                 360                 365

Arg His Phe Lys Gln Glu Ile Lys Gly Ala Leu Asp Tyr Val Tyr Arg
370             375                 380

His Trp Ser Glu Arg Gly Ile Gly Trp Gly Arg Asp Ser Leu Val Pro
385             390                 395                 400

Asp Leu Asn Thr Thr Ala Leu Gly Leu Arg Thr Leu Arg Met His Gly
            405                 410                 415

Tyr Asn Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Arg Ala
            450                 455                 460

Met Asp Asp Ala Arg Lys Phe Ala Glu Pro Tyr Leu Arg Glu Ala Leu
465             470                 475                 480

Ala Thr Lys Ile Ser Thr Asn Thr Lys Leu Phe Lys Glu Ile Glu Tyr
            485                 490                 495

Val Val Glu Tyr Pro Trp His Met Ser Ile Pro Arg Leu Glu Ala Arg
            500                 505                 510

Ser Tyr Ile Asp Ser Tyr Asp Asp Asn Tyr Val Trp Gln Arg Lys Thr
            515                 520                 525

Leu Tyr Arg Met Pro Ser Leu Ser Asn Ser Lys Cys Leu Glu Leu Ala
530             535                 540

Lys Leu Asp Phe Asn Ile Val Gln Ser Leu His Gln Glu Glu Leu Lys
545             550                 555                 560

Leu Leu Thr Arg Trp Trp Lys Glu Ser Gly Met Ala Asp Ile Asn Phe
            565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
610             615                 620

Leu Lys Ser Phe Thr Glu Gly Val Lys Arg Trp Asp Thr Ser Leu Leu
```

```
                625                 630                 635                 640
        His Glu Ile Pro Glu Cys Met Gln Thr Cys Phe Lys Val Trp Phe Lys
                            645                 650                 655

Leu Met Glu Glu Val Asn Asn Asp Val Val Lys Val Gln Gly Arg Asp
                    660                 665                 670

Met Leu Ala His Ile Arg Lys Pro Trp Glu Leu Tyr Phe Asn Cys Tyr
                    675                 680                 685

Val Gln Glu Arg Glu Trp Leu Glu Ala Gly Tyr Ile Pro Thr Phe Glu
                    690                 695                 700

Glu Tyr Leu Lys Thr Tyr Ala Ile Ser Val Gly Leu Gly Pro Cys Thr
        705                 710                 715                 720

Leu Gln Pro Ile Leu Leu Met Gly Glu Leu Val Lys Asp Asp Val Val
                            725                 730                 735

Glu Lys Val His Tyr Pro Ser Asn Met Phe Glu Leu Val Ser Leu Ser
                    740                 745                 750

Trp Arg Leu Thr Asn Asp Thr Lys Thr Tyr Gln Ala Glu Lys Ala Arg
                    755                 760                 765

Gly Gln Gln Ala Ser Gly Ile Ala Cys Tyr Met Lys Asp Asn Pro Gly
                    770                 775                 780

Ala Thr Glu Glu Asp Ala Ile Lys His Ile Cys Arg Val Val Asp Arg
        785                 790                 795                 800

Ala Leu Lys Glu Ala Ser Phe Glu Tyr Phe Lys Pro Ser Asn Asp Ile
                            805                 810                 815

Pro Met Gly Cys Lys Ser Phe Ile Phe Asn Leu Arg Leu Cys Val Gln
                    820                 825                 830

Ile Phe Tyr Lys Phe Ile Asp Gly Tyr Gly Ile Ala Asn Glu Glu Ile
                    835                 840                 845

Lys Asp Tyr Ile Arg Lys Val Tyr Ile Asp Pro Ile Gln Val
        850                 855                 860

<210> SEQ ID NO 119
<211> LENGTH: 774
<212> TYPE: PRT
<213> ORGANISM: Helianthus annuus
<220> FEATURE:
<223> OTHER INFORMATION: kaurene synthase
<300> PUBLICATION INFORMATION:
<308> DATABASE ACCESSION NUMBER: Genbank CBM82408
<309> DATABASE ENTRY DATE: 2010-06-15

<400> SEQUENCE: 119

Met Asn Ile Thr Ile Thr Gln Ser Met Thr Gly Pro Leu Ser Ile Thr
        1               5                   10                  15

Lys Pro Tyr Arg Ser Trp Ala Leu Ser Ala Ile His Thr Ala Pro Ser
                    20                  25                  30

His Val Gly Gln Ala Asn Pro Thr Asn Leu Ala Ile Asp Thr Thr Lys
                35                  40                  45

Glu Arg Ile Arg Lys Leu Phe Asn Asn Val Asp Leu Ser Val Ser Ser
            50                  55                  60

Tyr Asp Thr Ala Trp Val Ala Met Val Pro Ser Pro Ser Ser Pro Lys
        65                  70                  75                  80

Ser Pro Cys Phe Pro Glu Cys Leu Asn Trp Leu Val Asp Asn Gln Leu
                            85                  90                  95

Asp Asp Gly Ser Trp Gly Leu Val Asn His Ser Ser Thr His Pro Leu
                    100                 105                 110

Ile Lys Asp Ser Leu Ser Ser Thr Leu Ala Cys Ile Val Ala Leu Lys
```

-continued

```
            115                 120                 125
Arg Trp Asn Val Gly Glu Asp Gln Ile Asn Lys Gly Leu Arg Phe Ile
130                 135                 140

Glu Ser Asn Leu Ala Ser Ala Thr Asp Lys Ser Gln Pro Ser Pro Phe
145                 150                 155                 160

Gly Phe Asp Ile Ile Phe Pro Gly Met Leu Glu Tyr Ala Gln Gln Leu
                165                 170                 175

Asn Ile Asn Leu Arg Ser Lys Gln Thr Asp Phe Thr Leu Met Leu His
                180                 185                 190

Glu Arg Asp Leu Glu Leu Lys Arg Cys His Ser Asn Glu Met Glu Ala
            195                 200                 205

Tyr Leu Ala Tyr Asn Ser Glu Gly Leu Gly Asn Leu Tyr Asp Trp His
210                 215                 220

Met Val Lys Lys Tyr Gln Met Lys Asn Gly Ser Val Phe Asn Ser Pro
225                 230                 235                 240

Ser Ala Thr Ala Ala Phe Ile Asn Arg Gln Asp Thr Gly Cys Leu
                245                 250                 255

Asn Tyr Leu Thr Ser Leu Leu Glu Lys Phe Gly Asn Ala Val Pro Thr
                260                 265                 270

Val Tyr Pro Leu Glu Leu Tyr Ile Arg Leu Ser Met Val Asp Thr Leu
                275                 280                 285

Glu Arg Leu Gly Ile Ala Arg His Phe Ser Val Glu Ile Lys Asn Val
            290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Glu Glu Ile Thr Asn Glu Gly
                340                 345                 350

Ala Phe Lys Asp Glu Tyr Ala Ala Leu Glu Val Tyr Asn Ala Ser Gln
            355                 360                 365

Ile Leu Tyr Pro Lys Glu Leu Ala Phe Gly Glu Gln Ile Leu Arg Ser
370                 375                 380

Gly Asp Phe Leu Arg Arg Ile Thr Ser Thr Asp Ser Asn Arg Leu Ser
385                 390                 395                 400

Thr Phe Ile Gln Lys Glu Ala Glu Asn Ala Leu Lys Val Pro Phe Asn
                405                 410                 415

Thr Gly Ile Glu Arg Ile Asn Val Lys Arg Tyr Ile Asp His Tyr His
                420                 425                 430

Val Asp His Thr Arg Ile Leu Lys Thr Thr Tyr Arg Ser Ser Asn Ile
            435                 440                 445

Ser Asn Glu Asp Tyr Leu Lys Phe Ala Val Glu Asp Phe Asn Ser Cys
450                 455                 460

Gln Ser Ile Tyr Leu Glu Glu Met Lys Gly Phe Lys Arg Trp Leu Ala
465                 470                 475                 480

Glu Thr Lys Leu Asp Gln Leu Thr Phe Ala Arg Glu Lys Ser Ala Tyr
                485                 490                 495

Cys Tyr Phe Thr Ala Ala Ala Thr Leu Pro Ala Pro Glu Leu Ser Asp
                500                 505                 510

Ala Arg Leu Ser Trp Ala Lys Asn Ser Ile Leu Thr Ala Ile Thr Asp
            515                 520                 525

Asp Phe Ile Asp Gly Gly Ala Thr Ile Asp Glu Ser Ile Asn Leu Val
530                 535                 540
```

```
Tyr Cys Val Glu Lys Trp Asn Val Asp Val Asp Lys Asp Cys Cys Ser
545                 550                 555                 560

Glu Thr Val Arg Ile Leu Phe Ser Ala Ile Lys Asp Ala Ile Cys Trp
                565                 570                 575

Met Gly Asp Ala Gly Phe Lys Trp Gln Glu Arg Asp Val Thr Ser His
            580                 585                 590

Val Thr Gln Ile Trp Leu Asp Leu Leu Asn Ser Met Leu Thr Glu Ala
        595                 600                 605

Ile Trp Arg Arg Asp Ala Tyr Thr Pro Thr Met Asp Glu Tyr Met Lys
610                 615                 620

Asn Ala Ser Val Ser Phe Ala Leu Gly Pro Ile Val Leu Asn Thr Leu
625                 630                 635                 640

Tyr Phe Val Gly Pro Lys Leu Ser Glu Glu Ile Val Glu Ser Ser Glu
                645                 650                 655

Tyr His Asn Ile Phe Asp Gln Met Ser Val Met Gly Arg Leu Leu Asn
            660                 665                 670

Asp Ile Tyr Ser Phe Met Arg Glu Ile Lys Glu Leu Asn Ala Ile
        675                 680                 685

Glu Leu Gln Leu Arg Asn Gly Glu Ser Ala Thr Gly Glu Glu Val
    690                 695                 700

Ile Lys Glu Ile Thr Thr Val Ile Lys Asn Met Arg Lys Glu Ile Met
705                 710                 715                 720

Lys Leu Val Thr Glu Glu Lys Gly Ser Val Val Pro Arg Ala Cys Lys
                725                 730                 735

Asp Val Phe Leu Asn Met Ser Asn Val Leu Asn Leu Phe Tyr Ala Thr
            740                 745                 750

Asp Asp Gly Phe Thr Gly Asp Ala Ile Leu Gly Ile Val Lys Asp Thr
        755                 760                 765

Phe Tyr Glu Pro Leu Ser
    770
```

<210> SEQ ID NO 120
<211> LENGTH: 812
<212> TYPE: PRT
<213> ORGANISM: Oryza sativa
<220> FEATURE:
<223> OTHER INFORMATION: ent-kaurene synthase
<300> PUBLICATION INFORMATION:
<308> DATABASE ACCESSION NUMBER: Genbank BAE72099
<309> DATABASE ENTRY DATE: 2008-02-15

<400> SEQUENCE: 120

```
Met Met Met Leu Leu Leu Pro Ser Ser Ser Ser Cys Cys Cys Arg
1               5                   10                  15

Cys Pro Gly Gly Gln Phe His Gly Ala Pro Pro Arg Val Met Ala Pro
            20                  25                  30

Arg Arg Gly Val Thr Arg Val Tyr Ile Glu Lys Arg Leu Gly Val Gly
        35                  40                  45

Gly Gly Asn Ala Ser Ser Leu Gln Asp Met His Arg Lys Glu Leu Gln
    50                  55                  60

Ala Arg Thr Arg Asp Gln Leu Gln Thr Leu Glu Leu Ser Thr Ser Leu
65                  70                  75                  80

Tyr Asp Thr Ala Trp Val Ala Met Val Pro Leu Arg Gly Ser Arg Gln
                85                  90                  95

His Pro Cys Phe Pro Gln Cys Val Glu Trp Ile Leu Gln Asn Gln Gln
            100                 105                 110
```

-continued

Asp Asp Gly Ser Trp Gly Thr Arg Gly Phe Gly Val Ala Val Thr Arg
            115                 120                 125

Asp Val Leu Ser Ser Thr Leu Ala Cys Val Leu Ala Leu Lys Arg Trp
130                 135                 140

Asn Val Gly Gln Glu His Ile Arg Arg Gly Leu Asp Phe Ile Gly Arg
145                 150                 155                 160

Asn Phe Ser Ile Ala Met Asp Glu Gln Ile Ala Ala Pro Val Gly Phe
            165                 170                 175

Asn Ile Thr Phe Pro Gly Met Leu Ser Leu Ala Met Gly Met Asp Leu
            180                 185                 190

Glu Phe Pro Val Arg Gln Thr Asp Val Asp Arg Leu Leu His Leu Arg
            195                 200                 205

Glu Ile Glu Leu Glu Arg Glu Ala Gly Asp His Ser Tyr Gly Arg Lys
            210                 215                 220

Ala Tyr Met Ala Tyr Val Thr Glu Gly Leu Gly Asn Leu Leu Glu Trp
225                 230                 235                 240

Asp Glu Ile Met Met Phe Gln Arg Lys Asn Gly Ser Phe Phe Asn Cys
            245                 250                 255

Pro Ser Thr Thr Ala Ala Thr Leu Val Asn His Tyr Asn Asp Lys Ala
            260                 265                 270

Leu Gln Tyr Leu Asn Cys Leu Val Ser Lys Phe Gly Ser Ala Val Pro
            275                 280                 285

Thr Val Tyr Pro Leu Asn Ile Tyr Cys Gln Leu Ser Trp Val Asp Ala
            290                 295                 300

Leu Glu Lys Met Gly Ile Ser Gln Tyr Phe Val Ser Glu Ile Lys Ser
305                 310                 315                 320

Ile Leu Asp Thr Thr Tyr Val Ser Trp Leu Glu Arg Asp Glu Glu Ile
            325                 330                 335

Met Leu Asp Ile Thr Thr Cys Ala Met Ala Phe Arg Leu Leu Arg Met
            340                 345                 350

Asn Gly Tyr His Val Ser Ser Val Glu Leu Ser Pro Val Ala Glu Ala
            355                 360                 365

Ser Ser Phe Arg Glu Ser Leu Gln Gly Tyr Leu Asn Asp Lys Lys Ser
            370                 375                 380

Leu Ile Glu Leu Tyr Lys Ala Ser Lys Val Ser Lys Ser Glu Asn Glu
385                 390                 395                 400

Ser Ile Leu Asp Ser Ile Gly Ser Trp Ser Gly Ser Leu Leu Lys Glu
            405                 410                 415

Ser Val Cys Ser Asn Gly Val Lys Lys Ala Pro Ile Phe Glu Glu Met
            420                 425                 430

Lys Tyr Ala Leu Lys Phe Pro Phe Tyr Thr Thr Leu Asp Arg Leu Asp
            435                 440                 445

His Lys Arg Asn Ile Glu Arg Phe Asp Ala Lys Asp Ser Gln Met Leu
            450                 455                 460

Lys Thr Glu Tyr Leu Leu Pro His Ala Asn Gln Asp Ile Leu Ala Leu
465                 470                 475                 480

Ala Val Glu Asp Phe Ser Ser Ser Gln Ser Ile Tyr Gln Asp Glu Leu
            485                 490                 495

Asn Tyr Leu Glu Cys Trp Val Lys Asp Glu Lys Leu Asp Gln Leu Pro
            500                 505                 510

Phe Ala Arg Gln Lys Leu Thr Tyr Cys Tyr Leu Ser Ala Ala Ala Thr
            515                 520                 525

```
Ile Phe Pro Arg Glu Leu Ser Glu Ala Arg Ile Ala Trp Ala Lys Asn
            530                 535                 540

Gly Val Leu Thr Thr Val Val Asp Asp Phe Phe Asp Leu Gly Gly Ser
545                 550                 555                 560

Lys Glu Glu Leu Glu Asn Leu Ile Ala Leu Val Glu Lys Trp Asp Gly
                565                 570                 575

His Gln Glu Glu Phe Tyr Ser Glu Gln Val Arg Ile Val Phe Ser Ala
            580                 585                 590

Ile Tyr Thr Thr Val Asn Gln Leu Gly Ala Lys Ala Ser Ala Leu Gln
        595                 600                 605

Gly Arg Asp Val Thr Lys His Leu Thr Glu Ile Trp Leu Cys Leu Met
610                 615                 620

Arg Ser Met Met Thr Glu Ala Glu Trp Gln Arg Thr Lys Tyr Val Pro
625                 630                 635                 640

Thr Met Glu Glu Tyr Met Ala Asn Ala Val Ser Phe Ala Leu Gly
                645                 650                 655

Pro Ile Val Leu Pro Thr Leu Tyr Phe Val Gly Pro Lys Leu Gln Glu
                660                 665                 670

Asp Val Val Arg Asp His Glu Tyr Asn Glu Leu Phe Arg Leu Met Ser
            675                 680                 685

Thr Cys Gly Arg Leu Leu Asn Asp Ser Gln Gly Phe Glu Arg Glu Ser
690                 695                 700

Leu Glu Gly Lys Leu Asn Ser Val Ser Leu Leu Val His His Ser Gly
705                 710                 715                 720

Gly Ser Ile Ser Ile Asp Glu Ala Lys Met Lys Ala Gln Lys Ser Ile
                725                 730                 735

Asp Thr Ser Arg Arg Asn Leu Leu Arg Leu Val Leu Gly Glu Gln Gly
            740                 745                 750

Ala Val Pro Arg Pro Cys Lys Gln Leu Phe Trp Lys Met Cys Lys Ile
        755                 760                 765

Val His Met Phe Tyr Ser Arg Thr Asp Gly Phe Ser Ser Pro Lys Glu
770                 775                 780

Met Val Ser Ala Val Asn Ala Val Val Lys Glu Pro Leu Lys Leu Lys
785                 790                 795                 800

Val Ser Asp Pro Tyr Gly Ser Ile Leu Ser Gly Asn
                805                 810
```

<210> SEQ ID NO 121
<211> LENGTH: 820
<212> TYPE: PRT
<213> ORGANISM: Oryza sativa
<220> FEATURE:
<223> OTHER INFORMATION: stemer-13-ene synthase
<300> PUBLICATION INFORMATION:
<308> DATABASE ACCESSION NUMBER: Genbank BAD34478
<309> DATABASE ENTRY DATE: 2008-02-15

<400> SEQUENCE: 121

```
Met Met Leu Leu Ser Ser Ser Tyr Ser Gly Gly Gln Phe Pro Gly Val
1               5                   10                  15

Ser Pro Leu Gly Thr Arg Pro Lys Arg Ser Thr Thr Val Val Pro Arg
            20                  25                  30

Pro Val Val Thr Arg Ala Gly Gly Val Arg Asn Asn Leu Glu Val Val
        35                  40                  45

Gly Asn Ala Gly Thr Leu Gln Gly Met Asp Ile Asp Glu Leu Arg Val
    50                  55                  60
```

```
Ile Val Arg Lys Gln Leu Gln Gly Val Glu Leu Ser Pro Ser Ser Tyr
 65                  70                  75                  80

Asp Thr Ala Trp Val Ala Met Val Pro Val Gln Gly Ser Arg Gln Ser
                 85                  90                  95

Pro Cys Phe Pro Gln Cys Val Glu Trp Ile Leu Gln Asn Gln Gln Glu
            100                 105                 110

Asp Gly Ser Trp Gly His Ser Ala Gly Pro Ser Gly Glu Val Asn Lys
        115                 120                 125

Asp Ile Leu Leu Ser Thr Leu Ala Cys Val Leu Ala Leu Asn Ile Trp
130                 135                 140

Asn Val Gly Gln Asp His Ile Arg Arg Gly Leu Ser Phe Ile Gly Arg
145                 150                 155                 160

Asn Phe Ser Val Ala Ile Asp Gly Gln Cys Ala Ala Pro Val Gly Phe
                165                 170                 175

Asn Ile Thr Phe Ser Gly Met Leu Arg Leu Ala Ile Gly Met Gly Leu
            180                 185                 190

Lys Phe Pro Val Met Glu Thr Asp Ile Asp Ser Ile Phe Arg Leu Arg
        195                 200                 205

Glu Val Glu Phe Glu Arg Asp Ala Gly Thr Ala Ser Ala Arg Lys
210                 215                 220

Ala Phe Met Ala Tyr Val Ser Glu Gly Leu Gly Arg Glu Gln Asp Trp
225                 230                 235                 240

Asp His Val Met Ala Tyr Gln Arg Lys Asn Gly Ser Leu Phe Asn Ser
                245                 250                 255

Pro Ser Thr Thr Ala Ala Ser Ala Ile His Ser Cys Asn Asp Arg Ala
            260                 265                 270

Leu Asp Tyr Leu Val Ser Leu Thr Ser Lys Leu Gly Gly Pro Val Pro
        275                 280                 285

Ala Ile Tyr Pro Asp Lys Val Tyr Ser Gln Leu Cys Met Val Asp Thr
290                 295                 300

Leu Glu Lys Met Gly Ile Ser Ser Asp Phe Ala Cys Asp Ile Arg Asp
305                 310                 315                 320

Ile Leu Asp Met Thr Tyr Ser Cys Trp Met Gln Asp Glu Glu Ile
                325                 330                 335

Met Leu Asp Met Ala Thr Cys Ala Lys Ala Phe Arg Leu Leu Arg Met
            340                 345                 350

His Gly Tyr Asp Val Ser Ser Glu Gly Met Ala Arg Phe Ala Glu Arg
        355                 360                 365

Ser Ser Phe Asp Asp Ser Ile His Ala Tyr Leu Asn Asp Thr Lys Pro
370                 375                 380

Leu Leu Glu Leu Tyr Lys Ser Ser Gln Val His Phe Leu Glu Glu Asp
385                 390                 395                 400

Phe Ile Leu Glu Asn Ile Gly Ser Trp Ser Ala Lys Leu Leu Lys Gln
                405                 410                 415

Gln Leu Ser Phe Asn Lys Ile Ser Lys Ser Leu Met Pro Glu Val Glu
            420                 425                 430

Tyr Ala Leu Lys Tyr Pro Phe Tyr Ala Thr Val Glu Val Leu Glu His
        435                 440                 445

Lys Gly Asn Ile Glu Arg Phe Asn Val Asn Gly Phe Gln Arg Leu Lys
        450                 455                 460

Ser Gly Tyr Cys Gly Ser Gly Ala Asp Lys Glu Ile Leu Ala Leu Ala
465                 470                 475                 480

Val Asn Lys Phe His Tyr Ala Gln Ser Val Tyr Gln Gln Glu Leu Arg
```

```
            485                 490                 495

Tyr Leu Glu Ser Trp Val Ala Glu Phe Arg Leu Asp Glu Leu Lys Phe
            500                 505                 510

Ala Arg Val Ile Pro Leu Gln Ser Leu Leu Ser Ala Val Pro Leu
            515                 520                 525

Phe Pro Cys Glu Leu Ser Asp Ala Arg Ile Ala Trp Ser Gln Asn Ala
            530                 535                 540

Ile Leu Thr Ala Val Asp Asp Leu Phe Asp Gly Gly Ser Met
545                 550                 555                 560

Glu Glu Met Leu Asn Leu Val Ala Leu Phe Asp Lys Trp Asp Asp His
            565                 570                 575

Gly Glu Ile Gly Phe Cys Ser Ser Asn Val Glu Ile Met Phe Asn Ala
            580                 585                 590

Val Tyr Asn Thr Thr Lys Arg Ile Gly Ala Lys Ala Ala Leu Val Gln
            595                 600                 605

Lys Arg Cys Val Ile Asp His Ile Ala Glu Gln Trp Gln Val Met Val
            610                 615                 620

Arg Ala Met Leu Thr Glu Ala Glu Trp Ala Ala Gly Lys His Ile Pro
625                 630                 635                 640

Ala Thr Met Gly Glu Tyr Met Ser Val Ala Glu Pro Ser Phe Ala Leu
            645                 650                 655

Gly Pro Ile Val Pro Val Ser Ala Tyr Leu Leu Gly Glu Glu Leu Pro
            660                 665                 670

Glu Glu Ala Val Arg Ser Pro Glu Tyr Gly Arg Leu Leu Gly Leu Ala
            675                 680                 685

Ser Ala Val Gly Arg Leu Leu Asn Asp Val Met Thr Tyr Glu Lys Glu
            690                 695                 700

Met Gly Thr Gly Lys Leu Asn Ser Val Val Leu Gln Pro Leu Ala
705                 710                 715                 720

Ala Gly Gly Ala Ala Ser Arg Gly Gly Gly Ala Pro Ala Pro Ala
            725                 730                 735

Pro Ala Ser Val Glu Ala Ala Arg Ala Glu Val Arg Arg Ala Ile Gln
            740                 745                 750

Ala Ser Trp Arg Asp Leu His Gly Leu Val Phe Gly Ser Gly Gly
            755                 760                 765

Ser Ser Ser Ser Ile Ile Pro Arg Pro Cys Arg Glu Val Phe Trp His
            770                 775                 780

Thr Gly Lys Val Ala Ser Val Phe Tyr Gln Glu Gly Asp Gly Tyr Ala
785                 790                 795                 800

Arg Lys Ala Met Arg Ser Met Ala Asn Ala Val Ile Leu Glu Pro Leu
            805                 810                 815

His Leu Gln Glu
            820

<210> SEQ ID NO 122
<211> LENGTH: 816
<212> TYPE: PRT
<213> ORGANISM: Oryza sativa
<220> FEATURE:
<223> OTHER INFORMATION: stemodene synthase
<300> PUBLICATION INFORMATION:
<308> DATABASE ACCESSION NUMBER: Genbank AAZ76733
<309> DATABASE ENTRY DATE: 2006-05-30

<400> SEQUENCE: 122

Met Met Leu Leu Ser Ser Ser Tyr Ser Gly Gly Gln Phe Pro Gly Val
```

```
   1               5                  10                 15
Ser Pro Leu Gly Thr Arg Pro Lys Arg Ser Thr Thr Val Val Pro Leu
                20                 25                 30

Pro Val Val Thr Arg Ala Thr Ala Gly Gly Val Arg Asn Asn Leu Glu
                35                 40                 45

Val Val Gly Asn Ala Gly Thr Leu Gln Gly Met Asp Ile Asp Glu Leu
                50                 55                 60

Arg Val Ile Val Arg Lys Gln Leu Gln Gly Val Glu Leu Ser Pro Ser
 65                 70                 75                 80

Ser Tyr Asp Thr Ala Trp Val Ala Met Val Pro Val Gln Gly Ser Pro
                85                 90                 95

Gln Ser Pro Cys Phe Pro Gln Cys Val Glu Trp Ile Leu Gln Asn Gln
               100                105                110

Gln Glu Asp Gly Ser Trp Gly His Ser Ala Gly Pro Ser Gly Glu Val
               115                120                125

Asn Lys Asp Ile Leu Leu Ser Thr Leu Ala Cys Val Leu Ala Leu Asn
               130                135                140

Thr Trp Asn Val Gly Gln Asp His Ile Arg Arg Gly Leu Ser Phe Ile
145                150                155                160

Gly Arg Asn Phe Ser Val Ala Ile Asp Gly Gln Cys Ala Ala Pro Val
               165                170                175

Gly Phe Asn Ile Thr Phe Ser Gly Met Leu His Leu Ala Ile Gly Met
               180                185                190

Gly Leu Lys Phe Pro Val Met Glu Thr Asp Ile Asp Ser Ile Phe Arg
               195                200                205

Leu Arg Glu Val Glu Phe Glu Arg Asp Ala Gly Gly Thr Ala Ser Ala
               210                215                220

Arg Lys Ala Phe Met Ala Tyr Val Ser Glu Gly Leu Gly Arg Glu Gln
225                230                235                240

Asp Trp Asp His Val Met Ala Tyr Gln Arg Lys Asn Gly Ser Leu Phe
               245                250                255

Asn Ser Pro Ser Thr Thr Ala Ala Ser Ala Ile His Ser Cys Asn Asp
               260                265                270

Arg Ala Leu Asp Tyr Leu Val Ser Leu Thr Ser Lys Leu Gly Gly Pro
               275                280                285

Val Pro Ala Ile His Pro Asp Lys Val Tyr Ser Gln Leu Cys Met Val
               290                295                300

Asp Thr Leu Glu Lys Met Gly Ile Ser Ser Asp Phe Ala Cys Asp Ile
305                310                315                320

Arg Asp Ile Leu Asp Met Thr Tyr Ser Cys Trp Met Gln Asp Glu Glu
               325                330                335

Glu Ile Met Leu Asp Met Ala Thr Cys Ala Lys Ala Phe Arg Leu Leu
               340                345                350

Arg Met His Gly Tyr Asp Val Ser Ser Glu Gly Met Ala Arg Phe Ala
               355                360                365

Glu Arg Ser Ser Phe Asp Asp Ser Ile His Ala Tyr Leu Asn Asp Thr
               370                375                380

Lys Pro Leu Leu Glu Leu Tyr Lys Ser Ser Gln Leu His Phe Leu Glu
385                390                395                400

Glu Asp Leu Ile Leu Glu Asn Ile Ser Ser Trp Ser Ala Lys Leu Leu
               405                410                415

Lys Gln Gln Leu Ser Ser Asn Lys Ile Met Lys Ser Leu Met Pro Glu
               420                425                430
```

```
Val Glu Tyr Ala Leu Lys Tyr Pro Leu Tyr Ser Thr Val Asp Ala Leu
        435                 440                 445

Glu His Arg Gly Asn Ile Glu Arg Phe Asn Val Asn Gly Phe Gln Arg
450                 455                 460

Pro Lys Ser Gly Tyr Cys Gly Ser Gly Ala Asp Lys Glu Ile Leu Ala
465                 470                 475                 480

Leu Ala Val Asp Lys Phe His Tyr Asn Gln Ser Val Tyr Gln Gln Glu
                485                 490                 495

Leu Arg Tyr Leu Glu Ser Trp Val Ala Glu Phe Gly Leu Asp Glu Leu
                500                 505                 510

Lys Phe Ala Arg Val Ile Pro Leu Gln Ser Leu Leu Ser Ala Leu Val
                515                 520                 525

Pro Leu Phe Pro Ala Glu Leu Ser Asp Ala Arg Ile Ala Phe Ser Gln
530                 535                 540

Asn Cys Met Leu Thr Thr Met Val Asp Asp Phe Phe Asp Gly Gly Gly
545                 550                 555                 560

Ser Met Glu Glu Met Val Asn Phe Val Ala Leu Ile Asp Glu Trp Asp
                565                 570                 575

Asn His Gly Glu Ile Gly Phe Cys Ser Asn Asn Val Glu Ile Met Phe
                580                 585                 590

Asn Ala Ile Tyr Asn Thr Thr Lys Arg Asn Cys Ala Lys Ala Ala Leu
                595                 600                 605

Val Gln Asn Arg Cys Val Met Asp His Ile Ala Lys Gln Trp Gln Val
                610                 615                 620

Met Val Arg Ala Met Lys Thr Glu Ala Glu Trp Ala Ala Ser Arg His
625                 630                 635                 640

Ile Pro Ala Thr Met Glu Glu Tyr Met Ser Val Gly Glu Pro Ser Phe
                645                 650                 655

Ala Leu Gly Pro Ile Val Pro Leu Ser Ala Tyr Leu Leu Gly Glu Glu
                660                 665                 670

Leu Pro Glu Glu Ala Val Arg Ser Pro Glu Tyr Gly Gln Leu Leu Arg
                675                 680                 685

His Ala Ser Ala Val Gly Arg Leu Leu Asn Asp Val Met Thr Tyr Glu
                690                 695                 700

Lys Glu Val Leu Thr Trp Thr Pro Asn Ser Val Leu Leu Gln Ala Leu
705                 710                 715                 720

Ala Ala Ala Arg Gly Gly Gly Glu Ser Pro Thr Pro Ser Pro Ala
                725                 730                 735

Cys Ala Glu Ala Ala Arg Gly Glu Val Arg Arg Ala Ile Gln Ala Ser
                740                 745                 750

Trp Arg Asp Leu His Arg Leu Val Phe Arg Asp Asp Gly Ser Ser
                755                 760                 765

Ile Val Pro Arg Ala Cys Arg Glu Leu Phe Trp Gly Thr Ala Lys Val
770                 775                 780

Ala Asn Val Phe Tyr Gln Glu Val Asp Gly Tyr Thr Pro Lys Ala Met
785                 790                 795                 800

Arg Gly Met Ala Asn Ala Val Ile Leu Asp Pro Leu His Leu Gln Gln
                805                 810                 815

<210> SEQ ID NO 123
<211> LENGTH: 784
<212> TYPE: PRT
<213> ORGANISM: Stevia rebaudiana
<220> FEATURE:
```

<223> OTHER INFORMATION: copalyl pyrophosphate synthase
<300> PUBLICATION INFORMATION:
<308> DATABASE ACCESSION NUMBER: Genbank AAD34294
<309> DATABASE ENTRY DATE: 2000-03-22

<400> SEQUENCE: 123

```
Met Asn Leu Ser Leu Cys Ile Ala Ser Pro Leu Leu Thr Lys Ser Ser
 1               5                  10                  15

Arg Pro Thr Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Leu Phe Lys Asn Val Glu Ile Ser Val Ser Ser Tyr Asp
50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro Leu Asp Leu Tyr Ile Arg Leu Ser Met Val Asp Thr Ile
        275                 280                 285

Glu Arg Leu Gly Ile Ser His His Phe Arg Val Glu Ile Lys Asn Val
290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
370                 375                 380
```

```
Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
            405                 410                 415

Thr Gly Leu Glu Arg Ile Asn Thr Arg Arg Asn Ile Gln Leu Tyr Asn
        420                 425                 430

Val Asp Asn Thr Arg Ile Leu Lys Thr Thr Tyr His Ser Ser Asn Ile
    435                 440                 445

Ser Asn Thr Tyr Tyr Leu Arg Leu Ala Val Glu Asp Phe Tyr Thr Cys
450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
            485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
            565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
            645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
            725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
        755                 760                 765

Ile Ile Tyr Asn Pro Leu Val Leu Val Asn Glu Asn Glu Glu Gln Arg
    770                 775                 780

<210> SEQ ID NO 124
<211> LENGTH: 850
<212> TYPE: PRT
```

<213> ORGANISM: Pinus taeda
<220> FEATURE:
<223> OTHER INFORMATION: abietadiene/levopimaradiene synthase
<300> PUBLICATION INFORMATION:
<308> DATABASE ACCESSION NUMBER: Genbank Q50EK2
<309> DATABASE ENTRY DATE: 2005-06-07

<400> SEQUENCE: 124

```
Met Ala Leu Pro Ser Ser Leu Ser Ser Gln Ile His Thr Gly Ala
 1               5                  10                  15

Thr Thr Gln Cys Ile Pro His Phe His Gly Ser Leu Asn Ala Gly Thr
                20                  25                  30

Ser Ala Gly Lys Arg Arg Ser Leu Tyr Leu Arg Trp Gly Lys Gly Pro
            35                  40                  45

Ser Lys Ile Val Ala Cys Ala Gly Gln Asp Pro Phe Ser Val Pro Thr
    50                  55                  60

Leu Val Lys Arg Glu Phe Pro Pro Gly Phe Trp Lys Asp His Val Ile
65                  70                  75                  80

Glu Ser Leu Met Pro Ser Tyr Lys Val Ala Pro Ser Asp Glu Lys Arg
                85                  90                  95

Ile Glu Thr Leu Ile Thr Glu Ile Lys Asn Met Phe Arg Ser Met Gly
            100                 105                 110

Tyr Gly Glu Thr Asn Pro Ser Ala Tyr Asp Thr Ala Trp Val Ala Arg
        115                 120                 125

Ile Pro Ala Val Asp Gly Ser Glu Lys Pro Gln Phe Pro Glu Thr Leu
    130                 135                 140

Glu Trp Ile Leu Gln Asn Gln Leu Lys Asp Gly Ser Trp Gly Glu Glu
145                 150                 155                 160

Phe Tyr Phe Leu Ala Tyr Asp Arg Ile Leu Ala Thr Leu Ala Cys Ile
                165                 170                 175

Ile Thr Leu Thr Ile Trp Gln Thr Gly Asp Thr Gln Val Gln Lys Gly
            180                 185                 190

Ile Glu Phe Phe Lys Thr Gln Ala Gly Lys Ile Glu Glu Glu Ala Asp
        195                 200                 205

Ser His Arg Pro Ser Gly Phe Glu Ile Val Phe Pro Ala Met Leu Lys
    210                 215                 220

Glu Ala Lys Ala Leu Gly Leu Ala Leu Pro Tyr Glu Leu Pro Phe Ile
225                 230                 235                 240

Gln Gln Ile Ile Glu Lys Arg Glu Ala Lys Leu Gln Arg Leu Pro Pro
                245                 250                 255

Asp Leu Leu Tyr Ala Leu Pro Thr Thr Leu Leu Tyr Ser Leu Glu Gly
            260                 265                 270

Leu Gln Glu Ile Val Asp Trp Glu Lys Ile Met Lys Leu Gln Ser Lys
        275                 280                 285

Asp Gly Ser Phe Leu Ser Ser Pro Ala Ser Thr Ala Ala Val Phe Met
    290                 295                 300

Arg Thr Gly Asn Lys Lys Cys Leu Glu Phe Leu Asn Phe Val Leu Lys
305                 310                 315                 320

Lys Phe Gly Asn His Val Pro Cys His Tyr Pro Leu Asp Leu Phe Glu
                325                 330                 335

Arg Leu Trp Ala Val Asp Thr Val Glu Arg Leu Gly Ile Asp His His
            340                 345                 350

Phe Lys Glu Glu Ile Lys Asp Ala Leu Asp Tyr Val Tyr Ser His Trp
        355                 360                 365

Asp Glu Arg Gly Ile Gly Trp Ala Arg Glu Asn Pro Val Pro Asp Ile
```

```
                    370                 375                 380
Asp Asp Thr Ala Met Gly Leu Arg Ile Leu Arg Leu His Gly Tyr Asn
385                 390                 395                 400

Val Ser Ser Asp Val Leu Lys Thr Phe Arg Asp Glu Asn Gly Glu Phe
                405                 410                 415

Phe Cys Phe Leu Gly Gln Thr Gln Arg Gly Val Thr Asp Met Leu Asn
            420                 425                 430

Val Asn Arg Cys Ser His Val Ala Phe Pro Gly Glu Thr Ile Met Glu
        435                 440                 445

Glu Ala Lys Leu Cys Thr Glu Arg Tyr Leu Arg Asn Ala Leu Glu Asp
    450                 455                 460

Gly Gly Ala Ser Asp Lys Trp Ala Leu Lys Lys Asn Ile Arg Gly Glu
465                 470                 475                 480

Val Glu Tyr Ala Leu Lys Tyr Pro Trp His Arg Ser Met Pro Arg Leu
                485                 490                 495

Glu Ala Arg Ser Tyr Ile Glu Asn Tyr Gly Pro Asn Asp Val Trp Leu
            500                 505                 510

Gly Lys Thr Met Tyr Met Met Pro Asn Ile Ser Asn Glu Lys Tyr Leu
        515                 520                 525

Glu Leu Ala Lys Leu Asp Phe Asn Arg Val Gln Phe Phe His Arg Gln
    530                 535                 540

Glu Leu Gln Asp Ile Arg Arg Trp Trp Asn Ser Ser Gly Phe Ser Gln
545                 550                 555                 560

Leu Gly Phe Thr Arg Glu Arg Val Ala Glu Ile Tyr Phe Ser Pro Ala
                565                 570                 575

Ser Phe Leu Phe Glu Pro Glu Phe Ala Thr Cys Arg Ala Val Tyr Thr
            580                 585                 590

Lys Thr Ser Asn Phe Thr Val Ile Leu Asp Asp Leu Tyr Asp Ala His
        595                 600                 605

Gly Thr Leu Asp Asn Leu Lys Leu Phe Ser Glu Ser Val Lys Arg Trp
    610                 615                 620

Asp Leu Ser Leu Val Asp Gln Met Pro Gln Asp Met Lys Ile Cys Phe
625                 630                 635                 640

Lys Gly Phe Tyr Asn Thr Phe Asn Glu Ile Ala Glu Glu Gly Arg Lys
                645                 650                 655

Arg Gln Gly Arg Asp Val Leu Ser Tyr Ile Gln Lys Val Trp Glu Val
            660                 665                 670

Gln Leu Glu Ala Tyr Thr Lys Glu Ala Glu Trp Ser Ala Val Arg Tyr
        675                 680                 685

Val Pro Ser Tyr Asp Glu Tyr Ile Gly Asn Ala Ser Val Ser Ile Ala
    690                 695                 700

Leu Gly Thr Val Val Leu Ile Ser Ala Leu Phe Thr Gly Glu Ile Leu
705                 710                 715                 720

Thr Asp Asp Ile Leu Ser Lys Ile Gly Arg Asp Ser Arg Phe Leu Tyr
                725                 730                 735

Leu Met Gly Leu Thr Gly Arg Leu Val Asn Asp Thr Lys Thr Tyr Gln
            740                 745                 750

Ala Glu Arg Gly Gln Gly Glu Val Ala Ser Ala Val Gln Cys Tyr Met
        755                 760                 765

Lys Asp His Pro Glu Ile Ser Glu Glu Glu Ala Leu Lys His Val Tyr
    770                 775                 780

Thr Ile Met Asp Asn Ala Leu Asp Glu Leu Asn Arg Glu Phe Val Asn
785                 790                 795                 800
```

```
Asn Arg Asp Val Pro Asp Thr Cys Arg Arg Leu Val Phe Glu Thr Ala
            805                 810                 815

Arg Ile Met Gln Leu Phe Tyr Met Asp Gly Asp Gly Leu Thr Leu Ser
            820                 825                 830

His Asn Met Glu Ile Lys Glu His Val Lys Asn Cys Leu Phe Gln Pro
        835                 840                 845

Val Ala
    850

<210> SEQ ID NO 125
<211> LENGTH: 859
<212> TYPE: PRT
<213> ORGANISM: Picea abies
<220> FEATURE:
<223> OTHER INFORMATION: abietadiene/levopimaradiene synthase
<300> PUBLICATION INFORMATION:
<308> DATABASE ACCESSION NUMBER: Genbank AAS47691
<309> DATABASE ENTRY DATE: 2009-04-08

<400> SEQUENCE: 125

Met Ala Leu Leu Ser Ser Ser Leu Ser Ser Gln Ile Pro Thr Gly Ala
 1               5                  10                  15

His His Leu Thr Leu Asn Ala Tyr Ala Asn Thr Gln Cys Ile Pro His
            20                  25                  30

Phe Phe Ser Thr Leu Asn Ala Gly Thr Ser Ala Gly Lys Arg Ser Ser
        35                  40                  45

Leu Tyr Leu Arg Trp Gly Lys Gly Ser Asn Lys Ile Ile Ala Cys Val
    50                  55                  60

Gly Glu Asp Ser Leu Ser Ala Pro Thr Leu Val Lys Arg Glu Phe Pro
65                  70                  75                  80

Pro Gly Phe Trp Lys Asp His Val Ile Asp Ser Leu Thr Ser Ser His
                85                  90                  95

Lys Val Ala Ala Ser Asp Glu Lys Arg Ile Glu Thr Leu Ile Ser Glu
            100                 105                 110

Ile Lys Asn Met Phe Arg Ser Met Gly Tyr Gly Asp Thr Asn Pro Ser
        115                 120                 125

Ala Tyr Asp Thr Ala Trp Val Ala Arg Ile Pro Ala Val Asp Gly Ser
    130                 135                 140

Glu Gln Pro Glu Phe Pro Glu Thr Leu Glu Trp Ile Leu Gln Asn Gln
145                 150                 155                 160

Leu Lys Asp Gly Ser Trp Gly Glu Gly Phe Tyr Phe Leu Ala Tyr Asp
                165                 170                 175

Arg Ile Leu Ala Thr Leu Ala Cys Ile Ile Thr Leu Thr Leu Trp Arg
            180                 185                 190

Thr Gly Glu Ile Gln Val Gln Lys Gly Ile Glu Phe Phe Lys Thr Gln
        195                 200                 205

Ala Gly Lys Ile Glu Asp Glu Ala Asp Ser His Arg Pro Ser Gly Phe
    210                 215                 220

Glu Ile Val Phe Pro Ala Met Leu Lys Glu Ala Lys Val Leu Gly Leu
225                 230                 235                 240

Asp Leu Pro Tyr Glu Leu Pro Phe Ile Lys Gln Ile Ile Glu Lys Arg
                245                 250                 255

Glu Ala Lys Leu Glu Arg Leu Pro Thr Asn Ile Leu Tyr Ala Leu Pro
            260                 265                 270

Thr Thr Leu Leu Tyr Ser Leu Glu Gly Leu Gln Glu Ile Val Asp Trp
        275                 280                 285
```

-continued

```
Gln Lys Ile Ile Lys Leu Gln Ser Lys Asp Gly Ser Phe Leu Ser Ser
    290                 295                 300

Pro Ala Ser Thr Ala Ala Val Phe Met Arg Thr Gly Asn Lys Lys Cys
305                 310                 315                 320

Leu Glu Phe Leu Asn Phe Val Leu Lys Lys Phe Gly Asn His Val Pro
                    325                 330                 335

Cys His Tyr Pro Leu Asp Leu Phe Glu Arg Leu Trp Ala Val Asp Thr
                340                 345                 350

Ile Glu Arg Leu Gly Ile Asp Arg His Phe Lys Glu Ile Lys Asp
                    355                 360                 365

Ala Leu Asp Tyr Val Tyr Ser His Trp Asp Glu Arg Gly Ile Gly Trp
    370                 375                 380

Ala Arg Glu Asn Pro Val Pro Asp Ile Asp Asp Thr Ala Met Gly Leu
385                 390                 395                 400

Arg Ile Leu Arg Leu His Gly Tyr Asn Val Ser Ser Asp Val Leu Lys
                    405                 410                 415

Thr Phe Arg Asp Glu Asn Gly Glu Phe Phe Cys Phe Leu Gly Gln Thr
                420                 425                 430

Gln Arg Gly Val Thr Asp Met Leu Asn Val Asn Arg Cys Ser His Val
    435                 440                 445

Ala Phe Pro Gly Glu Thr Ile Met Glu Glu Ala Lys Thr Cys Thr Glu
    450                 455                 460

Arg Tyr Leu Arg Asn Ala Leu Glu Asp Val Gly Ala Phe Asp Lys Trp
465                 470                 475                 480

Ala Leu Lys Lys Asn Ile Arg Gly Glu Val Glu Tyr Ala Leu Lys Tyr
                    485                 490                 495

Pro Trp His Arg Ser Met Pro Arg Leu Glu Ala Arg Ser Tyr Ile Glu
            500                 505                 510

His Tyr Gly Pro Asn Asp Val Trp Leu Gly Lys Thr Met Tyr Met Met
        515                 520                 525

Pro Tyr Ile Ser Asn Glu Lys Tyr Leu Glu Leu Ala Lys Leu Asp Phe
    530                 535                 540

Asn His Val Gln Ser Leu His Gln Lys Glu Leu Arg Asp Leu Arg Arg
545                 550                 555                 560

Trp Trp Thr Ser Ser Gly Phe Thr Glu Leu Lys Phe Thr Arg Glu Arg
                565                 570                 575

Val Thr Glu Ile Tyr Phe Ser Pro Ala Ser Phe Met Phe Glu Pro Glu
            580                 585                 590

Phe Ala Thr Cys Arg Ala Val Tyr Thr Lys Thr Ser Asn Phe Thr Val
        595                 600                 605

Ile Leu Asp Asp Leu Tyr Asp Ala His Gly Thr Leu Asp Asp Leu Lys
    610                 615                 620

Leu Phe Ser Asp Ser Val Lys Lys Trp Asp Leu Ser Leu Val Asp Arg
625                 630                 635                 640

Met Pro Gln Asp Met Lys Ile Cys Phe Met Gly Phe Tyr Asn Thr Phe
                645                 650                 655

Asn Glu Ile Ala Glu Glu Gly Arg Lys Arg Gln Gly Arg Asp Val Leu
            660                 665                 670

Gly Tyr Ile Arg Asn Val Trp Glu Ile Gln Leu Glu Ala Tyr Thr Lys
        675                 680                 685

Glu Ala Glu Trp Ser Ala Ala Arg Tyr Val Pro Ser Phe Asp Glu Tyr
    690                 695                 700
```

```
Ile Asp Asn Ala Ser Val Ser Ile Ala Leu Gly Thr Val Leu Ile
705                 710                 715                 720

Ser Ala Leu Phe Thr Gly Glu Ile Leu Thr Asp Asp Val Leu Ser Lys
            725                 730                 735

Ile Gly Arg Gly Ser Arg Phe Leu Gln Leu Met Gly Leu Thr Gly Arg
        740                 745                 750

Leu Val Asn Asp Thr Lys Thr Tyr Glu Ala Glu Arg Gly Gln Gly Glu
            755                 760                 765

Val Ala Ser Ala Val Gln Cys Tyr Met Lys Asp His Pro Glu Ile Ser
        770                 775                 780

Glu Glu Glu Ala Leu Lys His Val Tyr Thr Val Met Glu Asn Ala Leu
785                 790                 795                 800

Asp Glu Leu Asn Arg Glu Phe Val Asn Asn Arg Glu Val Pro Asp Ser
            805                 810                 815

Cys Arg Arg Leu Val Phe Glu Thr Ala Arg Ile Met Gln Leu Phe Tyr
        820                 825                 830

Met Asp Gly Asp Gly Leu Thr Leu Ser His Gly Thr Glu Ile Lys Glu
            835                 840                 845

His Val Lys Asn Cys Leu Phe Gln Pro Val Ala
        850                 855

<210> SEQ ID NO 126
<211> LENGTH: 873
<212> TYPE: PRT
<213> ORGANISM: Ginkgo biloba
<220> FEATURE:
<223> OTHER INFORMATION: levopimaradiene synthase
<300> PUBLICATION INFORMATION:
<308> DATABASE ACCESSION NUMBER: Genbank AAS89668
<309> DATABASE ENTRY DATE: 2005-03-10

<400> SEQUENCE: 126

Met Ala Gly Val Leu Phe Ala Asn Leu Pro Cys Ser Leu Gln Leu Ser
1               5                   10                  15

Pro Lys Val Pro Phe Arg Gln Ser Thr Asn Ile Leu Ile Pro Phe His
            20                  25                  30

Lys Arg Ser Ser Phe Gly Phe Asn Ala Gln His Cys Val Arg Ser His
        35                  40                  45

Leu Arg Leu Arg Trp Asn Cys Val Gly Ile His Ala Ser Ala Ala Glu
    50                  55                  60

Thr Arg Pro Asp Gln Leu Pro Gln Glu Glu Arg Phe Val Ser Arg Leu
65                  70                  75                  80

Asn Ala Asp Tyr His Pro Ala Val Trp Lys Asp Phe Ile Asp Ser
                85                  90                  95

Leu Thr Ser Pro Asn Ser His Ala Thr Ser Lys Ser Ser Val Asp Glu
            100                 105                 110

Thr Ile Asn Lys Arg Ile Gln Thr Leu Val Lys Glu Ile Gln Cys Met
        115                 120                 125

Phe Gln Ser Met Gly Asp Gly Glu Thr Asn Pro Ser Ala Tyr Asp Thr
    130                 135                 140

Ala Trp Val Ala Arg Ile Pro Ser Ile Asp Gly Ser Gly Ala Pro Gln
145                 150                 155                 160

Phe Pro Gln Thr Leu Gln Trp Ile Leu Asn Asn Gln Leu Pro Asp Gly
                165                 170                 175

Ser Trp Gly Glu Glu Cys Ile Phe Leu Ala Tyr Asp Arg Val Leu Asn
            180                 185                 190
```

```
Thr Leu Ala Cys Leu Leu Thr Leu Lys Ile Trp Asn Lys Gly Asp Ile
            195                 200                 205

Gln Val Gln Lys Gly Val Glu Phe Val Arg Lys His Met Glu Glu Met
210                 215                 220

Lys Asp Glu Ala Asp Asn His Arg Pro Ser Gly Phe Glu Val Val Phe
225                 230                 235                 240

Pro Ala Met Leu Asp Glu Ala Lys Ser Leu Gly Leu Asp Leu Pro Tyr
            245                 250                 255

His Leu Pro Phe Ile Ser Gln Ile His Gln Lys Arg Gln Lys Lys Leu
            260                 265                 270

Gln Lys Ile Pro Leu Asn Val Leu His Asn His Gln Thr Ala Leu Leu
            275                 280                 285

Tyr Ser Leu Glu Gly Leu Gln Asp Val Val Asp Trp Gln Glu Ile Thr
290                 295                 300

Asn Leu Gln Ser Arg Asp Gly Ser Phe Leu Ser Ser Pro Ala Ser Thr
305                 310                 315                 320

Ala Cys Val Phe Met His Thr Gln Asn Lys Arg Cys Leu His Phe Leu
            325                 330                 335

Asn Phe Val Leu Ser Lys Phe Gly Asp Tyr Val Pro Cys His Tyr Pro
            340                 345                 350

Leu Asp Leu Phe Glu Arg Leu Trp Ala Val Asp Thr Val Glu Arg Leu
            355                 360                 365

Gly Ile Asp Arg Tyr Phe Lys Lys Glu Ile Lys Glu Ser Leu Asp Tyr
            370                 375                 380

Val Tyr Arg Tyr Trp Asp Ala Glu Arg Gly Val Gly Trp Ala Arg Cys
385                 390                 395                 400

Asn Pro Ile Pro Asp Val Asp Asp Thr Ala Met Gly Leu Arg Ile Leu
            405                 410                 415

Arg Leu His Gly Tyr Asn Val Ser Ser Asp Val Leu Glu Asn Phe Arg
            420                 425                 430

Asp Glu Lys Gly Asp Phe Phe Cys Phe Ala Gly Gln Thr Gln Ile Gly
            435                 440                 445

Val Thr Asp Asn Leu Asn Leu Tyr Arg Cys Ser Gln Val Cys Phe Pro
450                 455                 460

Gly Glu Lys Ile Met Glu Glu Ala Lys Thr Phe Thr Thr Asn His Leu
465                 470                 475                 480

Gln Asn Ala Leu Ala Lys Asn Asn Ala Phe Asp Lys Trp Ala Val Lys
            485                 490                 495

Lys Asp Leu Pro Gly Glu Val Glu Tyr Ala Ile Lys Tyr Pro Trp His
            500                 505                 510

Arg Ser Met Pro Arg Leu Glu Ala Arg Ser Tyr Ile Glu Gln Phe Gly
            515                 520                 525

Ser Asn Asp Val Trp Leu Gly Lys Thr Val Tyr Lys Met Leu Tyr Val
530                 535                 540

Ser Asn Glu Lys Tyr Leu Glu Leu Ala Lys Leu Asp Phe Asn Met Val
545                 550                 555                 560

Gln Ala Leu His Gln Lys Glu Thr Gln His Ile Val Ser Trp Trp Arg
            565                 570                 575

Glu Ser Gly Phe Asn Asp Leu Thr Phe Thr Arg Gln Arg Pro Val Glu
            580                 585                 590

Met Tyr Phe Ser Val Ala Val Ser Met Phe Glu Pro Glu Phe Ala Ala
            595                 600                 605

Cys Arg Ile Ala Tyr Ala Lys Thr Ser Cys Leu Ala Val Ile Leu Asp
```

```
                610              615              620
Asp Leu Tyr Asp Thr His Gly Ser Leu Asp Leu Lys Leu Phe Ser
625              630              635              640

Glu Ala Val Arg Arg Trp Asp Ile Ser Val Leu Asp Ser Val Arg Asp
                645              650              655

Asn Gln Leu Lys Val Cys Phe Leu Gly Leu Tyr Asn Thr Val Asn Gly
            660              665              670

Phe Gly Lys Asp Gly Leu Lys Glu Gln Gly Arg Asp Val Leu Gly Tyr
                675              680              685

Leu Arg Lys Val Trp Glu Gly Leu Leu Ala Ser Tyr Thr Lys Glu Ala
            690              695              700

Glu Trp Ser Ala Ala Lys Tyr Val Pro Thr Phe Asn Glu Tyr Val Glu
705              710              715              720

Asn Ala Lys Val Ser Ile Ala Leu Ala Thr Val Val Leu Asn Ser Ile
                725              730              735

Phe Phe Thr Gly Glu Leu Leu Pro Asp Tyr Ile Leu Gln Gln Val Asp
            740              745              750

Leu Arg Ser Lys Phe Leu His Leu Val Ser Leu Thr Gly Arg Leu Ile
            755              760              765

Asn Asp Thr Lys Thr Tyr Gln Ala Glu Arg Asn Arg Gly Glu Leu Val
770              775              780

Ser Ser Val Gln Cys Tyr Met Arg Glu Asn Pro Glu Cys Thr Glu Glu
785              790              795              800

Glu Ala Leu Ser His Val Tyr Gly Ile Ile Asp Asn Ala Leu Lys Glu
                805              810              815

Leu Asn Trp Glu Leu Ala Asn Pro Ala Ser Asn Ala Pro Leu Cys Val
            820              825              830

Arg Arg Leu Leu Phe Asn Thr Ala Arg Val Met Gln Leu Phe Tyr Met
            835              840              845

Tyr Arg Asp Gly Phe Gly Ile Ser Asp Lys Glu Met Lys Asp His Val
            850              855              860

Ser Arg Thr Leu Phe Asp Pro Val Ala
865              870

<210> SEQ ID NO 127
<211> LENGTH: 850
<212> TYPE: PRT
<213> ORGANISM: Pinus taeda
<220> FEATURE:
<223> OTHER INFORMATION: diterpene synthase
<300> PUBLICATION INFORMATION:
<308> DATABASE ACCESSION NUMBER: Genbank AAX07435
<309> DATABASE ENTRY DATE: 2005-06-02

<400> SEQUENCE: 127

Met Ala Leu Pro Ser Ser Leu Ser Ser Gln Ile His Thr Gly Ala
1               5               10              15

Thr Thr Gln Cys Ile Pro His Phe His Gly Ser Leu Asn Ala Gly Thr
                20              25              30

Ser Ala Gly Lys Arg Arg Ser Leu Tyr Leu Arg Trp Gly Lys Gly Pro
            35              40              45

Ser Lys Ile Val Ala Cys Ala Gly Gln Asp Pro Phe Ser Val Pro Thr
            50              55              60

Leu Val Lys Arg Glu Phe Pro Pro Gly Phe Trp Lys Asp His Val Ile
65              70              75              80

Glu Ser Leu Met Pro Ser Tyr Lys Val Ala Pro Ser Asp Glu Lys Arg
```

```
                85                  90                  95
Ile Glu Thr Leu Ile Thr Glu Ile Lys Asn Met Phe Arg Ser Met Gly
            100                 105                 110
Tyr Gly Glu Thr Asn Pro Ser Ala Tyr Asp Thr Ala Trp Val Ala Arg
            115                 120                 125
Ile Pro Ala Val Asp Gly Ser Glu Lys Pro Gln Phe Pro Glu Thr Leu
            130                 135                 140
Glu Trp Ile Leu Gln Asn Gln Leu Lys Asp Gly Ser Trp Gly Glu Glu
145                 150                 155                 160
Phe Tyr Phe Leu Ala Tyr Asp Arg Ile Leu Ala Thr Leu Ala Cys Ile
                165                 170                 175
Ile Thr Leu Thr Ile Trp Gln Thr Gly Asp Thr Gln Val Gln Lys Gly
            180                 185                 190
Ile Glu Phe Phe Lys Thr Gln Ala Gly Lys Ile Glu Glu Glu Ala Asp
            195                 200                 205
Ser His Arg Pro Ser Gly Phe Glu Ile Val Phe Pro Ala Met Leu Lys
        210                 215                 220
Glu Ala Lys Ala Leu Gly Leu Ala Leu Pro Tyr Glu Leu Pro Phe Ile
225                 230                 235                 240
Gln Gln Ile Ile Glu Lys Arg Glu Ala Lys Leu Gln Arg Leu Pro Pro
                245                 250                 255
Asp Leu Leu Tyr Ala Leu Pro Thr Thr Leu Leu Tyr Ser Leu Glu Gly
            260                 265                 270
Leu Gln Glu Ile Val Asp Trp Glu Lys Ile Met Lys Leu Gln Ser Lys
            275                 280                 285
Asp Gly Ser Phe Leu Ser Ser Pro Ala Ser Thr Ala Ala Val Phe Met
            290                 295                 300
Arg Thr Gly Asn Lys Lys Cys Leu Glu Phe Leu Asn Phe Val Leu Lys
305                 310                 315                 320
Lys Phe Gly Asn His Val Pro Cys His Tyr Pro Leu Asp Leu Phe Glu
                325                 330                 335
Arg Leu Trp Ala Val Asp Thr Val Glu Arg Leu Gly Ile Asp His His
            340                 345                 350
Phe Lys Glu Glu Ile Lys Asp Ala Leu Asp Tyr Val Tyr Ser His Trp
            355                 360                 365
Asp Glu Arg Gly Ile Gly Trp Ala Arg Glu Asn Pro Val Pro Asp Ile
            370                 375                 380
Asp Asp Thr Ala Met Gly Leu Arg Ile Leu Arg Leu His Gly Tyr Asn
385                 390                 395                 400
Val Ser Ser Asp Val Leu Lys Thr Phe Arg Asp Glu Asn Gly Glu Phe
                405                 410                 415
Phe Cys Phe Leu Gly Gln Thr Gln Arg Gly Val Thr Asp Met Leu Asn
            420                 425                 430
Val Asn Arg Cys Ser His Val Ala Phe Pro Gly Glu Thr Ile Met Glu
            435                 440                 445
Glu Ala Lys Leu Cys Thr Glu Arg Tyr Leu Arg Asn Ala Leu Glu Asp
            450                 455                 460
Gly Gly Ala Ser Asp Lys Trp Ala Leu Lys Lys Asn Ile Arg Gly Glu
465                 470                 475                 480
Val Glu Tyr Ala Leu Lys Tyr Pro Trp His Arg Ser Met Pro Arg Leu
                485                 490                 495
Glu Ala Arg Ser Tyr Ile Glu Asn Tyr Gly Pro Asn Asp Val Trp Leu
            500                 505                 510
```

```
Gly Lys Thr Met Tyr Met Met Pro Asn Ile Ser Asn Glu Lys Tyr Leu
        515                 520                 525

Glu Leu Ala Lys Leu Asp Phe Asn Arg Val Gln Phe Phe His Arg Gln
        530                 535                 540

Glu Leu Gln Asp Ile Arg Arg Trp Trp Asn Ser Ser Gly Phe Ser Gln
545                 550                 555                 560

Leu Gly Phe Thr Arg Glu Arg Val Ala Glu Ile Tyr Phe Ser Pro Ala
                565                 570                 575

Ser Phe Leu Phe Glu Pro Glu Phe Ala Thr Cys Arg Ala Val Tyr Thr
                580                 585                 590

Lys Thr Ser Asn Phe Thr Val Ile Leu Asp Asp Leu Tyr Asp Ala His
        595                 600                 605

Gly Thr Leu Asp Asn Leu Lys Leu Phe Ser Glu Ser Val Lys Arg Trp
        610                 615                 620

Asp Leu Ser Leu Val Asp Gln Met Pro Gln Asp Met Lys Ile Cys Phe
625                 630                 635                 640

Lys Gly Phe Tyr Asn Thr Phe Asn Glu Ile Ala Glu Glu Gly Arg Lys
                645                 650                 655

Arg Gln Gly Arg Asp Val Leu Ser Tyr Ile Gln Lys Val Trp Glu Val
                660                 665                 670

Gln Leu Glu Ala Tyr Thr Lys Glu Ala Glu Trp Ser Ala Val Arg Tyr
        675                 680                 685

Val Pro Ser Tyr Asp Glu Tyr Ile Gly Asn Ala Ser Val Ser Ile Ala
        690                 695                 700

Leu Gly Thr Val Val Leu Ile Ser Ala Leu Phe Thr Gly Glu Ile Leu
705                 710                 715                 720

Thr Asp Asp Ile Leu Ser Lys Ile Gly Arg Asp Ser Arg Phe Leu Tyr
                725                 730                 735

Leu Met Gly Leu Thr Gly Arg Leu Val Asn Asp Thr Lys Thr Tyr Gln
        740                 745                 750

Ala Glu Arg Gly Gln Gly Glu Val Ala Ser Ala Val Gln Cys Tyr Met
        755                 760                 765

Lys Asp His Pro Glu Ile Ser Glu Glu Ala Leu Lys His Val Tyr
        770                 775                 780

Thr Ile Met Asp Asn Ala Leu Asp Glu Leu Asn Arg Glu Phe Val Asn
785                 790                 795                 800

Asn Arg Asp Val Pro Asp Thr Cys Arg Arg Leu Val Phe Glu Thr Ala
                805                 810                 815

Arg Ile Met Gln Leu Phe Tyr Met Asp Gly Asp Gly Leu Thr Leu Ser
                820                 825                 830

His Asn Met Glu Ile Lys Glu His Val Lys Asn Cys Leu Phe Gln Pro
        835                 840                 845

Val Ala
    850

<210> SEQ ID NO 128
<211> LENGTH: 867
<212> TYPE: PRT
<213> ORGANISM: Picea abies
<220> FEATURE:
<223> OTHER INFORMATION: isopimaradiene synthase
<300> PUBLICATION INFORMATION:
<308> DATABASE ACCESSION NUMBER: Genbank Q675L5
<309> DATABASE ENTRY DATE: 2005-11-22

<400> SEQUENCE: 128
```

```
Met Ala Leu Leu Ser Ser Leu Ser Ser Gln Ile Pro Thr Gly Ser
 1               5                  10                 15

His Pro Leu Thr His Thr Gln Cys Ile Pro His Phe Ser Thr Ile
                20                  25                  30

Asn Ala Gly Ile Ser Ala Gly Lys Pro Arg Ser Phe Tyr Leu Arg Trp
            35                  40                  45

Gly Lys Gly Ser Asn Lys Ile Ile Ala Cys Val Gly Glu Gly Thr Thr
     50                  55                  60

Ser Leu Pro Tyr Gln Ser Ala Glu Lys Thr Asp Ser Leu Ser Ala Pro
 65                  70                  75                  80

Thr Leu Val Lys Arg Glu Phe Pro Pro Gly Phe Trp Lys Asp His Val
                 85                  90                  95

Ile Asp Ser Leu Thr Ser Ser His Lys Val Ser Ala Ala Glu Glu Lys
                100                 105                 110

Arg Met Glu Thr Leu Ile Ser Glu Ile Lys Asn Ile Phe Arg Ser Met
                115                 120                 125

Gly Tyr Gly Glu Thr Asn Pro Ser Ala Tyr Asp Thr Ala Trp Val Ala
        130                 135                 140

Arg Ile Pro Ala Val Asp Gly Ser Glu His Pro Glu Phe Pro Glu Thr
145                 150                 155                 160

Leu Glu Trp Ile Leu Gln Asn Gln Leu Lys Asp Gly Ser Trp Gly Glu
                165                 170                 175

Gly Phe Tyr Phe Leu Ala Tyr Asp Arg Ile Leu Ala Thr Leu Ala Cys
                180                 185                 190

Ile Ile Thr Leu Thr Leu Trp Arg Thr Gly Glu Thr Gln Ile Arg Lys
            195                 200                 205

Gly Ile Glu Phe Phe Lys Thr Gln Ala Gly Lys Ile Glu Asp Glu Ala
    210                 215                 220

Asp Ser His Arg Pro Ser Gly Phe Glu Ile Val Phe Pro Ala Met Leu
225                 230                 235                 240

Lys Glu Ala Lys Val Leu Gly Leu Asp Leu Pro Tyr Glu Leu Pro Phe
                245                 250                 255

Ile Lys Gln Ile Glu Lys Arg Glu Ala Lys Leu Glu Arg Leu Pro
                260                 265                 270

Thr Asn Ile Leu Tyr Ala Leu Pro Thr Thr Leu Leu Tyr Ser Leu Glu
        275                 280                 285

Gly Leu Gln Glu Ile Val Asp Trp Glu Lys Ile Ile Lys Leu Gln Ser
    290                 295                 300

Lys Asp Gly Ser Phe Leu Thr Ser Pro Ala Ser Thr Ala Ala Val Phe
305                 310                 315                 320

Met Arg Thr Gly Asn Lys Lys Cys Leu Glu Phe Leu Asn Phe Val Leu
                325                 330                 335

Lys Lys Phe Gly Asn His Val Pro Cys His Tyr Pro Leu Asp Leu Phe
            340                 345                 350

Glu Arg Leu Trp Ala Val Asp Thr Val Glu Arg Leu Gly Ile Asp His
                355                 360                 365

His Phe Lys Glu Glu Ile Lys Asp Ala Leu Asp Tyr Val Tyr Ser His
    370                 375                 380

Trp Asp Glu Arg Gly Ile Gly Trp Ala Arg Glu Asn Pro Ile Pro Asp
385                 390                 395                 400

Ile Asp Asp Thr Ala Met Gly Leu Arg Ile Leu Arg Leu His Gly Tyr
                405                 410                 415
```

-continued

```
Asn Val Ser Ser Asp Val Leu Lys Thr Phe Arg Asp Glu Asn Gly Glu
                420                 425                 430

Phe Phe Cys Phe Leu Gly Gln Thr Gln Arg Gly Val Thr Asp Met Leu
            435                 440                 445

Asn Val Asn Arg Cys Ser His Val Ala Phe Pro Gly Glu Thr Ile Met
        450                 455                 460

Gln Glu Ala Lys Leu Cys Thr Glu Arg Tyr Leu Arg Asn Ala Leu Glu
465                 470                 475                 480

Asp Val Gly Ala Phe Asp Lys Trp Ala Leu Lys Lys Asn Ile Arg Gly
                485                 490                 495

Glu Val Glu Tyr Ala Leu Lys Tyr Pro Trp His Arg Ser Met Pro Arg
            500                 505                 510

Leu Glu Ala Arg Ser Tyr Ile Glu His Tyr Gly Pro Asn Asp Val Trp
        515                 520                 525

Leu Gly Lys Thr Met Tyr Met Met Pro Tyr Ile Ser Asn Leu Lys Tyr
    530                 535                 540

Leu Glu Leu Ala Lys Leu Asp Phe Asn His Val Gln Ser Leu His Gln
545                 550                 555                 560

Lys Glu Leu Arg Asp Leu Arg Arg Trp Trp Lys Ser Ser Gly Leu Ser
                565                 570                 575

Glu Leu Lys Phe Thr Arg Glu Arg Val Thr Glu Ile Tyr Phe Ser Ala
            580                 585                 590

Ala Ser Phe Ile Phe Glu Pro Glu Phe Ala Thr Cys Arg Asp Val Tyr
        595                 600                 605

Thr Lys Ile Ser Ile Phe Thr Val Ile Leu Asp Asp Leu Tyr Asp Ala
    610                 615                 620

His Gly Thr Leu Asp Asn Leu Glu Leu Phe Ser Glu Gly Val Lys Arg
625                 630                 635                 640

Trp Asp Leu Ser Leu Val Asp Arg Met Pro Gln Asp Met Lys Ile Cys
                645                 650                 655

Phe Thr Val Leu Tyr Asn Thr Val Asn Glu Ile Ala Val Glu Gly Arg
            660                 665                 670

Lys Arg Gln Gly Arg Asp Val Leu Gly Tyr Ile Arg Asn Val Leu Glu
        675                 680                 685

Ile Leu Leu Ala Ala His Thr Lys Glu Ala Glu Trp Ser Ala Ala Arg
    690                 695                 700

Tyr Val Pro Ser Phe Asp Glu Tyr Ile Glu Asn Ala Ser Val Ser Ile
705                 710                 715                 720

Ser Leu Gly Thr Leu Val Leu Ile Ser Val Leu Phe Thr Gly Glu Ile
                725                 730                 735

Leu Thr Asp Asp Val Leu Ser Lys Ile Gly Arg Gly Ser Arg Phe Leu
            740                 745                 750

Gln Leu Met Gly Leu Thr Gly Arg Leu Val Asn Asp Thr Lys Thr Tyr
        755                 760                 765

Glu Ala Glu Arg Gly Gln Gly Glu Val Ala Ser Ala Val Gln Cys Tyr
    770                 775                 780

Met Lys Glu His Pro Glu Ile Ser Glu Glu Ala Leu Lys His Val
785                 790                 795                 800

Tyr Thr Val Met Glu Asn Ala Leu Asp Glu Leu Asn Arg Glu Phe Val
                805                 810                 815

Asn Asn Arg Asp Val Pro Asp Ser Cys Arg Arg Leu Val Phe Glu Thr
            820                 825                 830

Ala Arg Ile Met Gln Leu Phe Tyr Met Glu Gly Asp Gly Leu Thr Leu
```

```
                835                 840                 845
Ser His Glu Met Glu Ile Lys Glu His Val Lys Asn Cys Leu Phe Gln
    850                 855                 860

Pro Val Ala
865

<210> SEQ ID NO 129
<211> LENGTH: 792
<212> TYPE: PRT
<213> ORGANISM: Nicotiana tabacum
<220> FEATURE:
<223> OTHER INFORMATION: abienol synthase
<300> PUBLICATION INFORMATION:
<308> DATABASE ACCESSION NUMBER: Genbank CCD33019
<309> DATABASE ENTRY DATE: 2011-11-16

<400> SEQUENCE: 129

Met Val Leu Gly Leu Arg Ser Lys Ile Ile Pro Leu Pro Asp His Lys
1               5                   10                  15

Leu Gly Asn Ile Lys Leu Gly Ser Val Thr Asn Ala Ile Cys His Arg
            20                  25                  30

Pro Cys Arg Val Arg Cys Ser His Ser Thr Ala Ser Ser Met Glu Glu
        35                  40                  45

Ala Lys Glu Arg Ile Arg Glu Thr Phe Gly Lys Ile Glu Leu Ser Pro
    50                  55                  60

Ser Ser Tyr Asp Thr Ala Trp Val Ala Met Val Pro Ser Arg Tyr Ser
65                  70                  75                  80

Met Asn Gln Pro Cys Phe Pro Gln Cys Leu Asp Trp Ile Leu Glu Asn
                85                  90                  95

Gln Arg Glu Asp Gly Ser Trp Gly Leu Asn Pro Ser His Pro Leu Leu
            100                 105                 110

Val Lys Asp Ser Leu Ser Ser Thr Leu Ala Ser Leu Leu Ala Leu Arg
        115                 120                 125

Lys Trp Arg Ile Gly Asp Asn Gln Val Gln Arg Gly Leu Gly Phe Ile
    130                 135                 140

Glu Thr His Gly Trp Ala Val Asp Asn Lys Asp Gln Ile Ser Pro Leu
145                 150                 155                 160

Gly Phe Glu Ile Ile Phe Pro Cys Met Ile Asn Tyr Ala Glu Lys Leu
                165                 170                 175

Asn Leu Asp Leu Pro Leu Asp Pro Asn Leu Val Asn Met Met Leu Cys
            180                 185                 190

Glu Arg Glu Leu Thr Ile Glu Arg Ala Leu Lys Asn Glu Phe Glu Gly
        195                 200                 205

Asn Met Ala Asn Val Glu Tyr Phe Ala Glu Gly Leu Gly Glu Leu Cys
    210                 215                 220

His Trp Lys Glu Met Met Leu Arg Gln Arg His Asn Gly Ser Leu Phe
225                 230                 235                 240

Asp Ser Pro Ala Thr Thr Ala Ala Leu Ile Tyr His Gln Tyr Asp
                245                 250                 255

Glu Lys Cys Phe Gly Tyr Leu Asn Ser Ile Leu Lys Leu His Asp Asn
            260                 265                 270

Trp Val Pro Thr Ile Cys Pro Thr Lys Ile His Ser Asn Leu Phe Leu
        275                 280                 285

Val Asp Ala Leu Gln Asn Leu Gly Val Asp Arg Tyr Phe Lys Thr Glu
    290                 295                 300

Val Lys Arg Val Leu Asp Glu Ile Tyr Arg Leu Trp Leu Glu Lys Asn
```

-continued

```
            305                 310                 315                 320
        Glu Glu Ile Phe Ser Asp Val Ala His Cys Ala Met Ala Phe Arg Leu
                        325                 330                 335
        Leu Arg Met Asn Asn Tyr Glu Val Ser Ser Glu Glu Leu Glu Gly Phe
                        340                 345                 350
        Val Asp Gln Glu His Phe Phe Thr Thr Ser Gly Lys Leu Met Asn
                        355                 360                 365
        His Val Ala Ile Leu Glu Leu His Arg Ala Ser Gln Val Ala Ile His
                370                 375                 380
        Glu Arg Lys Asp His Ile Leu Asp Lys Ile Ser Thr Trp Thr Arg Asn
        385                 390                 395                 400
        Phe Met Glu Gln Lys Leu Leu Asp Lys His Ile Pro Asp Arg Ser Lys
                        405                 410                 415
        Lys Glu Met Glu Phe Ala Met Arg Lys Phe Tyr Gly Thr Phe Asp Arg
                        420                 425                 430
        Val Glu Thr Arg Arg Tyr Ile Glu Ser Tyr Lys Met Asp Ser Phe Lys
                        435                 440                 445
        Ile Leu Lys Ala Ala Tyr Arg Ser Ser Gly Ile Asn Asn Ile Asp Leu
                450                 455                 460
        Leu Lys Phe Ser Glu His Asp Phe Asn Leu Cys Gln Thr Arg His Lys
        465                 470                 475                 480
        Glu Glu Leu Gln Gln Met Lys Arg Trp Phe Thr Asp Cys Lys Leu Glu
                        485                 490                 495
        Gln Val Gly Leu Ser Gln Gln Tyr Leu Tyr Thr Ser Tyr Phe Ile Ile
                        500                 505                 510
        Ala Ala Ile Leu Phe Glu Pro Glu Tyr Ala Asp Ala Arg Leu Ala Tyr
                        515                 520                 525
        Ala Lys Tyr Ala Ile Ile Ile Thr Ala Val Asp Asp Phe Phe Asp Cys
                        530                 535                 540
        Phe Ile Cys Lys Glu Glu Leu Gln Asn Ile Ile Glu Leu Val Glu Arg
        545                 550                 555                 560
        Trp Glu Gly Tyr Ser Thr Val Gly Phe Arg Ser Glu Arg Val Arg Ile
                        565                 570                 575
        Phe Phe Leu Ala Leu Tyr Lys Met Val Glu Glu Ile Ala Ala Lys Ala
                        580                 585                 590
        Glu Thr Lys Gln Gly Arg Cys Val Lys Asp His Leu Ile Asn Leu Trp
                        595                 600                 605
        Ile Asp Met Leu Lys Cys Met Leu Val Glu Leu Asp Leu Trp Lys Ile
                        610                 615                 620
        Lys Ser Thr Thr Pro Ser Ile Glu Glu Tyr Leu Ser Val Ala Cys Val
        625                 630                 635                 640
        Thr Ile Gly Val Pro Cys Phe Val Leu Thr Ser Leu Tyr Leu Leu Gly
                        645                 650                 655
        Pro Lys Leu Ser Lys Asp Val Ile Glu Ser Ser Glu Val Ser Ala Leu
                        660                 665                 670
        Cys Asn Cys Thr Ala Ala Val Ala Arg Leu Ile Asn Asp Ile His Ser
                        675                 680                 685
        Tyr Lys Arg Glu Gln Ala Glu Ser Ser Thr Asn Met Val Ser Ile Leu
                        690                 695                 700
        Ile Thr Gln Ser Gln Gly Thr Ile Ser Glu Glu Ala Ile Arg Gln
        705                 710                 715                 720
        Ile Lys Glu Met Met Glu Ser Lys Arg Arg Glu Leu Leu Gly Met Val
                        725                 730                 735
```

```
Leu Gln Asn Lys Glu Ser Gln Leu Pro Gln Val Cys Lys Asp Leu Phe
            740                 745                 750

Trp Thr Thr Ile Asn Ala Ala Tyr Ser Ile His Thr His Gly Asp Gly
            755                 760                 765

Tyr Arg Phe Pro Glu Glu Phe Lys Asn His Ile Asn Asp Val Ile Tyr
770                 775                 780

Lys Pro Leu Asn Gln Tyr Ser Pro
785                 790

<210> SEQ ID NO 130
<211> LENGTH: 747
<212> TYPE: PRT
<213> ORGANISM: Nicotiana glutinosa
<220> FEATURE:
<223> OTHER INFORMATION: labdenediol diphosphate synthase

<400> SEQUENCE: 130

Met Cys Ala Pro Ile Asp Ala Ser Tyr Leu Gly Tyr Leu Asn Glu Leu
1               5                   10                  15

Glu Ser Asn Phe Ser Asn Asn Pro Glu Glu Lys Asp Ile Gln Val Ser
            20                  25                  30

Arg Thr Ile Gln Ile Lys Asn Leu Thr Glu Glu Ile Lys Cys Lys Leu
        35                  40                  45

Asn Ser Met Glu Asp Gly Arg Ser Ser Val Ser Ala Tyr Asp Thr Ala
    50                  55                  60

Trp Val Ser Phe Ile Pro Asn Thr Thr Asn Gly Asn Asp Gln Arg
65                  70                  75                  80

Pro Met Phe Pro Ser Cys Leu Gln Trp Ile Ile Asp Asn Gln Leu Cys
                85                  90                  95

Asp Gly Ser Trp Gly Glu Glu Ser Val Phe Cys Ile Tyr Asp Arg Leu
            100                 105                 110

Leu Asn Thr Leu Ala Cys Val Val Ala Leu Thr Leu Trp Asn Thr Cys
        115                 120                 125

Leu Pro Lys Arg Asn Lys Gly Val Met Phe Ile Lys Glu Asn Leu Ile
    130                 135                 140

Lys Leu Glu Thr Gly Glu Val Glu His Met Thr Cys Gly Phe Glu Phe
145                 150                 155                 160

Val Phe Pro Ala Leu Leu Glu Lys Ala Gln Gln Leu Asn Ile Asp Ile
                165                 170                 175

Pro Tyr Asp Ala Pro Val Leu Lys Asp Ile Tyr Ala Arg Arg Glu Val
            180                 185                 190

Lys Phe Thr Arg Ile Pro Lys Glu Ile Val His Thr Ile Pro Thr Thr
        195                 200                 205

Ala Leu Leu Ser Leu Glu Gly Leu Arg Asp Asp Leu Asp Trp Gln Arg
    210                 215                 220

Leu Leu Asn Phe Gln Met Pro Asp Gly Ser Phe Leu Ser Ala Pro Ala
225                 230                 235                 240

Ser Thr Ala Phe Ala Phe Met Lys Thr Asn Asp Glu Lys Cys Leu Ala
                245                 250                 255

Tyr Leu Gln Asn Val Val Gln Lys Ser Asn Gly Gly Ala Arg His Tyr
            260                 265                 270

Pro Leu Asp Leu Leu Thr Arg Leu Trp Ala Ile Asp Arg Leu Gln Arg
        275                 280                 285

Leu Gly Ile Ser Tyr Tyr Phe Ala Glu Glu Phe Lys Glu Leu Leu Asn
    290                 295                 300
```

-continued

His Val Phe Arg Tyr Trp Asp Glu Glu Asn Gly Ile Phe Ser Gly Arg
305                 310                 315                 320

Asn Ser Asn Val Cys Asp Val Asp Asp Thr Cys Met Ala Ile Arg Leu
            325                 330                 335

Leu Arg Leu His Gly Tyr Asp Val Ser Pro Asp Ala Leu Asn Asn Phe
            340                 345                 350

Thr Asp Gly Asp Gln Phe Phe Cys Leu Arg Gly Glu Val Asp Gly Ser
        355                 360                 365

Pro Thr His Met Phe Asn Leu Tyr Arg Cys Ser Gln Val Leu Phe Pro
    370                 375                 380

Gly Glu Lys Ile Leu Glu Glu Ala Lys Asn Phe Thr Tyr Asn Phe Leu
385                 390                 395                 400

Gln Gln Cys Leu Ala Asn Asn Arg Cys Leu Asp Lys Trp Val Ile Ala
                405                 410                 415

Lys Asp Ile Pro Gly Glu Ile Arg Tyr Ala Leu Lys Phe Pro Trp Tyr
            420                 425                 430

Ala Ser Leu Pro Arg Val Glu Ser Arg Leu Tyr Ile Glu Gln Tyr Gly
        435                 440                 445

Gly Ala Asn Asp Ile Trp Ile Gly Lys Thr Leu Tyr Arg Met Pro Asp
450                 455                 460

Val Ser Asn Asn Val Tyr Leu Gln Ala Ala Lys Leu Asp Tyr Asn Arg
465                 470                 475                 480

Cys Gln Ser Gln His Arg Phe Glu Trp Leu Ile Met Gln Trp Phe
                485                 490                 495

Asp Lys Cys Asn Phe Gln Gln Phe Gly Ile Ser Lys Lys Tyr Leu Leu
            500                 505                 510

Val Ser Tyr Phe Leu Ala Ala Ala Ser Ile Phe Glu Val Glu Lys Ser
        515                 520                 525

Arg Glu Arg Leu Ala Trp Ala Lys Ser Arg Ile Ile Cys Lys Met Ile
    530                 535                 540

Thr Ser Tyr Tyr Asn Glu Glu Ala Thr Thr Trp Thr Ser Arg Asn Ser
545                 550                 555                 560

Leu Leu Met Glu Phe Lys Gly Ser Asp Pro Ser Arg Lys Asn Gly
                565                 570                 575

Asn Glu Thr Lys Glu Ile Ile Val Leu Lys Asn Leu Arg Gln Phe Leu
            580                 585                 590

His Gln Leu Ser Glu Glu Thr Phe Glu Asp Leu Gly Lys Asp Ile His
        595                 600                 605

His Gln Leu Gln Asn Ala Trp Lys Thr Trp Leu Ala Phe Leu Arg Glu
    610                 615                 620

Glu Lys Asn Thr Cys Gln Glu Glu Ala Glu Leu Leu Val Arg Thr Ile
625                 630                 635                 640

Asn Leu Ser Gly Gly His Met Ile His Asp Glu Ile Leu Phe Asp Ala
                645                 650                 655

Asp Tyr Lys Asn Leu Ser Asn Leu Thr Asn Lys Val Cys Cys Met Leu
            660                 665                 670

Ser Glu Leu Gln Asn Asp Lys Val Thr Gly Ser Ser Lys Asn Thr Asp
        675                 680                 685

Ile Glu Leu Asn Met Gln Ala Leu Val Lys Leu Val Phe Gly Asn Thr
    690                 695                 700

Ser Ser Asn Ile Asn Gln Asp Ile Lys Gln Thr Phe Phe Thr Val Val
705                 710                 715                 720

```
Lys Thr Phe Tyr Tyr Ser Ala His Ala Ser Glu Glu Ile Ile Asn Phe
                725                 730                 735

His Ile Ser Lys Val Leu Leu Gln Gln Val Gln
            740                 745

<210> SEQ ID NO 131
<211> LENGTH: 755
<212> TYPE: PRT
<213> ORGANISM: Nicotiana glutinosa
<220> FEATURE:
<223> OTHER INFORMATION: sclareol synthase

<400> SEQUENCE: 131

Met Ser His Ser Thr Ala Ser Ser Leu Glu Glu Ala Lys Glu Arg Ile
  1               5                  10                  15

Arg Glu Thr Phe Gly Lys Asn Glu Leu Ser Pro Ser Tyr Asp Thr
                 20                  25                  30

Ala Trp Val Ala Met Val Pro Ser Arg Tyr Ser Met Asn Gln Pro Cys
             35                  40                  45

Phe Pro Arg Cys Leu Asp Trp Ile Leu Glu Asn Gln Arg Glu Asp Gly
 50                  55                  60

Ser Trp Gly Leu Asn Pro Ser His Pro Leu Leu Val Lys Asp Ser Leu
 65                  70                  75                  80

Ser Ser Thr Leu Ala Cys Leu Ala Leu Arg Lys Trp Arg Ile Gly
                 85                  90                  95

Asp Asn Gln Val Gln Arg Gly Leu Gly Phe Ile Glu Thr His Gly Trp
                100                 105                 110

Ala Val Asp Asn Val Asp Gln Ile Ser Pro Leu Gly Phe Asp Ile Ile
            115                 120                 125

Phe Pro Ser Met Ile Lys Tyr Ala Glu Lys Leu Asn Leu Asp Leu Pro
130                 135                 140

Phe Asp Pro Asn Leu Val Asn Met Met Leu Arg Glu Arg Glu Leu Thr
145                 150                 155                 160

Ile Glu Arg Ala Leu Lys Asn Glu Phe Glu Gly Asn Met Ala Asn Val
                165                 170                 175

Glu Tyr Phe Ala Glu Gly Leu Gly Glu Leu Cys His Trp Lys Glu Ile
            180                 185                 190

Met Leu His Gln Arg Arg Asn Gly Ser Pro Phe Asp Ser Pro Ala Thr
        195                 200                 205

Thr Ala Ala Leu Ile Tyr His Gln His Asp Glu Lys Cys Phe Gly
210                 215                 220

Tyr Leu Ser Ser Ile Leu Lys Leu His Glu Asn Trp Val Pro Thr Ile
225                 230                 235                 240

Tyr Pro Thr Lys Val His Ser Asn Leu Phe Phe Val Asp Ala Leu Gln
                245                 250                 255

Asn Leu Gly Val Asp Arg Tyr Phe Lys Thr Glu Leu Lys Ser Val Leu
            260                 265                 270

Asp Glu Ile Tyr Arg Leu Trp Leu Glu Lys Asn Glu Glu Ile Phe Ser
        275                 280                 285

Asp Ile Ala His Cys Ala Met Ala Phe Arg Leu Leu Arg Met Asn Asn
    290                 295                 300

Tyr Glu Val Ser Ser Glu Glu Leu Gly Phe Val Asp Gln Glu His
305                 310                 315                 320

Phe Phe Thr Thr Ser Gly Gly Lys Leu Ile Ser His Val Ala Ile Leu
                325                 330                 335
```

-continued

```
Glu Leu His Arg Ala Ser Gln Val Asp Ile Gln Glu Gly Lys Asp Leu
            340                 345                 350

Ile Leu Asp Lys Ile Ser Thr Trp Thr Arg Asn Phe Met Glu Gln Glu
        355                 360                 365

Leu Leu Asp Asn Gln Ile Leu Asp Arg Ser Lys Lys Glu Met Glu Phe
    370                 375                 380

Ala Met Arg Lys Phe Tyr Gly Thr Phe Asp Arg Val Glu Thr Arg Arg
385                 390                 395                 400

Tyr Ile Glu Ser Tyr Lys Met Asp Ser Phe Lys Ile Leu Lys Ala Ala
                405                 410                 415

Tyr Arg Ser Ser Asn Ile Asn Asn Ile Asp Leu Leu Lys Phe Ser Glu
            420                 425                 430

His Asp Phe Asn Leu Cys Gln Ala Arg His Lys Glu Glu Leu Gln Gln
        435                 440                 445

Ile Lys Arg Trp Phe Ala Asp Cys Lys Leu Glu Gln Val Gly Ser Ser
    450                 455                 460

Gln Asn Tyr Leu Tyr Thr Ser Tyr Phe Pro Ile Ala Ala Ile Leu Phe
465                 470                 475                 480

Glu Pro Glu Tyr Gly Asp Ala Arg Leu Ala Phe Ala Lys Cys Gly Ile
                485                 490                 495

Ile Ala Thr Thr Val Asp Asp Phe Phe Asp Gly Phe Ala Cys Asn Glu
            500                 505                 510

Glu Leu Gln Asn Ile Ile Glu Leu Val Glu Arg Trp Asp Gly Tyr Pro
        515                 520                 525

Thr Val Gly Phe Arg Ser Glu Arg Val Arg Ile Phe Phe Leu Ala Leu
    530                 535                 540

Tyr Lys Met Ile Glu Glu Ile Ala Ala Lys Ala Glu Thr Lys Gln Gly
545                 550                 555                 560

Arg Cys Val Lys Asp Leu Leu Ile Asn Leu Trp Ile Asp Leu Leu Lys
                565                 570                 575

Cys Met Leu Val Glu Leu Asp Leu Trp Lys Ile Lys Ser Thr Thr Pro
            580                 585                 590

Ser Ile Glu Glu Tyr Leu Ser Ile Ala Cys Val Thr Thr Gly Val Lys
        595                 600                 605

Cys Leu Ile Leu Ile Ser Leu His Leu Leu Gly Pro Lys Leu Ser Lys
    610                 615                 620

Asp Val Thr Glu Ser Ser Glu Val Ser Ala Leu Trp Asn Cys Thr Ala
625                 630                 635                 640

Val Val Ala Arg Leu Asn Asn Asp Ile His Ser Tyr Lys Arg Glu Gln
                645                 650                 655

Ala Glu Ser Ser Thr Asn Met Val Ala Ile Leu Ile Ser Gln Ser Gln
            660                 665                 670

Arg Thr Ile Ser Glu Glu Ala Ile Arg Gln Ile Lys Glu Met Met
        675                 680                 685

Glu Ser Lys Arg Arg Glu Leu Leu Gly Met Val Leu Gln Asn Lys Glu
    690                 695                 700

Ser Gln Leu Pro Gln Val Cys Lys Asp Leu Phe Trp Thr Thr Phe Lys
705                 710                 715                 720

Ala Ala Tyr Ser Ile Tyr Thr His Gly Asp Glu Tyr Arg Phe Pro Gln
                725                 730                 735
```

```
Glu Leu Lys Asn His Ile Asn Asp Val Ile Tyr Lys Pro Leu Asn Gln
            740                 745                 750
Tyr Ser Pro
        755
```